US006951738B2

(12) United States Patent
Ni et al.

(10) Patent No.: US 6,951,738 B2
(45) Date of Patent: Oct. 4, 2005

(54) HUMAN TUMOR NECROSIS FACTOR RECEPTORS TR13 AND TR14

(75) Inventors: Jian Ni, Germantown, MD (US); Kevin P. Baker, Darnestown, MD (US); Steven M. Ruben, Olney, MD (US); Paul E. Young, Gaithersburg, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 10/046,433

(22) Filed: Jan. 16, 2002

(65) Prior Publication Data

US 2003/0092101 A1 May 15, 2003

Related U.S. Application Data

(63) Continuation-in-part of application No. 09/618,570, filed on Jul. 14, 2000, now abandoned.
(60) Provisional application No. 60/144,087, filed on Jul. 16, 1999, provisional application No. 60/149,450, filed on Aug. 18, 1999, provisional application No. 60/149,712, filed on Aug. 20, 1999, provisional application No. 60/153,089, filed on Sep. 10, 1999, and provisional application No. 60/261, 960, filed on Jan. 17, 2001.

(51) Int. Cl.[7] .......................... C12N 15/09; C07H 21/04
(52) U.S. Cl. ................. 435/69.1; 536/23.5; 530/350; 435/320.1; 435/455; 435/252.3; 435/325
(58) Field of Search ................. 536/23.5; 530/350; 435/320.1, 252.3, 325, 69.1

(56) References Cited

U.S. PATENT DOCUMENTS

| | | | | |
|---|---|---|---|---|
| 5,194,596 A | * | 3/1993 | Tischer et al. | 530/399 |
| 5,350,836 A | * | 9/1994 | Kopchick et al. | 530/399 |
| 5,736,363 A | * | 4/1998 | Edwards et al. | 435/69.4 |
| 5,876,969 A | * | 3/1999 | Fleer et al. | 435/69.7 |
| 6,072,047 A | | 6/2000 | Rauch et al. | |

FOREIGN PATENT DOCUMENTS

| | | |
|---|---|---|
| DE | 19817948 | 10/1999 |
| GB | 9907113.6 | 3/1999 |
| GB | 9922858.7 | 9/1999 |
| WO | WO 9514772 | 6/1995 |
| WO | WO 9838304 | 9/1998 |
| WO | WO 9906548 | 2/1999 |
| WO | WO 9906550 | 2/1999 |
| WO | WO 9933967 | 7/1999 |
| WO | WO 9954461 | 10/1999 |
| WO | WO 0001817 | 1/2000 |
| WO | WO 0039284 | 7/2000 |
| WO | WO 0053758 | 9/2000 |
| WO | WO 0055351 | 9/2000 |
| WO | WO 00/58460 | * 10/2000 |
| WO | WO 0058460 | 10/2000 |
| WO | WO 0060076 | 10/2000 |
| WO | WO 0061741 | 10/2000 |
| WO | WO 0061757 | 10/2000 |
| WO | WO 0078802 | 12/2000 |
| WO | WO 0102568 | 1/2001 |
| WO | WO 01/05834 | * 1/2001 |
| WO | WO 0118542 | 3/2001 |
| WO | WO 0131003 | 5/2001 |
| WO | WO 0140466 | 6/2001 |
| WO | WO 0159117 | 8/2001 |
| WO | WO 0164835 | 9/2001 |

OTHER PUBLICATIONS

Vukicevic et al., 1996, PNAS USA 93:9021–9026.*
Latza et al., Eur. J. Immunol., 24: 677–683 (1994).
Latza et al., Tumor necrosis factor receptor superfamily member 4 precursor. SWISSPROT Accession No. P43489, Nov. 1, 1995, annotation updated Sep. 15, 2003.
Loparev et al., Tumor necrosis factor receptor II homolog. SWISSPROT Accession No. O57116, Jun. 1, 1998, annotation updated Feb. 1, 2003.
Naismith et al., TIBS, 23: 74–79 (1998).
International Search Report from PCT/US00/19343 (Jun. 5, 2003).
U.S. Appl. No. 09/912,293, Rosen et al.
Strausberg et al., qo16g05.x1 NCI_CGAP_Lu5 Homo sapiens cDNA clone IMAGE: 1980728 3' mRNA sequence. NCBI Accession No. AI301140, Feb. 1, 1999, National Center for Biotechnology Information, U.S.A.
International Search Report from PCT/US00/19343 (Dec. 18, 2000).
Rosenthal et al., Human endometrium tumour cDNA derived EST 11. GENESEQ Accession No. AAZ41991, Feb. 1, 1999, Geneseq Database Version 73.0 (Oct. 15, 2001).
Rosenthal et al., Human endometrium tumour EST encoded protein 32. GENESEQ Accession No. AAY59972, Feb. 1, 1999, Geneseq Database Version 73.0 (Oct. 15, 2001).
Lee et al., Human ovarian cancer cell expressed sequence 8094. GENESEQ Accession No. AAF98655, Jul. 2, 2001, Geneseq Database Version 73.0 (Oct. 15, 2001).
Lee et al., Human ovarian cancer cell expressed sequence 9957. GENESEQ Accession No. AAF98672, Jul. 2, 2001, Geneseq Database Verison 73.0 (Oct. 15, 2001).
Matsubara, K. and Okubo, K. Human gene signature HUMGS08479. GENESEQ Accession No. AAT26240, Nov. 13, 1996, Geneseq Database Verion 73.0 (Oct. 15, 2001).
Tang et al., Human polynucleotide SEQ ID No. 4330. GENESEQ Accession No. AAI84270, Nov. 16, 2001, Geneseq Database Version 75.0 (Nov. 14, 2001).

(Continued)

Primary Examiner—Lorraine Spector
Assistant Examiner—Eileen B. O'Hara
(74) Attorney, Agent, or Firm—Human Genome Sciences, Inc.

(57) ABSTRACT

The present invention relates to two novel proteins, TR13 and TR14, which are members of the tumor necrosis factor (TNF) receptor superfamily. In particular, isolated nucleic acid molecules are provided encoding the human TR13 and TR14 proteins. TR13 and TR14 polypeptides are also provided as are vectors, host cells and recombinant methods for producing the same. The invention further relates to screening methods for identifying agonists and antagonists of TR13 and TR14.

38 Claims, 37 Drawing Sheets

OTHER PUBLICATIONS

Williams et al., Novel human polynucleotide, SEQ ID No.: 735. GENESEQ Accession No. AAF64979, Apr. 9, 2001, Geneseq Database Verison 75.0 (Nov. 14, 2001).
Williams et al., Novel human polynucleotide, SEQ ID No.: 2193. GENESEQ Accession No. AAF66437, Apr. 9, 2001, Geneseq Database Version 75.0 (Nov. 14, 2001).
Ohara, O. et al., GenBank Accession No. AB037745 (Mar. 14, 2000).
NCI–CGAP, GenBank Accesion No. AW292764 (Jan. 16, 2000).
NCI–CGAP, GenBank Accession No. AI185703 (Oct. 29, 1998).
NCI–CGAP, GenBank Accession No. AI805813 (Dec. 13, 1999).
NCI–CGAP, GenBank Accession No. AA631436 (Oct. 30, 1997).
NCI–CGAP, GenBank Accession No. AI813293 (Dec. 21, 1999).
Adams, M.D. et al., GenBank Accession No. AA329106 (Apr. 20, 1997).
Dias Neto, E. et al., GenBank Accession No. AW994023 (Jun. 5, 2000).
NCI–CGAP, GenBank Accession No. AI672868 (Dec. 18, 1999).
Hegde, P. et al., GenBank Accession No. AW966212 (Jun. 1, 2000).
NCI–CGAP, GenBank Accession No. BE218431 (Jul. 3, 2000).
NCI–CGAP, GenBank Accession No. AW137691 (Oct. 29, 1999).
NCI–CGAP, GenBank Accession No. AA890726 (Jan. 4, 1999).
Dias Neto, E. et al., GenBank Accession No. BE081676 (Jun. 12, 2000).
Dias Neto, E. et al., GenBank Accession No. AI902568 (Mar. 30, 2000).
NCI–CGAP, GenBank Accession No. AI889507 (Mar. 7, 2000).
NCI–CGAP, GenBank Accession No. AI565067 (May 14, 1999).
Hillier, L. et al. GenBank Accession No. AA399077 (May 16, 1997).
NCI–CGAP, GenBank Accession No. AI683933 (Dec. 15, 1999).
NCI–CGAP, GenBank Accession No. AI923722 (Mar. 8, 2000).
Hegde, P. et al., GenBank Accession No. AW958161 (Jun. 1, 2000).
Hegde, P. et al., GenBank Accession No. AW965515 (Jun. 1, 2000).
NCI–CGAP, GenBank Accession No. AI131470 (Oct. 27, 1998).
NCI–CGAP, GenBank Accession No. AW272678 (Jan. 3, 2000).
NCI–CGAP, GenBank Accession No. AW337219 (Jan. 31, 2000).
Hegde, P. et al., GenBank Accession No. AW966239 (Jun. 1, 2000).
NCI–CGAP, Genbank Accession No. AI955187 (Mar. 9, 2000).
NCI–CGAP, GenBank Accession No. AA603475 (Oct. 8, 1997).
NCI–CGAP, GenBank Accession No. AI628844 (Mar. 7, 2000).
HCGAP, GenBank Accession No. AW391972 (Feb. 4, 2000).
NCI–CGAP, GenBank Accession No. AI683001 (Dec. 15, 1999).
Dias Neto, E., GenBank Accession No. AW864381 (May 22, 2000).
NCI–CGAP, GenBank Accession No. AI148969 (Nov. 10, 1998).
NCI–CGAP, GenBank Accession No. AI026747 (Aug. 27, 1998).
HCGP, GenBank Accession No. AW602657 (Mar. 23, 2000).
NCI–CGAP, GenBank Accession No. AI499493 (Apr. 14, 1999).
NCI–CGAP, GenBank Accession No. AA512881 (Aug. 20, 1997).
Dias Neto, E. et al., GenBank Accession No. AW864300 (May 22, 2000).
NCI–CGAP, GenBank Accession No. AI623092 (Dec. 15, 1999).
NCI–CGAP GenBank Accession No. AW139336 (Oct. 30, 1999).
NCI–CGAP, GenBank Accession No. AA552291 (Sep. 9, 1997).
NCI–CGAP, GenBank Accession No. AA557888 (Sep. 9, 1997).
Dias Neto, E. et al., GenBank Accession No. AW994408 (Jun. 5, 2000).
NCI–CGAP, GenBank Accession No. AI000966 (Jul. 27, 1998).
NCI–CGAP GenBank Accession No. AI363713 (Feb. 15, 1999).
Adams, M.D. et al., GenBank Accession No. AA337039 (Apr. 21, 1997).
NCI–CGAP, GenBank Accession No. AA552248 (Sep. 5, 1997).
NCI–CGAP, GenBank Accession No. AA508043 (Aug. 19, 1997).
NCI–CGAP, GenBank Accession No. AI963850 (Mar. 8, 2000).
NCI–CGAP, GenBank Accession No. AA888781 (Jan. 4, 1999).
Hillier, L. et al., GenBank Accession No. AA412133 (May 18, 1997).
Dias Neto, E. et al., GenBank Accession No. AW864697 (May 22, 2000).
Adams, M.D. et al., GenBank Accession No. AA336849 (Apr. 21, 1997).
HCGP, GenBank Accession No. AW392189 (Feb. 4,2000).
NCI–CGAP, GenBank Accession No. AW130027 (Oct. 27, 1999).
Adams, M.D. et al., GenBank Accession No. AA337895 (Apr. 21, 1997).
Dias Neto, E. et al., GenBank Accession No. AW864722 (Apr. 22, 2000).
Adams, M.D. et al., GenBank Accession No. AA335292 (Apr. 21, 1997).
Adams, M.D. et al., GenBank Accession No. AA337833 (Apr. 21, 1997).
NCI–CGAP, GenBank, Accession No. AA533583 (Aug. 21, 1997).

NCI–CGAP, GenBank Accession No. AI963678 (Mar. 8, 2000).

Adams, M.D. et al., GenBank Accession No. AA336964 (Apr. 21, 1997).

NCI–CGAP, GenBank Accession No. AI363749 (Jan. 7, 1999).

NCI–CGAP, GenBank Accession No. AI696598 (Dec. 16, 1999).

Adams, M.D. et al., GenBank Accession No. AA336993 (Apr. 21, 1997).

NCI–CGAP, GenBank Accession No. AW080858 (Oct. 14, 1999).

Marra, M. et al., GenBank Accession No. AI152363 (Sep. 30, 1998).

NCI–CGAP, GenBank Accession No. AA9996710 (Jun. 5, 1998).

NCI–CGAP, GenBank Accession No. AI687545 (Dec. 14, 1999).

NCI–CGAP, GenBank Accession No. BE046818 (Jun. 8, 2000).

* cited by examiner

1   GTCGACCCACGCGTCCGCAGCCTTCTCAGTATGGACCAAAGTACCCAAGCCTGTGCTGGT   60
1                                    M  D  Q  S  T  Q  A  C  A  G    10

61  GAGAAACATTGCCATAACAGGGGTGGCCTACACTTCAGAATGCTTCCCCTGCAAACCTGG  120
11  E  K  H  C  H  N  R  G  G  L  H  F  R  M  L  P  L  Q  T  W       30

121 CACGTATGCAGACAAGCAGGGCTCCTCTTTCTGCAAACTTTGCCCAGCAACTCTTATTCA  180
31  H  V  C  R  Q  A  G  L  L  F  L  Q  T  L  P  S  N  S  Y  S       50

181 AATAAAGGAGAAACTTCTTGCCACCAGTGTGACCCTGACAAATACTCAGAGAAAGGATCT  240
51  N  K  G  E  T  S  C  H  Q  C  D  P  D  K  Y  S  E  K  G  S̶       70

241 TCTTCCTGTAACGTGCGCCCAGCTTGCACAGACAAAGATTATTTCTACACACACACGGCC  300
71  S̶  S̶  C̶  N̶  V  R  P  A  C  T̳  D̳  K̳  D̳  Y  F  Y  T  H  T̳  A̳   90

301 TGCGATGCCAACGGAGAGACACAACTCATGTACAAATGGGCCAAGCCGAAAATCTGTAGC  360
91  C̳  D̳  A  N  G  E  T  Q  L  M  Y  K  W  A  K  P  K  I  C  S      110

361 GAGGACCTTGAGGGGGCAGTGAAGCTGCCTGCCTCTGGTGTGAAGACCCACTGCCCACCC  420
111 E  D  L  E  G  A  V  K  L  P  A  S  G  V  K  T  H  C  P  P      130

421 TGCAACCCAGGCTTCTTCAAAACCAACAACAGCACCTGCCAGCCCTGCCCATATGGTTCC  480
131 C  N  P  G  F  F  K  T  N  N  S  T  C  Q  P  C  P  Y  G̶  S̶      150

481 TACTCCAATGGCTCAGACTGTACCCGCTGCCCTGCAGGGACTGAACCTGCTGTGGGATTT  540
151 Y̶  S̶  N̶  G̶  S̶  D̶  C̶  T̶  R̶  C  P  A  G̶  T̶  E̶  P̶  A̶  V  G  F  170

541 GAATACAAATGGTGGAACACGCTGCCCACAAACATGGAAACGACCGTTCTCAGTGGGATC  600
171 E  Y  K  W  W  N  T  L  P  T̳  N̳  M̳  E̳  T  T  V  L  S  G  I      190

601 AACTTCGAGTACAAGGGCATGACAGGCTGGGAGGTGGCTGGTGATCACATTTACACAGCT  660

661  GCTGGAGCCTCAGACAATGACTTCATGATTCTCACTCTGGTTGTGCCAGGATTTAGACCT  720
211  A  G̶ A̶ S̶ D̶ N̶ D̶ F  M  I  L  T  L  V  V  P  G  F  R  P   230

721  CCGCAGTCGGTGATGGCAGACACAGAGAATAAAGAGGTGGCCAGAATCACATTTGTCTTT  780
231  P  Q  S  V  M  A  D  T  E  N  K  E  V  A  R  I  T  F  V  F   250

781  GAGACCCTCTGTTCTGTGAACTGTGAGCTCTACTTCATGGTGGGTGTGAATTCTAGGACC  840
251  E̶ T̶ L  C  S  V  N  C  E  L  Y  F  M  V  G  V  N  S  R  T   270

841  AACACTCCTGTGGAGACGTGGAAAGGTTCCAAAGGCAAACAGTCCTATACCTACATCATT  900
271  N  T  P  V  E  T  W  K  G  S  K  G  K  Q  S  Y  T  Y  I  I   290

901  GAGGAGAACACTACCACGAGCTTCACCTGGGCCTTCCAGAGGACCACTTTTCATGAGGCA  960
291  E  E  N  T  T  T  S  F  T  W  A  F  Q  R  T  T  F  H  E  A   310
        **********

961  AGCAGGAAGTACACCAATGACGTTGCCAAGATCTACTCCATCAATGTCACCAATGTTATG  1020
311  S  R  K  Y  T  N  D  V  A  K  I  Y  S  I  N  V  T  N  V  M   330

1021 AATGGCGTGGCCTCCTACTGCCGTCCCTGTGCCCTAGAAGCCTCTGATGTGGGCTCCTCC  1080
331  N  G  V  A  S  Y  C  R  P  C  A  L  E  A  S  D  V  G  S  S   350

1081 TGCACCTCTTGTCCTGCTGGTTACTATATTGACCGAGATTCAGGAACCTGCCACTCCTGC  1140
351  C  T  S  C  P  A  G  Y  Y  I  D  R  D  S  G̶ T̶ C̶ H̶ S̶ C̶   370

1141 CCCCCTAACACAATTCTGAAAGCCCACCAGCCTTATGGTGTCCAGGCCTGTGTGCCCTGT  1200
371  P  P  N  T  I  L  K  A  H  Q  P  Y  G̶ V̶ Q̶ A̶ C  V  P  C   390

1201 GGTCCAGGGACCAAGAACAACAAGATCCACTCTCTGTGCTACAATGATTGCACCTTCTCA  1260
391  G  P  G̶ T̶ K̶ N̶ N̶ K  I  H  S  L  C  Y  N  D  C  T  F  S   410
```

FIG.1B

```
1261 CGCAACACTCCAACCAGGACTTTCAACTACAACTTCTCCGCTTTGGCAAACACCGTCACT 1320
 411  R  N  T  P  T  R  T  F  N  Y  N  F  S  A  L  A  N  T  V  T  430

1321 CTTGCTGGAGGGCCAAGCTTCACTTCCAAAGGGTTGAAATACTTCCATCACTTTACCCTC 1380
 431  L  A  G  G  P  S  F  T  S  K  G  L  K  Y  F  H  H  F  T  L  450
                           **********

1381 AGTCTCTGTGGAAACCAGGGTAGGAAAATGTCTGTGTGCACCGACAATGTCACTGACCTC 1440
 451  S  L  C  G  N  Q  G  R  K  M  S  V  C  T  D  N  V  T  D  L  470

1441 CGGATTCCTGAGGGTGAGTCAGGGTTCTCCAAATCTATCACAGCCTACGTCTGCCAGGCA 1500
 471  R  I  P  E  G  E  S  G  F  S  K  S  I  T  A  Y  V  C  Q  A  490

1501 GTCATCATCCCCCCAGAGGTGACAGGCTACAAGGCCGGGGTTTCCTCACAGCCTGTCAGC 1560
 491  V  I  I  P  P  E  V  T  G  Y  K  A  G  V  S  S  Q  P  V  S  510

1561 CTTGCTGATCGACTTATTGGGGTGACAACAGATATGACTCTGGATGGAATCACCTCCCCA 1620
 511  L  A  D  R  L  I  G  V  T  T  D  M  T  L  D  G  I  T  S  P  530

1621 GCTGAACTTTTCCACCTGGAGTCCTTGGGAATACCGGACGTGATCTTCTTTTATAGGTCC 1680
 531  A  E  L  F  H  L  E  S  L  G  I  P  D  V  I  F  F  Y  R  S  550

1681 AATGATGTGACCCAGTCCTGCAGTTCTGGGAGATCAACCACCATCCGCGTCAGGTGCAGT 1740
 551  N  D  V  T  Q  S  C  S  S  G  R  S  T  T  I  R  V  R  C  S  570

1741 CCACAGAAAACTGTCCCTGGAAGTTTGCTGCTGCCAGGAACGTGCTCAGATGGGACCTGT 1800
 571  P  Q  K  T  V  P  G  S  L  L  L  P  G  T  C  S  D  G  T  C  590

1801 GATGGCTGCAACTTCCACTTCCTGTGGGAGAGCGCGGCTGCTTGCCCGCTCTGCTCAGTG 1860
 591  D  G  C  N  F  H  F  L  W  E  S  A  A  A  C  P  L  C  S  V  610

1861 GCTGACTACCATGCTATCGTCAGCAGCTGTGTGGCTGGGATCCAGAAGACTACTTACGTG 1920
```

1921 TGGCGAGAACCCAAGCTATGCTCTGGTGGCATTTCTCTGCCTGAGCAGAGAGTCACCATC  1980
631  W R E P K L C S G G I S L P E Q R V T I                          650

1981 TGCAAAACCATAGATTTCTGGCTGAAAGTGGGCATCTCTGCAGGCACCTGTACTGCCATC  2040
651  C K T I D F W L K V G̶ I̶ S̶ A̶ G̶ T̶ C̶ T̶ A̶ I̶                          670

2041 CTGCTCACCGTCTTGACCTGCTACTTTTGGAAAAAGAATCAAAAACTAGAGTACAAGTAC  2100
671  L L T V L T C Y F W K K N Q K L E Y K Y                          690

2101 TCCAAGCTGGTGATGAATGCTACTCTCAAGGACTGTGACCTGCCAGCAGCTGACAGCTGC  2160
691  S K L V M N A T L K D C D L P A A D S C                          710

2161 GCCATCATGGAAGGCGAGGATGTAGAGGACGACCTCATCTTTACCAGCAAGAATCACTCT  2220
711  A I M E G E D V E D D L I F T S K N H S                          730

2221 TTGGGAAGATCAAATCATTTACCTCCAAGAGGACTCCTGATGGATTTGACTCAGTGCCGC  2280
731  L G R S N H L P P R G L L M D L T Q C R                          750

2281 TGAAGACATCCTCAGGAGGCCCAGACATGGACCTGTGAGAGGCACTGCCTGCCTCACCTG  2340
751  *                                                                751

2341 CCTCCTCACCTTGCATAGCACCTTTGCAAGCCTGCGGCGATTTGGGTGCCAGCATCCTGC  2400

2401 AACACCCACTGCTGGAAATCTCTTCATTGTGGCCTTATCAGATGTTTGAATTTCAGATCT  2460

2461 TTTTTTATAGAGTACCCAAACCCTCCTTTCTGCTTGCCTCAAACCTGCCAAATATACCCA  2520

2521 CACTTTGTTTGTAAATTAAAAAAAAAAAAAAAAA  2554
```

FIG.1D

```
          10                  20                  30
1    M D Q S T Q A C A G E K H C H N R G G L H F R M L P L Q T W   TR13.aa
1    M - - - - - - C V G A R R - L G R G P - - - - - - - - - - -   gi|472958 OX40 homologue 40                  50                  60
31   H V C R Q A G L L F L Q T L P S N S Y S N K G E T S C H Q C   TR13.aa
13   - - C - - A L L L L - G L G L S T V T G - - - - - - L H C     gi|472958 OX40 homologue 70                  80                  90
61   D P D K Y S E K G S S S C N V R P A C T D K D Y F Y T H T A   TR13.aa
32   V G D T Y P S N D R C C H E C R P G - - - - - - - - - - - -   gi|472958 OX40 homologue 100                 110                 120
91   C D A N G E T Q L M Y K W A K P K I C S E D L E G A V K L P   TR13.aa
50   - - - - - - - - - - - - - - - - - - - N G M V S R C           gi|472958 OX40 homologue 130                 140                 150
121  A S G V K T H C P P C N P G F F K T N N S T C Q P C P Y G S   TR13.aa
57   S R S Q N T V C R P C G P G F Y N - D V V S S K P C - - - -   gi|472958 OX40 homologue 160                 170                 180
151  Y S N G S D C T R C P A G T E P A V G F E Y K W W N T L P T   TR13.aa
82   - - - - K P C T W C - - - - - - - - - - - - - - - - - - - -   gi|472958 OX40 homologue 190                 200                 210
181  N M E T T V L S G I N F E Y K G M T G W E V A G D H I Y T A   TR13.aa
88   - - - - - - - - - - - - - - - - - - - - - - - - - - - - - -   gi|472958 OX40 homologue
```

FIG. 2A

```
                          220              230              240
211  A G A S D N D F M I L T L V V P G F R P P Q S V M A D T E N    TR13.aa
 88  - - - - - - - - - - - - - - - - - - - N L R S G S E R          gi|472958 OX40 homologue 250              260              270
241  K E V A R I T F V F E T L C S V N C E L Y F M V G V N S R T    TR13.aa
 96  K Q L C T A T Q - - D T V C R - - C - - - - - - - - - - - -    gi|472958 OX40 homologue 280              290              300
271  N T P V E T W K G S K G K Q S Y T Y I I E E N T T T S F T W    TR13.aa
110  - - - - - - R A G T Q P L D S Y K - - - - - - - - - - - - -    gi|472958 OX40 homologue 310              320              330
301  A F Q R T T F H E A S R K Y T N D V A K I Y S I N V T N V M    TR13.aa
121  - - - - - - - - - - - - - - - - - - - - - - - - - - - - -     gi|472958 OX40 homologue 340              350              360
331  N G V A S Y C R P C A L E A S D V G S S C T S C P A G Y Y I    TR13.aa
121  - - - - - - - - - - - - P G V D C A P C P P G H F -            gi|472958 OX40 homologue 370              380              390
361  D R D S G T C H S C P P N T I L K A H Q P Y G V Q A C V P C    TR13.aa
134  - - S P G D N Q A C K P - - - - - - - - - - - - - - - -       gi|472958 OX40 homologue 400              410              420
391  G P G T K N N K I H S L C Y N D C T F S R N T P T R T F N Y    TR13.aa
144  - - - - - - - - - - - W T N C T - - - - - - - - - -            gi|472958 OX40 homologue
```

FIG. 2B

```
        430           440           450
421 |N F S A L A N T V T L A G G P S F T S K G L K Y F H H F T L|  TR13.aa
149 - - - -|L A|G K H|T L|Q P A S N S S D - - - - - - - - - - - -  gi|472958 OX40 homologue 460           470           480
451 |S L C G N Q G R K M S V C T D N V T D L R I P E G E S G F S|  TR13.aa
164 - - - - - - - - - A I|C E D|R D P P A T Q|P|Q E T Q|G|- -  gi|472958 OX40 homologue 490           500           510
481 |K S I T A Y V C Q A V I I P P E V T G Y K A G V S S Q P V S|  TR13.aa
182 - - - - - - - - - - - -|P P|- - - - - - - - - - A R|P|I T  gi|472958 OX40 homologue 520           530           540
511 |L A D R L I G V T T D M T L D G I T S P A E L F H L E S L G|  TR13.aa
189 V Q - - - - - - - - - - - - -|P|T E|A - - - - - - -  gi|472958 OX40 homologue 550           560           570
541 |I P D V I F F Y R S N D V T Q S C S S G R S T T I R V R C S|  TR13.aa
195 - - - - - - - - - - - - - - - - - - - - - - - - - - - - - -  gi|472958 OX40 homologue 580           590           600
571 |P Q K T V P G S L L L P G T C S D G T C D G C N F H F L W E|  TR13.aa
195 - - - - - - - - - - - - - - - - - - - - - - - - - -|W|P  gi|472958 OX40 homologue 610           620           630
601 |S A A A C P L C S V A D Y H A I V S S C V A G I Q K T T Y V|  TR13.aa
197 R T S Q G|P|- - - - - - - - - - - - - - - - - - - - - -  gi|472958 OX40 homologue
```

FIG. 2C

```
       640              650            660
631 WREPKLCSGGISLPEQRVTICKTIDFWLKV       TR13.aa
203 ------STRPVEVPGGR-AVAAILGLGLVL       gi|472958 OX40 homologue 670              680            690
661 GISAGTCTAILLTVLTCYFWKKNQKLEYKY       TR13.aa
226 GLLGPL--AILLAL---YLLRRDQRLPPDA       gi|472958 OX40 homologue 700              710            720
691 SKLVMNATLKDCDLPAADSCAIMEGEDVED       TR13.aa
251 HKPPGGSFR-----------TPIQEEQADA       gi|472958 OX40 homologue 730              740            750
721 DLIFTSKNHSLGRSNHLPPRGLLMDLTQCR       TR13.aa
271 HSTLA------------------------K       gi|472958 OX40 homologue 751                                      TR13.aa
277 I                                    gi|472958 OX40 homologue
```

FIG. 2D

```
  1 TGAGGTGGATTTGTACCGGAGTCCCATTTGGGAGCAAGAGCCATCTACTCGTCCGTTACC    60

61 GGCCTTCCCACCATGGATTGCCAAGAAAATGAGTACTGGGACCAATGGGGACGGTGTGTC   120
  1                        M  S  T  G  T̶  N̶  G̶  D̶  G  V  S          11

121 ACCTGCCAACGGTGTGGTCCTGGACAGGAGCTATCCAAGGATTGTGGTTATGGAGAGGGT   180
 12  P  A  N  G  V  V  L  D  R  S  Y  P  R  I  V  V  M  E  R  V     31

181 GGAGATGCCTACTGCACAGCCTGCCCTCCTCGCAGTACAAAAGCAGCTGGGGCCACCACA   240
 32  E  M  P  T  A  Q  P  A  L  L  A  V  Q  K  Q  L  G  P  P  Q     51

241 AATGTGCAGAGTTGCATGCACCTGTGCTGTCATCAATCGTGTTCAGAAGGTCAACTGCAC   300
 52  M  C  R  V  A  C  T  C  A  V  I  N  R  V  Q  K  V  N̂  C  T     71

301 ACCTACCTCTAATGCTGTCTGTGGGGACTGTTTGCCCAGGTTCTACCGAAAGACACGCAT   360
 72  P  T  S  N  A  V  C  G  D  C  L  P  R  F  Y  R  K  T  R  I     91

361 TGGAGGCCTGCAGGACCAAGAGTGCATCCCGTGCACGAAGCAGACCCCCACCTCTGAGGT   420
 92  G  G  L  Q  D  Q  E  C  I  P  C  T  K  Q  T  P  T  S  E  V    111

421 TCAATGTGCCTTCCAGTTGAGCTTAGTGGAGGCAGATGCACCCACAGTGCCCCCTCAGGA   480
112  Q  C  A  F  Q  L  S̶  L̶  V̶  E̶  A  D  A  P  T  V  P  P  Q  E    131

481 GGCCACACTTGTTGCACTGGTGAGCAGCCTGCTAGTGGTGTTTACCCTGGCCTTCCTGGG   540
132  A  T  L  V  A  L  V  S  S  L  L  V  V  F  T  L  A  F  L  g    151

541 GCTCTTCTTCCTCTACTGCAAGCAGTTCTTCAACAGACATTGCCAGCGTGGAGGTTTGCT   600
152  l  f  f  l  y  c  k  q  f  f  n  r  h  c  q  r  g  g  l  l    171
                        * * * * * * * *
601 GCAGTTTGAGGCTGATAAAACAGCAAAGGAGGAATCTCTCTTCCCCGTGCCACCCAGCAA   660
172  q  f  e  a  d  k  t̶  a̶  k̶  e̶  e  s  l  f  p  v  p  p  s  k    191
```

FIG.4A

```
661  GGAGACCAGTGCTGAGTCCCAAGTCTCTTGGGCCCCTGGCAGCCTTGCCCAGTTGTTCTC   720
192   e  t  s  a  e  s  q  v  s  w  a  p  g  s  l  a  q  l  f  s    211

721  TCTGGACTCTGTTCCTATACCACAACAGCAGCAGGGGCCTGAAATGTGATGTCCACAAGA   780
212   l  d  s  v  p  i  p  q  q  q  g  p  e  m  *                   227

781  GCTAATACCCTACAGATGGGGCATATCCTATCCCATCCCACCAGAGGATTGATTCTCCAT   840

841  TTCACAAGGACTGATCTGGAGCATTTCTTGCTTCCCTGTTGTAGTCTGGGGAGCCAGATT   900

901  CCACATTCATGGGACTACCAGACATGTTCCTAGCTCAACTTGATTATAGAGAAGAGGAGA   960

961  GAGGACAGTGAATGGGGTAGGGTTTTCATGTCTGCATTTTTGGTCAGGTAAGCCTCTCAA   1020

1021 AATTGTGTTGGCACATCTACCTAGCACTTTAGGGACAAAATCAAACCCTTCTCCCCTTTT   1080

1081 AGCTCCTCCACACTGCCTCCCTCCTCAACACACACACACACACATACACACACATATACA   1140

1141 TAGACACACAAACACACACACACACATTAATATCTATCTTGGGGAAGCCTCGTGCCATA   1200

1201 ATTCCCAAGTCATGTCTCAGACTGCTGCATTGCAGCATGACGCAGGGCAAACACTTTCCC   1260

1261 TCTAGATCCCTGGGGCCTGACCCTGTATTTGAGGTTCTCACCACCCTCAGCAGGGAGAAG   1320

1321 GGCTGAAGTTCGCCATTTTGGAACCTTACAGAACATTTCTGAGCCAAAGTAATCTTCCTT   1380

1381 CTGGGGCCTGAGTTCCCCAAACTACCCCACAGCAGTCCCTCAAAGACAGCCCTCAATCCA   1440

1441 TGTAGGGACATCTGAGTATGCCTCTTTCTATTGAAATGTCAATTCAATCCCAGCTTTCTC   1500

1501 ACCACCGTTCCCCTTTGATTCTTTCTCAATTGTCTTTTTGCCTTTAGCTCCCACCTATAC   1560
```

FIG.4B

```
1561  ATCTCATGCTCAGAGAAAAACAAGTTCCTTAGAGGTTGTATTCTTTATTCTCCAAGAATC  1620

1621  TGTCTGAAACTTGTACAGCTAGTTCCTGTCCCACAACTATTAAGTGGTTTATTAAGTACA  1680

1681  TTAGGCAGAATGTGCACTTCATCACCAGGTTCTAGCTCTGGCAAAGGAGTGCTGTCTACA  1740

1741  GCAAGATTTTTGCTTTTAGAATTTTATTAACTACATCTTTTGGGTTCATCCATCTACAAA  1800

1801  CACTGATTAAGGGCCCCTGGGGCAACCAATTGATCAGATTACTAAAAGGACTTGGGAAAA  1860

1861  AGCAAAAAGGTCCCATTGTACTGGACTGAGGATTAGAAGCAATTGAAATACAAGCCTGTA  1920

1921  CCAAGCAAGCAGCCTGGCCCCACACAGGTATTAGCAAATATGTGGTAACCAAGGTTTTAG  1980

1981  GCCTTGGCCCCTAGGTTTCCTGTTTTTTTTTCGTTTTGGTTTCCGTTTTCGTTTTTTGCA  2040

2041  ACAGGTTATTCTTATCTCACTGGCTTTCACTGATCATGTTTAGACCTTCTGGTAGAAGAA  2100

2101  ATAATATCCAGACAGGGGATGATTTGGCTTCAGCAGGCTGCAGGTGTTCAAAGGTTGCCA  2160

2161  TGTGGCTGGCAGTGGTTCAAGCCCACATTTGACACTGCTGCTCTAGAGGAAAGATAATGA  2220

2221  TGGTAACACAGTAATAATAATAATAATAACAAAAATATGATAAAGTGAAAGAGTAGATTT  2280

2281  CTTTCAGTGTGCTTGCTCCATGGCATGAATGCTATGTGGACAGCCCAAGCCATACCCAGA  2340

2341  ATCACCTTAATTCCAACTTTTTGAGGTTCAGCAATTGGAGGTGGCAATTGGCTTTGCATT  2400

2401  TTAAAGTATTTCGGGTAAAGGTGAAGTGAACGATTTTCGTCTTTATAATTTCTGTTTGGC  2460

2461  CATGGCAAATACCATAGTTGAGTATTTGCTTCAGGAGAGTTCTTTTTACAGTTTTACTTT  2520
```

FIG.4C

```
2521  TCAATGCTGAGGCATATTTCTTTGAGCACTGTGCTTTTATGTGTCTTTCTACAAAGGGGT  2580

2581  TATTGGTCAGTGGAAGAACAAAGTACACTTGATAAAAACATTTTCAACATACATTGAGCC  2640

2641  TAAACAGCAGTTAAGTTGTCTCTAATGAACTAGCAAAAAAAAAAAATGTAGTTTTTGTTT  2700

2701  GTAAGGAAGGGGAGGTATTTCCTGAGAATGAATTTTTTTTTTTTTGGATTACTGTTTTTC  2760

2761  TCTCCATATACCTTGACTTGGATTTTGACAGGAGGGAGTCTGGGAAAATAATTTTTTCCT  2820

2821  CCAAGATTCTCAGATCCAGGTTAGGAAAGGATTCAGCACTACAGCATACCCCTCTACAAC  2880

2881  ATACAGCCCTGTCACATTGAGATCATAATCCCTCCTGTCCCACTCCTCTCTACCAACCCC  2940

2941  ACCCTACTAGCTAGGTCTTCAGTGTTTTACATTGAATATTGGTACATTTTAATTATTTTT  3000

3001  TCTCATAAATGGGTTATTTATAGAGATTTTGTTAACTCTTGAGCCATATGCATGTGTAGA  3060

3061  TACTGGCAGGGCTATGTTTGTTTATGATGCTCTGCAAACATTTCATATTGGCCAATAAAC  3120

3121  AGAAATATATCCAAAAAAAAAAAAAAAAAAtntaRmssngsgnatdATGGATTGCCAAGAA  3180

3181  AATGAGTACTGGGACCAATGGGGACGGTGTGTCACCTGCCAACGGTGTGGTCCTGGACAG  3240

3241  GAGCTATCCAAGGATTGTGGTTATGGAGAGGGTGGAGATGCCTACTGCACAGCCTGCCCT  3300

3301  CCTCGCAGTACAAAAGGCAGCTGGGGCCACCACAAATGTCAGAGTTGCATCACCTGTGCT  3360

3361  GTCATCAATCGTGTTCAGAAGGTCAACTGCACAGCTACCTCTAATGCTGTCTGTGGGGAC  3420

3421  TGTTTGCCCAGGTTCTACCGAAAGACACGCATTGGAGGCCTGCAGGACCAAGAGTGCATC  3480
```

FIG.4D

```
3481  CCGTGCACGAAGCAGACCCCCACCTCTGAGGTTCAATGTGCCTTCCAGTTGAGCTTAGTG  3540

3541  GAGGCAGATGCACCCACAGTGCCCCCTCAGGAGGCCACACTTGTTGCACTGGTGAGCAGC  3600

3601  CTGCTAGTGGTGTTTACCCTGGCCTTCCTGGGGCTCTTCTTCCTCTACTGCAAGCAGTTC  3660

3661  TTCAACAGACATTGCCAGCGTGGAGGTTTGCTGCAGTTTGACGCTGATAAAACAGCAAAG  3720

3721  GAGGAATCTCTCTTCCCCGTGCCACCCAGCAAGGAGACCAGTGCTGAGTCCCAAGTCTCT  3780

3781  TGGGCCCCTGGCAGCCTTGCCCAGTTGTTCTCTCTGGACTCTGTTCCTATACCACAACAG  3840

3841  CAGCAGGGGCCTGAAATGTGA  3861
```

```
                    10                  20                  30
1    M S T G T N G D G V S P A N G V V L D R S Y P R I V V M E R    TR14.aa
1    M A P V A - - - - V W A A L A V G L E L W A A A H A L P A Q   gi|339758 Tumor Necrosis Factor 40                  50                  60
31   V E M P - - T A Q P A L L A V Q K Q L - - G P P Q M C R V A    TR14.aa
27   V A F T P Y A P E P G S T C R L R E Y Y D Q T A Q M C C S K    gi|339758 Tumor Necrosis Factor 70                  80                  90
57   C T C A V I N R V Q K V N C T P T S N A V C G D C L P R F Y    TR14.aa
57   C S P G - - - Q H A K V F C T K T S D T V C D S C E D S T Y    gi|339758 Tumor Necrosis Factor 100                 110                 120
87   - - - - - - - - - - - - - - - - - - - - - - - - - - - - -    TR14.aa
84   T Q L W N W V P E C L S C G S R C S S D Q V E T Q A C T R E    gi|339758 Tumor Necrosis Factor 130                 140                 150
87   - - - - - - - - R K T R I G G L Q D Q E - - - - - - - - - -    TR14.aa
114  Q N R I C T C R P G W Y C A L S K Q E G C R L C A P L R K C    gi|339758 Tumor Necrosis Factor 160                 170                 180
99   - - - - - - - - - - - - - - C I P C T K Q T - - - - -         TR14.aa
144  R P G F G V A R P G T E T S D V V C K P C A P G T F S N T T    gi|339758 Tumor Necrosis Factor 190                 200                 210
107  - - - - - - - - - - - - - - - - - - - P T S E V Q C A - -    TR14.aa
174  S S T D I C R P H Q I C N V V A I P G N A S R D A V C T S T    gi|339758 Tumor Necrosis Factor 220                 230                 240
115  - - - - - - - - - - - - F Q L S L V E A D A P T V P P Q E A    TR14.aa
204  S P T R S M A P G A V H L P Q P V S T R S Q H T Q P T P E P    gi|339758 Tumor Necrosis Factor
```

FIG. 5B

```
              250              260              270
133 T L V A L V S S L L V V - - - - - - - - - - - F T L A F -   TR14.aa
234 S T A P S T S F L L P M G P S P P A E G S T G D F A L P V G  gi|339758 Tumor Necrosis Factor 280              290              300
150 - - - - - - - L G L F F L - - - Y C K Q F F N R H - - - - C   TR14.aa
264 L I V G V T A L G L L I I G V V N C V I M T Q V K K K P L C  gi|339758 Tumor Necrosis Factor 310              320              330
166 - Q R G G L L - Q F E A D K T - - - - - A K E E S L F P V P   TR14.aa
294 L Q R E A K V P H L P A D K A R G T Q G P E Q Q H L L I T A  gi|339758 Tumor Necrosis Factor 340              350              360
189 P S K - - - - - - - - - - - - - - - - - - - - - - - - - -   TR14.aa
324 P S S S S S L E S S A S A L D R R A P T R N Q P Q A P G V   gi|339758 Tumor Necrosis Factor 370              380              390
192 - - - - - - - - - - - - - - - - - - - - - - - - - - - - -   TR14.aa
354 E A S G A G E A R A S T G S S D S S P G G H G T Q V N V T C  gi|339758 Tumor Necrosis Factor 400              410              420
192 - - - - - - - - - - - - - - - - - - - - - - - - - - - - -   TR14.aa
384 I V N V C S S S D H S S Q C S S Q A S S T M G D T D S S P S  gi|339758 Tumor Necrosis Factor 430              440              450
192 E T S A E S Q V S W A - - - - - - - - - - - - - P G S L A Q L   TR14.aa
414 E S P K D E Q V P F S K E E C A F R S Q L E T P E T L L G S   gi|339758 Tumor Necrosis Factor 460
210 F S L D S V P I P Q Q Q Q G P E M                             TR14.aa
444 T E E K P L P L G V P D A G M K P S                           gi|339758 Tumor Necrosis Factor
```

```
  1 GCAGAAGCAGCAGCCGCAGCACCTGAGCCGCTACTGCCGCTCACTCAGGACAACGCTATG    60
  1                                                           M     1
                    ******              ******
 61 GCTGAGCCTGGGCACAGCCACCATCTCTCCGCCAGAGTCAGGGGAAGAACTGAGAGGCGC   120
  2  A  E  P  G  H  S  H  H  L  S  A  R  V  R  G  R  T  E  R  R    21

121 ATACCCCGGCTGTGGCGGCTGCTGCTCTGGGCTGGGACCGCCTTCCAGGTGACCCAGGGA   180
 22  I  P  R  L  W  R  L  L  L  W  A  G  T  A  F  Q  V  T  Q  G    41

181 ACGGGACCGGAGCTTCACGCCTGCAAAGAGTCTGAGTACCACTATGAGTACACGGCGTGT   240
 42  T  G  P  E  L  H  A  C  K  E  S  E  Y  H  Y  E  Y  T  A  C    61
                                                    +++++++++++++++
241 GACAGCACGGGTTCCAGGTGGAGGGTCGCCGTGCCGCATACCCCGGGCCTGTGCACCAGC   300
 62  D  S  T  G  S  R  W  R  V  A  V  P  H  T  P  G  L  C  T  S    81
     +              +++++++++++++++
301 CTGCCTGACCCCGTCAAGGGCACCGAGTGCTCCTTCTCCTGCAACGCCGGGGAGTTTCTG   360
 82  L  P  D  P  V  K  G  T  E  C  S  F  S  C  N  A  G  E  F  L   101
              ******
361 GATATGAAGGACCAGTCATGTAAGCCATGCGCTGAGGGCCGCTACTCCCTCGGCACAGGC   420
102  D  M  K  D  Q  S  C  K  P  C  A  E  G  R  Y  S  L  G  T  G   121

421 ATTCGGTTTGATGAGTGGGATGAGCTGCCCCATGGCTTTGCCAGCCTCTCAGCCAACATG   480
122  I  R  F  D  E  W  D  E  L  P  H  G  F  A  S  L  S  A  N  M   141
                                 .+++++++++++******.
481 GAGCTGGATGACAGTGCTGCTGAGTCCACCGGGAACTGTACTTCGTCCAAGTGGGTTCCC   540
142  E  L  D  D  S  A  A  E  S  T  G  N  C  T  S  S  K  W  V  P   161

541 CGGGGCGACTACATCGCCTTCAACACGGACGAATGCACAGCCACACTGATGTACGCCGTC   600
162  R  G  D  Y  I  A  F  N  T  D  E  C  T  A  T  L  M  Y  A  V   181

601 AACCTGAAGCAATCTGGCACCGTTAACTTCGAATACTACTATCCAGACTCCAGCATCATC   660
182  N  L  K  Q  S  G  T  V  N  F  E  Y  Y  Y  P  D  S  S  I  I   201
```

FIG. 7A

```
661  TTTGAGTTTTTCGTTCAGAATGACCAGTGCCAGCCCAATGCAGATGACTCCAGGTGGATG  720
202   F  E  F  F  V  Q  N  D  Q  C  Q  P  N  A  D  D  S  R  W  M   221
         ******

721  AAGACCACAGAGAAAGGATGGGAATTCCACAGTGTGGAGCTAAATCGAGGCAATAATGTC  780
222   K  T  T  E  K  G  W  E  F  H  S  V  E  L  N  R  G  N  N  V   241

781  CTCTATTGGAGAACCACAGCCTTCTCAGTATGGACCAAAGTACCCAAGCCTGTGCTGGTG  840
242   L  Y  W  R  T  T  A  F  S  V  W  T  K  V  P  K  P  V  L  V   261
                     +++++++++++++++

841  AGAAACATTGCCATAACAGGGGTGGCCTACACTTCAGAATGCTTCCCCTGCAAACCTGGC  900
262   R  N  I  A  I  T  G  V  A  Y  T  S  E  C  F  P  C  K  P  G   281
                   ++++++++++++++++

901  ACGTATGCAGACAAGCAGGGCTCCTCTTTCTGCAAACTTTGCCCAGCCAACTCTTATTCA  960
282   T̶  Y̶  A̶  D̶  K  Q  G  S  S  F  C  K  L  C  P  A  N  S  Y  S   301
                                                  ******   ++++.

961  AATAAAGGAGAAACTTCTTGCCACCAGTGTGACCCTGACAAATACTCAGAGAAAGGATCT  1020
302   N  K  G  E  T  S  C  H  Q  C  D  P  D  K  Y  S  E  K  G  S   321
      ++++++++++           ******

1021 TCTTCCTGTAACGTGCGCCCAGCTTGCACAGACAAAGATTATTTCTACACACACACGGCC  1080
322   S  S  C  N  V  R  P  A  C  T̶  D̶  K̶  D̶  Y  F  Y  T  H  T̶  A̶   341

1081 TGCGATGCCAACGGAGAGACACAACTCATGTACAAATGGGCCAAGCCGAAAATCTGTAGC  1140
342   C̶  D̶  A  N  G  E  T  Q  L  M  Y  K  W  A  K  P  K  I  C  S   361

1141 GAGGACCTTGAGGGGGCAGTGAAGCTGCCTGCCTCTGGTGTGAAGACCCACTGCCCACCC  1200
362   E  D  L  E  G  A  V  K  L  P  A  S  G  V  K  T  H  C  P  P   381
                                                              ++++.

1201 TGCAACCCAGGCTTCTTCAAAACCAACAACAGCACCTGCCAGCCCTGCCCATATGGTTCC  1260
382   C  N  P  G  F  F  K  T  N  N  S  T  C  Q  P  C  P  Y  G  S   401
      ++++++++++++++++++++++++++     +++++++++++++++++

1261 TACTCCAATGGCTCAGACTGTACCCGCTGCCCTGCAGGGACTGAACCTGCTGTGGGATTT  1320
402   Y  S  N  G  S  D  C  T  R  C  P  A  G  T  E  P  A  V  G  F   421
```

FIG. 7B

```
1321  GAATACAAATGGTGGAACACGCTGCCCACAAACATGGAAACGACCGTTCTCAGTGGGATC  1380
 422   E  Y  K  W  W  N  T  L  P  T̶  N̶  M̶  E̶  T  T  V  L  S  G  I    441

1381  AACTTCGAGTACAAGGGCATGACAGGCTGGGAGGTGGCTGGTGATCACATTTACACAGCT  1440
 442   N  F  E  Y  K  G  M  T̶  G̶  W̶  E̶  V  A  G  D  H  I  Y  T  A    461
          ++++++++++++++++.
1441  GCTGGAGCCTCAGACAATGACTTCATGATTCTCACTCTGGTTGTGCCAGGATTTAGACCT  1500
 462   A  G  A  S̶  D̶  N̶  D̶  F  M  I  L  T  L  V  V  P  G  F  R  P    481

1501  CCGCAGTCGGTGATGGCAGACACAGAGAATAAAGAGGTGGCCAGAATCACATTTGTCTTT  1560
 482   P  Q  S  V  M  A  D  T  E  N  K  E  V  A  R  I  T  F  V  F    501

1561  GAGACCCTCTGTTCTGTGAACTGTGAGCTCTACTTCATGGTGGGTGTGAATTCTAGGACC  1620
 502   E  T  L  C  S  V  N  C  E  L  Y  F  M  V  G  V  N  S  R  T    521
                      ******
1621  AACACTCCTGTGGAGACGTGGAAAGGTTCCAAAGGCAAACAGTCCTATACCTACATCATT  1680
 522   N  T̶  P̶  V̶  E̶  T  W  K  G  S  K  G  K  Q  S  Y  T  Y  I  I    541

1681  GAGGAGAACACTACCACGAGCTTCACCTGGGCCTTCCAGAGGACCACTTTTCATGAGGCA  1740
 542   E  E  N  T  T  T  S  F  T  W  A  F  Q  R  T  T̶  F̶  H̶  E̶  A    561
       ******
1741  AGCAGGAAGTACACCAATGACGTTGCCAAGATCTACTCCATCAATGTCACCAATGTTATG  1800
 562   S  R  K  Y  T  N  D  V  A  K  I  Y  S  I  N  V  T  N  V  M    581
                                                    . +++++++ .
1801  AATGGCGTGGCCTCCTACTGCCGTCCCTGTGCCCTAGAAGCCTCTGATGTGGGCTCCTCC  1860
 582   N  G  V  A  S  Y  C  R  P  C  A  L  E  A  S  D  V  G  S  S    601
       +++++++ .                          . ++++++++++++++ .
1861  TGCACCTCTTGTCCTGCTGGTTACTATATTGACCGAGATTCAGGAACCTGCCACTCCTGC  1920
 602   C  T  S  C  P  A  G  Y  Y  I  D  R  D  S  G  T  C  H  S  C    621
                               .  ++++++++++++++++  .
1921  CCCCCTAACACAATTCTGAAAGCCCACCAGCCTTATGGTGTCCAGGCCTGTGTGCCCTGT  1980
 622   P  P  N  T  I  L  K  A  H  Q  P  Y  G  V  Q  A  C  V  P  C    641
```

FIG. 7C

```
                  +++++++++++++++++
1981  GGTCCAGGGACCAAGAACAACAAGATCCACTCTCTGTGCTACAATGATTGCACCTTCTCA  2040
 642  G  P  G  T  K  N  N  K  I  H  S  L  C  Y  N  D  C  T  F  S    661

2041  CGCAACACTCCAACCAGGACTTTCAACTACAACTTCTCCGCTTTGGCAAACACCGTCACT  2100
 662  R  N  T  P  T  R  T  F  N  Y  N  F  S  A  L  A  N  T  V  T    681
                       ******
2101  CTTGCTGGAGGGCCAAGCTTCACTTCCAAAGGGTTGAAATACTTCCATCACTTTACCCTC  2160
 682  L  A  G  G  P  S  F  T  S  K  G  L  K  Y  F  H  H  F  T  L    701

2161  AGTCTCTGTGGAAACCAGGGTAGGAAAATGTCTGTGTGCACCGACAATGTCACTGACCTC  2220
 702  S  L  C  G  N  Q  G  R  K  M  S  V  C  T  D  N  V  T  D  L    721

2221  CGGATTCCTGAGGGTGAGTCAGGGTTCTCCAAATCTATCACAGCCTACGTCTGCCAGGCA  2280
 722  R  I  P  E  G  E  S  G  F  S  K  S  I  T  A  Y  V  C  Q  A    741

2281  GTCATCATCCCCCCAGAGGTGACAGGCTACAAGGCCGGGGTTTCCTCACAGCCTGTCAGC  2340
 742  V  I  I  P  P  E  V  T  G  Y  K  A  G  V  S  S  Q  P  V  S    761

2341  CTTGCTGATCGACTTATTGGGGTGACAACAGATATGACTCTGGATGGAATCACCTCCCCA  2400
 762  L  A  D  R  L  I  G  V  T  T  D  M  T  L  D  G  I  T  S  P    781

2401  GCTGAACTTTTCCACCTGGAGTCCTTGGGAATACCGGACGTGATCTTCTTTTATAGGTCC  2460
 782  A  E  L  F  H  L  E  S  L  G  I  P  D  V  I  F  F  Y  R  S    801
                         ******              ******
2461  AATGATGTGACCCAGTCCTGCAGTTCTGGGAGATCAACCACCATCCGCGTCAGGTGCAGT  2520
 802  N  D  V  T  Q  S  C  S  S  G  R  S  T  T  I  R  V  R  C  S    821
                                                    . +++++++ .
2521  CCACAGAAAACTGTCCCTGGAAGTTTGCTGCTGCCAGGAACGTGCTCAGATGGGACCTGT  2580
 822  P  Q  K  T  V  P  G  S  L  L  L  P  G  T  C  S  D  G  T  C    841
      ++++++
2581  GATGGCTGCAACTTCCACTTCCTGTGGGAGAGCGCGGCTGCTTGCCCGCTCTGCTCAGTG  2640
 842  D  G  C  N  F  H  F  L  W  E  S  A  A  A  C  P  L  C  S  V    861
```

FIG. 7D

```
                                          ++++++++++++++++
2641  GCTGACTACCATGCTATCGTCAGCAGCTGTGTGGCTGGGATCCAGAAGACTACTTACGTG  2700
 862  A-D- Y  H  A  I  V  S  S  C  V  A  G  I  Q  K  T  T  Y  V     881

2701  TGGCGAGAACCCAAGCTATGCTCTGGTGGCATTTCTCTGCCTGAGCAGAGAGTCACCATC  2760
 882  W  R  E  P  K  L  C  S  G  G  I  S- L- P- E- Q  R  V  T  I    901
              .  ++++++++++++++++++++++++++++++++ .
2761  TGCAAAACCATAGATTTCTGGCTGAAAGTGGGCATCTCTGCAGGCACCTGTACTGCCATC  2820
 902  C  K  T  I  D  F  W  L  K  V  G  I  S  A  G  T  C  T  A  I    921

2821  CTGCTCACCGTCTTGACCTGCTACTTTTGGAAAAAGAATCAAAAACTAGAGTACAAGTAC  2880
 922  L  L  T  V  L  T  C  Y  F  W  k  k  n  q  k  l  e  y  k  y    941
                              *******
2881  TCCAAGCTGGTGATGAATGCTACTCTCAAGGACTGTGACCTGCCAGCAGCTGACAGCTGC  2940
 942  s  k  l  v  m  n  a  t- l- k- d- c  d  l  p  a  a  d  s  c    961
                                          *******
2941  GCCATCATGGAAGGCGAGGATGTAGAGGACGACCTCATCTTTACCAGCAAGAATCACTCT  3000
 962  a  i  m  e  g  e  d  v  e  d  d  l  i  f  t  s  k  n  h  s    981

3001  TTGGGAAGATCAAATCATTTACCTCCAAGAGGACTCCTGATGGATTTGACTCAGTGCCGC  3060
 982  l  g  r  s  n  h  l  p  p  r  g  l  l  m  d  l  t  q  c  r   1001

3061  TGAAGACATCCTCAGGAGGCCCAGACATGGACCTGTGAGAGGCACTGCCTGCCTCACCTG  3120
1002  *                                                             1002

3121  CCTCCTCACCTTGCATAGCACCTTTGCAAGCCTGCGGCGATTTGGGTGCCAGCATCCTGC  3180

3181  AACACCCACTGCTGGAAATCTCTTCATTGTGGCCTTATCAGATGTTTGAATTTCAGATCT  3240

3241  TTTTTTATAGAGTACCCAAACCCTCCTTTCTGCTTGCCTCAAACCTGCCAAATATACCCA  3300

3301  CACTTTGTTTGTAAATTAAAAAAAAAAAAAAAAA  3334
```

```
              10              20              30
     ┌──────────────────────────────────────────────┐
1    │ M A E P G H S H H L S A R V R G R T E R R I P R L W R L L L │  TR13-alpha.aa
1    │ M - - - - - - - - - - - - - - - - - - - - - - - - - - - - - │  gb|AAB94382.1 TNF Receptor II 40              50              60
     ┌──────────────────────────────────────────────┐
31   │ W A G T A F Q V T Q G T G P E L H A C K E S E Y H Y E Y T A │  TR13-alpha.aa
2      - - - - - - - - - - - - - - - - - K S V L Y S Y I L - -       gb|AAB94382.1 TNF Receptor II 70              80              90
     ┌──────────────────────────────────────────────┐
61   │ C D S T G S R W R V A V P H T P G L C T S L P D P V K G T E │  TR13-alpha.aa
11     - - - - - - - - - - - - - - - - - - - - - - - - - - - - -    gb|AAB94382.1 TNF Receptor II 100             110             120
     ┌──────────────────────────────────────────────┐
91   │ C S F S C N A G E F L D M K D Q S C K P C A E G R Y S L G T │  TR13-alpha.aa
11     - - - - - - - - F L - - - - - S C - - - - - - - - - - - - -  gb|AAB94382.1 TNF Receptor II 130             140             150
     ┌──────────────────────────────────────────────┐
121  │ G I R F D E W D E L P H G F A S L S A N M E L D D S A A E S │  TR13-alpha.aa
15     - I I I N G R D V A P Y - - - - - - - - - - - - - A P S      gb|AAB94382.1 TNF Receptor II 160             170             180
     ┌──────────────────────────────────────────────┐
151  │ T G N C T S S K W V P R G D Y I A F N T D E C T A T L M Y A │  TR13-alpha.aa
29     N G K C K D N E - - - - - - - - - - - - - - - - - - - - -   gb|AAB94382.1 TNF Receptor II 190             200             210
     ┌──────────────────────────────────────────────┐
181  │ V N L K Q S G T V N F E Y Y Y P D S S I I F E F F V Q N D Q │  TR13-alpha.aa
37     - - - - - - - - - - - - - - - - - - - - - Y N R H N L       gb|AAB94382.1 TNF Receptor II 220             230             240
     ┌──────────────────────────────────────────────┐
211  │ C Q P N A D D S R W M K T T E K G W E F H S V E L N R G N N │  TR13-alpha.aa
43     C - - - - - - - - - - - - - - - - - - - - - - - - - - - -   gb|AAB94382.1 TNF Receptor II 250             260             270
     ┌──────────────────────────────────────────────┐
241  │ V L Y W R T T A F S V W T K V P K P V L V R N I A I T G V A │  TR13-alpha.aa
44     - - - - - - - - - - - - - - - - - - - - - - - - - - - - -   gb|AAB94382.1 TNF Receptor II
```

FIG. 8B

```
              280         290         300
271  YTSECFPCKPGTYADKQGSSFCKLCPANSY      TR13-alpha.aa
 44  ----CLSCPPGTYASR-------LCDSKT-      gb|AAB94382.1 TNF Receptor II 310         320         330
301  SNKGETSCHQCDPDKYSEKGSSSCNVRPAC      TR13-alpha.aa
 62  --NTNTQCTPCGSDTFTSRNNHL----PAC      gb|AAB94382.1 TNF Receptor II 340         350         360
331  TDKDYFYTHTACDANGETQLMYKWAKPKIC      TR13-alpha.aa
 86  -----LSCNGRCDSNQVETRSCNTTHNRIC      gb|AAB94382.1 TNF Receptor II 370         380         390
361  SEDLEGAVKLPASGVKTHCPPCNPGFFKTN      TR13-alpha.aa
111  D-------------------CAPGYY---       gb|AAB94382.1 TNF Receptor II 400         410         420
391  NSTCQPCPYGSYSNGSDCTRCPAGTEPAVG      TR13-alpha.aa
118  ------CLL----KGSGCKACVSQTKCGIG      gb|AAB94382.1 TNF Receptor II 430         440         450
421  FEYKWWNTLPTNMETTVLSGINFEYKGMTG      TR13-alpha.aa
138  Y--------------------------GVSG     gb|AAB94382.1 TNF Receptor II 460         470         480
451  WEVAGDHIYTAAGASDNDFMILTLVVPGFR      TR13-alpha.aa
143  HTPTGDVI---------------------       gb|AAB94382.1 TNF Receptor II 490         500         510
481  PPQSVMADTENKEVARITFVFETLCSVNCE      TR13-alpha.aa
151  ------------------------------      gb|AAB94382.1 TNF Receptor II 520         530         540
511  LYFMVGVNSRTNTPVETWKGSKGKQSYTYI      TR13-alpha.aa
151  ------------------------------      gb|AAB94382.1 TNF Receptor II
```

FIG. 8C

```
                550               560               570
541  I E E N T T T S F T W A F Q R T T F H E A S R K Y T N D V A   TR13-alpha.aa
151  - - - - - - - - - - - - - - - - - - - - - - - - - - - - - -   gb|AAB94382.1 TNF Receptor II 580               590               600
571  K I Y S I N V T N V M N G V A S Y C R P C A L E A S D V G S   TR13-alpha.aa
151  - - - - - - - - - - - - - - - C S P C G L - - - - - - -       gb|AAB94382.1 TNF Receptor II 610               620               630
601  S C T S C P A G Y Y I D R D S G T C H S C P P N T I L K A H   TR13-alpha.aa
157  - - - - - - - G T Y - - - - - - - - - - - - - - - - S H       gb|AAB94382.1 TNF Receptor II 640               650               660
631  Q P Y G V Q A C V P C G P G T K N N K I H S L C Y N D C T F   TR13-alpha.aa
162  T V S S A D K C E P - - - - - - - - - - - - - - - - - - -     gb|AAB94382.1 TNF Receptor II 670               680               690
661  S R N T P T R T F N Y N F S A L A N T V T L A G G P S F T S   TR13-alpha.aa
172  - - - V P S N T F N Y - - - - I D V E I N L - - - - - Y P V   gb|AAB94382.1 TNF Receptor II 700               710               720
691  K G L K Y F H H F T L S L C G N Q G R K M S V C T - D N V T   TR13-alpha.aa
190  N D - - - - - - - - - - - - - - - - - T S C T R T T T T       gb|AAB94382.1 TNF Receptor II 730               740               750
720  D L R I P E G E S G F S K S I T A Y V C Q A V I I P P E V T   TR13-alpha.aa
201  G L S E S I S T S E L T I T M N H K D C D P V - - - - - - -   gb|AAB94382.1 TNF Receptor II 760               770               780
750  G Y K A G V S S Q P V S L A D R L I G V T T D M T L D G I T   TR13-alpha.aa
224  - F R D G Y F S - - - - - - - - - - - - - - - V L N K V A     gb|AAB94382.1 TNF Receptor II 790               800               810
780  S P A E L F H L E S L G I P D V I F F Y R S N D V T Q S C S   TR13-alpha.aa
237  T S G - - - - - - - - - - - - - F F T G E N R Y Q N T S       gb|AAB94382.1 TNF Receptor II
```

FIG. 8D

```
                    820              830              840
810  S G R S T T I R V R C S P Q K T V P G S L L L P G T C S D G   TR13-alpha.aa
252  N V C T L N F E I K C N N K D S S S K Q L - - - - - - - - -   gb|AAB94382.1 TNF Receptor II 850              860              870
840  T C D G C N F H F L W E S A A A C P L C S V A D Y H A I V S   TR13-alpha.aa
273  - - - - - - - - - - - T K T K N D T I M P H S E T V T L V G   gb|AAB94382.1 TNF Receptor II 880              890              900
870  S C V A G I Q K T T Y V W R E P K L C S G G I S L P E Q R V   TR13-alpha.aa
292  D C L S S V D - - I Y I - - - - - L Y S N T - - - - - - - -   gb|AAB94382.1 TNF Receptor II 910              920              930
900  T I C K T I D F W L K V G I S A G T C T A I L L T V L T C Y   TR13-alpha.aa
307  - - - N T Q D Y - - - - - - - - - - - - - - - - - - - - - -   gb|AAB94382.1 TNF Receptor II 940              950              960
930  F W K K N Q K L E Y K Y S K L V M N A T L K D C D L P A A D   TR13-alpha.aa
312  - - - E T D T I S Y H A G N V L - - - - - - D V D S H M P G   gb|AAB94382.1 TNF Receptor II 970              980              990
960  S C A I M E G E D V E D D L I F T S K N H S L G R S N H L P   TR13-alpha.aa
333  S C D I - - - - - - - - - - - - - - - - H K L I T N S Q N P   gb|AAB94382.1 TNF Receptor II 1000
990  P R G L L M D L T Q C R                                       TR13-alpha.aa
347  T H - - - - - - - - F L                                       gb|AAB94382.1 TNF Receptor II
```

| | | |
|---|---|---|
| 1 | GGATTTGTACCGGAGTCCCATTTGGGAGCAAGAGCCATCTACTCGTCCGTTACCGGCCTT | 60 |
| 61 | CCCACCATGGATTGCCAAGAAAATGAGTACTGGGACCAATGGGACGGTGTGTCACCTGC | 120 |
| 1 | M D C Q E N E Y W D Q W G R C V T C | 18 |
| 121 | CAACGGTGTGGTCCTGGACAGGAGCTATCCAAGGATTGTGGTTATGGAGAGGTGGAGAT | 180 |
| 19 | Q R C G P G Q E L S K D C G Y G E G G D | 38 |
| 181 | GCCTACTGGCACAGCCTGCCCTCCTCGCAGTACAAAAGCAGTGGGCCACCACAAATGT | 240 |
| 39 | A Y W H S L P S S Q Y K S S W G H H K C | 58 |
| 241 | CAGAGTTGCATCACCTGTGCTGTCATCAATCGTGTTCAGAAGGTCAACTGCCACACCTACC | 300 |
| 59 | Q S C I T C A V I N R V Q K V N C T P T | 78 |

FIG. 10A

```
301 TCTAATGCTGTCTGTGGGACTGTTTGCCCAGTTCTACCGAAAGACACGCATTGGAGGC    360
 79  S   N   A   V   C   G   D   C   L   P   R   F   Y   R   K   T   R   I   G   G      98

361 CTGCAGGACCAAGAGTGCATCCCGTGCACGAAGCAGACCCCCACCTCTGAGGTTCAATGT    420
 99  L   Q   D   Q   E   C   I   P   C   T   K   Q   T   P   T   S   E   V   Q   C     118

421 GCCTTCCAGTTGAGCTTAGTGGAGGCAGATGCACCCACAGTGCCCCCTCAGGAGGCCACA    480
119  A   F   Q   L   S   L   V   E   A   D   A   P   T   V   P   P   Q   E   A   T     138

481 CTTGTTGCACTGGTGAGCAGCCTGCTAGTGGTGTTCACCCTGGCCTTCCTGGGGCTCTTC    540
139  L   V   A   L   V   S   S   L   L   V   V   F   T   L   A   F   L   G   L   F     158

541 TTCCTCTACTGCAAGCAGTTCTTCAACAGACATTGCCAGCGTGGAGGTTTGCTGCAGTTT    600
159  F   L   Y   C   K   Q   F   F   N   R   H   C   Q   R   G   G   L   L   Q   F     178
```

FIG. 10B

```
601  GAGGCTGATAAAACAGCAAAGGAGGAATCTCTTCCCCGTGCCACCCAGCAAGGAGACC      660
179   E   A   D   K   T   A   K   E   E   S   L   F   P   V   P   P   S   K   E   T    198

661  AGTGCTGAGTCTCCAAGTCTCTTGGGCCCCTTGCCAGCCTTGTTCTCTCTGGAC          720
199   S   A   E   S   Q   V   S   W   A   P   G   S   L   A   Q   L   F   S   L   D    218

721  TCTGTTCCTATACCACAAACAGCAGGGGCCTGAAATGTGATGTCCACAAGAGCTAATA     780
219   S   V   P   I   P   Q   Q   Q   Q   G   P   E   M   *                            232

781  CCCTACAGATGGGGGCATATATCCTATCCCACCCAGAGGATTGATTCTCCATTTCACAA    840

841  GGACTGATCTGAGCATTTCTTGCTTCCCTGTTGTAGTCTCGGGAGCCAGATTCCCACATT  900

901  CATGGGACTACCAGACATGTTCCTAGCTCAACTTGATTATAGAGAAGAGAGAGAGGACA    960
```

FIG. 10C

```
 961  GTGAATGGGGTAGGGTTTTCATGTCTGCATTTTTGGTCAGTTAAGCCTCTCAAAATTGTG   1020
1021  TTGGCACACATCTACCTAGCACTTTAGGGACAAAAATCAAACCCTTTCTCCCCTTTTAGCTCCT   1080
1081  CCACACTGCCCTCCCCTCCCTCAACACACACACACACACACACATATACACATATAGACAC   1140
1141  ACAAACACACACACACACATTAAATATCTATCTTGGGGAAGCCCTCGTGCCATAATTCCA   1200
1201  AGTCATGTCTCAGACTGCTGCATTGCAGCATGACGCAGGGCAAAACACTTTCCCTCTAGAT   1260
1261  CCCTGGGGCCTCACCCTGTATTTGAGGTTCTCACCACCCTCAGCAGGGAGAAGGGCTGAA   1320
1321  GTTCGCCCATTTGGAACCTTACAGAACATTTCTGAGCCAAAGTAATCTTCCTTCTGGGGC   1380
```

FIG. 10D

```
1381  CTGAGTTCCCCAAAACTACCCCACAGCAGTCCCTCAAAGACAGCCCTCAATCCATGTAGG      1440
1441  ACATCTGAGTATGCCCTCTTTCTATTGAAATGTCAATTCAATCCCAGCTTTCTCACCACCG   1500
1501  TTCCCCTTTGATTCTTTCTCAATTGTCTTTTTGCCTTTAGCTCCCACCTATACATCTCAT    1560
1561  GCTCAGAGAAAAAACAAGTTCCTTAGAGGTTGTATTCTTTATTCTCCAAGAATCTGTCTGA   1620
1621  AACTTGTACAGCTAGTTCCTGTCCCAACTATTAAGTGGTTTATTAAGTACATTAGGCA      1680
1681  GAATGTGCACTTCATCACCAGTTCTAGCTCTCTGGCAAAGGAGTGCTGTCTACAGCAAGAT   1740
1741  TTTTGCTTTTAGAATTTATTAACTACATCTCTTGGGTTCATCCATCTACAAACACTGAT     1800
```

FIG. 10E

```
1801  TAAGGGCCCCTGGGCAACCAATTGATCAGATTACTAAAAGGACTTGGAAAAAGCAAAA  1860
1861  AGGTCCCATTGTACTGGTACTGAGGATTAGAAGCAATTGAAATACAAGCCTGTACCAAGC  1920
1921  AAGCAGCCTGGCCCCACACAGGTATTAGCAAATATGTGGTAACCAAGGTTTTAGGCCTTG  1980
1981  GSCYCTAGTTTCCTGTTTTTTTCGTTTTTTCCGTTTTCGTTTTTTGCAACAGT  2040
2041  TATTCTTATCTCACTGGCTTTCACTGATCATGTTTAGACCTTTCTGGTAGAAGAAATAATA  2100
2101  TCCAGACAGGGGATGATTGGCTTCAGCAGGCTGCAGGTGTTCAAAGTTGCCATGTGGC  2160
2161  TGGCAGTGGTTCAAGCCCACATTTGACACTGCTGCTCTAGAGGAAAGATAATGATGGTAA  2220
```

FIG. 10F

```
2221  CACAGTAATAATAATAATAACAAAAATATGATAAAGTGAAAGAGTAGATTCTTTCA  2280
2281  GTGTGCTTGCTCCATGGCATGAATGCTATGTGGACAGCCCAAGCCATACCCAGAATCACC  2340
2341  TTAATTCCAACTTTTTGAGGTTCAGCAATTGGAGGTGGCAATTGGCTTTGCATTTTAAAG  2400
2401  TATTTCGGGTAAAGGTGAAGTGAAGGATTTCGTCTTTATAATTTCGTTTGGCCATGGC  2460
2461  AAATACCATAGTTGAGTATTGCTTCAGGAGAGTTCTTTTTACAGTTTTACTTTTTCAATG  2520
2521  CTGAGGCATATTTCTTTGAGCACTGTGCTTTTATGTGTCTTTCTACAAAGGGGTTATTGG  2580
2581  TCAGTGGAAGAACAAAGTACACTTGATAAAAACATTTCAACATACATTGAGCCTAAACA  2640
2641  GCAGTTAAGTTGTCTCTAATGAACTAGCAAAAAAAAAATGTAGTTTTTGTTTGTAAGG  2700
```

FIG. 10G

```
2701  AAGGGGAGGTATTCCTGAGAATGAATTTTTTTTTTGGATTACTGTTTTTCTCCA  2760
2761  TATACCTTGAACTTGGGATTTTGAACAGGAGGAAGTCCTGGGAAAAATAATTTTTTCCC  2820
2821  TCCAAGATTCTCAGATCCCAGGTTAGGAAAGGATTCAGCACTAACAGCATAACCCCTCTA  2880
2881  CAACATACAGCCCTGTCACATTGAGATCATAATCCCTCCTGTCCCACTCCTCTCTACCAA  2940
2941  CCCCACCCTACTAGCTAGTCTTCAGTGTTTACATTGAATATGGTACATTTTAATTAT  3000
3001  TTTTTCTCATAAATGGGTTATTTTATAGAGATTTGTTAACTCTTGAGCCATATGCATGTG  3060
3061  TAGATACTGGGCAGGGCTATGTTGTTTGTTTATGATGCTCTGCAAACATTTCATATTGGCCAAT  3120
3121  AAACAGAAATATATCCAAAAAAAAAAAAAAAA  3152
```

FIG. 10H

SEQUENCE LISTING

```
<160> NUMBER OF SEQ ID NOS: 61

<210> SEQ ID NO 1
<211> LENGTH: 2554
<212> TYPE: DNA
<213> ORGANISM: Homo sapiens
<220> FEATURE:
<221> NAME/KEY: CDS
<222> LOCATION: (31)..(2283)

<400> SEQUENCE: 1
gtcgacccac gcgtccgcag ccttctcagt atg gac caa agt acc caa gcc tgt      54
```

-continued

```
                    Met Asp Gln Ser Thr Gln Ala Cys
                     1               5 gct ggt gag aaa cat tgc cat aac agg ggt ggc cta cac ttc aga atg       102
Ala Gly Glu Lys His Cys His Asn Arg Gly Gly Leu His Phe Arg Met
     10              15                  20 ctt ccc ctg caa acc tgg cac gta tgc aga caa gca ggc ctc ctc ttt       150
Leu Pro Leu Gln Thr Trp His Val Cys Arg Gln Ala Gly Leu Leu Phe
 25              30                  35                  40 ctg caa act ttg ccc agc aac tct tat tca aat aaa gga gaa act tct       198
Leu Gln Thr Leu Pro Ser Asn Ser Tyr Ser Asn Lys Gly Glu Thr Ser
             45                  50                  55 tgc cac cag tgt gac cct gac aaa tac tca gag aaa gga tct tct tcc       246
Cys His Gln Cys Asp Pro Asp Lys Tyr Ser Glu Lys Gly Ser Ser Ser
                 60                  65                  70 tgt aac gtg cgc cca gct tgc aca gac aaa gat tat ttc tac aca cac       294
Cys Asn Val Arg Pro Ala Cys Thr Asp Lys Asp Tyr Phe Tyr Thr His
         75                  80                  85 acg gcc tgc gat gcc aac gga gag aca caa ctc atg tac aaa tgg gcc       342
Thr Ala Cys Asp Ala Asn Gly Glu Thr Gln Leu Met Tyr Lys Trp Ala
     90                  95                 100 aag ccg aaa atc tgt agc gag gac ctt gag ggg gca gtg aag ctg cct       390
Lys Pro Lys Ile Cys Ser Glu Asp Leu Glu Gly Ala Val Lys Leu Pro
105                 110                 115                 120 gcc tct ggt gtg aag acc cac tgc cca ccc tgc aac cca ggc ttc ttc       438
Ala Ser Gly Val Lys Thr His Cys Pro Pro Cys Asn Pro Gly Phe Phe
                125                 130                 135 aaa acc aac aac agc acc tgc cag ccc tgc cca tat ggt tcc tac tcc       486
Lys Thr Asn Asn Ser Thr Cys Gln Pro Cys Pro Tyr Gly Ser Tyr Ser
            140                 145                 150 aat ggc tca gac tgt acc cgc tgc cct gca ggg act gaa cct gct gtg       534
Asn Gly Ser Asp Cys Thr Arg Cys Pro Ala Gly Thr Glu Pro Ala Val
        155                 160                 165 gga ttt gaa tac aaa tgg tgg aac acg ctg ccc aca aac atg gaa acg       582
Gly Phe Glu Tyr Lys Trp Trp Asn Thr Leu Pro Thr Asn Met Glu Thr
    170                 175                 180 acc gtt ctc agt ggg atc aac ttc gag tac aag ggc atg aca ggc tgg       630
Thr Val Leu Ser Gly Ile Asn Phe Glu Tyr Lys Gly Met Thr Gly Trp
185                 190                 195                 200 gag gtg gct ggt gat cac att tac aca gct gct gga gcc tca gac aat       678
Glu Val Ala Gly Asp His Ile Tyr Thr Ala Ala Gly Ala Ser Asp Asn
                205                 210                 215 gac ttc atg att ctc act ctg gtt gtg cca gga ttt aga cct ccg cag       726
Asp Phe Met Ile Leu Thr Leu Val Val Pro Gly Phe Arg Pro Pro Gln
            220                 225                 230 tcg gtg atg gca gac aca gag aat aaa gag gtg gcc aga atc aca ttt       774
Ser Val Met Ala Asp Thr Glu Asn Lys Glu Val Ala Arg Ile Thr Phe
        235                 240                 245 gtc ttt gag acc ctc tgt tct gtg aac tgt gag ctc tac ttc atg gtg       822
Val Phe Glu Thr Leu Cys Ser Val Asn Cys Glu Leu Tyr Phe Met Val
    250                 255                 260 ggt gtg aat tct agg acc aac act cct gtg gag acg tgg aaa ggt tcc       870
Gly Val Asn Ser Arg Thr Asn Thr Pro Val Glu Thr Trp Lys Gly Ser
265                 270                 275                 280 aaa ggc aaa cag tcc tat acc tac atc att gag gag aac act acc acg       918
Lys Gly Lys Gln Ser Tyr Thr Tyr Ile Ile Glu Glu Asn Thr Thr Thr
                285                 290                 295 agc ttc acc tgg gcc ttc cag agg acc act ttt cat gag gca agc agg       966
Ser Phe Thr Trp Ala Phe Gln Arg Thr Thr Phe His Glu Ala Ser Arg
            300                 305                 310
```

-continued

```
aag tac acc aat gac gtt gcc aag atc tac tcc atc aat gtc acc aat     1014
Lys Tyr Thr Asn Asp Val Ala Lys Ile Tyr Ser Ile Asn Val Thr Asn
        315                 320                 325 gtt atg aat ggc gtg gcc tcc tac tgc cgt ccc tgt gcc cta gaa gcc     1062
Val Met Asn Gly Val Ala Ser Tyr Cys Arg Pro Cys Ala Leu Glu Ala
330                 335                 340 tct gat gtg ggc tcc tcc tgc acc tct tgt cct gct ggt tac tat att     1110
Ser Asp Val Gly Ser Ser Cys Thr Ser Cys Pro Ala Gly Tyr Tyr Ile
345                 350                 355                 360 gac cga gat tca gga acc tgc cac tcc tgc ccc cct aac aca att ctg     1158
Asp Arg Asp Ser Gly Thr Cys His Ser Cys Pro Pro Asn Thr Ile Leu
                365                 370                 375 aaa gcc cac cag cct tat ggt gtc cag gcc tgt gtg ccc tgt ggt cca     1206
Lys Ala His Gln Pro Tyr Gly Val Gln Ala Cys Val Pro Cys Gly Pro
            380                 385                 390 ggg acc aag aac aac aag atc cac tct ctg tgc tac aat gat tgc acc     1254
Gly Thr Lys Asn Asn Lys Ile His Ser Leu Cys Tyr Asn Asp Cys Thr
        395                 400                 405 ttc tca cgc aac act cca acc agg act ttc aac tac aac ttc tcc gct     1302
Phe Ser Arg Asn Thr Pro Thr Arg Thr Phe Asn Tyr Asn Phe Ser Ala
410                 415                 420 ttg gca aac acc gtc act ctt gct gga ggg cca agc ttc act tcc aaa     1350
Leu Ala Asn Thr Val Thr Leu Ala Gly Gly Pro Ser Phe Thr Ser Lys
425                 430                 435                 440 ggg ttg aaa tac ttc cat cac ttt acc ctc agt ctc tgt gga aac cag     1398
Gly Leu Lys Tyr Phe His His Phe Thr Leu Ser Leu Cys Gly Asn Gln
                445                 450                 455 ggt agg aaa atg tct gtg tgc acc gac aat gtc act gac ctc cgg att     1446
Gly Arg Lys Met Ser Val Cys Thr Asp Asn Val Thr Asp Leu Arg Ile
            460                 465                 470 cct gag ggt gag tca ggg ttc tcc aaa tct atc aca gcc tac gtc tgc     1494
Pro Glu Gly Glu Ser Gly Phe Ser Lys Ser Ile Thr Ala Tyr Val Cys
        475                 480                 485 cag gca gtc atc atc ccc cca gag gtg aca ggc tac aag gcc ggg gtt     1542
Gln Ala Val Ile Ile Pro Pro Glu Val Thr Gly Tyr Lys Ala Gly Val
490                 495                 500 tcc tca cag cct gtc agc ctt gct gat cga ctt att ggg gtg aca aca     1590
Ser Ser Gln Pro Val Ser Leu Ala Asp Arg Leu Ile Gly Val Thr Thr
505                 510                 515                 520 gat atg act ctg gat gga atc acc tcc cca gct gaa ctt ttc cac ctg     1638
Asp Met Thr Leu Asp Gly Ile Thr Ser Pro Ala Glu Leu Phe His Leu
                525                 530                 535 gag tcc ttg gga ata ccg gac gtg atc ttc ttt tat agg tcc aat gat     1686
Glu Ser Leu Gly Ile Pro Asp Val Ile Phe Phe Tyr Arg Ser Asn Asp
            540                 545                 550 gtg acc cag tcc tgc agt tct ggg aga tca acc acc atc cgc gtc agg     1734
Val Thr Gln Ser Cys Ser Ser Gly Arg Ser Thr Thr Ile Arg Val Arg
        555                 560                 565 tgc agt cca cag aaa act gtc cct gga agt ttg ctg ctg cca gga acg     1782
Cys Ser Pro Gln Lys Thr Val Pro Gly Ser Leu Leu Leu Pro Gly Thr
570                 575                 580 tgc tca gat ggg acc tgt gat ggc tgc aac ttc cac ttc ctg tgg gag     1830
Cys Ser Asp Gly Thr Cys Asp Gly Cys Asn Phe His Phe Leu Trp Glu
585                 590                 595                 600 agc gcg gct gct tgc ccg ctc tgc tca gtg gct gac tac cat gct atc     1878
Ser Ala Ala Ala Cys Pro Leu Cys Ser Val Ala Asp Tyr His Ala Ile
                605                 610                 615 gtc agc agc tgt gtg gct ggg atc cag aag act act tac gtg tgg cga     1926
Val Ser Ser Cys Val Ala Gly Ile Gln Lys Thr Thr Tyr Val Trp Arg
            620                 625                 630
```

-continued

```
gaa ccc aag cta tgc tct ggt ggc att tct ctg cct gag cag aga gtc     1974
Glu Pro Lys Leu Cys Ser Gly Gly Ile Ser Leu Pro Glu Gln Arg Val
            635                 640                 645 acc atc tgc aaa acc ata gat ttc tgg ctg aaa gtg ggc atc tct gca     2022
Thr Ile Cys Lys Thr Ile Asp Phe Trp Leu Lys Val Gly Ile Ser Ala
650                 655                 660 ggc acc tgt act gcc atc ctg ctc acc gtc ttg acc tgc tac ttt tgg     2070
Gly Thr Cys Thr Ala Ile Leu Leu Thr Val Leu Thr Cys Tyr Phe Trp
665                 670                 675                 680 aaa aag aat caa aaa cta gag tac aag tac tcc aag ctg gtg atg aat     2118
Lys Lys Asn Gln Lys Leu Glu Tyr Lys Tyr Ser Lys Leu Val Met Asn
            685                 690                 695 gct act ctc aag gac tgt gac ctg cca gca gct gac agc tgc gcc atc     2166
Ala Thr Leu Lys Asp Cys Asp Leu Pro Ala Ala Asp Ser Cys Ala Ile
700                 705                 710 atg gaa ggc gag gat gta gag gac gac ctc atc ttt acc agc aag aat     2214
Met Glu Gly Glu Asp Val Glu Asp Asp Leu Ile Phe Thr Ser Lys Asn
            715                 720                 725 cac tct ttg gga aga tca aat cat tta cct cca aga gga ctc ctg atg     2262
His Ser Leu Gly Arg Ser Asn His Leu Pro Pro Arg Gly Leu Leu Met
730                 735                 740 gat ttg act cag tgc cgc tga agacatcctc aggaggccca gacatggacc        2313
Asp Leu Thr Gln Cys Arg
745                 750 tgtgagaggc actgcctgcc tcacctgcct cctcaccttg catagcacct ttgcaagcct   2373
gcggcgattt gggtgccagc atcctgcaac acccactgct ggaaatctct tcattgtggc   2433
cttatcagat gtttgaattt cagatctttt tttatagagt acccaaaccc tcctttctgc   2493
ttgcctcaaa cctgccaaat atacccacac tttgtttgta aattaaaaaa aaaaaaaaaa   2553
a                                                                    2554

<210> SEQ ID NO 2
<211> LENGTH: 750
<212> TYPE: PRT
<213> ORGANISM: Homo sapiens

<400> SEQUENCE: 2

Met Asp Gln Ser Thr Gln Ala Cys Ala Gly Glu Lys His Cys His Asn
1               5                   10                  15

Arg Gly Gly Leu His Phe Arg Met Leu Pro Leu Gln Thr Trp His Val
                20                  25                  30

Cys Arg Gln Ala Gly Leu Leu Phe Leu Gln Thr Leu Pro Ser Asn Ser
            35                  40                  45

Tyr Ser Asn Lys Gly Glu Thr Ser Cys His Gln Cys Asp Pro Asp Lys
        50                  55                  60

Tyr Ser Glu Lys Gly Ser Ser Cys Asn Val Arg Pro Ala Cys Thr
65                  70                  75                  80

Asp Lys Asp Tyr Phe Tyr Thr His Thr Ala Cys Asp Ala Asn Gly Glu
                85                  90                  95

Thr Gln Leu Met Tyr Lys Trp Ala Lys Pro Lys Ile Cys Ser Glu Asp
                100                 105                 110

Leu Glu Gly Ala Val Lys Leu Pro Ala Ser Gly Val Lys Thr His Cys
            115                 120                 125

Pro Pro Cys Asn Pro Gly Phe Phe Lys Thr Asn Asn Ser Thr Cys Gln
        130                 135                 140

Pro Cys Pro Tyr Gly Ser Tyr Ser Asn Gly Ser Asp Cys Thr Arg Cys
```

-continued

```
            145                 150                 155                 160
       Pro Ala Gly Thr Glu Pro Ala Val Gly Phe Glu Tyr Lys Trp Trp Asn
                       165                 170                 175
       Thr Leu Pro Thr Asn Met Glu Thr Thr Val Leu Ser Gly Ile Asn Phe
                       180                 185                 190
       Glu Tyr Lys Gly Met Thr Gly Trp Glu Val Ala Gly Asp His Ile Tyr
                       195                 200                 205
       Thr Ala Ala Gly Ala Ser Asp Asn Asp Phe Met Ile Leu Thr Leu Val
                       210                 215                 220
       Val Pro Gly Phe Arg Pro Pro Gln Ser Val Met Ala Asp Thr Glu Asn
       225                 230                 235                 240
       Lys Glu Val Ala Arg Ile Thr Phe Val Phe Glu Thr Leu Cys Ser Val
                       245                 250                 255
       Asn Cys Glu Leu Tyr Phe Met Val Gly Val Asn Ser Arg Thr Asn Thr
                       260                 265                 270
       Pro Val Glu Thr Trp Lys Gly Ser Lys Gly Lys Gln Ser Tyr Thr Tyr
                       275                 280                 285
       Ile Ile Glu Glu Asn Thr Thr Thr Ser Phe Thr Trp Ala Phe Gln Arg
       290                 295                 300
       Thr Thr Phe His Glu Ala Ser Arg Lys Tyr Thr Asn Asp Val Ala Lys
       305                 310                 315                 320
       Ile Tyr Ser Ile Asn Val Thr Asn Val Met Asn Gly Val Ala Ser Tyr
                       325                 330                 335
       Cys Arg Pro Cys Ala Leu Glu Ala Ser Asp Val Gly Ser Ser Cys Thr
                       340                 345                 350
       Ser Cys Pro Ala Gly Tyr Tyr Ile Asp Arg Asp Ser Gly Thr Cys His
                       355                 360                 365
       Ser Cys Pro Pro Asn Thr Ile Leu Lys Ala His Gln Pro Tyr Gly Val
                       370                 375                 380
       Gln Ala Cys Val Pro Cys Gly Pro Gly Thr Lys Asn Asn Lys Ile His
       385                 390                 395                 400
       Ser Leu Cys Tyr Asn Asp Cys Thr Phe Ser Arg Asn Thr Pro Thr Arg
                       405                 410                 415
       Thr Phe Asn Tyr Asn Phe Ser Ala Leu Ala Asn Thr Val Thr Leu Ala
                       420                 425                 430
       Gly Gly Pro Ser Phe Thr Ser Lys Gly Leu Lys Tyr Phe His His Phe
                       435                 440                 445
       Thr Leu Ser Leu Cys Gly Asn Gln Gly Arg Lys Met Ser Val Cys Thr
                       450                 455                 460
       Asp Asn Val Thr Asp Leu Arg Ile Pro Glu Gly Glu Ser Gly Phe Ser
       465                 470                 475                 480
       Lys Ser Ile Thr Ala Tyr Val Cys Gln Ala Val Ile Pro Pro Glu
                       485                 490                 495
       Val Thr Gly Tyr Lys Ala Gly Val Ser Ser Gln Pro Val Ser Leu Ala
                       500                 505                 510
       Asp Arg Leu Ile Gly Val Thr Thr Asp Met Thr Leu Asp Gly Ile Thr
                       515                 520                 525
       Ser Pro Ala Glu Leu Phe His Leu Glu Ser Leu Gly Ile Pro Asp Val
                       530                 535                 540
       Ile Phe Phe Tyr Arg Ser Asn Asp Val Thr Gln Ser Cys Ser Ser Gly
       545                 550                 555                 560
       Arg Ser Thr Thr Ile Arg Val Arg Cys Ser Pro Gln Lys Thr Val Pro
                       565                 570                 575
```

-continued

```
Gly Ser Leu Leu Leu Pro Gly Thr Cys Ser Asp Gly Thr Cys Asp Gly
            580                 585                 590

Cys Asn Phe His Phe Leu Trp Glu Ser Ala Ala Cys Pro Leu Cys
        595                 600                 605

Ser Val Ala Asp Tyr His Ala Ile Val Ser Ser Cys Val Ala Gly Ile
        610                 615                 620

Gln Lys Thr Thr Tyr Val Trp Arg Glu Pro Lys Leu Cys Ser Gly Gly
625                 630                 635                 640

Ile Ser Leu Pro Glu Gln Arg Val Thr Ile Cys Lys Thr Ile Asp Phe
                645                 650                 655

Trp Leu Lys Val Gly Ile Ser Ala Gly Thr Cys Thr Ala Ile Leu Leu
                660                 665                 670

Thr Val Leu Thr Cys Tyr Phe Trp Lys Lys Asn Gln Lys Leu Glu Tyr
            675                 680                 685

Lys Tyr Ser Lys Leu Val Met Asn Ala Thr Leu Lys Asp Cys Asp Leu
        690                 695                 700

Pro Ala Ala Asp Ser Cys Ala Ile Met Glu Gly Glu Asp Val Glu Asp
705                 710                 715                 720

Asp Leu Ile Phe Thr Ser Lys Asn His Ser Leu Gly Arg Ser Asn His
                725                 730                 735

Leu Pro Pro Arg Gly Leu Leu Met Asp Leu Thr Gln Cys Arg
            740                 745                 750

<210> SEQ ID NO 3
<211> LENGTH: 277
<212> TYPE: PRT
<213> ORGANISM: Homo sapiens

<400> SEQUENCE: 3

Met Cys Val Gly Ala Arg Arg Leu Gly Arg Gly Pro Cys Ala Ala Leu
  1               5                  10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
```

```
                    195                 200                     205
        Val Pro Gly Gly Arg Ala Val Ala Ala Ile Leu Gly Leu Gly Leu Val
            210                 215                 220

Leu Gly Leu Leu Gly Pro Leu Ala Ile Leu Leu Ala Leu Tyr Leu Leu
        225                 230                 235                 240

Arg Arg Asp Gln Arg Leu Pro Pro Asp Ala His Lys Pro Pro Gly Gly
                        245                 250                 255

Gly Ser Phe Arg Thr Pro Ile Gln Glu Gln Ala Asp Ala His Ser
                        260                 265                 270

Thr Leu Ala Lys Ile
                275

<210> SEQ ID NO 4
<211> LENGTH: 3861
<212> TYPE: DNA
<213> ORGANISM: Homo sapiens
<220> FEATURE:
<221> NAME/KEY: CDS
<222> LOCATION: (89)..(769)
<221> NAME/KEY: misc_feature
<222> LOCATION: (3151)
<223> OTHER INFORMATION: n equals a,t,g, or c
<221> NAME/KEY: misc_feature
<222> LOCATION: (3158)
<223> OTHER INFORMATION: n equals a,t,g, or c
<221> NAME/KEY: misc_feature
<222> LOCATION: (3162)
<223> OTHER INFORMATION: n equals a,t,g, or c

<400> SEQUENCE: 4
tgaggtggat ttgtaccgga gtcccatttg ggagcaagag ccatctactc gtccgttacc      60
ggccttccca ccatggattg ccaagaaa atg agt act ggg acc aat ggg gac        112
                                 Met Ser Thr Gly Thr Asn Gly Asp
                                   1               5 ggt gtg tca cct gcc aac ggt gtg gtc ctg gac agg agc tat cca agg        160
Gly Val Ser Pro Ala Asn Gly Val Val Leu Asp Arg Ser Tyr Pro Arg
 10                  15                  20 att gtg gtt atg gag agg gtg gag atg cct act gca cag cct gcc ctc        208
Ile Val Val Met Glu Arg Val Glu Met Pro Thr Ala Gln Pro Ala Leu
 25                  30                  35                  40 ctc gca gta caa aag cag ctg ggg cca cca caa atg tgc aga gtt gca        256
Leu Ala Val Gln Lys Gln Leu Gly Pro Pro Gln Met Cys Arg Val Ala
                 45                  50                  55 tgc acc tgt gct gtc atc aat cgt gtt cag aag gtc aac tgc aca cct        304
Cys Thr Cys Ala Val Ile Asn Arg Val Gln Lys Val Asn Cys Thr Pro
             60                  65                  70 acc tct aat gct gtc tgt ggg gac tgt ttg ccc agg ttc tac cga aag        352
Thr Ser Asn Ala Val Cys Gly Asp Cys Leu Pro Arg Phe Tyr Arg Lys
         75                  80                  85 aca cgc att gga ggc ctg cag gac caa gag tgc atc ccg tgc acg aag        400
Thr Arg Ile Gly Gly Leu Gln Asp Gln Glu Cys Ile Pro Cys Thr Lys
     90                  95                 100 cag acc ccc acc tct gag gtt caa tgt gcc ttc cag ttg agc tta gtg        448
Gln Thr Pro Thr Ser Glu Val Gln Cys Ala Phe Gln Leu Ser Leu Val
105                 110                 115                 120 gag gca gat gca ccc aca gtg ccc cct cag gag gcc aca ctt gtt gca        496
Glu Ala Asp Ala Pro Thr Val Pro Pro Gln Glu Ala Thr Leu Val Ala
                125                 130                 135 ctg gtg agc agc ctg cta gtg gtg ttt acc ctg gcc ttc ctg ggg ctc        544
Leu Val Ser Ser Leu Leu Val Val Phe Thr Leu Ala Phe Leu Gly Leu
            140                 145                 150
```

-continued

| | | |
|---|---|---|
| ttc ttc ctc tac tgc aag cag ttc ttc aac aga cat tgc cag cgt gga<br>Phe Phe Leu Tyr Cys Lys Gln Phe Phe Asn Arg His Cys Gln Arg Gly<br>                155                        160                      165 | 592 |
| ggt ttg ctg cag ttt gag gct gat aaa aca gca aag gag gaa tct ctc<br>Gly Leu Leu Gln Phe Glu Ala Asp Lys Thr Ala Lys Glu Glu Ser Leu<br>    170                        175                        180 | 640 |
| ttc ccc gtg cca ccc agc aag gag acc agt gct gag tcc caa gtc tct<br>Phe Pro Val Pro Pro Ser Lys Glu Thr Ser Ala Glu Ser Gln Val Ser<br>185                        190                        195                      200 | 688 |
| tgg gcc cct ggc agc ctt gcc cag ttg ttc tct ctg gac tct gtt cct<br>Trp Ala Pro Gly Ser Leu Ala Gln Leu Phe Ser Leu Asp Ser Val Pro<br>                205                        210                        215 | 736 |
| ata cca caa cag cag cag ggg cct gaa atg tga tgtccacaag agctaatacc<br>Ile Pro Gln Gln Gln Gln Gly Pro Glu Met<br>              220                        225 | 789 |
| ctacagatgg ggcatatcct atcccatccc accagaggat tgattctcca tttcacaagg | 849 |
| actgatctgg agcatttctt gcttccctgt tgtagtctgg ggagccagat tccacattca | 909 |
| tgggactacc agacatgttc ctagctcaac ttgattatag agaagaggag agaggacagt | 969 |
| gaatggggta gggttttcat gtctgcattt ttggtcaggt aagcctctca aaattgtgtt | 1029 |
| ggcacatcta cctagcactt tagggacaaa atcaaaccct tctccccttt tagctcctcc | 1089 |
| acactgcctc cctcctcaac acacacacac acacatacac acacatatac atagacacac | 1149 |
| aaacacacac acacacatta atatctatct tggggggaagc ctcgtgccat aattcccaag | 1209 |
| tcatgtctca gactgctgca ttgcagcatg acgcagggca aacactttcc ctctagatcc | 1269 |
| ctggggcctc accctgtatt tgaggttctc accaccctca gcagggagaa gggctgaagt | 1329 |
| tcgccatttt ggaaccttac agaacatttc tgagccaaag taatcttcct tctgggcct | 1389 |
| gagttcccca aactacccca cagcagtccc tcaaagacag ccctcaatcc atgtagggac | 1449 |
| atctgagtat gcctctttct attgaaatgt caattcaatc ccagctttct caccaccgtt | 1509 |
| cccctttgat tctttctcaa ttgtcttttt gcctttagct cccacctata catctcatgc | 1569 |
| tcagagaaaa acaagttcct tagaggttgt attctttatt ctccaagaat ctgtctgaaa | 1629 |
| cttgtacagc tagttcctgt cccacaacta ttaagtggtt tattaagtac attaggcaga | 1689 |
| atgtgcactt catcaccagg ttctagctct ggcaaaggag tgctgtctac agcaagattt | 1749 |
| ttgcttttag aattttatta actacatctt ttgggttcat ccatctacaa acactgatta | 1809 |
| agggccctg gggcaaccaa ttgatcagat tactaaaagg acttgggaaa aagcaaaaag | 1869 |
| gtcccattgt actggactga ggattagaag caattgaaat acaagcctgt accaagcaag | 1929 |
| cagcctggcc ccacacaggt attagcaaat atgtggtaac caaggtttta ggccttggcc | 1989 |
| cctaggtttc ctgttttttt ttcgttttgg tttccgtttt cgtttttgc aacaggttat | 2049 |
| tcttatctca ctggctttca ctgatcatgt ttagaccttc tggtagaaga ataatatcc | 2109 |
| agacagggga tgatttggct tcagcaggct gcaggtgttc aaaggttgcc atgtggctgg | 2169 |
| cagtggttca agcccacatt tgacactgct gctctagagg aaagataatg atggtaacac | 2229 |
| agtaataata ataataataa caaaaatatg ataaagtgaa agagtagatt tctttcagtg | 2289 |
| tgcttgctcc atggcatgaa tgctatgtgg acagcccaag ccatacccag aatcacctta | 2349 |
| attccaactt tttgaggttc agcaattgga ggtggcaatt ggctttgcat tttaaagtat | 2409 |
| ttcgggtaaa ggtgaagtga aggattttcg tctttataat ttctgtttgg ccatggcaaa | 2469 |
| taccatagtt gagtatttgc ttcaggagag ttctttttac agttttactt ttcaatgctg | 2529 |
| aggcatattt cttttgagcac tgtgctttta tgtgtctttc tacaaagggg ttattggtca | 2589 |

-continued

```
gtggaagaac aaagtacact tgataaaaac attttcaaca tacattgagc ctaaacagca    2649
gttaagttgt ctctaatgaa ctagcaaaaa aaaaaaatgt agttttttgtt tgtaaggaag    2709 gggaggtatt tcctgagaat gaattttttt tttttttggat tactgttttt ctctccatat    2769
accttgactt ggattttgac aggagggagt ctgggaaaat aattttttcc tccaagattc    2829
tcagatccag gttaggaaag gattcagcac tacagcatac ccctctacaa catacagccc    2889
tgtcacattg agatcataat ccctcctgtc ccactcctct ctaccaaccc caccctacta    2949
gctaggtctt cagtgtttta cattgaatat tggtacattt taattatttt ttctcataaa    3009
tgggttattt atagagattt tgttaactct tgagccatat gcatgtgtag atactggcag    3069
ggctatgttt gtttatgatg ctctgcaaac atttcatatt ggccaataaa cagaaatata    3129
tccaaaaaaa aaaaaaaaaa tntarmssng sgnatdatgg attgccaaga aaatgagtac    3189
tgggaccaat ggggacggtg tgtcacctgc aacggtgtg gtcctggaca ggagctatcc    3249
aaggattgtg gttatggaga gggtggagat gcctactgca cagcctgccc tcctcgcagt    3309
acaaaaggca gctggggcca ccacaaatgt cagagttgca tcacctgtgc tgtcatcaat    3369
cgtgttcaga aggtcaactg cacagctacc tctaatgctg tctgtgggga ctgtttgccc    3429
aggttctacc gaaagacacg cattggaggc ctgcaggacc aagagtgcat cccgtgcacg    3489
aagcagaccc ccacctctga ggttcaatgt gccttccagt tgagcttagt ggaggcagat    3549
gcacccacag tgcccctca ggaggccaca cttgttgcac tggtgagcag cctgctagtg    3609
gtgtttaccc tggccttcct ggggctcttc ttcctctact gcaagcagtt cttcaacaga    3669
cattgccagc gtggaggttt gctgcagttt gaggctgata aaacagcaaa ggaggaatct    3729
ctcttccccg tgccacccag caaggagacc agtgctgagt cccaagtctc ttgggcccct    3789
ggcagccttg cccagttgtt ctctctggac tctgttccta taccacaaca gcagcagggg    3849
cctgaaatgt ga                                                        3861
```

<210> SEQ ID NO 5
<211> LENGTH: 226
<212> TYPE: PRT
<213> ORGANISM: Homo sapiens

<400> SEQUENCE: 5

```
Met Ser Thr Gly Thr Asn Gly Asp Gly Val Ser Pro Ala Asn Gly Val
  1               5                  10                  15

Val Leu Asp Arg Ser Tyr Pro Arg Ile Val Val Met Glu Arg Val Glu
                 20                  25                  30

Met Pro Thr Ala Gln Pro Ala Leu Leu Ala Val Gln Lys Gln Leu Gly
             35                  40                  45

Pro Pro Gln Met Cys Arg Val Ala Cys Thr Cys Ala Val Ile Asn Arg
         50                  55                  60

Val Gln Lys Val Asn Cys Thr Pro Thr Ser Asn Ala Val Cys Gly Asp
 65                  70                  75                  80

Cys Leu Pro Arg Phe Tyr Arg Lys Thr Arg Ile Gly Gly Leu Gln Asp
                 85                  90                  95

Gln Glu Cys Ile Pro Cys Thr Lys Gln Thr Pro Thr Ser Glu Val Gln
            100                 105                 110

Cys Ala Phe Gln Leu Ser Leu Val Glu Ala Asp Ala Pro Thr Val Pro
            115                 120                 125

Pro Gln Glu Ala Thr Leu Val Ala Leu Val Ser Ser Leu Leu Val Val
        130                 135                 140
```

```
Phe Thr Leu Ala Phe Leu Gly Leu Phe Phe Leu Tyr Cys Lys Gln Phe
145                 150                 155                 160

Phe Asn Arg His Cys Gln Arg Gly Gly Leu Leu Gln Phe Glu Ala Asp
                165                 170                 175

Lys Thr Ala Lys Glu Glu Ser Leu Phe Pro Val Pro Pro Ser Lys Glu
            180                 185                 190

Thr Ser Ala Glu Ser Gln Val Ser Trp Ala Pro Gly Ser Leu Ala Gln
        195                 200                 205

Leu Phe Ser Leu Asp Ser Val Pro Ile Pro Gln Gln Gln Gln Gly Pro
    210                 215                 220

Glu Met
225

<210> SEQ ID NO 6
<211> LENGTH: 461
<212> TYPE: PRT
<213> ORGANISM: Homo sapiens

<400> SEQUENCE: 6

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Ser Ser Ser Thr
                165                 170                 175

Asp Ile Cys Arg Pro His Gln Ile Cys Asn Val Val Ala Ile Pro Gly
            180                 185                 190

Asn Ala Ser Arg Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
```

```
                      275                 280                 285
Lys Lys Pro Leu Cys Leu Gln Arg Glu Ala Lys Val Pro His Leu Pro
            290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
                340                 345                 350

Val Glu Ala Ser Ala Gly Glu Ala Arg Ala Ser Thr Gly Ser Ser
            355                 360                 365

Asp Ser Ser Pro Gly Gly His Gly Thr Gln Val Asn Val Thr Cys Ile
            370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
                420                 425                 430

Gln Leu Glu Thr Pro Glu Thr Leu Leu Gly Ser Thr Glu Glu Lys Pro
            435                 440                 445

Leu Pro Leu Gly Val Pro Asp Ala Gly Met Lys Pro Ser
            450                 455                 460

<210> SEQ ID NO 7
<211> LENGTH: 159
<212> TYPE: PRT
<213> ORGANISM: Homo sapiens

<400> SEQUENCE: 7

Met Ser Thr Gly Thr Asn Gly Asp Gly Val Ser Pro Ala Asn Gly Val
1               5                   10                  15

Val Leu Asp Arg Ser Tyr Pro Arg Ile Val Met Glu Arg Val Glu
            20                  25                  30

Met Pro Thr Ala Gln Pro Ala Leu Leu Ala Val Gln Lys Gln Leu Gly
            35                  40                  45

Pro Pro Gln Met Cys Arg Val Ala Cys Thr Cys Ala Val Ile Asn Arg
    50                  55                  60

Val Gln Lys Val Asn Cys Thr Pro Thr Ser Asn Ala Val Cys Gly Asp
65                  70                  75                  80

Cys Leu Pro Arg Phe Tyr Arg Lys Thr Arg Ile Gly Gly Leu Gln Asp
                85                  90                  95

Gln Glu Cys Ile Pro Cys Thr Lys Gln Thr Pro Thr Ser Glu Val Gln
            100                 105                 110

Cys Ala Phe Gln Leu Ser Leu Val Glu Ala Asp Ala Pro Thr Val Pro
            115                 120                 125

Pro Gln Glu Ala Thr Leu Val Ala Leu Val Ser Ser Leu Leu Val Val
        130                 135                 140

Phe Thr Leu Ala Phe Leu Gly Leu Phe Phe Leu Tyr Cys Lys Gln
145                 150                 155

<210> SEQ ID NO 8
<211> LENGTH: 342
<212> TYPE: DNA
<213> ORGANISM: Homo sapiens
<220> FEATURE:
```

```
<221> NAME/KEY: misc_feature
<222> LOCATION: (28)
<223> OTHER INFORMATION: n equals a,t,g, or c
<221> NAME/KEY: misc_feature
<222> LOCATION: (31)
<223> OTHER INFORMATION: n equals a,t,g, or c
<221> NAME/KEY: misc_feature
<222> LOCATION: (40)
<223> OTHER INFORMATION: n equals a,t,g, or c
<221> NAME/KEY: misc_feature
<222> LOCATION: (181)
<223> OTHER INFORMATION: n equals a,t,g, or c
<221> NAME/KEY: misc_feature
<222> LOCATION: (276)
<223> OTHER INFORMATION: n equals a,t,g, or c
<221> NAME/KEY: misc_feature
<222> LOCATION: (282)
<223> OTHER INFORMATION: n equals a,t,g, or c

<400> SEQUENCE: 8
ggaccttgag ggggcagtga agctgctngc ntctggtgtn aagacccact gcccaccctg      60
caacccaggc ttcttcaaaa ccaacaacag cacctgccag ccctgcccat atggttccta    120
ctccaatggc tcagactgta cccgctgccc tgcagggact gaacctgctg tgggatttga    180
ntacaaatgg tggaacacgc tgcccacaaa catggaaacg accgttctca gtgggatcaa    240
cttcgagtac aagggcatga caggctggga ggtggntggt gntcacattt acacagctgc    300
tggagcctca gacaatgact tcatgattct aaatctggtt gt                       342

<210> SEQ ID NO 9
<211> LENGTH: 291
<212> TYPE: DNA
<213> ORGANISM: Homo sapiens
<220> FEATURE:
<221> NAME/KEY: misc_feature
<222> LOCATION: (244)
<223> OTHER INFORMATION: n equals a, t, g or c

<400> SEQUENCE: 9
ctcctgtgga gacgtggaaa ggttccaaag gcaaacagtc ctatacctac atcattgagg      60
agaacactac cacgagcttc acctgggcct tccagaggac cacttttcat gaggcaagca    120
ggaagtacac caatgacgtt gccaagatct actccatcaa tgtcaccaat gttatgaatg    180
gcgtggcctc ctactgccgt ccctgtgccc tagaagcctc tgatgtgggc tcctcctgca    240
cctnttgtcc tgctggttac tatattgacc gagattcagg aacctgccac t             291

<210> SEQ ID NO 10
<211> LENGTH: 267
<212> TYPE: DNA
<213> ORGANISM: Homo sapiens
<220> FEATURE:
<221> NAME/KEY: misc_feature
<222> LOCATION: (41)
<223> OTHER INFORMATION: n equals a,t,g, or c
<221> NAME/KEY: misc_feature
<222> LOCATION: (171)
<223> OTHER INFORMATION: n equals a,t,g, or c
<221> NAME/KEY: misc_feature
<222> LOCATION: (207)
<223> OTHER INFORMATION: n equals a,t,g, or c

<400> SEQUENCE: 10
ccaagatcta ctccatcaat gtcaccaatg ttatgaatgg ngtggcctcc tactgccgtc      60
cctgtgccct agaagcctct gatgtgggct cctcctgcac ctcttgtcct gctggttact    120
atattgaccg agattcagga acctgccact cctgcccccc taacacaatt ntgaaagccc    180
```

```
accagcctta tggtgtccag gcctgtntgc cctgtggtcc agggaccaag aacaacaaga      240
tccactctct gtgctacaat gattgca                                          267
```

<210> SEQ ID NO 11
<211> LENGTH: 274
<212> TYPE: DNA
<213> ORGANISM: Homo sapiens
<220> FEATURE:
<221> NAME/KEY: misc_feature
<222> LOCATION: (107)
<223> OTHER INFORMATION: n equals a,t,g, or c
<221> NAME/KEY: misc_feature
<222> LOCATION: (196)
<223> OTHER INFORMATION: n equals a,t,g, or c

<400> SEQUENCE: 11

```
aaagaatcaa aaactagagt acaagtactc caagctggtg atgaatgcta ctctcaagga       60
ctgtgacctg ccagcagctg acagctcgcc atcatggaag gcgaggntgt agaggacgac      120
ctcatcttta ccagcaagaa gtcactcttt gggaagatca aatcatttac ctccaagagg      180
actcctgatg gatttnactc agtgccgctg aagacatcct caggaggccc agacatggac      240
ctgtgagagg cactgcctgc ctcacctgct tcct                                   274
```

<210> SEQ ID NO 12
<211> LENGTH: 245
<212> TYPE: DNA
<213> ORGANISM: Homo sapiens

<400> SEQUENCE: 12

```
ccaagccgaa aatctgtagc gaggaccttg aggggggcagt gaagctgctg cctctggtgt      60
gaagacccac tgcccaccct gcaacccagg cttcttcaaa accaacaaca gcacctgcca     120
gccctgccca tatggttcct actccaatgg ctcagactgt acccgctgcc ctgcagggac     180
tgaacctgct gtgggatttg aatacaaatg gtggaacacg ctgcccacaa acatgggaaa     240
cgacc                                                                  245
```

<210> SEQ ID NO 13
<211> LENGTH: 292
<212> TYPE: DNA
<213> ORGANISM: Homo sapiens
<220> FEATURE:
<221> NAME/KEY: misc_feature
<222> LOCATION: (5)
<223> OTHER INFORMATION: n equals a,t,g, or c
<221> NAME/KEY: misc_feature
<222> LOCATION: (202)
<223> OTHER INFORMATION: n equals a,t,g, or c
<221> NAME/KEY: misc_feature
<222> LOCATION: (245)
<223> OTHER INFORMATION: n equals a,t,g, or c
<221> NAME/KEY: misc_feature
<222> LOCATION: (246)
<223> OTHER INFORMATION: n equals a,t,g, or c
<221> NAME/KEY: misc_feature
<222> LOCATION: (291)
<223> OTHER INFORMATION: n equals a,t,g, or c
<221> NAME/KEY: misc_feature
<222> LOCATION: (292)
<223> OTHER INFORMATION: n equals a,t,g, or c

<400> SEQUENCE: 13

```
ggcanaggga atttgactca gtgccgctga agacatcctc aggaggccca gacatggacc       60
tgtgagaggc actgcctgcc tcacctgcct cctcaccttg catagcacct ttgcaagcct     120
```

```
gcgggaattt gggtgccagc atcctgcaac acccactgct gggaaatctc ttcattgtgg      180
ccttatcaga tgtttgaatt tnagatcttt ttttatagag tacccaaacc ctcctttctg      240
cttgnntcaa acctgccaaa tatacccaca ctttgtttgt aaaaaaaaaa nn              292
```

<210> SEQ ID NO 14
<211> LENGTH: 220
<212> TYPE: DNA
<213> ORGANISM: Homo sapiens
<220> FEATURE:
<221> NAME/KEY: misc_feature
<222> LOCATION: (164)
<223> OTHER INFORMATION: n equals a, t, g or c

<400> SEQUENCE: 14

```
atcttctttt ataggtccaa tgatgtgacc cagtcctgca gttctgggag atcaaccacc       60
atccgcgtca ggtgcagtcc acagaaaact gtccctggaa gtttgctgct gccaggaacg      120
tgctcagatg ggacctgtga tggctgcaac ttccacttcc tgtnggagag cgcggctgct      180
tgcccgctct gctcagtggc tgactaccat gctatcgtca                            220
```

<210> SEQ ID NO 15
<211> LENGTH: 427
<212> TYPE: DNA
<213> ORGANISM: Homo sapiens
<220> FEATURE:
<221> NAME/KEY: misc_feature
<222> LOCATION: (44)
<223> OTHER INFORMATION: n equals a,t,g, or c
<221> NAME/KEY: misc_feature
<222> LOCATION: (77)
<223> OTHER INFORMATION: n equals a,t,g, or c
<221> NAME/KEY: misc_feature
<222> LOCATION: (234)
<223> OTHER INFORMATION: n equals a,t,g, or c
<221> NAME/KEY: misc_feature
<222> LOCATION: (260)
<223> OTHER INFORMATION: n equals a,t,g, or c
<221> NAME/KEY: misc_feature
<222> LOCATION: (268)
<223> OTHER INFORMATION: n equals a,t,g, or c
<221> NAME/KEY: misc_feature
<222> LOCATION: (271)
<223> OTHER INFORMATION: n equals a,t,g, or c
<221> NAME/KEY: misc_feature
<222> LOCATION: (272)
<223> OTHER INFORMATION: n equals a,t,g, or c
<221> NAME/KEY: misc_feature
<222> LOCATION: (275)
<223> OTHER INFORMATION: n equals a,t,g, or c
<221> NAME/KEY: misc_feature
<222> LOCATION: (305)
<223> OTHER INFORMATION: n equals a,t,g, or c
<221> NAME/KEY: misc_feature
<222> LOCATION: (308)
<223> OTHER INFORMATION: n equals a,t,g, or c
<221> NAME/KEY: misc_feature
<222> LOCATION: (331)
<223> OTHER INFORMATION: n equals a,t,g, or c
<221> NAME/KEY: misc_feature
<222> LOCATION: (353)
<223> OTHER INFORMATION: n equals a,t,g, or c
<221> NAME/KEY: misc_feature
<222> LOCATION: (359)
<223> OTHER INFORMATION: n equals a,t,g, or c
<221> NAME/KEY: misc_feature
<222> LOCATION: (368)
<223> OTHER INFORMATION: n equals a,t,g, or c
<221> NAME/KEY: misc_feature
<222> LOCATION: (372)
<223> OTHER INFORMATION: n equals a,t,g, or c
<221> NAME/KEY: misc_feature
<222> LOCATION: (381)

```
<223> OTHER INFORMATION: n equals a,t,g, or c
<221> NAME/KEY: misc_feature
<222> LOCATION: (388)
<223> OTHER INFORMATION: n equals a,t,g, or c
<221> NAME/KEY: misc_feature
<222> LOCATION: (398)
<223> OTHER INFORMATION: n equals a,t,g, or c
<221> NAME/KEY: misc_feature
<222> LOCATION: (400)
<223> OTHER INFORMATION: n equals a,t,g, or c
<221> NAME/KEY: misc_feature
<222> LOCATION: (407)
<223> OTHER INFORMATION: n equals a,t,g, or c
<221> NAME/KEY: misc_feature
<222> LOCATION: (427)
<223> OTHER INFORMATION: n equals a,t,g, or c

<400> SEQUENCE: 15
aattcggcag agctcagaca atgacttcat gattctcact ctgnttgtgc caggatttag    60
acctccgcag tcggtgntgg cagacacaga gaataaagag gtggccagaa tcacatttgt   120
ctttgagacc ctctgttctg tgaactgtga gctctacttc atggtgggtg tggaattcta   180
gggaccaaca cttcctgtgg aggacgtggg aaaggttcca aagggcaaac agtnccttat   240
tacctgacat gcattgaggn aggaacantt nnccnggagg tttcaactgg ggcctttccc   300
gaggnacnac ttttttcatg gagggccaag ncaggggagt tacaacccat tgnacgttng   360
gccaaggntc tnatttccat ncaatgtnca accaatgntn atggaanggg tgttggggcc   420 ttgctttn                                                            427

<210> SEQ ID NO 16
<211> LENGTH: 333
<212> TYPE: DNA
<213> ORGANISM: Homo sapiens
<220> FEATURE:
<221> NAME/KEY: misc_feature
<222> LOCATION: (20)
<223> OTHER INFORMATION: n equals a,t,g, or c
<221> NAME/KEY: misc_feature
<222> LOCATION: (23)
<223> OTHER INFORMATION: n equals a,t,g, or c
<221> NAME/KEY: misc_feature
<222> LOCATION: (76)
<223> OTHER INFORMATION: n equals a,t,g, or c
<221> NAME/KEY: misc_feature
<222> LOCATION: (80)
<223> OTHER INFORMATION: n equals a,t,g, or c
<221> NAME/KEY: misc_feature
<222> LOCATION: (85)
<223> OTHER INFORMATION: n equals a,t,g, or c
<221> NAME/KEY: misc_feature
<222> LOCATION: (103)
<223> OTHER INFORMATION: n equals a,t,g, or c
<221> NAME/KEY: misc_feature
<222> LOCATION: (129)
<223> OTHER INFORMATION: n equals a,t,g, or c
<221> NAME/KEY: misc_feature
<222> LOCATION: (152)
<223> OTHER INFORMATION: n equals a,t,g, or c
<221> NAME/KEY: misc_feature
<222> LOCATION: (171)
<223> OTHER INFORMATION: n equals a,t,g, or c
<221> NAME/KEY: misc_feature
<222> LOCATION: (244)
<223> OTHER INFORMATION: n equals a,t,g, or c
<221> NAME/KEY: misc_feature
<222> LOCATION: (260)
<223> OTHER INFORMATION: n equals a,t,g, or c
<221> NAME/KEY: misc_feature
<222> LOCATION: (269)
<223> OTHER INFORMATION: n equals a,t,g, or c
<221> NAME/KEY: misc_feature
<222> LOCATION: (275)
```

```
<223> OTHER INFORMATION: n equals a,t,g, or c
<221> NAME/KEY: misc_feature
<222> LOCATION: (293)
<223> OTHER INFORMATION: n equals a,t,g, or c
<221> NAME/KEY: misc_feature
<222> LOCATION: (307)
<223> OTHER INFORMATION: n equals a,t,g, or c
<221> NAME/KEY: misc_feature
<222> LOCATION: (320)
<223> OTHER INFORMATION: n equals a,t,g, or c

<400> SEQUENCE: 16
taactctggt tgtcccaggn ttnaaacctc cgcagtcggt gaatggcaga cacagagaat      60
aaagaggtgg ccagantcan atttnttttt aaaaccctct gtnctgtgaa actgtgaagc    120
tctacttgna tggtgggtgt gaaattctag gnaccaacac tcctgtggag nacgtggaaa    180
aggttccaaa ggcaaacagt cctataccta catcattgaa ggaggaacac taccacgagg    240
ttgnacctgg gcccttccan agggaccant tttcnatgag ggcaagcagg gangtacacc    300
attgagngtt gcccaggttn tattccttca atg                                  333

<210> SEQ ID NO 17
<211> LENGTH: 70
<212> TYPE: DNA
<213> ORGANISM: Homo sapiens
<220> FEATURE:
<221> NAME/KEY: misc_feature
<222> LOCATION: (40)
<223> OTHER INFORMATION: n equals a,t,g, or c
<221> NAME/KEY: misc_feature
<222> LOCATION: (60)
<223> OTHER INFORMATION: n equals a,t,g, or c
<221> NAME/KEY: misc_feature
<222> LOCATION: (66)
<223> OTHER INFORMATION: n equals a,t,g, or c

<400> SEQUENCE: 17
ggcacaggca aagattattt ctacacacac acggcctgcn atgccaacgg agagacacan     60 ctcatntaca                                                             70

<210> SEQ ID NO 18
<211> LENGTH: 568
<212> TYPE: DNA
<213> ORGANISM: Homo sapiens
<220> FEATURE:
<221> NAME/KEY: misc_feature
<222> LOCATION: (396)
<223> OTHER INFORMATION: n equals a,t,g, or c
<221> NAME/KEY: misc_feature
<222> LOCATION: (465)
<223> OTHER INFORMATION: n equals a,t,g, or c
<221> NAME/KEY: misc_feature
<222> LOCATION: (472)
<223> OTHER INFORMATION: n equals a,t,g, or c
<221> NAME/KEY: misc_feature
<222> LOCATION: (480)
<223> OTHER INFORMATION: n equals a,t,g, or c
<221> NAME/KEY: misc_feature
<222> LOCATION: (505)
<223> OTHER INFORMATION: n equals a,t,g, or c
<221> NAME/KEY: misc_feature
<222> LOCATION: (545)
<223> OTHER INFORMATION: n equals a,t,g, or c
<221> NAME/KEY: misc_feature
<222> LOCATION: (549)
<223> OTHER INFORMATION: n equals a,t,g, or c

<400> SEQUENCE: 18
gcttcagtgt gcttgctcat ggcatgaatg ctatgtggac agcccaagcc atacccagaa     60
```

```
tcaccttaat tccaactttt tgaggttcag caattggagg tggcaattgg ctttgcattt      120
taaagtattt cgggtaaagg tgaagtgaag gattttcgtc tttataattt ctgttcggcc      180
atggcaaata ccatagttga gtatttgctt caggagagtt cttttttacag ttttactttt     240 caatgctgag gcatatttct ttgagcactg tgcttttatg tgtctttcta caaagggggt     300
attggtcagt ggaagaacaa agtacacttg ataaaaacat tttcaacata cattgagcct      360
aaacagcagt taagttgtct ctaaatgaac tagcanaaaa aaaaaatgta gttttttgttt    420 gtaaggaagg ggaggtattt cctgagaatg aatttttttt ttttnggaaa cnggtttctn     480
tccataacct tgcttggatt ttacnggagg gaccctggga aaaaaatttt tcctccaaaa     540
ttttnaaanc cggtttggaa agggttca                                         568

<210> SEQ ID NO 19
<211> LENGTH: 554
<212> TYPE: DNA
<213> ORGANISM: Homo sapiens
<220> FEATURE:
<221> NAME/KEY: misc_feature
<222> LOCATION: (396)
<223> OTHER INFORMATION: n equals a,t,g, or c
<221> NAME/KEY: misc_feature
<222> LOCATION: (407)
<223> OTHER INFORMATION: n equals a,t,g, or c
<221> NAME/KEY: misc_feature
<222> LOCATION: (473)
<223> OTHER INFORMATION: n equals a,t,g, or c
<221> NAME/KEY: misc_feature
<222> LOCATION: (494)
<223> OTHER INFORMATION: n equals a,t,g, or c
<221> NAME/KEY: misc_feature
<222> LOCATION: (541)
<223> OTHER INFORMATION: n equals a,t,g, or c
<221> NAME/KEY: misc_feature
<222> LOCATION: (542)
<223> OTHER INFORMATION: n equals a,t,g, or c
<221> NAME/KEY: misc_feature
<222> LOCATION: (548)
<223> OTHER INFORMATION: n equals a,t,g, or c

<400> SEQUENCE: 19
gcttcagtgt gcttgctcat ggcatgaatg ctatgtggac agcccaagcc atacccagaa       60
tcaccttaat tccaactttt tgaggttcag caattggagg tggcaattgg ctttgcattt      120
taaagtattt cgggtaaagg tgaagtgaag gattttcgtc tttataattt ctgttcggcc      180
atggcaaata ccatagttga gtatttgctt caggagagtt cttttttacag ttttactttt     240 caatgctgag gcatatttct ttgagcactg tgcttttatg tgtctttcta caaagggggt     300
attggtcagt ggaagaacaa agtacacttg ataaaaacat tttcaacata cattgagcct      360
aaacagcagt taagttgtct ctaaatgaac tagcanaaaa aaaaaangta gttttttgttt    420 gtaaggaagg ggaggtattt cctgagaatg aatttttttt ttttggata acnggttttc      480 tctccataaa cctngcttgg attttacagg agggaccctg ggaaaaaaat ttttcctcca     540
nnattttnaa atcc                                                        554

<210> SEQ ID NO 20
<211> LENGTH: 310
<212> TYPE: DNA
<213> ORGANISM: Homo sapiens
<220> FEATURE:
<221> NAME/KEY: misc_feature
<222> LOCATION: (83)
<223> OTHER INFORMATION: n equals a,t,g, or c

<400> SEQUENCE: 20
```

```
ctgagtatgc ctctttctat tgaaatgtca attcaatccc agctttctca ccaccgttcc     60
cctttgattc tttctcaatt gtnttttgc ctttagctcc cacctataca tctcatgctc    120
agagaaaaac aagttcctta gaggttgtat tctttattct ccaagaatct gtctgaaact    180
tgtacagcta gttcctgtcc cacaactatt aagtggttta ttaagtacat taggcagaat    240
gtgcacttca tcaccaggtt ctagctctgg caaaggagtg ctgtctacag caaggatttt    300
tgcttttaga                                                           310
```

```
<210> SEQ ID NO 21
<211> LENGTH: 546
<212> TYPE: DNA
<213> ORGANISM: Homo sapiens
<220> FEATURE:
<221> NAME/KEY: misc_feature
<222> LOCATION: (317)
<223> OTHER INFORMATION: n equals a,t,g, or c
<221> NAME/KEY: misc_feature
<222> LOCATION: (340)
<223> OTHER INFORMATION: n equals a,t,g, or c
<221> NAME/KEY: misc_feature
<222> LOCATION: (351)
<223> OTHER INFORMATION: n equals a,t,g, or c
<221> NAME/KEY: misc_feature
<222> LOCATION: (389)
<223> OTHER INFORMATION: n equals a,t,g, or c
<221> NAME/KEY: misc_feature
<222> LOCATION: (398)
<223> OTHER INFORMATION: n equals a,t,g, or c
<221> NAME/KEY: misc_feature
<222> LOCATION: (428)
<223> OTHER INFORMATION: n equals a,t,g, or c
<221> NAME/KEY: misc_feature
<222> LOCATION: (429)
<223> OTHER INFORMATION: n equals a,t,g, or c
<221> NAME/KEY: misc_feature
<222> LOCATION: (433)
<223> OTHER INFORMATION: n equals a,t,g, or c
<221> NAME/KEY: misc_feature
<222> LOCATION: (452)
<223> OTHER INFORMATION: n equals a,t,g, or c
<221> NAME/KEY: misc_feature
<222> LOCATION: (468)
<223> OTHER INFORMATION: n equals a,t,g, or c
<221> NAME/KEY: misc_feature
<222> LOCATION: (483)
<223> OTHER INFORMATION: n equals a,t,g, or c
<221> NAME/KEY: misc_feature
<222> LOCATION: (534)
<223> OTHER INFORMATION: n equals a,t,g, or c
<221> NAME/KEY: misc_feature
<222> LOCATION: (541)
<223> OTHER INFORMATION: n equals a,t,g, or c

<400> SEQUENCE: 21
cgcgctgagg tggatttgta ccggagtccc atttgggagc aagagccatc tactcgtccg     60
ttaccggcct tcccaccatg gattgccaag aaaatgagta ctgggaccaa tggggacggt    120
gtgtcacctg ccaacggtgt ggtcctggac aggagctatc caaggattgt ggttatggag    180
agggtggaga tgcctactgc acagcctgcc ctcctcgcag gtacaaaagc agctggggcc    240
accacaaatg tcagagttgc atcacctgtg ctgtcatcaa tcgtgttcag aaggtccaac    300
tgcacagcta acctctnatg ctgtctgtgg ggatgtttgn cccaagttct naccgaaaag    360
acacgccatg ggaaggctgg caggaccang aatggccntc ccgtgcaga aagccagacc    420 ccccaacnnc tgnaggttcc aatgtggcct tnccatttgg aagcttantg ggaaggcaga    480
tgncaaccca aagtggcccc ttcagggagg ccaaaatttg ttggcaatgg gtgnagcagc    540
```

```
<210> SEQ ID NO 22
<211> LENGTH: 474
<212> TYPE: DNA
<213> ORGANISM: Homo sapiens
<220> FEATURE:
<221> NAME/KEY: misc_feature
<222> LOCATION: (308)
<223> OTHER INFORMATION: n equals a,t,g, or c
<221> NAME/KEY: misc_feature
<222> LOCATION: (315)
<223> OTHER INFORMATION: n equals a,t,g, or c
<221> NAME/KEY: misc_feature
<222> LOCATION: (333)
<223> OTHER INFORMATION: n equals a,t,g, or c
<221> NAME/KEY: misc_feature
<222> LOCATION: (412)
<223> OTHER INFORMATION: n equals a,t,g, or c
<221> NAME/KEY: misc_feature
<222> LOCATION: (431)
<223> OTHER INFORMATION: n equals a,t,g, or c
<221> NAME/KEY: misc_feature
<222> LOCATION: (436)
<223> OTHER INFORMATION: n equals a,t,g, or c
<221> NAME/KEY: misc_feature
<222> LOCATION: (444)
<223> OTHER INFORMATION: n equals a,t,g, or c
<221> NAME/KEY: misc_feature
<222> LOCATION: (473)
<223> OTHER INFORMATION: n equals a,t,g, or c

<400> SEQUENCE: 22
cgcgctgagg tggatttgta ccggagtccc atttgggagc aagagccatc tactcgtccg      60
ttaccggcct tcccaccatg gattgccaag aaaatgagta ctgggaccaa tggggacggt    120
gtgtcacctg ccaacggtgt ggtcctggac aggagctatc caaggattgt ggttatggag    180
agggtggaga tgcctactgc acagcctgcc ctcctcgcag tacaaaagca gctggggcca    240
ccacaaatgt cagagttgca tcacctgtgc tgtcatcaat cgtgttcaga aggttcaact    300
gcacagtnac ctctnatgct gtctgtgggg ganggtttgc ccaagtttct aaccgaaaga    360
cacgccattg gaaggctgcc aggaccaagg atggcatccc gtggcacaaa gncagacccc    420
caacttctga nggttncaaa gtgncttttcc aattggagct taatgggagg cana         474

<210> SEQ ID NO 23
<211> LENGTH: 24
<212> TYPE: DNA
<213> ORGANISM: Homo sapiens

<400> SEQUENCE: 23
cgcccatgga tggaccaaag tacc                                             24

<210> SEQ ID NO 24
<211> LENGTH: 24
<212> TYPE: DNA
<213> ORGANISM: Homo sapiens

<400> SEQUENCE: 24
cgcccatgga tgagtactgg gacc                                             24

<210> SEQ ID NO 25
<211> LENGTH: 34
<212> TYPE: DNA
<213> ORGANISM: Homo sapiens

<400> SEQUENCE: 25
```

-continued gcagcatcta gagcggcact gagtcaaatc catc    34

<210> SEQ ID NO 26
<211> LENGTH: 26
<212> TYPE: DNA
<213> ORGANISM: Homo sapiens

<400> SEQUENCE: 26
cgcaagcttc attcaggccc ctgctg    26

<210> SEQ ID NO 27
<211> LENGTH: 28
<212> TYPE: DNA
<213> ORGANISM: Homo sapiens

<400> SEQUENCE: 27
cgcggatcca tggatggacc aaagtacc    28

<210> SEQ ID NO 28
<211> LENGTH: 28
<212> TYPE: DNA
<213> ORGANISM: Homo sapiens

<400> SEQUENCE: 28
cgcggatcca tggatgagta ctgggacc    28

<210> SEQ ID NO 29
<211> LENGTH: 27
<212> TYPE: DNA
<213> ORGANISM: Homo sapiens

<400> SEQUENCE: 29
cgcggtaccg cggcactgag tcaaatc    27

<210> SEQ ID NO 30
<211> LENGTH: 26
<212> TYPE: DNA
<213> ORGANISM: Homo sapiens

<400> SEQUENCE: 30
cgcggtaccc attcaggccc ctgctg    26

<210> SEQ ID NO 31
<211> LENGTH: 27
<212> TYPE: DNA
<213> ORGANISM: Homo sapiens

<400> SEQUENCE: 31
cgcggatcca tggaccaaag tacccaa    27

<210> SEQ ID NO 32
<211> LENGTH: 57
<212> TYPE: DNA
<213> ORGANISM: Homo sapiens

<400> SEQUENCE: 32
cgctctagat caagcgtagt ctgggacgtc gtatgggtag cggcactgag tcaaatc    57

<210> SEQ ID NO 33
<211> LENGTH: 56
<212> TYPE: DNA
<213> ORGANISM: Homo sapiens

<400> SEQUENCE: 33

```
cgctctagat caagcgtagt ctgggacgtc gtatgggtac attcaggccc ctgctg          56

<210> SEQ ID NO 34
<211> LENGTH: 33
<212> TYPE: DNA
<213> ORGANISM: Homo sapiens

<400> SEQUENCE: 34
cgcggatccg ccatcatgga ccaaagtacc aat                                   33

<210> SEQ ID NO 35
<211> LENGTH: 27
<212> TYPE: DNA
<213> ORGANISM: Homo sapiens

<400> SEQUENCE: 35
cgcggtaccg cggcactgag tcaaatc                                          27

<210> SEQ ID NO 36
<211> LENGTH: 24
<212> TYPE: DNA
<213> ORGANISM: Homo sapiens

<400> SEQUENCE: 36
cgcggatcca tgagtactgg gacc                                             24

<210> SEQ ID NO 37
<211> LENGTH: 28
<212> TYPE: DNA
<213> ORGANISM: Homo sapiens

<400> SEQUENCE: 37
cgcggtacct tcattcaggc ccctgctg                                         28

<210> SEQ ID NO 38
<211> LENGTH: 733
<212> TYPE: DNA
<213> ORGANISM: Homo sapiens

<400> SEQUENCE: 38
gggatccgga gcccaaatct tctgacaaaa ctcacacatg cccaccgtgc ccagcacctg      60
aattcgaggg tgcaccgtca gtcttcctct ccccccaaa acccaaggac accctcatga      120
tctcccggac tcctgaggtc acatgcgtgg tggtggacgt aagccacgaa gaccctgagg      180
tcaagttcaa ctggtacgtg gacggcgtgg aggtgcataa tgccaagaca aagccgcggg      240
aggagcagta acagcacgt accgtgtgg tcagcgtcct caccgtcctg caccaggact      300
ggctgaatgg caaggagtac aagtgcaagg tctccaacaa agccctccca ccccccatcg      360
agaaaaccat ctccaaagcc aaagggcagc ccgagaacc acaggtgtac accctgcccc      420
catcccggga tgagctgacc aagaaccagg tcagcctgac ctgcctggtc aaaggcttct      480
atccaagcga catcgccgtg gagtgggaga gcaatgggca gccggagaac aactacaaga      540
ccacgcctcc cgtgctggac tccgacggct ccttcttcct ctacagcaag ctcaccgtgg      600
acaagagcag gtggcagcag gggaacgtct tctcatgctc cgtgatgcat gaggctctgc      660
acaaccacta cacgcagaag agcctctccc tgtctccggg taaatgagtg cgacggccgc      720
gactctagag gat                                                        733

<210> SEQ ID NO 39
```

```
<211> LENGTH: 3334
<212> TYPE: DNA
<213> ORGANISM: Homo sapiens
<220> FEATURE:
<221> NAME/KEY: CDS
<222> LOCATION: (58)..(3063)

<400> SEQUENCE: 39
gcagaagcag cagccgcagc acctgagccg ctactgccgc tcactcagga caacgct          57 atg gct gag cct ggg cac agc cac cat ctc tcc gcc aga gtc agg gga        105
Met Ala Glu Pro Gly His Ser His His Leu Ser Ala Arg Val Arg Gly
 1               5                  10                  15 aga act gag agg cgc ata ccc cgg ctg tgg cgg ctg ctc tgg gct            153
Arg Thr Glu Arg Arg Ile Pro Arg Leu Trp Arg Leu Leu Leu Trp Ala
                20                  25                  30 ggg acc gcc ttc cag gtg acc cag gga acg gga ccg gag ctt cac gcc        201
Gly Thr Ala Phe Gln Val Thr Gln Gly Thr Gly Pro Glu Leu His Ala
             35                  40                  45 tgc aaa gag tct gag tac cac tat gag tac acg gcg tgt gac agc acg        249
Cys Lys Glu Ser Glu Tyr His Tyr Glu Tyr Thr Ala Cys Asp Ser Thr
 50                  55                  60 ggt tcc agg tgg agg gtc gcc gtg ccg cat acc ccg ggc ctg tgc acc        297
Gly Ser Arg Trp Arg Val Ala Val Pro His Thr Pro Gly Leu Cys Thr
 65                  70                  75                  80 agc ctg cct gac ccc gtc aag ggc acc gag tgc tcc ttc tcc tgc aac        345
Ser Leu Pro Asp Pro Val Lys Gly Thr Glu Cys Ser Phe Ser Cys Asn
                 85                  90                  95 gcc ggg gag ttt ctg gat atg aag gac cag tca tgt aag cca tgc gct        393
Ala Gly Glu Phe Leu Asp Met Lys Asp Gln Ser Cys Lys Pro Cys Ala
            100                 105                 110 gag ggc cgc tac tcc ctc ggc aca ggc att cgg ttt gat gag tgg gat        441
Glu Gly Arg Tyr Ser Leu Gly Thr Gly Ile Arg Phe Asp Glu Trp Asp
        115                 120                 125 gag ctg ccc cat ggc ttt gcc agc ctc tca gcc aac atg gag ctg gat        489
Glu Leu Pro His Gly Phe Ala Ser Leu Ser Ala Asn Met Glu Leu Asp
    130                 135                 140 gac agt gct gct gag tcc acc ggg aac tgt act tcg tcc aag tgg gtt        537
Asp Ser Ala Ala Glu Ser Thr Gly Asn Cys Thr Ser Ser Lys Trp Val
145                 150                 155                 160 ccc cgg ggc gac tac atc gcc ttc aac acg gac gaa tgc aca gcc aca        585
Pro Arg Gly Asp Tyr Ile Ala Phe Asn Thr Asp Glu Cys Thr Ala Thr
                165                 170                 175 ctg atg tac gcc gtc aac ctg aag caa tct ggc acc gtt aac ttc gaa        633
Leu Met Tyr Ala Val Asn Leu Lys Gln Ser Gly Thr Val Asn Phe Glu
            180                 185                 190 tac tac tat cca gac tcc agc atc atc ttt gag ttt ttc gtt cag aat        681
Tyr Tyr Tyr Pro Asp Ser Ser Ile Ile Phe Glu Phe Phe Val Gln Asn
        195                 200                 205 gac cag tgc cag ccc aat gca gat gac tcc agg tgg atg aag acc aca        729
Asp Gln Cys Gln Pro Asn Ala Asp Asp Ser Arg Trp Met Lys Thr Thr
    210                 215                 220 gag aaa gga tgg gaa ttc cac agt gtg gag cta aat cga ggc aat aat        777
Glu Lys Gly Trp Glu Phe His Ser Val Glu Leu Asn Arg Gly Asn Asn
225                 230                 235                 240 gtc ctc tat tgg aga acc aca gcc ttc tca gta tgg acc aaa gta ccc        825
Val Leu Tyr Trp Arg Thr Thr Ala Phe Ser Val Trp Thr Lys Val Pro
                245                 250                 255 aag cct gtg ctg gtg aga aac att gcc ata aca ggg gtg gcc tac act        873
Lys Pro Val Leu Val Arg Asn Ile Ala Ile Thr Gly Val Ala Tyr Thr
            260                 265                 270
```

-continued

| | |
|---|---|
| tca gaa tgc ttc ccc tgc aaa cct ggc acg tat gca gac aag cag ggc<br>Ser Glu Cys Phe Pro Cys Lys Pro Gly Thr Tyr Ala Asp Lys Gln Gly<br>275                          280                      285 | 921 |
| tcc tct ttc tgc aaa ctt tgc cca gcc aac tct tat tca aat aaa gga<br>Ser Ser Phe Cys Lys Leu Cys Pro Ala Asn Ser Tyr Ser Asn Lys Gly<br>290                          295                      300 | 969 |
| gaa act tct tgc cac cag tgt gac cct gac aaa tac tca gag aaa gga<br>Glu Thr Ser Cys His Gln Cys Asp Pro Asp Lys Tyr Ser Glu Lys Gly<br>305                          310                      315                      320 | 1017 |
| tct tct tcc tgt aac gtg cgc cca gct tgc aca gac aaa gat tat ttc<br>Ser Ser Ser Cys Asn Val Arg Pro Ala Cys Thr Asp Lys Asp Tyr Phe<br>                  325                      330                      335 | 1065 |
| tac aca cac acg gcc tgc gat gcc aac gga gag aca caa ctc atg tac<br>Tyr Thr His Thr Ala Cys Asp Ala Asn Gly Glu Thr Gln Leu Met Tyr<br>              340                      345                      350 | 1113 |
| aaa tgg gcc aag ccg aaa atc tgt agc gag gac ctt gag ggg gca gtg<br>Lys Trp Ala Lys Pro Lys Ile Cys Ser Glu Asp Leu Glu Gly Ala Val<br>355                          360                      365 | 1161 |
| aag ctg cct gcc tct ggt gtg aag acc cac tgc cca ccc tgc aac cca<br>Lys Leu Pro Ala Ser Gly Val Lys Thr His Cys Pro Pro Cys Asn Pro<br>370                          375                      380 | 1209 |
| ggc ttc ttc aaa acc aac aac agc acc tgc cag ccc tgc cca tat ggt<br>Gly Phe Phe Lys Thr Asn Asn Ser Thr Cys Gln Pro Cys Pro Tyr Gly<br>385                          390                      395                      400 | 1257 |
| tcc tac tcc aat ggc tca gac tgt acc cgc tgc cct gca ggg act gaa<br>Ser Tyr Ser Asn Gly Ser Asp Cys Thr Arg Cys Pro Ala Gly Thr Glu<br>                  405                      410                      415 | 1305 |
| cct gct gtg gga ttt gaa tac aaa tgg tgg aac acg ctg ccc aca aac<br>Pro Ala Val Gly Phe Glu Tyr Lys Trp Trp Asn Thr Leu Pro Thr Asn<br>                  420                      425                      430 | 1353 |
| atg gaa acg acc gtt ctc agt ggg atc aac ttc gag tac aag ggc atg<br>Met Glu Thr Thr Val Leu Ser Gly Ile Asn Phe Glu Tyr Lys Gly Met<br>435                          440                      445 | 1401 |
| aca ggc tgg gag gtg gct ggt gat cac att tac aca gct gct gga gcc<br>Thr Gly Trp Glu Val Ala Gly Asp His Ile Tyr Thr Ala Ala Gly Ala<br>450                          455                      460 | 1449 |
| tca gac aat gac ttc atg att ctc act ctg gtt gtg cca gga ttt aga<br>Ser Asp Asn Asp Phe Met Ile Leu Thr Leu Val Val Pro Gly Phe Arg<br>465                          470                      475                      480 | 1497 |
| cct ccg cag tcg gtg atg gca gac aca gag aat aaa gag gtg gcc aga<br>Pro Pro Gln Ser Val Met Ala Asp Thr Glu Asn Lys Glu Val Ala Arg<br>                          485                      490                      495 | 1545 |
| atc aca ttt gtc ttt gag acc ctc tgt tct gtg aac tgt gag ctc tac<br>Ile Thr Phe Val Phe Glu Thr Leu Cys Ser Val Asn Cys Glu Leu Tyr<br>                  500                      505                      510 | 1593 |
| ttc atg gtg ggt gtg aat tct agg acc aac act cct gtg gag acg tgg<br>Phe Met Val Gly Val Asn Ser Arg Thr Asn Thr Pro Val Glu Thr Trp<br>                515                      520                      525 | 1641 |
| aaa ggt tcc aaa ggc aaa cag tcc tat acc tac atc att gag gag aac<br>Lys Gly Ser Lys Gly Lys Gln Ser Tyr Thr Tyr Ile Ile Glu Glu Asn<br>530                          535                      540 | 1689 |
| act acc acg agc ttc acc tgg gcc ttc cag agg acc act ttt cat gag<br>Thr Thr Thr Ser Phe Thr Trp Ala Phe Gln Arg Thr Thr Phe His Glu<br>545                          550                      555                      560 | 1737 |
| gca agc agg aag tac acc aat gac gtt gcc aag atc tac tcc atc aat<br>Ala Ser Arg Lys Tyr Thr Asn Asp Val Ala Lys Ile Tyr Ser Ile Asn<br>                  565                      570                      575 | 1785 |
| gtc acc aat gtt atg aat ggc gtg gcc tcc tac tgc cgt ccc tgt gcc<br>Val Thr Asn Val Met Asn Gly Val Ala Ser Tyr Cys Arg Pro Cys Ala<br>                  580                      585                      590 | 1833 |

-continued

| | |
|---|---|
| cta gaa gcc tct gat gtg ggc tcc tcc tgc acc tct tgt cct gct ggt<br>Leu Glu Ala Ser Asp Val Gly Ser Ser Cys Thr Ser Cys Pro Ala Gly<br>595                          600                   605 | 1881 |
| tac tat att gac cga gat tca gga acc tgc cac tcc tgc ccc cct aac<br>Tyr Tyr Ile Asp Arg Asp Ser Gly Thr Cys His Ser Cys Pro Pro Asn<br>610                         615                   620 | 1929 |
| aca att ctg aaa gcc cac cag cct tat ggt gtc cag gcc tgt gtg ccc<br>Thr Ile Leu Lys Ala His Gln Pro Tyr Gly Val Gln Ala Cys Val Pro<br>625                          630                   635                 640 | 1977 |
| tgt ggt cca ggg acc aag aac aac aag atc cac tct ctg tgc tac aat<br>Cys Gly Pro Gly Thr Lys Asn Asn Lys Ile His Ser Leu Cys Tyr Asn<br>                 645                   650                   655 | 2025 |
| gat tgc acc ttc tca cgc aac act cca acc agg act ttc aac tac aac<br>Asp Cys Thr Phe Ser Arg Asn Thr Pro Thr Arg Thr Phe Asn Tyr Asn<br>            660                   665                   670 | 2073 |
| ttc tcc gct ttg gca aac acc gtc act ctt gct gga ggg cca agc ttc<br>Phe Ser Ala Leu Ala Asn Thr Val Thr Leu Ala Gly Gly Pro Ser Phe<br>675                         680                   685 | 2121 |
| act tcc aaa ggg ttg aaa tac ttc cat cac ttt acc ctc agt ctc tgt<br>Thr Ser Lys Gly Leu Lys Tyr Phe His His Phe Thr Leu Ser Leu Cys<br>690                         695                   700 | 2169 |
| gga aac cag ggt agg aaa atg tct gtg tgc acc gac aat gtc act gac<br>Gly Asn Gln Gly Arg Lys Met Ser Val Cys Thr Asp Asn Val Thr Asp<br>705                         710                   715                 720 | 2217 |
| ctc cgg att cct gag ggt gag tca ggg ttc tcc aaa tct atc aca gcc<br>Leu Arg Ile Pro Glu Gly Glu Ser Gly Phe Ser Lys Ser Ile Thr Ala<br>                   725                   730                   735 | 2265 |
| tac gtc tgc cag gca gtc atc atc ccc cca gag gtg aca ggc tac aag<br>Tyr Val Cys Gln Ala Val Ile Ile Pro Pro Glu Val Thr Gly Tyr Lys<br>            740                   745                   750 | 2313 |
| gcc ggg gtt tcc tca cag cct gtc agc ctt gct gat cga ctt att ggg<br>Ala Gly Val Ser Ser Gln Pro Val Ser Leu Ala Asp Arg Leu Ile Gly<br>755                         760                   765 | 2361 |
| gtg aca aca gat atg act ctg gat gga atc acc tcc cca gct gaa ctt<br>Val Thr Thr Asp Met Thr Leu Asp Gly Ile Thr Ser Pro Ala Glu Leu<br>770                         775                   780 | 2409 |
| ttc cac ctg gag tcc ttg gga ata ccg gac gtg atc ttc ttt tat agg<br>Phe His Leu Glu Ser Leu Gly Ile Pro Asp Val Ile Phe Phe Tyr Arg<br>785                         790                   795                 800 | 2457 |
| tcc aat gat gtg acc cag tcc tgc agt tct ggg aga tca acc acc atc<br>Ser Asn Asp Val Thr Gln Ser Cys Ser Ser Gly Arg Ser Thr Thr Ile<br>                   805                   810                   815 | 2505 |
| cgc gtc agg tgc agt cca cag aaa act gtc cct gga agt ttg ctg ctg<br>Arg Val Arg Cys Ser Pro Gln Lys Thr Val Pro Gly Ser Leu Leu Leu<br>            820                   825                   830 | 2553 |
| cca gga acg tgc tca gat ggg acc tgt gat ggc tgc aac ttc cac ttc<br>Pro Gly Thr Cys Ser Asp Gly Thr Cys Asp Gly Cys Asn Phe His Phe<br>835                         840                   845 | 2601 |
| ctg tgg gag agc gcg gct gct tgc ccg ctc tgc tca gtg gct gac tac<br>Leu Trp Glu Ser Ala Ala Ala Cys Pro Leu Cys Ser Val Ala Asp Tyr<br>850                         855                   860 | 2649 |
| cat gct atc gtc agc agc tgt gtg gct ggg atc cag aag act act tac<br>His Ala Ile Val Ser Ser Cys Val Ala Gly Ile Gln Lys Thr Thr Tyr<br>865                         870                   875                 880 | 2697 |
| gtg tgg cga gaa ccc aag cta tgc tct ggt ggc att tct ctg cct gag<br>Val Trp Arg Glu Pro Lys Leu Cys Ser Gly Gly Ile Ser Leu Pro Glu<br>                   885                   890                   895 | 2745 |
| cag aga gtc acc atc tgc aaa acc ata gat ttc tgg ctg aaa gtg ggc<br>Gln Arg Val Thr Ile Cys Lys Thr Ile Asp Phe Trp Leu Lys Val Gly | 2793 |

-continued

```
                     900                 905                 910
atc tct gca ggc acc tgt act gcc atc ctg ctc acc gtc ttg acc tgc          2841
Ile Ser Ala Gly Thr Cys Thr Ala Ile Leu Leu Thr Val Leu Thr Cys
            915                 920                 925 tac ttt tgg aaa aag aat caa aaa cta gag tac aag tac tcc aag ctg          2889
Tyr Phe Trp Lys Lys Asn Gln Lys Leu Glu Tyr Lys Tyr Ser Lys Leu
    930                 935                 940 gtg atg aat gct act ctc aag gac tgt gac ctg cca gca gct gac agc          2937
Val Met Asn Ala Thr Leu Lys Asp Cys Asp Leu Pro Ala Ala Asp Ser
945                 950                 955                 960 tgc gcc atc atg gaa ggc gag gat gta gag gac gac ctc atc ttt acc          2985
Cys Ala Ile Met Glu Gly Glu Asp Val Glu Asp Asp Leu Ile Phe Thr
                965                 970                 975 agc aag aat cac tct ttg gga aga tca aat cat tta cct cca aga gga          3033
Ser Lys Asn His Ser Leu Gly Arg Ser Asn His Leu Pro Pro Arg Gly
            980                 985                 990 ctc ctg atg gat ttg act cag tgc cgc tga agacatcctc aggaggccca            3083
Leu Leu Met Asp Leu Thr Gln Cys Arg
        995                 1000 gacatggacc tgtgagaggc actgcctgcc tcacctgcct cctcaccttg catagcacct        3143
ttgcaagcct gcggcgattt gggtgccagc atcctgcaac acccactgct ggaaatctct        3203
tcattgtggc cttatcagat gtttgaattt cagatctttt tttatagagt acccaaaccc        3263
tcctttctgc ttgcctcaaa cctgccaaat atacccacac tttgtttgta aattaaaaaa        3323
aaaaaaaaaa a                                                             3334

<210> SEQ ID NO 40
<211> LENGTH: 1001
<212> TYPE: PRT
<213> ORGANISM: Homo sapiens

<400> SEQUENCE: 40

Met Ala Glu Pro Gly His Ser His His Leu Ser Ala Arg Val Arg Gly
  1               5                  10                  15

Arg Thr Glu Arg Arg Ile Pro Arg Leu Trp Arg Leu Leu Leu Trp Ala
             20                  25                  30

Gly Thr Ala Phe Gln Val Thr Gln Gly Thr Gly Pro Glu Leu His Ala
         35                  40                  45

Cys Lys Glu Ser Glu Tyr His Tyr Glu Tyr Thr Ala Cys Asp Ser Thr
     50                  55                  60

Gly Ser Arg Trp Arg Val Ala Val Pro His Thr Pro Gly Leu Cys Thr
 65                  70                  75                  80

Ser Leu Pro Asp Pro Val Lys Gly Thr Glu Cys Ser Phe Ser Cys Asn
                 85                  90                  95

Ala Gly Glu Phe Leu Asp Met Lys Asp Gln Ser Cys Lys Pro Cys Ala
            100                 105                 110

Glu Gly Arg Tyr Ser Leu Gly Thr Gly Ile Arg Phe Asp Glu Trp Asp
        115                 120                 125

Glu Leu Pro His Gly Phe Ala Ser Leu Ser Ala Asn Met Glu Leu Asp
    130                 135                 140

Asp Ser Ala Ala Glu Ser Thr Gly Asn Cys Thr Ser Ser Lys Trp Val
145                 150                 155                 160

Pro Arg Gly Asp Tyr Ile Ala Phe Asn Thr Asp Glu Cys Thr Ala Thr
                165                 170                 175

Leu Met Tyr Ala Val Asn Leu Lys Gln Ser Gly Thr Val Asn Phe Glu
            180                 185                 190
```

```
Tyr Tyr Tyr Pro Asp Ser Ser Ile Ile Phe Glu Phe Phe Val Gln Asn
            195                 200                 205

Asp Gln Cys Gln Pro Asn Ala Asp Asp Ser Arg Trp Met Lys Thr Thr
    210                 215                 220

Glu Lys Gly Trp Glu Phe His Ser Val Glu Leu Asn Arg Gly Asn Asn
225                 230                 235                 240

Val Leu Tyr Trp Arg Thr Thr Ala Phe Ser Val Trp Thr Lys Val Pro
                245                 250                 255

Lys Pro Val Leu Val Arg Asn Ile Ala Ile Thr Gly Val Ala Tyr Thr
            260                 265                 270

Ser Glu Cys Phe Pro Cys Lys Pro Gly Thr Tyr Ala Asp Lys Gln Gly
        275                 280                 285

Ser Ser Phe Cys Lys Leu Cys Pro Ala Asn Ser Tyr Ser Asn Lys Gly
    290                 295                 300

Glu Thr Ser Cys His Gln Cys Asp Pro Asp Lys Tyr Ser Glu Lys Gly
305                 310                 315                 320

Ser Ser Ser Cys Asn Val Arg Pro Ala Cys Thr Asp Lys Asp Tyr Phe
                325                 330                 335

Tyr Thr His Thr Ala Cys Asp Ala Asn Gly Glu Thr Gln Leu Met Tyr
            340                 345                 350

Lys Trp Ala Lys Pro Lys Ile Cys Ser Glu Asp Leu Glu Gly Ala Val
        355                 360                 365

Lys Leu Pro Ala Ser Gly Val Lys Thr His Cys Pro Pro Cys Asn Pro
    370                 375                 380

Gly Phe Phe Lys Thr Asn Asn Ser Thr Cys Gln Pro Cys Pro Tyr Gly
385                 390                 395                 400

Ser Tyr Ser Asn Gly Ser Asp Cys Thr Arg Cys Pro Ala Gly Thr Glu
                405                 410                 415

Pro Ala Val Gly Phe Glu Tyr Lys Trp Trp Asn Thr Leu Pro Thr Asn
            420                 425                 430

Met Glu Thr Thr Val Leu Ser Gly Ile Asn Phe Glu Tyr Lys Gly Met
        435                 440                 445

Thr Gly Trp Glu Val Ala Gly Asp His Ile Tyr Thr Ala Ala Gly Ala
    450                 455                 460

Ser Asp Asn Asp Phe Met Ile Leu Thr Leu Val Val Pro Gly Phe Arg
465                 470                 475                 480

Pro Pro Gln Ser Val Met Ala Asp Thr Glu Asn Lys Glu Val Ala Arg
                485                 490                 495

Ile Thr Phe Val Phe Glu Thr Leu Cys Ser Val Asn Cys Glu Leu Tyr
            500                 505                 510

Phe Met Val Gly Val Asn Ser Arg Thr Asn Thr Pro Val Glu Thr Trp
        515                 520                 525

Lys Gly Ser Lys Gly Lys Gln Ser Tyr Thr Tyr Ile Ile Glu Glu Asn
    530                 535                 540

Thr Thr Thr Ser Phe Thr Trp Ala Phe Gln Arg Thr Thr Phe His Glu
545                 550                 555                 560

Ala Ser Arg Lys Tyr Thr Asn Asp Val Ala Lys Ile Tyr Ser Ile Asn
                565                 570                 575

Val Thr Asn Val Met Asn Gly Val Ala Ser Tyr Cys Arg Pro Cys Ala
            580                 585                 590

Leu Glu Ala Ser Asp Val Gly Ser Ser Cys Thr Ser Cys Pro Ala Gly
        595                 600                 605
```

| | | | | | | | | | | | | |
|---|---|---|---|---|---|---|---|---|---|---|---|---|
|Tyr|Tyr|Ile|Asp|Arg|Asp|Ser|Gly|Thr|Cys|His|Ser|Cys|Pro|Pro|Asn|
| |610| | | | |615| | | |620| | | | | |

Tyr Tyr Ile Asp Arg Asp Ser Gly Thr Cys His Ser Cys Pro Pro Asn
    610             615              620

Thr Ile Leu Lys Ala His Gln Pro Tyr Gly Val Gln Ala Cys Val Pro
625             630              635              640

Cys Gly Pro Gly Thr Lys Asn Asn Lys Ile His Ser Leu Cys Tyr Asn
            645              650              655

Asp Cys Thr Phe Ser Arg Asn Thr Pro Thr Arg Thr Phe Asn Tyr Asn
        660              665              670

Phe Ser Ala Leu Ala Asn Thr Val Thr Leu Ala Gly Pro Ser Phe
        675              680              685

Thr Ser Lys Gly Leu Lys Tyr Phe His His Phe Thr Leu Ser Leu Cys
    690              695              700

Gly Asn Gln Gly Arg Lys Met Ser Val Cys Thr Asp Asn Val Thr Asp
705             710              715              720

Leu Arg Ile Pro Glu Gly Glu Ser Gly Phe Ser Lys Ser Ile Thr Ala
            725              730              735

Tyr Val Cys Gln Ala Val Ile Ile Pro Pro Glu Val Thr Gly Tyr Lys
            740              745              750

Ala Gly Val Ser Ser Gln Pro Val Ser Leu Ala Asp Arg Leu Ile Gly
    755              760              765

Val Thr Thr Asp Met Thr Leu Asp Gly Ile Thr Ser Pro Ala Glu Leu
770             775              780

Phe His Leu Glu Ser Leu Gly Ile Pro Asp Val Ile Phe Phe Tyr Arg
785             790              795              800

Ser Asn Asp Val Thr Gln Ser Cys Ser Ser Gly Arg Ser Thr Thr Ile
            805              810              815

Arg Val Arg Cys Ser Pro Gln Lys Thr Val Pro Gly Ser Leu Leu
            820              825              830

Pro Gly Thr Cys Ser Asp Gly Thr Cys Asp Gly Cys Asn Phe His Phe
            835              840              845

Leu Trp Glu Ser Ala Ala Cys Pro Leu Cys Ser Val Ala Asp Tyr
    850              855              860

His Ala Ile Val Ser Ser Cys Val Ala Gly Ile Gln Lys Thr Thr Tyr
865             870              875              880

Val Trp Arg Glu Pro Lys Leu Cys Ser Gly Gly Ile Ser Leu Pro Glu
            885              890              895

Gln Arg Val Thr Ile Cys Lys Thr Ile Asp Phe Trp Leu Lys Val Gly
            900              905              910

Ile Ser Ala Gly Thr Cys Thr Ala Ile Leu Leu Thr Val Leu Thr Cys
    915              920              925

Tyr Phe Trp Lys Lys Asn Gln Lys Leu Glu Tyr Lys Tyr Ser Lys Leu
    930              935              940

Val Met Asn Ala Thr Leu Lys Asp Cys Asp Leu Pro Ala Ala Asp Ser
945             950              955              960

Cys Ala Ile Met Glu Gly Glu Asp Val Glu Asp Leu Ile Phe Thr
            965              970              975

Ser Lys Asn His Ser Leu Gly Arg Ser Asn His Leu Pro Pro Arg Gly
            980              985              990

Leu Leu Met Asp Leu Thr Gln Cys Arg
            995             1000

<210> SEQ ID NO 41
<211> LENGTH: 350
<212> TYPE: PRT

<213> ORGANISM: Homo sapiens

<400> SEQUENCE: 41

```
Met Lys Ser Val Leu Tyr Ser Tyr Ile Leu Phe Leu Ser Cys Ile Ile
 1               5                  10                  15
Ile Asn Gly Arg Asp Val Ala Pro Tyr Ala Pro Ser Asn Gly Lys Cys
                20                  25                  30
Lys Asp Asn Glu Tyr Asn Arg His Asn Leu Cys Cys Leu Ser Cys Pro
             35                  40                  45
Pro Gly Thr Tyr Ala Ser Arg Leu Cys Asp Ser Lys Thr Asn Thr Asn
 50                  55                  60
Thr Gln Cys Thr Pro Cys Gly Ser Asp Thr Phe Thr Ser Arg Asn Asn
 65                  70                  75                  80
His Leu Pro Ala Cys Leu Ser Cys Asn Gly Arg Cys Asp Ser Asn Gln
                 85                  90                  95
Val Glu Thr Arg Ser Cys Asn Thr Thr His Asn Arg Ile Cys Asp Cys
                100                 105                 110
Ala Pro Gly Tyr Tyr Cys Leu Leu Lys Gly Ser Gly Cys Lys Ala Cys
            115                 120                 125
Val Ser Gln Thr Lys Cys Gly Ile Gly Tyr Gly Val Ser Gly His Thr
130                 135                 140
Pro Thr Gly Asp Val Ile Cys Ser Pro Cys Gly Leu Gly Thr Tyr Ser
145                 150                 155                 160
His Thr Val Ser Ser Ala Asp Lys Cys Glu Pro Val Pro Ser Asn Thr
                165                 170                 175
Phe Asn Tyr Ile Asp Val Glu Ile Asn Leu Tyr Pro Val Asn Asp Thr
            180                 185                 190
Ser Cys Thr Arg Thr Thr Thr Gly Leu Ser Glu Ser Ile Ser Thr
            195                 200                 205
Ser Glu Leu Thr Ile Thr Met Asn His Lys Asp Cys Asp Pro Val Phe
210                 215                 220
Arg Asp Gly Tyr Phe Ser Val Leu Asn Lys Val Ala Thr Ser Gly Phe
225                 230                 235                 240
Phe Thr Gly Glu Asn Arg Tyr Gln Asn Thr Ser Asn Val Cys Thr Leu
                245                 250                 255
Asn Phe Glu Ile Lys Cys Asn Asn Lys Asp Ser Ser Lys Gln Leu
            260                 265                 270
Thr Lys Thr Lys Asn Asp Thr Ile Met Pro His Ser Glu Thr Val Thr
            275                 280                 285
Leu Val Gly Asp Cys Leu Ser Ser Val Asp Ile Tyr Ile Leu Tyr Ser
290                 295                 300
Asn Thr Asn Thr Gln Asp Tyr Glu Thr Asp Thr Ile Ser Tyr His Ala
305                 310                 315                 320
Gly Asn Val Leu Asp Val Asp Ser His Met Pro Gly Ser Cys Asp Ile
                325                 330                 335
His Lys Leu Ile Thr Asn Ser Gln Asn Pro Thr His Phe Leu
            340                 345                 350
```

<210> SEQ ID NO 42
<211> LENGTH: 30
<212> TYPE: DNA
<213> ORGANISM: Homo sapiens

<400> SEQUENCE: 42
gcagcacata tgatggctga gcctgggcac                                    30

<210> SEQ ID NO 43
<211> LENGTH: 34
<212> TYPE: DNA
<213> ORGANISM: Homo sapiens

<400> SEQUENCE: 43
gcagcatcta gagcggcagt gagtcaaatc catc                        34

<210> SEQ ID NO 44
<211> LENGTH: 48
<212> TYPE: DNA
<213> ORGANISM: Homo sapiens

<400> SEQUENCE: 44
gcagcatcta gaccgccatc atggctgagc ctgggcacag ccaccatc         48

<210> SEQ ID NO 45
<211> LENGTH: 30
<212> TYPE: DNA
<213> ORGANISM: Homo sapiens

<400> SEQUENCE: 45
gcagcatcta gagcggcact gagtcaaatc                             30

<210> SEQ ID NO 46
<211> LENGTH: 27
<212> TYPE: DNA
<213> ORGANISM: Homo sapiens

<400> SEQUENCE: 46
cgcggatcca tggctgagcc tgggcac                                27

<210> SEQ ID NO 47
<211> LENGTH: 57
<212> TYPE: DNA
<213> ORGANISM: Homo sapiens

<400> SEQUENCE: 47
cgctctagat caagcgtagt ctgggacgtc gtatgggtag cggcactgag tcaaatc    57

<210> SEQ ID NO 48
<211> LENGTH: 342
<212> TYPE: DNA
<213> ORGANISM: Homo sapiens
<220> FEATURE:
<221> NAME/KEY: misc_feature
<222> LOCATION: (28)
<223> OTHER INFORMATION: n equals a,t,g, or c
<221> NAME/KEY: misc_feature
<222> LOCATION: (31)
<223> OTHER INFORMATION: n equals a,t,g, or c
<221> NAME/KEY: misc_feature
<222> LOCATION: (40)
<223> OTHER INFORMATION: n equals a,t,g, or c
<221> NAME/KEY: misc_feature
<222> LOCATION: (181)
<223> OTHER INFORMATION: n equals a,t,g, or c
<221> NAME/KEY: misc_feature
<222> LOCATION: (276)
<223> OTHER INFORMATION: n equals a,t,g, or c
<221> NAME/KEY: misc_feature
<222> LOCATION: (282)
<223> OTHER INFORMATION: n equals a,t,g, or c

<400> SEQUENCE: 48
ggaccttgag ggggcagtga agctgctngc ntctggtgtn aagacccact gcccaccctg    60

```
caacccaggc ttcttcaaaa ccaacaacag cacctgccag ccctgcccat atggttccta      120
ctccaatggc tcagactgta cccgctgccc tgcagggact gaacctgctg tgggatttga      180
ntacaaatgg tggaacacgc tgcccacaaa catggaaacg accgttctca gtgggatcaa      240
cttcgagtac aagggcatga caggctggga ggtggntggt gntcacattt acacagctgc      300
tggagcctca gacaatgact tcatgattct aaatctggtt gt                         342

<210> SEQ ID NO 49
<211> LENGTH: 291
<212> TYPE: DNA
<213> ORGANISM: Homo sapiens
<220> FEATURE:
<221> NAME/KEY: misc_difference
<222> LOCATION: (244)
<223> OTHER INFORMATION: n equals a, t, g or c

<400> SEQUENCE: 49
ctcctgtgga gacgtggaaa ggttccaaag gcaaacagtc ctatacctac atcattgagg      60
agaacactac cacgagcttc acctgggcct tccagaggac cacttttcat gaggcaagca      120
ggaagtacac caatgacgtt gccaagatct actccatcaa tgtcaccaat gttatgaatg      180
gcgtggcctc ctactgccgt ccctgtgccc tagaagcctc tgatgtgggc tcctcctgca      240
cctnttgtcc tgctggttac tatattgacc gagattcagg aacctgccac t              291

<210> SEQ ID NO 50
<211> LENGTH: 294
<212> TYPE: DNA
<213> ORGANISM: Homo sapiens
<220> FEATURE:
<221> NAME/KEY: misc_feature
<222> LOCATION: (75)
<223> OTHER INFORMATION: n equals a, t, g or c

<400> SEQUENCE: 50
ggaacgggac cggagcttca cgcctgcaaa gagtctgagt accactatga gtacacggcg      60
tgtgacagca cgggnttcca ggtggagggt cgccgtgccg catacccggg cctgtgcac      120 cagcctgcct gacccgtca agggcaccga gtgctccttc tcctgcaacg ccggggagtt      180
tctggatatg aaggaccagt catgtaagcc atgcgctgag ggccgctact ccctcggcac      240
aggcattcgg tttgatgagt gggatgagct tgccccatgg ctttgcagcc tttt           294

<210> SEQ ID NO 51
<211> LENGTH: 267
<212> TYPE: DNA
<213> ORGANISM: Homo sapiens
<220> FEATURE:
<221> NAME/KEY: misc_feature
<222> LOCATION: (41)
<223> OTHER INFORMATION: n equals a,t,g, or c
<221> NAME/KEY: misc_feature
<222> LOCATION: (171)
<223> OTHER INFORMATION: n equals a,t,g, or c
<221> NAME/KEY: misc_feature
<222> LOCATION: (207)
<223> OTHER INFORMATION: n equals a,t,g, or c

<400> SEQUENCE: 51
ccaagatcta ctccatcaat gtcaccaatg ttatgaatgg ngtggcctcc tactgccgtc      60
cctgtgccct agaagcctct gatgtgggct cctcctgcac ctcttgtcct gctggttact     120
atattgaccg agattcagga acctgccact cctgcccccc taacacaatt ntgaaagccc     180
```

| accagcctta tggtgtccag gcctgtntgc cctgtggtcc agggaccaag aacaacaaga | 240 |
| tccactctct gtgctacaat gattgca | 267 |

<210> SEQ ID NO 52
<211> LENGTH: 274
<212> TYPE: DNA
<213> ORGANISM: Homo sapiens
<220> FEATURE:
<221> NAME/KEY: misc_feature
<222> LOCATION: (107)
<223> OTHER INFORMATION: n equals a, t, g or c
<221> NAME/KEY: misc_feature
<222> LOCATION: (196)
<223> OTHER INFORMATION: n equals a, t, g or c

<400> SEQUENCE: 52

| aaagaatcaa aaactagagt acaagtactc caagctggtg atgaatgcta ctctcaagga | 60 |
| ctgtgacctg ccagcagctg acagctcgcc atcatggaag gcgaggntgt agaggacgac | 120 |
| ctcatcttta ccagcaagaa gtcactcttt gggaagatca aatcatttac ctccaagagg | 180 |
| actcctgatg gatttnactc agtgccgctg aagacatcct caggaggccc agacatggac | 240 |
| ctgtgagagg cactgcctgc ctcacctgct tcct | 274 |

<210> SEQ ID NO 53
<211> LENGTH: 245
<212> TYPE: DNA
<213> ORGANISM: Homo sapiens

<400> SEQUENCE: 53

| ccaagccgaa aatctgtagc gaggaccttg aggggggcagt gaagctgctg cctctggtgt | 60 |
| gaagaccccac tgcccaccct gcaacccagg cttcttcaaa accaacaaca gcacctgcca | 120 |
| gccctgccca tatggttcct actccaatgg ctcagactgt accgctgcc ctgcagggac | 180 |
| tgaacctgct gtgggatttg aatacaaatg gtggaacacg ctgcccacaa acatgggaaa | 240 |
| cgacc | 245 |

<210> SEQ ID NO 54
<211> LENGTH: 292
<212> TYPE: DNA
<213> ORGANISM: Homo sapiens
<220> FEATURE:
<221> NAME/KEY: misc_feature
<222> LOCATION: (5)
<223> OTHER INFORMATION: n equals a, t, g or c
<221> NAME/KEY: misc_feature
<222> LOCATION: (202)
<223> OTHER INFORMATION: n equals a, t, g or c
<221> NAME/KEY: misc_feature
<222> LOCATION: (245)
<223> OTHER INFORMATION: n equals a, t, g or c
<221> NAME/KEY: misc_feature
<222> LOCATION: (246)
<223> OTHER INFORMATION: n equals a, t, g or c
<221> NAME/KEY: misc_feature
<222> LOCATION: (291)
<223> OTHER INFORMATION: n equals a, t, g or c
<221> NAME/KEY: misc_difference
<222> LOCATION: (292)
<223> OTHER INFORMATION: n equals a, t, g or c

<400> SEQUENCE: 54

| ggcanaggga atttgactca gtgccgctga agacatcctc aggaggccca gacatggacc | 60 |
| tgtgagaggc actgcctgcc tcacctgcct cctcacctttg catagcacct ttgcaagcct | 120 |
| gcgggaattt gggtgccagc atcctgcaac acccactgct gggaaatctc ttcattgtgg | 180 |

-continued

```
ccttatcaga tgtttgaatt tnagatcttt ttttatagag tacccaaacc ctcctttctg    240
cttgnntcaa acctgccaaa tatacccaca ctttgtttgt aaaaaaaaaa nn           292
```

<210> SEQ ID NO 55
<211> LENGTH: 220
<212> TYPE: DNA
<213> ORGANISM: Homo sapiens
<220> FEATURE:
<221> NAME/KEY: misc_feature
<222> LOCATION: (164)
<223> OTHER INFORMATION: n equals a, t, g or c
<400> SEQUENCE: 55

```
atcttctttt ataggtccaa tgatgtgacc cagtcctgca gttctgggag atcaaccacc    60
atccgcgtca ggtgcagtcc acagaaaact gtccctggaa gtttgctgct gccaggaacg   120
tgctcagatg ggacctgtga tggctgcaac ttccacttcc tgtnggagag cgcggctgct   180
tgcccgctct gctcagtggc tgactaccat gctatcgtca                         220
```

<210> SEQ ID NO 56
<211> LENGTH: 427
<212> TYPE: DNA
<213> ORGANISM: Homo sapiens
<220> FEATURE:
<221> NAME/KEY: misc_feature
<222> LOCATION: (44)
<223> OTHER INFORMATION: n equals a, t, g or c
<221> NAME/KEY: misc_feature
<222> LOCATION: (77)
<223> OTHER INFORMATION: n equals a, t, g or c
<221> NAME/KEY: misc_feature
<222> LOCATION: (234)
<223> OTHER INFORMATION: n equals a, t, g or c
<221> NAME/KEY: misc_feature
<222> LOCATION: (260)
<223> OTHER INFORMATION: n equals a, t, g or c
<221> NAME/KEY: misc_feature
<222> LOCATION: (268)
<223> OTHER INFORMATION: n equals a, t, g or c
<221> NAME/KEY: misc_feature
<222> LOCATION: (271)
<223> OTHER INFORMATION: n equals a, t, g or c
<221> NAME/KEY: misc_feature
<222> LOCATION: (272)
<223> OTHER INFORMATION: n equals a, t, g or c
<221> NAME/KEY: misc_feature
<222> LOCATION: (275)
<223> OTHER INFORMATION: n equals a, t, g or c
<221> NAME/KEY: misc_feature
<222> LOCATION: (305)
<223> OTHER INFORMATION: n equals a, t, g or c
<221> NAME/KEY: misc_feature
<222> LOCATION: (308)
<223> OTHER INFORMATION: n equals a, t, g or c
<221> NAME/KEY: misc_feature
<222> LOCATION: (331)
<223> OTHER INFORMATION: n equals a, t, g or c
<221> NAME/KEY: misc_feature
<222> LOCATION: (355)
<223> OTHER INFORMATION: n equals a, t, g or c
<221> NAME/KEY: misc_feature
<222> LOCATION: (359)
<223> OTHER INFORMATION: n equals a, t, g or c
<221> NAME/KEY: misc_feature
<222> LOCATION: (368)
<223> OTHER INFORMATION: n equals a, t, g or c
<221> NAME/KEY: misc_feature
<222> LOCATION: (372)
<223> OTHER INFORMATION: n equals a, t, g or c
<221> NAME/KEY: misc_feature
<222> LOCATION: (381)
<223> OTHER INFORMATION: n equals a, t, g or c
<221> NAME/KEY: misc_feature
<222> LOCATION: (388)
<223> OTHER INFORMATION: n equals a, t, g or c
<221> NAME/KEY: misc_feature
<222> LOCATION: (398)
<223> OTHER INFORMATION: n equals a, t, g or c
<221> NAME/KEY: misc_feature
<222> LOCATION: (400)
<223> OTHER INFORMATION: n equals a, t, g or c
<221> NAME/KEY: misc_feature
<222> LOCATION: (407)
<223> OTHER INFORMATION: n equals a, t, g or c
<221> NAME/KEY: misc_feature
<222> LOCATION: (427)
<223> OTHER INFORMATION: n equals a, t, g or c

<400> SEQUENCE: 56

```
aattcggcag agctcagaca atgacttcat gattctcact ctgnttgtgc caggatttag    60
acctccgcag tcggtgntgg cagacacaga gaataaagag gtggccagaa tcacatttgt   120
ctttgagacc ctctgttctg tgaactgtga gctctacttc atggtgggtg tggaattcta   180
gggaccaaca cttcctgtgg aggacgtggg aaaggttcca aagggcaaac agtnccttat   240
tacctgacat gcattgaggn aggaacantt nnccnggagg tttcaactgg ggcctttccc   300
gaggnacnac tttttttcatg gagggccaag ncagggagt tacaacccat tgnacgttng   360
gccaaggntc tnatttccat ncaatgtnca accaatgntn atggaanggg tgttggggcc   420
ttgcttn                                                             427
```

<210> SEQ ID NO 57
<211> LENGTH: 367
<212> TYPE: DNA
<213> ORGANISM: Homo sapiens
<220> FEATURE:
<221> NAME/KEY: misc_feature
<222> LOCATION: (5)
<223> OTHER INFORMATION: n equals a, t, g or c
<221> NAME/KEY: misc_feature
<222> LOCATION: (55)
<223> OTHER INFORMATION: n equals a, t, g or c
<221> NAME/KEY: misc_feature
<222> LOCATION: (66)
<223> OTHER INFORMATION: n equals a, t, g or c
<221> NAME/KEY: misc_feature
<222> LOCATION: (67)
<223> OTHER INFORMATION: n equals a, t, g or c
<221> NAME/KEY: misc_feature
<222> LOCATION: (116)
<223> OTHER INFORMATION: n equals a, t, g or c
<221> NAME/KEY: misc_feature
<222> LOCATION: (123)
<223> OTHER INFORMATION: n equals a, t, g or c
<221> NAME/KEY: misc_feature
<222> LOCATION: (275)
<223> OTHER INFORMATION: n equals a, t, g or c
<221> NAME/KEY: misc_feature
<222> LOCATION: (315)
<223> OTHER INFORMATION: n equals a, t, g or c
<221> NAME/KEY: misc_feature
<222> LOCATION: (340)
<223> OTHER INFORMATION: n equals a, t, g or c
<221> NAME/KEY: misc_feature
<222> LOCATION: (348)
<223> OTHER INFORMATION: n equals a, t, g or c
<221> NAME/KEY: misc_feature
<222> LOCATION: (356)
<223> OTHER INFORMATION: n equals a, t, g or c

<400> SEQUENCE: 57

```
ggcanaggct gagtccaccg ggaactgtac ttcgtccaag tgggttcccc ggggngactt    60
gatcgnntcc aacacggacg aatgcacagc cacactgatg tacgccgtca acctgnaagc   120
```

-continued

```
agnctggtca ccgttgaact tcggaatact actatccaga ctccatcatc atctttgaag      180
tttttcgttc agaatgacca gtgccagccc aatgcagatg actccaggtg gatgaagacc      240
acagagaaag gatgggaatt ccacagtgtg agctnaaatc gaggcaataa tgtccgttat      300
tgggggaacc acagncttct tcaatgatgg gaccaaagtn acccaagnct gtgctnggtg      360
gaggaaa                                                                367
```

<210> SEQ ID NO 58
<211> LENGTH: 333
<212> TYPE: DNA
<213> ORGANISM: Homo sapiens
<220> FEATURE:
<221> NAME/KEY: misc_feature
<222> LOCATION: (20)
<223> OTHER INFORMATION: n equals a, t, g or c
<221> NAME/KEY: misc_feature
<222> LOCATION: (23)
<223> OTHER INFORMATION: n equals a, t, g or c
<221> NAME/KEY: misc_feature
<222> LOCATION: (76)
<223> OTHER INFORMATION: n equals a, t, g or c
<221> NAME/KEY: misc_feature
<222> LOCATION: (80)
<223> OTHER INFORMATION: n equals a, t, g or c
<221> NAME/KEY: misc_feature
<222> LOCATION: (85)
<223> OTHER INFORMATION: n equals a, t, g or c
<221> NAME/KEY: misc_feature
<222> LOCATION: (103)
<223> OTHER INFORMATION: n equals a, t, g or c
<221> NAME/KEY: misc_feature
<222> LOCATION: (129)
<223> OTHER INFORMATION: n equals a, t, g or c
<221> NAME/KEY: misc_feature
<222> LOCATION: (152)
<223> OTHER INFORMATION: n equals a, t, g or c
<221> NAME/KEY: misc_feature
<222> LOCATION: (171)
<223> OTHER INFORMATION: n equals a, t, g or c
<221> NAME/KEY: misc_feature
<222> LOCATION: (244)
<223> OTHER INFORMATION: n equals a, t, g or c
<221> NAME/KEY: misc_feature
<222> LOCATION: (260)
<223> OTHER INFORMATION: n equals a, t, g or c
<221> NAME/KEY: misc_feature
<222> LOCATION: (269)
<223> OTHER INFORMATION: n equals a, t, g or c
<221> NAME/KEY: misc_feature
<222> LOCATION: (275)
<223> OTHER INFORMATION: n equals a, t, g or c
<221> NAME/KEY: misc_feature
<222> LOCATION: (293)
<223> OTHER INFORMATION: n equals a, t, g or c
<221> NAME/KEY: misc_feature
<222> LOCATION: (307)
<223> OTHER INFORMATION: n equals a, t, g or c
<221> NAME/KEY: misc_feature
<222> LOCATION: (320)
<223> OTHER INFORMATION: n equals a, t, g or c

<400> SEQUENCE: 58

```
taactctggt tgtcccaggn ttnaaacctc cgcagtcggt gaatggcaga cacagagaat      60
aaagaggtgg ccagantcan atttnttttt aaaaccctct gtnctgtgaa actgtgaagc     120
tctacttgna tggtgggtgt gaaattctag gnaccaacac tcctgtggag nacgtggaaa     180
aggttccaaa ggcaaacagt cctataccta catcattgaa ggaggaacac taccacgagg     240
ttgnacctgg gcccttccan agggaccant tttcnatgag gcaagcagg gangtacacc      300 attgagngtt gcccaggttn tattccttca atg                                   333
```

<210> SEQ ID NO 59
<211> LENGTH: 70
<212> TYPE: DNA
<213> ORGANISM: Homo sapiens
<220> FEATURE:
<221> NAME/KEY: misc_feature
<222> LOCATION: (40)
<223> OTHER INFORMATION: n equals a, t, g or c
<221> NAME/KEY: misc_feature
<222> LOCATION: (60)
<223> OTHER INFORMATION: n equals a, t, g or c
<221> NAME/KEY: misc_feature
<222> LOCATION: (66)
<223> OTHER INFORMATION: n equals a, t, g or c

<400> SEQUENCE: 59

| | | | | | |
|---|---|---|---|---|---|
| ggcacaggca | aagattattt | ctacacacac | acggcctgcn | atgccaacgg | agagacacan | 60 |
| ctcatntaca | | | | | | 70 |

<210> SEQ ID NO 60
<211> LENGTH: 3152
<212> TYPE: DNA
<213> ORGANISM: Homo sapiens

<400> SEQUENCE: 60

| | | | | | |
|---|---|---|---|---|---|
| ggatttgtac | cggagtccca | tttgggagca | agagccatct | actcgtccgt | taccggcctt | 60 |
| cccaccatgg | attgccaaga | aaatgagtac | tgggaccaat | ggggacggtg | tgtcacctgc | 120 |
| caacggtgtg | gtcctggaca | ggagctatcc | aaggattgtg | gttatggaga | gggtggagat | 180 |
| gcctactggc | acagcctgcc | ctcctcgcag | tacaaaagca | gctggggcca | ccacaaatgt | 240 |
| cagagttgca | tcacctgtgc | tgtcatcaat | cgtgttcaga | aggtcaactg | cacacctacc | 300 |
| tctaatgctg | tctgtgggga | ctgtttgccc | aggttctacc | gaaagacacg | cattggaggc | 360 |
| ctgcaggacc | aagagtgcat | cccgtgcacg | aagcagaccc | ccacctctga | ggttcaatgt | 420 |
| gccttccagt | tgagcttagt | ggaggcagat | gcacccacag | tgccccctca | ggaggccaca | 480 |
| cttgttgcac | tggtgagcag | cctgctagtg | gtgtttaccc | tggccttcct | ggggctcttc | 540 |
| ttcctctact | gcaagcagtt | cttcaacaga | cattgccagc | gtggaggttt | gctgcagttt | 600 |
| gaggctgata | aaacagcaaa | ggaggaatct | ctcttcccgc | tgccacccag | caaggagacc | 660 |
| agtgctgagt | cccaagtctc | ttgggcccct | ggcagccttg | cccagttgtt | ctctctggac | 720 |
| tctgttccta | taccaacaac | gcagcagggg | cctgaaatgt | gatgtccaca | agagctaata | 780 |
| ccctacagat | ggggcatatc | ctatcccatc | ccaccagagg | attgattctc | catttcacaa | 840 |
| ggactgatct | ggagcatttc | ttgcttccct | gttgtagtct | gggagccag | attccacatt | 900 |
| catgggacta | ccagacatgt | tcctagctca | acttgattat | agagaagagg | agagaggaca | 960 |
| gtgaatgggg | tagggttttc | atgtctgcat | ttttggtcag | gtaagcctct | caaaattgtg | 1020 |
| ttggcacatc | tacctagcac | tttagggaca | aaatcaaacc | cttctcccct | tttagctcct | 1080 |
| ccacactgcc | tccctcctca | acacacacac | acacacatac | acacacatat | acatagacac | 1140 |
| acaaacacac | acacacacat | taatatctat | cttgggggaa | gcctcgtgcc | ataattccca | 1200 |
| agtcatgtct | cagactgctg | cattgcagca | tgacgcaggg | caaacacttt | ccctctagat | 1260 |
| ccctgggggcc | tcaccctgta | tttgaggttc | tcaccaccct | cagcagggag | aagggctgaa | 1320 |
| gttcgccatt | ttggaacctt | acagaacatt | tctgagccaa | agtaatcttc | cttctggggc | 1380 |
| ctgagttccc | caaactaccc | cacagcagtc | cctcaaagac | agccctcaat | ccatgtaggg | 1440 |

-continued

```
acatctgagt atgcctcttt ctattgaaat gtcaattcaa tcccagcttt ctcaccaccg    1500
ttcccctttg attctttctc aattgtcttt ttgcctttag ctcccaccta tacatctcat    1560
gctcagagaa aaacaagttc cttagaggtt gtattcttta ttctccaaga atctgtctga    1620
aacttgtaca gctagttcct gtcccacaac tattaagtgg tttattaagt acattaggca    1680
gaatgtgcac ttcatcacca ggttctagct ctggcaaagg agtgctgtct acagcaagat    1740
ttttgctttt agaattttat taactacatc tcttgggttc atccatctac aaacactgat    1800
taagggcccc tggggcaacc aattgatcag attactaaaa ggacttggga aaaagcaaaa    1860
aggtcccatt gtactggtac tgaggattag aagcaattga aatacaagcc tgtaccaagc    1920
aagcagcctg gccccacaca ggtattagca aatatgtggt aaccaaggtt ttaggccttg    1980
gscyctaggt ttcctgtttt ttttcgtttt tggtttccgt tttcgttttt tgcaacaggt    2040
tattcttatc tcactggctt tcactgatca tgtttagacc ttctggtaga agaaataata    2100
tccagacagg ggatgatttg gcttcagcag gctgcaggtg ttcaaaggtt gccatgtggc    2160
tggcagtggt tcaagcccac atttgacact gctgctctag aggaaagata atgatggtaa    2220
cacagtaata ataataataa taacaaaaat atgataaagt gaaagagtag atttcttttca    2280 gtgtgcttgc tccatggcat gaatgctatg tggacagccc aagccatacc cagaatcacc    2340
ttaattccaa cttttttgagg ttcagcaatt ggaggtggca attggctttg catttttaaag   2400 tatttcgggt aaaggtgaag tgaaggattt tcgtctttat aatttctgtt tggccatggc    2460
aaataccata gttgagtatt tgcttcagga gagttctttt tacagtttta ctttttcaatg    2520 ctgaggcata tttctttgag cactgtgctt ttatgtgtct ttctacaaag gggttattgg    2580
tcagtggaag aacaaagtac acttgataaa aacatttttca acatacattg agcctaaaca    2640
gcagttaagt tgtctctaat gaactagcaa aaaaaaaaaa tgtagttttt gtttgtaagg    2700
aaggggaggt atttcctgag aatgaatttt ttttttttttg gattactgtt tttctctcca    2760
tataccttga acttgggatt ttgaacagga gggaagtcct gggaaaaata atttttttccc    2820 tccaagattc tcagatccca ggttaggaaa ggattcagca ctaacagcat aacccctcta    2880
caacatacag ccctgtcaca ttgagatcat aatccctcct gtcccactcc tctctaccaa    2940
ccccacccta ctagctaggt cttcagtgtt ttacattgaa tattggtaca ttttaattat    3000
tttttctcat aaatgggtta tttatagaga ttttgttaac tcttgagcca tatgcatgtg    3060
tagatactgg cagggctatg tttgtttatg atgctctgca aacatttcat attggccaat    3120
aaacagaaat atatccaaaa aaaaaaaaaa aa                                  3152
```

<210> SEQ ID NO 61
<211> LENGTH: 231
<212> TYPE: PRT
<213> ORGANISM: Homo sapiens

<400> SEQUENCE: 61

```
Met Asp Cys Gln Glu Asn Glu Tyr Trp Asp Gln Trp Gly Arg Cys Val
  1               5                   10                  15

Thr Cys Gln Arg Cys Gly Pro Gly Gln Glu Leu Ser Lys Asp Cys Gly
             20                  25                  30

Tyr Gly Glu Gly Gly Asp Ala Tyr Trp His Ser Leu Pro Ser Ser Gln
         35                  40                  45

Tyr Lys Ser Ser Trp Gly His His Lys Cys Gln Ser Cys Ile Thr Cys
     50                  55                  60

Ala Val Ile Asn Arg Val Gln Lys Val Asn Cys Thr Pro Thr Ser Asn
```

-continued

```
                65                  70                  75                  80
Ala Val Cys Gly Asp Cys Leu Pro Arg Phe Tyr Arg Lys Thr Arg Ile
                85                  90                  95

Gly Gly Leu Gln Asp Gln Glu Cys Ile Pro Cys Thr Lys Gln Thr Pro
               100                 105                110

Thr Ser Glu Val Gln Cys Ala Phe Gln Leu Ser Leu Val Glu Ala Asp
           115                 120                 125

Ala Pro Thr Val Pro Pro Gln Glu Ala Thr Leu Val Ala Leu Val Ser
       130                 135                 140

Ser Leu Leu Val Val Phe Thr Leu Ala Phe Leu Gly Leu Phe Phe Leu
145                 150                 155                 160

Tyr Cys Lys Gln Phe Phe Asn Arg His Cys Gln Arg Gly Gly Leu Leu
               165                 170                 175

Gln Phe Glu Ala Asp Lys Thr Ala Lys Glu Glu Ser Leu Phe Pro Val
               180                 185                 190

Pro Pro Ser Lys Glu Thr Ser Ala Glu Ser Gln Val Ser Trp Ala Pro
           195                 200                 205

Gly Ser Leu Ala Gln Leu Phe Ser Leu Asp Ser Val Pro Ile Pro Gln
       210                 215                 220

Gln Gln Gln Gly Pro Glu Met
225                 230
```

HUMAN TUMOR NECROSIS FACTOR RECEPTORS TR13 AND TR14

CROSS REFERENCE TO A RELATED APPLICATION

This application is a continuation-in-part of, and claims benefit under 35 U.S.C. § 120 to, U.S. patent application Ser. No. 09/618,570, filed Jul. 14, 2000 now abandoned; which claims benefit under 35 U.S.C. § 119(e) of U.S. Provisional Application Nos. 60/144,087, 60/149,450, 60/149,712, and 60/153,089, which were filed on Jul. 16, 1999, Aug. 18, 1999, Aug. 20, 1999, and Sep. 10, 1999, respectively; and also claims benefit under 35 U.S.C. § 119(e) of U.S. Provisional Application No. 60/261,960, filed Jan. 17, 2001, each of which is hereby incorporated by reference in its entirety.

BACKGROUND OF THE INVENTION

1. Field of the Invention

The present invention relates to two novel members of the tumor necrosis factor family of receptors. More specifically, isolated nucleic acid molecules are provided encoding the novel human tumor necrosis factor receptors, TR13 and TR14. TR13 and TR14 polypeptides are also provided, as are vectors, host cells, and recombinant methods for producing the same. The invention further relates to screening methods for identifying agonists and antagonists of TR13 and/or TR14 activity.

2. Related Art

Many biological actions, for instance, response to certain stimuli and natural biological processes, are controlled by factors, such as cytokines. Many cytokines act through receptors by engaging the receptor and producing an intracellular response.

For example, tumor necrosis factors (TNF) alpha and beta are cytokines, which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized.

Among the ligands there are included TNF-$\alpha$, lymphotoxin-$\alpha$ (LT-$\alpha$, also known as TNF-$\beta$), LT-$\beta$ (found in complex heterotrimer LT-2-$\beta$), FasL, CD40L, CD27L, CD30L, 4-1BBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (A. Meager, Biologicals 22:291–295 (1994)).

Many members of the TNF-ligand superfamily are expressed by activated T-cells, implying that they are necessary for T-cell interactions with other cell types which underlie cell ontogeny and functions. (A. Meager, supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (R. Watanabe-Fukunaga et al., Nature 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (R. C. Allen et al., Science 259:990 (1993)). Targeted mutations of the low affinity nerve growth factor receptor cause a disorder characterized by faulty sensory innovation of peripheral structures (K. F. Lee et al., Cell 69:737 (1992)).

TNF-$\alpha$ and LT-$\alpha$ are capable of binding to two TNF receptors (the 55- and 75-kd TNF receptors). A large number of biological effects elicited by TNF-$\alpha$ and LT-$\alpha$, acting through their receptors, include hemorrhagic necrosis of transplanted tumors, cytotoxicity, a role in endotoxic shock, inflammation, immunoregulation, proliferation and antiviral responses, as well as protection against the deleterious effects of ionizing radiation. TNF-$\alpha$ and LT-$\alpha$ are involved in the pathogenesis of a wide range of diseases, including endotoxic shock, cerebral malaria, tumors, autoimmune disease, AIDS and graft-host rejection (B. Beutler and C. Von Huffel, Science 264:667–668 (1994)). Mutations in the p55 receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., Cell 74:845 (1993)).

Apoptosis, or programmed cell death, is a physiologic process essential to the normal development and homeostasis of multicellular organisms (H. Steller, Science 267:1445–1449 (1995)). Derangements of apoptosis contribute to the pathogenesis of several human diseases including cancer, neurodegenerative disorders, and acquired immune deficiency syndrome (C. B. Thompson, Science 267:1456–1462 (1995)). Recently, much attention has focused on the signal transduction and biological function of two cell surface death receptors, Fas/APO-1 and TNFR-1 (J. L. Cleveland et al., Cell 81:479–482 (1995); A. Fraser et al., Cell 85:781–784 (1996); S. Nagata et al., Science 267:1449–56 (1995)). Both are members of the TNF receptor family, which also include TNFR-2, low affinity NGFR, CD40, and CD30, among others (C. A. Smith et al., Science 248: 1019–23 (1990); M. Tewari et al., in Modular Texts in Molecular and Cell Biology M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain," which is distantly related to the Drosophila suicide gene, reaper (P. Golstein et al., Cell 81:185–6 (1995); K. White et al., Science 264:677–83 (1994)). This shared death domain suggests that both receptors interact with a related set of signal transducing molecules that, until recently, remained unidentified. Activation of Fas/APO-1 recruits the death domain-containing adapter molecule FADD/MORT1 (A. M. Chinnaiyan et al., Cell 81:505–512 (1995); M. P. Boldin et al., J. Biol. Chem. 270:7795–8 (1995); F. C. Kischkel et al., EMBO 14:5579–5588 (1995)), which in turn binds and presumably activates FLICE/MACH1, a member of the ICE/CED-3 family of pro-apoptotic proteases (M. Muzio et al., Cell 85: 817–827 (1996); M. P. Boldin et al., Cell 85:803–815 (1996)). While the central role of Fas/APO-1 is to trigger cell death, TNFR-1 can signal an array of diverse biological activities-many of which stem from its ability to activate NF-kB (L. A. Tartaglia et al., Immunol Today 13:151–153 (1992)).

Accordingly, TNFR-1 recruits the multivalent adapter molecule TRADD, which like FADD, also contains a death domain (H. Hsu et al, Cell 81:495–504 (1995); H. Hsu et al., Cell 84:299–308 (1996)). Through its associations with a number of signaling molecules including FADD, TRAF2, and RIP, TRADD can signal both apoptosis and NF-kB activation(H. Hsu et al, Cell 84:299–308 (1996); H. Hsu et al., Immunity 4:387–396 (1996)).

Recently, a new apoptosis inducing TNF ligand has been discovered. S. R. Wiley et al., Immunity 3:673–682 (1995), named the new molecule, "TNF-related apoptosis-inducing ligand" or "TRAIL." R. M. Pitti et al., J. Biol. Chem. 271:12687–12690 (1996), named the molecule "Apo-2 ligand" or "Apo-2L." This molecule was also disclosed in co-pending U.S. provisional patent application No. 60/013405. For convenience, this molecule will be referred to herein as TRAIL.

Unlike FAS ligand, whose transcripts appear to be largely restricted to stimulated T-cells, significant levels of TRAIL are detected in many human tissues (e.g., spleen, lung, prostate, thymus, ovary, small intestine, colon, peripheral blood lymphocytes, placenta, kidney), and it is constitutively transcribed by some cell lines. It has been shown that TRAIL acts independently from the FAS ligand (S. R. Wiley et al., supra). It has also been shown that TRAIL activates apoptosis rapidly, within a time frame that is similar to death signaling by Fas/Apo-1L, but much faster than TNF-induced apoptosis. S. A. Marsters et al., Current Biology 6:750–752 (1996). The inability of TRAIL to bind TNFR-1, Fas, or the recently identified DR3, suggests that TRAIL may interact with a unique receptor(s).

Work to date suggests that there are several unique TNF receptors for TRAIL. In co-pending U.S. provisional patent application No. 60/035,722, one novel death domain containing receptor for TRAIL, DR4, was disclosed. See, Pan et al., Science 276:111–113 (April 1997). In co-pending U.S. provisional patent application No. 60/040,846, a novel death domain containing receptor, DR5 (TR7), was disclosed. This receptor has now been shown to bind TRAIL. In co-pending U.S. provisional patent application No. 60/035,496, another receptor, TR5, was disclosed. This receptor has also now been shown to bind TRAIL, however, TR5 has been shown to be a non-signaling decoy receptor which antagonizes apoptosis.

The effects of TNF family ligands and receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize additional novel receptors that bind TRAIL.

SUMMARY OF THE INVENTION

The present invention provides isolated nucleic acid molecules comprising a polynucleotide encoding the TR13 receptor having the amino acid sequence shown in SEQ ID NO:2 (FIGS. 1A–D, amino acid sequence shown in SEQ ID NO:40 (FIGS. 7A–E) or the amino acid sequence encoded by the eDNA clone deposited as American Type Culture Collection ("ATCC") Deposit No. PTA-349 (HWLHM70) on Jul. 13, 1999, and/or the amino acid sequence encoded by the cDNA clone deposited as American Type Culture Collection ("ATCC") Deposit No. PTA-507 (HWLHN83) on Aug. 12, 1999. The ATCC is located at 10801 University Boulevard, Manassas, Virginia 20110-2209. It would be apparent to the skilled artisan that the various methods of use, including but not limited to diagnostic and therapeutic uses described herein, for the TR13 receptor polynucleotides and polypeptides would apply equally to all variants and fragments thereof (e.g., fragments of the TR13 receptor disclosed and described herein in FIGS. 1A–D, FIG. 7A–E, SEQ ID NO:1, SEQ ID NO:2, SEQ ID NO:39, SEQ ID NO:40 and/or contained or encoded by one or both of the deposited cDNA clones HWLHM70 and HWLHN83).

The present invention also relates to recombinant vectors, which include the isolated nucleic acid molecules of the present invention, and to host cells containing the recombinant vectors, as well as to methods of making such vectors and host cells and for using them for production of TR13 polypeptides (e.g., the TR13 polypeptide sequence shown in FIGS. 1A–D and/or FIGS. 7A–E, or a fragment thereof) by recombinant techniques.

The invention further provides an isolated TR13 polypeptide (e.g., the TR13 polypeptide sequence shown in FIGS. 1A–D and/or FIGS. 7A–E or fragments thereof) having an amino acid sequence encoded by a polynucleotide described herein (e.g., the polynucleotide sequence shown in SEQ ID NO:1 and/or SEQ ID NO:39, or a fragment thereof).

The present invention also provides diagnostic assays such as quantitative and diagnostic assays for detecting levels of TR13 polynucleotide and/or protein (e.g., the TR13 protein shown in FIGS. 1A–D and/or FIGS. 7A–E or fragments thereof). Thus, for instance, a diagnostic assay in accordance with the invention for detecting over-expression of TR13, or soluble form thereof, compared to normal control tissue samples may be used to detect the presence of tumors.

The present invention provides isolated nucleic acid molecules comprising a polynucleotide encoding the TR14 receptor having the amino acid sequence shown in SEQ ID NO:61 (FIGS. 10A–), and/or the amino acid sequence encoded by the cDNA clone deposited as American Type Culture Collection ("ATCC") Deposit No. PTA-348 (HMSHK47) on Jul. 13, 1999. While the sequence of SEQ ID NO:61 and FIGS. 10A–H are preferred embodiments of TR14 receptor protein, the present invention provides alternative isolated nucleic acid molecule embodiments comprising a polynucleotide encoding the TR14 receptor having the amino acid sequence shown in SEQ ID NO:5 (FIGS. 4A–E. The sequence of amino acid residues T-78 to M-231 of SEQ ID NO:61 is identical to the sequence of amino acid residues T-73 to M-226 of SEQ ID NO:5. It would be apparent to the skilled artisan that the various methods of use, including, but not limited to, diagnostic and therapeutic uses described herein, for the TR13 receptor polynucleotides and polypeptides would apply equally to all variants and fragments thereof (e.g., fragments of the TR14 receptor disclosed and described in FIGS. 10A–H and SEQ ID NOS:60 and 61, or, alternatively, FIGS. 4A–E and SEQ ID NO:4, SEQ ID NO:5 and/or contained or encoded by the deposited cDNA clone (HMSHK47)).

The present invention also relates to recombinant vectors, which include the isolated nucleic acid molecules of the present invention, and to host cells containing the recombinant vectors, as well as to methods of making such vectors and host cells and for using them for production of TR14 polypeptides by recombinant techniques.

The invention further provides an isolated TR14 polypeptide (e.g., the TR14 polypeptide sequence shown in FIGS. 10A–H or, alternatively, FIGS. 4A–E, or fragments thereof) having an amino acid sequence encoded by a polynucleotide described herein (e.g., the polynucleotide sequence shown in SEQ ID NO:60, or, alternatively SEQ ID NO:4, or fragments thereof).

The present invention also provides diagnostic assays such as quantitative and diagnostic assays for detecting levels of TR14 polynucleotide and/or protein (e.g., the TR14 polypeptide sequence disclosed in FIGS. 10A–H or 4A–E, or fragments thereof). Thus, for instance, a diagnostic assay in accordance with the invention for detecting overexpression of TR14, or soluble form thereof, compared to normal control tissue samples may be used to detect the presence of tumors.

Tumor Necrosis Factor (TNF) family ligands are known to be among the most pleiotropic cytokines, inducing a large number of cellular responses, including cell proliferation, cytotoxicity, anti-viral activity, immunoregulatory activities, hematopoiesis, and the transcriptional regulation of several genes. Cellular response to TNF-family ligands include not only normal physiological responses, but also diseases associated with increased apoptosis or the inhibition of apoptosis. Apoptosis-programmed cell death is a physiological mechanism involved in the deletion of peripheral T lymphocytes of the immune system, and its dysregulation can lead to a number of different pathogenic processes. Diseases associated with increased cell survival, unregulated cell proliferation, or the inhibition of apoptosis, include cancers, autoimmune disorders, viral infections, inflammation, graft vs. host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia, and anorexia.

Thus, the invention further provides a method for inhibiting TR13 mediated signaling and/or apoptosis induced by a TNF-family ligand, which involves administering to a cell which expresses the TR13 polypeptide (i.e., the TR13 polypeptide shown in FIGS. 1A–D and/or FIGS. 7A–E, or a fragment thereof) an effective amount of a TR13 antagonist capable of decreasing TR13 mediated apoptosis and/or decreasing TR13 mediated signaling. Preferably, TR13 mediated signaling is decreased to treat a disease wherein increased apoptosis is exhibited.

Thus, the invention further provides a method for promoting TR13 mediated signalling and/or apoptosis induced by a TNF-family ligand, which involves administering to a cell which expresses the TR13 polypeptide (e.g., the TR13 polypeptide shown in FIGS. 1A–D and/or FIGS. 7A–E, or a fragment thereof) an effective amount of a TR13 agonist capable of increasing TR13 mediated apoptosis and/or increasing TR13 mediated signaling. Preferably, TR13 mediated signaling is increased to treat a disease wherein decreased apoptosis is exhibited.

Thus, the invention further provides a method for inhibiting TR14 mediated signaling and/or apoptosis induced by a TNF-family ligand, which involves administering to a cell which expresses the TR14 polypeptide an effective amount of a TR14 antagonist capable of decreasing TR14 mediated apoptosis and/or capable of decreasing TR14 mediated signaling. Preferably, TR14 mediated signaling is decreased to treat a disease wherein increased apoptosis is exhibited.

Thus, the invention further provides a method for promoting TR14 mediated signaling and/or apoptosis induced by a TNF-family ligand, which involves administering to a cell which expresses the TR14 polypeptide an effective amount of a TR14 agonist capable of increasing TR14 mediated apoptosis and/or capable of increasing TR14 mediated signaling. Preferably, TR14 mediated signaling is increased to treat a disease wherein decreased apoptosis is exhibited.

In a further aspect, the present invention is directed to a method for enhancing TR13 mediated signaling induced by a TNF-family ligand (e.g., Fas Ligand and/or AIM-II ("LIGHT") (International application publication number WO 97/34911, published Sep. 25, 1997)) which involves administering to a cell which expresses the TR13 polypeptide (e.g., the polypeptide shown in FIGS. 1A–D and/or FIGS. 7A–E or a fragment thereof) an effective amount of an agonist capable of increasing TR13 mediated activity. Preferably, TR13 mediated activity is increased to treat a disease wherein decreased apoptosis is exhibited.

Whether any candidate "agonist" or "antagonist" of the present invention can enhance or inhibit TR13 mediated signaling can be determined using art-known TNF-family ligand/receptor cellular response assays, including those described in more detail below. Thus, in a further aspect, a screening method is provided for determining whether a candidate agonist or antagonist is capable of enhancing or inhibiting a cellular response to a TR13 TNF-family ligand. The method involves contacting cells which express the TR13 polypeptide (e.g., the polypeptide shown in FIGS. 1A–D and/or FIGS. 7A–E, or a fragment thereof) with a candidate compound and a TNF-family ligand (e.g., Fas Ligand and/or AIM-II (International application publication number WO 97/34911, published Sep. 25, 1997)), assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By the invention, a cell expressing a TR13 polypeptide (e.g., the polypeptide shown in FIGS. 1A–D and/or FIGS. 7A–E or a fragment thereof) can be contacted with either an endogenous or exogenously administered TNF-family ligand.

In a further aspect, the present invention is directed to a method for enhancing apoptosis TR14 mediated signaling induced by a TNF-family ligand, which involves administering to a cell which expresses the TR14 polypeptide (e.g., the polypeptide shown in FIGS. 10A–H, or, alternatively 4A–E, or a fragment thereof) an effective amount of an agonist capable of increasing TR14 mediated activity. Preferably, TR14 mediated activity is increased to treat a disease wherein decreased apoptosis is exhibited.

In specific, preferred embodiments, TR14 polynucleotides and polypeptides, as well as antibodies that agonize TR14 receptor (as described in the section on Antibodies, above), stimulate epithelial cell proliferation and/or development to ameliorate the diseases and disorders described in this section. Members of the TNF family of proteins are known to signal through the NF-κB singaling pathway. NF-κB is a transcription factor activated by a wide certain agents to stimulate cell activation and differentiation. It is believed that the TR14 receptor of the instant invention signals through the NF-κB pathway to activate proliferation and development of cells. Thus, TR14 polynucleotides and polypeptides of the invention as well as antibodies and peptides that agonize TR14 may be used in accordance with the invention to stimulate NF-κB-mediated epithelial cell proliferation, including but not limited to ectodermal dysplasia.

Whether any candidate "agonist" or "antagonist" of the present invention can enhance or inhibit TR14 mediated signaling can be determined using art-known TR14 TNF-family ligand/receptor cellular response assays, including those described in more detail below. Thus, in a further aspect, a screening method is provided for determining whether a candidate agonist or antagonist is capable of enhancing or inhibiting a cellular response to a TNF-family ligand. The method involves contacting cells which express the TR14 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By the invention, a cell expressing the TR14 polypeptide (e.g., the polypeptide shown in FIGS. 10A–H, or, alternatively 4A–E) can be contacted with either an endogenous or exogenously administered TNF-family ligand.

BRIEF DESCRIPTION OF THE FIGURES

FIGS. 1A–D shows the nucleotide (SEQ ID NO:1) and deduced amino acid sequence (SEQ ID NO:2) of the TR13 receptor. Predicted amino acids from about 105 to about 170, about 251 to about 265, about 331 to about 410, and about 580 to about 610 constitute the cysteine-rich domains (amino acid residues from about 105 to about 170, about 251 to about 265, about 331 to about 410, and about 580 to about 610 in SEQ ID NO:2) and are represented by the underlined amino acid regions; amino acids from about 139 to about 142, about 140 to about 143, about 153 to about 156, about 293 to about 296, about 325 to about 328, about 421 to about 424, about 466 to about 469, about 696 to about 699, and about 728 to about 731 constitute potential sites of N-glycosylation (amino acid residues from about 139 to about 142, about 140 to about 143, about 153 to about 156, about 293 to about 296, about 325 to about 328, about 421 to about 424, about 466 to about 469, about 696 to about 699, and about 728 to about 731 in SEQ ID NO:2) which are represented by the bolded amino acids; amino acids from about 312 to about 315, and about 458 to about 461, constitute potential cAMP phosphorylation sites (amino acid residues from about from about 312 to about 315, and about 458 to about 461 in SEQ ID NO:2) and are represented by asterisks (*) above the amino acid residues; amino acids from about 50 to about 53, about 66 to about 69, about 80 to about 83, about 276 to about 279, about 311 to about 314, about 438 to about 441, about 559 to about 562, about 564 to about 567, about 698 to about 701, and about 725 to about 728 constitute potential sites of protein kinase C (PKC) phosphorylation (amino acid residues from about 50 to about 53, about 66 to about 69, about 80 to about 83, about 276 to about 279, about 311 to about 314, about 438 to about 441, about 559 to about 562, about 564 to about 567, about 698 to about 701, and about 725 to about 728 in SEQ ID NO:2) and are represented by the italicized amino acid residues; amino acids from about 80 to about 83, about 89 to about 92, about 180 to about 183, about 198 to about 201, about 214 to about 217, about 272 to about 275, about 306 to about 309, about 510 to about 513, about 529 to about 532, about 584 to about 587, about 609 to about 312, about 642 to about 645, and about 698 to about 701 casein kinase II phosphorylation sites (amino acid residues from about 80 to about 83, about 89 to about 92, about 180 to about 183, about 198 to about 201, about 214 to about 217, about 272 to about 275, about 306 to about 309, about 510 to about 513, about 529 to about 532, about 584 to about 587, about 609 to about 312, about 642 to about 645, and about 698 to about 701 in SEQ ID NO:2) and are represented by the double underlined amino acids; amino acids from about 69 to about 74, about 149 to about 154, about 154 to about 159, about 163 to about 168, about 212 to about 217, about 248 to about 253, about 365 to about 370, about 383 to about 388, about 393 to about 398, about 588 to about 593, about 623 to about 628, about 661 to about 666, and about 665 to about 670 N-myristoylation sites (amino acids from about 69 to about 74, about 149 to about 154, about 154 to about 159, about 163 to about 168, about 212 to about 217, about 248 to about 253, about 365 to about 370, about 383 to about 388, about 393 to about 398, about 588 to about 593, about 623 to about 628, about 661 to about 666, and about 665 to about 670 in SEQ ID NO:2) and are represented by the strikethrough amino acids (e.g. Q); and amino acids from about 456 to about 459 constitute a potential amidylation site (amino acid residues from about 456 to about 459 of SEQ ID NO:5) and is represented by the lowercase amino acids.

FIGS. 2A–D show the regions of similarity between the amino acid sequences of the TR13 receptor protein (SEQ ID NO:2), and the OX40 protein (SEQ ID NO:3).

FIGS. 4A–E shows the nucleotide (SEQ ID NO:4) and deduced amino acid sequence (SEQ ID NO:5) of the TR14 receptor. The predicted extracellular domain constitutes amino acids from about 1 to about 133 (amino acid residues from 1 to 133 of SEQ ID NO:5) and are represented by the underlined amino acids; amino acids from about 65 to about 85 constitute a conserved cysteine-rich domain (amino acid residues from about 65 to about 85 of SEQ ID NO:5) and is represented by the italized amino acid residues; amino acids from about 134 to about 150 constitute the predicted transmembrane domain (amino acid residues from about 134 to about 150 in SEQ ID NO:5) which are represented by the double underlined amino acid residues; amino acid residues from about 151 to about 226 constitutes the predicted intracellular domain (amino acid residues from about 151 to about 226 of SEQ ID NO:5) and are represented by the lower case amino acid residues; amino acids from about 178 to about 180 constitute potential protein kinase C (PKC) phosphorylation sites (amino acid residues from about 178 to about 180 of SEQ ID NO:5) and are represented by asterisks (*) above the amino acid residues; amino acids from about 5 to about 8, about 118 to about 121, about 178 to about 181, and about 193 to about 196 constitute potential sites of casein kinase II phosphorylation (amino acid residues from about 5 to about 8, about 118 to about 121, about 178 to about 181, about 193 to about 196 of SEQ ID NO:5) and are represented by the strikethrough amino acid residues; and amino acids from about 9 to about 14 contitutes a potential N-myristoylation site (amino acid residues from about 9 to about 14 of SEQ ID NO:5) and is represented by the bold amino acids.

FIGS. 5A–B show the regions of similarity between the amino acid sequences of the TR14 receptor protein (SEQ ID NO: 5), and the Tumor Necrosis Factor Receptor protein (SEQ ID NO: 6).

FIGS. 7A–E shows the nucleotide (SEQ ID NO:39) and deduced amino acid sequence (SEQ ID NO:40) of the full-length TR13 receptor. The predicted signal sequence constitutes amino acids from about 1 to about 41 (amino acid residues from about 1 to about 41 of SEQ ID NO:40) and are represented by the dotted underlined amino acids; amino acids from about 42 to about 906 constitutes the predicted extracellular domain (amino acid residues from 42 to 906 of SEQ ID NO:40) and are represented by the single underlined amino acids; amino acids from about 271 to about 421 and from about 585 to about 595 constitute conserved cysteine-rich domains (amino acid residues from about 271 to about 421 and from about 585 to about 595 of SEQ ID NO:40) and is represented by the italized amino acid residues; amino acids from about 907 to about 931 constitute the predicted transmembrane domain (amino acid residues from about 907 to about 931 in SEQ ID NO:40) which are represented by the double underlined amino acid residues; amino acid residues from about 932 to about 1001 constitutes the predicted intracellular domain (amino acid residues from about 932 to about 1001 of SEQ ID NO:40) and are represented by the lower case amino acid residues; amino acids from about 11 to about 13, about 18 to about 20, 107 to about 109, about 156 to about 158, about 224 to about 226, about 301 to about 303, about 317 to about 319, about 331 to about 333, about 527 to about 529, about 562 to about 564, about 689 to about 691, about 810 to about 812, about 815 to about 817, about 949 to about 951, and about 976 to about 978 constitute potential protein kinase C (PKC) phosphorylation sites (amino acid residues from about 11 to about 13, about 18 to about 20, 107 to about 109, about 156 to about 158, about 224 to about 226, about 301 to about 303, about 317 to about 319, about 331 to about 333, about 527 to about 529, about 562 to about 564, about 689 to about 691, about 810 to about 812, about 815 to about 817, about 949 to about 951, and about 976 to about 978 of SEQ ID NO:40) and are represented by asterisks (*) above the amino acid residues; amino acids from about 42 to about 45, about 59 to about 62, about 81 to about 84, about 146 to about 149, about 282 to about 285, about 331 to about 334, about 340 to about 343, about 431 to about 434, about 449 to about 452, about 465 to about 468, about 523 to about 526, about 557 to about 560, about 761 to about 764, about 780 to about 783, about 780 to about 783, about 835 to about 838, about 860 to about 863, about 893 to about 896, and about 949 to about 952 constitute potential sites of casein kinase II phosphorylation (amino acid residues from about 42 to about 45, about 59 to about 62, about 81 to about 84, about 146 to about 149, about 282 to about 285, about 331 to about 334, about 340 to about 343, about 431 to about 434, about 449 to about 452, about 465 to about 468, about 523 to about 526, about 557 to about 560, about 761 to about 764, about 780 to about 783, about 780 to about 783, about 835 to about 838, about 860 to about 863, about 893 to about 896, and about 949 to about 952 of SEQ ID NO:40) and are represented by the strikethrough amino acid residues; amino acids from about 77 to about 82, about 88 to about 93, about 152 to about 157, about 268 to about 273, about 288 to about 293, about 320 to about 325, about 400 to about 405, about 414 to about 419, about 463 to about 468, about 599 to about 604, about 616 to about 621, about 634 to about 639, about 644 to about 649, about 839 to about 844, about 874 to about 879, about 912 to about 917, and about 916 to about 921 constitute potential N-myristoylation sites (amino acid residues from about 77 to about 82, about 88 to about 93, about 152 to about 157, about 268 to about 273, about 288 to about 293, about 320 to about 325, about 400 to about 405, about 414 to about 419, about 463 to about 468, about 599 to about 604, about 616 to about 621, about 634 to about 639, about 644 to about 649, about 839 to about 844, about 874 to about 879, about 912 to about 917, and about 916 to about 921 of SEQ ID NO:40) and are represented by a plus sign ("+") above the amino acids; amino acids from about 50 to about 56, and 109 to about 116 constitute potential tyrosinc phosphorylation sites (amino acids from about 50 to about 56, and about 109 to about 116 of SEQ ID NO:40) are represented by the double strikethrough amino acids; and amino acids from about 153 to about 156, 390 to about 393, 391 to about 394, about 404 to about 407, about 544 to about 547, about 576 to about 579, about 672 to about 675, about 717 to about 720, about 947 to about 950, and about 979 to about 982 constitute potential N-glycosylation sites (ammo acids from about 153 to about 156, 390 to about 393, 391 to about 394, about 404 to about 407, about 544 to about 547, about 576 to about 579, about 672 to about 675, about 717 to about 720, about 947 to about 950, and about 979 to about 982 of SEQ ID NO:40) which are represented by the shaded amino acids.

FIGS. 8A–D show the regions of similarity between the amino acid sequences of the full-length TR13 receptor protein (SEQ ID NO:40), and the Tumor Necrosis Factor Receptor H homolog (gb|AAB94382.1) (SEQ ID NO:41).

FIGS. 10A–H show a preferred nucleotide (SEQ ID NO: 60) and deduced amino acid sequence (SEQ ID NO: 61) of the TR14 receptor. The transmembrane domain from amino acids L-139 to L-155 is underlined.

DETAILED DESCRIPTION OF THE PREFERRED EMBODIMENTS

Figure 3:
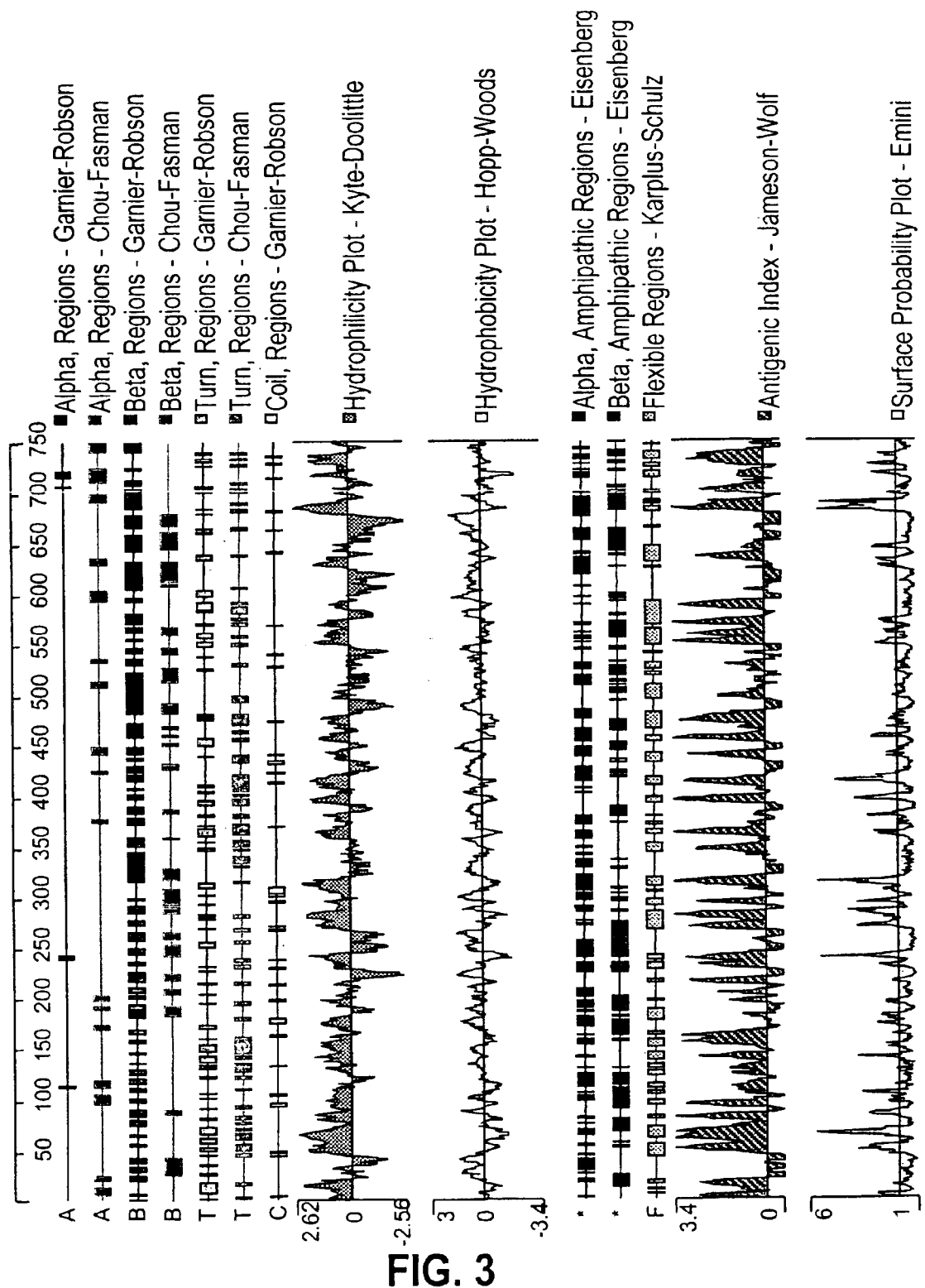
FIG. 3 shows an analysis of the TR13 amino acid sequence (SEQ ID NQ:2). Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues from about M1 to about A9, about K12 to about L20, about N47 to about T55, about H58 to about 566, about D63 to about S71, about P77 to about F85, about A90 to about Q98, about F136 to about Q144, about S152 to about C160, about R159 to about A167, about A211 to about M219, about M235 to about V243, about V266 to about V274, about W277 to about S285, about I290 to about F298, about A310 to about V318, about E343 to about C351, about I360 to about H368, about G391 to about I399, about F409 to about T417, about S436 to about Y444, about C453 to about S461, about I472 to about S480, about Y548 to about S556, about C557 to about I565, about V567 to about V575, about T584 to about G592, about R632 to about G640, about W680 to about Y688, about Q684 to about K692, about T698 to about A706, about S726 to about S734, and about S734 to about L742 of SEQ ID NO:2 (FIGS. 1A–C) correspond to the highly antigenic regions of the TR13 protein, predicted using the Jameson-Wolf antigenic index (See FIG. 3 and Table I). These highly antigenic fragments correspond to the amino acid residues illustrated in FIGS. 1A–D and in SEQ ID NO:2.

The present invention provides isolated nucleic acid molecules comprising a polynucleotide encoding a TR13 polypeptide having the amino acid sequence shown in FIGS. 1A–D (SEQ ID NO:2) and/or FIGS. 7A–E (SEQ ID NO:40) and/or fragments or variants thereof. The TR13 polypeptide of the present invention shares sequence homology with the human OX40 homologue (FIGS. 2A–D) and the tumor necrosis factor receptor II homolog (FIGS. 8A–D). The nucleotide sequence shown in FIGS. 1A–D (SEQ ID NO:1) was obtained by sequencing a cDNA clone (HWLHM70), which was deposited on Jul. 13, 1999 at the American Type Culture Collection, and given Accession Number PTA-349. The nucleotide sequence shown in FIGS. 7A–E (SEQ ID NO:39) was obtained, in part, by sequencing a cDNA clone (HWLHN83), which was deposited on Aug. 12, 1999 at the American Type Culture Collection, and given Accession Number PTA-507. The deposited clone is inserted in the pSport1 clone (Life Technologies, Rockville, Md.) using the SalI and NotI restriction endonuclease cleavage sites.

The present invention provides isolated nucleic acid molecules comprising a polynucleotide encoding a TR14 polypeptide having the amino acid sequence shown in FIGS. 10A–H (SEQ ID NO:51), or, alternatively 4A–E (SEQ ID NO:5) and/or fragments or variants thereof, which were determined by sequencing a cloned cDNA. The TR14 polypeptide of the present invention shares sequence homology with the Tumor Necrosis Factor Receptor (FIGS. 5A–B). The nucleotide sequence shown in FIGS. 10A–H (SEQ ID NO:60) was obtained by sequencing a cDNA clone (HMSHK47), which was deposited on Jul. 13, 1999 at the American Type Culture Collection, and given Accession Number PTA-348. The deposited clone is inserted in the pBluescript clone (Life Technologies, Rockville, Md.) using the EcoRI restriction endonuclease cleavage sites. While SEQ ID NO:60 is a preferred sequence for TR14, an alternative TR14 related sequence is shown in FIGS. 4A–E (SEQ ID NO:4).

Nucleic Acid Molecules

Unless otherwise indicated, all nucleotide sequences determined by sequencing a DNA molecule herein were determined using an automated DNA sequencer (such as the Model 3700 and Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleic acid sequence set out in SEQ ID NO: 1 and/or SEQ ID NO: 39, a nucleic acid molecule of the present invention encoding a TR13 polypeptide may be obtained using standard cloning and screening procedures, such as those for cloning cDNAs using mRNA as starting material. Illustrative of the invention, the nucleic acid molecule described in SEQ ID NO: 1 was discovered in a cDNA library derived from activated monocytes. Further, illustrative of the invention, the nucleic acid molecule described in SEQ ID NO: 39 was discovered in a cDNA library derived from normal human colon. TR13 polynucleotides of the invention have also been identified in cDNA libraries from the following tissues: pancreas tumor, endometrial tumor, adult small intestine, colon cancer, breast cancer cell line, resting T-cell, amygdala, rectum, T-cell helper, pineal gland, apoptotic T-cell, epididymus, greater omentum, prostate BPH, osteoclastoma, endometrial stromal cells, stromal cell, substantia nigra, activated T-cell, tonsil, and testes tissue.

The determined TR13 nucleotide sequence of SEQ ID NO:1 contains an open reading frame encoding a protein of about 750 amino acid residues, and a deduced molecular weight of about 82 kDa. The amino acid sequence of the predicted TR13 receptor is shown in SEQ ID NO:2 from amino acid residue about 1 to residue about 750. Of known members of the TNF receptor family, this TR13 polypeptide shares the greatest degree of homology with human OX40 (See FIGS. 2A–D), including significant sequence homology over multiple cysteine rich domains.

The determined TR13 nucleotide sequence of SEQ ID NO:39 contains an open reading frame encoding a protein of about 1001 amino acid residues, with a predicted signal encompassing amino acids about 1 to about 41, a predicted extracellular domain encompassing amino acids from about 42 to about 906, a transmembrane domain encompassing amino acids from about 907 to about 931, and an intracellular domain encompassing amino acids from about 932 to 1001, of SEQ ID NO:40, and a deduced molecular weight of about 110 kDa. The amino acid sequence of the predicted TR13 receptor is shown in SEQ ID NO:40 from amino acid residue about 1 to residue about 1001. Of known members of the TNF receptor family, this TR13 polypeptide shares the greatest degree of homology with the tumor necrosis factor receptor II homolog (See FIGS. 8A–D), including significant sequence homology over multiple cysteine rich domains.

Using the information provided herein, such as the nucleic acid sequence set out, preferably, in SEQ ID NO: 60, or, alternatively SEQ ID NO: 4, a nucleic acid molecule of the present invention encoding a TR14 polypeptide may be obtained using standard cloning and screening procedures, such as those for cloning cDNAs using mRNA as starting material. Illustrative of the invention, the nucleic acid molecule contained in deposited clone HMSHK47 (described in SEQ ID NO:60) was discovered in a cDNA library derived from colon. The gene of the present invention has also been identified in cDNA libraries from the following tissues: activated T-cell, endometrial tumor, thymus, and 12 week early stage human tissue.

The determined nucleotide sequence of the TR14 cDNA of SEQ ID NO:60 contains an open reading frame encoding a protein of about 231 amino acid residues, with a predicted extracellular domain encompassing amino acids from about 1 to about 138, a transmembrane domain encompassing amino acids from about 139 to about 155, and an intracellular domain encompassing amino acids from about 156 to about 231 of SEQ ID NO:61 and a deduced molecular weight of about 25 kDa.

The TR14 nucleotide sequence of SEQ ID NO: 4 contains an open reading frame encoding a protein of about 226 amino acid residues, with a predicted extracellular domain encompassing amino acids from about 1 to about 133, a transmembrane domain encompassing amino acids from about 134 to about 150 (from about 139 to about 155 of SEQ ID NO:61), and an intracellular domain encompassing amino acids from about 151 to about 226 of SEQ ID NO:4 (acids from about 156 to about 231 of SEQ ID NO:61) and a deduced molecular weight of about 24.5 kDa. Of known members of the TNF receptor family, the TR14 polypeptide of the SEQ ID NO:5 shares the greatest degree of homology with tumor necrosis factor receptor (See FIGS. 5A–B).

As indicated, the present invention also encompasses mature form(s) of the TR13 and/or TR14 polypeptides of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide.

Therefore, the present invention provides a nucleotide sequence encoding the mature form of the TR13 polypeptide having the amino acid sequence encoded by the cDNA clone identified as ATCC Deposit No. PTA-349 (HWLHM70), and/or of the amino acid sequence shown in FIGS. 1A–D (SEQ ID NO:2). By the mature form of TR13 polypeptide having the amino acid sequence encoded by, for example, the cDNA clone identified as ATCC Deposit No. PTA-349 (HWLHM70) is meant, the mature form(s) of the TR13 receptor produced by expression in a mammalian cell (e.g., COS cells, as described below) of the complete open reading frame encoded by the human DNA sequence of the clone contained in the deposited vector. As indicated herein, the mature form of the TR13 polypeptide having the amino acid sequence encoded by the cDNA clone contained in ATCC Deposit No. PTA-349 (HWLHM70), may or may not differ from the predicted mature TR13 protein shown in SEQ ID NO:2 (amino acids from about 1 to about 750) depending on the accuracy of the predicted cleavage site based on computer analysis. Polypeptides encoded by the nucleotide sequences are also encompassed by the invention.

Therefore, the present invention provides a nucleotide sequence encoding the mature form of the TR13 polypeptide having the amino acid sequence encoded by the cDNA clone identified as ATCC Deposit No. PTA-507 (HWLHN83), and/or of the amino acid sequence as shown in FIGS. 7A–E (SEQ ID NO:40). By the mature form of the TR13 polypeptide having the amino acid sequence encoded by, for example, the cDNA clone identified as ATCC Deposit No. PTA-507 (HWLHN83), is meant, the mature form(s) of the TR13 receptor produced by expression in a mammalian cell (e.g., COS cells, as described below) of the complete open reading frame encoded by the human DNA sequence of the clone contained in the deposited vector. As indicated herein, the mature form of the TR13 polypeptide having the amino acid sequence encoded by the cDNA clone contained in ATCC Deposit No. PTA-507 (HWLHN83), may or may not differ from the predicted mature TR13 protein shown in SEQ ID NO:40 (amino acids from about 42 to about 1001) depending on the accuracy of the predicted cleavage site based on computer analysis. Polypeptides encoded by these nucleotide sequences are also encompassed by the invention.

Methods for predicting whether a protein has a secretory leader as well as the cleavage point for that leader sequence are available. For instance, the method of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the TR13 polypeptide of the present invention was analyzed by a computer program ("PSORT"). See K. Nakai and M. Kanehisa, *Genomics* 14:897–911 (1992). PSORT is an expert system for predicting the cellular location of a protein based on the amino acid sequence. As part of this computational prediction of localization, the methods of McGeoch and von Heinje are incorporated. Thereafter, the complete amino acid sequences were further analyzed by visual inspection, applying a simple form of the (−1,−3) rule of von Heinje. von Heinje, supra. Thus, the TR13 protein is predicted to consist of residues from about 1–750 in SEQ ID NO: 2, and/or 1–1001 in SEQ ID NO: 40. The mature form of the polypeptide sequence disclosed in SEQ ID NO: 40 is predicted to consist of residues from about 42 to 1001.

As one of ordinary skill would appreciate, due to the possibilities of sequencing errors, as well as the variability of cleavage sites for leaders in different known proteins, the predicted full-length TR13 polypeptide encoded by the deposited cDNA clones comprises about 1001 amino acids, but may be anywhere in the range of about 700 to about 1200 amino acids. It will further be appreciated that, the domains described herein have been predicted by computer analysis, and accordingly, depending on the analytical criteria used for identifying various functional domains, the exact "address" of, for example, the extracellular domain, intracellular domain, cysteine-rich domains, and transmembrane domain of TR13 may differ slightly (e.g., the address may "shift" by about 1 to about 20 residues, more likely about 1 to about 5 residues). For example, the exact location of the TR13 cysteine-rich domains in FIGS. 1A–D (SEQ ID NO:2) and/or FIGS. 7A–E (SEQ ID NO:40) may vary slightly (e.g., the address may "shift" by about 1 to about 20 residues, more likely about 1 to about 5 residues) depending on the criteria used to define the motifs. In any event, as discussed further below, the invention further provides polypeptides having various residues deleted from the N-terminus and/or C-terminus of the full-length TR13, including polypeptides lacking one or more amino acids from the N-termini of the extracellular domain described herein, which constitute soluble forms of the extracellular domain of the TR13 polypeptides.

As one of ordinary skill would appreciate, due to the possibilities of sequencing errors, the preferred predicted full-length TR14 polypeptide encoded by the deposited cDNA clone comprises about 231 amino acids as shown in SEQ ID NO:61, but may be anywhere in the range of 175–275 amino acids. In an alternative embodiment, predicted full-length TR14 polypeptide comprises about 226 amino acids, but may be anywhere in the range of 175–275 amino acids, but may be anywhere in the range of about 45 to about 200 amino acids. It will further be appreciated that, the domains described herein have been predicted by computer analysis, and accordingly, that depending on the analytical criteria used for identifying various functional domains, the exact "address" of, for example, the extracellular domain, intracellular domain, cysteine-rich domains, and transmembrane domain of TR14 may differ slightly (e.g., the address may "shift" by about 1 to about 20 residues, more likely about 1 to about 5 residues). For example, the exact location of the TR14 extracellular domain and/or cysteine-rich domains in FIGS. 10A–H (SEQ ID NO:61) or, alternatively FIGS. 4A–E (SEQ ID NO:5) may vary slightly (e.g., the address may "shift" by about 1 to about 20 residues, more likely about 1 to about 5 residues) depending on the criteria used to define the domain. Additionally, in the event the polypeptide sequence of TR14 is longer than the sequence depicted in FIGS. 10A–H or, alternatively FIGS. 4A–E, the skilled artisan would appreciate that the sequence could affect the ultimate location of the extracellular, transmembrane, or intracellular domain. In any event, as discussed further below, the invention further provides polypeptides having various residues deleted from the N-terminus and/or C-terminus of the full-length TR14, including polypeptides lacking one or more amino acids from the N-termini of the extracellular domain described herein, which constitute soluble forms of the extracellular domain of the TR14 polypeptides.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically. However, a nucleic acid molecule contained in a clone that is a member of a mixed clone library (e.g., a genomic or cDNA library) and that has not been isolated from other clones of the library (e.g., in the form of a homogeneous solution containing the clone without other members of the library) or a chromosome isolated or removed from a cell or a cell lysate (e.g., a "chromosome spread", as in a karyotype), is not "isolated" for the purposes of this invention.

Isolated nucleic acid molecules of the present invention include, for example, DNA molecules comprising, or alternatively consisting of, an open reading frame (ORF) shown in FIGS. 1A–D (SEQ ID NO:1), FIGS. 7A–E (SEQ ID NO:39) and/or contained in a deposited eDNA clone (e.g., HWLHM70 and HWLHN83); DNA molecules comprising, or alternatively consisting of, the coding sequence for the mature TR13 protein shown in FIGS. 1A–D (SEQ ID NO:1) and/or FIGS. 7A–E (SEQ ID NO:39) and/or contained in a deposited cDNA clone (e.g., HWLHM70 and HWLHN83); DNA molecules comprising, or alternatively consisting of, a fragment of the coding sequence for the full-length TR13 protein disclosed in FIGS. 1A–D and/or FIGS. 7A–E and/or encoded by a deposited eDNA clone; and DNA molecules which comprise, or alternatively consist of, a sequence substantially different from those described above, but which, due to the degeneracy of the, genetic code, still encode TR13 polypeptides (including fragments of variants thereof). Of course, the genetic code is well known in the art. Thus, it would be routine for one skilled in the art to generate such degenerate variants.

Isolated nucleic acid molecules of the present invention include, for example, DNA molecules comprising, or alternatively consisting of, an open reading frame (ORF) shown preferably in FIGS. 10A–H (SEQ ID NO:60) or, alternatively, in FIGS. 4A–E (SEQ ID NO:4) and/or contained in the deposited cDNA clone (HMSHK47); DNA molecules comprising, or alternatively consisting of, the coding sequence for the mature TR14 protein shown preferably in FIGS. 10A–H (amino acids 1–164 of SEQ ID NO:6 1), or alternatively, in FIGS. 74A–E (SEQ ID NO:4) and/or contained in the deposited cDNA clone (HMSHK47); DNA molecules comprising, or alternatively consisting of, a fragment of the coding sequence for the full-length TR14 protein disclosed in preferably in FIGS. 10A–H or, alternatively, in FIGS. 4A–E and/or encoded by the deposited cDNA clone (HMSLIK47); and DNA molecules which comprise a sequence substantially different from those described above, but which, due to the degeneracy of the genetic code, still encode TR14 polypeptides (including fragments or variants thereof). Of course, the genetic code is well known in the art. Thus, it would be routine for one skilled in the art to generate such degenerate variants.

In another aspect, the invention provides isolated nucleic acid molecules encoding the TR13 polypeptide having an amino acid sequence encoded by the cDNA clone contained in ATCC Deposit No. PTA-349 (HWLHM70). In a further embodiment, nucleic acid molecules are provided that encode the mature form of the TR13 polypeptide disclosed in FIGS. 1A–D and/or encoded by the cDNA contained in ATCC Deposit No. PTA-349. In a further embodiment, nucleic acids are provided that the full-length TR13 polypeptide disclosed in FIGS. 1A–D and/or encoded by the deposited eDNA clone, but lacking the N-terminal methionine. In a further embodiment, nucleic acid molecules are provided that encode The invention further provides an isolated nucleic acid molecule having the nucleotide sequence shown in SEQ ID NO:1 or the nucleotide sequence of the TR13 cDNA contained in the above-described deposited cDNA clone, or a nucleic acid molecule having a sequence complementary to one of the above sequences. Such isolated molecules, particularly DNA molecules, are useful, for example, as probes for gene mapping by in situ hybridization with chromosomes, and for detecting expression of the TR13 gene in human tissue, for instance, by Northern blot analysis.

In another aspect, the invention provides isolated nucleic acid molecules encoding the TR13 polypeptide having an amino acid sequence as encoded by the cDNA clone contained in ATCC Deposit No. PTA-507 (HWLHN83). In a further embodiment, nucleic acid molecules are provided that encode the mature form of the TR13 polypeptide disclosed in FIGS. 7A–E, and/or encoded by the cDNA contained in ATCC Deposit No. PTA-507. In a further embodiment, nucleic acid molecules are provided that encode the full-length TR13 polypeptide disclosed in FIGS. 7A–E, and/or encoded by the deposited eDNA clone, but lacking the N-terminal methionine. The invention further provides an isolated nucleic acid molecule having the nucleotide sequence shown in SEQ ID NO:39 or the nucleotide sequence of the TR13 cDNA contained in the above-described deposited cDNA clone, or a nucleic acid molecule having a sequence complementary to one of the above sequences. Such isolated molecules, particularly DNA molecules, are useful, for example, as probes for gene mapping by in situ hybridization with chromosomes, and for detecting expression of the TR13 gene in human tissue, for instance, by Northern blot analysis.

In another aspect, the invention provides isolated nucleic acid molecules encoding the TR14 polypeptide having an amino acid sequence encoded by the cDNA clone contained in ATCC Deposit No. PTA-348 (HMSHK47). In a further embodiment, nucleic acid molecules are provided that encode the full-length TR14 polypeptide disclosed in FIGS. 10A–H or, alternatively, in FIGS. 4A–E, and/or encoded by the deposited cDNA clone, but lacking the N-terminal methionine. The invention further provides an isolated nucleic acid molecule having the nucleotide sequence shown preferably in SEQ ID NO:60 or, alternatively, in SEQ ID NO:4 or the nucleotide sequence of the TR14 cDNA contained in the above-described deposited cDNA clone, or a nucleic acid molecule having a sequence complementary to one of the above sequences. Such isolated molecules, particularly DNA molecules, are useful, for example, as probes for gene mapping by in situ hybridization with chromosomes, and for detecting expression of the TR14 gene in human tissue, for instance, by Northern blot analysis.

In addition, the invention provides nucleic acid molecules having nucleotide sequences related to extensive portions of SEQ ID NO: 1 which have been determined from the following related cDNA clones: HETAQ12R (SEQ ID NO: 8), HETAK82R (SEQ ID NO:9), HETBH18R (SEQ ID NO:10), HEPAB26R (SEQ ID NO:11), HETAN38R (SEQ ID NO:12), HPWDD30R (SEQ ID NO:13), HETAT05R (SEQ ID NO:14), HETDQ39R (SEQ ID NO:15), HETEM84R (SEQ ID NO:16), and HSIDV42R (SEQ ID NO:17).

In addition, the invention provides nucleic acid molecules having nucleotide sequences related to extensive portions of SEQ ID NO:39 which have been determined from the following related cDNA clones: HETAQ12R (SEQ ID NO:48), HETAK82R (SEQ ID NO:49), HETBM71R (SEQ ID NO:50), HETBH18R (SEQ ID NO:51), HEPAB26R (SEQ ID NO:52), HETAN38R (SEQ ID NO:53), HPWDD30R (SEQ ID NO:54), HETAT05R (SEQ ID NO:55), HETDQ39R (SEQ ID NO:56), HPWBL93R (SEQ ID NO:57), HETEM84R (SEQ ID NO:58), and HSIDV42R (SEQ ID NO:59).

In addition, the invention provides nucleic acid molecules having nucleotide sequences related to extensive portions of SEQ ID NOS: 60 and 4 which have been determined from the following related cDNA clones: HSABD50R (SEQ ID NO:18), HTXMX53R (SEQ ID NO:19), HE2OR74R (SEQ ID NO:20), HMSHK47R (SEQ ID NO:21), and HMSHK59R (SEQ ID NO:22).

The present invention is further directed to fragments of the isolated TR13 nucleic acid molecules described herein. By a fragment of an isolated DNA molecule having the nucleotide sequence of a deposited cDNA clone (e.g., HWLHN83 and/or HWLHM70), or the nucleotide sequence shown in FIGS. 1A–D (SEQ ID NO:1) and/or FIGS. 7A–E (SEQ ID NO:39), or the complementary strand thereto, is intended DNA fragments at least about 15 nt, and more preferably at least about 20 nt, or at least 25 nt, still more preferably at least about 30 nt, or at least 35 nt, and even more preferably, at least about 40 nt, or at least about 50 nt in length which are useful, for example, as diagnostic probes and primers as discussed herein. Of course, larger fragments 50–1500 nt in length are also useful according to the present invention, as are fragments corresponding to most, if not all, of the nucleotide sequence of the deposited cDNA or as shown in SEQ ID NO:1 and/or SEQ ID NO:39. By a fragment at least 20 nt in length, for example, is intended fragments which include 20 or more contiguous bases from the nucleotide sequence of a deposited cDNA clone or the nucleotide sequence as shown in FIGS. 1A–D (SEQ ID NO:1) and/or FIGS. 7A–E (SEQ ID NO:39). In this context "about" includes the particularly recited size, or may be larger or smaller by several (5, 4, 3, 2, or 1) nucleotides, at either terminus or at both termini.

The present invention is further directed to fragments of the isolated TR14 nucleic acid molecules described herein.

By a fragment of an isolated DNA molecule having the nucleotide sequence of the deposited cDNA clone (HMSHK47), or the nucleotide sequence shown preferably in FIGS. 10A–H (SEQ ID NO:60) or, alternatively in FIGS. 4A–E (SEQ ID NO:4), or the complementary strand thereto, is intended DNA fragments at least about 15 nt, and more preferably at least about 20 nt, or at least 25 nt, still more preferably at least about 30 nt, or at least 35 nt, and even more preferably, at least about 40 nt, or at least 50 nt, in length which are useful, for example, as diagnostic probes and primers as discussed herein. Of course, larger fragments 50–1500 nt in length are also useful according to the present invention, as are fragments corresponding to most, if not all, of the nucleotide sequence of the deposited cDNA or as shown preferably in FIGS. 10A–H (SEQ ID NO:60) or, alternatively in FIGS. 4A–E (SEQ ID NO:4). By a fragment at least 20 nt in length, for example, is intended fragments which include 20 or more contiguous bases from the nucleotide sequence of the deposited cDNA or the nucleotide sequence as shown in preferably in SEQ ID NO:60, or, alternatively, in SEQ ID NO:4. In this context "about" includes the particularly recited size, or may be larger or smaller by several (5, 4, 3, 2, or 1) nucleotides, at either terminus or at both termini.

Representative examples of TR13 polynucleotide fragments of the invention include, for example, fragments that comprise, or alternatively, consist of, a sequence from about nucleotide 1 to about 50, from about 51 to about 108, from about 109 to about 159, from about 160 to about 210, from about 211 to about 261, from about 262 to about 273, from about 274 to about 324, from about 325 to about 375, from about 376 to about 426, from about 427 to about 477, from about 478 to about 528, from about 529 to about 579, from about 580 to about 630, from about 631 to about 681, from about 682 to about 732, from about 733 to about 744, from about 745 to about 798, from about 799 to about 849, from about 850 to about 900, from about 901 to about 951, from about 952 to about 1002, from about 1003 to about 1053, from about 1054 to about 1104, from about 1105 to about 1155, from about 1156 to about 1164, from about 1165 to about 1197, from about 1198 to about 1248, from about 1249 to about 1266, from about 1267 to about 1317, from about 1318 to about 1368, from about 1369 to about 1419, from about 1420 to about 1470, from about 1471 to about 1521, from about 1522 to about 1572, from about 1573 to about 1623, from about 1624 to about 1674, from about 1675 to about 1725, from about 1726 to about 1776, from about 1777 to about 1827, from about 1828 to about 1878, from about 1879 to about 1929, from about 1930 to about 1980, from about 1981 to about 2031, from about 2032 to about 2082, from about 2083 to about 2133, from about 2134 to about 2184, from about 2185 to about 2235, from about 2236 to about 2286, from about 2287 to about 2337, from about 2338 to about 2388, from about 2389 to about 2489, from about 2490 to about 2540, from about 2451 to about 2501, from about 2502 to about 2554 of the polynucleotide sequence shown in FIGS. 1A–D (SEQ ID NO:1), or the complementary strand thereto, or the cDNA contained in the deposited clone (HWLHM70). Other representative examples of polynucleotide fragments of the invention include, for example, fragments that comprise, or alternatively consist of, a sequence from about nucleotide 1 to about 362, from about 705 to about 830, from about 31 to about 2280, from about 343 to about 414, from about 415 to about 459, from about 460 to about 540, 343 to about 540, from about 781 to about 804, from about 805 to about 830, about 781 to about 822, from about 1021 to about 1260, from about 1768 to about 1812, from about 1813 to about 1866, from about 1768 to about 1866, from about 31 to about 540, from about 660 to about 984, from about 1057 to about 1470, from about 1672 to about 1806, and/or from about 1924 to about 2256 of the polynucleotide sequence shown in FIGS. 1A–D (SEQ ID NO:1), or the complementary strand thereto. In this context "about" includes the particularly recited ranges, larger or smaller by several (5, 4, 3, 2, or 1) nucleotides, at either terminus or at both termini. Polynucleotides which hybridize to any 1, 2, 3, 4, 5 or more of these polynucleotide fragments are also encompassed by the invention. Moreover, polypeptides encoded by these polynucleotides and/or polynucleotide fragments are also encompassed by the invention.

Additional representative examples of TR13 polynucleotide fragments of the invention include, for example, fragments that comprise, or alternatively, consist of, a sequence from about nucleotide 1 to about 50, from about 51 to about 108, from about 109 to about 159, from about 160 to about 210, from about 211 to about 261, from about 262 to about 273, from about 274 to about 324, from about 325 to about 375, from about 376 to about 426, from about 427 to about 477, from about 478 to about 528, from about 529 to about 579, from about 580 to about 630, from about 631 to about 681, from about 682 to about 732, from about 733 to about 744, from about 745 to about 798, from about 799 to about 849, from about 850 to about 900, from about 901 to about 951, from about 952 to about 1002, from about 1003 to about 1053, from about 1054 to about 1104, from about 1105 to about 1155, from about 1156 to about 1164, from about 1165 to about 1197, from about 1198 to about 1248, from about 1249 to about 1266, from about 1267 to about 1317, from about 1318 to about 1368, from about 1369 to about 1419, from about 1420 to about 1470, from about 1471 to about 1521, from about 1522 to about 1572, from about 1573 to about 1623, from about 1624 to about 1674, from about 1675 to about 1725, from about 1726 to about 1776, from about 1777 to about 1827, from about 1828 to about 1878, from about 1879 to about 1929, from about 1930 to about 1980, from about 1981 to about 2031, from about 2032 to about 2082, from about 2083 to about 2133, from about 2134 to about 2184, from about 2185 to about 2235, from about 2236 to about 2286, from about 2287 to about 2337, from about 2338 to about 2388, from about 2389 to about2489, from about 2490 to about 2540, from about 2451 to about 2501, from about 2502 to about 2554, about 2600 to about 2650, about 2651 to about 2700, about 2701 to about 2750, about 2751 to about 2800, about 2801 to about 2850, about 2851 to about 2900, about 2901 to about 2950, about 2951 to about 3000, about 3001 to about 3050, about 3051 to about 3100, about 3101 to about 3150, about 3151 to about 3200, about 3201 to about 3250, about 3251 to about 3300, and about 3301 to about 3334 of the polynucleotide sequence shown in FIGS. 7A–E (SEQ ID NO:39), or the complementary strand thereto, or the cDNA contained in the deposited clone (HWLHN83). Other representative examples of polynucleotide fragments of the invention include, for example, fragments that comprise, or alternatively consist of, a sequence from about nucleotide 1 to about 42, from about 181 to about 2775, from about 984 to about 1142, from about 1485 to about 1610, from about 2361 to about 2718, from about 61 to about 3060, from about 58 to about 3060, from about 58 to about 183, from about 58 to about 2775, from about 2776 to about 2850, from about 2851 to about 3060, from about 868 to about 1320, from about 868 to about 915, from about 925 to about 957, about 960 to about 1017, about 1042 to about 1140, about 1267 to about 1320, about 870 to about 1320, about 1810 to about 1842, about 2038 to about 2079, about 2185 to about 2289, about 2995 to about 3054, about 190 to about 237, about 418 to about 462, about 58 to about 843, about 847 to about 1326, about 1366 to about 2424, about 1812 to about 1842, about 2776 to about 2850, about 2428 to about 3060, about 2851 to about 3060, and/or from about 490 to about 537 of the polynucleotide sequence shown in FIGS. 7A–E (SEQ ID NO:39), or the complementary strand thereto. In this context "about" includes the particularly recited ranges, larger or smaller by several (5, 4, 3, 2, or 1) nucleotides, at either terminus or at both termini. Polynucleotides which hybridize to any 1, 2, 3, 4, 5 or more of these polynucleotide fragments are also encompassed by the invention. Moreover, polypeptides encoded by these polynucleotides and/or polynucleotide fragments are also encompassed by the invention. Moreover, polypeptides encoded by the polynucleotides and/or polynucleotide fragments are also encompassed by the invention. which demonstrates a TR13 functional activity. By a polypeptide demonstrating a TR13 "functional activity" is meant, a polypeptide capable of displaying one or more known functional activities associated with a full-length (complete) TR13 protein. Such functional activities include, but are not limited to, biological activity (e.g., cell proliferation activity, ability to cause cell death including ability to induce apoptosis), antigenicity (ability to bind (or compete with a TR13 polypeptide for binding) to an anti-TR13 antibody), immunogenicity (ability to generate antibody which binds to a TR13 polypeptide), ability to form multimers with TR13 polypeptides of the invention, and ability to bind to a receptor or ligand for a TR13 polypeptide.

In one embodiment where one is assaying for the ability to bind or compete with full-length TR13 polypeptide for binding to anti-TR13 antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and in immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a TR13 ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., *Microbiol. Rev.* 59:94–123 (1995). In another embodiment, physiological correlates of TR13 binding to its substrates (signal transduction) can be assayed.

In addition, assays described herein (see, for example, Examples 5, and 16–21) and those otherwise known in the art may routinely be applied to measure the ability of TR13 polypeptides and fragments, variants derivatives and analogs thereof to elicit a particular biological activity (e.g., to inhibit Fas ligand and/or TRAIL induced apoptosis, to enhance Fas ligand induced apoptosis, to regulate (e.g., inhibit) B cell proliferation (see, e.g., Example 33), to regulate proliferation of other cells, and/or to inhibit hematopoiesis in vitro or in vivo). For example, techniques known in the art (such as for example assaying for thy thymidine incorporation), may be applied or routinely modified to assay for the ability of the compositions of the invention to regulate (e.g., inhibit and/or enhance apoptosis) and/or to regulate (e.g., inhibit and/or enhance) proliferation of hematopoietic cells. Additionally, assays desribed herein (see e.g., Example 15 and Example 33) and otherwise known in the art may be applied or routinely modified to assay for the ability of the compositions of the invention to inhibit or stimulate B cell proliferation.

Representative examples of TR14 polynucleotide fragments of the invention include, for example, fragments that comprise, or alternatively, consist of, a sequence from about nucleotide 1 to about 50, from about 51 to about 108, from about 109 to about 159, from about 160 to about 210, from about 211 to about 261, from about 262 to about 273, from about 274 to about 324, from about 325 to about 375, from about 376 to about 426, from about 427 to about 477, from about 478 to about 528, from about 529 to about 579, from about 580 to about 630, from about 631 to about 681, from about 682 to about 732, from about 733 to about 744, from about 745 to about 798, from about 799 to about 849, from about 850 to about 900, from about 901 to about 951, from about 952 to about 1002, from about 1003 to about 1053, from about 1054 to about 1104, from about 1105 to about 1155, from about 1156 to about 1164, from about 1165 to about 1197, from about 1198 to about 1248, from about 1249 to about 1266, from about 1267 to about 1317, from about 1318 to about 1368, from about 1369 to about 1419, from about 1420 to about 1470, from about 1471 to about 1521, from about 1522 to about 1572, from about 1573 to about 1623, from about 1624 to about 1674, from about 1675 to about 1725, from about 1726 to about 1776, from about 1777 to about 1827, from about 1828 to about 1878, from about 1879 to about 1929, from about 1930 to about 1980, from about 1981 to about 2031, from about 2032 to about 2082, from about 2083 to about 2133, from about 2134 to about 2184, from about 2185 to about 2235, from about 2236 to about 2286, from about 2287 to about 2337, from about 2338 to about 2388, from about 2389 to about 2489, from about 2490 to about 2540, from about 2451 to about 2501, from about 2502 to about 2552, from about 2553 to about 2603, from about 2604 to about 2654, from about 2655 to about 2705, from about 2706 to about 2756, from about 2806 to about 2856, from about 2857 to about 2907, from about 2908 to about 2958, from about 2959 to about 3009, from about 3010 to about 3060, from about 3061 to about 3111, and/or from about 3112 to about 3152 of the polynucleotide sequence shown in FIGS. 10A–H (SEQ ID NO:60), or the complementary strand thereto, or the cDNA contained in the deposited clone (HMSHK47). Other representative examples of polynucleotide fragments of the invention include, for example, fragments that comprise, or alternatively, consist of, a sequence from about nucleotide 1 to about 1451, from about 1761 to about 2251, from about 89 to about 766, from about 89 to about 487, from about 488 to about 538, from about 539 to about 766, from about 92 to about 160, from about 212 to about 243, from about 281 to about 313, from about 314 to about 343, from about 281 to about 343, from about 325 to about 433, and/or 550 to about 766 of the polynucleotide sequence shown in FIGS. 10A–H (SEQ ID NO:60), or the complementary strand thereto. In this context "about" includes the particularly recited ranges, larger or smaller by several (5, 4, 3, 2, or 1) nucleotides, at either terminus or at both termini. Polynucleotides which hybridize to any 1, 2, 3, 4, 5 or more of these polynucleotide fragments are also encompassed by the invention. Moreover, polypeptides encoded by these polynucleotides and/or polynucleotide fragments are also encompassed by the invention.

Alternative representative examples of TR14 polynucleotide fragments of the invention include, for example, fragments that comprise, or alternatively, consist of, a sequence from about nucleotide 1 to about 50, from about 51 to about 108, from about 109 to about 159, from about 160 to about 210, from about 211 to about 261, from about 262 to about 273, from about 274 to about 324, from about 325 to about 375, from about 376 to about 426, from about 427 to about 477, from about 478 to about 528, from about 529 to about 579, from about 580 to about 630, from about 631 to about 681, from about 682 to about 732, from about 733 to about 744, from about 745 to about 798, from about 799 to about 849, from about 850 to about 900, from about 901 to about 951, from about 952 to about 1002, from about 1003 to about 1053, from about 1054 to about 1104, from about 1105 to about 1155, from about 1156 to about 1164, from about 1165 to about 1197, from about 1198 to about 1248, from about 1249 to about 1266, from about 1267 to about 1317, from about 1318 to about 1368, from about 1369 to about 1419, from about 1420 to about 1470, from about 1471 to about 1521, from about 1522 to about 1572, from about 1573 to about 1623, from about 1624 to about 1674, from about 1675 to about 1725, from about 1726 to about 1776, from about 1777 to about 1827, from about 1828 to about 1878, from about 1879 to about 1929, from about 1930 to about 1980, from about 1981 to about 2031, from about 2032 to about 2082, from about 2083 to about 2133, from about 2134 to about 2184, from about 2185 to about 2235, from about 2236 to about 2286, from about 2287 to about 2337, from about 2338 to about 2388, from about 2389 to about 2489, from about 2490 to about 2540, from about 2451 to about 2501, from about 2502 to about 2552, from about 2553 to about 2603, from about 2604 to about 2654, from about 2655 to about 2705, from about 2706 to about 2756, from about 2806 to about 2856, from about 2857 to about 2907, from about 2908 to about 2958, from about 2959 to about 3009, from about 3010 to about 3060, from about 3061 to about 3111, from about 3112 to about 3162, from about 3163 to about 3213, from about 3214 to about 3264, from about 3265 to about 3315, from about 3316 to about 3366, from about 3367 to about 3417, from about 3418 to about 3468, from about 3469 to about 3519, from about 3520 to about 3566, from about 3567 to about 3599, from about 3600 to about 3649, from about 3650 to about 3699, from about 3700 to about 3749, from about 3750 to about 3799, and/or from 3800 to about 3861 of the polynucleotide sequence shown in FIGS. 4A–E (SEQ ID NO:4), or the complementary strand thereto, or the cDNA contained in the deposited clone (HMSHK47). Other representative examples of polynucleotide fragments of the invention include, for example, fragments that comprise, or alternatively, consist of, a sequence from about nucleotide 1 to about 1451, from about 1761 to about 2251, from about 3133 to about 3861, from about 89 to about 766, from about 89 to about 487, from about 488 to about 538, from about 539 to about 766, from about 92 to about 160, from about 212 to about 243, from about 281 to about 313, from about 314 to about 343, from about 281 to about 343, from about 325 to about 433, and/or 550 to about 766 of the polynucleotide sequence shown in FIGS. 4A–E (SEQ ID NO:4), or the complementary strand thereto. In this context "about" includes the particularly recited ranges, larger or smaller by several (5, 4, 3, 2, or 1) nucleotides, at either terminus or at both termini. Polynucleotides which hybridize to any 1, 2, 3, 4, 5 or more of these polynucleotide fragments are also encompassed by the invention. Moreover, polypeptides encoded by these polynucleotides and/or polynucleotide fragments are also encompassed by the invention.

Preferably, the polynucleotide fragments of the invention encode a polypeptide which demonstrates a TR14 functional activity. By a polypeptide demonstrating a TR14 "functional activity" is meant, a polypeptide capable of displaying one or more known functional activities associated with a full-length (complete) TR14 protein. Such functional activities include, but are not limited to, biological activity, antigenicity (ability to bind (or compete with a TR14 polypeptide for binding) to an anti-TR14 antibody), immunogenicity (ability to generate antibody which binds to a TR14 polypeptide), ability to form multimers with TR14 polypeptides of the invention, and ability to bind to a receptor or ligand for a TR14 polypeptide.

In one embodiment where one is assaying for the ability to bind or compete with full-length TR14 polypeptide for binding to anti-TR14 antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a TR14 ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky et al., *Microbiol. Rev.* 59:94–123 (1995). In another embodiment, physiological correlates of TR14 binding to its substrates (signal transduction) can be assayed.

In addition, assays described herein (see, for example, Examples 5 and 15–21 and 33 and those otherwise known in the art may routinely be applied to measure the ability of TR14 polypeptides and fragments, variants derivatives and analogs thereof to elicit a particular biological activity (e.g., to inhibit TRAIL induced apoptosis, to regulate (e.g., inhibit) B cell proliferation (see, e.g., Example 33), and/or to inhibit hematopoiesis in vitro or in vivo). For example, techniques known in the art (such as for example assaying for thymidine incorporation), may be applied or routinely modified to assay for the ability of the compositions of the invention to regulate (e.g., inhibit apoptosis) and/or to regulate (e.g., inhibit) proliferation of hematopoietic cells. Additionally, assays desribed herein (see e.g., Example 15 and Example 33) and otherwise known in the art may be applied or routinely modified to assay for the ability of the compositions of the invention to inhibit or stimulate B cell proliferation.

Other methods will be known to the skilled artisan and are within the scope of the invention.

Preferred nucleic acid fragments of the present invention include nucleic acid molecules encoding a member selected from the group: a polypeptide comprising or alternatively, consisting of any combination of one, two, three or all four TR13 cysteine rich domains (amino acid residues from about 105 to about 170, from about 251 to about 264, from about 331 to about 410 and from about 580 to about 610 in FIGS. 1A–D (amino acids from about 105 to about 170, from about 251 to about 265, from about 331 to about 410 and from about 580 to about 610 in SEQ ID NO:1). Since, as discussed above, the location of these domains have been predicted by computer analysis, one of ordinary skill would appreciate that the amino acid residues constituting these domains may be the particularly recited ranges for each domain or may vary slightly (e.g., by about 1, 2, 3, 4, 5, 10, or 15 residues at either extreme or at both extremes) depending on the criteria used to define each domain.

Additional preferred nucleic acid fragments of the present invention include nucleic acid molecules encoding a member selected from the group: a polypeptide comprising or alternatively, consisting of the TR13 receptor extracellular domain (amino acids 1 to 906 in FIGS. 7A–E); a polypeptide comprising or alternatively, consisting of, the mature TR13 receptor extracellular domain (amino acids 42 to 906 in FIGS. 7A–E); a polypeptide comprising or alternatively, consisting of, one or more of the TR13 cysteine rich domains disclosed in FIGS. 7A–E (e.g., amino acid residues from about 271 to about 421, from about 271 to about 286, about 290 to about 300, about 301 to about 320, about 329 to about 361, about 404 to about 421, and from about 585 to about 595 in FIGS. 7A–E (amino acid residues from about 271 to about 421, from about 271 to about 286, about 290 to about 300, about 301 to about 320, about 329 to about 361, about 404 to about 421, and from about 585 to about 595 in SEQ ID NO:39 and SEQ ID NO:40); a polypeptide comprising, or alternatively, consisting of the TRL13 transmembrane domain (amino acids 907 to 931 in FIGS. 7A–E); and a polypeptide comprising, or alternatively consisting of the TR13 intracellular domain (amino acid 932 to 1001 in FIGS. 7A–E). As above, since the location of these domains have been predicted by computer analysis, one of ordinary skill would appreciate that the amino acid residues constituting these domains may be the particularly recited ranges for each domain or may vary slightly (e.g., by about 1, 2, 3, 4, 5, 10, or 15 residues at either extreme or at both extremes) depending on the criteria used to define each domain.

It is believed that the cysteine rich motifs of TR13 disclosed in FIGS. 1A–D are important for interactions between TR13 and its ligands. Accordingly, specific embodiments of the invention are directed to polynucleotides encoding polypeptides which comprise, or alternatively consist of, the amino acid sequence of amino acid residues from about 105 to about 170, from about 251 to about 265, from about 331 to about 410, and from about 580 to about 610 of SEQ ID NO:5 (corresponding to amino acid residues from about 105 to about 170, from about 251 to about 265, from about 331 to about 410, and from about 580 to about 610 of FIGS. 4A–E). In a specific embodiment, the polynucleotides encoding TR13 polypeptides of the invention comprise or alternatively consist of, polynucleotide sequences encoding any combination of 2, 3, or all four of the cysteine-rich motifs of TR13. In this context, "about" includes the particularly recited ranges, larger or smaller by several (5, 4, 3, 2, or 1) nucleotides, at either terminus or at both termini. Polypeptides encoded by these polynucleotides are also encompassed by the invention.

Further, specific embodiments of the invention are directed to polynucleotides encoding polypeptides which comprise, or alternatively consist of, the amino acid sequence of amino acid residues from about 271 to about 421, from about 271 to about 286, from about 290 to about 300, from about 301 to about 320, about 329 to about 361, about 404 to about 421, and about 585 to about 595 of SEQ ID NO:40 (corresponding to amino acid residues from about 271 to about 421, from about 271 to about 286, from about 290 to about 300, from about 301 to about 320, about 329 to about 361, about 404 to about 421, and about 585 to about 595 of FIGS. 7A–E). In a specific embodiment, the polynucleotides encoding TR13 polypeptides of the invention comprise or alternatively consist of, polynucleotide sequences encoding any combination of 2, 3, or all four of the cysteine-rich motifs of TR13 disclosed in FIGS. 7A–E. In this context, "about" includes the particularly recited ranges, larger or smaller by several (5, 4, 3, 2, or 1) nucleotides, at either terminus or at both termini. Polypeptides encoded by these polynucleotides are also encompassed by the invention.

Preferred nucleic acid fragments of the invention encode a full-length TR13 polypeptide lacking the nucleotides encoding the amino terminal methionine (e.g., nucleotides 34–750 in SEQ ID NO:1), as it is known that the methionine is cleaved naturally and such sequences may be useful in genetically engineering TR13 expression vectors. Polypeptides encoded by such nucleic acids are also contemplated by the invention.

Preferred nucleic acid fragments of the invention encode a full-length TR13 polypeptide lacking the nucleotides encoding the amino terminal methionine (e.g., nucleotides 61–1001 in FIGS. 7A–E and SEQ ID NO:39), as it is known that the methionine is cleaved naturally and such sequences may be useful in genetically engineering TR13 expression vectors. Polypeptides encoded by such nucleic acids are also contemplated by the invention.

Preferred nucleic acid fragments of the present invention further include nucleic acid molecules encoding epitope-bearing portions of the TR13 receptor protein. In particular, such nucleic acid fragments of the present invention include nucleic acid molecules encoding: a polypeptide comprising or alternatively consisting of, amino acid residues from about 1 to about 170 in FIGS. 1A–D (corresponding to about amino acid 1 to about 170 in SEQ ID NO:2); a polypeptide comprising or alternatively consisting of, amino acid residues from about 210 to about 318 in FIGS. 1A–D (corresponding to about amino acid 210 to about 318 in SEQ ID NO:2); a polypeptide comprising or alternatively consisting of, amino acid residues from about 343 to about 480 in FIGS. 1A–D (corresponding to about amino acid 343 to about 480 in SEQ ID NO:2); a polypeptide comprising or alternatively consisting of, amino acid residues from about 548 to about 592 in FIGS. 1A–D (corresponding to about amino acid 548 to about 592 in SEQ ID NO:2); and a polypeptide comprising or alternatively consisting of, amino acid residues from about 632 to about 742 in FIGS. 1A–D (corresponding to about amino acid 632 to about 742 in SEQ ID NO:2). The inventors have determined that the above polypeptide fragments are antigenic regions of the TR13 protein. Methods for determining other such epitope-bearing portions of the TR13 protein are described in detail below.

Preferred nucleic acid fragments of the present invention further include nucleic acid molecules encoding antigenic fragments of the TR13 receptor protein. In particular, such nucleic acid fragments of the present invention include nucleic acid molecules encoding: a polypeptide comprising or alternatively consisting of, amino acid residues from about M1 to about A9, about K12 to about L20, about N47 to about T55, about H58 to about S66, about D63 to about S71, about P77 to about F85, about A90 to about Q98, about F136 to about Q144, about S152 to about C160, about R159 to about A167, about A211 to about M219, about M235 to about V243, about V266 to about V274, about W277 to about S285, about I290 to about F298, about A310 to about V318, about E343 to about C351, about I360 to about H368, about G391 to about I399, about F409 to about T417, about S436 to about Y444, about C453 to about S461, about I472 to about S480, about Y548 to about S556, about C557 to about I565, about V567 to about V575, about T584 to about G592, about R632 to about G640, about W680 to about Y688, about Q684 to about K692, about T698 to about A706, about S726 to about S734, and about S734 to about L742 of SEQ ID NO:2 (FIGS. 1A–D) correspond to the highly antigenic regions of the TR13 protein, predicted using the Jameson-Wolf antigenic index (See FIG. 3 and Table I). These highly antigenic fragments correspond to the amino acid residues illustrated in FIG. 1A-D and in SEQ ID NO:2. In this context, "about" includes the particularly recited ranges, larger or smaller by several (5, 4, 3, 2, or 1) nucleotides, at either terminus or at both termini. Methods for determining other such antigenic fragments of the TR13 protein are described in detail below.

Additional preferred nucleic acid fragments of the present invention further include nucleic acid fragments encoding: a polypeptide comprising or alternatively consisting of, amino acid residues from about 1 to about 262 in FIGS. 7A–E (corresponding to about amino acid 1 to about 262 in SEQ ID NO:40); a polypeptide comprising or alternatively consisting of, amino acid residues from about 264 to about 423 in FIGS. 7A–E (corresponding to about amino acid 264 to about 423 in SEQ ID NO:40); a polypeptide comprising or alternatively consisting of, amino acid residues from about 437 to about 789 in FIGS. 7A–E (corresponding to about amino acid 437 to about 789 in SEQ ID NO:40); and a polypeptide comprising or alternatively consisting of, amino acid residues from about 791 to about 1001 in FIGS. 7A–E (corresponding to about amino acid 791 to about 1001 in SEQ ID NO:40). The inventors have determined that the above polypeptide fragments are antigenic regions of the TR13 protein. Methods for determining other such epitope-bearing portions of the TR13 protein are described in detail below.

Figure 9:
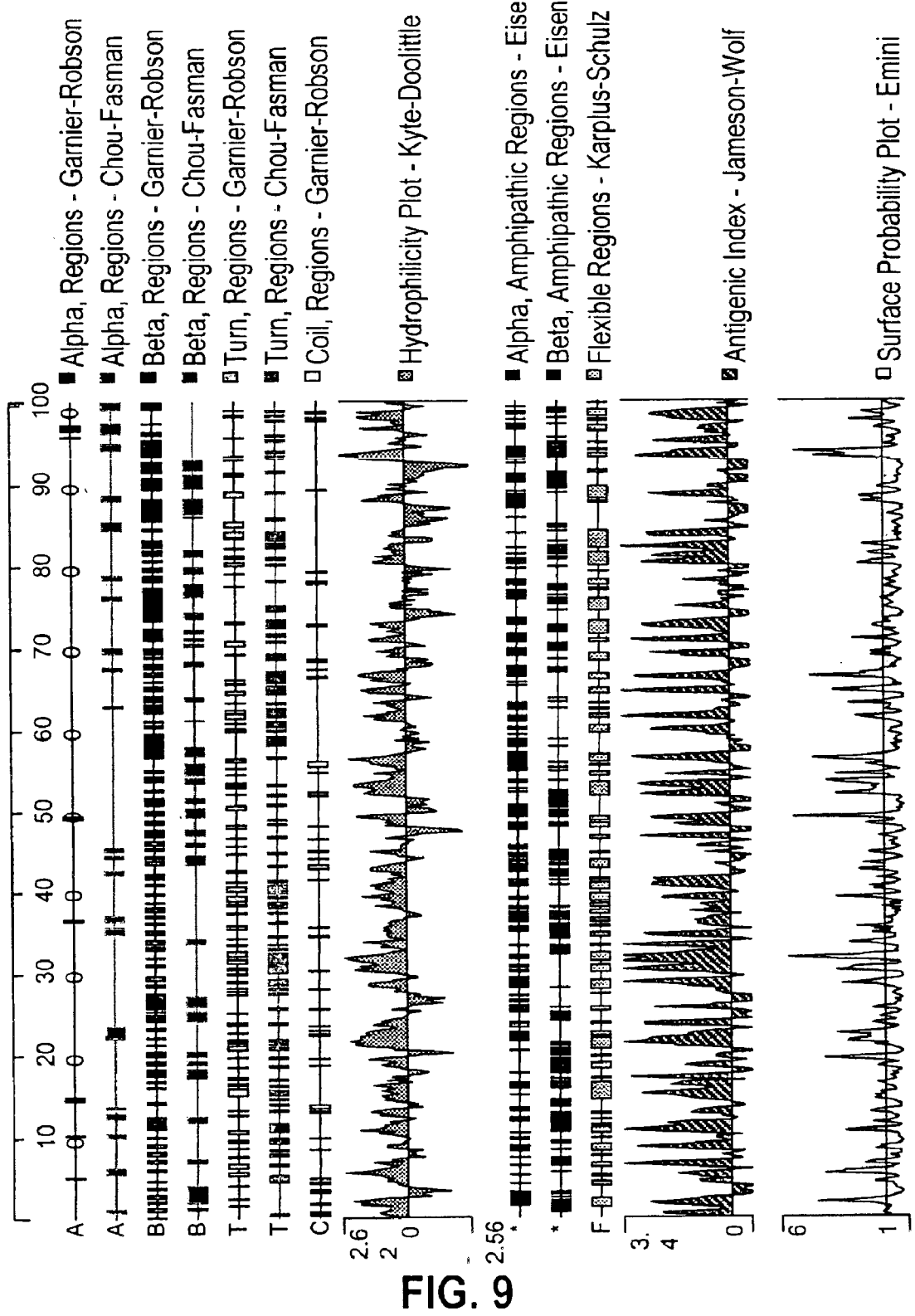
FIG. 9 shows an analysis of the full-length TR13 amino acid sequence disclosed in FIGS. 7A–E (SEQ ID NO:40). Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues from about M1 to about H9, about V14 to about I22, about H47 to about H55, about C61 to about R69, about L82 to about E90, about D102 to about P110, about K109 to about S117, about F124 to about H132, about M141 to about E149, about S146 to about C154, about S157 to about W165, about F168 to about T176, about N182 to about N190, about Q207 to about A215, about P213 to about M221, about M221 to about E229, about V233 to about V241, about T253 to about V261, about T282 to about S290, about N298 to about T306, about C308 to about Y316, about K315 to about S323, about P328 to about F336, about A341 to about Q349, about F387 to about Q395, about 5403 to about C411, about T409 to about P417, about F443 to about N451, about W451 to about Y459, about A462 to about M470, about G478 to about M486, about A487 to about A495, about V517 to about V525, about T527 to about Q535, about I541 to about F549, about A561 to about V569, about E594 to about C602, about I611 to about H619, about G643 to about I650, about P686 to about K694, about C704 to about S712, about R722 to about I730, about E727 to about T735, about P746 to about G754, about D776 to about L784, about Y799 to about S807, about C808 to about I816, about V818 to about V826, about T835 to about G843, about R883 to about G891, about K932 to about K940, about Q935 to about K943, about T949 to about A957, about S977 to about S985, about S981 to about P989, and about N986 to about L994 of SEQ ID NO:40 (FIGS. 7A–E) correspond to the highly antigenic regions of the TR13 protein, predicted using the Jameson-Wolf antigenic index (See FIG. 9 and Table III). These highly antigenic fragments correspond to the amino acid residues illustrated in FIGS. 7A–E and in SEQ ID NO:40.

Additional preferred nucleic acid fragments of the present invention encoding antigenic fragments of the TR13 receptor protein include nucleic acid molecules encoding: a polypeptide comprising or alternatively consisting of, amino acid residues from about M1 to about H9, about V14 to about I22, about H47 to about H55, about C61 to about R69, about L82 to about E90, about D102 to about P110, about K109 to about S117, about F124 to about H132, about M141 to about E149, about S146 to about C154, about S157 to about W165, about F168 to about T176, about N182 to about N190, about Q207 to about A215, about P213 to about M221, about M221 to about E229, about V233 to about V241, about T253 to about T261, about T282 to about S290, about N298 to about T306, about C308 to about Y316, about K315 to about S323, about P328 to about F336, about A341 to about Q349, about F387 to about Q395, about S403 to about C411, about T409 to about P417, about F443 to about N451, about W451 to about Y459, about A462 to about M470, about G478 to about M486, about A487 to about A495, about V517 to about V525, about T527 to about Q535, about I541 to about F549, about A561 to about V569, about E594 to about C602, about I611 to about H619, about G643 to about I650, about P686 to about K694, about C704 to about S712, about R722 to about I730, about E727 to about T735, about P746 to about G754, about D776 to about L784, about Y799 to about S807, about C808 to about I816, about V818 to about V826, about T835 to about G843, about R883 to about G891, about K932 to about K940, about Q935 to about K943, about T949 to about A957, about S977 to about S985, about S981 to about P989, and about N986 to about L994 of SEQ ID NO:40 (FIGS. 7A–E) correspond to the highly antigenic regions of the TR13 protein, predicted using the Jameson-Wolf antigenic index (See FIG. 9 and Table III). These highly antigenic fragments correspond to the amino acid residues illustrated in FIG. 7A–E and in SEQ ID NO:40. In this context, "about" includes the particularly recited ranges, larger or smaller by several (5, 4, 3, 2, or 1) nucleotides, at either terminus or at both termini. Methods for determining other such antigenic fragments of the TR13 protein are described in detail below.

Additionally, it is believed that the extracellular cysteine rich motif of TR14 disclosed in FIGS. 10A–H or, alternatively, FIGS. 4A–E is important for interactions between TR14 and its ligands. Accordingly, specific embodiments of the invention are directed to nucleic acid molecules encoding polypeptides which comprise, or alternatively consist of, preferably amino acids Cys-31 to Cys-104 of FIGS. 10A–B and SEQ ID NO:61, or, alternatively, the amino acid sequence of amino acid residues from about 70 to about 90 of FIG. 10A and SEQ ID NO:61 (corresponding to amino acid residues from about 65 to about 85 of FIGS. 4A–E or SEQ ID NO:5). In this context, "about" includes the particularly recited ranges, larger or smaller by several (5, 4, 3, 2, or 1) nucleotides, at either terminus or at both termini. Polypeptides encoded by these polynucleotides are also encompassed by the invention.

Preferred nucleic acid fragments of the present invention include nucleic acid molecules encoding a member selected from the group: a polypeptide comprising or alternatively, consisting of, the TR14 receptor extracellular domain (preferably amino acid residues from about 1 to 138 in FIGS. 10A–H or, alternatively, from about 1 to about 133 in FIGS. 4A–E); a polypeptide comprising or alternatively, consisting of, the TR14 cysteine rich domain (preferably amino acid residues from about 31 to about 104 of FIGS. 10A–H, or amino acid residues from about 70 to 90 in FIGS. 10A, or, alternatively, from about 65 to about 85 in FIGS. 4A–E); a polypeptide comprising or alternatively, consisting of the TR14 transmembrane domain (preferably amino acid residues from about 139 to 155 in FIGS. 10A–H or, alternatively, 134 to about 150 in FIGS. 4A–E); and a polypeptide comprising or alternatively, consisting of, the TR14 intracellular domain (preferably amino acid residues from about 156 to about 231 in FIGS. 10A–H or, alternatively, amino acid residues from about 151 to about 226 in FIGS. 4A–E). Since the location of these domains have been predicted by computer analysis, one of ordinary skill would appreciate that the amino acid residues constituting these domains may be the particularly recited ranges for each domain or may vary slightly (e.g., by about 1, 2, 3, 4, 5, 10, or 15 residues at either extreme or at both extremes) depending on the criteria used to define each domain.

Preferred nucleic acid fragments of the invention encode a full-length TR14 polypeptide lacking the nucleotides encoding the amino terminal methionine (e.g., nucleotides 70–759 of FIGS. 10A–H or SEQ ID NO:60, or nucleotides 102–765 in SEQ ID NO:4), as it is known that the methionine is cleaved naturally and such sequences may be useful in genetically engineering TR14 expression vectors. Polypeptides encoded by such nucleic acids are also contemplated by the invention.

Preferred nucleic acid fragments of the present invention further include nucleic acid molecules encoding epitope-bearing portions of the TR14 receptor protein. In particular, preferred epitope-bearing polypeptides of the present invention comprise, or alternatively consist of, one, two, three, four, five, six, or all six of the immunogenic epitopes of the TR14 protein shown in SEQ ID NO:61 as residues: Asp-2 to Asp-10, Thr-17 to Asp-38, Pro-45 to Ser-52, Pro-88 to Arg-95, Thr-108 to Glu-115, Thr-131 to Glu-136, Phe-166 to Gly-174, Ala-180 to Ala-200, and Gln-224 to Met-231. Fragments and/or variants of these polypeptides, such as, for example, fragments and/or variants as described herein, are encompassed by the invention. Polynucleotides encoding these polypeptides (including fragments and/or variants) are also encompassed by the invention, as are antibodies that bind these polypeptides.

Alternatively, such nucleic acid fragments of the present invention include nucleic acid molecules encoding: a polypeptide comprising or alternatively consisting of, amino acid residues from about 2 to about 24 in FIGS. 4A–E (corresponding to about amino acid 2 to about 24 in SEQ ID NO:5); a polypeptide comprising or alternatively consisting of, amino acid residues from about 42 to about 52 in FIGS. 4A–E (corresponding to about amino acid 42 to about 52 in SEQ ID NO:5); a polypeptide comprising or alternatively consisting of, amino acid residues from about 80 to about 115 in FIGS. 4A–E (corresponding to about amino acid 80 to about 115 in SEQ ID NO:5 and about amino acid 85 to about 120 of SEQ ID NO:61); and a polypeptide comprising or alternatively consisting of, amino acid residues from about 155 to about 226 in FIGS. 4A–E (corresponding to about amino acid 155 to about 226 in SEQ ID NO:5 and about amino acid 160 to about amino acid 231 of SEQ ID NO:61). The inventors have determined that the above polypeptide fragments are antigenic regions of the TR14 protein. Methods for determining other such epitope-bearing portions of the TR14 protein are described in detail below.

Alternative nucleic acid fragments of the present invention further include nucleic acid molecules encoding antigenic fragments of the TR14 receptor protein. In particular, such nucleic acid fragments of the present invention include nucleic acid molecules encoding: a polypeptide comprising or alternatively consisting of, amino acid residues of SEQ ID NO:5 (FIGS. 4A–E) from about T3 to about S11, from about V16 to about R24, from about Q44 to about M52, from about F85 to about G93 (about F90 to about G98 of SEQ ID NO:61), from about T103 to about V111 (about T108 to about V116 of SEQ ID NO:61), from about F161 to about G169 (about F165 to about G174 of SEQ ID NO:61), from about V187 to about A195 (from about V192 to about A200 of SEQ ID NO:61), from about P218 to about M226 (about P223 to about M231 of SEQ ID NO:61) correspond to the highly antigenic regions of the TR14 protein, predicted using the Jameson-Wolf antigenic index (See FIG. 11 and Table IV). These highly antigenic fragments correspond to the amino acid residues illustrated in FIG. 4A-E and in SEQ ID NO:5 (or FIGS. 10A–H and SEQ ID NO:61, as indicated above). In this context, "about" includes the particularly recited ranges, larger or smaller by several (5, 4, 3, 2, or 1) nucleotides, at either terminus or at both termini. Methods for determining other such antigenic fragments of the TR14 protein are described in detail below.

The data presented in FIG. 3 are also represented in tabular form in Table I. The columns in Table I are labeled with the headings "Res", "Position", and Roman Numerals I–XIV. The column headings refer to the following features of the amino acid sequence presented in FIG. 3 and Table I: "Res": amino acid residue of SEQ ID NO:2 and FIGS. 1A–D; "Position": position of the corresponding residue within SEQ ID NO:2 and FIGS. 1A–D; I: Alpha, Regions—Garnier-Robson; II: Alpha, Regions—Chou-Fasman; III: Beta, Regions—Garnier-Rubson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

The data presented in FIG. 9 are also represented in tabular form in Table III. The columns in Table III are labeled with the headings "Res", "Position", and Roman Numerals I–XIV. The column headings refer to the following features of the amino acid sequence presented In FIG. 9 and Table III: "Res": amino acid residue of SEQ ID NO:40 and FIGS. 7A–E; "Position": position of the corresponding residue within SEQ ID NO:40 and FIGS. 7A–E; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Aniphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

In additional embodiments, the nucleic acid molecule of the invention encodes a polypeptide comprising, or alternatively consisting of, a functional attribute of TR13. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of TR13.

The data representing the structural or functional attributes of TR13 (SEQ ID NO:40) set forth in FIG. 9 and/or Table III, as described above, was generated using the various modules and algorithms of the DNA*STAR set on default parameters. In a preferred embodiment, the data presented in columns VIII, IX, XIII, and XIV of Table III can be used to determine regions of TR13 which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table I, be represented or identified by using tabular representations of the data presented in FIG. 3. The DNA*STAR computer algorithm used to generate FIG. 3 (set on the original default parameters) was used to present the data in FIG. 3 in a tabular format (See Table I). The tabular format of the data in FIG. 3 may be used to easily determine specific boundaries of a preferred region.

Certain preferred regions in these regards are set out in FIG. 9, but may, as shown in Table III, be represented or identified by using tabular representations of the data presented in FIG. 9. The DNA*STAR computer algorithm used to generate FIG. 9 (set on the original default parameters) was used to present the data in FIG. 9 in a tabular format (See Table III). The tabular format of the data in FIG. 9 may be used to easily determine specific boundaries of a preferred region.

The above-mentioned preferred regions set out in FIG. 3 and in Table I include, but are not limited to, regions of the aforementioned types identified by analysis of the amino acid sequence set out in FIGS. 1A–D. As set out in FIG. 3 and in Table I, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions.

The above-mentioned preferred regions set out in FIG. 9 and in Table III include, but are not limited to, regions of the aforementioned types identified by analysis of the amino acid sequence set out in FIG. 9. As set out in FIG. 9 and in Table III, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions.

Figure 11:
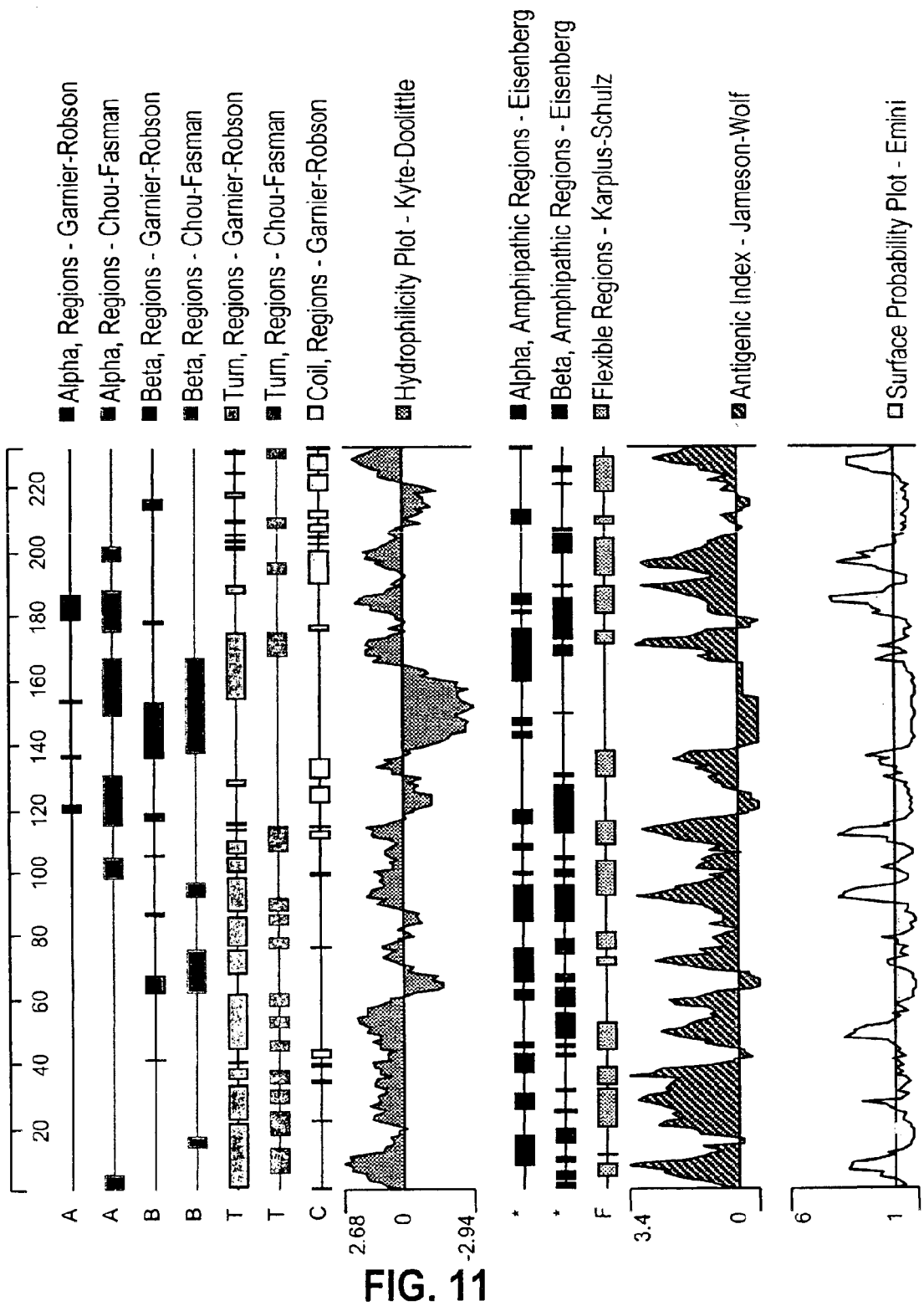
FIG. 11 shows an analysis of the full-length TR14 amino acid sequence disclosed in FIGS. 10A–H (SEQ ID NO: 61). Alpha, beta, turn and coil regions; hydrophilicity and hydrophobicity; amphipathic regions; flexible regions; antigenic index and surface probability are shown. The data are presented in tabular form, amino acid by amino acid, in Table IV, below.

The data presented in FIG. 11 are also represented in tabular form in Table IV. The columns in Table IV are labeled with the headings "Res", "Pos", and Roman Numerals I–XIV. The column headings refer to the following features of the amino acid sequence presented in FIGS. 10A–H, and 11: "Res": amino acid residue of SEQ ID NO:61 and FIGS. 10A–H; "Pos": position of the corresponding residue within SEQ ID NO:61 and FIGS. 10A–H; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XIII: Flexible Regions—Karplus-Schulz; XII: Antigenic Index—Jameson-Wolf; and XIV: Surface Probability Plot—Emini.

Figure 6:
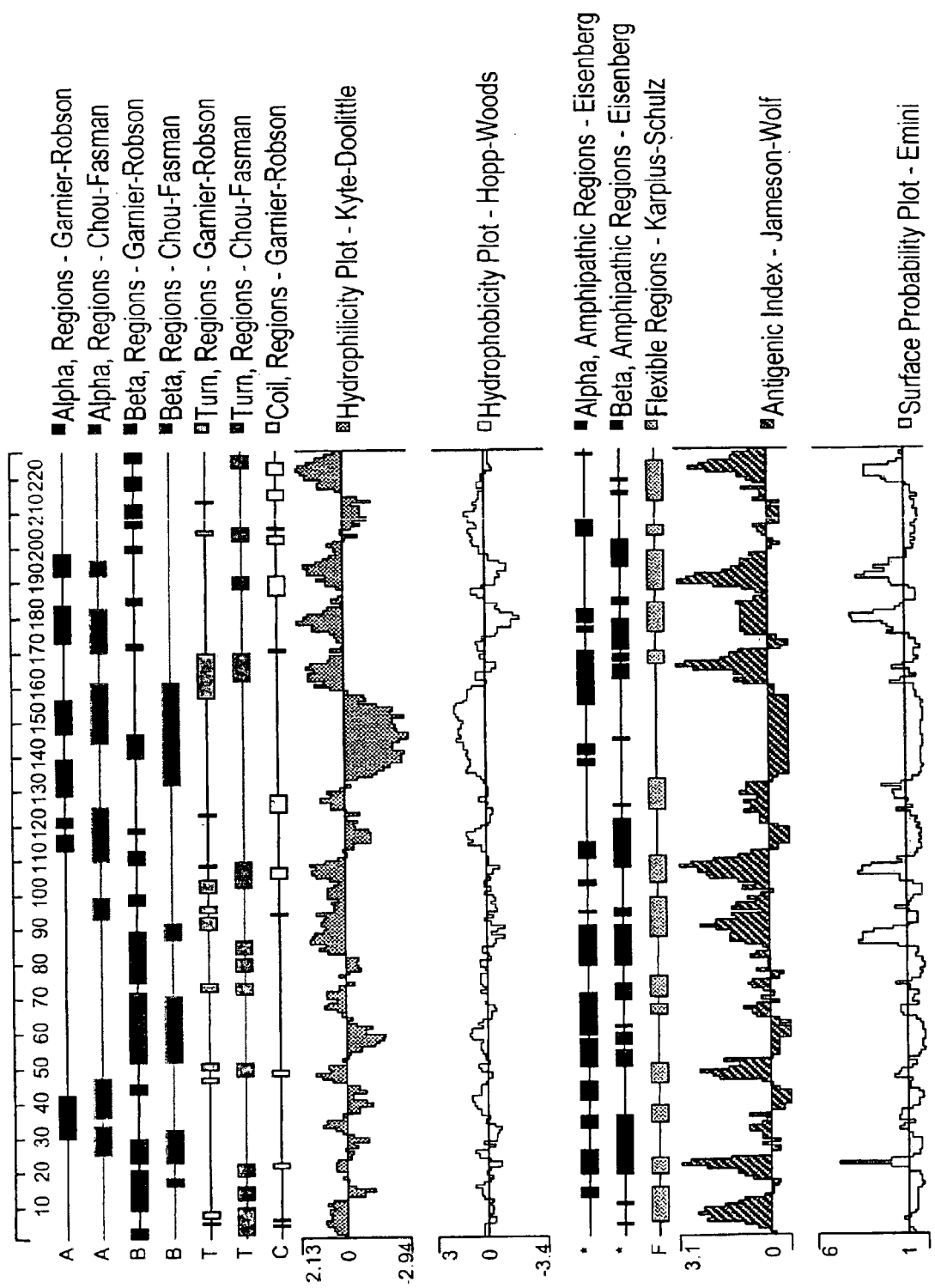
FIG. 6 shows an analysis of the TR14 amino acid sequence (SEQ ID NO:5). Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues from about T3 to about S11, from about V16 to about R24, from about Q44 to about M52, from about F85 to about G93, from about T103 to about V111, from about F161 to about G169, from about V187 to about A195, from about P218 to about M226 of SEQ ID NO:5 (FIGS. 4A–E) correspond to the highly antigenic regions of the TR14 protein, predicted using the Jameson-Wolf antigenic index (See FIG. 6 and Table II). These highly antigenic fragments correspond to the amino acid residues illustrated in FIGS. 4A–E and in SEQ ID NO:5.

The data presented in FIG. 6 are also represented in tabular form in Table II. As above, the columns in Table II are labeled with the headings "Res", "Position", and Roman Numerals I–XIV. The column headings refer to the following features of the amino acid sequence presented in FIG. 6 and Table II: "Res": amino acid residue of SEQ ID NO:5 and FIGS. 4A–E; "Position": position of the corresponding residue within SEQ ID NO:5 and FIGS. 4A–E; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

In additional embodiments, the polynucleotides of the invention encode functional attributes of TR14. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of TR14.

The data representing the structural or functional attributes of TR13 (SEQ ID NO:2) set forth in FIG. 3 and/or Table I, as described above, was generated using the various modules and algorithms of the DNA*STAR set on default parameters. In a preferred embodiment, the data presented in columns VIII, IX, XIII, and XIV of Table I can be used to determine regions of TR13 which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

The data representing the structural or functional attributes of TR14 (SEQ ID NO:61, as set forth in FIG. 11 and/or Table IV; or, alternatively, SEQ ID NO:5, as set forth in FIG. 6 and/or Table II), as described above, were generated using the various modules and algorithms of the DNA*STAR set on default parameters. In a preferred embodiment, the data presented in columns VIII, IX, XIII, and XIV of Table II can be used to determine regions of TR14 which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 6, but may, as shown in Table II, be represented or identified by using tabular representations of the data presented in FIG. 6. The DNA*STAR computer algorithm used to generate FIG. 6 (set on the original default parameters) was used to present the data in FIG. 6 in a tabular format (See Table II). The tabular format of the data in FIG. 6 may be used to easily determine specific boundaries of a preferred region.

Certain even more preferred regions in these regards are set out in FIG. 11, but may, as shown in Table IV, be represented or identified by using tabular representations of the data presented in FIG. 11. The DNA*STAR computer algorithm used to generate FIG. 11 (set on the original default parameters) was used to present the data in FIG. 11 in a tabular format (See Table IV). The tabular format of the data in FIG. 11 may be used to easily determine specific boundaries of a preferred region.

The above-mentioned preferred regions set out in FIG. 11 and in Table IV include, but are not limited to, regions of the aforementioned types identified by analysis of the amino acid sequence set out in FIGS. 10A–H. As set out in FIG. 11 and in Table IV, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions.

The above-mentioned preferred regions set out in FIG. 6 and in Table II include, but are not limited to, regions of the aforementioned types identified by analysis of the amino acid sequence set out in FIGS. 4A–E. As set out in FIG. 6 and in Table II, such preferred regions include Garnier-Robson alpha-regions, beta-regions, turn-regions, and coil-regions, Chou-Fasman alpha-regions, beta-regions, and turn-regions, Kyte-Doolittle hydrophilic regions and Hopp-Woods hydrophobic regions, Eisenberg alpha- and beta-amphipathic regions, Karplus-Schulz flexible regions, Jameson-Wolf regions of high antigenic index and Emini surface-forming regions.

TABLE I

| Res | Pos | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.73 | −0.31 | . | . | . | 1.40 | 1.44 |
| Asp | 2 | . | . | . | . | . | T | T | . | 1.12 | −0.26 | . | . | . | 2.25 | 1.62 |
| Gln | 3 | . | . | . | . | . | T | T | . | 0.92 | −0.29 | * | . | . | 2.50 | 2.20 |
| Ser | 4 | . | . | . | . | . | T | C | 0.64 | −0.21 | . | . | . | 2.05 | 2.24 |
| Thr | 5 | . | . | B | . | . | T | . | 0.44 | −0.26 | . | . | F | 1.60 | 0.72 |
| Gln | 6 | . | A | B | . | . | . | . | 0.70 | 0.24 | . | . | F | 0.35 | 0.42 |
| Ala | 7 | . | A | B | . | . | . | . | 0.70 | 0.27 | . | . | . | −0.05 | 0.31 |
| Cys | 8 | . | A | . | . | T | . | . | 0.74 | −0.11 | . | . | . | 0.70 | 0.37 |
| Ala | 9 | . | A | . | . | T | . | . | 1.01 | −0.60 | . | . | . | 1.00 | 0.43 |
| Gly | 10 | . | A | . | . | T | . | . | 0.66 | −0.50 | . | . | F | 0.85 | 0.58 |
| Glu | 11 | . | A | . | . | T | . | . | 0.62 | −0.43 | . | . | F | 0.85 | 0.58 |
| Lys | 12 | . | A | . | . | T | . | . | 1.21 | −0.50 | . | . | F | 1.10 | 0.78 |
| His | 13 | . | A | . | . | T | . | . | 1.99 | −0.60 | . | * | . | 1.65 | 1.27 |
| Cys | 14 | . | A | . | . | T | . | . | 2.23 | −1.03 | . | . | . | 1.90 | 1.43 |
| His | 15 | . | . | . | . | T | . | . | 2.23 | −0.60 | . | * | . | 2.20 | 0.71 |
| Asn | 16 | . | . | . | . | T | T | . | 1.42 | −0.17 | . | * | F | 2.50 | 0.52 |
| Arg | 17 | . | . | . | . | T | T | . | 1.34 | 0.01 | * | * | F | 1.65 | 0.79 |
| Gly | 18 | . | . | . | . | T | T | . | 0.68 | −0.06 | * | * | F | 2.00 | 0.79 |
| Gly | 19 | . | . | . | . | T | T | . | 1.46 | 0.23 | * | * | F | 1.15 | 0.43 |
| Leu | 20 | . | A | . | . | . | . | C | 0.89 | −0.17 | * | * | . | 0.75 | 0.43 |
| His | 21 | . | A | B | . | . | . | . | 0.08 | 0.44 | * | * | . | −0.60 | 0.43 |
| Phe | 22 | . | A | B | . | . | . | . | −0.24 | 0.70 | . | * | . | −0.60 | 0.36 |
| Arg | 23 | . | A | B | . | . | . | . | −0.71 | 0.70 | . | * | . | −0.60 | 0.67 |
| Met | 24 | . | A | B | . | . | . | . | −0.37 | 0.70 | . | * | . | −0.60 | 0.40 |
| Leu | 25 | . | A | B | . | . | . | . | 0.13 | 0.60 | . | * | . | −0.60 | 0.81 |
| Pro | 26 | . | A | . | . | . | . | C | −0.12 | 0.30 | . | * | . | −0.10 | 0.60 |
| Leu | 27 | . | . | . | B | T | . | . | 0.54 | 1.21 | * | . | . | −0.20 | 0.63 |
| Gln | 28 | . | . | . | B | T | . | . | −0.42 | 1.10 | . | . | . | −0.05 | 1.05 |
| Thr | 29 | . | . | . | B | T | . | . | −0.49 | 1.06 | * | . | . | −0.20 | 0.50 |
| Trp | 30 | . | . | B | B | . | . | . | 0.43 | 1.20 | * | . | . | −0.60 | 0.33 |
| His | 31 | . | . | B | B | . | . | . | 0.64 | 0.51 | * | . | . | −0.60 | 0.37 |
| Val | 32 | . | . | B | B | . | . | . | 0.87 | 0.51 | * | . | . | −0.60 | 0.44 |
| Cys | 33 | . | . | B | B | . | . | . | 0.52 | 0.53 | * | . | . | −0.60 | 0.43 |
| Arg | 34 | . | . | B | B | . | . | . | 0.02 | 0.04 | * | . | . | −0.30 | 0.31 |
| Gln | 35 | . | . | . | B | T | . | . | −0.50 | 0.23 | * | . | . | 0.10 | 0.34 |
| Ala | 36 | . | . | . | B | T | . | . | −1.17 | 0.27 | * | . | . | 0.10 | 0.53 |
| Gly | 37 | . | . | . | B | T | . | . | −1.12 | 0.49 | * | . | . | −0.20 | 0.23 |
| Leu | 38 | . | . | B | B | . | . | . | −0.46 | 1.17 | * | . | . | −0.60 | 0.11 |
| Leu | 39 | . | . | B | B | . | . | . | −0.88 | 1.17 | * | . | . | −0.60 | 0.19 |
| Phe | 40 | . | . | B | B | . | . | . | −1.69 | 1.16 | * | . | . | −0.60 | 0.28 |
| Leu | 41 | . | . | B | B | . | . | . | −1.31 | 1.41 | * | . | . | −0.60 | 0.28 |
| Gln | 42 | . | . | B | B | . | . | . | −1.27 | 1.16 | . | . | . | −0.60 | 0.52 |
| Thr | 43 | . | . | B | B | . | . | . | −0.46 | 0.86 | . | . | F | −0.45 | 0.81 |
| Leu | 44 | . | . | B | B | . | . | . | 0.06 | 0.47 | . | . | F | −0.30 | 1.57 |
| Pro | 45 | . | . | . | . | . | T | C | 0.51 | 0.17 | * | . | F | 0.60 | 1.22 |
| Ser | 46 | . | . | . | . | T | T | . | 1.02 | 0.53 | . | . | F | 0.50 | 1.32 |
| Asn | 47 | . | . | . | . | T | T | . | 1.02 | 0.43 | . | . | F | 0.84 | 2.15 |
| Ser | 48 | . | . | . | . | T | T | C | 1.38 | 0.14 | . | . | F | 1.28 | 2.24 |
| Tyr | 49 | . | . | . | . | . | T | . | 1.84 | −0.29 | . | . | F | 2.22 | 3.34 |
| Ser | 50 | . | . | . | . | . | . | C | 2.06 | −0.24 | . | . | F | 2.36 | 2.05 |
| Asn | 51 | . | . | . | . | T | T | . | 2.04 | −0.64 | . | . | F | 3.40 | 2.65 |
| Lys | 52 | . | . | . | . | T | T | . | 1.74 | −0.54 | . | . | F | 3.06 | 2.44 |
| Gly | 53 | . | . | . | . | T | T | . | 1.38 | −0.91 | . | * | F | 2.72 | 2.44 |
| Glu | 54 | . | . | . | . | T | T | . | 1.59 | −0.73 | * | * | F | 2.23 | 0.81 |
| Thr | 55 | . | . | . | . | T | T | . | 1.89 | −0.63 | * | . | F | 1.89 | 0.55 |
| Ser | 56 | . | . | . | B | . | T | . | 1.22 | −0.23 | * | . | F | 0.85 | 0.97 |
| Cys | 57 | . | . | . | B | . | T | . | 1.18 | −0.09 | . | * | . | 1.04 | 0.30 |
| His | 58 | . | . | . | B | . | T | . | 1.31 | −0.09 | . | * | . | 1.38 | 0.35 |
| Gln | 59 | . | . | . | . | T | . | . | 1.31 | −0.14 | . | . | . | 1.92 | 0.40 |
| Cys | 60 | . | . | . | . | T | . | . | 1.67 | −0.53 | . | . | . | 2.71 | 1.25 |
| Asp | 61 | . | . | . | . | T | T | . | 1.72 | −1.10 | . | . | F | 3.40 | 1.84 |

TABLE I-continued

| Res | Pos | I | II | III | IV | V | VI | VII | VIII | IX | X | XI | XII | XIII | XIV |
|---|---|---|---|---|---|---|---|---|---|---|---|---|---|---|---|
| Pro | 62 | . | . | . | . | T | T | . | 2.09 | −0.84 | . | . | F | 3.06 | 1.66 |
| Asp | 63 | . | . | . | . | T | T | . | 2.12 | −0.86 | . | . | F | 3.06 | 4.15 |
| Lys | 64 | . | . | . | . | T | T | . | 2.17 | −1.43 | * | * | F | 3.06 | 4.31 |
| Tyr | 65 | . | . | B | . | . | T | . | 2.49 | −1.43 | * | . | F | 2.66 | 5.57 |
| Ser | 66 | . | . | B | . | . | T | . | 2.19 | −1.43 | * | . | F | 2.66 | 3.30 |
| Glu | 67 | . | . | . | . | T | T | . | 2.10 | −1.04 | * | . | F | 3.40 | 2.21 |
| Lys | 68 | . | . | . | . | T | T | . | 1.80 | −0.66 | * | * | F | 3.06 | 1.89 |
| Gly | 69 | . | . | . | . | T | . | . | 1.09 | −1.03 | * | * | F | 2.52 | 1.89 |
| Ser | 70 | . | . | . | . | T | T | . | 1.33 | −0.84 | . | * | F | 2.23 | 0.59 |
| Ser | 71 | . | . | . | . | T | T | . | 0.78 | −0.44 | . | * | F | 1.59 | 0.47 |
| Ser | 72 | . | . | . | . | T | T | . | 0.89 | 0.20 | . | * | F | 0.65 | 0.35 |
| Cys | 73 | . | . | . | . | T | T | . | 0.63 | −0.23 | . | * | F | 1.25 | 0.52 |
| Asn | 74 | . | . | . | . | T | . | . | 0.39 | −0.19 | . | * | . | 0.90 | 0.60 |
| Val | 75 | . | . | B | . | . | . | . | 0.02 | −0.07 | * | * | . | 0.50 | 0.45 |
| Arg | 76 | . | . | B | . | . | T | . | 0.01 | 0.11 | . | * | . | 0.10 | 0.45 |
| Pro | 77 | . | . | B | . | . | T | . | 0.31 | 0.03 | . | * | . | 0.44 | 0.40 |
| Ala | 78 | . | . | B | . | . | T | . | 1.02 | −0.37 | . | * | . | 1.38 | 0.91 |
| Cys | 79 | . | . | B | . | . | T | . | 1.02 | −1.01 | . | * | . | 2.02 | 0.93 |
| Thr | 80 | . | . | B | . | . | . | . | 1.63 | −1.01 | * | * | F | 2.31 | 1.00 |
| Asp | 81 | . | . | . | . | T | T | . | 0.82 | −0.69 | * | . | F | 3.40 | 1.55 |
| Lys | 82 | . | . | . | . | T | T | . | 0.79 | −0.40 | . | . | F | 2.76 | 2.50 |
| Asp | 83 | . | . | . | . | T | T | . | 1.07 | −0.21 | . | . | F | 2.42 | 2.72 |
| Tyr | 84 | . | . | B | . | . | T | . | 1.70 | −0.21 | . | . | . | 1.53 | 2.35 |
| Phe | 85 | . | . | B | B | . | . | . | 1.70 | 0.29 | . | . | . | 0.19 | 1.60 |
| Tyr | 86 | . | . | B | B | . | . | . | 1.11 | 0.77 | . | . | . | −0.45 | 1.38 |
| Thr | 87 | . | . | B | B | . | . | . | 0.40 | 1.27 | . | . | . | −0.60 | 0.89 |
| His | 88 | . | . | B | B | . | . | . | 0.40 | 1.09 | . | . | . | −0.60 | 0.55 |
| Thr | 89 | . | . | B | B | . | . | . | 0.06 | 0.30 | . | . | . | −0.30 | 0.59 |
| Ala | 90 | . | . | B | B | . | . | . | 0.76 | 0.04 | . | * | . | 0.00 | 0.41 |
| Cys | 91 | . | . | . | B | T | . | . | 0.66 | −0.04 | . | * | . | 1.30 | 0.49 |
| Asp | 92 | . | . | . | . | T | T | . | 0.97 | −0.11 | . | * | . | 2.00 | 0.33 |
| Ala | 93 | . | . | . | . | . | T | C | 0.69 | −0.60 | . | * | F | 2.55 | 0.57 |
| Asn | 94 | . | . | . | . | . | T | C | 1.00 | −0.61 | . | * | F | 3.00 | 1.54 |
| Gly | 95 | . | . | . | . | . | T | C | 0.78 | −0.79 | . | * | F | 2.70 | 1.60 |
| Glu | 96 | . | A | . | . | . | . | C | 0.84 | −0.10 | . | * | F | 1.70 | 1.30 |
| Thr | 97 | . | A | B | . | . | . | . | 0.60 | 0.01 | . | * | F | 0.45 | 0.80 |
| Gln | 98 | . | A | B | . | . | . | . | 1.23 | 0.37 | * | * | F | 0.30 | 1.27 |
| Leu | 99 | . | A | B | . | . | . | . | 0.94 | −0.06 | * | * | . | 0.45 | 1.47 |
| Met | 100 | . | A | B | . | . | . | . | 0.70 | 0.86 | * | * | . | −0.45 | 1.07 |
| Tyr | 101 | . | A | B | . | . | . | . | 0.74 | 0.87 | * | * | . | −0.60 | 0.62 |
| Lys | 102 | . | A | . | . | T | . | . | 0.84 | 0.47 | * | * | . | −0.05 | 1.51 |
| Trp | 103 | . | A | . | . | T | . | . | 0.89 | 0.21 | * | * | . | 0.25 | 2.36 |
| Ala | 104 | . | A | . | . | . | . | C | 0.81 | −0.40 | * | * | F | 0.80 | 3.01 |
| Lys | 105 | . | A | . | . | . | . | C | 0.74 | −0.47 | * | * | F | 0.80 | 1.06 |
| Pro | 106 | . | A | . | . | T | . | . | 0.69 | 0.10 | . | * | F | 0.25 | 0.54 |
| Lys | 107 | . | . | . | . | T | . | . | 0.64 | −0.43 | . | * | F | 1.05 | 0.71 |
| Ile | 108 | . | . | B | . | . | . | . | 0.93 | −0.93 | . | * | . | 0.80 | 0.62 |
| Cys | 109 | . | . | B | . | . | T | . | 0.71 | −0.93 | . | * | . | 1.00 | 0.67 |
| Ser | 110 | . | . | B | . | . | T | . | 0.67 | −0.67 | . | * | F | 1.15 | 0.28 |
| Glu | 111 | . | . | B | . | . | T | . | 0.53 | −0.67 | . | . | F | 1.15 | 0.68 |
| Asp | 112 | A | . | . | . | . | T | . | −0.10 | −0.93 | * | * | F | 1.30 | 1.26 |
| Leu | 113 | A | A | . | . | . | . | . | −0.07 | −1.00 | * | * | F | 0.75 | 0.95 |
| Glu | 114 | A | A | . | . | . | . | . | 0.64 | −0.74 | * | * | F | 0.75 | 0.41 |
| Gly | 115 | A | A | . | . | . | . | . | 0.13 | −0.74 | * | * | F | 0.75 | 0.49 |
| Ala | 116 | . | A | B | . | . | . | . | −0.08 | −0.06 | * | * | . | 0.30 | 0.49 |
| Val | 117 | . | A | B | . | . | . | . | −0.67 | −0.31 | * | * | . | 0.30 | 0.43 |
| Lys | 118 | . | A | B | . | . | . | . | −0.16 | 0.19 | * | * | . | −0.30 | 0.44 |
| Leu | 119 | . | A | B | . | . | . | . | −0.50 | 0.14 | * | * | . | −0.30 | 0.59 |
| Pro | 120 | . | . | B | . | . | T | . | −1.01 | 0.07 | * | * | . | 0.10 | 0.78 |
| Ala | 121 | . | . | . | . | T | T | . | −0.38 | 0.07 | * | * | F | 0.65 | 0.29 |
| Ser | 122 | . | . | . | . | T | T | . | 0.17 | 0.07 | * | * | F | 0.65 | 0.70 |
| Gly | 123 | . | . | . | . | T | T | . | 0.09 | −0.13 | * | * | F | 1.25 | 0.66 |
| Val | 124 | . | . | B | . | . | . | . | 0.23 | −0.06 | . | . | F | 0.79 | 0.89 |
| Lys | 125 | . | . | B | . | . | . | . | 0.23 | 0.01 | . | . | F | 0.33 | 0.35 |
| Thr | 126 | . | . | B | . | . | . | . | 0.61 | 0.06 | . | . | F | 0.47 | 0.55 |
| His | 127 | . | . | B | . | . | . | . | 0.24 | 0.06 | * | . | . | 0.61 | 1.15 |
| Cys | 128 | . | . | B | . | . | T | . | 0.59 | −0.01 | . | . | . | 1.40 | 0.31 |
| Pro | 129 | . | . | B | . | . | T | . | 1.23 | 0.39 | * | * | F | 0.81 | 0.34 |
| Pro | 130 | . | . | . | . | T | T | . | 0.84 | 0.33 | . | . | F | 1.07 | 0.39 |
| Cys | 131 | . | . | . | . | T | T | . | 0.46 | 0.26 | . | . | F | 0.93 | 0.72 |
| Asn | 132 | . | . | . | . | . | T | C | −0.21 | 0.47 | . | . | F | 0.29 | 0.40 |
| Pro | 133 | . | . | . | . | T | T | . | 0.50 | 0.83 | . | . | F | 0.35 | 0.23 |
| Gly | 134 | . | . | . | . | T | T | . | 0.40 | 0.40 | . | . | . | 0.20 | 0.85 |
| Phe | 135 | . | . | B | . | . | T | . | 0.61 | 0.31 | . | . | . | 0.10 | 0.76 |
| Phe | 136 | . | . | B | . | . | . | . | 1.28 | 0.31 | . | . | F | 0.30 | 0.79 |
| Lys | 137 | . | . | . | . | T | . | . | 0.98 | 0.29 | . | . | F | 1.10 | 1.28 |
| Thr | 138 | . | . | . | . | T | . | . | 0.88 | 0.24 | . | . | F | 1.35 | 1.99 |

TABLE I-continued

| Res | Pos | I | II | III | IV | V | VI | VII | VIII | IX | X | XI | XII | XIII | XIV |
|---|---|---|---|---|---|---|---|---|---|---|---|---|---|---|---|
| Asn | 139 | . | . | . | . | T | . | . | 0.56 | −0.06 | * | . | F | 2.20 | 3.31 |
| Asn | 140 | . | . | . | . | T | T | . | 1.26 | −0.27 | * | . | F | 2.50 | 0.89 |
| Ser | 141 | . | . | . | . | T | T | . | 1.74 | 0.13 | * | * | F | 1.80 | 1.06 |
| Thr | 142 | . | . | . | . | T | T | . | 1.03 | 0.07 | . | . | F | 1.55 | 1.02 |
| Cys | 143 | . | . | . | . | T | T | . | 1.13 | 0.24 | . | . | F | 1.15 | 0.34 |
| Gln | 144 | . | . | B | . | . | . | . | 0.89 | 0.27 | . | . | F | 0.30 | 0.39 |
| Pro | 145 | . | . | B | . | . | . | . | 0.54 | 0.64 | . | . | F | −0.25 | 0.43 |
| Cys | 146 | . | . | B | . | . | T | . | 0.54 | 0.59 | . | . | . | −0.20 | 0.79 |
| Pro | 147 | . | . | B | . | . | T | . | 0.61 | 0.40 | . | . | . | −0.20 | 0.61 |
| Tyr | 148 | . | . | . | . | T | T | . | 0.98 | 0.76 | . | . | . | 0.20 | 0.62 |
| Gly | 149 | . | . | . | . | T | T | . | 0.98 | 0.71 | . | . | . | 0.35 | 1.55 |
| Ser | 150 | . | . | . | . | T | . | . | 0.84 | 0.54 | . | . | F | 0.30 | 1.61 |
| Tyr | 151 | . | . | . | . | T | T | . | 1.21 | 0.54 | . | . | F | 0.50 | 1.02 |
| Ser | 152 | . | . | . | . | T | T | . | 1.42 | 0.17 | . | . | F | 1.11 | 1.38 |
| Asn | 153 | . | . | . | . | T | T | . | 1.00 | −0.26 | . | . | F | 2.02 | 1.71 |
| Gly | 154 | . | . | . | . | T | T | . | 1.03 | −0.07 | * | . | F | 2.18 | 0.59 |
| Ser | 155 | . | . | . | . | T | T | . | 1.44 | −0.34 | * | . | F | 2.49 | 0.63 |
| Asp | 156 | . | . | . | . | T | T | . | 1.02 | −0.73 | * | . | F | 3.10 | 0.77 |
| Cys | 157 | . | . | B | . | . | T | . | 1.11 | −0.56 | * | * | F | 2.39 | 0.42 |
| Thr | 158 | . | . | B | . | . | T | . | 0.52 | −0.56 | * | * | F | 2.39 | 0.48 |
| Arg | 159 | . | . | B | . | . | . | . | 0.52 | −0.44 | * | . | F | 1.89 | 0.29 |
| Cys | 160 | . | . | B | . | . | T | . | 0.51 | −0.01 | . | . | . | 1.94 | 0.54 |
| Pro | 161 | . | . | . | . | T | T | . | 0.51 | −0.10 | . | . | . | 2.34 | 0.54 |
| Ala | 162 | . | . | . | . | T | T | . | 0.97 | −0.59 | . | * | F | 3.10 | 0.47 |
| Gly | 163 | . | . | . | . | . | T | C | 0.69 | −0.16 | * | * | F | 2.44 | 1.37 |
| Thr | 164 | . | . | . | . | . | . | C | −0.28 | −0.23 | . | * | F | 1.78 | 0.89 |
| Glu | 165 | . | . | B | . | . | . | . | 0.04 | −0.01 | . | . | F | 1.27 | 0.66 |
| Pro | 166 | . | . | B | . | . | . | . | −0.44 | −0.09 | . | * | F | 0.96 | 0.66 |
| Ala | 167 | . | . | B | . | . | . | . | 0.14 | 0.27 | . | * | . | −0.10 | 0.39 |
| Val | 168 | . | . | B | . | . | . | . | 0.24 | −0.21 | . | * | . | 0.50 | 0.39 |
| Gly | 169 | . | . | B | . | . | . | . | 0.60 | 0.54 | . | * | . | −0.40 | 0.40 |
| Phe | 170 | . | A | B | . | . | . | . | 0.31 | 0.11 | . | * | . | −0.30 | 0.79 |
| Glu | 171 | . | A | B | . | . | . | . | 0.23 | 0.53 | . | * | . | −0.45 | 1.12 |
| Tyr | 172 | . | A | . | . | T | . | . | 0.82 | 0.80 | * | * | . | −0.05 | 1.19 |
| Lys | 173 | . | A | . | . | T | . | . | 1.37 | 0.77 | * | * | . | −0.05 | 2.21 |
| Trp | 174 | . | A | . | . | T | . | . | 0.90 | 0.47 | * | * | . | −0.05 | 1.84 |
| Trp | 175 | . | A | . | . | T | . | . | 1.39 | 1.16 | * | * | . | −0.20 | 0.97 |
| Asn | 176 | . | . | . | . | . | . | C | 1.08 | 0.83 | * | * | . | −0.20 | 0.75 |
| Thr | 177 | . | . | . | . | . | . | C | 1.32 | 1.31 | * | * | F | 0.10 | 1.03 |
| Leu | 178 | . | . | . | . | . | . | C | 0.68 | 0.80 | * | * | F | 0.10 | 1.57 |
| Pro | 179 | . | . | . | . | . | T | C | 0.97 | 0.50 | . | * | F | 0.12 | 0.97 |
| Thr | 180 | . | . | . | . | . | T | C | 0.94 | 0.10 | * | * | F | 0.54 | 1.16 |
| Asn | 181 | . | . | . | . | . | T | C | 0.63 | 0.10 | * | * | F | 0.51 | 2.03 |
| Met | 182 | . | . | B | . | . | T | . | 0.09 | −0.10 | . | * | F | 0.88 | 1.90 |
| Glu | 183 | . | . | B | B | . | . | . | 0.09 | 0.11 | . | * | F | −0.30 | 0.98 |
| Thr | 184 | . | . | B | B | . | . | . | −0.00 | 0.31 | . | . | F | −0.27 | 0.50 |
| Thr | 185 | . | . | B | B | . | . | . | −0.03 | 0.30 | . | . | F | −0.24 | 0.68 |
| Val | 186 | . | . | B | B | . | . | . | −0.92 | 0.11 | * | * | F | −0.21 | 0.39 |
| Leu | 187 | . | . | B | B | . | . | . | −0.32 | 0.80 | * | * | F | −0.48 | 0.19 |
| Ser | 188 | . | . | B | B | . | . | . | −1.02 | 0.71 | . | * | F | −0.45 | 0.21 |
| Gly | 189 | . | . | . | B | . | . | C | −0.71 | 1.01 | * | * | . | −0.40 | 0.24 |
| Ile | 190 | . | A | B | B | . | . | . | −0.64 | 0.37 | * | * | . | −0.30 | 0.51 |
| Asn | 191 | . | A | B | B | . | . | . | 0.26 | 0.44 | * | * | . | −0.60 | 0.60 |
| Phe | 192 | . | A | B | B | . | . | . | 0.72 | 0.06 | * | * | . | −0.15 | 1.21 |
| Glu | 193 | . | A | B | B | . | . | . | 0.42 | 0.06 | * | * | . | −0.15 | 1.71 |
| Tyr | 194 | . | . | B | . | . | T | . | 0.46 | −0.01 | * | * | . | 0.85 | 1.05 |
| Lys | 195 | . | . | . | . | T | T | . | 1.00 | 0.07 | * | * | F | 0.80 | 1.76 |
| Gly | 196 | . | . | . | . | T | T | . | 0.71 | −0.29 | * | * | F | 1.40 | 1.00 |
| Met | 197 | . | . | . | . | . | T | C | 1.41 | 0.63 | . | * | F | 0.15 | 0.67 |
| Thr | 198 | . | . | . | . | . | . | C | 0.56 | −0.13 | * | * | F | 0.85 | 0.58 |
| Gly | 199 | . | A | . | . | . | . | C | 0.21 | 0.51 | . | * | . | −0.40 | 0.44 |
| Trp | 200 | . | A | B | . | . | . | . | −0.18 | 0.59 | * | * | . | −0.42 | 0.45 |
| Glu | 201 | . | A | B | . | . | . | . | 0.17 | 0.40 | * | . | . | −0.24 | 0.31 |
| Val | 202 | . | A | B | . | . | . | . | 0.73 | −0.09 | * | . | . | 0.84 | 0.52 |
| Ala | 203 | . | A | B | . | . | . | . | 0.16 | −0.01 | * | . | . | 1.02 | 0.67 |
| Gly | 204 | . | . | . | . | T | . | . | 0.26 | −0.24 | * | . | . | 1.80 | 0.27 |
| Asp | 205 | . | . | . | B | T | . | . | 0.23 | 0.51 | * | . | . | 0.52 | 0.57 |
| His | 206 | . | . | B | B | . | . | . | −0.36 | 0.36 | * | . | . | 0.24 | 0.82 |
| Ile | 207 | . | . | B | B | . | . | . | −0.09 | 0.36 | . | . | . | 0.06 | 0.83 |
| Tyr | 208 | . | . | B | B | . | . | . | 0.16 | 0.43 | * | . | . | −0.42 | 0.50 |
| Thr | 209 | . | . | B | B | . | . | . | −0.09 | 0.86 | . | . | . | −0.60 | 0.37 |
| Ala | 210 | . | . | B | B | . | . | . | −0.39 | 0.86 | . | . | . | −0.60 | 0.53 |
| Ala | 211 | . | . | B | . | . | . | . | −0.36 | 0.56 | . | . | . | −0.12 | 0.45 |
| Gly | 212 | . | . | . | . | . | . | C | 0.53 | −0.20 | . | . | . | 1.26 | 0.52 |
| Ala | 213 | . | . | . | . | . | . | C | 0.78 | −0.29 | . | . | F | 1.69 | 0.83 |
| Ser | 214 | . | . | . | . | . | T | C | 0.39 | −0.79 | . | . | F | 2.62 | 1.38 |
| Asp | 215 | . | . | . | . | T | T | . | 0.38 | −0.50 | . | . | F | 2.80 | 1.21 |

TABLE I-continued

| Res | Pos | I | II | III | IV | V | VI | VII | VIII | IX | X | XI | XII | XIII | XIV |
|---|---|---|---|---|---|---|---|---|---|---|---|---|---|---|---|
| Asn | 216 | . | . | . | . | . | T | C | 0.08 | −0.31 | . | . | F | 2.32 | 1.18 |
| Asp | 217 | . | . | B | . | . | T | . | −0.39 | −0.13 | . | . | F | 1.69 | 0.62 |
| Phe | 218 | . | . | B | B | . | . | . | −0.11 | 0.17 | . | . | . | 0.26 | 0.30 |
| Met | 219 | . | . | B | B | . | . | . | −0.62 | 0.66 | . | . | . | −0.32 | 0.27 |
| Ile | 220 | . | . | B | B | . | . | . | −1.48 | 0.94 | . | . | . | −0.60 | 0.14 |
| Leu | 221 | . | . | B | B | . | . | . | −2.33 | 1.59 | . | . | . | −0.60 | 0.12 |
| Thr | 222 | . | . | B | B | . | . | . | −2.54 | 1.44 | . | . | . | −0.60 | 0.09 |
| Leu | 223 | . | . | B | B | . | . | . | −2.19 | 1.26 | . | . | . | −0.60 | 0.19 |
| Val | 224 | . | . | B | B | . | . | . | −2.29 | 1.00 | * | * | . | −0.60 | 0.23 |
| Val | 225 | . | . | B | B | . | . | . | −1.29 | 1.10 | * | * | . | −0.60 | 0.14 |
| Pro | 226 | . | . | B | . | . | . | . | −0.69 | 0.61 | * | * | . | −0.40 | 0.33 |
| Gly | 227 | . | . | . | . | T | . | . | −0.59 | 0.36 | * | . | F | 0.45 | 0.68 |
| Phe | 228 | . | . | B | . | . | . | . | 0.22 | 0.14 | * | . | F | 0.45 | 1.42 |
| Arg | 229 | . | . | . | . | . | . | C | 0.78 | −0.10 | * | * | F | 1.50 | 1.59 |
| Pro | 230 | . | . | . | . | . | T | C | 0.78 | −0.14 | * | . | F | 1.95 | 2.16 |
| Pro | 231 | . | . | . | . | T | T | . | 0.39 | 0.07 | * | * | F | 1.80 | 1.85 |
| Gln | 232 | . | . | . | . | T | T | . | 0.14 | −0.10 | * | * | F | 2.50 | 0.93 |
| Ser | 233 | . | . | B | . | . | T | . | 0.84 | 0.40 | * | * | F | 0.95 | 0.61 |
| Val | 234 | . | . | B | . | . | . | . | 0.42 | −0.03 | * | * | . | 1.55 | 0.66 |
| Met | 235 | . | . | B | . | . | . | . | 0.63 | 0.03 | . | . | . | 1.00 | 0.55 |
| Ala | 236 | . | . | B | . | . | . | . | 0.84 | −0.37 | . | * | . | 1.65 | 0.71 |
| Asp | 237 | . | . | B | . | . | . | . | 0.89 | −0.36 | . | . | F | 2.20 | 1.54 |
| Thr | 238 | . | . | . | . | . | T | C | 1.19 | −1.00 | . | . | F | 3.00 | 3.11 |
| Glu | 239 | A | . | . | . | . | T | . | 1.19 | −1.61 | . | . | F | 2.50 | 5.33 |
| Asn | 240 | A | . | . | . | . | T | . | 1.20 | −1.47 | * | * | F | 2.20 | 2.37 |
| Lys | 241 | A | . | . | . | . | . | . | 1.90 | −0.97 | * | * | F | 1.70 | 1.66 |
| Glu | 242 | A | . | . | . | . | . | . | 1.01 | −1.46 | * | * | F | 1.40 | 1.88 |
| Val | 243 | A | . | . | B | . | . | . | 1.01 | −0.77 | * | * | . | 0.60 | 0.82 |
| Ala | 244 | . | . | B | B | . | . | . | 0.31 | −0.69 | * | * | . | 0.60 | 0.59 |
| Arg | 245 | . | . | B | B | . | . | . | −0.54 | 0.10 | * | * | . | −0.30 | 0.29 |
| Ile | 246 | . | . | B | B | . | . | . | −1.29 | 0.74 | * | * | . | −0.60 | 0.29 |
| Thr | 247 | . | . | B | B | . | . | . | −1.29 | 0.89 | * | * | . | −0.60 | 0.25 |
| Phe | 248 | . | . | B | B | . | . | . | −0.74 | 0.39 | * | * | . | −0.30 | 0.22 |
| Val | 249 | . | . | B | B | . | . | . | −0.97 | 0.87 | * | * | . | −0.60 | 0.46 |
| Phe | 250 | . | . | B | B | . | . | . | −1.74 | 0.87 | * | * | . | −0.60 | 0.26 |
| Glu | 251 | . | . | B | B | . | . | . | −1.16 | 0.96 | * | * | . | −0.60 | 0.16 |
| Thr | 252 | . | . | . | B | T | . | . | −1.70 | 0.56 | * | * | . | −0.20 | 0.29 |
| Leu | 253 | . | . | . | B | T | . | . | −1.00 | 0.56 | * | * | . | −0.20 | 0.25 |
| Cys | 254 | . | . | . | B | T | . | . | −0.81 | 0.17 | * | * | . | 0.10 | 0.23 |
| Ser | 255 | . | . | . | . | T | T | . | −0.11 | 0.74 | * | * | . | 0.20 | 0.09 |
| Val | 256 | . | . | . | . | T | T | . | −0.92 | 0.26 | * | * | . | 0.50 | 0.18 |
| Asn | 257 | . | . | B | . | T | T | . | −0.86 | 0.26 | . | * | . | 0.50 | 0.28 |
| Cys | 258 | . | . | B | . | . | T | . | −0.74 | 0.44 | . | * | . | −0.20 | 0.33 |
| Glu | 259 | . | . | B | B | . | . | . | −0.68 | 0.84 | . | * | . | −0.60 | 0.38 |
| Leu | 260 | . | . | B | B | . | . | . | −1.23 | 0.81 | . | * | . | −0.60 | 0.24 |
| Tyr | 261 | . | . | B | B | . | . | . | −0.72 | 1.06 | . | * | . | −0.60 | 0.33 |
| Phe | 262 | . | . | B | B | . | . | . | −1.58 | 0.91 | . | * | . | −0.60 | 0.19 |
| Met | 263 | . | . | B | B | . | . | . | −0.91 | 1.56 | . | * | . | −0.60 | 0.17 |
| Val | 264 | . | . | B | B | . | . | . | −1.21 | 1.27 | . | * | . | −0.60 | 0.17 |
| Gly | 265 | . | . | B | B | . | . | . | −0.29 | 0.90 | . | * | . | −0.32 | 0.27 |
| Val | 266 | . | . | B | B | . | . | . | −0.36 | 0.11 | . | * | . | 0.26 | 0.53 |
| Asn | 267 | . | . | . | . | . | T | C | 0.34 | −0.01 | . | * | F | 2.04 | 1.03 |
| Ser | 268 | . | . | . | . | . | T | C | 0.63 | −0.26 | . | * | F | 2.32 | 1.67 |
| Arg | 269 | . | . | . | . | T | T | . | 1.28 | −0.20 | . | * | F | 2.80 | 3.24 |
| Thr | 270 | . | . | . | . | T | T | . | 0.77 | −0.41 | . | * | F | 2.52 | 3.12 |
| Asn | 271 | . | . | . | . | . | . | C | 1.62 | −0.17 | * | * | F | 1.84 | 1.73 |
| Thr | 272 | . | . | . | . | . | . | C | 1.31 | −0.56 | * | * | F | 1.86 | 1.53 |
| Pro | 273 | . | . | B | . | . | . | . | 1.32 | −0.07 | * | * | F | 1.08 | 1.53 |
| Val | 274 | . | . | B | . | . | . | . | 1.26 | 0.36 | . | * | F | 0.05 | 1.00 |
| Glu | 275 | . | . | B | . | . | . | . | 1.22 | −0.04 | . | * | F | 0.80 | 1.38 |
| Thr | 276 | . | . | B | . | . | . | . | 0.92 | −0.10 | * | . | F | 0.99 | 0.88 |
| Trp | 277 | . | . | B | . | . | . | . | 1.28 | −0.14 | . | . | F | 1.48 | 1.60 |
| Lys | 278 | . | . | . | . | T | . | . | 1.14 | −0.79 | . | . | F | 2.52 | 1.85 |
| Gly | 279 | . | . | . | . | T | . | . | 2.04 | −0.36 | . | . | F | 2.56 | 1.27 |
| Ser | 280 | . | . | . | . | T | T | . | 2.04 | −0.84 | . | . | F | 3.40 | 2.41 |
| Lys | 281 | . | . | . | . | . | T | C | 2.06 | −1.36 | . | . | F | 2.86 | 2.08 |
| Gly | 282 | . | . | . | . | T | T | . | 2.10 | −0.97 | . | . | F | 2.72 | 2.82 |
| Lys | 283 | . | . | . | . | T | T | . | 1.74 | −0.64 | . | . | F | 2.38 | 3.30 |
| Gln | 284 | . | . | . | B | T | . | . | 1.84 | −0.54 | * | . | F | 1.64 | 2.38 |
| Ser | 285 | . | . | B | B | . | . | . | 1.26 | 0.21 | * | * | F | 0.00 | 3.77 |
| Tyr | 286 | . | . | B | B | . | . | . | 0.32 | 0.47 | * | * | . | −0.45 | 1.32 |
| Thr | 287 | . | . | B | B | . | . | . | 0.67 | 1.16 | * | . | . | −0.60 | 0.53 |
| Tyr | 288 | . | . | B | B | . | . | . | 0.62 | 0.76 | . | . | . | −0.60 | 0.69 |
| Ile | 289 | . | . | B | B | . | . | . | 0.62 | 0.37 | * | . | . | −0.30 | 0.76 |
| Ile | 290 | . | . | B | B | . | . | . | 0.61 | 0.01 | . | . | . | −0.04 | 0.85 |
| Glu | 291 | . | . | B | B | . | . | . | 0.54 | 0.01 | . | . | F | 0.37 | 0.78 |
| Glu | 292 | . | . | B | . | . | . | . | 0.54 | −0.26 | . | . | F | 1.58 | 1.61 |

TABLE I-continued

| Res | Pos | I | II | III | IV | V | VI | VII | VIII | IX | X | XI | XII | XIII | XIV |
|---|---|---|---|---|---|---|---|---|---|---|---|---|---|---|---|
| Asn | 293 | . | . | . | B | T | . | . | 0.49 | −0.46 | . | . | F | 2.04 | 3.32 |
| Thr | 294 | . | . | . | B | T | . | . | 0.68 | −0.76 | . | . | F | 2.60 | 2.57 |
| Thr | 295 | . | . | . | B | . | . | C | 1.26 | 0.03 | . | * | F | 1.24 | 1.29 |
| Thr | 296 | . | . | . | B | . | . | C | 0.97 | 0.51 | . | . | F | 0.68 | 1.15 |
| Ser | 297 | . | . | . | B | . | . | C | 0.38 | 1.03 | * | * | F | 0.27 | 0.84 |
| Phe | 298 | . | . | B | B | . | . | . | −0.32 | 1.04 | * | * | . | −0.34 | 0.59 |
| Thr | 299 | . | . | B | B | . | . | . | −0.01 | 1.34 | * | . | . | −0.60 | 0.35 |
| Trp | 300 | . | . | B | B | . | . | . | 0.41 | 1.26 | * | . | . | −0.60 | 0.46 |
| Ala | 301 | . | . | . | B | . | . | C | 0.41 | 0.87 | * | . | . | −0.25 | 1.03 |
| Phe | 302 | . | . | . | B | T | . | . | 0.40 | 0.57 | * | * | . | −0.05 | 1.03 |
| Gln | 303 | . | . | . | B | T | . | . | 0.40 | 0.57 | * | * | . | −0.05 | 1.42 |
| Arg | 304 | . | . | . | B | . | . | C | 0.68 | 0.44 | . | . | F | −0.10 | 1.21 |
| Thr | 305 | . | . | . | B | . | . | C | 0.97 | 0.44 | . | . | F | −0.10 | 1.91 |
| Thr | 306 | . | . | . | B | . | . | C | 0.97 | −0.34 | . | . | F | 0.80 | 1.91 |
| Phe | 307 | . | . | . | B | . | . | C | 1.37 | −0.24 | * | * | . | 0.50 | 0.98 |
| His | 308 | . | . | . | B | . | . | C | 1.48 | 0.14 | * | * | . | −0.10 | 0.91 |
| Glu | 309 | . | . | . | B | . | . | C | 1.41 | −0.34 | * | * | . | 0.65 | 1.24 |
| Ala | 310 | . | . | . | . | T | . | C | 1.48 | −0.83 | * | . | F | 1.84 | 2.86 |
| Ser | 311 | . | . | . | . | T | . | . | 1.48 | −0.86 | * | . | F | 2.18 | 3.30 |
| Arg | 312 | . | . | . | . | T | . | . | 2.18 | −0.87 | * | . | F | 2.52 | 2.75 |
| Lys | 313 | . | . | . | . | T | . | . | 2.21 | −0.47 | * | . | F | 2.56 | 4.38 |
| Tyr | 314 | . | . | . | . | T | T | . | 1.36 | −0.97 | * | . | F | 3.40 | 5.45 |
| Thr | 315 | . | . | . | . | T | T | . | 1.36 | −0.71 | * | . | F | 3.06 | 2.07 |
| Asn | 316 | . | . | B | . | . | T | . | 1.70 | −0.21 | * | . | F | 2.02 | 1.04 |
| Asp | 317 | . | . | B | . | . | T | . | 0.70 | −0.21 | * | . | F | 1.68 | 1.33 |
| Val | 318 | . | . | B | B | . | . | . | 0.41 | −0.29 | * | . | F | 0.79 | 0.65 |
| Ala | 319 | . | . | B | B | . | . | . | 0.36 | −0.01 | * | . | . | 0.30 | 0.63 |
| Lys | 320 | . | . | B | B | . | . | . | −0.22 | −0.03 | * | . | . | 0.30 | 0.51 |
| Ile | 321 | . | . | B | B | . | . | . | −0.22 | 0.66 | * | . | . | −0.60 | 0.48 |
| Tyr | 322 | . | . | B | B | . | . | . | −1.08 | 0.41 | . | . | . | −0.60 | 0.76 |
| Ser | 323 | . | . | B | B | . | . | . | −0.53 | 0.56 | . | . | . | −0.60 | 0.28 |
| Ile | 324 | . | . | B | B | . | . | . | 0.06 | 1.04 | . | . | . | −0.60 | 0.58 |
| Asn | 325 | . | . | B | B | . | . | . | −0.84 | 0.76 | . | . | . | −0.60 | 0.60 |
| Val | 326 | . | . | B | B | . | . | . | −0.56 | 0.64 | . | . | . | −0.60 | 0.33 |
| Thr | 327 | . | . | B | B | . | . | . | −0.31 | 0.87 | . | * | . | −0.60 | 0.47 |
| Asn | 328 | . | . | B | B | . | . | . | −0.36 | 0.59 | * | * | . | −0.60 | 0.47 |
| Val | 329 | . | . | B | . | . | T | . | −0.32 | 0.61 | * | . | . | −0.20 | 0.62 |
| Met | 330 | . | . | B | . | . | T | . | −0.91 | 0.61 | * | . | . | −0.20 | 0.32 |
| Asn | 331 | . | . | B | . | . | T | . | −0.36 | 0.63 | * | . | . | −0.20 | 0.20 |
| Gly | 332 | . | . | B | . | . | T | . | −0.29 | 0.61 | * | . | . | −0.20 | 0.36 |
| Val | 333 | . | . | B | . | . | . | . | −0.96 | 0.73 | * | . | . | −0.40 | 0.57 |
| Ala | 334 | . | . | B | . | . | T | . | 0.01 | 0.69 | * | . | . | −0.20 | 0.19 |
| Ser | 335 | . | . | B | . | . | T | . | 0.40 | 0.29 | * | . | . | 0.10 | 0.38 |
| Tyr | 336 | . | . | B | . | . | T | . | −0.27 | 0.29 | * | * | . | 0.10 | 0.79 |
| Cys | 337 | . | . | B | . | . | T | . | −0.51 | 0.21 | * | . | . | 0.10 | 0.42 |
| Arg | 338 | . | . | B | . | . | T | . | −0.47 | 0.21 | . | . | . | 0.10 | 0.32 |
| Pro | 339 | . | . | B | . | . | T | . | 0.12 | 0.51 | . | . | . | −0.20 | 0.17 |
| Cys | 340 | . | . | B | . | . | T | . | −0.17 | −0.24 | . | . | . | 0.70 | 0.54 |
| Ala | 341 | . | . | B | . | . | T | . | −0.22 | −0.31 | * | . | . | 0.70 | 0.28 |
| Leu | 342 | . | . | B | . | . | . | . | 0.44 | 0.07 | * | . | . | −0.10 | 0.24 |
| Glu | 343 | . | . | B | . | . | . | . | −0.52 | −0.36 | * | . | . | 0.75 | 0.75 |
| Ala | 344 | . | . | B | . | . | . | . | −0.66 | −0.29 | . | . | F | 1.15 | 0.55 |
| Ser | 345 | . | . | B | . | . | . | . | −0.29 | −0.36 | . | . | F | 1.40 | 0.66 |
| Asp | 346 | . | . | . | . | T | T | . | 0.00 | −0.66 | . | . | F | 2.55 | 0.51 |
| Val | 347 | . | . | . | . | T | T | . | 0.14 | −0.27 | . | . | F | 2.50 | 0.68 |
| Gly | 348 | . | . | . | . | T | T | . | −0.17 | −0.20 | * | . | F | 2.25 | 0.27 |
| Ser | 349 | . | . | . | . | T | T | . | 0.12 | −0.10 | * | . | F | 2.00 | 0.23 |
| Ser | 350 | . | . | . | . | T | . | . | −0.24 | 0.29 | * | . | F | 0.95 | 0.42 |
| Cys | 351 | . | . | B | . | . | T | . | −0.46 | 0.21 | . | . | F | 0.50 | 0.23 |
| Thr | 352 | . | . | B | . | . | T | . | −0.19 | 0.21 | . | . | F | 0.25 | 0.26 |
| Ser | 353 | . | . | B | . | . | T | . | −0.19 | 0.33 | . | . | F | 0.25 | 0.20 |
| Cys | 354 | . | . | B | . | . | T | . | −0.13 | 0.37 | . | . | . | 0.10 | 0.37 |
| Pro | 355 | . | . | B | . | . | T | . | −0.08 | 0.56 | . | . | . | −0.20 | 0.40 |
| Ala | 356 | . | . | . | . | T | T | . | −0.30 | 0.83 | . | . | . | 0.20 | 0.47 |
| Gly | 357 | . | . | B | . | . | T | . | 0.01 | 1.13 | * | . | . | −0.20 | 0.61 |
| Tyr | 358 | . | . | B | . | . | T | . | 0.42 | 0.56 | * | . | . | −0.20 | 0.66 |
| Tyr | 359 | . | . | B | B | . | . | . | 1.09 | 0.13 | * | . | . | 0.19 | 1.28 |
| Ile | 360 | . | . | B | B | . | . | . | 1.00 | −0.37 | * | . | . | 1.13 | 2.16 |
| Asp | 361 | . | . | B | B | . | . | . | 1.24 | −0.41 | * | . | . | 1.47 | 1.84 |
| Arg | 362 | . | . | . | . | T | . | . | 1.28 | −0.74 | * | . | F | 2.86 | 1.16 |
| Asp | 363 | . | . | . | . | T | T | . | 0.86 | −1.01 | * | . | F | 3.40 | 2.40 |
| Ser | 364 | . | . | . | . | T | T | . | 1.07 | −1.13 | * | . | F | 2.91 | 0.77 |
| Gly | 365 | . | . | . | . | T | T | . | 1.66 | −0.63 | * | . | F | 2.57 | 0.53 |
| Thr | 366 | . | . | . | . | T | T | . | 0.99 | −0.24 | . | . | F | 1.93 | 0.43 |
| Cys | 367 | . | . | . | . | T | T | . | 0.67 | 0.33 | . | * | . | 0.84 | 0.17 |
| His | 368 | . | . | . | . | T | T | . | 0.46 | 0.37 | . | . | . | 0.50 | 0.27 |
| Ser | 369 | . | . | . | . | T | T | . | 0.76 | 0.37 | . | . | . | 0.50 | 0.29 |

TABLE I-continued

| Res | Pos | I | II | III | IV | V | VI | VII | VIII | IX | X | XI | XII | XIII | XIV |
|---|---|---|---|---|---|---|---|---|---|---|---|---|---|---|---|
| Cys | 370 | . | . | B | . | . | T | . | 0.79 | 0.29 | . | . | . | 0.10 | 0.86 |
| Pro | 371 | . | . | . | . | . | T | C | 0.21 | 0.20 | . | . | F | 0.45 | 0.91 |
| Pro | 372 | . | . | . | . | T | T | . | 0.07 | 0.39 | * | . | F | 0.65 | 0.48 |
| Asn | 373 | . | . | . | . | T | T | . | 0.14 | 0.69 | * | * | F | 0.35 | 0.74 |
| Thr | 374 | . | . | B | . | . | T | . | −0.14 | 0.11 | * | * | F | 0.25 | 0.95 |
| Ile | 375 | . | A | B | . | . | . | . | 0.49 | 0.19 | * | . | . | −0.30 | 0.62 |
| Leu | 376 | . | A | B | . | . | . | . | 0.70 | 0.26 | * | . | . | −0.30 | 0.53 |
| Lys | 377 | . | A | B | . | . | . | . | 0.70 | 0.26 | * | . | . | −0.30 | 0.63 |
| Ala | 378 | . | A | B | . | . | . | . | 0.46 | 0.20 | * | . | . | −0.15 | 1.39 |
| His | 379 | . | A | B | . | . | . | . | 0.42 | 0.27 | . | . | . | −0.15 | 2.64 |
| Gln | 380 | . | . | B | . | . | T | . | 0.46 | 0.01 | * | * | F | 0.40 | 1.31 |
| Pro | 381 | . | . | . | . | T | T | . | 1.27 | 0.66 | . | * | . | 0.20 | 0.96 |
| Tyr | 382 | . | . | . | . | T | T | . | 0.63 | 0.56 | . | * | . | 0.35 | 1.22 |
| Gly | 383 | . | . | . | . | T | T | . | 0.56 | 0.56 | . | * | . | 0.20 | 0.71 |
| Val | 384 | . | . | B | B | . | . | . | −0.27 | 0.73 | . | * | . | −0.60 | 0.25 |
| Gln | 385 | . | . | B | B | . | . | . | −0.48 | 0.94 | . | * | . | −0.60 | 0.12 |
| Ala | 386 | . | . | B | B | . | . | . | −0.93 | 0.61 | . | * | . | −0.60 | 0.18 |
| Cys | 387 | . | . | B | B | . | . | . | −1.03 | 0.76 | . | * | . | −0.60 | 0.13 |
| Val | 388 | . | . | B | B | . | . | . | −0.90 | 0.54 | . | * | . | −0.60 | 0.08 |
| Pro | 389 | . | . | B | . | . | . | . | −0.39 | 0.57 | . | * | . | −0.40 | 0.12 |
| Cys | 390 | . | . | B | . | . | . | . | −0.70 | 0.50 | . | . | . | −0.40 | 0.21 |
| Gly | 391 | . | . | B | . | . | T | . | −0.07 | 0.41 | . | . | F | 0.29 | 0.42 |
| Pro | 392 | . | . | . | . | T | T | . | 0.60 | −0.23 | . | . | F | 1.93 | 0.54 |
| Gly | 393 | . | . | . | . | T | T | . | 1.46 | −0.26 | . | . | F | 2.42 | 1.61 |
| Thr | 394 | . | . | . | . | T | T | . | 1.71 | −0.43 | . | . | F | 2.76 | 2.62 |
| Lys | 395 | . | . | . | . | T | T | . | 1.49 | −0.86 | . | . | F | 3.40 | 3.39 |
| Asn | 396 | . | . | . | . | T | T | . | 1.80 | −0.60 | . | . | F | 3.06 | 2.40 |
| Asn | 397 | . | . | B | . | . | T | . | 1.71 | −0.53 | . | . | F | 2.32 | 2.26 |
| Lys | 398 | . | . | B | . | . | T | . | 1.24 | −0.63 | . | . | F | 1.98 | 1.52 |
| Ile | 399 | . | . | B | . | . | . | . | 0.89 | 0.06 | . | . | . | 0.24 | 0.78 |
| His | 400 | . | . | B | . | . | T | . | 0.60 | 0.23 | . | . | . | 0.10 | 0.26 |
| Ser | 401 | . | . | B | . | . | T | . | 0.60 | 0.59 | . | . | . | −0.20 | 0.20 |
| Leu | 402 | . | . | B | . | . | T | . | 0.60 | 0.99 | * | . | . | −0.20 | 0.47 |
| Cys | 403 | . | . | B | . | . | T | . | −0.11 | 0.30 | * | . | . | 0.10 | 0.57 |
| Tyr | 404 | . | . | . | . | T | . | . | 0.47 | 0.37 | . | . | . | 0.30 | 0.23 |
| Asn | 405 | . | . | . | . | T | T | . | −0.20 | 0.47 | . | . | . | 0.20 | 0.40 |
| Asp | 406 | . | . | . | . | T | T | . | −0.20 | 0.57 | * | . | . | 0.20 | 0.65 |
| Cys | 407 | . | . | B | . | . | T | . | 0.72 | 0.39 | * | . | . | 0.10 | 0.55 |
| Thr | 408 | . | . | B | . | . | T | . | 1.39 | −0.37 | . | . | . | 0.70 | 0.67 |
| Phe | 409 | . | . | B | . | . | . | . | 1.32 | −0.37 | . | . | . | 0.80 | 0.65 |
| Ser | 410 | . | . | . | . | T | T | . | 1.11 | 0.11 | . | . | F | 1.40 | 1.75 |
| Arg | 411 | . | . | . | . | T | T | . | 0.80 | −0.03 | . | . | F | 2.30 | 1.87 |
| Asn | 412 | . | . | . | . | . | T | C | 1.58 | −0.03 | . | . | F | 2.40 | 3.12 |
| Thr | 413 | . | . | . | . | . | T | C | 1.58 | −0.81 | . | . | F | 3.00 | 4.55 |
| Pro | 414 | . | . | . | . | . | T | C | 1.58 | −0.71 | * | . | F | 2.70 | 3.36 |
| Thr | 415 | . | . | . | . | T | T | . | 1.88 | 0.07 | * | . | F | 1.70 | 1.81 |
| Arg | 416 | . | . | B | . | . | T | . | 1.52 | 0.07 | * | . | F | 1.00 | 2.01 |
| Thr | 417 | . | . | B | . | . | T | . | 1.52 | 0.34 | * | * | F | 0.70 | 2.04 |
| Phe | 418 | . | . | B | . | . | . | . | 1.13 | 0.31 | * | * | . | 0.05 | 2.27 |
| Asn | 419 | . | . | B | . | . | T | . | 1.04 | 0.61 | * | * | . | −0.05 | 1.01 |
| Tyr | 420 | . | . | B | . | . | T | . | 0.77 | 1.00 | * | . | . | −0.20 | 0.93 |
| Asn | 421 | . | . | B | . | . | T | . | −0.16 | 1.01 | * | * | . | −0.05 | 1.09 |
| Phe | 422 | . | . | B | . | . | T | . | −0.43 | 0.91 | * | * | . | −0.20 | 0.56 |
| Ser | 423 | . | A | . | . | . | . | C | 0.27 | 1.01 | * | * | . | −0.40 | 0.36 |
| Ala | 424 | . | A | . | . | . | . | C | −0.04 | 0.66 | * | * | . | −0.40 | 0.36 |
| Leu | 425 | . | A | B | . | . | . | . | −0.66 | 0.74 | * | * | . | −0.60 | 0.60 |
| Ala | 426 | . | A | B | . | . | . | . | −0.97 | 0.60 | . | * | . | −0.60 | 0.33 |
| Asn | 427 | . | A | B | . | . | . | . | −1.08 | 0.70 | * | . | . | −0.60 | 0.47 |
| Thr | 428 | . | . | B | B | . | . | . | −1.37 | 0.89 | * | . | . | −0.60 | 0.47 |
| Val | 429 | . | . | B | B | . | . | . | −1.12 | 0.70 | . | . | . | −0.60 | 0.47 |
| Thr | 430 | . | . | B | B | . | . | . | −0.66 | 0.63 | . | . | . | −0.60 | 0.29 |
| Leu | 431 | . | . | B | B | . | . | . | −0.28 | 0.66 | . | . | . | −0.60 | 0.20 |
| Ala | 432 | . | . | B | B | . | . | . | −0.58 | 0.60 | . | . | . | −0.60 | 0.42 |
| Gly | 433 | . | . | . | B | . | . | C | −0.97 | 0.34 | . | * | F | 0.05 | 0.39 |
| Gly | 434 | . | . | . | . | . | T | C | −0.42 | 0.64 | . | . | F | 0.15 | 0.41 |
| Pro | 435 | . | . | . | . | . | T | C | −0.41 | 0.44 | . | * | F | 0.15 | 0.58 |
| Ser | 436 | . | . | . | . | . | T | C | 0.44 | 0.33 | . | * | F | 0.73 | 0.79 |
| Phe | 437 | . | . | B | . | . | T | . | 0.69 | −0.10 | . | . | F | 1.56 | 1.59 |
| Thr | 438 | . | . | B | . | . | . | . | 0.22 | −0.10 | * | . | F | 1.64 | 1.02 |
| Ser | 439 | . | . | B | . | . | T | . | 0.61 | 0.16 | * | . | F | 1.37 | 0.63 |
| Lys | 440 | . | . | . | . | T | T | . | 0.58 | −0.23 | * | . | F | 2.80 | 1.45 |
| Gly | 441 | . | . | . | . | T | T | . | 0.18 | −0.26 | * | . | F | 2.52 | 1.57 |
| Leu | 442 | . | . | . | . | . | T | C | 0.84 | 0.04 | * | . | F | 1.44 | 1.02 |
| Lys | 443 | . | A | B | . | . | . | . | 1.12 | 0.16 | * | . | . | 0.26 | 0.69 |
| Tyr | 444 | . | A | B | . | . | . | . | 0.72 | 0.66 | * | . | . | −0.32 | 0.95 |
| Phe | 445 | . | A | B | . | . | . | . | 0.37 | 1.01 | * | * | . | −0.60 | 1.00 |
| His | 446 | . | A | B | . | . | . | . | −0.10 | 0.81 | * | * | . | −0.60 | 0.72 |

TABLE I-continued

| Res | Pos | I | II | III | IV | V | VI | VII | VIII | IX | X | XI | XII | XIII | XIV |
|---|---|---|---|---|---|---|---|---|---|---|---|---|---|---|---|
| His | 447 | . | A | B | . | . | . | . | 0.41 | 1.50 | * | * | . | −0.60 | 0.38 |
| Phe | 448 | . | A | B | . | . | . | . | −0.44 | 1.13 | * | * | . | −0.60 | 0.59 |
| Thr | 449 | . | A | B | . | . | . | . | −0.87 | 1.03 | . | * | . | −0.60 | 0.36 |
| Leu | 450 | . | A | . | . | T | . | . | −0.51 | 1.10 | . | * | . | −0.20 | 0.14 |
| Ser | 451 | . | . | . | B | T | . | . | −0.48 | 1.03 | . | * | . | −0.20 | 0.16 |
| Leu | 452 | . | . | . | B | T | . | . | −0.44 | 0.64 | . | * | . | 0.14 | 0.18 |
| Cys | 453 | . | . | . | B | T | . | . | −0.09 | 0.56 | . | * | . | 0.48 | 0.37 |
| Gly | 454 | . | . | . | B | T | . | . | 0.33 | 0.30 | * | . | F | 1.27 | 0.28 |
| Asn | 455 | . | . | . | . | T | T | . | 1.19 | −0.09 | * | . | F | 2.61 | 0.66 |
| Gln | 456 | . | . | . | . | T | T | . | 0.89 | −0.77 | * | . | F | 3.40 | 2.45 |
| Gly | 457 | . | . | . | . | T | T | . | 1.40 | −0.73 | * | . | F | 3.06 | 2.45 |
| Arg | 458 | . | . | . | . | T | T | . | 1.21 | −0.77 | * | . | F | 2.72 | 2.04 |
| Lys | 459 | . | . | B | B | . | . | . | 0.89 | −0.53 | * | . | F | 1.43 | 0.87 |
| Met | 460 | . | . | B | B | . | . | . | 0.58 | −0.36 | * | . | . | 0.64 | 0.47 |
| Ser | 461 | . | . | B | B | . | . | . | 0.58 | −0.30 | * | . | . | 0.30 | 0.35 |
| Val | 462 | . | . | B | B | . | . | . | 0.92 | −0.30 | * | . | . | 0.30 | 0.29 |
| Cys | 463 | . | . | B | . | . | T | . | −0.04 | 0.10 | * | . | . | 0.10 | 0.47 |
| Thr | 464 | . | . | B | . | . | T | . | −0.40 | 0.13 | * | * | . | 0.10 | 0.26 |
| Asp | 465 | . | . | B | . | . | T | . | 0.20 | 0.23 | * | . | F | 0.25 | 0.51 |
| Asn | 466 | . | . | B. | . | . | T | . | −0.31 | −0.41 | * | * | F | 1.00 | 1.59 |
| Val | 467 | . | . | B | B | . | . | . | 0.66 | −0.30 | . | * | F | 0.45 | 0.91 |
| Thr | 468 | . | . | B | B | . | . | . | 0.43 | −0.79 | . | * | F | 0.90 | 1.07 |
| Asp | 469 | . | . | B | B | . | . | . | 0.53 | −0.10 | . | * | F | 0.45 | 0.46 |
| Leu | 470 | . | . | B | B | . | . | . | 0.53 | −0.07 | . | * | F | 0.76 | 0.97 |
| Arg | 471 | . | . | B | B | . | . | . | 0.19 | −0.71 | . | * | F | 1.52 | 1.16 |
| Ile | 472 | . | . | B | . | . | T | . | 1.04 | −0.77 | . | * | F | 2.08 | 0.69 |
| Pro | 473 | . | . | B | . | . | T | . | 1.06 | −0.77 | . | * | F | 2.54 | 1.44 |
| Glu | 474 | . | . | . | . | T | T | . | 0.71 | −1.07 | . | * | F | 3.10 | 0.99 |
| Gly | 475 | . | . | . | . | . | T | C | 0.82 | −0.64 | . | * | F | 2.74 | 1.40 |
| Glu | 476 | . | . | . | . | T | T | . | 0.41 | −0.54 | * | . | F | 2.48 | 0.78 |
| Ser | 477 | . | . | . | . | . | T | C | 1.34 | −0.59 | * | . | F | 2.10 | 0.60 |
| Gly | 478 | . | . | . | . | T | T | . | 1.26 | −0.59 | * | . | F | 2.27 | 1.22 |
| Phe | 479 | . | . | . | . | T | T | . | 0.37 | −0.63 | * | . | F | 1.94 | 0.95 |
| Ser | 480 | . | . | . | . | . | T | C | 0.40 | 0.06 | * | . | F | 0.97 | 0.49 |
| Lys | 481 | . | . | . | . | T | T | . | −0.19 | 0.16 | * | . | F | 1.30 | 0.72 |
| Ser | 482 | . | . | . | . | T | T | . | −0.13 | 0.23 | * | . | F | 1.17 | 0.84 |
| Ile | 483 | . | . | B | . | . | T | . | −0.64 | 0.20 | * | . | . | 0.49 | 0.98 |
| Thr | 484 | . | . | B | B | . | . | . | −0.61 | 0.46 | * | . | . | −0.34 | 0.37 |
| Ala | 485 | . | . | B | B | . | . | . | −0.31 | 1.03 | * | . | . | −0.47 | 0.15 |
| Tyr | 486 | . | . | B | B | . | . | . | −0.94 | 1.04 | * | . | . | −0.60 | 0.36 |
| Val | 487 | . | . | B | B | . | . | . | −1.50 | 0.86 | . | . | . | −0.60 | 0.25 |
| Cys | 488 | . | . | B | B | . | . | . | −1.50 | 1.01 | . | . | . | −0.60 | 0.19 |
| Gln | 489 | . | . | B | B | . | . | . | −2.08 | 1.20 | . | . | . | −0.60 | 0.08 |
| Ala | 490 | . | . | B | B | . | . | . | −1.70 | 1.13 | . | . | . | −0.60 | 0.08 |
| Val | 491 | . | . | B | B | . | . | . | −1.67 | 0.91 | . | . | . | −0.60 | 0.23 |
| Ile | 492 | . | . | B | B | . | . | . | −0.81 | 0.77 | . | . | . | −0.60 | 0.20 |
| Ile | 493 | . | . | B | B | . | . | . | −1.00 | 0.37 | . | . | . | −0.30 | 0.35 |
| Pro | 494 | . | . | B | . | . | T | . | −1.31 | 0.51 | . | * | . | −0.20 | 0.35 |
| Pro | 495 | . | . | B | . | . | T | . | −1.07 | 0.36 | . | * | F | 0.42 | 0.71 |
| Glu | 496 | . | . | B | . | . | T | . | −0.46 | 0.10 | . | . | F | 0.74 | 1.01 |
| Val | 497 | . | . | B | . | . | T | . | 0.48 | 0.17 | . | . | F | 0.91 | 1.02 |
| Thr | 498 | . | . | B | . | . | T | . | 0.78 | −0.26 | . | * | F | 1.68 | 1.32 |
| Gly | 499 | . | . | B | . | . | T | . | 0.64 | −0.19 | . | . | F | 1.70 | 0.77 |
| Tyr | 500 | . | . | B | . | . | T | . | 0.00 | 0.24 | . | . | F | 1.08 | 1.03 |
| Lys | 501 | . | . | B | . | . | T | . | −0.30 | 0.24 | . | . | F | 0.76 | 0.53 |
| Ala | 502 | . | . | B | . | . | . | . | 0.26 | 0.14 | . | * | F | 0.39 | 0.71 |
| Gly | 503 | . | . | B | . | . | . | . | 0.57 | 0.10 | . | * | F | 0.22 | 0.61 |
| Val | 504 | . | . | B | . | . | . | . | 0.70 | −0.26 | . | * | F | 0.65 | 0.53 |
| Ser | 505 | . | . | B | . | . | . | . | 0.09 | 0.17 | . | * | F | 0.05 | 0.81 |
| Ser | 506 | . | . | B | . | . | . | . | −0.26 | 0.31 | . | * | F | 0.05 | 0.61 |
| Gln | 507 | . | . | B | . | . | . | . | −0.48 | 0.27 | . | . | F | 0.20 | 1.10 |
| Pro | 508 | . | . | B | . | . | . | . | −0.72 | 0.31 | . | . | F | 0.05 | 0.67 |
| Val | 509 | . | A | B | . | . | . | . | 0.13 | 0.43 | * | * | F | −0.45 | 0.51 |
| Ser | 510 | . | A | B | . | . | . | . | 0.54 | 0.04 | * | * | . | −0.30 | 0.49 |
| Leu | 511 | . | A | B | . | . | . | . | 0.03 | −0.36 | * | * | . | 0.30 | 0.62 |
| Ala | 512 | . | A | B | . | . | . | . | −0.86 | −0.10 | * | * | . | 0.30 | 0.69 |
| Asp | 513 | . | A | B | B | . | . | . | −0.99 | −0.06 | * | * | . | 0.30 | 0.36 |
| Arg | 514 | . | A | B | B | . | . | . | −0.99 | −0.01 | * | * | . | 0.30 | 0.43 |
| Leu | 515 | . | . | B | B | . | . | . | −1.00 | −0.06 | * | . | . | 0.30 | 0.32 |
| Ile | 516 | . | . | B | B | . | . | . | −0.50 | −0.07 | * | . | . | 0.30 | 0.28 |
| Gly | 517 | . | . | B | B | . | . | . | 0.09 | 0.41 | * | . | . | −0.60 | 0.20 |
| Val | 518 | . | . | B | B | . | . | . | −0.51 | 0.41 | * | . | . | −0.60 | 0.41 |
| Thr | 519 | . | . | B | B | . | . | . | −0.93 | 0.34 | . | * | F | −0.15 | 0.58 |
| Thr | 520 | . | . | B | B | . | . | . | −0.93 | 0.14 | . | * | F | −0.15 | 0.85 |
| Asp | 521 | . | . | B | B | . | . | . | −0.04 | 0.40 | . | * | F | −0.45 | 0.94 |
| Met | 522 | . | . | B | B | . | . | . | −0.04 | −0.24 | . | * | F | 0.60 | 1.09 |
| Thr | 523 | . | . | B | B | . | . | . | −0.08 | −0.30 | . | * | . | 0.30 | 0.75 |

TABLE I-continued

| Res | Pos | I | II | III | IV | V | VI | VII | VIII | IX | X | XI | XII | XIII | XIV |
|---|---|---|---|---|---|---|---|---|---|---|---|---|---|---|---|
| Leu | 524 | . | . | B | B | . | . | . | -0.08 | -0.10 | * | * | F | 0.45 | 0.31 |
| Asp | 525 | . | . | . | B | T | . | . | -0.07 | 0.39 | * | * | F | 0.25 | 0.46 |
| Gly | 526 | . | . | . | B | T | . | . | -0.28 | 0.16 | * | * | F | 0.34 | 0.42 |
| Ile | 527 | . | . | . | B | . | . | C | -0.27 | 0.10 | * | . | F | 0.23 | 0.79 |
| Thr | 528 | . | . | . | B | . | . | C | 0.04 | -0.09 | * | * | F | 0.92 | 0.48 |
| Ser | 529 | . | . | . | . | . | T | C | 0.04 | -0.09 | * | . | F | 1.41 | 0.84 |
| Pro | 530 | . | . | . | . | . | T | C | -0.66 | 0.17 | * | . | F | 0.90 | 0.99 |
| Ala | 531 | . | . | B | . | . | T | . | -0.34 | 0.27 | * | . | F | 0.61 | 0.59 |
| Glu | 532 | . | . | B | . | . | T | . | -0.27 | 0.29 | . | * | . | 0.37 | 0.60 |
| Leu | 533 | . | A | B | . | . | . | . | 0.04 | 0.59 | . | . | . | -0.42 | 0.32 |
| Phe | 534 | . | A | B | . | . | . | . | 0.04 | 0.16 | . | . | . | -0.21 | 0.55 |
| His | 535 | . | A | B | . | . | . | . | -0.56 | 0.04 | . | . | . | -0.30 | 0.43 |
| Leu | 536 | . | A | B | . | . | . | . | -0.31 | 0.73 | . | . | . | -0.60 | 0.43 |
| Glu | 537 | . | A | B | . | . | . | . | -1.20 | 0.47 | . | . | . | -0.60 | 0.49 |
| Ser | 538 | . | . | . | . | T | . | . | -0.60 | 0.37 | . | . | . | 0.30 | 0.25 |
| Leu | 539 | . | . | . | . | T | . | . | 0.10 | 0.30 | . | . | . | 0.30 | 0.47 |
| Gly | 540 | . | . | . | . | . | . | C | -0.72 | -0.39 | . | . | . | 0.70 | 0.45 |
| Ile | 541 | . | . | . | B | . | . | C | -0.80 | 0.26 | . | . | F | 0.05 | 0.25 |
| Pro | 542 | . | . | B | B | . | . | . | -1.50 | 0.56 | . | . | F | -0.45 | 0.21 |
| Asp | 543 | . | . | B | B | . | . | . | -1.90 | 0.66 | . | . | . | -0.60 | 0.19 |
| Val | 544 | . | . | B | B | . | . | . | -1.33 | 1.01 | * | * | . | -0.60 | 0.23 |
| Ile | 545 | . | . | B | B | . | . | . | -0.88 | 1.09 | * | . | . | -0.60 | 0.23 |
| Phe | 546 | . | . | B | B | . | . | . | -0.29 | 0.66 | . | * | . | -0.60 | 0.27 |
| Phe | 547 | . | . | B | B | . | . | . | -0.08 | 1.04 | . | * | . | -0.60 | 0.50 |
| Tyr | 548 | . | . | B | . | . | . | . | -0.08 | 0.80 | . | * | . | 0.09 | 1.14 |
| Arg | 549 | . | . | . | . | T | T | . | -0.08 | 0.11 | . | . | F | 1.48 | 2.19 |
| Ser | 550 | . | . | . | . | T | T | . | 0.50 | -0.03 | . | . | F | 2.42 | 1.88 |
| Asn | 551 | . | . | . | . | T | T | . | 1.20 | -0.33 | * | . | F | 2.76 | 1.73 |
| Asp | 552 | . | . | . | . | T | T | . | 1.60 | -0.69 | * | . | F | 3.40 | 1.53 |
| Val | 553 | . | . | . | . | T | . | . | 1.18 | -0.30 | . | . | F | 2.56 | 1.53 |
| Thr | 554 | . | . | B | . | . | . | . | 0.77 | -0.11 | * | . | F | 1.67 | 0.51 |
| Gln | 555 | . | . | B | . | . | . | . | 0.77 | -0.13 | * | . | F | 1.33 | 0.41 |
| Ser | 556 | . | . | B | . | . | . | . | 0.42 | 0.26 | * | * | F | 0.67 | 0.74 |
| Cys | 557 | . | . | B | . | . | T | . | 0.53 | 0.04 | * | * | F | 0.81 | 0.51 |
| Ser | 558 | . | . | . | . | T | T | . | 1.09 | -0.44 | * | * | F | 2.09 | 0.57 |
| Ser | 559 | . | . | . | . | T | T | . | 1.09 | -0.46 | * | * | F | 2.37 | 0.57 |
| Gly | 560 | . | . | . | . | T | T | . | 0.78 | -0.36 | . | . | F | 2.80 | 1.54 |
| Arg | 561 | . | . | . | B | T | . | . | 0.19 | -0.44 | . | * | F | 2.12 | 1.66 |
| Ser | 562 | . | . | . | B | T | . | . | 0.97 | -0.14 | * | * | F | 1.69 | 0.87 |
| Thr | 563 | . | . | B | B | . | . | . | 0.41 | -0.53 | * | * | F | 1.46 | 1.72 |
| Thr | 564 | . | . | B | B | . | . | . | 0.82 | -0.31 | . | * | F | 0.73 | 0.65 |
| Ile | 565 | . | . | B | B | . | . | . | 0.50 | -0.31 | . | * | F | 0.45 | 0.95 |
| Arg | 566 | . | . | B | B | . | . | . | 0.09 | -0.13 | . | * | . | 0.30 | 0.35 |
| Val | 567 | . | . | B | B | . | . | . | 0.18 | -0.23 | . | * | . | 0.64 | 0.33 |
| Arg | 568 | . | . | B | B | . | . | . | 0.49 | -0.29 | . | * | . | 0.98 | 0.73 |
| Cys | 569 | . | . | B | B | . | . | . | 0.84 | -0.57 | . | * | . | 1.62 | 0.64 |
| Ser | 570 | . | . | . | . | . | T | C | 1.42 | -0.57 | * | * | F | 2.86 | 1.73 |
| Pro | 571 | . | . | . | . | T | T | . | 0.46 | -0.73 | * | * | F | 3.40 | 1.27 |
| Gln | 572 | . | . | . | . | T | T | . | 1.10 | -0.09 | * | * | F | 2.76 | 1.76 |
| Lys | 573 | . | . | B | . | . | T | . | 0.64 | -0.23 | . | * | F | 2.02 | 2.03 |
| Thr | 574 | . | . | B | . | . | . | . | 1.01 | -0.19 | . | . | F | 1.48 | 1.30 |
| Val | 575 | . | . | B | . | . | . | . | 0.50 | -0.23 | . | . | F | 1.34 | 1.01 |
| Pro | 576 | . | . | B | . | . | T | . | -0.10 | 0.06 | . | . | F | 0.25 | 0.42 |
| Gly | 577 | . | . | B | . | . | T | . | -0.91 | 0.74 | . | . | F | -0.05 | 0.24 |
| Ser | 578 | . | . | B | . | . | T | . | -1.17 | 0.94 | . | . | F | -0.05 | 0.26 |
| Leu | 579 | . | . | B | . | . | . | . | -1.20 | 0.73 | . | * | F | -0.25 | 0.26 |
| Leu | 580 | . | . | B | . | . | . | . | -0.66 | 0.73 | . | * | F | -0.40 | 0.26 |
| Leu | 581 | . | . | B | . | . | T | . | -1.11 | 0.79 | . | . | F | -0.05 | 0.28 |
| Pro | 582 | . | . | B | . | . | T | . | -1.07 | 0.97 | . | . | F | -0.05 | 0.18 |
| Gly | 583 | . | . | . | . | T | T | . | -0.77 | 0.67 | . | . | F | 0.35 | 0.30 |
| Thr | 584 | . | . | B | . | . | T | . | -0.30 | -0.01 | . | . | F | 1.16 | 0.61 |
| Cys | 585 | . | . | . | . | T | T | . | 0.20 | -0.27 | . | . | F | 1.87 | 0.39 |
| Ser | 586 | . | . | . | . | T | T | . | 0.34 | -0.21 | . | . | F | 2.18 | 0.57 |
| Asp | 587 | . | . | . | . | T | T | . | 0.56 | -0.07 | . | . | F | 2.49 | 0.21 |
| Gly | 588 | . | . | . | . | T | T | . | 0.56 | -0.56 | . | . | F | 3.10 | 0.66 |
| Thr | 589 | . | . | . | . | T | . | . | 0.20 | -0.70 | * | . | F | 2.59 | 0.48 |
| Cys | 590 | . | . | . | . | T | T | . | 0.87 | -0.51 | * | . | F | 2.48 | 0.16 |
| Asp | 591 | . | . | . | . | T | T | . | 0.47 | -0.11 | . | . | F | 1.87 | 0.25 |
| Gly | 592 | . | . | . | . | T | T | . | 0.43 | 0.24 | . | * | F | 0.96 | 0.15 |
| Cys | 593 | . | . | . | . | T | T | . | 0.08 | 0.26 | . | . | . | 0.50 | 0.38 |
| Asn | 594 | . | A | B | . | . | . | . | -0.42 | 0.47 | . | . | . | -0.60 | 0.20 |
| Phe | 595 | . | A | B | . | . | . | . | -0.04 | 1.16 | . | * | . | -0.60 | 0.17 |
| His | 596 | . | A | B | . | . | . | . | -0.04 | 1.64 | . | . | . | -0.60 | 0.33 |
| Phe | 597 | . | A | B | . | . | . | . | 0.00 | 1.07 | * | * | . | -0.60 | 0.35 |
| Leu | 598 | . | A | . | . | T | . | . | 0.08 | 1.06 | . | * | . | -0.20 | 0.54 |
| Trp | 599 | . | A | . | . | T | . | . | -0.51 | 0.77 | . | * | . | -0.20 | 0.40 |
| Glu | 600 | . | A | . | . | T | . | . | -0.40 | 0.77 | . | * | . | -0.20 | 0.47 |

TABLE I-continued

| Res | Pos | I | II | III | IV | V | VI | VII | VIII | IX | X | XI | XII | XIII | XIV |
|---|---|---|---|---|---|---|---|---|---|---|---|---|---|---|---|
| Ser | 601 | . | A | . | . | T | . | . | −1.03 | 0.49 | . | . | . | −0.20 | 0.58 |
| Ala | 602 | . | A | . | . | T | . | . | −0.54 | 0.37 | . | . | . | 0.10 | 0.29 |
| Ala | 603 | . | A | . | . | T | . | . | −0.54 | −0.11 | . | . | . | 0.70 | 0.26 |
| Ala | 604 | . | A | . | . | T | . | . | −0.92 | 0.57 | . | . | . | −0.20 | 0.16 |
| Cys | 605 | . | . | . | . | . | T | C | −1.22 | 0.76 | . | . | . | 0.00 | 0.09 |
| Pro | 606 | . | . | B | . | . | T | . | −1.78 | 0.64 | . | . | . | −0.20 | 0.11 |
| Leu | 607 | . | . | B | . | . | T | . | −1.78 | 0.79 | * | . | . | −0.20 | 0.08 |
| Cys | 608 | . | . | B | . | . | T | . | −1.19 | 0.79 | * | . | . | −0.20 | 0.16 |
| Ser | 609 | . | . | B | B | . | . | . | −0.84 | 0.21 | . | . | . | −0.30 | 0.17 |
| Val | 610 | . | . | B | B | . | . | . | −0.21 | 0.54 | . | . | . | −0.60 | 0.32 |
| Ala | 611 | . | . | B | B | . | . | . | −0.59 | 0.36 | . | . | . | −0.30 | 0.82 |
| Asp | 612 | . | . | B | . | . | . | . | −0.67 | 0.29 | . | . | . | −0.10 | 0.62 |
| Tyr | 613 | . | . | B | B | . | . | . | −0.86 | 0.59 | . | . | . | −0.60 | 0.58 |
| His | 614 | . | . | B | B | . | . | . | −0.86 | 0.59 | . | . | . | −0.60 | 0.43 |
| Ala | 615 | . | . | B | B | . | . | . | −0.30 | 0.47 | . | . | . | −0.60 | 0.34 |
| Ile | 616 | . | . | B | B | . | . | . | −0.38 | 0.86 | . | * | . | −0.60 | 0.29 |
| Val | 617 | . | . | B | B | . | . | . | −1.23 | 0.67 | . | . | . | −0.60 | 0.12 |
| Ser | 618 | . | . | B | B | . | . | . | −1.58 | 0.81 | . | . | . | −0.60 | 0.09 |
| Ser | 619 | . | . | B | B | . | . | . | −1.89 | 0.81 | . | . | . | −0.60 | 0.12 |
| Cys | 620 | . | . | B | B | . | . | . | −2.19 | 0.56 | * | . | . | −0.60 | 0.16 |
| Val | 621 | . | . | B | B | . | . | . | −1.30 | 0.60 | * | . | . | −0.60 | 0.09 |
| Ala | 622 | . | . | B | B | . | . | . | −0.40 | 0.61 | * | . | . | −0.60 | 0.11 |
| Gly | 623 | . | . | B | B | . | . | . | −0.41 | 0.23 | * | . | . | −0.30 | 0.41 |
| Ile | 624 | . | . | B | B | . | . | . | −0.42 | 0.14 | * | . | . | −0.30 | 0.80 |
| Gln | 625 | . | . | B | B | . | . | . | 0.00 | −0.01 | . | . | F | 0.60 | 1.15 |
| Lys | 626 | . | . | B | B | . | . | . | 0.00 | 0.24 | * | . | F | 0.00 | 1.82 |
| Thr | 627 | . | . | B | B | . | . | . | 0.30 | 0.46 | * | * | F | −0.30 | 1.92 |
| Thr | 628 | . | . | B | B | . | . | . | 0.76 | 0.69 | * | . | F | −0.30 | 1.17 |
| Tyr | 629 | . | . | B | B | . | . | . | 1.64 | 0.29 | * | . | . | −0.15 | 1.14 |
| Val | 630 | . | A | B | B | . | . | . | 1.43 | 0.29 | * | . | . | −0.15 | 1.37 |
| Trp | 631 | . | A | B | B | . | . | . | 1.43 | 0.23 | * | * | . | −0.15 | 1.47 |
| Arg | 632 | . | A | B | B | . | . | . | 0.93 | −0.26 | * | . | F | 0.60 | 1.88 |
| Glu | 633 | . | A | B | B | . | . | . | 0.58 | −0.33 | * | . | F | 0.85 | 2.09 |
| Pro | 634 | . | A | . | . | T | . | . | 0.52 | −0.40 | * | . | F | 1.50 | 1.06 |
| Lys | 635 | . | A | . | . | T | . | . | 1.03 | −0.93 | * | . | F | 1.90 | 0.73 |
| Leu | 636 | . | A | . | . | T | . | . | 0.98 | −0.50 | * | . | F | 1.85 | 0.42 |
| Cys | 637 | . | . | . | . | T | T | . | −0.02 | −0.07 | * | . | F | 2.50 | 0.27 |
| Ser | 638 | . | . | . | . | T | T | . | −0.32 | 0.19 | . | * | F | 1.65 | 0.09 |
| Gly | 639 | . | . | . | . | T | T | . | −0.92 | 0.57 | * | * | F | 1.10 | 0.15 |
| Gly | 640 | . | . | . | . | T | T | . | −1.18 | 0.57 | * | . | F | 0.85 | 0.23 |
| Ile | 641 | . | . | . | . | . | . | C | −0.37 | 0.43 | * | . | F | 0.20 | 0.27 |
| Ser | 642 | . | . | . | . | . | . | C | 0.30 | 0.04 | . | * | F | 0.25 | 0.47 |
| Leu | 643 | . | . | B | . | . | . | . | 0.71 | 0.01 | . | * | F | 0.05 | 0.82 |
| Pro | 644 | . | . | B | . | . | . | . | 0.20 | −0.41 | . | * | F | 0.80 | 2.30 |
| Glu | 645 | . | . | B | B | . | . | . | 0.23 | −0.46 | . | * | F | 0.60 | 1.27 |
| Gln | 646 | . | . | B | B | . | . | . | 0.23 | −0.36 | . | * | F | 0.60 | 2.23 |
| Arg | 647 | . | . | B | B | . | . | . | −0.13 | −0.36 | . | * | F | 0.60 | 1.01 |
| Val | 648 | . | . | B | B | . | . | . | 0.72 | −0.21 | . | * | . | 0.30 | 0.31 |
| Thr | 649 | . | . | B | B | . | . | . | 0.62 | −0.21 | . | * | . | 0.30 | 0.36 |
| Ile | 650 | . | . | B | B | . | . | . | −0.27 | −0.13 | . | * | . | 0.30 | 0.27 |
| Cys | 651 | . | . | B | B | . | . | . | −0.27 | 0.56 | . | * | . | −0.60 | 0.25 |
| Lys | 652 | . | . | B | B | . | . | . | −1.08 | −0.09 | * | * | . | 0.30 | 0.29 |
| Thr | 653 | . | . | B | B | . | . | . | −0.51 | 0.21 | * | * | . | −0.30 | 0.36 |
| Ile | 654 | . | . | B | B | . | . | . | −1.01 | 0.44 | * | * | . | −0.60 | 0.71 |
| Asp | 655 | . | . | B | B | . | . | . | −0.08 | 0.56 | * | * | . | −0.60 | 0.29 |
| Phe | 656 | . | . | B | B | . | . | . | −0.27 | 0.56 | * | * | . | −0.60 | 0.40 |
| Trp | 657 | . | . | B | B | . | . | . | −0.66 | 0.71 | * | * | . | −0.60 | 0.43 |
| Leu | 658 | . | . | B | B | . | . | . | −1.23 | 0.46 | * | * | . | −0.60 | 0.25 |
| Lys | 659 | . | . | B | B | . | . | . | −0.64 | 1.14 | * | * | . | −0.60 | 0.20 |
| Val | 660 | . | . | . | B | T | . | . | −1.23 | 0.74 | * | * | . | −0.20 | 0.26 |
| Gly | 661 | . | . | . | B | T | . | . | −0.88 | 0.33 | * | * | . | 0.10 | 0.32 |
| Ile | 662 | . | . | . | B | T | . | . | −0.90 | 0.07 | * | * | . | 0.10 | 0.16 |
| Ser | 663 | . | . | . | . | . | T | C | −0.76 | 0.56 | * | * | . | 0.00 | 0.31 |
| Ala | 664 | . | . | . | . | T | T | . | −1.11 | 0.49 | . | * | F | 0.35 | 0.17 |
| Gly | 665 | . | . | . | . | T | T | . | −0.84 | 0.54 | * | . | F | 0.35 | 0.34 |
| Thr | 666 | . | . | B | . | . | T | . | −1.39 | 0.36 | . | . | F | 0.25 | 0.26 |
| Cys | 667 | . | . | B | B | . | . | . | −1.31 | 0.66 | . | . | . | −0.60 | 0.18 |
| Thr | 668 | . | . | B | B | . | . | . | −1.82 | 0.84 | . | . | . | −0.60 | 0.15 |
| Ala | 669 | . | . | B | B | . | . | . | −1.54 | 1.10 | . | . | . | −0.60 | 0.09 |
| Ile | 670 | . | . | B | B | . | . | . | −2.06 | 1.10 | . | . | . | −0.60 | 0.23 |
| Leu | 671 | . | . | B | B | . | . | . | −2.56 | 1.17 | . | . | . | −0.60 | 0.12 |
| Leu | 672 | . | . | B | B | . | . | . | −2.20 | 1.37 | . | . | . | −0.60 | 0.10 |
| Thr | 673 | . | . | B | B | . | . | . | −2.56 | 1.36 | . | . | . | −0.60 | 0.20 |
| Val | 674 | . | . | B | B | . | . | . | −2.21 | 1.24 | . | . | . | −0.60 | 0.13 |
| Leu | 675 | . | . | B | B | . | . | . | −2.02 | 1.31 | . | . | . | −0.60 | 0.25 |
| Thr | 676 | . | . | B | B | . | . | . | −1.50 | 1.41 | * | . | . | −0.60 | 0.15 |
| Cys | 677 | . | . | B | B | . | . | . | −0.64 | 1.84 | * | . | . | −0.60 | 0.21 |

TABLE I-continued

| Res | Pos | I | II | III | IV | V | VI | VII | VIII | IX | X | XI | XII | XIII | XIV |
|---|---|---|---|---|---|---|---|---|---|---|---|---|---|---|---|
| Tyr | 678 | . | . | B | B | . | . | . | −0.29 | 1.20 | . | . | . | −0.60 | 0.51 |
| Phe | 679 | . | . | . | B | T | . | . | 0.57 | 0.51 | . | . | . | −0.20 | 0.70 |
| Trp | 680 | . | . | . | B | T | . | . | 1.38 | 0.43 | * | . | . | 0.29 | 2.10 |
| Lys | 681 | . | . | . | . | . | T | C | 1.73 | 0.26 | * | . | F | 1.28 | 2.32 |
| Lys | 682 | . | . | . | . | . | T | T | . | 1.59 | −0.50 | * | * | F | 2.42 | 5.37 |
| Asn | 683 | . | . | . | . | . | T | C | 1.83 | −0.60 | * | * | F | 2.86 | 4.21 |
| Gln | 684 | . | . | . | . | . | T | T | . | 2.29 | −1.51 | * | * | F | 3.40 | 3.65 |
| Lys | 685 | . | . | B | . | . | . | . | 2.62 | −0.76 | * | * | F | 2.46 | 2.86 |
| Leu | 686 | . | . | B | . | . | . | . | 2.33 | −0.76 | * | * | F | 2.32 | 3.55 |
| Glu | 687 | . | . | B | . | . | . | . | 1.99 | −0.40 | * | * | . | 1.73 | 3.21 |
| Tyr | 688 | . | . | B | . | . | T | . | 2.03 | −0.41 | * | * | . | 1.79 | 2.15 |
| Lys | 689 | . | . | B | . | . | T | . | 1.22 | −0.41 | * | * | F | 1.80 | 5.22 |
| Tyr | 690 | . | . | B | . | . | T | . | 0.32 | −0.41 | * | * | F | 2.00 | 2.49 |
| Ser | 691 | . | . | B | . | . | T | . | 0.53 | 0.23 | * | * | F | 1.20 | 1.18 |
| Lys | 692 | . | A | B | . | . | . | . | 0.53 | 0.09 | * | * | F | 0.45 | 0.58 |
| Leu | 693 | . | A | B | . | . | . | . | 0.19 | 0.49 | * | * | . | −0.20 | 0.60 |
| Val | 694 | . | A | B | . | . | . | . | −0.17 | 0.23 | * | * | . | −0.10 | 0.45 |
| Met | 695 | . | A | B | . | . | . | . | −0.73 | 0.33 | * | * | . | −0.30 | 0.33 |
| Asn | 696 | . | A | B | . | . | . | . | −0.39 | 1.01 | . | * | . | −0.60 | 0.33 |
| Ala | 697 | . | A | B | . | . | . | . | −0.43 | 0.33 | * | * | . | −0.30 | 0.88 |
| Thr | 698 | . | A | B | . | . | . | . | −0.29 | −0.31 | . | * | . | 0.65 | 1.48 |
| Leu | 699 | . | A | B | . | . | . | . | 0.57 | −0.36 | * | . | F | 0.85 | 0.49 |
| Lys | 700 | . | A | B | . | . | . | . | 0.36 | −0.76 | . | * | F | 1.35 | 0.82 |
| Asp | 701 | . | . | . | . | T | T | . | 0.14 | −0.57 | . | * | F | 2.35 | 0.47 |
| Cys | 702 | . | . | B | . | . | T | . | 0.14 | −0.63 | . | . | . | 2.00 | 0.87 |
| Asp | 703 | . | . | B | . | . | T | . | −0.13 | −0.81 | . | . | . | 1.80 | 0.44 |
| Leu | 704 | . | . | B | . | . | T | . | 0.68 | −0.31 | . | . | . | 1.30 | 0.27 |
| Pro | 705 | . | . | B | . | . | . | . | 0.33 | −0.31 | . | . | . | 0.90 | 0.83 |
| Ala | 706 | . | . | . | . | T | . | . | −0.33 | −0.50 | . | * | . | 1.10 | 0.67 |
| Ala | 707 | A | . | . | . | . | . | . | −0.26 | 0.07 | . | . | . | −0.10 | 0.43 |
| Asp | 708 | A | . | . | . | . | T | . | −1.14 | −0.11 | . | . | . | 0.70 | 0.28 |
| Ser | 709 | . | . | B | . | . | T | . | −0.93 | 0.14 | . | . | . | 0.10 | 0.20 |
| Cys | 710 | . | . | B | . | . | T | . | −0.72 | 0.26 | . | . | . | 0.10 | 0.19 |
| Ala | 711 | . | . | B | . | . | T | . | −0.48 | −0.24 | . | . | . | 0.70 | 0.20 |
| Ile | 712 | . | A | B | . | . | . | . | 0.11 | 0.19 | . | . | . | −0.30 | 0.15 |
| Met | 713 | . | A | B | . | . | . | . | 0.11 | −0.20 | . | . | . | 0.30 | 0.48 |
| Glu | 714 | . | A | B | . | . | . | . | −0.44 | −0.77 | . | . | F | 0.75 | 0.79 |
| Gly | 715 | . | A | . | . | . | . | C | 0.22 | −0.63 | * | . | F | 0.95 | 0.83 |
| Glu | 716 | A | A | . | . | . | . | . | 0.81 | −1.31 | * | . | F | 0.90 | 1.46 |
| Asp | 717 | A | A | . | . | . | . | . | 1.70 | −1.93 | * | . | F | 0.90 | 1.41 |
| Val | 718 | A | A | . | . | . | . | . | 1.49 | −1.93 | * | . | F | 0.90 | 2.38 |
| Glu | 719 | A | A | . | . | . | . | . | 0.60 | −1.67 | * | . | F | 0.90 | 1.13 |
| Asp | 720 | A | A | . | . | . | . | . | 0.24 | −0.99 | * | . | F | 0.75 | 0.48 |
| Asp | 721 | A | A | . | . | . | . | . | −0.07 | −0.20 | . | * | F | 0.45 | 0.55 |
| Leu | 722 | A | A | . | . | . | . | . | −0.37 | −0.36 | * | * | . | 0.30 | 0.46 |
| Ile | 723 | A | A | . | . | . | . | . | 0.53 | 0.03 | . | * | . | −0.30 | 0.37 |
| Phe | 724 | . | A | B | . | . | . | . | 0.53 | 0.03 | . | . | . | −0.30 | 0.44 |
| Thr | 725 | . | A | B | . | . | . | . | 0.50 | 0.43 | . | . | F | −0.45 | 0.87 |
| Ser | 726 | . | . | . | . | . | T | C | 0.20 | 0.24 | . | . | F | 0.60 | 1.68 |
| Lys | 727 | . | . | . | . | . | T | T | . | 0.20 | −0.06 | . | . | F | 1.40 | 2.60 |
| Asn | 728 | . | . | . | . | . | T | C | 0.74 | −0.16 | * | * | F | 1.48 | 1.49 |
| His | 729 | . | . | . | . | . | T | C | 1.56 | −0.21 | * | * | F | 1.76 | 1.10 |
| Ser | 730 | . | . | . | . | . | . | C | 1.57 | −0.60 | . | * | . | 1.99 | 1.07 |
| Leu | 731 | . | . | . | . | T | . | . | 1.87 | −0.21 | . | * | . | 2.02 | 0.90 |
| Gly | 732 | . | . | . | . | T | T | . | 1.79 | −0.21 | . | . | F | 2.80 | 1.06 |
| Arg | 733 | . | . | . | . | T | T | . | 0.98 | −0.21 | * | . | F | 2.52 | 1.07 |
| Ser | 734 | . | . | . | . | T | T | . | 0.80 | 0.09 | * | . | F | 1.88 | 1.07 |
| Asn | 735 | . | . | . | . | T | T | . | 0.89 | −0.17 | * | * | F | 2.44 | 1.68 |
| His | 736 | . | . | . | . | . | . | C | 1.81 | −0.17 | * | * | F | 2.00 | 1.33 |
| Leu | 737 | . | . | . | . | . | . | C | 1.81 | −0.17 | * | * | F | 1.96 | 1.94 |
| Pro | 738 | . | . | . | . | . | T | C | 0.89 | −0.13 | * | * | F | 2.40 | 1.19 |
| Pro | 739 | . | . | . | . | . | T | T | . | 0.38 | 0.16 | . | * | F | 1.61 | 0.72 |
| Arg | 740 | . | . | . | . | . | T | T | . | −0.22 | 0.34 | . | * | F | 1.37 | 0.72 |
| Gly | 741 | . | . | B | . | . | . | T | . | −0.19 | 0.27 | . | * | F | 0.73 | 0.46 |
| Leu | 742 | . | A | B | . | . | . | . | −0.19 | −0.16 | . | * | . | 0.54 | 0.50 |
| Leu | 743 | . | A | B | . | . | . | . | −0.29 | 0.10 | * | . | . | −0.30 | 0.21 |
| Met | 744 | . | A | B | . | . | . | . | −0.08 | 0.59 | * | . | . | −0.60 | 0.31 |
| Asp | 745 | . | A | B | . | . | . | . | −0.86 | 0.56 | * | . | . | −0.60 | 0.64 |
| Leu | 746 | . | A | B | . | . | . | . | −0.40 | 0.44 | . | . | . | −0.60 | 0.42 |
| Thr | 747 | . | A | B | . | . | . | . | 0.02 | −0.24 | . | * | . | 0.30 | 0.83 |
| Gln | 748 | . | A | B | . | . | . | . | 0.44 | −0.43 | . | . | F | 0.45 | 0.63 |
| Cys | 749 | . | A | B | . | . | . | . | 0.66 | 0.00 | . | . | . | −0.30 | 0.98 |
| Arg | 750 | . | A | B | . | . | . | . | 0.27 | −0.26 | . | . | . | 0.30 | 0.87 |

TABLE II

| Res | Pos | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | T | . | 0.80 | 0.20 | . | . | . | -0.10 | 0.71 |
| Ser | 2 | . | . | B | . | . | . | T | . | 0.47 | 0.26 | . | . | . | 0.10 | 0.80 |
| Thr | 3 | . | . | B | . | . | . | T | . | 0.51 | 0.23 | . | . | . | 0.50 | 1.01 |
| Gly | 4 | . | . | . | . | . | . | T | C | 0.90 | 0.23 | . | * | . | 0.95 | 1.01 |
| Thr | 5 | . | . | . | . | . | T | T | . | 0.94 | -0.39 | . | . | F | 2.15 | 1.26 |
| Asn | 6 | . | . | . | . | . | . | T | C | 0.69 | -0.34 | . | . | F | 2.05 | 0.86 |
| Gly | 7 | . | . | . | . | . | T | T | . | 0.69 | -0.19 | . | . | F | 2.50 | 0.65 |
| Asp | 8 | . | . | . | . | . | T | T | . | 0.79 | -0.23 | . | . | F | 2.25 | 0.60 |
| Gly | 9 | . | . | B | . | . | . | T | . | 0.54 | -0.29 | . | . | F | 1.60 | 0.58 |
| Val | 10 | . | . | B | . | . | . | . | . | 0.86 | -0.19 | . | * | F | 1.15 | 0.59 |
| Ser | 11 | . | . | B | . | . | . | . | . | 0.51 | -0.21 | . | . | F | 0.90 | 0.57 |
| Pro | 12 | . | . | B | . | . | . | T | . | 0.00 | 0.21 | * | . | F | 0.25 | 0.57 |
| Ala | 13 | . | . | B | . | . | . | T | . | -0.86 | 0.43 | * | . | F | -0.05 | 0.57 |
| Asn | 14 | . | . | B | . | . | . | T | . | -1.32 | 0.43 | * | . | F | -0.05 | 0.31 |
| Gly | 15 | . | . | B | . | . | . | T | . | -0.47 | 0.73 | . | . | . | -0.20 | 0.17 |
| Val | 16 | . | . | B | B | . | . | . | . | -0.06 | 0.30 | . | . | . | -0.30 | 0.28 |
| Val | 17 | . | . | B | B | . | . | . | . | -0.14 | -0.20 | . | . | . | 0.60 | 0.34 |
| Leu | 18 | . | . | B | B | . | . | . | . | 0.20 | -0.21 | . | . | . | 0.90 | 0.46 |
| Asp | 19 | . | . | B | . | . | . | T | . | -0.01 | 0.11 | * | * | F | 1.15 | 0.96 |
| Arg | 20 | . | . | B | . | . | . | T | . | 0.44 | -0.10 | * | * | F | 2.20 | 2.01 |
| Ser | 21 | . | . | . | . | . | T | T | C | 0.41 | -0.74 | * | * | F | 3.00 | 4.77 |
| Tyr | 22 | . | . | . | . | . | T | T | C | 0.41 | -0.74 | * | * | F | 2.70 | 2.00 |
| Pro | 23 | . | . | B | B | . | . | . | . | 0.37 | -0.10 | * | * | F | 1.35 | 0.76 |
| Arg | 24 | . | . | B | B | . | . | . | . | -0.23 | 0.54 | * | * | . | 0.00 | 0.42 |
| Ile | 25 | . | A | B | B | . | . | . | . | -0.34 | 0.77 | * | * | . | -0.30 | 0.27 |
| Val | 26 | . | A | B | B | . | . | . | . | 0.07 | 0.01 | . | * | . | -0.30 | 0.30 |
| Val | 27 | . | A | B | B | . | . | . | . | -0.54 | -0.41 | . | * | . | 0.30 | 0.30 |
| Met | 28 | . | A | B | B | . | . | . | . | -0.33 | 0.23 | . | * | . | -0.30 | 0.31 |
| Glu | 29 | . | A | B | B | . | . | . | . | -1.04 | -0.46 | . | * | . | 0.30 | 0.73 |
| Arg | 30 | A | A | . | B | . | . | . | . | -0.37 | -0.49 | . | * | . | 0.30 | 0.98 |
| Val | 31 | A | A | . | B | . | . | . | . | 0.18 | -0.70 | . | * | . | 0.75 | 1.53 |
| Glu | 32 | A | A | . | B | . | . | . | . | 0.44 | -0.83 | * | * | . | 0.75 | 1.27 |
| Met | 33 | A | A | . | . | . | . | . | . | 1.04 | -0.33 | * | * | . | 0.30 | 0.66 |
| Pro | 34 | A | . | . | . | . | . | . | . | 0.83 | 0.07 | * | * | F | 0.20 | 1.53 |
| Thr | 35 | A | . | . | . | . | . | . | . | 0.13 | -0.14 | * | * | F | 0.80 | 1.37 |
| Ala | 36 | A | A | . | . | . | . | . | . | 0.18 | 0.36 | . | . | F | 0.00 | 1.40 |
| Gln | 37 | A | A | . | . | . | . | . | . | -0.63 | 0.43 | . | . | F | -0.45 | 0.75 |
| Pro | 38 | A | A | . | . | . | . | . | . | -0.62 | 0.69 | . | . | F | -0.45 | 0.43 |
| Ala | 39 | A | A | . | . | . | . | . | . | -1.27 | 0.70 | . | . | . | -0.60 | 0.43 |
| Leu | 40 | A | A | . | . | . | . | . | . | -0.96 | 0.84 | * | . | . | -0.60 | 0.18 |
| Leu | 41 | A | A | . | . | . | . | . | . | -0.32 | 0.84 | * | . | . | -0.60 | 0.20 |
| Ala | 42 | A | A | . | . | . | . | . | . | -0.32 | 0.41 | * | . | . | -0.60 | 0.40 |
| Val | 43 | . | A | B | . | . | . | . | . | -0.92 | 0.31 | * | . | . | -0.30 | 0.85 |
| Gln | 44 | . | A | B | . | . | . | . | . | -0.68 | 0.31 | * | . | . | -0.06 | 0.85 |
| Lys | 45 | . | A | B | . | . | . | . | . | -0.08 | 0.06 | * | . | F | 0.33 | 0.83 |
| Gln | 46 | . | A | . | . | T | . | . | . | 0.52 | -0.01 | . | . | F | 1.72 | 1.74 |
| Leu | 47 | . | A | . | . | T | . | . | . | 1.11 | -0.23 | . | . | F | 1.96 | 1.55 |
| Gly | 48 | . | . | . | . | . | T | T | C | 1.37 | -0.23 | . | . | F | 2.40 | 1.34 |
| Pro | 49 | . | . | . | . | . | T | T | C | 0.70 | 0.39 | . | . | F | 1.41 | 0.77 |
| Pro | 50 | . | . | . | . | T | T | T | . | 0.77 | 0.56 | * | * | F | 1.07 | 0.50 |
| Gln | 51 | . | . | . | . | T | T | T | . | -0.09 | -0.13 | * | * | . | 1.58 | 0.99 |
| Met | 52 | . | . | B | B | . | . | . | . | 0.13 | 0.09 | * | * | . | -0.06 | 0.47 |
| Cys | 53 | . | . | B | B | . | . | . | . | -0.19 | 0.16 | * | * | . | -0.30 | 0.31 |
| Arg | 54 | . | . | B | B | . | . | . | . | -0.29 | 0.30 | * | * | . | -0.30 | 0.10 |
| Val | 55 | . | . | B | B | . | . | . | . | -0.74 | 0.39 | * | . | . | -0.30 | 0.14 |
| Ala | 56 | . | . | B | B | . | . | . | . | -1.33 | 0.34 | * | * | . | -0.30 | 0.14 |
| Cys | 57 | . | . | B | B | . | . | . | . | -1.59 | 0.27 | * | * | . | -0.30 | 0.07 |
| Thr | 58 | . | . | B | B | . | . | . | . | -1.81 | 0.91 | . | * | . | -0.60 | 0.07 |
| Cys | 59 | . | . | B | B | . | . | . | . | -1.92 | 0.96 | * | * | . | -0.60 | 0.05 |
| Ala | 60 | . | . | B | B | . | . | . | . | -0.96 | 0.86 | * | . | . | -0.60 | 0.15 |
| Val | 61 | . | . | B | B | . | . | . | . | -1.22 | 0.29 | * | * | . | -0.30 | 0.20 |
| Ile | 62 | . | . | B | B | . | . | . | . | -0.56 | 0.44 | * | . | . | -0.60 | 0.28 |
| Asn | 63 | . | . | B | B | . | . | . | . | -0.20 | 0.27 | * | . | . | -0.30 | 0.48 |
| Arg | 64 | . | . | B | B | . | . | . | . | -0.39 | -0.23 | * | . | . | 0.45 | 1.30 |
| Val | 65 | . | . | B | B | . | . | . | . | 0.20 | -0.23 | * | . | F | 0.60 | 1.38 |
| Gln | 66 | . | . | B | B | . | . | . | . | 0.39 | -0.51 | * | . | F | 0.90 | 1.38 |
| Lys | 67 | . | . | B | B | . | . | . | . | 0.97 | -0.34 | * | . | F | 0.45 | 0.38 |
| Val | 68 | . | . | B | B | . | . | . | . | 0.76 | 0.14 | * | . | . | -0.30 | 0.73 |
| Asn | 69 | . | . | B | B | . | . | . | . | 0.33 | -0.07 | * | * | . | 0.30 | 0.65 |
| Cys | 70 | . | . | B | B | . | . | . | . | 0.89 | 0.01 | * | * | F | -0.15 | 0.47 |
| Thr | 71 | . | . | B | . | . | . | T | . | 0.89 | 0.40 | . | * | F | 0.25 | 0.85 |
| Pro | 72 | . | . | . | . | T | T | . | . | 0.26 | 0.16 | * | * | F | 0.65 | 0.85 |
| Thr | 73 | . | . | . | . | T | T | . | . | 0.26 | 0.26 | * | * | F | 0.80 | 1.61 |
| Ser | 74 | . | . | . | . | T | T | . | . | -0.41 | 0.33 | * | * | F | 0.65 | 0.83 |
| Asn | 75 | . | . | B | . | . | . | . | . | -0.09 | 0.41 | . | . | F | -0.25 | 0.29 |
| Ala | 76 | . | . | B | . | . | . | . | . | 0.22 | 0.41 | . | . | . | -0.40 | 0.20 |
| Val | 77 | . | . | B | . | . | . | . | . | -0.23 | -0.07 | . | . | . | 0.50 | 0.24 |

TABLE II-continued

| Res | Pos | I | II | III | IV | V | VI | VII | VIII | IX | X | XI | XII | XIII | XIV |
|---|---|---|---|---|---|---|---|---|---|---|---|---|---|---|---|
| Cys | 78 | . | . | B | . | . | T | . | -0.73 | 0.11 | . | . | . | 0.10 | 0.08 |
| Gly | 79 | . | . | B | . | . | T | . | -0.64 | 0.40 | * | * | . | 0.10 | 0.07 |
| Asp | 80 | . | . | B | . | . | T | . | -0.53 | 0.33 | * | * | . | 0.10 | 0.14 |
| Cys | 81 | . | . | B | . | . | T | . | -0.64 | -0.31 | * | * | . | 0.70 | 0.51 |
| Leu | 82 | . | . | B | . | . | . | . | -0.03 | -0.10 | * | * | . | 0.50 | 0.44 |
| Pro | 83 | . | . | B | . | . | T | . | 0.74 | 0.23 | * | * | . | 0.10 | 0.42 |
| Arg | 84 | . | . | B | . | . | T | . | 1.13 | 0.23 | * | * | . | 0.25 | 1.52 |
| Phe | 85 | . | . | B | . | . | T | . | 0.82 | -0.34 | * | * | . | 0.85 | 3.69 |
| Tyr | 86 | . | . | B | . | . | T | . | 1.60 | -0.54 | * | * | . | 1.38 | 3.44 |
| Arg | 87 | . | . | B | B | . | . | . | 1.52 | -0.97 | * | * | F | 1.36 | 3.44 |
| Lys | 88 | . | . | B | B | . | . | . | 1.39 | -0.29 | * | * | F | 1.29 | 2.79 |
| Thr | 89 | . | . | B | B | . | . | . | 0.93 | -0.64 | * | * | F | 1.82 | 1.76 |
| Arg | 90 | . | . | . | B | T | . | . | 0.82 | -0.97 | * | * | F | 2.30 | 0.89 |
| Ile | 91 | . | . | . | B | T | . | . | 1.07 | -0.29 | . | . | F | 1.77 | 0.37 |
| Gly | 92 | . | . | . | . | T | . | . | 0.96 | 0.11 | . | . | F | 1.14 | 0.44 |
| Gly | 93 | . | A | . | . | T | . | . | 0.91 | -0.37 | . | * | F | 1.31 | 0.38 |
| Leu | 94 | . | A | . | . | . | . | C | 1.22 | 0.03 | * | * | F | 0.28 | 0.93 |
| Gln | 95 | . | A | . | . | T | . | . | 0.44 | -0.66 | . | * | F | 1.30 | 1.62 |
| Asp | 96 | . | A | . | . | T | . | . | 0.44 | -0.51 | . | . | F | 1.15 | 0.88 |
| Gln | 97 | . | A | B | . | . | . | . | 0.58 | -0.26 | . | . | F | 0.45 | 0.75 |
| Glu | 98 | . | A | B | . | . | . | . | 0.26 | -0.51 | . | . | F | 0.75 | 0.67 |
| Cys | 99 | . | A | B | . | . | . | . | 0.76 | -0.34 | . | . | . | 0.30 | 0.21 |
| Ile | 100 | . | . | B | . | . | . | . | 0.80 | 0.14 | . | . | . | -0.10 | 0.18 |
| Pro | 101 | . | . | . | . | T | . | . | 0.80 | -0.26 | . | . | . | 0.90 | 0.21 |
| Cys | 102 | . | . | . | . | T | T | . | 0.49 | 0.14 | * | . | . | 0.50 | 0.67 |
| Thr | 103 | . | . | . | . | T | T | . | 0.28 | 0.06 | * | . | F | 1.10 | 1.37 |
| Lys | 104 | . | . | . | . | T | T | . | 0.63 | -0.20 | . | . | F | 2.00 | 1.37 |
| Gln | 105 | . | . | . | . | . | T | C | 1.22 | -0.14 | . | . | F | 2.10 | 3.69 |
| Thr | 106 | . | . | . | . | . | T | C | 1.43 | -0.33 | . | . | F | 2.40 | 3.43 |
| Pro | 107 | . | . | . | . | . | T | C | 1.24 | -0.81 | . | * | F | 3.00 | 2.97 |
| Thr | 108 | . | . | . | . | . | T | T | 1.56 | -0.17 | . | * | F | 2.60 | 1.27 |
| Ser | 109 | . | . | B | . | . | . | T | 0.84 | -0.17 | . | * | F | 1.90 | 1.53 |
| Glu | 110 | . | A | B | . | . | . | . | 0.26 | -0.09 | * | * | F | 1.05 | 0.53 |
| Val | 111 | . | A | B | . | . | . | . | -0.13 | -0.01 | * | * | . | 0.60 | 0.37 |
| Gln | 112 | . | A | B | . | . | . | . | 0.08 | 0.29 | * | * | . | -0.30 | 0.24 |
| Cys | 113 | A | A | . | . | . | . | . | -0.42 | 0.30 | * | * | . | -0.30 | 0.24 |
| Ala | 114 | A | A | . | . | . | . | . | -0.42 | 0.99 | * | * | . | -0.60 | 0.27 |
| Phe | 115 | A | A | . | . | . | . | . | -1.23 | 0.73 | . | * | . | -0.60 | 0.21 |
| Gln | 116 | A | A | . | . | . | . | . | -1.23 | 1.01 | . | * | . | -0.60 | 0.32 |
| Leu | 117 | A | A | . | . | . | . | . | -1.23 | 1.09 | . | * | . | -0.60 | 0.23 |
| Ser | 118 | . | A | B | . | . | . | . | -1.16 | 0.59 | . | * | . | -0.60 | 0.47 |
| Leu | 119 | . | A | B | . | . | . | . | -0.57 | 0.30 | . | * | . | -0.30 | 0.27 |
| Val | 120 | A | A | . | . | . | . | . | -0.46 | -0.10 | . | * | . | 0.30 | 0.55 |
| Glu | 121 | A | A | . | . | . | . | . | -0.67 | -0.29 | . | * | . | 0.30 | 0.41 |
| Ala | 122 | A | A | . | . | . | . | . | -0.17 | -0.24 | . | . | . | 0.30 | 0.78 |
| Asp | 123 | . | A | . | . | T | . | . | -0.72 | -0.44 | . | . | . | 0.85 | 1.51 |
| Ala | 124 | . | A | . | . | . | . | C | -0.12 | -0.44 | . | . | F | 0.65 | 0.65 |
| Pro | 125 | . | A | . | . | . | . | C | 0.52 | -0.01 | . | * | F | 0.65 | 0.99 |
| Thr | 126 | . | . | . | . | . | . | C | 0.52 | -0.09 | . | . | F | 0.85 | 0.92 |
| Val | 127 | . | . | . | . | . | . | C | 1.11 | 0.31 | . | . | F | 0.40 | 1.57 |
| Pro | 128 | . | . | . | . | . | . | C | 0.52 | -0.19 | . | . | F | 1.00 | 1.76 |
| Pro | 129 | A | . | . | . | . | . | . | 0.80 | -0.11 | . | . | F | 0.80 | 1.23 |
| Gln | 130 | A | . | . | . | . | . | . | 0.20 | -0.11 | . | . | F | 0.80 | 2.40 |
| Glu | 131 | A | . | . | . | . | . | . | -0.34 | -0.07 | . | . | F | 0.80 | 1.28 |
| Ala | 132 | A | . | . | B | . | . | . | -0.08 | 0.14 | . | . | F | -0.15 | 0.61 |
| Thr | 133 | A | . | . | B | . | . | . | -0.68 | 0.21 | . | . | . | -0.30 | 0.36 |
| Leu | 134 | A | . | . | B | . | . | . | -1.32 | 0.50 | . | . | . | -0.60 | 0.17 |
| Val | 135 | A | . | . | B | . | . | . | -1.62 | 1.14 | . | . | . | -0.60 | 0.13 |
| Ala | 136 | A | . | . | B | . | . | . | -1.92 | 1.03 | . | . | . | -0.60 | 0.12 |
| Leu | 137 | A | . | . | B | . | . | . | -2.14 | 0.93 | * | . | . | -0.60 | 0.19 |
| Val | 138 | A | . | . | B | . | . | . | -2.64 | 0.93 | * | . | . | -0.60 | 0.21 |
| Ser | 139 | A | . | . | B | . | . | . | -2.69 | 0.97 | . | . | . | -0.60 | 0.17 |
| Ser | 140 | . | . | B | B | . | . | . | -2.69 | 1.11 | * | . | . | -0.60 | 0.15 |
| Leu | 141 | . | . | B | B | . | . | . | -2.80 | 1.07 | * | . | . | -0.60 | 0.15 |
| Leu | 142 | . | . | B | B | . | . | . | -2.30 | 1.21 | * | . | . | -0.60 | 0.10 |
| Val | 143 | . | . | B | B | . | . | . | -2.26 | 1.31 | . | . | . | -0.60 | 0.11 |
| Val | 144 | . | A | B | B | . | . | . | -2.54 | 1.61 | . | * | . | -0.60 | 0.11 |
| Phe | 145 | . | A | B | B | . | . | . | -2.94 | 1.43 | . | . | . | -0.60 | 0.13 |
| Thr | 146 | . | A | B | B | . | . | . | -2.94 | 1.53 | . | . | . | -0.60 | 0.15 |
| Leu | 147 | A | A | . | B | . | . | . | -2.48 | 1.57 | . | . | . | -0.60 | 0.17 |
| Ala | 148 | A | A | . | B | . | . | . | -2.43 | 1.36 | . | . | . | -0.60 | 0.19 |
| Phe | 149 | A | A | . | B | . | . | . | -2.28 | 1.26 | . | . | . | -0.60 | 0.11 |
| Leu | 150 | A | A | . | B | . | . | . | -2.28 | 1.56 | . | . | . | -0.60 | 0.12 |
| Gly | 151 | A | A | . | B | . | . | . | -2.78 | 1.66 | . | . | . | -0.60 | 0.10 |
| Leu | 152 | A | A | . | B | . | . | . | -2.21 | 1.84 | . | . | . | -0.60 | 0.10 |
| Phe | 153 | A | A | . | B | . | . | . | -2.29 | 1.81 | . | . | . | -0.60 | 0.18 |
| Phe | 154 | A | A | . | B | . | . | . | -1.54 | 1.70 | * | . | . | -0.60 | 0.10 |

TABLE II-continued

| Res | Pos | I | II | III | IV | V | VI | VII | VIII | IX | X | XI | XII | XIII | XIV |
|---|---|---|---|---|---|---|---|---|---|---|---|---|---|---|---|
| Leu | 155 | A | A | . | B | . | . | . | −0.73 | 1.27 | * | . | . | −0.60 | 0.24 |
| Tyr | 156 | A | A | . | B | . | . | . | −1.09 | 0.99 | * | . | . | −0.60 | 0.48 |
| Cys | 157 | . | A | . | B | T | . | . | −0.98 | 0.99 | * | . | . | −0.20 | 0.48 |
| Lys | 158 | . | A | . | B | T | . | . | −0.28 | 0.99 | * | . | . | −0.20 | 0.50 |
| Gln | 159 | . | A | . | B | T | . | . | 0.53 | 0.70 | * | . | . | −0.20 | 0.51 |
| Phe | 160 | . | A | . | B | T | . | . | 1.31 | −0.06 | * | . | . | 0.85 | 1.88 |
| Phe | 161 | . | A | . | B | T | . | . | 0.89 | −0.13 | * | . | . | 1.16 | 1.28 |
| Asn | 162 | . | . | . | . | T | T | . | 1.56 | 0.44 | * | * | . | 0.82 | 0.39 |
| Arg | 163 | . | . | . | . | T | T | . | 1.62 | 0.44 | * | * | . | 1.13 | 0.79 |
| His | 164 | . | . | . | . | T | T | . | 1.28 | −0.34 | * | * | . | 2.49 | 1.79 |
| Cys | 165 | . | . | . | . | T | T | . | 1.63 | −0.70 | * | * | . | 3.10 | 1.10 |
| Gln | 166 | . | . | . | . | T | T | . | 1.52 | −0.67 | * | . | F | 2.79 | 0.56 |
| Arg | 167 | . | . | . | . | T | T | . | 0.71 | 0.01 | * | * | F | 1.58 | 0.34 |
| Gly | 168 | . | . | . | . | T | T | . | 0.60 | 0.20 | * | * | F | 1.27 | 0.52 |
| Gly | 169 | . | . | . | . | T | T | . | −0.07 | 0.03 | * | . | F | 0.96 | 0.52 |
| Leu | 170 | . | A | . | . | . | . | C | 0.60 | 0.41 | . | * | . | −0.40 | 0.23 |
| Leu | 171 | . | A | B | . | . | . | . | 0.01 | 0.41 | . | * | . | −0.60 | 0.40 |
| Gln | 172 | . | A | B | . | . | . | . | −0.10 | 0.49 | . | * | . | −0.60 | 0.41 |
| Phe | 173 | A | A | . | . | . | . | . | 0.29 | 0.06 | . | * | . | −0.30 | 0.83 |
| Glu | 174 | A | A | . | . | . | . | . | 0.32 | −0.63 | . | * | . | 0.75 | 2.01 |
| Ala | 175 | A | A | . | . | . | . | . | 0.54 | −0.83 | * | * | F | 0.90 | 1.67 |
| Asp | 176 | A | A | . | . | . | . | . | 1.40 | −0.73 | * | * | F | 0.90 | 1.95 |
| Lys | 177 | A | A | . | . | . | . | . | 1.40 | −1.51 | * | * | F | 0.90 | 2.26 |
| Thr | 178 | A | A | . | . | . | . | . | 2.10 | −1.51 | * | * | F | 0.90 | 3.87 |
| Ala | 179 | A | A | . | . | . | . | . | 1.80 | −2.01 | * | . | F | 0.90 | 4.01 |
| Lys | 180 | A | A | . | . | . | . | . | 1.58 | −1.63 | * | . | F | 0.90 | 2.69 |
| Glu | 181 | A | A | . | . | . | . | . | 0.88 | −0.94 | * | . | F | 0.90 | 1.54 |
| Glu | 182 | A | A | . | . | . | . | . | 0.62 | −0.64 | . | . | F | 0.90 | 1.32 |
| Ser | 183 | A | . | . | . | . | . | . | 0.08 | −0.71 | . | * | F | 1.10 | 1.02 |
| Leu | 184 | . | . | B | . | . | . | . | 0.46 | −0.07 | . | * | . | 0.50 | 0.44 |
| Phe | 185 | . | . | B | . | . | . | . | 0.20 | 0.36 | . | . | . | 0.20 | 0.39 |
| Pro | 186 | . | . | . | . | . | . | C | −0.10 | 0.79 | . | . | . | 0.40 | 0.45 |
| Val | 187 | . | . | . | . | . | . | C | −0.06 | 0.79 | . | . | F | 0.85 | 0.73 |
| Pro | 188 | . | . | . | . | . | T | C | 0.24 | 0.10 | . | . | F | 1.80 | 1.69 |
| Pro | 189 | . | . | . | . | . | T | C | 0.74 | −0.69 | . | . | F | 3.00 | 1.89 |
| Ser | 190 | . | . | . | . | . | T | C | 1.14 | −0.63 | . | . | F | 2.70 | 3.67 |
| Lys | 191 | . | . | . | . | . | T | C | 0.77 | −0.89 | . | . | F | 2.40 | 3.18 |
| Glu | 192 | A | A | . | . | . | . | . | 1.62 | −0.81 | . | . | F | 1.50 | 2.08 |
| Thr | 193 | A | A | . | . | . | . | . | 1.53 | −1.24 | . | . | F | 1.20 | 2.69 |
| Ser | 194 | A | A | . | . | . | . | . | 1.74 | −1.24 | . | * | F | 0.90 | 1.80 |
| Ala | 195 | A | A | . | . | . | . | . | 1.19 | −0.84 | . | * | F | 0.90 | 1.80 |
| Glu | 196 | A | A | . | . | . | . | . | 0.84 | −0.20 | . | * | F | 0.45 | 0.93 |
| Ser | 197 | A | . | . | . | . | . | . | 0.56 | −0.30 | . | * | F | 0.65 | 0.93 |
| Gln | 198 | A | . | . | . | . | . | . | 0.28 | 0.23 | . | * | F | 0.05 | 0.96 |
| Val | 199 | . | . | B | . | . | . | . | 0.37 | 0.23 | . | * | . | −0.10 | 0.56 |
| Ser | 200 | . | . | B | . | . | . | . | 0.61 | 0.66 | . | * | . | −0.40 | 0.65 |
| Trp | 201 | . | . | . | . | . | . | C | 0.31 | 0.70 | . | * | . | −0.20 | 0.37 |
| Ala | 202 | . | . | . | . | . | T | C | −0.20 | 0.69 | . | . | . | 0.00 | 0.67 |
| Pro | 203 | . | . | . | . | . | T | C | −0.79 | 0.73 | * | . | F | 0.15 | 0.41 |
| Gly | 204 | . | . | . | . | T | T | . | 0.07 | 0.84 | * | . | F | 0.35 | 0.40 |
| Ser | 205 | . | . | . | . | . | T | C | −0.44 | 0.33 | * | . | F | 0.45 | 0.68 |
| Leu | 206 | . | . | B | . | . | . | . | −0.86 | 0.51 | * | . | . | −0.40 | 0.36 |
| Ala | 207 | . | . | B | . | . | . | . | −0.57 | 0.87 | * | . | . | −0.40 | 0.32 |
| Gln | 208 | . | . | B | . | . | . | . | −1.17 | 0.83 | . | . | . | −0.40 | 0.32 |
| Leu | 209 | . | . | B | . | . | . | . | −0.82 | 1.13 | . | . | . | −0.40 | 0.32 |
| Phe | 210 | . | . | B | . | . | . | . | −0.82 | 0.44 | . | . | . | −0.40 | 0.52 |
| Ser | 211 | . | . | B | . | . | . | . | −0.87 | 0.33 | . | . | . | −0.10 | 0.40 |
| Leu | 212 | . | . | B | . | . | . | . | −0.49 | 0.57 | . | . | . | −0.40 | 0.36 |
| Asp | 213 | . | . | . | . | T | . | . | −1.38 | 0.31 | . | . | F | 0.45 | 0.65 |
| Ser | 214 | . | . | . | . | . | . | C | −0.78 | 0.21 | . | . | F | 0.25 | 0.34 |
| Val | 215 | . | . | . | . | . | . | C | −0.08 | 0.26 | . | * | F | 0.25 | 0.64 |
| Pro | 216 | . | . | . | . | . | . | C | 0.22 | −0.03 | . | . | F | 0.85 | 0.66 |
| Ile | 217 | . | . | B | . | . | . | . | 1.03 | 0.37 | . | . | F | 0.05 | 0.86 |
| Pro | 218 | . | . | B | . | . | . | . | 1.03 | 0.39 | . | . | F | 0.46 | 2.00 |
| Gln | 219 | . | . | B | . | . | . | . | 0.99 | 0.14 | . | * | F | 0.72 | 2.24 |
| Gln | 220 | . | . | B | . | . | . | . | 1.63 | 0.14 | . | . | F | 0.98 | 3.16 |
| Gln | 221 | . | . | . | . | . | . | C | 1.84 | −0.11 | . | . | F | 2.04 | 3.16 |
| Gln | 222 | . | . | . | . | . | . | C | 2.13 | −0.54 | . | . | F | 2.60 | 3.16 |
| Gly | 223 | . | . | . | . | . | T | C | 1.96 | −0.33 | . | . | F | 2.24 | 1.80 |
| Pro | 224 | . | . | . | . | . | T | C | 1.57 | −0.30 | . | . | F | 1.98 | 1.33 |
| Glu | 225 | . | . | B | . | . | T | . | 1.18 | −0.27 | . | . | . | 1.22 | 0.98 |
| Met | 226 | . | . | B | . | . | T | . | 0.79 | −0.24 | * | . | . | 1.11 | 1.27 |

TABLE III

| Res | Pos | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.20 | -0.17 | . | . | . | 0.93 | 1.00 |
| Ala | 2 | . | . | B | . | . | . | . | 0.56 | -0.17 | . | . | . | 1.06 | 0.78 |
| Glu | 3 | . | . | . | . | . | T | C | 0.64 | -0.10 | . | . | . | 1.74 | 0.83 |
| Pro | 4 | . | . | . | . | . | T | C | 1.00 | -0.14 | . | . | . | 2.17 | 1.12 |
| Gly | 5 | . | . | . | . | T | T | . | 1.36 | -0.26 | . | . | F | 2.80 | 1.51 |
| His | 6 | . | . | . | . | . | T | C | 1.14 | -0.26 | . | . | . | 2.17 | 1.18 |
| Ser | 7 | . | A | . | . | . | . | C | 1.43 | 0.43 | . | . | . | 0.44 | 0.63 |
| His | 8 | . | A | . | . | . | . | C | 0.84 | 0.39 | . | * | . | 0.46 | 0.86 |
| His | 9 | . | A | . | . | . | . | C | 1.17 | 0.46 | . | * | . | -0.12 | 0.64 |
| Leu | 10 | . | A | B | . | . | . | . | 0.66 | -0.04 | . | * | . | 0.30 | 0.93 |
| Ser | 11 | . | A | B | B | . | . | . | 0.80 | 0.21 | . | * | . | -0.30 | 0.51 |
| Ala | 12 | . | A | B | B | . | . | . | 0.76 | -0.29 | . | * | . | 0.30 | 0.73 |
| Arg | 13 | . | A | B | B | . | . | . | 0.90 | -0.36 | . | * | . | 0.30 | 0.87 |
| Val | 14 | . | . | B | B | . | . | . | 0.62 | -1.04 | . | * | F | 1.16 | 1.28 |
| Arg | 15 | . | . | B | B | . | . | . | 1.43 | -0.94 | * | * | F | 1.42 | 1.83 |
| Gly | 16 | . | . | . | . | T | . | . | 1.84 | -1.44 | * | * | F | 2.28 | 1.61 |
| Arg | 17 | . | . | B | . | . | . | . | 2.54 | -1.44 | * | * | F | 2.14 | 4.26 |
| Thr | 18 | . | . | . | . | . | . | C | 1.54 | -2.09 | * | * | F | 2.60 | 4.26 |
| Glu | 19 | . | . | B | . | . | . | . | 2.19 | -1.40 | * | * | F | 2.14 | 3.02 |
| Arg | 20 | . | . | B | B | . | . | . | 2.19 | -1.40 | * | * | F | 1.68 | 2.38 |
| Arg | 21 | . | . | B | B | . | . | . | 1.72 | -1.40 | * | * | F | 1.42 | 3.23 |
| Ile | 22 | . | . | B | B | . | . | . | 1.32 | -1.20 | * | * | F | 1.16 | 1.54 |
| Pro | 23 | . | . | B | B | . | . | . | 1.74 | -0.29 | * | . | F | 0.45 | 0.83 |
| Arg | 24 | . | . | . | B | T | . | . | 0.93 | -0.29 | * | . | F | 0.85 | 0.83 |
| Leu | 25 | . | . | B | B | . | . | . | 0.01 | 0.40 | * | . | . | -0.30 | 0.97 |
| Trp | 26 | . | . | B | B | . | . | . | -0.91 | 0.40 | * | * | . | -0.30 | 0.52 |
| Arg | 27 | . | . | B | B | . | . | . | -0.31 | 0.66 | * | . | . | -0.60 | 0.22 |
| Leu | 28 | . | . | B | B | . | . | . | -0.69 | 1.57 | * | . | . | -0.60 | 0.28 |
| Leu | 29 | . | . | B | B | . | . | . | -1.14 | 1.39 | * | . | . | -0.60 | 0.27 |
| Leu | 30 | . | . | B | B | . | . | . | -0.64 | 0.90 | * | * | . | -0.60 | 0.14 |
| Trp | 31 | . | . | . | B | . | . | C | -0.94 | 1.39 | * | * | . | -0.40 | 0.24 |
| Ala | 32 | . | . | . | B | . | . | C | -1.76 | 1.20 | * | * | . | -0.40 | 0.29 |
| Gly | 33 | . | . | . | B | . | . | C | -0.94 | 1.30 | . | . | . | -0.40 | 0.30 |
| Thr | 34 | . | . | . | B | . | . | C | -0.99 | 1.01 | . | . | . | -0.40 | 0.50 |
| Ala | 35 | . | . | B | B | . | . | . | -0.49 | 0.74 | . | . | . | -0.60 | 0.37 |
| Phe | 36 | . | . | B | B | . | . | . | -0.20 | 0.73 | . | . | . | -0.60 | 0.54 |
| Gln | 37 | . | . | B | B | . | . | . | 0.04 | 0.70 | . | . | . | -0.60 | 0.64 |
| Val | 38 | . | . | B | B | . | . | . | 0.08 | 0.64 | . | . | . | -0.60 | 0.63 |
| Thr | 39 | . | . | B | B | . | . | . | 0.04 | 0.63 | . | . | F | -0.30 | 1.05 |
| Gln | 40 | . | . | . | B | T | . | . | 0.42 | 0.27 | . | . | F | 0.25 | 0.60 |
| Gly | 41 | . | . | . | . | T | . | . | 1.12 | 0.30 | . | . | F | 0.60 | 1.25 |
| Thr | 42 | . | . | . | . | . | . | C | 0.31 | -0.34 | * | . | F | 1.00 | 1.50 |
| Gly | 43 | . | . | . | . | T | . | C | 1.13 | -0.14 | . | . | F | 1.05 | 0.72 |
| Pro | 44 | . | . | . | . | T | . | C | 0.86 | -0.04 | . | . | F | 1.05 | 0.98 |
| Glu | 45 | . | . | B | . | . | T | . | 0.19 | 0.03 | . | . | F | 0.25 | 0.69 |
| Leu | 46 | . | . | B | . | . | T | . | 0.58 | 0.11 | . | . | . | 0.10 | 0.37 |
| His | 47 | . | . | B | . | . | . | . | 0.89 | -0.31 | . | . | . | 0.50 | 0.48 |
| Ala | 48 | . | . | . | . | . | . | C | 0.93 | -0.74 | . | . | . | 1.00 | 0.48 |
| Cys | 49 | A | . | . | . | T | . | . | 1.14 | -0.36 | . | . | . | 0.70 | 0.78 |
| Lys | 50 | A | . | . | . | T | . | . | 0.90 | -1.04 | . | . | F | 1.15 | 1.00 |
| Glu | 51 | A | . | . | . | T | . | . | 1.68 | -0.79 | . | . | F | 1.30 | 1.55 |
| Ser | 52 | . | . | . | . | T | T | . | 1.47 | -0.79 | * | . | F | 1.70 | 3.93 |
| Glu | 53 | . | A | . | . | T | . | . | 2.06 | -0.60 | . | . | F | 1.30 | 3.08 |
| Tyr | 54 | . | A | . | . | T | . | . | 2.48 | -0.60 | . | . | . | 1.15 | 3.08 |
| His | 55 | . | A | . | . | T | . | . | 2.12 | 0.16 | . | * | . | 0.25 | 3.60 |
| Tyr | 56 | . | A | . | . | T | . | . | 1.53 | 0.26 | . | * | . | 0.25 | 3.00 |
| Glu | 57 | . | A | B | . | . | . | . | 1.17 | 0.76 | . | . | . | -0.45 | 1.93 |
| Tyr | 58 | . | A | B | . | . | . | . | 1.17 | 0.57 | . | . | . | -0.60 | 0.76 |
| Thr | 59 | . | A | B | . | . | . | . | 1.11 | 0.07 | . | . | . | -0.30 | 0.81 |
| Ala | 60 | . | A | B | . | . | . | . | 0.83 | -0.30 | . | . | . | 0.64 | 0.63 |
| Cys | 61 | . | A | B | . | . | . | . | 0.73 | 0.19 | . | . | . | 0.38 | 0.58 |
| Asp | 62 | . | A | . | . | T | . | . | 0.43 | -0.14 | . | . | F | 1.87 | 0.40 |
| Ser | 63 | . | . | . | . | T | T | . | 0.79 | -0.24 | * | . | F | 2.61 | 0.53 |
| Thr | 64 | . | . | . | . | T | T | . | 0.81 | -0.74 | * | * | F | 3.40 | 1.92 |
| Gly | 65 | . | . | . | . | T | T | . | 1.51 | -0.40 | * | * | F | 2.76 | 1.21 |
| Ser | 66 | . | . | . | . | T | T | . | 1.32 | -0.40 | * | * | F | 2.42 | 1.77 |
| Arg | 67 | . | . | . | B | T | . | . | 0.73 | -0.14 | * | * | F | 1.53 | 0.91 |
| Trp | 68 | . | . | B | B | . | . | . | 0.18 | -0.13 | . | * | . | 0.64 | 0.93 |
| Arg | 69 | . | . | B | B | . | . | . | 0.28 | 0.09 | . | * | . | -0.30 | 0.51 |
| Val | 70 | . | . | B | B | . | . | . | 0.59 | 0.13 | . | * | . | -0.30 | 0.41 |
| Ala | 71 | . | . | B | B | . | . | . | 0.58 | 0.63 | . | * | . | -0.60 | 0.53 |
| Val | 72 | . | . | B | B | . | . | . | 0.26 | 0.20 | . | * | . | -0.30 | 0.39 |
| Pro | 73 | . | . | . | . | T | . | . | 0.20 | 0.63 | * | . | . | 0.00 | 0.81 |
| His | 74 | . | . | . | . | T | . | . | -0.72 | 0.41 | * | * | . | 0.00 | 0.79 |
| Thr | 75 | . | . | . | . | T | T | C | -0.53 | 0.60 | . | . | F | 0.15 | 0.88 |
| Pro | 76 | . | . | . | . | T | T | . | -0.26 | 0.53 | . | . | F | 0.35 | 0.30 |
| Gly | 77 | . | . | . | . | T | T | . | 0.30 | 0.59 | . | . | F | 0.35 | 0.32 |

TABLE III-continued

| Res | Pos | I | II | III | IV | V | VI | VII | VIII | IX | X | XI | XII | XIII | XIV |
|-----|-----|---|----|-----|----|----|-----|-----|------|-----|----|-----|-----|------|-----|
| Leu | 78  | . | .  | B   | .  | .  | T   | .   | −0.30 | 0.47 | . | .  | .   | −0.20 | 0.30 |
| Cys | 79  | . | .  | B   | .  | .  | .   | .   | −0.48 | 0.67 | . | .  | .   | −0.40 | 0.16 |
| Thr | 80  | . | .  | B   | .  | .  | .   | .   | −0.17 | 0.67 | . | .  | .   | −0.40 | 0.25 |
| Ser | 81  | . | .  | B   | .  | .  | .   | .   | −0.17 | 0.24 | * | .  | F   | 0.05 | 0.51 |
| Leu | 82  | . | .  | B   | .  | .  | T   | .   | −0.68 | −0.01 | * | .  | F   | 1.30 | 1.46 |
| Pro | 83  | . | .  | B   | .  | .  | T   | .   | 0.18 | 0.06 | * | *  | F   | 0.85 | 0.75 |
| Asp | 84  | . | .  | .   | .  | .  | T   | C   | 0.50 | −0.43 | * | *  | F   | 2.10 | 1.12 |
| Pro | 85  | . | .  | .   | .  | T  | T   | .   | 0.50 | −0.39 | * | .  | F   | 2.60 | 1.34 |
| Val | 86  | . | .  | .   | .  | T  | .   | .   | 0.80 | −0.59 | * | .  | F   | 3.00 | 1.25 |
| Lys | 87  | . | .  | B   | .  | .  | .   | .   | 0.94 | −1.01 | * | .  | F   | 2.30 | 1.30 |
| Gly | 88  | . | .  | B   | .  | .  | .   | .   | 0.86 | −0.44 | * | .  | F   | 1.55 | 0.45 |
| Thr | 89  | . | .  | B   | .  | .  | .   | .   | 0.16 | −0.49 | * | .  | F   | 1.25 | 0.81 |
| Glu | 90  | . | .  | B   | .  | .  | .   | .   | 0.07 | −0.34 | . | .  | F   | 0.95 | 0.35 |
| Cys | 91  | . | .  | B   | .  | .  | T   | .   | 0.26 | 0.04 | . | *  | .   | 0.10 | 0.48 |
| Ser | 92  | . | .  | B   | .  | .  | T   | .   | 0.21 | 0.19 | . | *  | .   | 0.10 | 0.18 |
| Phe | 93  | . | .  | B   | .  | .  | T   | .   | −0.03 | 0.10 | . | *  | .   | 0.10 | 0.16 |
| Ser | 94  | . | .  | .   | .  | T  | T   | .   | −0.07 | 0.60 | . | *  | .   | 0.20 | 0.31 |
| Cys | 95  | . | .  | .   | .  | T  | .   | .   | −0.07 | 0.46 | . | *  | .   | 0.00 | 0.23 |
| Asn | 96  | . | .  | .   | .  | T  | T   | .   | −0.10 | 0.07 | * | .  | .   | 0.50 | 0.46 |
| Ala | 97  | . | .  | .   | .  | .  | T   | C   | −0.61 | 0.07 | * | .  | .   | 0.30 | 0.30 |
| Gly | 98  | . | .  | .   | .  | .  | T   | C   | 0.09 | 0.37 | * | .  | F   | 0.45 | 0.46 |
| Glu | 99  | A | .  | .   | .  | .  | T   | .   | −0.21 | −0.20 | . | *  | .   | 0.70 | 0.47 |
| Phe | 100 | . | A  | B   | .  | .  | .   | .   | 0.50 | 0.01 | . | .  | .   | −0.30 | 0.46 |
| Leu | 101 | . | A  | B   | .  | .  | .   | .   | 0.50 | −0.49 | . | .  | .   | 0.30 | 0.94 |
| Asp | 102 | A | A  | .   | .  | .  | .   | .   | 1.09 | −0.91 | . | .  | .   | 0.94 | 0.90 |
| Met | 103 | . | A  | .   | .  | T  | .   | .   | 1.13 | −0.51 | . | .  | .   | 1.83 | 1.81 |
| Lys | 104 | . | A  | .   | .  | T  | .   | .   | 0.47 | −0.91 | * | .  | F   | 2.32 | 2.94 |
| Asp | 105 | . | .  | .   | .  | T  | T   | .   | 1.21 | −1.03 | * | .  | F   | 2.91 | 0.94 |
| Gln | 106 | . | .  | .   | .  | T  | T   | .   | 1.81 | −1.03 | . | *  | F   | 3.40 | 1.90 |
| Ser | 107 | . | .  | .   | .  | T  | T   | .   | 1.14 | −1.21 | . | .  | F   | 3.06 | 1.47 |
| Cys | 108 | . | .  | .   | .  | T  | T   | .   | 1.16 | −0.64 | . | *  | F   | 2.57 | 0.47 |
| Lys | 109 | . | .  | B   | .  | .  | T   | .   | 1.11 | −0.14 | . | *  | F   | 1.53 | 0.28 |
| Pro | 110 | . | .  | B   | .  | .  | T   | .   | 0.77 | −0.54 | . | *  | F   | 1.69 | 0.36 |
| Cys | 111 | . | .  | B   | .  | .  | T   | .   | 0.88 | −0.50 | . | *  | .   | 1.10 | 0.66 |
| Ala | 112 | . | .  | B   | .  | .  | T   | .   | 0.93 | −1.07 | . | *  | F   | 1.75 | 0.64 |
| Glu | 113 | . | .  | B   | .  | .  | .   | .   | 1.30 | −0.31 | . | *  | F   | 1.45 | 0.65 |
| Gly | 114 | . | .  | B   | .  | .  | T   | .   | 0.44 | −0.36 | . | *  | F   | 2.00 | 1.63 |
| Arg | 115 | . | .  | B   | .  | .  | T   | .   | 0.31 | −0.24 | . | *  | F   | 1.80 | 1.33 |
| Tyr | 116 | . | .  | B   | .  | .  | T   | .   | 0.67 | −0.31 | . | *  | .   | 1.30 | 0.76 |
| Ser | 117 | . | .  | B   | .  | .  | T   | .   | 0.91 | 0.17 | . | *  | .   | 0.65 | 1.11 |
| Leu | 118 | . | .  | B   | B  | .  | .   | .   | 0.02 | 0.17 | * | *  | .   | −0.10 | 0.56 |
| Gly | 119 | . | .  | .   | B  | T  | .   | .   | 0.48 | 0.86 | * | *  | F   | −0.05 | 0.25 |
| Thr | 120 | . | .  | B   | B  | .  | .   | .   | −0.33 | 0.10 | * | *  | F   | −0.15 | 0.37 |
| Gly | 121 | . | .  | B   | B  | .  | .   | .   | −0.09 | 0.50 | * | *  | F   | −0.45 | 0.39 |
| Ile | 122 | . | A  | B   | B  | .  | .   | .   | 0.21 | −0.19 | * | *  | .   | 0.30 | 0.65 |
| Arg | 123 | . | A  | B   | B  | .  | .   | .   | 0.73 | −0.61 | . | *  | .   | 0.60 | 0.78 |
| Phe | 124 | . | A  | B   | B  | .  | .   | .   | 1.08 | −0.19 | . | *  | .   | 0.30 | 0.83 |
| Asp | 125 | . | A  | .   | B  | .  | .   | C   | 1.39 | −0.61 | . | *  | .   | 0.95 | 1.97 |
| Glu | 126 | . | A  | .   | .  | T  | .   | .   | 0.92 | −1.30 | . | *  | F   | 1.30 | 1.75 |
| Trp | 127 | . | A  | .   | .  | T  | .   | .   | 1.60 | −0.61 | . | *  | F   | 1.30 | 1.66 |
| Asp | 128 | . | A  | .   | .  | .  | .   | C   | 1.46 | −0.97 | . | *  | F   | 1.10 | 1.54 |
| Glu | 129 | . | A  | .   | .  | .  | .   | C   | 1.81 | −0.47 | * | .  | F   | 0.80 | 1.21 |
| Leu | 130 | . | .  | .   | .  | .  | T   | C   | 1.11 | −0.04 | * | .  | .   | 1.05 | 1.14 |
| Pro | 131 | . | .  | .   | .  | .  | T   | C   | 0.52 | −0.17 | * | .  | .   | 0.90 | 0.59 |
| His | 132 | . | .  | .   | .  | T  | T   | .   | 0.51 | 0.33 | * | .  | .   | 0.50 | 0.34 |
| Gly | 133 | . | .  | .   | .  | .  | T   | C   | −0.30 | 0.71 | * | .  | .   | 0.00 | 0.56 |
| Phe | 134 | . | A  | .   | .  | .  | .   | C   | −0.60 | 0.71 | * | .  | .   | −0.40 | 0.30 |
| Ala | 135 | . | A  | .   | .  | .  | .   | C   | −0.38 | 0.67 | * | *  | .   | −0.40 | 0.29 |
| Ser | 136 | . | A  | .   | .  | .  | .   | C   | −0.17 | 0.67 | . | *  | .   | −0.40 | 0.30 |
| Leu | 137 | . | A  | .   | .  | .  | .   | C   | −0.73 | 0.64 | . | *  | .   | −0.40 | 0.56 |
| Ser | 138 | . | .  | .   | .  | .  | T   | C   | −0.39 | 0.47 | . | *  | .   | 0.00 | 0.55 |
| Ala | 139 | . | .  | .   | .  | .  | T   | C   | −0.50 | −0.03 | . | *  | .   | 0.90 | 0.71 |
| Asn | 140 | . | .  | B   | .  | .  | T   | .   | 0.09 | 0.27 | . | *  | .   | 0.10 | 0.71 |
| Met | 141 | . | .  | B   | .  | .  | T   | .   | 0.39 | −0.41 | . | *  | .   | 0.70 | 0.88 |
| Glu | 142 | . | .  | B   | .  | .  | .   | .   | 0.90 | −0.80 | . | *  | .   | 0.95 | 1.45 |
| Leu | 143 | A | .  | .   | .  | .  | T   | .   | 0.61 | −0.91 | . | *  | .   | 1.15 | 1.21 |
| Asp | 144 | A | .  | .   | .  | .  | T   | .   | 0.61 | −0.81 | . | *  | F   | 1.30 | 1.24 |
| Asp | 145 | A | .  | .   | .  | .  | T   | .   | 0.61 | −0.93 | . | *  | F   | 1.15 | 0.72 |
| Ser | 146 | A | .  | .   | .  | .  | T   | .   | 0.91 | −0.93 | . | .  | F   | 1.58 | 1.51 |
| Ala | 147 | A | .  | .   | .  | .  | .   | .   | 0.60 | −1.23 | . | .  | F   | 1.66 | 1.22 |
| Ala | 148 | A | .  | .   | .  | .  | .   | .   | 1.07 | −0.74 | . | .  | F   | 1.94 | 1.05 |
| Glu | 149 | . | .  | .   | .  | T  | .   | .   | 1.07 | −0.31 | . | .  | F   | 2.17 | 0.78 |
| Ser | 150 | . | .  | .   | .  | T  | T   | .   | 0.40 | −0.30 | * | .  | F   | 2.80 | 1.23 |
| Thr | 151 | . | .  | .   | .  | T  | T   | .   | 0.39 | −0.23 | . | .  | F   | 2.37 | 0.66 |
| Gly | 152 | . | .  | .   | .  | T  | T   | .   | 0.68 | −0.24 | . | .  | F   | 2.09 | 0.55 |
| Asn | 153 | . | .  | .   | .  | T  | T   | .   | 0.97 | 0.14 | . | .  | F   | 1.21 | 0.55 |
| Cys | 154 | . | .  | .   | .  | T  | T   | .   | 1.01 | 0.14 | . | .  | F   | 0.93 | 0.51 |

TABLE III-continued

| Res | Pos | I | II | III | IV | V | VI | VII | VIII | IX | X | XI | XII | XIII | XIV |
|---|---|---|---|---|---|---|---|---|---|---|---|---|---|---|---|
| Thr | 155 | . | . | . | . | T | T | . | 1.02 | −0.34 | . | . | F | 1.40 | 1.02 |
| Ser | 156 | . | . | . | . | T | T | . | 0.48 | 0.14 | . | . | F | 0.65 | 0.67 |
| Ser | 157 | . | . | . | . | T | T | . | 0.61 | 0.39 | * | * | F | 0.88 | 0.93 |
| Lys | 158 | . | . | . | . | T | . | . | 0.72 | 0.24 | * | * | F | 0.91 | 0.99 |
| Trp | 159 | . | . | B | . | . | . | . | 1.04 | −0.24 | * | * | F | 1.49 | 1.45 |
| Val | 160 | . | . | B | . | . | . | . | 1.36 | −0.20 | * | * | F | 1.92 | 1.07 |
| Pro | 161 | . | . | B | . | . | T | . | 1.41 | −0.59 | * | * | F | 2.30 | 0.90 |
| Arg | 162 | . | . | . | . | T | T | . | 0.82 | 0.17 | * | * | F | 1.72 | 1.33 |
| Gly | 163 | . | . | B | . | . | T | . | 0.19 | −0.06 | * | * | F | 1.69 | 1.26 |
| Asp | 164 | . | . | . | . | T | . | . | −0.22 | −0.20 | * | * | F | 1.51 | 0.82 |
| Tyr | 165 | . | . | B | . | . | . | . | 0.63 | 0.16 | * | . | . | 0.13 | 0.36 |
| Ile | 166 | . | . | B | . | . | . | . | 0.53 | 0.56 | . | * | . | −0.40 | 0.59 |
| Ala | 167 | . | . | B | . | . | . | . | 0.42 | 0.61 | . | * | . | −0.40 | 0.51 |
| Phe | 168 | . | . | B | . | . | . | . | 0.77 | 0.61 | . | . | . | −0.09 | 0.54 |
| Asn | 169 | . | . | B | . | . | T | . | 0.10 | −0.14 | . | . | . | 1.47 | 1.35 |
| Thr | 170 | . | . | . | . | . | T | C | 0.03 | −0.26 | . | . | F | 1.98 | 0.71 |
| Asp | 171 | . | . | . | . | T | T | . | 0.33 | −0.27 | . | * | F | 2.64 | 1.19 |
| Glu | 172 | . | . | . | . | T | T | . | 0.61 | −0.56 | . | . | F | 3.10 | 0.75 |
| Cys | 173 | . | . | . | B | T | . | . | 0.50 | −0.47 | . | . | . | 1.94 | 0.75 |
| Thr | 174 | . | . | B | B | . | . | . | −0.10 | −0.27 | . | . | . | 1.23 | 0.37 |
| Ala | 175 | . | . | B | B | . | . | . | −0.03 | 0.34 | . | . | . | 0.32 | 0.21 |
| Thr | 176 | . | . | B | B | . | . | . | −0.62 | 1.10 | . | . | . | −0.29 | 0.62 |
| Leu | 177 | . | . | B | B | . | . | . | −1.48 | 1.03 | * | * | . | −0.60 | 0.43 |
| Met | 178 | . | . | B | B | . | . | . | −0.81 | 1.19 | . | * | . | −0.60 | 0.32 |
| Tyr | 179 | . | . | B | B | . | . | . | −1.31 | 1.09 | . | * | . | −0.60 | 0.35 |
| Ala | 180 | . | . | B | B | . | . | . | −0.68 | 1.29 | . | * | . | −0.60 | 0.35 |
| Val | 181 | . | . | B | B | . | . | . | −0.37 | 0.60 | . | * | . | −0.60 | 0.71 |
| Asn | 182 | . | . | B | B | . | . | . | 0.14 | 0.39 | . | * | . | −0.30 | 0.79 |
| Leu | 183 | . | . | B | B | . | . | . | 0.40 | 0.01 | . | * | F | 0.21 | 1.05 |
| Lys | 184 | . | . | B | B | . | . | . | 0.33 | −0.06 | . | * | F | 1.02 | 1.40 |
| Gln | 185 | . | . | . | . | T | T | . | 0.07 | −0.21 | . | * | F | 2.03 | 1.25 |
| Ser | 186 | . | . | . | . | . | T | C | 0.92 | 0.03 | . | * | F | 1.44 | 1.13 |
| Gly | 187 | . | . | . | . | . | T | C | 0.22 | −0.26 | . | * | F | 2.10 | 0.91 |
| Thr | 188 | . | . | B | . | . | T | . | 1.03 | 0.53 | . | * | F | 0.79 | 0.45 |
| Val | 189 | . | . | B | B | . | . | . | 0.74 | 0.13 | . | * | F | 0.48 | 0.59 |
| Asn | 190 | . | . | B | B | . | . | . | 0.50 | 0.50 | . | * | . | −0.18 | 0.93 |
| Phe | 191 | . | . | B | B | . | . | . | 0.56 | 0.83 | . | * | . | −0.24 | 1.01 |
| Glu | 192 | . | . | B | B | . | . | . | 0.69 | 1.10 | . | * | . | −0.45 | 2.13 |
| Tyr | 193 | . | . | B | B | . | . | . | 1.00 | 0.89 | . | * | . | −0.45 | 2.04 |
| Tyr | 194 | . | . | . | . | T | . | . | 1.56 | 0.49 | . | * | . | 0.15 | 3.94 |
| Tyr | 195 | . | . | . | . | . | T | C | 1.26 | 0.09 | . | * | . | 0.45 | 3.05 |
| Pro | 196 | . | . | . | . | T | T | . | 1.07 | 0.47 | . | . | F | 0.50 | 2.61 |
| Asp | 197 | . | . | . | . | T | T | . | 0.18 | 0.40 | . | . | F | 0.50 | 1.17 |
| Ser | 198 | . | . | . | . | . | T | C | −0.28 | 0.33 | . | . | F | 0.45 | 0.52 |
| Ser | 199 | . | . | B | B | . | . | . | −0.03 | 0.36 | . | * | F | −0.15 | 0.29 |
| Ile | 200 | . | . | B | B | . | . | . | −0.49 | −0.07 | . | * | . | 0.30 | 0.30 |
| Ile | 201 | . | . | B | B | . | . | . | −0.98 | 0.71 | . | * | . | −0.60 | 0.20 |
| Phe | 202 | . | . | B | B | . | . | . | −1.83 | 1.11 | * | * | . | −0.60 | 0.13 |
| Glu | 203 | . | . | B | B | . | . | . | −1.53 | 1.37 | . | * | . | −0.60 | 0.13 |
| Phe | 204 | . | . | B | B | . | . | . | −1.23 | 1.09 | . | * | . | −0.60 | 0.33 |
| Phe | 205 | . | . | B | B | . | . | . | −0.34 | 0.80 | * | * | . | −0.60 | 0.62 |
| Val | 206 | . | . | . | B | T | . | . | 0.54 | 0.01 | * | . | . | 0.10 | 0.59 |
| Gln | 207 | . | . | . | . | T | T | . | 0.58 | 0.41 | . | * | F | 0.50 | 1.19 |
| Asn | 208 | . | . | . | . | T | T | . | 0.58 | 0.20 | . | . | F | 0.65 | 0.73 |
| Asp | 209 | . | . | . | . | T | T | . | 1.07 | −0.19 | . | . | F | 1.40 | 1.71 |
| Gln | 210 | . | . | . | . | T | T | . | 1.77 | −0.40 | . | . | F | 1.74 | 1.53 |
| Cys | 211 | . | . | . | . | T | . | . | 2.03 | −0.40 | . | * | F | 1.88 | 1.53 |
| Gln | 212 | . | . | B | . | . | T | . | 2.03 | −0.30 | . | * | F | 1.87 | 0.93 |
| Pro | 213 | . | . | B | . | . | T | . | 2.03 | −0.30 | . | * | F | 2.21 | 0.89 |
| Asn | 214 | . | . | . | . | T | T | . | 1.73 | −0.70 | . | . | F | 3.40 | 2.78 |
| Ala | 215 | . | . | . | . | T | T | . | 1.84 | −0.89 | . | * | F | 3.06 | 2.15 |
| Asp | 216 | . | . | . | . | T | . | . | 2.22 | −1.29 | . | . | F | 2.75 | 2.73 |
| Asp | 217 | . | . | . | . | T | T | . | 1.62 | −0.80 | * | . | F | 2.84 | 1.78 |
| Ser | 218 | . | . | . | . | . | T | C | 1.88 | −0.59 | * | . | F | 2.53 | 1.75 |
| Arg | 219 | . | . | . | . | T | T | . | 1.57 | −1.09 | * | . | F | 2.62 | 2.09 |
| Trp | 220 | . | . | B | . | . | T | . | 1.84 | −0.60 | * | . | . | 2.30 | 1.81 |
| Met | 221 | . | A | B | . | . | . | . | 1.84 | −0.11 | * | . | . | 1.37 | 1.95 |
| Lys | 222 | . | A | B | . | . | . | . | 1.89 | −0.50 | * | * | F | 1.29 | 1.72 |
| Thr | 223 | . | A | . | . | . | . | C | 1.84 | −0.50 | * | . | F | 1.26 | 3.27 |
| Thr | 224 | . | A | . | . | . | . | C | 1.44 | −0.99 | * | . | F | 1.33 | 3.27 |
| Glu | 225 | . | A | . | . | . | . | C | 1.73 | −0.69 | * | . | F | 1.10 | 1.72 |
| Lys | 226 | . | A | . | . | . | . | C | 1.63 | −0.69 | * | * | F | 1.10 | 2.06 |
| Gly | 227 | . | A | . | . | T | . | . | 1.56 | −0.39 | * | . | F | 1.00 | 1.24 |
| Trp | 228 | . | A | . | . | . | . | C | 1.57 | −0.37 | . | . | . | 0.50 | 0.97 |
| Glu | 229 | . | A | . | . | . | . | C | 1.02 | 0.01 | . | . | . | −0.10 | 0.65 |
| Phe | 230 | . | A | B | . | . | . | . | 1.02 | 0.66 | . | . | . | −0.60 | 0.49 |
| His | 231 | . | A | B | . | . | . | . | 0.17 | 0.23 | . | . | . | −0.30 | 0.81 |

TABLE III-continued

| Res | Pos | I | II | III | IV | V | VI | VII | VIII | IX | X | XI | XII | XIII | XIV |
|---|---|---|---|---|---|---|---|---|---|---|---|---|---|---|---|
| Ser | 232 | . | A | B | . | . | . | . | 0.51 | 0.00 | . | . | . | −0.30 | 0.38 |
| Val | 233 | . | A | B | . | . | . | . | 0.91 | 0.40 | * | . | . | −0.26 | 0.71 |
| Glu | 234 | . | A | . | . | . | . | C | 0.57 | −0.39 | . | . | . | 1.33 | 1.03 |
| Leu | 235 | . | A | . | . | . | . | C | 1.27 | −0.46 | . | . | . | 1.52 | 0.76 |
| Asn | 236 | . | . | . | . | T | T | . | 1.30 | −0.44 | . | . | F | 2.76 | 1.64 |
| Arg | 237 | . | . | . | . | T | T | . | 0.74 | −0.69 | * | . | F | 3.40 | 1.52 |
| Gly | 238 | . | . | . | . | T | T | . | 0.79 | −0.04 | * | . | F | 2.76 | 1.37 |
| Asn | 239 | . | . | . | . | T | T | . | 0.54 | −0.04 | * | . | F | 2.27 | 0.70 |
| Asn | 240 | . | . | . | B | . | . | C | 1.07 | 0.31 | * | * | F | 0.73 | 0.56 |
| Val | 241 | . | . | B | B | . | . | . | 1.18 | 1.23 | . | * | . | −0.26 | 0.60 |
| Leu | 242 | . | . | B | B | . | . | . | 0.76 | 0.80 | . | * | . | −0.60 | 0.73 |
| Tyr | 243 | . | . | B | B | . | . | . | 0.79 | 0.89 | . | * | . | −0.60 | 0.65 |
| Trp | 244 | . | . | B | B | . | . | . | 0.20 | 0.97 | . | * | . | −0.45 | 1.27 |
| Arg | 245 | . | . | B | B | . | . | . | −0.50 | 0.83 | . | . | . | −0.45 | 1.56 |
| Thr | 246 | . | . | B | B | . | . | . | 0.06 | 0.93 | . | . | F | −0.45 | 0.86 |
| Thr | 247 | . | . | B | B | . | . | . | 0.01 | 0.56 | . | * | . | −0.45 | 1.10 |
| Ala | 248 | . | . | B | B | . | . | . | −0.03 | 0.29 | . | . | . | −0.30 | 0.42 |
| Phe | 249 | . | . | B | B | . | . | . | −0.06 | 1.20 | . | * | . | −0.60 | 0.30 |
| Ser | 250 | . | . | B | B | . | . | . | −0.12 | 1.20 | . | * | . | −0.60 | 0.30 |
| Val | 251 | . | . | . | B | T | . | . | −0.67 | 0.71 | * | * | . | −0.20 | 0.60 |
| Trp | 252 | . | . | B | B | . | . | . | −0.57 | 0.86 | * | . | . | −0.36 | 0.51 |
| Thr | 253 | . | . | B | B | . | . | . | 0.07 | 0.50 | * | . | F | 0.03 | 0.59 |
| Lys | 254 | . | . | . | B | . | . | C | 0.56 | 0.11 | * | * | F | 0.92 | 1.60 |
| Val | 255 | . | . | . | . | . | T | C | −0.00 | −0.10 | * | . | F | 2.16 | 2.35 |
| Pro | 256 | . | . | . | . | . | T | C | 0.04 | −0.37 | * | . | F | 2.40 | 1.21 |
| Lys | 257 | . | . | B | . | . | T | . | −0.52 | −0.17 | * | * | F | 1.81 | 0.50 |
| Pro | 258 | . | . | B | . | . | T | . | −0.10 | 0.47 | * | * | F | 0.67 | 0.50 |
| Val | 259 | . | . | B | B | . | . | . | −0.14 | −0.17 | * | . | . | 0.78 | 0.63 |
| Leu | 260 | . | . | B | B | . | . | . | −0.18 | −0.20 | . | . | . | 0.54 | 0.51 |
| Val | 261 | . | . | B | B | . | . | . | −0.56 | 0.49 | . | . | . | −0.60 | 0.23 |
| Arg | 262 | . | . | B | B | . | . | . | −1.49 | 0.56 | . | . | . | −0.60 | 0.31 |
| Asn | 263 | . | . | B | B | . | . | . | −1.59 | 0.60 | * | . | . | −0.60 | 0.27 |
| Ile | 264 | . | . | B | B | . | . | . | −1.08 | 0.40 | . | . | . | −0.60 | 0.52 |
| Ala | 265 | . | . | B | B | . | . | . | −1.12 | 0.19 | * | . | . | −0.30 | 0.26 |
| Ile | 266 | . | . | B | B | . | . | . | −0.86 | 0.83 | * | . | . | −0.60 | 0.12 |
| Thr | 267 | . | . | B | B | . | . | . | −1.21 | 0.93 | . | . | . | −0.60 | 0.17 |
| Gly | 268 | . | . | B | B | . | . | . | −1.52 | 1.00 | . | * | . | −0.60 | 0.27 |
| Val | 269 | . | . | B | B | . | . | . | −0.93 | 0.99 | . | . | . | −0.60 | 0.56 |
| Ala | 270 | . | . | B | B | . | . | . | −0.34 | 0.69 | . | . | . | −0.60 | 0.52 |
| Tyr | 271 | . | . | B | B | . | . | . | −0.12 | 0.20 | * | . | . | −0.30 | 0.90 |
| Thr | 272 | . | . | B | . | . | T | . | −0.51 | 0.34 | . | . | F | 0.25 | 0.65 |
| Ser | 273 | . | . | B | . | T | T | . | −0.38 | 0.49 | . | . | F | 0.35 | 0.56 |
| Glu | 274 | . | . | . | . | T | T | . | −0.19 | 0.41 | . | . | F | 0.35 | 0.55 |
| Cys | 275 | . | . | B | . | . | T | . | 0.44 | 0.23 | . | . | . | 0.10 | 0.20 |
| Phe | 276 | . | . | B | . | . | . | . | 0.48 | −0.26 | . | . | . | 0.50 | 0.31 |
| Pro | 277 | . | . | . | . | T | . | . | 0.44 | −0.21 | . | . | . | 0.90 | 0.27 |
| Cys | 278 | . | . | . | . | T | . | . | 0.43 | 0.21 | . | . | . | 0.30 | 0.50 |
| Lys | 279 | . | . | . | . | . | T | C | 0.19 | 0.13 | . | . | F | 0.45 | 0.84 |
| Pro | 280 | . | . | . | . | T | T | . | 0.27 | 0.10 | . | * | F | 0.65 | 0.85 |
| Gly | 281 | . | . | . | . | T | T | . | 0.97 | 0.17 | * | * | F | 0.80 | 1.60 |
| Thr | 282 | . | . | B | . | . | T | . | 1.22 | −0.40 | * | . | F | 1.34 | 1.34 |
| Tyr | 283 | . | . | B | . | . | . | . | 1.89 | −0.40 | * | . | F | 1.48 | 1.73 |
| Ala | 284 | . | . | B | . | . | . | . | 1.50 | −0.43 | * | . | F | 1.82 | 3.03 |
| Asp | 285 | . | . | B | . | . | T | . | 1.41 | −0.43 | * | . | F | 2.36 | 2.08 |
| Lys | 286 | . | . | . | . | T | T | . | 1.46 | −0.53 | * | . | F | 3.40 | 1.78 |
| Gln | 287 | . | . | . | . | T | T | . | 1.07 | −0.90 | * | . | F | 3.06 | 2.36 |
| Gly | 288 | . | . | . | . | T | T | . | 0.64 | −0.61 | * | . | F | 2.72 | 1.22 |
| Ser | 289 | . | . | . | . | T | T | . | 1.28 | −0.04 | * | . | F | 1.93 | 0.33 |
| Ser | 290 | . | . | B | . | T | T | . | 0.47 | −0.04 | * | . | F | 1.59 | 0.38 |
| Phe | 291 | . | . | B | . | . | T | . | −0.24 | 0.24 | * | . | . | 0.10 | 0.32 |
| Cys | 292 | . | . | B | . | . | T | . | −0.46 | 0.39 | * | . | . | 0.10 | 0.13 |
| Lys | 293 | . | . | B | . | . | . | . | −0.70 | 0.43 | * | . | . | −0.40 | 0.15 |
| Leu | 294 | . | . | B | . | . | . | . | −0.40 | 0.54 | . | . | . | −0.40 | 0.17 |
| Cys | 295 | . | . | B | . | . | . | . | −0.40 | 0.16 | . | . | . | −0.10 | 0.51 |
| Pro | 296 | . | . | B | . | . | . | . | 0.06 | −0.03 | . | . | . | 0.50 | 0.34 |
| Ala | 297 | . | . | . | . | T | . | . | 0.42 | 0.73 | . | . | . | 0.00 | 0.65 |
| Asn | 298 | . | . | . | . | T | T | . | 0.38 | 0.43 | . | . | F | 0.84 | 1.62 |
| Ser | 299 | . | . | . | . | T | T | . | 1.23 | 0.26 | * | . | F | 1.48 | 1.69 |
| Tyr | 300 | . | . | . | . | T | T | . | 1.56 | −0.17 | . | . | F | 2.42 | 3.34 |
| Ser | 301 | . | . | . | . | T | T | C | 1.77 | −0.24 | * | . | F | 2.56 | 2.05 |
| Asn | 302 | . | . | . | . | T | T | . | 2.04 | −0.64 | * | . | F | 3.40 | 2.65 |
| Lys | 303 | . | . | . | . | T | T | . | 1.74 | −0.54 | . | . | F | 3.06 | 2.44 |
| Gly | 304 | . | . | . | . | T | T | . | 1.38 | −0.91 | . | * | F | 2.72 | 2.44 |
| Glu | 305 | . | . | . | . | T | T | . | 1.59 | −0.73 | * | . | F | 2.23 | 0.81 |
| Thr | 306 | . | . | . | . | T | T | . | 1.89 | −0.63 | * | . | F | 1.89 | 0.55 |
| Ser | 307 | . | . | B | . | . | T | . | 1.22 | −0.23 | * | . | F | 0.85 | 0.97 |
| Cys | 308 | . | . | B | . | . | T | . | 1.18 | −0.09 | . | * | . | 1.04 | 0.30 |

TABLE III-continued

| Res | Pos | I | II | III | IV | V | VI | VII | VIII | IX | X | XI | XII | XIII | XIV |
|---|---|---|---|---|---|---|---|---|---|---|---|---|---|---|---|
| His | 309 | . | . | B | . | . | T | . | 1.31 | −0.09 | . | . | . | 1.38 | 0.35 |
| Gln | 310 | . | . | . | . | T | . | . | 1.31 | −0.14 | . | . | . | 1.92 | 0.40 |
| Cys | 311 | . | . | . | . | T | . | . | 1.67 | −0.53 | . | . | . | 2.71 | 1.25 |
| Asp | 312 | . | . | . | . | T | T | . | 1.72 | −1.10 | . | . | F | 3.40 | 1.84 |
| Pro | 313 | . | . | . | . | T | T | . | 2.09 | −0.84 | . | . | F | 3.06 | 1.66 |
| Asp | 314 | . | . | . | . | T | T | . | 2.12 | −0.86 | . | . | F | 3.06 | 4.15 |
| Lys | 315 | . | . | . | . | T | T | . | 2.17 | −1.43 | * | . | F | 3.06 | 4.31 |
| Tyr | 316 | . | . | B | . | . | T | . | 2.49 | −1.43 | * | . | F | 2.66 | 5.57 |
| Ser | 317 | . | . | B | . | . | T | . | 2.19 | −1.43 | * | . | F | 2.66 | 3.30 |
| Glu | 318 | . | . | . | . | T | T | . | 2.10 | −1.04 | * | . | F | 3.40 | 2.21 |
| Lys | 319 | . | . | . | . | T | T | . | 1.80 | −0.66 | * | . | F | 3.06 | 1.89 |
| Gly | 320 | . | . | . | . | T | . | . | 1.09 | −1.03 | * | * | F | 2.52 | 1.89 |
| Ser | 321 | . | . | . | . | T | T | . | 1.33 | −0.84 | . | * | F | 2.23 | 0.59 |
| Ser | 322 | . | . | . | . | T | T | . | 0.78 | −0.44 | . | * | F | 1.59 | 0.47 |
| Ser | 323 | . | . | . | . | T | T | . | 0.89 | 0.20 | . | * | F | 0.65 | 0.35 |
| Cys | 324 | . | . | . | . | T | T | . | 0.63 | −0.23 | . | * | F | 1.25 | 0.52 |
| Asn | 325 | . | . | . | . | T | . | . | 0.39 | −0.19 | . | * | . | 0.90 | 0.60 |
| Val | 326 | . | . | B | . | . | . | . | 0.02 | −0.07 | . | * | . | 0.50 | 0.45 |
| Arg | 327 | . | . | B | . | . | T | . | 0.01 | 0.11 | . | * | . | 0.10 | 0.45 |
| Pro | 328 | . | . | B | . | . | T | . | 0.31 | 0.03 | . | * | . | 0.44 | 0.40 |
| Ala | 329 | . | . | B | . | . | T | . | 1.02 | −0.37 | . | * | . | 1.38 | 0.91 |
| Cys | 330 | . | . | B | . | . | T | . | 1.02 | −1.01 | . | * | . | 2.02 | 0.93 |
| Thr | 331 | . | . | B | . | . | . | . | 1.63 | −1.01 | * | . | F | 2.31 | 1.00 |
| Asp | 332 | . | . | . | . | T | T | . | 0.82 | −0.69 | * | . | F | 3.40 | 1.55 |
| Lys | 333 | . | . | . | . | T | T | . | 0.79 | −0.40 | . | . | F | 2.76 | 2.50 |
| Asp | 334 | . | . | . | . | T | T | . | 1.07 | −0.21 | . | . | F | 2.42 | 2.72 |
| Tyr | 335 | . | . | B | . | . | T | . | 1.70 | −0.21 | . | . | . | 1.53 | 2.35 |
| Phe | 336 | . | . | B | B | . | . | . | 1.70 | 0.29 | . | . | . | 0.19 | 1.60 |
| Tyr | 337 | . | . | B | B | . | . | . | 1.11 | 0.77 | . | . | . | −0.45 | 1.38 |
| Thr | 338 | . | . | B | B | . | . | . | 0.40 | 1.27 | . | . | . | −0.60 | 0.89 |
| His | 339 | . | . | B | B | . | . | . | 0.40 | 1.09 | . | . | . | −0.60 | 0.55 |
| Thr | 340 | . | . | B | B | . | . | . | 0.06 | 0.30 | . | . | . | −0.30 | 0.59 |
| Ala | 341 | . | . | B | B | . | . | . | 0.76 | 0.04 | . | * | . | 0.00 | 0.41 |
| Cys | 342 | . | . | . | B | T | . | . | 0.66 | −0.04 | . | * | . | 1.30 | 0.49 |
| Asp | 343 | . | . | . | . | T | T | . | 0.97 | −0.11 | . | * | . | 2.00 | 0.33 |
| Ala | 344 | . | . | . | . | . | T | C | 0.69 | −0.60 | . | * | F | 2.55 | 0.57 |
| Asn | 345 | . | . | . | . | . | T | C | 1.00 | −0.61 | . | * | F | 3.00 | 1.54 |
| Gly | 346 | . | . | . | . | . | T | C | 0.78 | −0.79 | . | * | F | 2.70 | 1.60 |
| Glu | 347 | . | A | . | . | . | . | C | 0.84 | −0.10 | . | * | F | 1.70 | 1.30 |
| Thr | 348 | . | A | B | . | . | . | . | 0.60 | 0.01 | . | * | F | 0.45 | 0.80 |
| Gln | 349 | . | A | B | . | . | . | . | 1.23 | 0.37 | * | * | F | 0.30 | 1.27 |
| Leu | 350 | . | A | B | . | . | . | . | 0.94 | −0.06 | * | * | . | 0.45 | 1.47 |
| Met | 351 | . | A | B | . | . | . | . | 0.70 | 0.86 | * | * | . | −0.45 | 1.07 |
| Tyr | 352 | . | A | B | . | . | . | . | 0.74 | 0.87 | * | * | . | −0.60 | 0.62 |
| Lys | 353 | . | A | . | . | T | . | . | 0.84 | 0.47 | * | * | . | −0.05 | 1.51 |
| Trp | 354 | . | A | . | . | T | . | . | 0.89 | 0.21 | * | * | . | 0.25 | 2.36 |
| Ala | 355 | . | A | . | . | . | . | C | 0.81 | −0.40 | . | * | F | 0.80 | 3.01 |
| Lys | 356 | . | A | . | . | . | . | C | 0.74 | −0.47 | * | * | F | 0.80 | 1.06 |
| Pro | 357 | . | A | . | . | T | . | . | 0.69 | 0.10 | . | * | F | 0.25 | 0.54 |
| Lys | 358 | . | . | . | . | T | . | . | 0.64 | −0.43 | . | * | F | 1.05 | 0.71 |
| Ile | 359 | . | . | B | . | . | . | . | 0.93 | −0.93 | . | * | . | 0.80 | 0.62 |
| Cys | 360 | . | . | B | . | . | T | . | 0.71 | −0.93 | . | . | . | 1.00 | 0.67 |
| Ser | 361 | . | . | B | . | . | T | . | 0.67 | −0.67 | . | * | F | 1.15 | 0.28 |
| Glu | 362 | . | . | B | . | . | T | . | 0.53 | −0.67 | * | . | F | 1.15 | 0.68 |
| Asp | 363 | A | . | . | . | . | T | . | −0.10 | −0.93 | * | * | F | 1.30 | 1.26 |
| Leu | 364 | A | A | . | . | . | . | . | −0.07 | −1.00 | * | * | F | 0.75 | 0.95 |
| Glu | 365 | A | A | . | . | . | . | . | 0.64 | −0.74 | * | * | F | 0.75 | 0.41 |
| Gly | 366 | A | A | . | . | . | . | . | 0.13 | −0.74 | * | * | F | 0.75 | 0.49 |
| Ala | 367 | . | A | B | . | . | . | . | −0.08 | −0.06 | * | * | . | 0.30 | 0.49 |
| Val | 368 | . | A | B | . | . | . | . | −0.67 | −0.31 | * | * | . | 0.30 | 0.43 |
| Lys | 369 | . | A | B | . | . | . | . | −0.16 | 0.19 | * | * | . | −0.30 | 0.44 |
| Leu | 370 | . | A | B | . | . | . | . | −0.50 | 0.14 | * | * | . | −0.30 | 0.59 |
| Pro | 371 | . | . | B | . | . | T | . | −1.01 | 0.07 | * | * | . | 0.10 | 0.78 |
| Ala | 372 | . | . | . | . | T | T | . | −0.38 | 0.07 | * | * | F | 0.65 | 0.29 |
| Ser | 373 | . | . | . | . | T | T | . | 0.17 | 0.07 | * | * | F | 0.65 | 0.70 |
| Gly | 374 | . | . | . | . | T | T | . | 0.09 | −0.13 | * | * | F | 1.25 | 0.66 |
| Val | 375 | . | . | B | . | . | . | . | 0.23 | −0.06 | . | . | F | 0.79 | 0.89 |
| Lys | 376 | . | . | B | . | . | . | . | 0.23 | 0.01 | . | . | F | 0.33 | 0.35 |
| Thr | 377 | . | . | B | . | . | . | . | 0.61 | 0.06 | . | . | F | 0.47 | 0.55 |
| His | 378 | . | . | B | . | . | . | . | 0.24 | 0.06 | * | . | . | 0.61 | 1.15 |
| Cys | 379 | . | . | B | . | . | T | . | 0.59 | −0.01 | . | . | . | 1.40 | 0.31 |
| Pro | 380 | . | . | B | . | . | T | . | 1.23 | 0.39 | * | * | F | 0.81 | 0.34 |
| Pro | 381 | . | . | . | . | T | T | . | 0.84 | 0.33 | . | . | F | 1.07 | 0.39 |
| Cys | 382 | . | . | . | . | T | T | . | 0.46 | 0.26 | . | . | F | 0.93 | 0.72 |
| Asn | 383 | . | . | . | . | T | C | . | −0.21 | 0.47 | . | . | F | 0.29 | 0.40 |
| Pro | 384 | . | . | . | . | T | T | . | 0.50 | 0.83 | . | . | F | 0.35 | 0.23 |
| Gly | 385 | . | . | . | . | T | T | . | 0.40 | 0.40 | . | . | . | 0.20 | 0.85 |

TABLE III-continued

| Res | Pos | I | II | III | IV | V | VI | VII | VIII | IX | X | XI | XII | XIII | XIV |
|---|---|---|---|---|---|---|---|---|---|---|---|---|---|---|---|
| Phe | 386 | . | . | B | . | . | T | . | 0.61 | 0.31 | . | . | . | 0.10 | 0.76 |
| Phe | 387 | . | . | B | . | . | . | . | 1.28 | 0.31 | . | . | F | 0.30 | 0.79 |
| Lys | 388 | . | . | . | . | T | . | . | 0.98 | 0.29 | . | . | F | 1.10 | 1.28 |
| Thr | 389 | . | . | . | . | T | . | . | 0.88 | 0.24 | . | . | F | 1.35 | 1.99 |
| Asn | 390 | . | . | . | . | T | . | . | 0.56 | −0.06 | * | . | F | 2.20 | 3.31 |
| Asn | 391 | . | . | . | . | T | T | . | 1.26 | −0.27 | * | . | F | 2.50 | 0.89 |
| Ser | 392 | . | . | . | . | T | T | . | 1.74 | 0.13 | * | . | F | 1.80 | 1.06 |
| Thr | 393 | . | . | . | . | T | T | . | 1.03 | 0.07 | . | . | F | 1.55 | 1.02 |
| Cys | 394 | . | . | . | . | T | T | . | 1.13 | 0.24 | . | . | F | 1.15 | 0.34 |
| Gln | 395 | . | . | B | . | . | . | . | 0.89 | 0.27 | . | . | F | 0.30 | 0.39 |
| Pro | 396 | . | . | B | . | . | . | . | 0.54 | 0.64 | . | . | F | −0.25 | 0.43 |
| Cys | 397 | . | . | B | . | . | T | . | 0.54 | 0.59 | . | . | . | −0.20 | 0.79 |
| Pro | 398 | . | . | B | . | . | T | . | 0.61 | 0.40 | . | . | . | −0.20 | 0.61 |
| Tyr | 399 | . | . | . | . | T | T | . | 0.98 | 0.76 | . | . | . | 0.20 | 0.62 |
| Gly | 400 | . | . | . | . | T | T | . | 0.98 | 0.71 | . | . | . | 0.35 | 1.55 |
| Ser | 401 | . | . | . | . | T | . | . | 0.84 | 0.54 | . | . | F | 0.30 | 1.61 |
| Tyr | 402 | . | . | . | . | T | T | . | 1.21 | 0.54 | . | . | F | 0.50 | 1.02 |
| Ser | 403 | . | . | . | . | T | T | . | 1.42 | 0.17 | . | . | F | 1.11 | 1.38 |
| Asn | 404 | . | . | . | . | T | T | . | 1.00 | −0.26 | . | . | F | 2.02 | 1.71 |
| Gly | 405 | . | . | . | . | T | T | . | 1.03 | −0.07 | * | . | F | 2.18 | 0.59 |
| Ser | 406 | . | . | . | . | T | T | . | 1.44 | −0.34 | * | . | F | 2.49 | 0.63 |
| Asp | 407 | . | . | . | . | T | T | . | 1.02 | −0.73 | * | . | F | 3.10 | 0.77 |
| Cys | 408 | . | . | B | . | . | T | . | 1.11 | −0.56 | * | * | F | 2.39 | 0.42 |
| Thr | 409 | . | . | B | . | . | T | . | 0.52 | −0.56 | * | * | F | 2.39 | 048 |
| Arg | 410 | . | . | B | . | . | . | . | 0.52 | −0.44 | * | . | F | 1.89 | 0.29 |
| Cys | 411 | . | . | B | . | . | T | . | 0.51 | −0.01 | . | . | . | 1.94 | 0.54 |
| Pro | 412 | . | . | . | . | T | T | . | 0.51 | −0.10 | . | . | . | 2.34 | 0.54 |
| Ala | 413 | . | . | . | . | T | T | . | 0.97 | −0.59 | . | * | F | 3.10 | 0.47 |
| Gly | 414 | . | . | . | . | . | T | C | 0.69 | −0.16 | * | * | F | 2.44 | 1.37 |
| Thr | 415 | . | . | . | . | . | . | C | −0.28 | −0.23 | . | * | F | 1.78 | 0.89 |
| Glu | 416 | . | . | B | . | . | . | . | 0.04 | −0.01 | . | . | F | 1.27 | 0.66 |
| Pro | 417 | . | . | B | . | . | . | . | −0.44 | −0.09 | . | . | F | 0.96 | 0.66 |
| Ala | 418 | . | . | B | . | . | . | . | 0.14 | 0.27 | . | * | . | −0.10 | 0.39 |
| Val | 419 | . | . | B | . | . | . | . | 0.24 | −0.21 | . | * | . | 0.50 | 0.39 |
| Gly | 420 | . | . | B | . | . | . | . | 0.60 | 0.54 | . | * | . | −0.40 | 0.40 |
| Phe | 421 | . | A | B | . | . | . | . | 0.31 | 0.11 | . | * | . | −0.30 | 0.79 |
| Glu | 422 | . | A | B | . | . | . | . | 0.23 | 0.53 | . | * | . | −0.45 | 1.12 |
| Tyr | 423 | . | A | . | . | T | . | . | 0.82 | 0.80 | * | * | . | −0.05 | 1.19 |
| Lys | 424 | . | A | . | . | T | . | . | 1.37 | 0.77 | * | * | . | −0.05 | 2.21 |
| Trp | 425 | . | A | . | . | T | . | . | 0.90 | 0.47 | * | * | . | −0.05 | 1.84 |
| Trp | 426 | . | A | . | . | T | . | . | 1.39 | 1.16 | * | * | . | −0.20 | 0.97 |
| Asn | 427 | . | . | . | . | . | . | C | 1.08 | 0.83 | * | * | . | −0.20 | 0.75 |
| Thr | 428 | . | . | . | . | . | . | C | 1.32 | 1.31 | * | . | F | 0.10 | 1.03 |
| Leu | 429 | . | . | . | . | . | . | C | 0.68 | 0.80 | * | * | F | 0.10 | 1.57 |
| Pro | 430 | . | . | . | . | . | T | C | 0.97 | 0.50 | * | . | F | 0.12 | 0.97 |
| Thr | 431 | . | . | . | . | . | T | C | 0.94 | 0.10 | * | . | F | 0.54 | 1.16 |
| Asn | 432 | . | . | . | . | . | T | C | 0.63 | 0.10 | * | * | F | 0.51 | 2.03 |
| Met | 433 | . | . | B | . | . | T | . | 0.09 | −0.10 | . | * | F | 0.88 | 1.90 |
| Glu | 434 | . | . | B | B | . | . | . | 0.09 | 0.11 | . | * | F | −0.30 | 0.98 |
| Thr | 435 | . | . | B | B | . | . | . | −0.00 | 0.31 | . | . | F | −0.27 | 0.50 |
| Thr | 436 | . | . | B | B | . | . | . | −0.03 | 0.30 | * | . | F | −0.24 | 0.68 |
| Val | 437 | . | . | B | B | . | . | . | −0.92 | 0.11 | * | * | F | −0.21 | 0.39 |
| Leu | 438 | . | . | B | B | . | . | . | −0.32 | 0.80 | * | * | F | −0.48 | 0.19 |
| Ser | 439 | . | . | B | B | . | . | . | −1.02 | 0.71 | . | * | F | −0.45 | 0.21 |
| Gly | 440 | . | . | . | B | . | . | C | −0.71 | 1.01 | * | * | . | −0.40 | 0.24 |
| Ile | 441 | . | A | B | B | . | . | . | −0.64 | 0.37 | * | * | . | −0.30 | 0.51 |
| Asn | 442 | . | A | B | B | . | . | . | 0.26 | 0.44 | * | * | . | −0.60 | 0.60 |
| Phe | 443 | . | A | B | B | . | . | . | 0.72 | 0.06 | * | * | . | −0.15 | 1.21 |
| Glu | 444 | . | A | B | B | . | . | . | 0.42 | 0.06 | * | * | . | −0.15 | 1.71 |
| Tyr | 445 | . | . | B | . | . | T | . | 0.46 | −0.01 | * | * | . | 0.85 | 1.05 |
| Lys | 446 | . | . | . | . | T | T | . | 1.00 | 0.07 | * | * | F | 0.80 | 1.76 |
| Gly | 447 | . | . | . | . | T | T | . | 0.71 | −0.29 | * | * | F | 1.40 | 1.00 |
| Met | 448 | . | . | . | . | . | T | C | 1.41 | 0.63 | . | * | F | 0.15 | 0.67 |
| Thr | 449 | . | . | . | . | . | . | C | 0.56 | −0.13 | * | * | F | 0.85 | 0.58 |
| Gly | 450 | . | A | . | . | . | . | C | 0.21 | 0.51 | * | * | . | −0.40 | 0.44 |
| Trp | 451 | . | A | B | . | . | . | . | −0.18 | 0.59 | * | * | . | −0.42 | 0.45 |
| Glu | 452 | . | A | B | . | . | . | . | 0.17 | 0.40 | * | . | . | −0.24 | 0.31 |
| Val | 453 | . | A | B | . | . | . | . | 0.73 | −0.09 | * | . | . | 0.84 | 0.52 |
| Ala | 454 | . | A | B | . | . | . | . | 0.16 | −0.01 | * | . | . | 1.02 | 0.67 |
| Gly | 455 | . | . | . | . | T | . | . | 0.26 | −0.24 | * | . | . | 1.80 | 0.27 |
| Asp | 456 | . | . | . | B | T | . | . | 0.23 | 0.51 | * | . | . | 0.52 | 0.57 |
| His | 457 | . | . | B | B | . | . | . | −0.36 | 0.36 | * | . | . | 0.24 | 0.82 |
| Ile | 458 | . | . | B | B | . | . | . | −0.09 | 0.36 | * | . | . | 0.06 | 0.83 |
| Tyr | 459 | . | . | B | B | . | . | . | 0.16 | 0.43 | * | . | . | −0.42 | 0.50 |
| Thr | 460 | . | . | B | B | . | . | . | −0.09 | 0.86 | . | . | . | −0.60 | 0.37 |
| Ala | 461 | . | . | B | B | . | . | . | −0.39 | 0.86 | . | . | . | −0.60 | 0.53 |
| Ala | 462 | . | . | B | . | . | . | . | −0.36 | 0.56 | . | . | . | −0.12 | 0.45 |

TABLE III-continued

| Res | Pos | I | II | III | IV | V | VI | VII | VIII | IX | X | XI | XII | XIII | XIV |
|-----|-----|---|----|----|----|---|----|----|------|-----|---|----|-----|------|-----|
| Gly | 463 | . | . | . | . | . | . | C | 0.53 | −0.20 | . | . | . | 1.26 | 0.52 |
| Ala | 464 | . | . | . | . | . | . | C | 0.78 | −0.29 | . | . | F | 1.69 | 0.83 |
| Ser | 465 | . | . | . | . | . | T | C | 0.39 | −0.79 | . | . | F | 2.62 | 1.38 |
| Asp | 466 | . | . | . | . | T | T | . | 0.38 | −0.50 | . | . | F | 2.80 | 1.21 |
| Asn | 467 | . | . | . | . | . | T | C | 0.08 | −0.31 | . | . | F | 2.32 | 1.18 |
| Asp | 468 | . | . | B | . | . | T | . | −0.39 | −0.13 | . | . | F | 1.69 | 0.62 |
| Phe | 469 | . | . | B | B | . | . | . | −0.11 | 0.17 | . | . | . | 0.26 | 0.30 |
| Met | 470 | . | . | B | B | . | . | . | −0.62 | 0.66 | . | . | . | −0.32 | 0.27 |
| Ile | 471 | . | . | B | B | . | . | . | −1.48 | 0.94 | . | . | . | −0.60 | 0.14 |
| Leu | 472 | . | . | B | B | . | . | . | −2.33 | 1.59 | . | . | . | −0.60 | 0.12 |
| Thr | 473 | . | . | B | B | . | . | . | −2.54 | 1.44 | . | . | . | −0.60 | 0.09 |
| Leu | 474 | . | . | B | B | . | . | . | −2.19 | 1.26 | . | . | . | −0.60 | 0.19 |
| Val | 475 | . | . | B | B | . | . | . | −2.29 | 1.00 | * | * | . | −0.60 | 0.23 |
| Val | 476 | . | . | B | B | . | . | . | −1.29 | 1.10 | . | . | . | −0.60 | 0.14 |
| Pro | 477 | . | . | B | . | . | . | . | −0.69 | 0.61 | * | * | . | −0.40 | 0.33 |
| Gly | 478 | . | . | . | . | T | . | . | −0.59 | 0.36 | * | . | F | 0.45 | 0.68 |
| Phe | 479 | . | . | B | . | . | . | . | 0.22 | 0.14 | * | . | F | 0.45 | 1.42 |
| Arg | 480 | . | . | . | . | . | . | C | 0.78 | −0.10 | * | * | F | 1.50 | 1.59 |
| Pro | 481 | . | . | . | . | . | T | C | 0.78 | −0.14 | * | . | F | 1.95 | 2.16 |
| Pro | 482 | . | . | . | . | T | T | . | 0.39 | 0.07 | * | * | F | 1.80 | 1.85 |
| Gln | 483 | . | . | . | . | T | T | . | 0.14 | −0.10 | * | * | F | 2.50 | 0.93 |
| Ser | 484 | . | . | B | . | . | T | . | 0.84 | 0.40 | * | * | F | 0.95 | 0.61 |
| Val | 485 | . | . | B | . | . | . | . | 0.42 | −0.03 | * | * | . | 1.55 | 0.66 |
| Met | 486 | . | . | B | . | . | . | . | 0.63 | 0.03 | . | . | . | 1.00 | 0.55 |
| Ala | 487 | . | . | B | . | . | . | . | 0.84 | −0.37 | . | * | . | 1.65 | 0.71 |
| Asp | 488 | . | . | B | . | . | T | . | 0.89 | −0.36 | . | . | F | 2.20 | 1.54 |
| Thr | 489 | . | . | . | . | . | T | C | 1.19 | −1.00 | . | . | F | 3.00 | 3.11 |
| Glu | 490 | A | . | . | . | . | T | . | 1.19 | −1.61 | . | . | F | 2.50 | 5.33 |
| Asn | 491 | A | . | . | . | . | T | . | 1.20 | −1.47 | * | * | F | 2.20 | 2.37 |
| Lys | 492 | A | . | . | . | . | . | . | 1.90 | −0.97 | * | * | F | 1.70 | 1.66 |
| Glu | 493 | A | . | . | . | . | . | . | 1.01 | −1.46 | * | * | F | 1.40 | 1.88 |
| Val | 494 | A | . | . | B | . | . | . | 1.01 | −0.77 | * | * | . | 0.60 | 0.82 |
| Ala | 495 | . | . | B | B | . | . | . | 0.31 | −0.69 | * | * | . | 0.60 | 0.59 |
| Arg | 496 | . | . | B | B | . | . | . | −0.54 | 0.10 | * | * | . | −0.30 | 0.29 |
| Ile | 497 | . | . | B | B | . | . | . | −1.29 | 0.74 | * | * | . | −0.60 | 0.29 |
| Thr | 498 | . | . | B | B | . | . | . | −1.29 | 0.89 | * | * | . | −0.60 | 0.25 |
| Phe | 499 | . | . | B | B | . | . | . | −0.74 | 0.39 | * | * | . | −0.30 | 0.22 |
| Val | 500 | . | . | B | B | . | . | . | −0.97 | 0.87 | * | * | . | −0.60 | 0.46 |
| Phe | 501 | . | . | B | B | . | . | . | −1.74 | 0.87 | * | * | . | −0.60 | 0.26 |
| Glu | 502 | . | . | B | B | . | . | . | −1.16 | 0.96 | * | * | . | −0.60 | 0.16 |
| Thr | 503 | . | . | . | B | T | . | . | −1.70 | 0.56 | * | . | . | −0.20 | 0.29 |
| Leu | 504 | . | . | . | B | T | . | . | −1.00 | 0.56 | * | * | . | −0.20 | 0.25 |
| Cys | 505 | . | . | . | B | T | . | . | −0.81 | 0.17 | * | * | . | 0.10 | 0.23 |
| Ser | 506 | . | . | . | . | T | T | . | −0.11 | 0.74 | * | * | . | 0.20 | 0.09 |
| Val | 507 | . | . | . | . | T | T | . | −0.92 | 0.26 | * | * | . | 0.50 | 0.18 |
| Asn | 508 | . | . | B | . | T | T | . | −0.86 | 0.26 | . | * | . | 0.50 | 0.28 |
| Cys | 509 | . | . | B | . | . | T | . | −0.74 | 0.44 | . | * | . | −0.20 | 0.33 |
| Glu | 510 | . | . | B | B | . | . | . | −0.68 | 0.84 | . | * | . | −0.60 | 0.38 |
| Leu | 511 | . | . | B | B | . | . | . | −1.23 | 0.81 | . | * | . | −0.60 | 0.24 |
| Tyr | 512 | . | . | B | B | . | . | . | −0.72 | 1.06 | . | * | . | −0.60 | 0.33 |
| Phe | 513 | . | . | B | B | . | . | . | −1.58 | 0.91 | . | * | . | −0.60 | 0.19 |
| Met | 514 | . | . | B | B | . | . | . | −0.91 | 1.56 | . | * | . | −0.60 | 0.17 |
| Val | 515 | . | . | B | B | . | . | . | −1.21 | 1.27 | . | * | . | −0.60 | 0.17 |
| Gly | 516 | . | . | B | B | . | . | . | −0.29 | 0.90 | . | * | . | −0.32 | 0.27 |
| Val | 517 | . | . | B | B | . | . | . | −0.36 | 0.11 | . | * | . | 0.26 | 0.53 |
| Asn | 518 | . | . | . | . | . | T | C | 0.34 | −0.01 | . | * | F | 2.04 | 1.03 |
| Ser | 519 | . | . | . | . | . | T | C | 0.63 | −0.26 | . | * | F | 2.32 | 1.67 |
| Arg | 520 | . | . | . | . | T | T | . | 1.28 | −0.20 | . | * | F | 2.80 | 3.24 |
| Thr | 521 | . | . | . | . | T | T | . | 0.77 | −0.41 | . | * | F | 2.52 | 3.12 |
| Asn | 522 | . | . | . | . | . | . | C | 1.62 | −0.17 | * | * | F | 1.84 | 1.73 |
| Thr | 523 | . | . | . | . | . | . | C | 1.31 | −0.56 | * | * | F | 1.86 | 1.53 |
| Pro | 524 | . | . | B | . | . | . | . | 1.32 | −0.07 | * | * | F | 1.08 | 1.53 |
| Val | 525 | . | . | B | . | . | . | . | 1.26 | 0.36 | * | * | F | 0.05 | 1.00 |
| Glu | 526 | . | . | B | . | . | . | . | 1.22 | −0.04 | * | . | F | 0.80 | 1.38 |
| Thr | 527 | . | . | B | . | . | . | . | 0.92 | −0.10 | * | . | F | 0.99 | 0.88 |
| Trp | 528 | . | . | B | . | . | . | . | 1.28 | −0.14 | . | . | F | 1.48 | 1.60 |
| Lys | 529 | . | . | . | . | T | . | . | 1.14 | −0.79 | . | . | F | 2.52 | 1.85 |
| Gly | 530 | . | . | . | . | T | . | . | 2.04 | −0.36 | . | . | F | 2.56 | 1.27 |
| Ser | 531 | . | . | . | . | T | T | . | 2.04 | −0.84 | . | . | F | 3.40 | 2.41 |
| Lys | 532 | . | . | . | . | . | T | C | 2.06 | −1.36 | . | . | F | 2.86 | 2.08 |
| Gly | 533 | . | . | . | . | T | T | . | 2.10 | −0.97 | . | . | F | 2.72 | 2.82 |
| Lys | 534 | . | . | . | . | T | T | . | 1.74 | −0.64 | . | . | F | 2.38 | 3.30 |
| Gln | 535 | . | . | . | B | T | . | . | 1.84 | −0.54 | . | . | F | 1.64 | 2.38 |
| Ser | 536 | . | . | B | B | . | . | . | 1.26 | 0.21 | * | * | F | 0.00 | 3.77 |
| Tyr | 537 | . | . | B | B | . | . | . | 0.32 | 0.47 | * | * | . | −0.45 | 1.32 |
| Thr | 538 | . | . | B | B | . | . | . | 0.67 | 1.16 | * | . | . | −0.60 | 0.53 |
| Tyr | 539 | . | . | B | B | . | . | . | 0.62 | 0.76 | . | . | . | −0.60 | 0.69 |

TABLE III-continued

| Res | Pos | I | II | III | IV | V | VI | VII | VIII | IX | X | XI | XII | XIII | XIV |
|---|---|---|---|---|---|---|---|---|---|---|---|---|---|---|---|
| Ile | 540 | . | . | B | B | . | . | . | 0.62 | 0.37 | * | . | . | −0.30 | 0.76 |
| Ile | 541 | . | . | B | B | . | . | . | 0.61 | 0.01 | * | . | . | −0.04 | 0.85 |
| Glu | 542 | . | . | B | B | . | . | . | 0.54 | 0.01 | . | . | F | 0.37 | 0.78 |
| Glu | 543 | . | . | B | . | . | . | . | 0.54 | −0.26 | . | . | F | 1.58 | 1.61 |
| Asn | 544 | . | . | . | B | T | . | . | 0.49 | −0.46 | . | . | F | 2.04 | 3.32 |
| Thr | 545 | . | . | . | B | T | . | . | 0.68 | −0.76 | . | . | F | 2.60 | 2.57 |
| Thr | 546 | . | . | . | B | . | . | C | 1.26 | 0.03 | . | * | F | 1.24 | 1.29 |
| Thr | 547 | . | . | . | B | . | . | C | 0.97 | 0.51 | . | . | F | 0.68 | 1.15 |
| Ser | 548 | . | . | . | B | . | . | C | 0.38 | 1.03 | * | * | F | 0.27 | 0.84 |
| Phe | 549 | . | . | B | B | . | . | . | −0.32 | 1.04 | * | * | . | −0.34 | 0.59 |
| Thr | 550 | . | . | B | B | . | . | . | −0.01 | 1.34 | * | . | . | −0.60 | 0.35 |
| Trp | 551 | . | . | B | B | . | . | . | 0.41 | 1.26 | * | . | . | −0.60 | 0.46 |
| Ala | 552 | . | . | . | B | . | . | C | 0.41 | 0.87 | * | . | . | −0.25 | 1.03 |
| Phe | 553 | . | . | . | B | T | . | . | 0.40 | 0.57 | * | * | . | −0.05 | 1.03 |
| Gln | 554 | . | . | . | B | T | . | . | 0.40 | 0.57 | * | * | . | −0.05 | 1.42 |
| Arg | 555 | . | . | . | B | . | . | C | 0.68 | 0.44 | . | . | F | −0.10 | 1.21 |
| Thr | 556 | . | . | . | B | . | . | C | 0.97 | 0.44 | . | . | F | −0.10 | 1.91 |
| Thr | 557 | . | . | . | B | . | . | C | 0.97 | −0.34 | * | . | F | 0.80 | 1.91 |
| Phe | 558 | . | . | . | B | . | . | C | 1.37 | −0.24 | * | * | . | 0.50 | 0.98 |
| His | 559 | . | . | . | B | . | . | C | 1.48 | 0.14 | * | * | . | −0.10 | 0.91 |
| Glu | 560 | . | . | . | B | . | . | C | 1.41 | −0.34 | * | * | . | 0.65 | 1.24 |
| Ala | 561 | . | . | . | . | T | . | C | 1.48 | −0.83 | * | . | F | 1.84 | 2.86 |
| Ser | 562 | . | . | . | . | T | . | . | 1.48 | −0.86 | * | . | F | 2.18 | 3.30 |
| Arg | 563 | . | . | . | . | T | . | . | 2.18 | −0.87 | * | . | F | 2.52 | 2.75 |
| Lys | 564 | . | . | . | . | T | . | . | 2.21 | −0.47 | * | . | F | 2.56 | 4.38 |
| Tyr | 565 | . | . | . | . | T | T | . | 1.36 | −0.97 | * | . | F | 3.40 | 5.45 |
| Thr | 566 | . | . | . | . | T | T | . | 1.36 | −0.71 | * | . | F | 3.06 | 2.07 |
| Asn | 567 | . | . | B | . | . | T | . | 1.70 | −0.21 | * | . | F | 2.02 | 1.04 |
| Asp | 568 | . | . | B | . | . | T | . | 0.70 | −0.21 | * | . | F | 1.68 | 1.33 |
| Val | 569 | . | . | B | B | . | . | . | 0.41 | −0.29 | * | . | F | 0.79 | 0.65 |
| Ala | 570 | . | . | B | B | . | . | . | 0.36 | −0.01 | * | . | . | 0.30 | 0.63 |
| Lys | 571 | . | . | B | B | . | . | . | −0.22 | −0.03 | * | . | . | 0.30 | 0.51 |
| Ile | 572 | . | . | B | B | . | . | . | −0.22 | 0.66 | * | . | . | −0.60 | 0.48 |
| Tyr | 573 | . | . | B | B | . | . | . | −1.08 | 0.41 | . | . | . | −0.60 | 0.76 |
| Ser | 574 | . | . | B | B | . | . | . | −0.53 | 0.56 | . | . | . | −0.60 | 0.28 |
| Ile | 575 | . | . | B | B | . | . | . | 0.06 | 1.04 | . | . | . | −0.60 | 0.58 |
| Asn | 576 | . | . | B | B | . | . | . | −0.84 | 0.76 | . | . | . | −0.60 | 0.60 |
| Val | 577 | . | . | B | B | . | . | . | −0.56 | 0.64 | . | . | . | −0.60 | 0.33 |
| Thr | 578 | . | . | B | B | . | . | . | −0.31 | 0.87 | . | . | * | −0.60 | 0.47 |
| Asn | 579 | . | . | B | B | . | . | . | −0.36 | 0.59 | * | * | . | −0.60 | 0.47 |
| Val | 580 | . | . | B | . | . | T | . | −0.32 | 0.61 | * | . | . | −0.20 | 0.62 |
| Met | 581 | . | . | B | . | . | T | . | −0.91 | 0.61 | * | . | . | −0.20 | 0.32 |
| Asn | 582 | . | . | B | . | . | T | . | −0.36 | 0.63 | * | . | . | −0.20 | 0.20 |
| Gly | 583 | . | . | B | . | . | T | . | −0.29 | 0.61 | * | . | . | −0.20 | 0.36 |
| Val | 584 | . | . | B | . | . | . | . | −0.96 | 0.73 | . | . | . | −0.40 | 0.57 |
| Ala | 585 | . | . | B | . | . | T | . | 0.01 | 0.69 | * | . | . | −0.20 | 0.19 |
| Ser | 586 | . | . | B | . | . | T | . | 0.40 | 0.29 | * | . | . | 0.10 | 0.38 |
| Tyr | 587 | . | . | B | . | . | T | . | −0.27 | 0.29 | * | * | . | 0.10 | 0.79 |
| Cys | 588 | . | . | B | . | . | T | . | −0.51 | 0.21 | * | . | . | 0.10 | 0.42 |
| Arg | 589 | . | . | B | . | . | T | . | −0.47 | 0.21 | . | . | . | 0.10 | 0.32 |
| Pro | 590 | . | . | B | . | . | T | . | 0.12 | 0.51 | . | . | . | −0.20 | 0.17 |
| Cys | 591 | . | . | B | . | . | T | . | −0.17 | −0.24 | . | . | . | 0.70 | 0.54 |
| Ala | 592 | . | . | B | . | . | T | . | −0.22 | −0.31 | * | . | . | 0.70 | 0.28 |
| Leu | 593 | . | . | B | . | . | . | . | 0.44 | 0.07 | * | . | . | −0.10 | 0.24 |
| Glu | 594 | . | . | B | . | . | . | . | −0.52 | −0.36 | * | . | . | 0.75 | 0.75 |
| Ala | 595 | . | . | B | . | . | . | . | −0.66 | −0.29 | . | . | F | 1.15 | 0.55 |
| Ser | 596 | . | . | B | . | . | . | . | −0.29 | −0.36 | . | . | F | 1.40 | 0.66 |
| Asp | 597 | . | . | . | . | T | T | . | 0.00 | −0.66 | . | . | F | 2.55 | 0.51 |
| Val | 598 | . | . | . | . | T | T | . | 0.14 | −0.27 | . | . | F | 2.50 | 0.68 |
| Gly | 599 | . | . | . | . | T | T | . | −0.17 | −0.20 | * | . | F | 2.25 | 0.27 |
| Ser | 600 | . | . | . | . | T | T | . | 0.12 | −0.10 | * | . | F | 2.00 | 0.23 |
| Ser | 601 | . | . | . | . | T | . | . | −0.24 | 0.29 | * | . | F | 0.95 | 0.42 |
| Cys | 602 | . | . | B | . | . | T | . | −0.46 | 0.21 | . | . | F | 0.50 | 0.23 |
| Thr | 603 | . | . | B | . | . | T | . | −0.19 | 0.21 | . | . | F | 0.25 | 0.26 |
| Ser | 604 | . | . | B | . | . | T | . | −0.19 | 0.33 | . | . | F | 0.25 | 0.20 |
| Cys | 605 | . | . | B | . | . | T | . | −0.13 | 0.37 | . | . | . | 0.10 | 0.37 |
| Pro | 606 | . | . | B | . | . | T | . | −0.08 | 0.56 | . | . | . | −0.20 | 0.40 |
| Ala | 607 | . | . | . | . | T | T | . | −0.30 | 0.83 | . | . | . | 0.20 | 0.47 |
| Gly | 608 | . | . | B | . | . | T | . | 0.01 | 1.13 | * | . | . | −0.20 | 0.61 |
| Tyr | 609 | . | . | B | . | . | T | . | 0.42 | 0.56 | * | . | . | −0.20 | 0.66 |
| Tyr | 610 | . | . | B | B | . | . | . | 1.09 | 0.13 | * | . | . | 0.19 | 1.28 |
| Ile | 611 | . | . | B | B | . | . | . | 1.00 | −0.37 | * | . | . | 1.13 | 2.16 |
| Asp | 612 | . | . | B | B | . | . | . | 1.24 | −0.41 | * | . | . | 1.47 | 1.84 |
| Arg | 613 | . | . | . | . | T | . | . | 1.28 | −0.74 | * | . | F | 2.86 | 1.16 |
| Asp | 614 | . | . | . | . | T | T | . | 0.86 | −1.01 | * | . | F | 3.40 | 2.40 |
| Ser | 615 | . | . | . | . | T | T | . | 1.07 | −1.13 | * | . | F | 2.91 | 0.77 |
| Gly | 616 | . | . | . | . | T | T | . | 1.66 | −0.63 | * | . | F | 2.57 | 0.53 |

TABLE III-continued

| Res | Pos | I | II | III | IV | V | VI | VII | VIII | IX | X | XI | XII | XIII | XIV |
|---|---|---|---|---|---|---|---|---|---|---|---|---|---|---|---|
| Thr | 617 | . | . | . | . | T | T | . | 0.99 | −0.24 | . | . | F | 1.93 | 0.43 |
| Cys | 618 | . | . | . | . | T | T | . | 0.67 | 0.33 | . | . | . | 0.84 | 0.17 |
| His | 619 | . | . | . | . | T | T | . | 0.46 | 0.37 | . | . | . | 0.50 | 0.27 |
| Ser | 620 | . | . | . | . | T | T | . | 0.76 | 0.37 | . | . | . | 0.50 | 0.29 |
| Cys | 621 | . | . | B | . | . | T | . | 0.79 | 0.29 | . | . | . | 0.10 | 0.86 |
| Pro | 622 | . | . | . | . | . | T | C | 0.21 | 0.20 | . | . | F | 0.45 | 0.91 |
| Pro | 623 | . | . | . | . | T | T | . | 0.07 | 0.39 | * | . | F | 0.65 | 0.48 |
| Asn | 624 | . | . | . | . | T | T | . | 0.14 | 0.69 | * | . | F | 0.35 | 0.74 |
| Thr | 625 | . | . | B | . | . | T | . | −0.14 | 0.11 | * | * | F | 0.25 | 0.95 |
| Ile | 626 | . | A | B | . | . | . | . | 0.49 | 0.19 | * | . | . | −0.30 | 0.62 |
| Leu | 627 | . | A | B | . | . | . | . | 0.70 | 0.26 | * | . | . | −0.30 | 0.53 |
| Lys | 628 | . | A | B | . | . | . | . | 0.70 | 0.26 | * | . | . | −0.30 | 0.63 |
| Ala | 629 | . | A | B | . | . | . | . | 0.46 | 0.20 | * | . | . | −0.15 | 1.39 |
| His | 630 | . | A | B | . | . | . | . | 0.42 | 0.27 | * | . | . | −0.15 | 2.64 |
| Gln | 631 | . | . | B | . | . | T | . | 0.46 | 0.01 | * | . | F | 0.40 | 1.31 |
| Pro | 632 | . | . | . | . | T | T | . | 1.27 | 0.66 | . | * | . | 0.20 | 0.96 |
| Tyr | 633 | . | . | . | . | T | T | . | 0.63 | 0.56 | . | * | . | 0.35 | 1.22 |
| Gly | 634 | . | . | . | . | T | T | . | 0.56 | 0.56 | . | * | . | 0.20 | 0.71 |
| Val | 635 | . | . | B | B | . | . | . | −0.27 | 0.73 | . | . | . | −0.60 | 0.25 |
| Gln | 636 | . | . | B | B | . | . | . | −0.48 | 0.94 | . | * | . | −0.60 | 0.12 |
| Ala | 637 | . | . | B | B | . | . | . | −0.93 | 0.61 | . | * | . | −0.60 | 0.18 |
| Cys | 638 | . | . | B | B | . | . | . | −1.03 | 0.76 | . | * | . | −0.60 | 0.13 |
| Val | 639 | . | . | B | B | . | . | . | −0.90 | 0.54 | . | . | . | −0.60 | 0.08 |
| Pro | 640 | . | . | B | . | . | . | . | −0.39 | 0.57 | . | * | . | −0.40 | 0.12 |
| Cys | 641 | . | . | B | . | . | . | . | −0.70 | 0.50 | . | . | . | −0.40 | 0.21 |
| Gly | 642 | . | . | B | . | . | . | T | . | −0.07 | 0.41 | . | . | F | 0.29 | 0.42 |
| Pro | 643 | . | . | . | . | T | T | . | 0.60 | −0.23 | . | . | F | 1.93 | 0.54 |
| Gly | 644 | . | . | . | . | T | T | . | 1.46 | −0.26 | . | . | F | 2.42 | 1.61 |
| Thr | 645 | . | . | . | . | T | T | . | 1.71 | −0.43 | . | . | F | 2.76 | 2.62 |
| Lys | 646 | . | . | . | . | T | T | . | 1.49 | −0.86 | . | . | F | 3.40 | 3.39 |
| Asn | 647 | . | . | . | . | T | T | . | 1.80 | −0.60 | . | . | F | 3.06 | 2.40 |
| Asn | 648 | . | . | B | . | . | T | . | 1.71 | −0.53 | . | . | F | 2.32 | 2.26 |
| Lys | 649 | . | . | B | . | . | T | . | 1.24 | −0.63 | . | . | F | 1.98 | 1.52 |
| Ile | 650 | . | . | B | . | . | . | . | 0.89 | 0.06 | . | . | . | 0.24 | 0.78 |
| His | 651 | . | . | B | . | . | T | . | 0.60 | 0.23 | . | . | . | 0.10 | 0.26 |
| Ser | 652 | . | . | B | . | . | T | . | 0.60 | 0.59 | . | . | . | −0.20 | 0.20 |
| Leu | 653 | . | . | B | . | . | T | . | 0.60 | 0.99 | * | . | . | −0.20 | 0.47 |
| Cys | 654 | . | . | B | . | . | T | . | −0.11 | 0.30 | * | . | . | 0.10 | 0.57 |
| Tyr | 655 | . | . | . | . | T | . | . | 0.47 | 0.37 | . | . | . | 0.30 | 0.23 |
| Asn | 656 | . | . | . | . | T | T | . | −0.20 | 0.47 | . | . | . | 0.20 | 0.40 |
| Asp | 657 | . | . | . | . | T | T | . | −0.20 | 0.57 | * | . | . | 0.20 | 0.65 |
| Cys | 658 | . | . | B | . | . | T | . | 0.72 | 0.39 | * | . | . | 0.10 | 0.55 |
| Thr | 659 | . | . | B | . | . | T | . | 1.39 | −0.37 | . | . | . | 0.70 | 0.67 |
| Phe | 660 | . | . | B | . | . | . | . | 1.32 | −0.37 | . | . | . | 0.80 | 0.65 |
| Ser | 661 | . | . | . | . | T | T | . | 1.11 | 0.11 | . | . | F | 1.40 | 1.75 |
| Arg | 662 | . | . | . | . | T | T | . | 0.80 | −0.03 | . | . | F | 2.30 | 1.87 |
| Asn | 663 | . | . | . | . | . | T | C | 1.58 | −0.03 | . | . | F | 2.40 | 3.12 |
| Thr | 664 | . | . | . | . | . | T | C | 1.58 | −0.81 | . | . | F | 3.00 | 4.55 |
| Pro | 665 | . | . | . | . | . | T | C | 1.58 | −0.71 | * | . | F | 2.70 | 3.36 |
| Thr | 666 | . | . | . | . | T | T | . | 1.88 | 0.07 | * | . | F | 1.70 | 1.81 |
| Arg | 667 | . | . | B | . | . | T | . | 1.52 | 0.07 | * | . | F | 1.00 | 2.01 |
| Thr | 668 | . | . | B | . | . | T | . | 1.52 | 0.34 | * | * | F | 0.70 | 2.04 |
| Phe | 669 | . | . | B | . | . | . | . | 1.13 | 0.31 | * | * | . | 0.05 | 2.27 |
| Asn | 670 | . | . | B | . | . | T | . | 1.04 | 0.61 | * | * | . | −0.05 | 1.01 |
| Tyr | 671 | . | . | B | . | . | T | . | 0.77 | 1.00 | * | . | . | −0.20 | 0.93 |
| Asn | 672 | . | . | B | . | . | T | . | −0.16 | 1.01 | * | * | . | −0.05 | 1.09 |
| Phe | 673 | . | . | B | . | . | T | . | −0.43 | 0.91 | * | * | . | −0.20 | 0.56 |
| Ser | 674 | . | A | . | . | . | . | C | 0.27 | 1.01 | * | * | . | −0.40 | 0.36 |
| Ala | 675 | . | A | . | . | . | . | C | −0.04 | 0.66 | * | * | . | −0.40 | 0.36 |
| Leu | 676 | . | A | B | . | . | . | . | −0.66 | 0.74 | * | . | . | −0.60 | 0.60 |
| Ala | 677 | . | A | B | . | . | . | . | −0.97 | 0.60 | * | * | . | −0.60 | 0.33 |
| Asn | 678 | . | A | B | . | . | . | . | −1.08 | 0.70 | * | . | . | −0.60 | 0.47 |
| Thr | 679 | . | . | B | B | . | . | . | −1.37 | 0.89 | * | . | . | −0.60 | 0.47 |
| Val | 680 | . | . | B | B | . | . | . | −1.12 | 0.70 | . | . | . | −0.60 | 0.47 |
| Thr | 681 | . | . | B | B | . | . | . | −0.66 | 0.63 | . | . | . | −0.60 | 0.29 |
| Leu | 682 | . | . | B | B | . | . | . | −0.28 | 0.66 | . | . | . | −0.60 | 0.20 |
| Ala | 683 | . | . | B | B | . | . | . | −0.58 | 0.60 | . | . | . | −0.60 | 0.42 |
| Gly | 684 | . | . | . | B | . | . | C | −0.97 | 0.34 | . | . | F | 0.05 | 0.39 |
| Gly | 685 | . | . | . | . | . | T | C | −0.42 | 0.64 | . | . | F | 0.15 | 0.41 |
| Pro | 686 | . | . | . | . | . | T | C | −0.41 | 0.44 | . | * | F | 0.15 | 0.58 |
| Ser | 687 | . | . | . | . | . | T | C | 0.44 | 0.33 | . | * | F | 0.73 | 0.79 |
| Phe | 688 | . | . | B | . | . | T | . | 0.69 | −0.10 | . | . | F | 1.56 | 1.59 |
| Thr | 689 | . | . | B | . | . | T | . | 0.22 | −0.10 | * | . | F | 1.64 | 1.02 |
| Ser | 690 | . | . | B | . | . | T | . | 0.61 | 0.16 | * | . | F | 1.37 | 0.63 |
| Lys | 691 | . | . | . | . | T | T | . | 0.58 | −0.23 | * | . | F | 2.80 | 1.45 |
| Gly | 692 | . | . | . | . | T | T | . | 0.18 | −0.26 | * | . | F | 2.52 | 1.57 |
| Leu | 693 | . | . | . | . | . | T | C | 0.84 | 0.04 | * | . | F | 1.44 | 1.02 |

TABLE III-continued

| Res | Pos | I | II | III | IV | V | VI | VII | VIII | IX | X | XI | XII | XIII | XIV |
|---|---|---|---|---|---|---|---|---|---|---|---|---|---|---|---|
| Lys | 694 | . | A | B | . | . | . | . | 1.12 | 0.16 | * | . | . | 0.26 | 0.69 |
| Tyr | 695 | . | A | B | . | . | . | . | 0.72 | 0.66 | * | . | . | -0.32 | 0.95 |
| Phe | 696 | . | A | B | . | . | . | . | 0.37 | 1.01 | * | * | . | -0.60 | 1.00 |
| His | 697 | . | A | B | . | . | . | . | -0.10 | 0.81 | * | * | . | -0.60 | 0.72 |
| His | 698 | . | A | B | . | . | . | . | 0.41 | 1.50 | * | * | . | -0.60 | 0.38 |
| Phe | 699 | . | A | B | . | . | . | . | -0.44 | 1.13 | * | * | . | -0.60 | 0.59 |
| Thr | 700 | . | A | B | . | . | . | . | -0.87 | 1.03 | . | * | . | -0.60 | 0.36 |
| Leu | 701 | . | A | . | . | T | . | . | -0.51 | 1.10 | . | * | . | -0.20 | 0.14 |
| Ser | 702 | . | . | . | B | T | . | . | -0.48 | 1.03 | . | * | . | -0.20 | 0.16 |
| Leu | 703 | . | . | . | B | T | . | . | -0.44 | 0.64 | . | * | . | 0.14 | 0.18 |
| Cys | 704 | . | . | . | B | T | . | . | -0.09 | 0.56 | . | * | . | 0.48 | 0.37 |
| Gly | 705 | . | . | . | B | T | . | . | 0.33 | 0.30 | * | . | F | 1.27 | 0.28 |
| Asn | 706 | . | . | . | . | T | T | . | 1.19 | -0.09 | * | . | F | 2.61 | 0.66 |
| Gln | 707 | . | . | . | . | T | T | . | 0.89 | -0.77 | * | . | F | 3.40 | 2.45 |
| Gly | 708 | . | . | . | . | T | T | . | 1.40 | -0.73 | * | . | F | 3.06 | 2.45 |
| Arg | 709 | . | . | . | . | T | T | . | 1.21 | -0.77 | * | . | F | 2.72 | 2.04 |
| Lys | 710 | . | . | B | B | . | . | . | 0.89 | -0.53 | * | . | F | 1.43 | 0.87 |
| Met | 711 | . | . | B | B | . | . | . | 0.58 | -0.36 | * | . | . | 0.64 | 0.47 |
| Ser | 712 | . | . | B | B | . | . | . | 0.58 | -0.30 | * | . | . | 0.30 | 0.35 |
| Val | 713 | . | . | B | B | . | . | . | 0.92 | -0.30 | * | . | . | 0.30 | 0.29 |
| Cys | 714 | . | . | B | . | . | T | . | -0.04 | 0.10 | * | . | . | 0.10 | 0.47 |
| Thr | 715 | . | . | B | . | . | T | . | -0.40 | 0.13 | * | * | . | 0.10 | 0.26 |
| Asp | 716 | . | . | B | . | . | T | . | 0.20 | 0.23 | * | . | F | 0.25 | 0.51 |
| Asn | 717 | . | . | B | . | . | T | . | -0.31 | -0.41 | * | * | F | 1.00 | 1.59 |
| Val | 718 | . | . | B | B | . | . | . | 0.66 | -0.30 | . | * | F | 0.45 | 0.91 |
| Thr | 719 | . | . | B | B | . | . | . | 0.43 | -0.79 | . | * | F | 0.90 | 1.07 |
| Asp | 720 | . | . | B | B | . | . | . | 0.53 | -0.10 | . | * | F | 0.45 | 0.46 |
| Leu | 721 | . | . | B | B | . | . | . | 0.53 | -0.07 | . | * | F | 0.76 | 0.97 |
| Arg | 722 | . | . | B | B | . | . | . | 0.19 | -0.71 | . | * | F | 1.52 | 1.16 |
| Ile | 723 | . | . | B | . | . | T | . | 1.04 | -0.77 | . | * | F | 2.08 | 0.69 |
| Pro | 724 | . | . | B | . | . | T | . | 1.06 | -0.77 | . | * | F | 2.54 | 1.44 |
| Glu | 725 | . | . | . | . | T | T | . | 0.71 | -1.07 | . | * | F | 3.10 | 0.99 |
| Gly | 726 | . | . | . | . | . | T | C | 0.82 | -0.64 | . | * | F | 2.74 | 1.40 |
| Glu | 727 | . | . | . | . | T | T | . | 0.41 | -0.54 | * | . | F | 2.48 | 0.78 |
| Ser | 728 | . | . | . | . | . | T | C | 1.34 | -0.59 | * | . | F | 2.10 | 0.60 |
| Gly | 729 | . | . | . | . | T | T | . | 1.26 | -0.59 | * | . | F | 2.27 | 1.22 |
| Phe | 730 | . | . | . | . | T | T | . | 0.37 | -0.63 | * | . | F | 1.94 | 0.95 |
| Ser | 731 | . | . | . | . | . | T | C | 0.40 | 0.06 | * | . | F | 0.97 | 0.49 |
| Lys | 732 | . | . | . | . | T | T | . | -0.19 | 0.16 | * | . | F | 1.30 | 0.72 |
| Ser | 733 | . | . | . | . | T | T | . | -0.13 | 0.23 | * | . | F | 1.17 | 0.84 |
| Ile | 734 | . | . | B | . | . | T | . | -0.64 | 0.20 | * | . | . | 0.49 | 0.98 |
| Thr | 735 | . | . | B | B | . | . | . | -0.61 | 0.46 | * | . | . | -0.34 | 0.37 |
| Ala | 736 | . | . | B | B | . | . | . | -0.31 | 1.03 | * | . | . | -0.47 | 0.15 |
| Tyr | 737 | . | . | B | B | . | . | . | -0.94 | 1.04 | * | . | . | -0.60 | 0.36 |
| Val | 738 | . | . | B | B | . | . | . | -1.50 | 0.86 | . | . | . | -0.60 | 0.25 |
| Cys | 739 | . | . | B | B | . | . | . | -1.50 | 1.01 | . | . | . | -0.60 | 0.19 |
| Gln | 740 | . | . | B | B | . | . | . | -2.08 | 1.20 | . | . | . | -0.60 | 0.08 |
| Ala | 741 | . | . | B | B | . | . | . | -1.70 | 1.13 | . | . | . | -0.60 | 0.08 |
| Val | 742 | . | . | B | B | . | . | . | -1.67 | 0.91 | . | . | . | -0.60 | 0.23 |
| Ile | 743 | . | . | B | B | . | . | . | -0.81 | 0.77 | . | . | . | -0.60 | 0.20 |
| Ile | 744 | . | . | B | B | . | . | . | -1.00 | 0.37 | . | . | . | -0.30 | 0.35 |
| Pro | 745 | . | . | B | . | . | T | . | -1.31 | 0.51 | . | * | . | -0.20 | 0.35 |
| Pro | 746 | . | . | B | . | . | T | . | -1.07 | 0.36 | . | * | F | 0.42 | 0.71 |
| Glu | 747 | . | . | B | . | . | T | . | -0.46 | 0.10 | . | . | F | 0.74 | 1.01 |
| Val | 748 | . | . | B | . | . | T | . | 0.48 | 0.17 | . | . | F | 0.91 | 1.02 |
| Thr | 749 | . | . | B | . | . | T | . | 0.78 | -0.26 | . | * | F | 1.68 | 1.32 |
| Gly | 750 | . | . | B | . | . | T | . | 0.64 | -0.19 | . | . | F | 1.70 | 0.77 |
| Tyr | 751 | . | . | B | . | . | T | . | 0.00 | 0.24 | . | . | F | 1.08 | 1.03 |
| Lys | 752 | . | . | B | . | . | T | . | -0.30 | 0.24 | . | . | F | 0.76 | 0.53 |
| Ala | 753 | . | . | B | . | . | . | . | 0.26 | 0.14 | . | * | F | 0.39 | 0.71 |
| Gly | 754 | . | . | B | . | . | . | . | 0.57 | 0.10 | . | * | F | 0.22 | 0.61 |
| Val | 755 | . | . | B | . | . | . | . | 0.70 | -0.26 | . | * | F | 0.65 | 0.53 |
| Ser | 756 | . | . | B | . | . | . | . | 0.09 | 0.17 | . | * | F | 0.05 | 0.81 |
| Ser | 757 | . | . | B | . | . | . | . | -0.26 | 0.31 | . | * | F | 0.05 | 0.61 |
| Gln | 758 | . | . | B | . | . | . | . | -0.48 | 0.27 | . | . | F | 0.20 | 1.10 |
| Pro | 759 | . | . | B | . | . | . | . | -0.72 | 0.31 | . | . | F | 0.05 | 0.67 |
| Val | 760 | . | A | B | . | . | . | . | 0.13 | 0.43 | * | * | F | -0.45 | 0.51 |
| Ser | 761 | . | A | B | . | . | . | . | 0.54 | 0.04 | * | * | . | -0.30 | 0.49 |
| Leu | 762 | . | A | B | . | . | . | . | 0.03 | -0.36 | * | . | . | 0.30 | 0.62 |
| Ala | 763 | . | A | B | . | . | . | . | -0.86 | -0.10 | * | . | . | 0.30 | 0.69 |
| Asp | 764 | . | A | B | B | . | . | . | -0.99 | -0.66 | * | * | . | 0.30 | 0.36 |
| Arg | 765 | . | A | B | B | . | . | . | -0.99 | -0.01 | * | * | . | 0.30 | 0.43 |
| Leu | 766 | . | . | B | B | . | . | . | -1.00 | -0.06 | * | . | . | 0.30 | 0.32 |
| Ile | 767 | . | . | B | B | . | . | . | -0.50 | -0.07 | * | . | . | 0.30 | 0.28 |
| Gly | 768 | . | . | B | B | . | . | . | 0.09 | 0.41 | * | . | . | -0.60 | 0.20 |
| Val | 769 | . | . | B | B | . | . | . | -0.51 | 0.41 | * | . | . | -0.60 | 0.41 |
| Thr | 770 | . | . | B | B | . | . | . | -0.93 | 0.34 | * | * | F | -0.15 | 0.58 |

TABLE III-continued

| Res | Pos | I | II | III | IV | V | VI | VII | VIII | IX | X | XI | XII | XIII | XIV |
|---|---|---|---|---|---|---|---|---|---|---|---|---|---|---|---|
| Thr | 771 | . | . | B | B | . | . | . | -0.93 | 0.14 | . | * | F | -0.15 | 0.85 |
| Asp | 772 | . | . | B | B | . | . | . | -0.04 | 0.40 | . | * | F | -0.45 | 0.94 |
| Met | 773 | . | . | B | B | . | . | . | -0.04 | -0.24 | . | * | F | 0.60 | 1.09 |
| Thr | 774 | . | . | B | B | . | . | . | -0.08 | -0.30 | . | * | . | 0.30 | 0.75 |
| Leu | 775 | . | . | B | B | . | . | . | -0.08 | -0.10 | * | * | F | 0.45 | 0.31 |
| Asp | 776 | . | . | . | B | T | . | . | -0.07 | 0.39 | * | * | F | 0.25 | 0.46 |
| Gly | 777 | . | . | . | B | T | . | . | -0.28 | 0.16 | * | * | F | 0.34 | 0.42 |
| Ile | 778 | . | . | . | B | . | . | C | -0.27 | 0.10 | * | . | F | 0.23 | 0.79 |
| Thr | 779 | . | . | . | B | . | . | C | 0.04 | -0.09 | * | * | F | 0.92 | 0.48 |
| Ser | 780 | . | . | . | . | . | T | C | 0.04 | -0.09 | * | . | F | 1.41 | 0.84 |
| Pro | 781 | . | . | . | . | . | T | C | -0.66 | 0.17 | * | . | F | 0.90 | 0.99 |
| Ala | 782 | . | . | B | . | . | T | . | -0.34 | 0.27 | * | . | F | 0.61 | 0.59 |
| Glu | 783 | . | . | B | . | . | T | . | -0.27 | 0.29 | . | * | . | 0.37 | 0.60 |
| Leu | 784 | . | A | B | . | . | . | . | 0.04 | 0.59 | . | . | . | -0.42 | 0.32 |
| Phe | 785 | . | A | B | . | . | . | . | 0.04 | 0.16 | . | . | . | -0.21 | 0.55 |
| His | 786 | . | A | B | . | . | . | . | -0.56 | 0.04 | . | . | . | -0.30 | 0.43 |
| Leu | 787 | . | A | B | . | . | . | . | -0.31 | 0.73 | . | . | . | -0.60 | 0.43 |
| Glu | 788 | . | A | B | . | . | . | . | -1.20 | 0.47 | . | . | . | -0.60 | 0.49 |
| Ser | 789 | . | . | . | . | T | . | . | -0.60 | 0.37 | . | . | . | 0.30 | 0.25 |
| Leu | 790 | . | . | . | . | T | . | . | 0.10 | 0.30 | . | . | . | 0.30 | 0.47 |
| Gly | 791 | . | . | . | . | . | . | C | -0.72 | -0.39 | . | . | . | 0.70 | 0.45 |
| Ile | 792 | . | . | . | B | . | . | C | -0.80 | 0.26 | . | . | F | 0.05 | 0.25 |
| Pro | 793 | . | . | B | B | . | . | . | -1.50 | 0.56 | . | . | F | -0.45 | 0.21 |
| Asp | 794 | . | . | B | B | . | . | . | -1.90 | 0.66 | . | . | . | -0.60 | 0.19 |
| Val | 795 | . | . | B | B | . | . | . | -1.33 | 1.01 | * | * | . | -0.60 | 0.23 |
| Ile | 796 | . | . | B | B | . | . | . | -0.88 | 1.09 | * | . | . | -0.60 | 0.23 |
| Phe | 797 | . | . | B | B | . | . | . | -0.29 | 0.66 | * | * | . | -0.60 | 0.27 |
| Phe | 798 | . | . | B | B | . | . | . | -0.08 | 1.04 | . | * | . | -0.60 | 0.50 |
| Tyr | 799 | . | . | B | . | . | . | . | -0.08 | 0.80 | . | . | . | 0.09 | 1.14 |
| Arg | 800 | . | . | . | . | T | T | . | -0.08 | 0.11 | . | . | F | 1.48 | 2.19 |
| Ser | 801 | . | . | . | . | T | T | . | 0.50 | -0.03 | . | . | F | 2.42 | 1.88 |
| Asn | 802 | . | . | . | . | T | T | . | 1.20 | -0.33 | * | . | F | 2.76 | 1.73 |
| Asp | 803 | . | . | . | . | T | T | . | 1.60 | -0.69 | * | . | F | 3.40 | 1.53 |
| Val | 804 | . | . | . | . | T | . | . | 1.18 | -0.30 | . | . | F | 2.56 | 1.53 |
| Thr | 805 | . | . | . | B | . | . | . | 0.77 | -0.11 | . | . | F | 1.67 | 0.51 |
| Gln | 806 | . | . | . | B | . | . | . | 0.77 | -0.13 | * | . | F | 1.33 | 0.41 |
| Ser | 807 | . | . | . | B | . | . | . | 0.42 | 0.26 | * | * | F | 0.67 | 0.74 |
| Cys | 808 | . | . | . | B | . | T | . | 0.53 | 0.04 | * | * | F | 0.81 | 0.51 |
| Ser | 809 | . | . | . | . | T | T | . | 1.09 | -0.44 | * | * | F | 2.09 | 0.57 |
| Ser | 810 | . | . | . | . | T | T | . | 1.09 | -0.46 | . | * | F | 2.37 | 0.57 |
| Gly | 811 | . | . | . | . | T | T | . | 0.78 | -0.36 | . | . | F | 2.80 | 1.54 |
| Arg | 812 | . | . | . | B | T | . | . | 0.19 | -0.44 | . | . | F | 2.12 | 1.66 |
| Ser | 813 | . | . | . | B | T | . | . | 0.97 | -0.14 | * | * | F | 1.69 | 0.87 |
| Thr | 814 | . | . | B | B | . | . | . | 0.41 | -0.53 | * | * | F | 1.46 | 1.72 |
| Thr | 815 | . | . | B | B | . | . | . | 0.82 | -0.31 | . | * | F | 0.73 | 0.65 |
| Ile | 816 | . | . | B | B | . | . | . | 0.50 | -0.31 | . | * | F | 0.45 | 0.95 |
| Arg | 817 | . | . | B | B | . | . | . | 0.09 | -0.13 | . | * | . | 0.30 | 0.35 |
| Val | 818 | . | . | B | B | . | . | . | 0.18 | -0.23 | . | * | . | 0.64 | 0.33 |
| Arg | 819 | . | . | B | B | . | . | . | 0.49 | -0.29 | . | * | . | 0.98 | 0.73 |
| Cys | 820 | . | . | B | B | . | . | . | 0.84 | -0.57 | . | * | . | 1.62 | 0.64 |
| Ser | 821 | . | . | . | . | . | T | C | 1.42 | -0.57 | * | * | F | 2.86 | 1.73 |
| Pro | 822 | . | . | . | . | T | T | . | 0.46 | -0.73 | * | * | F | 3.40 | 1.27 |
| Gln | 823 | . | . | . | . | T | T | . | 1.10 | -0.09 | * | * | F | 2.76 | 1.76 |
| Lys | 824 | . | . | B | . | . | T | . | 0.64 | -0.23 | . | * | F | 2.02 | 2.03 |
| Thr | 825 | . | . | B | . | . | . | . | 1.01 | -0.19 | . | . | F | 1.48 | 1.30 |
| Val | 826 | . | . | B | . | . | T | . | 0.50 | -0.23 | . | . | F | 1.34 | 1.01 |
| Pro | 827 | . | . | B | . | . | T | . | -0.10 | 0.06 | . | . | F | 0.25 | 0.42 |
| Gly | 828 | . | . | B | . | . | T | . | -0.91 | 0.74 | . | . | F | -0.05 | 0.24 |
| Ser | 829 | . | . | B | . | . | T | . | -1.17 | 0.94 | . | . | F | -0.05 | 0.26 |
| Leu | 830 | . | . | B | . | . | . | . | -1.20 | 0.73 | . | * | F | -0.25 | 0.26 |
| Leu | 831 | . | . | B | . | . | . | . | -0.66 | 0.73 | . | * | F | -0.40 | 0.26 |
| Leu | 832 | . | . | B | . | . | T | . | -1.11 | 0.79 | . | . | F | -0.05 | 0.28 |
| Pro | 833 | . | . | B | . | . | T | . | -1.07 | 0.97 | . | . | F | -0.05 | 0.18 |
| Gly | 834 | . | . | . | . | T | T | . | -0.77 | 0.67 | . | . | . | 0.35 | 0.30 |
| Thr | 835 | . | . | B | . | . | T | . | -0.30 | -0.01 | . | . | F | 1.16 | 0.61 |
| Cys | 836 | . | . | . | . | T | T | . | 0.20 | -0.27 | . | . | F | 1.87 | 0.39 |
| Ser | 837 | . | . | . | . | T | T | . | 0.34 | -0.21 | . | . | F | 2.18 | 0.57 |
| Asp | 838 | . | . | . | . | T | T | . | 0.56 | -0.07 | . | . | F | 2.49 | 0.21 |
| Gly | 839 | . | . | . | . | T | T | . | 0.56 | -0.56 | . | . | F | 3.10 | 0.66 |
| Thr | 840 | . | . | . | . | T | . | . | 0.20 | -0.70 | * | . | F | 2.59 | 0.48 |
| Cys | 841 | . | . | . | . | T | T | . | 0.87 | -0.51 | * | . | F | 2.48 | 0.16 |
| Asp | 842 | . | . | . | . | T | T | . | 0.47 | -0.11 | . | . | F | 1.87 | 0.25 |
| Gly | 843 | . | . | . | . | T | T | . | 0.43 | 0.24 | . | * | F | 0.96 | 0.15 |
| Cys | 844 | . | . | . | . | T | T | . | 0.08 | 0.26 | . | . | . | 0.50 | 0.38 |
| Asn | 845 | . | A | B | . | . | . | . | -0.42 | 0.47 | . | . | . | -0.60 | 0.20 |
| Phe | 846 | . | A | B | . | . | . | . | -0.04 | 1.16 | . | * | . | -0.60 | 0.17 |
| His | 847 | . | A | B | . | . | . | . | -0.04 | 1.64 | . | * | . | -0.60 | 0.33 |

TABLE III-continued

| Res | Pos | I | II | III | IV | V | VI | VII | VIII | IX | X | XI | XII | XIII | XIV |
|---|---|---|---|---|---|---|---|---|---|---|---|---|---|---|---|
| Phe | 848 | . | A | B | . | . | . | . | 0.00 | 1.07 | * | * | . | -0.60 | 0.35 |
| Leu | 849 | . | A | . | . | T | . | . | 0.08 | 1.06 | . | * | . | -0.20 | 0.54 |
| Trp | 850 | . | A | . | . | T | . | . | -0.51 | 0.77 | . | * | . | -0.20 | 0.40 |
| Glu | 851 | . | A | . | . | T | . | . | -0.40 | 0.77 | . | * | . | -0.20 | 0.47 |
| Ser | 852 | . | A | . | . | T | . | . | -1.03 | 0.49 | . | . | . | -0.20 | 0.58 |
| Ala | 853 | . | A | . | . | T | . | . | -0.54 | 0.37 | . | . | . | 0.10 | 0.29 |
| Ala | 854 | . | A | . | . | T | . | . | -0.54 | -0.11 | . | . | . | 0.70 | 0.26 |
| Ala | 855 | . | A | . | . | T | . | . | -0.92 | 0.57 | . | . | . | -0.20 | 0.16 |
| Cys | 856 | . | . | . | . | . | T | C | -1.22 | 0.76 | . | . | . | 0.00 | 0.09 |
| Pro | 857 | . | . | B | . | . | T | . | -1.78 | 0.64 | . | . | . | -0.20 | 0.11 |
| Leu | 858 | . | . | B | . | . | T | . | -1.78 | 0.79 | * | . | . | -0.20 | 0.08 |
| Cys | 859 | . | . | B | . | . | T | . | -1.19 | 0.79 | * | . | . | -0.20 | 0.16 |
| Ser | 860 | . | . | B | B | . | . | . | -0.84 | 0.21 | . | . | . | -0.30 | 0.17 |
| Val | 861 | . | . | B | B | . | . | . | -0.21 | 0.54 | . | . | . | -0.60 | 0.32 |
| Ala | 862 | . | . | B | B | . | . | . | -0.59 | 0.36 | . | . | . | -0.30 | 0.82 |
| Asp | 863 | . | . | B | . | . | . | . | -0.67 | 0.29 | . | . | . | -0.10 | 0.62 |
| Tyr | 864 | . | . | B | B | . | . | . | -0.86 | 0.59 | . | . | . | -0.60 | 0.58 |
| His | 865 | . | . | B | B | . | . | . | -0.86 | 0.59 | . | . | . | -0.60 | 0.43 |
| Ala | 866 | . | . | B | B | . | . | . | -0.30 | 0.47 | . | . | . | -0.60 | 0.34 |
| Ile | 867 | . | . | B | B | . | . | . | -0.38 | 0.86 | . | . | . | -0.60 | 0.29 |
| Val | 868 | . | . | B | B | . | . | . | -1.23 | 0.67 | . | . | . | -0.60 | 0.12 |
| Ser | 869 | . | . | B | B | . | . | . | -1.58 | 0.81 | . | . | . | -0.60 | 0.09 |
| Ser | 870 | . | . | B | B | . | . | . | -1.89 | 0.81 | . | . | . | -0.60 | 0.12 |
| Cys | 871 | . | . | B | B | . | . | . | -2.19 | 0.56 | * | . | . | -0.60 | 0.16 |
| Val | 872 | . | . | B | B | . | . | . | -1.30 | 0.60 | * | . | . | -0.60 | 0.09 |
| Ala | 873 | . | . | B | B | . | . | . | -0.40 | 0.61 | * | . | . | -0.60 | 0.11 |
| Gly | 874 | . | . | B | B | . | . | . | -0.41 | 0.23 | * | . | . | -0.30 | 0.41 |
| Ile | 875 | . | . | B | B | . | . | . | -0.42 | 0.14 | * | . | . | -0.30 | 0.80 |
| Gln | 876 | . | . | B | B | . | . | . | 0.00 | -0.01 | . | . | F | 0.60 | 1.15 |
| Lys | 877 | . | . | B | B | . | . | . | 0.00 | 0.24 | * | . | F | 0.00 | 1.82 |
| Thr | 878 | . | . | B | B | . | . | . | 0.30 | 0.46 | * | * | F | -0.30 | 1.92 |
| Thr | 879 | . | . | B | B | . | . | . | 0.76 | 0.69 | * | . | F | -0.30 | 1.17 |
| Tyr | 880 | . | . | B | B | . | . | . | 1.64 | 0.29 | * | . | . | -0.15 | 1.14 |
| Val | 881 | . | A | B | B | . | . | . | 1.43 | 0.29 | * | . | . | -0.15 | 1.37 |
| Trp | 882 | . | A | B | B | . | . | . | 1.43 | 0.23 | * | * | . | -0.15 | 1.47 |
| Arg | 883 | . | A | B | B | . | . | . | 0.93 | -0.26 | * | . | F | 0.60 | 1.88 |
| Glu | 884 | . | A | B | B | . | . | . | 0.58 | -0.33 | * | . | F | 0.85 | 2.09 |
| Pro | 885 | . | A | . | . | T | . | . | 0.52 | -0.40 | * | . | F | 1.50 | 1.06 |
| Lys | 886 | . | A | . | . | T | . | . | 1.03 | -0.93 | * | . | F | 1.90 | 0.73 |
| Leu | 887 | . | A | . | . | T | . | . | 0.98 | -0.50 | * | . | F | 1.85 | 0.42 |
| Cys | 888 | . | . | . | . | T | T | . | -0.02 | -0.07 | * | . | F | 2.50 | 0.27 |
| Ser | 889 | . | . | . | . | T | T | . | -0.32 | 0.19 | . | * | F | 1.65 | 0.09 |
| Gly | 890 | . | . | . | . | T | T | . | -0.92 | 0.57 | * | * | F | 1.10 | 0.15 |
| Gly | 891 | . | . | . | . | T | T | . | -1.18 | 0.57 | * | . | F | 0.85 | 0.23 |
| Ile | 892 | . | . | . | . | . | . | C | -0.37 | 0.43 | * | . | F | 0.20 | 0.27 |
| Ser | 893 | . | . | . | . | . | . | C | 0.30 | 0.04 | . | . | F | 0.25 | 0.47 |
| Leu | 894 | . | . | B | . | . | . | . | 0.71 | 0.01 | . | * | F | 0.05 | 0.82 |
| Pro | 895 | . | . | B | . | . | . | . | 0.20 | -0.41 | . | * | F | 0.80 | 2.30 |
| Glu | 896 | . | . | B | B | . | . | . | 0.23 | -0.46 | . | * | F | 0.60 | 1.27 |
| Gln | 897 | . | . | B | B | . | . | . | 0.23 | -0.36 | . | * | F | 0.60 | 2.23 |
| Arg | 898 | . | . | B | B | . | . | . | -0.13 | -0.36 | . | * | F | 0.60 | 1.01 |
| Val | 899 | . | . | B | B | . | . | . | 0.72 | -0.21 | . | * | . | 0.30 | 0.31 |
| Thr | 900 | . | . | B | B | . | . | . | 0.62 | -0.21 | . | * | . | 0.30 | 0.36 |
| Ile | 901 | . | . | B | B | . | . | . | -0.27 | -0.13 | . | * | . | 0.30 | 0.27 |
| Cys | 902 | . | . | B | B | . | . | . | -0.27 | 0.56 | . | * | . | -0.60 | 0.25 |
| Lys | 903 | . | . | B | B | . | . | . | -1.08 | -0.09 | . | * | . | 0.30 | 0.29 |
| Thr | 904 | . | . | B | B | . | . | . | -0.51 | 0.21 | * | * | . | -0.30 | 0.36 |
| Ile | 905 | . | . | B | B | . | . | . | -1.01 | 0.44 | * | * | . | -0.60 | 0.71 |
| Asp | 906 | . | . | B | B | . | . | . | -0.08 | 0.56 | * | * | . | -0.60 | 0.29 |
| Phe | 907 | . | . | B | B | . | . | . | -0.27 | 0.56 | * | * | . | -0.60 | 0.40 |
| Trp | 908 | . | . | B | B | . | . | . | -0.66 | 0.71 | * | * | . | -0.60 | 0.43 |
| Leu | 909 | . | . | B | B | . | . | . | -1.23 | 0.46 | * | * | . | -0.60 | 0.25 |
| Lys | 910 | . | . | B | B | . | . | . | -0.64 | 1.14 | * | * | . | -0.60 | 0.20 |
| Val | 911 | . | . | . | B | T | . | . | -1.23 | 0.74 | * | * | . | -0.20 | 0.26 |
| Gly | 912 | . | . | . | B | T | . | . | -0.88 | 0.33 | * | * | . | 0.10 | 0.32 |
| Ile | 913 | . | . | . | B | T | . | . | -0.90 | 0.07 | * | * | . | 0.10 | 0.16 |
| Ser | 914 | . | . | . | . | . | T | C | -0.76 | 0.56 | * | * | . | 0.00 | 0.31 |
| Ala | 915 | . | . | . | . | T | T | . | -1.11 | 0.49 | . | * | F | 0.35 | 0.17 |
| Gly | 916 | . | . | . | . | T | T | . | -0.84 | 0.54 | * | . | F | 0.35 | 0.34 |
| Thr | 917 | . | . | B | . | . | T | . | -1.39 | 0.36 | * | . | F | 0.25 | 0.26 |
| Cys | 918 | . | . | B | B | . | . | . | -1.31 | 0.66 | . | . | . | -0.60 | 0.18 |
| Thr | 919 | . | . | B | B | . | . | . | -1.82 | 0.84 | . | . | . | -0.60 | 0.15 |
| Ala | 920 | . | . | B | B | . | . | . | -1.54 | 1.10 | . | . | . | -0.60 | 0.09 |
| Ile | 921 | . | . | B | B | . | . | . | -2.06 | 1.10 | . | . | . | -0.60 | 0.23 |
| Leu | 922 | . | . | B | B | . | . | . | -2.56 | 1.17 | . | . | . | -0.60 | 0.12 |
| Leu | 923 | . | . | B | B | . | . | . | -2.20 | 1.37 | . | . | . | -0.60 | 0.10 |
| Thr | 924 | . | . | B | B | . | . | . | -2.56 | 1.36 | . | . | . | -0.60 | 0.20 |

TABLE III-continued

| Res | Pos | I | II | III | IV | V | VI | VII | VIII | IX | X | XI | XII | XIII | XIV |
|---|---|---|---|---|---|---|---|---|---|---|---|---|---|---|---|
| Val | 925 | . | . | B | B | . | . | . | −2.21 | 1.24 | . | . | . | −0.60 | 0.13 |
| Leu | 926 | . | . | B | B | . | . | . | −2.02 | 1.31 | . | . | . | −0.60 | 0.25 |
| Thr | 927 | . | . | B | B | . | . | . | −1.50 | 1.41 | * | . | . | −0.60 | 0.15 |
| Cys | 928 | . | . | B | B | . | . | . | −0.64 | 1.84 | * | . | . | −0.60 | 0.21 |
| Tyr | 929 | . | . | B | B | . | . | . | −0.29 | 1.20 | . | . | . | −0.60 | 0.51 |
| Phe | 930 | . | . | . | B | T | . | . | 0.57 | 0.51 | . | . | . | −0.20 | 0.70 |
| Trp | 931 | . | . | . | B | T | . | . | 1.38 | 0.43 | * | . | . | 0.29 | 2.10 |
| Lys | 932 | . | . | . | . | . | T | C | 1.73 | 0.26 | * | . | F | 1.28 | 2.32 |
| Lys | 933 | . | . | . | . | T | T | . | 1.59 | −0.50 | * | * | F | 2.42 | 5.37 |
| Asn | 934 | . | . | . | . | . | T | C | 1.83 | −0.60 | * | * | F | 2.86 | 4.21 |
| Gln | 935 | . | . | . | . | T | T | . | 2.29 | −1.51 | * | * | F | 3.40 | 3.65 |
| Lys | 936 | . | . | B | . | . | . | . | 2.62 | −0.76 | * | * | F | 2.46 | 2.86 |
| Leu | 937 | . | . | B | . | . | . | . | 2.33 | −0.76 | * | * | F | 2.32 | 3.55 |
| Glu | 938 | . | . | B | . | . | . | . | 1.99 | −0.40 | * | * | . | 1.73 | 3.21 |
| Tyr | 939 | . | . | B | . | . | T | . | 2.03 | −0.41 | * | * | . | 1.79 | 2.15 |
| Lys | 940 | . | . | B | . | . | T | . | 1.22 | −0.41 | * | * | F | 1.80 | 5.22 |
| Tyr | 941 | . | . | B | . | . | T | . | 0.32 | −0.41 | * | * | F | 2.00 | 2.49 |
| Ser | 942 | . | . | B | . | . | T | . | 0.53 | 0.23 | * | * | F | 1.20 | 1.18 |
| Lys | 943 | . | A | B | . | . | . | . | 0.53 | 0.09 | * | * | F | 0.45 | 0.58 |
| Leu | 944 | . | A | B | . | . | . | . | 0.19 | 0.49 | * | . | . | −0.20 | 0.60 |
| Val | 945 | . | A | B | . | . | . | . | −0.17 | 0.23 | * | * | . | −0.10 | 0.45 |
| Met | 946 | . | A | B | . | . | . | . | −0.73 | 0.33 | * | * | . | −0.30 | 0.33 |
| Asn | 947 | . | A | B | . | . | . | . | −0.39 | 1.01 | . | * | . | −0.60 | 0.33 |
| Ala | 948 | . | A | B | . | . | . | . | −0.43 | 0.33 | * | * | . | −0.30 | 0.88 |
| Thr | 949 | . | A | B | . | . | . | . | −0.29 | −0.31 | . | * | . | 0.65 | 1.48 |
| Leu | 950 | . | A | B | . | . | . | . | 0.57 | −0.36 | * | . | F | 0.85 | 0.49 |
| Lys | 951 | . | A | B | . | . | . | . | 0.36 | −0.76 | * | . | F | 1.35 | 0.82 |
| Asp | 952 | . | . | . | . | T | T | . | 0.14 | −0.57 | . | * | F | 2.35 | 0.47 |
| Cys | 953 | . | . | B | . | . | T | . | 0.14 | −0.63 | . | . | . | 2.00 | 0.87 |
| Asp | 954 | . | . | B | . | . | T | . | −0.13 | −0.81 | . | . | . | 1.80 | 0.44 |
| Leu | 955 | . | . | B | . | . | T | . | 0.68 | −0.31 | . | . | . | 1.30 | 0.27 |
| Pro | 956 | . | . | B | . | . | . | . | 0.33 | −0.31 | . | . | . | 0.90 | 0.83 |
| Ala | 957 | . | . | . | . | T | . | . | −0.33 | −0.50 | . | * | . | 1.10 | 0.67 |
| Ala | 958 | A | . | . | . | . | . | . | −0.26 | 0.07 | . | . | . | −0.10 | 0.43 |
| Asp | 959 | A | . | . | . | . | T | . | −1.14 | −0.11 | . | . | . | 0.70 | 0.28 |
| Ser | 960 | . | . | B | . | . | T | . | −0.93 | 0.14 | . | . | . | 0.10 | 0.20 |
| Cys | 961 | . | . | B | . | . | T | . | −0.72 | 0.26 | . | . | . | 0.10 | 0.19 |
| Ala | 962 | . | . | B | . | . | T | . | −0.48 | −0.24 | . | . | . | 0.70 | 0.20 |
| Ile | 963 | . | A | B | . | . | . | . | 0.11 | 0.19 | . | . | . | −0.30 | 0.15 |
| Met | 964 | . | A | B | . | . | . | . | 0.11 | −0.20 | . | . | . | 0.30 | 0.48 |
| Glu | 965 | . | A | B | . | . | . | . | −0.44 | −0.77 | . | . | F | 0.75 | 0.79 |
| Gly | 966 | . | A | . | . | . | . | C | 0.22 | −0.63 | * | . | F | 0.95 | 0.83 |
| Glu | 967 | A | A | . | . | . | . | . | 0.81 | −1.31 | * | . | F | 0.90 | 1.46 |
| Asp | 968 | A | A | . | . | . | . | . | 1.70 | −1.93 | * | . | F | 0.90 | 1.41 |
| Val | 969 | A | A | . | . | . | . | . | 1.49 | −1.93 | * | . | F | 0.90 | 2.38 |
| Glu | 970 | A | A | . | . | . | . | . | 0.60 | −1.67 | * | . | F | 0.90 | 1.13 |
| Asp | 971 | A | A | . | . | . | . | . | 0.24 | −0.99 | * | . | F | 0.75 | 0.48 |
| Asp | 972 | A | A | . | . | . | . | . | −0.07 | −0.20 | . | * | F | 0.45 | 0.55 |
| Leu | 973 | A | A | . | . | . | . | . | −0.37 | −0.36 | * | . | . | 0.30 | 0.46 |
| Ile | 974 | A | A | . | . | . | . | . | 0.53 | 0.03 | * | * | . | −0.30 | 0.37 |
| Phe | 975 | . | A | B | . | . | . | . | 0.53 | 0.03 | . | . | . | −0.30 | 0.44 |
| Thr | 976 | . | A | B | . | . | . | . | 0.50 | 0.43 | . | . | F | −0.45 | 0.87 |
| Ser | 977 | . | . | . | . | . | T | C | 0.20 | 0.24 | . | . | F | 0.60 | 1.68 |
| Lys | 978 | . | . | . | . | T | T | . | 0.20 | −0.06 | . | . | F | 1.40 | 2.60 |
| Asn | 979 | . | . | . | . | . | T | C | 0.74 | −0.16 | * | . | F | 1.48 | 1.49 |
| His | 980 | . | . | . | . | . | T | C | 1.56 | −0.21 | * | * | F | 1.76 | 1.10 |
| Ser | 981 | . | . | . | . | . | . | C | 1.57 | −0.60 | . | * | . | 1.99 | 1.07 |
| Leu | 982 | . | . | . | . | T | . | . | 1.87 | −0.21 | . | . | . | 2.02 | 0.90 |
| Gly | 983 | . | . | . | . | T | T | . | 1.79 | −0.21 | . | . | F | 2.80 | 1.06 |
| Arg | 984 | . | . | . | . | T | T | . | 0.98 | −0.21 | * | . | F | 2.52 | 1.07 |
| Ser | 985 | . | . | . | . | T | T | . | 0.80 | 0.09 | * | . | F | 1.88 | 1.07 |
| Asn | 986 | . | . | . | . | T | T | . | 0.89 | −0.17 | * | * | F | 2.44 | 1.68 |
| His | 987 | . | . | . | . | . | . | C | 1.81 | −0.17 | * | * | F | 2.00 | 1.33 |
| Leu | 988 | . | . | . | . | . | . | C | 1.81 | −0.17 | * | * | F | 1.96 | 1.94 |
| Pro | 989 | . | . | . | . | . | T | C | 0.89 | −0.13 | * | * | F | 2.40 | 1.19 |
| Pro | 990 | . | . | . | . | T | T | . | 0.38 | 0.16 | . | * | F | 1.61 | 0.72 |
| Arg | 991 | . | . | . | . | T | T | . | −0.22 | 0.34 | * | * | F | 1.37 | 0.72 |
| Gly | 992 | . | . | B | . | . | T | . | −0.19 | 0.27 | * | * | F | 0.73 | 0.46 |
| Leu | 993 | . | A | B | . | . | . | . | −0.19 | −0.16 | * | * | . | 0.54 | 0.50 |
| Leu | 994 | . | A | B | . | . | . | . | −0.29 | 0.10 | * | . | . | −0.30 | 0.21 |
| Met | 995 | . | A | B | . | . | . | . | −0.08 | 0.59 | * | . | . | −0.60 | 0.31 |
| Asp | 996 | . | A | B | . | . | . | . | −0.86 | 0.56 | * | . | . | −0.60 | 0.64 |
| Leu | 997 | . | A | B | . | . | . | . | −0.40 | 0.44 | . | . | . | −0.60 | 0.42 |
| Thr | 998 | . | A | B | . | . | . | . | 0.02 | −0.24 | . | . | . | 0.30 | 0.83 |
| Gln | 999 | . | A | B | . | . | . | . | 0.44 | −0.43 | . | . | F | 0.45 | 0.63 |

TABLE III-continued

| Res | Pos | I | II | III | IV | V | VI | VII | VIII | IX | X | XI | XII | XIII | XIV |
|---|---|---|---|---|---|---|---|---|---|---|---|---|---|---|---|
| Cys | 1000 | . | A | B | . | . | . | . | 0.66 | 0.00 | . | . | . | −0.30 | 0.98 |
| Arg | 1001 | . | A | B | . | . | . | . | 0.27 | −0.26 | . | . | . | 0.30 | 0.87 |

TABLE IV

| Res | Pos | I | II | III | IV | V | VI | VII | VIII | IX | X | XI | XII | XIII | XIV |
|---|---|---|---|---|---|---|---|---|---|---|---|---|---|---|---|
| Met | 1 | . | A | . | . | . | . | C | 0.68 | −0.13 | . | * | . | 0.50 | 0.57 |
| Asp | 2 | . | A | . | . | T | . | . | 1.07 | −0.56 | . | * | . | 1.00 | 0.78 |
| Cys | 3 | . | A | . | . | T | . | . | 1.46 | −0.59 | . | . | . | 1.34 | 0.98 |
| Gln | 4 | . | A | . | . | T | . | . | 1.60 | −1.01 | . | * | . | 1.83 | 1.71 |
| Glu | 5 | . | A | . | . | T | . | . | 1.70 | −0.87 | . | * | F | 2.32 | 1.61 |
| Asn | 6 | . | . | . | . | T | T | . | 2.30 | 0.04 | . | * | F | 2.16 | 3.15 |
| Glu | 7 | . | . | . | . | T | T | . | 2.30 | −0.53 | . | . | F | 3.40 | 3.04 |
| Tyr | 8 | . | . | . | . | T | T | . | 2.68 | −0.53 | * | . | F | 3.06 | 3.04 |
| Trp | 9 | . | . | . | . | T | T | . | 2.33 | 0.39 | * | * | . | 1.67 | 1.99 |
| Asp | 10 | . | . | . | . | T | T | . | 2.44 | 0.41 | * | * | . | 1.03 | 1.14 |
| Gln | 11 | . | . | . | . | T | T | . | 1.78 | 0.41 | * | . | F | 0.84 | 1.42 |
| Trp | 12 | . | . | . | . | T | T | . | 0.92 | 0.23 | * | . | . | 0.50 | 0.72 |
| Gly | 13 | . | . | . | . | T | T | . | 0.86 | −0.04 | * | . | . | 1.10 | 0.32 |
| Arg | 14 | . | . | . | B | T | . | . | 0.48 | 0.44 | * | . | . | −0.20 | 0.27 |
| Cys | 15 | . | . | . | B | T | . | . | 0.48 | 0.61 | * | * | . | −0.20 | 0.14 |
| Val | 16 | . | . | . | B | T | . | . | 0.59 | 0.10 | * | * | . | 0.35 | 0.24 |
| Thr | 17 | . | . | . | B | T | . | . | 0.21 | −0.33 | * | . | . | 1.20 | 0.24 |
| Cys | 18 | . | . | . | . | T | T | . | 0.21 | 0.24 | . | * | . | 1.25 | 0.24 |
| Gln | 19 | . | . | . | . | T | T | . | −0.11 | 0.10 | . | * | . | 1.50 | 0.32 |
| Arg | 20 | . | . | . | . | T | T | . | 0.21 | −0.11 | . | . | F | 2.50 | 0.34 |
| Cys | 21 | . | . | . | . | T | T | . | 1.07 | −0.17 | . | . | F | 2.25 | 0.63 |
| Gly | 22 | . | . | . | . | . | T | C | 1.38 | −0.34 | . | . | F | 1.80 | 0.63 |
| Pro | 23 | . | . | . | . | . | T | T | 1.23 | −0.74 | . | . | F | 2.05 | 0.56 |
| Gly | 24 | . | . | . | . | . | T | T | 0.93 | −0.06 | . | . | F | 1.81 | 0.86 |
| Gln | 25 | . | . | . | . | . | T | T | 0.87 | −0.24 | . | * | F | 2.02 | 1.16 |
| Glu | 26 | . | . | . | . | . | T | . | 1.53 | −0.67 | * | . | F | 2.43 | 1.50 |
| Leu | 27 | . | . | . | . | . | T | . | 1.21 | −1.10 | * | . | F | 2.74 | 2.54 |
| Ser | 28 | . | . | . | . | . | T | T | 1.08 | −0.96 | * | . | F | 3.10 | 0.79 |
| Lys | 29 | . | . | . | . | . | T | T | 1.18 | −0.93 | * | . | F | 2.79 | 0.45 |
| Asp | 30 | . | . | . | . | . | T | T | 0.83 | −0.17 | * | . | F | 2.18 | 0.85 |
| Cys | 31 | . | . | . | . | . | T | T | 0.83 | −0.43 | . | * | F | 2.21 | 0.63 |
| Gly | 32 | . | . | . | . | . | T | . | 1.30 | −0.81 | . | . | . | 2.19 | 0.55 |
| Tyr | 33 | . | . | . | . | . | T | . | 1.26 | −0.39 | . | . | F | 2.07 | 0.32 |
| Gly | 34 | . | . | . | . | . | T | C | 1.21 | 0.04 | . | . | F | 1.81 | 0.60 |
| Glu | 35 | . | . | . | . | . | T | T | 0.62 | −0.53 | . | . | F | 3.40 | 1.01 |
| Gly | 36 | . | . | . | . | . | T | T | 1.04 | −0.46 | . | . | F | 2.61 | 0.65 |
| Gly | 37 | . | . | . | . | . | T | T | 1.10 | −0.46 | . | . | F | 2.42 | 1.03 |
| Asp | 38 | . | . | . | . | . | T | . | 1.31 | 0.03 | * | . | F | 1.13 | 0.62 |
| Ala | 39 | . | . | . | . | . | . | C | 1.36 | 0.53 | * | . | . | 0.14 | 0.86 |
| Tyr | 40 | . | . | . | . | . | T | . | 0.54 | 0.49 | * | . | . | 0.15 | 1.16 |
| Trp | 41 | . | . | B | . | . | . | . | 0.68 | 0.74 | * | . | . | −0.40 | 0.57 |
| His | 42 | . | . | . | . | . | . | C | 0.72 | 1.17 | * | * | . | −0.20 | 0.88 |
| Ser | 43 | . | . | . | . | . | . | C | 0.42 | 1.06 | . | . | . | −0.20 | 0.75 |
| Leu | 44 | . | . | . | . | . | T | C | 1.01 | 0.69 | . | . | F | 0.15 | 0.96 |
| Pro | 45 | . | . | . | . | . | T | T | 1.01 | 0.17 | * | * | F | 1.04 | 1.22 |
| Ser | 46 | . | . | . | . | . | T | T | 1.34 | 0.43 | * | . | F | 0.98 | 1.42 |
| Ser | 47 | . | . | . | . | . | T | T | 1.08 | 0.04 | . | . | F | 1.52 | 3.45 |
| Gln | 48 | . | . | . | . | . | T | . | 1.08 | −0.26 | . | * | F | 2.16 | 2.99 |
| Tyr | 49 | . | . | . | . | . | T | . | 1.60 | −0.30 | . | * | F | 2.40 | 2.99 |
| Lys | 50 | . | . | . | . | . | T | . | 1.47 | 0.23 | . | * | F | 1.56 | 2.35 |
| Ser | 51 | . | . | . | . | . | T | T | 1.73 | 0.27 | . | * | F | 1.52 | 1.34 |
| Ser | 52 | . | . | . | . | . | T | T | 2.00 | 0.37 | . | * | F | 1.28 | 1.17 |
| Trp | 53 | . | . | . | . | . | T | T | 2.04 | 0.11 | . | * | . | 0.74 | 0.79 |
| Gly | 54 | . | . | . | . | . | T | T | 1.62 | 0.11 | . | * | . | 0.87 | 1.18 |
| His | 55 | . | . | . | . | . | T | . | 1.58 | 0.30 | . | * | . | 0.74 | 0.47 |
| His | 56 | . | . | . | . | . | T | . | 1.58 | 0.31 | . | . | . | 0.96 | 0.78 |
| Lys | 57 | . | . | . | . | . | T | . | 1.21 | −0.21 | . | * | . | 1.93 | 1.06 |
| Cys | 58 | . | . | . | . | . | T | T | 0.61 | −0.07 | . | * | . | 2.20 | 0.42 |
| Gln | 59 | . | . | . | . | . | T | T | 0.64 | 0.11 | * | * | . | 1.38 | 0.21 |
| Ser | 60 | . | . | . | . | . | T | T | 0.01 | 0.10 | * | * | . | 1.16 | 0.15 |
| Cys | 61 | . | . | . | . | . | T | T | −0.54 | 0.67 | * | * | . | 0.64 | 0.15 |
| Ile | 62 | . | . | . | B | B | . | . | −1.44 | 0.60 | * | * | . | −0.38 | 0.09 |
| Thr | 63 | . | . | . | B | B | . | . | −1.67 | 0.84 | * | . | . | −0.60 | 0.05 |
| Cys | 64 | . | . | . | B | B | . | . | −1.67 | 1.14 | . | . | . | −0.60 | 0.07 |
| Ala | 65 | . | . | . | B | B | . | . | −1.26 | 0.97 | * | * | . | −0.60 | 0.15 |
| Val | 66 | . | . | . | B | B | . | . | −1.44 | 0.29 | * | * | . | −0.30 | 0.20 |
| Ile | 67 | . | . | . | B | B | . | . | −0.56 | 0.44 | * | * | . | −0.34 | 0.28 |

TABLE IV-continued

| Res | Pos | I | II | III | IV | V | VI | VII | VIII | IX | X | XI | XII | XIII | XIV |
|---|---|---|---|---|---|---|---|---|---|---|---|---|---|---|---|
| Asn | 68 | . | . | . | B | T | . | . | −0.20 | 0.27 | * | . | . | 0.62 | 0.48 |
| Arg | 69 | . | . | . | B | T | . | . | −0.39 | −0.23 | * | . | . | 1.63 | 1.30 |
| Val | 70 | . | . | . | B | T | . | . | 0.20 | −0.23 | * | . | F | 2.04 | 1.38 |
| Gln | 71 | . | . | . | B | T | . | . | 0.39 | −0.51 | * | . | F | 2.60 | 1.38 |
| Lys | 72 | . | . | . | B | T | . | . | 0.97 | −0.34 | * | . | F | 1.89 | 0.38 |
| Val | 73 | . | . | . | B | T | . | . | 0.76 | 0.14 | * | . | . | 0.88 | 0.73 |
| Asn | 74 | . | . | . | B | T | . | . | 0.33 | −0.07 | * | * | . | 1.22 | 0.65 |
| Cys | 75 | . | . | . | B | T | . | . | 0.89 | 0.01 | * | * | F | 0.51 | 0.47 |
| Thr | 76 | . | . | . | . | . | T | C | 0.89 | 0.40 | . | * | F | 0.45 | 0.85 |
| Pro | 77 | . | . | . | . | . | T | T | 0.26 | 0.16 | . | * | F | 0.65 | 0.85 |
| Thr | 78 | . | . | . | . | . | T | T | 0.26 | 0.26 | . | * | F | 0.80 | 1.61 |
| Ser | 79 | . | . | . | . | . | T | T | −0.41 | 0.33 | . | . | F | 0.65 | 0.83 |
| Asn | 80 | . | . | . | . | . | T | . | −0.09 | 0.41 | . | . | F | 0.15 | 0.29 |
| Ala | 81 | . | . | . | . | . | T | . | 0.22 | 0.41 | . | . | . | 0.00 | 0.20 |
| Val | 82 | . | . | . | . | . | T | . | −0.23 | −0.07 | . | . | . | 0.90 | 0.24 |
| Cys | 83 | . | . | . | . | . | T | T | −0.73 | 0.11 | . | . | . | 0.50 | 0.08 |
| Gly | 84 | . | . | . | . | . | T | T | −0.64 | 0.40 | * | * | . | 0.50 | 0.07 |
| Asp | 85 | . | . | . | . | . | T | T | −0.53 | 0.33 | * | * | . | 0.50 | 0.14 |
| Cys | 86 | . | . | B | . | . | . | T | −0.64 | −0.31 | * | * | . | 0.70 | 0.51 |
| Leu | 87 | . | . | B | . | . | . | . | −0.03 | −0.10 | * | * | . | 0.81 | 0.44 |
| Pro | 88 | . | . | . | . | . | T | T | 0.74 | 0.23 | * | * | . | 1.12 | 0.42 |
| Arg | 89 | . | . | . | . | . | T | T | 1.13 | 0.23 | * | * | . | 1.58 | 1.52 |
| Phe | 90 | . | . | . | . | . | T | T | 0.82 | −0.34 | * | * | . | 2.49 | 3.69 |
| Tyr | 91 | . | . | . | . | . | T | T | 1.60 | −0.54 | * | * | . | 3.10 | 3.44 |
| Arg | 92 | . | . | . | B | T | . | . | 1.52 | −0.97 | * | * | F | 2.54 | 3.44 |
| Lys | 93 | . | . | . | B | T | . | . | 1.39 | −0.29 | * | * | F | 1.93 | 2.79 |
| Thr | 94 | . | . | . | B | T | . | . | 0.93 | −0.64 | * | * | F | 1.92 | 1.76 |
| Arg | 95 | . | . | . | B | T | . | . | 0.82 | −0.97 | * | * | F | 1.46 | 0.89 |
| Ile | 96 | . | . | . | B | T | . | . | 1.07 | −0.29 | . | . | F | 0.85 | 0.37 |
| Gly | 97 | . | . | . | . | . | T | . | 0.96 | 0.11 | . | . | F | 0.45 | 0.44 |
| Gly | 98 | . | A | . | . | . | T | . | 0.91 | −0.37 | . | . | F | 0.85 | 0.38 |
| Leu | 99 | . | A | . | . | . | . | C | 1.22 | 0.03 | * | * | F | 0.05 | 0.93 |
| Gln | 100 | . | A | . | . | T | . | . | 0.44 | −0.66 | . | * | F | 1.30 | 1.62 |
| Asp | 101 | . | A | . | . | T | . | . | 0.44 | −0.51 | . | . | F | 1.15 | 0.88 |
| Gln | 102 | . | A | . | . | T | . | . | 0.58 | −0.26 | . | . | F | 0.85 | 0.75 |
| Glu | 103 | . | A | . | . | T | . | . | 0.26 | −0.51 | . | . | F | 1.15 | 0.67 |
| Cys | 104 | . | A | . | . | T | . | . | 0.76 | −0.34 | . | * | . | 0.70 | 0.21 |
| Ile | 105 | . | . | B | . | . | . | . | 0.80 | 0.14 | . | . | . | −0.10 | 0.18 |
| Pro | 106 | . | . | . | . | T | . | . | 0.80 | −0.26 | . | . | . | 0.90 | 0.21 |
| Cys | 107 | . | . | . | . | T | T | . | 0.49 | 0.14 | * | . | . | 0.50 | 0.67 |
| Thr | 108 | . | . | . | . | T | T | . | 0.28 | 0.06 | * | . | F | 1.10 | 1.37 |
| Lys | 109 | . | . | . | . | T | T | . | 0.63 | −0.20 | . | . | F | 2.00 | 1.37 |
| Gln | 110 | . | . | . | . | . | T | C | 1.22 | −0.14 | . | . | F | 2.10 | 3.69 |
| Thr | 111 | . | . | . | . | . | T | C | 1.43 | −0.33 | . | . | F | 2.40 | 3.43 |
| Pro | 112 | . | . | . | . | . | T | C | 1.24 | −0.81 | . | * | F | 3.00 | 2.97 |
| Thr | 113 | . | . | . | . | T | T | . | 1.56 | −0.17 | . | * | F | 2.60 | 1.27 |
| Ser | 114 | . | . | . | . | . | T | C | 0.84 | −0.17 | . | * | F | 2.10 | 1.53 |
| Glu | 115 | . | A | . | . | T | . | . | 0.26 | −0.09 | * | * | F | 1.45 | 0.53 |
| Val | 116 | . | A | B | . | . | . | . | −0.13 | −0.01 | * | * | . | 0.60 | 0.37 |
| Gln | 117 | . | A | B | . | . | . | . | 0.08 | 0.29 | * | * | . | −0.30 | 0.24 |
| Cys | 118 | . | A | B | . | . | . | . | −0.42 | 0.30 | * | * | . | −0.30 | 0.24 |
| Ala | 119 | A | A | . | . | . | . | . | −0.42 | 0.99 | * | * | . | −0.60 | 0.27 |
| Phe | 120 | A | A | . | . | . | . | . | −1.23 | 0.73 | . | * | . | −0.60 | 0.21 |
| Gln | 121 | A | A | . | . | . | . | . | −1.23 | 1.01 | . | * | . | −0.60 | 0.32 |
| Leu | 122 | . | A | . | . | . | . | C | −1.23 | 1.09 | . | * | . | −0.40 | 0.23 |
| Ser | 123 | . | A | . | . | . | . | C | −1.16 | 0.59 | . | * | . | −0.40 | 0.47 |
| Leu | 124 | . | A | . | . | . | . | C | −0.57 | 0.30 | . | * | . | −0.10 | 0.27 |
| Val | 125 | . | A | . | . | . | . | C | −0.46 | −0.10 | . | * | . | 0.50 | 0.55 |
| Glu | 126 | . | A | . | . | . | . | C | −0.67 | −0.29 | . | * | . | 0.50 | 0.41 |
| Ala | 127 | . | A | . | . | T | . | . | −0.17 | −0.24 | . | . | . | 0.70 | 0.78 |
| Asp | 128 | . | A | . | . | T | . | . | −0.72 | −0.44 | . | . | . | 0.85 | 1.51 |
| Ala | 129 | . | A | . | . | . | . | C | −0.12 | −0.44 | . | * | F | 0.65 | 0.65 |
| Pro | 130 | . | A | . | . | . | . | C | 0.52 | −0.01 | . | * | F | 0.85 | 0.99 |
| Thr | 131 | . | . | . | . | . | . | C | 0.52 | −0.09 | . | . | F | 1.25 | 0.92 |
| Val | 132 | . | . | . | . | . | . | C | 1.11 | 0.31 | . | . | F | 1.00 | 1.57 |
| Pro | 133 | . | . | . | . | . | . | C | 0.52 | −0.19 | . | . | F | 1.80 | 1.76 |
| Pro | 134 | . | . | . | . | . | . | C | 0.80 | −0.11 | . | . | F | 2.00 | 1.23 |
| Gln | 135 | . | . | . | . | . | . | C | 0.20 | −0.11 | . | . | F | 1.80 | 2.40 |
| Glu | 136 | A | . | B | . | . | . | . | −0.34 | −0.07 | . | . | F | 1.40 | 1.28 |
| Ala | 137 | . | . | B | B | . | . | . | −0.08 | 0.14 | . | . | F | 0.25 | 0.61 |
| Thr | 138 | . | . | B | B | . | . | . | −0.68 | 0.21 | . | . | . | −0.10 | 0.36 |
| Leu | 139 | . | . | B | B | . | . | . | −1.32 | 0.50 | . | . | . | −0.60 | 0.17 |
| Val | 140 | . | . | B | B | . | . | . | −1.62 | 1.14 | . | . | . | −0.60 | 0.13 |
| Ala | 141 | . | . | B | B | . | . | . | −1.92 | 1.03 | . | . | . | −0.60 | 0.12 |
| Leu | 142 | . | . | B | B | . | . | . | −2.14 | 0.93 | * | . | . | −0.60 | 0.19 |
| Val | 143 | . | . | B | B | . | . | . | −2.64 | 0.93 | * | . | . | −0.60 | 0.21 |
| Ser | 144 | . | . | B | B | . | . | . | −2.69 | 0.97 | . | . | . | −0.60 | 0.17 |

TABLE IV-continued

| Res | Pos | I | II | III | IV | V | VI | VII | VIII | IX | X | XI | XII | XIII | XIV |
|---|---|---|---|---|---|---|---|---|---|---|---|---|---|---|---|
| Ser | 145 | . | . | B | B | . | . | . | −2.69 | 1.11 | * | . | . | −0.60 | 0.15 |
| Leu | 146 | . | . | B | B | . | . | . | −2.80 | 1.07 | * | . | . | −0.60 | 0.15 |
| Leu | 147 | . | . | B | B | . | . | . | −2.30 | 1.21 | * | . | . | −0.60 | 0.10 |
| Val | 148 | . | . | B | B | . | . | . | −2.26 | 1.31 | . | . | . | −0.60 | 0.11 |
| Val | 149 | . | A | B | B | . | . | . | −2.54 | 1.61 | . | * | . | −0.60 | 0.11 |
| Phe | 150 | . | A | B | B | . | . | . | −2.94 | 1.43 | . | . | . | −0.60 | 0.13 |
| Thr | 151 | . | A | B | B | . | . | . | −2.94 | 1.53 | . | . | . | −0.60 | 0.15 |
| Leu | 152 | . | A | B | B | . | . | . | −2.48 | 1.57 | . | . | . | −0.60 | 0.17 |
| Ala | 153 | A | A | . | B | . | . | . | −2.43 | 1.36 | . | . | . | −0.60 | 0.19 |
| Phe | 154 | . | A | . | B | T | . | . | −2.28 | 1.26 | . | . | . | −0.20 | 0.11 |
| Leu | 155 | . | A | . | B | T | . | . | −2.28 | 1.56 | . | . | . | −0.20 | 0.12 |
| Gly | 156 | . | A | . | B | T | . | . | −2.78 | 1.66 | . | . | . | −0.20 | 0.10 |
| Leu | 157 | . | A | . | B | T | . | . | −2.21 | 1.84 | . | . | . | −0.20 | 0.10 |
| Phe | 158 | . | A | . | B | T | . | . | −2.29 | 1.81 | . | . | . | −0.20 | 0.18 |
| Phe | 159 | . | A | . | B | T | . | . | −1.54 | 1.70 | * | . | . | −0.20 | 0.10 |
| Leu | 160 | . | A | . | B | T | . | . | −0.73 | 1.27 | * | . | . | −0.20 | 0.24 |
| Tyr | 161 | . | A | . | B | T | . | . | −1.09 | 0.99 | * | . | . | −0.20 | 0.48 |
| Cys | 162 | . | A | . | B | T | . | . | −0.98 | 0.99 | * | . | . | −0.20 | 0.48 |
| Lys | 163 | . | A | . | B | T | . | . | −0.28 | 0.99 | * | . | . | −0.20 | 0.50 |
| Gln | 164 | . | A | . | B | T | . | . | 0.53 | 0.70 | * | . | . | −0.20 | 0.51 |
| Phe | 165 | . | A | . | B | T | . | . | 1.31 | −0.06 | * | . | . | 0.85 | 1.88 |
| Phe | 166 | . | A | . | B | T | . | . | 0.89 | −0.13 | * | . | . | 1.16 | 1.28 |
| Asn | 167 | . | . | . | . | T | T | . | 1.56 | 0.44 | * | * | . | 0.82 | 0.39 |
| Arg | 168 | . | . | . | . | T | T | . | 1.62 | 0.44 | * | * | . | 1.13 | 0.79 |
| His | 169 | . | . | . | . | T | T | . | 1.28 | −0.34 | * | * | . | 2.49 | 1.79 |
| Cys | 170 | . | . | . | . | T | T | . | 1.63 | −0.70 | * | * | . | 3.10 | 1.10 |
| Gln | 171 | . | . | . | . | T | T | . | 1.52 | −0.67 | * | . | F | 2.79 | 0.56 |
| Arg | 172 | . | . | . | . | T | T | . | 0.71 | 0.01 | * | * | F | 1.58 | 0.34 |
| Gly | 173 | . | . | . | . | T | T | . | 0.60 | 0.20 | * | * | F | 1.27 | 0.52 |
| Gly | 174 | . | . | . | . | T | T | . | −0.07 | 0.03 | * | * | F | 0.96 | 0.52 |
| Leu | 175 | . | A | . | . | . | . | C | 0.60 | 0.41 | * | * | . | −0.40 | 0.23 |
| Leu | 176 | . | A | . | . | . | . | C | 0.01 | 0.41 | . | * | . | −0.40 | 0.40 |
| Gln | 177 | . | A | B | . | . | . | . | −0.10 | 0.49 | . | * | . | −0.60 | 0.41 |
| Phe | 178 | . | A | B | . | . | . | . | 0.29 | 0.06 | . | * | . | −0.30 | 0.83 |
| Glu | 179 | A | A | . | . | . | . | . | 0.32 | −0.63 | . | * | . | 0.75 | 2.01 |
| Ala | 180 | A | A | . | . | . | . | . | 0.54 | −0.83 | * | * | F | 0.90 | 1.67 |
| Asp | 181 | A | A | . | . | . | . | . | 1.40 | −0.73 | * | * | F | 0.90 | 1.95 |
| Lys | 182 | A | A | . | . | . | . | . | 1.40 | −1.51 | . | * | F | 0.90 | 2.26 |
| Thr | 183 | A | A | . | . | . | . | . | 2.10 | −1.51 | * | * | F | 0.90 | 3.87 |
| Ala | 184 | A | A | . | . | . | . | . | 1.80 | −2.01 | * | * | F | 1.20 | 4.01 |
| Lys | 185 | A | A | . | . | . | . | . | 1.58 | −1.63 | * | . | F | 1.50 | 2.69 |
| Glu | 186 | A | A | . | . | . | . | . | 0.88 | −0.94 | * | . | F | 1.80 | 1.54 |
| Glu | 187 | . | A | . | . | T | . | . | 0.62 | −0.64 | . | . | F | 2.50 | 1.32 |
| Ser | 188 | . | . | . | . | T | . | . | 0.08 | −0.71 | . | * | F | 3.00 | 1.02 |
| Leu | 189 | . | . | . | . | T | . | . | 0.46 | −0.07 | . | * | . | 2.10 | 0.44 |
| Phe | 190 | . | . | . | . | . | . | C | 0.20 | 0.36 | . | . | . | 1.00 | 0.39 |
| Pro | 191 | . | . | . | . | . | . | C | −0.10 | 0.79 | . | . | . | 0.70 | 0.45 |
| Val | 192 | . | . | . | . | . | . | C | −0.06 | 0.79 | . | . | F | 0.85 | 0.73 |
| Pro | 193 | . | . | . | . | . | T | C | 0.24 | 0.10 | . | . | F | 1.50 | 1.69 |
| Pro | 194 | . | . | . | . | . | T | C | 0.74 | −0.69 | . | . | F | 2.70 | 1.89 |
| Ser | 195 | . | . | . | . | . | T | C | 1.14 | −0.63 | . | . | F | 3.00 | 3.67 |
| Lys | 196 | . | . | . | . | . | T | C | 0.77 | −0.89 | . | . | F | 2.70 | 3.18 |
| Glu | 197 | . | A | . | . | . | . | C | 1.62 | −0.81 | . | . | F | 2.00 | 2.08 |
| Thr | 198 | . | A | . | . | . | . | C | 1.53 | −1.24 | . | . | F | 1.70 | 2.69 |
| Ser | 199 | . | A | . | . | . | . | C | 1.74 | −1.24 | . | * | F | 1.40 | 1.80 |
| Ala | 200 | . | A | . | . | . | . | C | 1.19 | −0.84 | . | * | F | 1.10 | 1.80 |
| Glu | 201 | . | A | . | . | T | . | . | 0.84 | −0.20 | . | * | F | 0.85 | 0.93 |
| Ser | 202 | . | . | . | . | . | . | C | 0.56 | −0.30 | . | * | F | 0.85 | 0.93 |
| Gln | 203 | . | . | . | . | T | . | . | 0.28 | 0.23 | . | * | F | 0.45 | 0.96 |
| Val | 204 | . | . | . | . | . | . | C | 0.37 | 0.23 | . | * | . | 0.10 | 0.56 |
| Ser | 205 | . | . | . | . | T | . | . | 0.61 | 0.66 | . | * | . | 0.00 | 0.65 |
| Trp | 206 | . | . | . | . | . | . | C | 0.31 | 0.70 | . | * | . | −0.20 | 0.37 |
| Ala | 207 | . | . | . | . | . | T | C | −0.20 | 0.69 | . | . | . | 0.00 | 0.67 |
| Pro | 208 | . | . | . | . | . | T | C | −0.79 | 0.73 | * | . | F | 0.15 | 0.41 |
| Gly | 209 | . | . | . | . | T | T | . | 0.07 | 0.84 | * | . | F | 0.35 | 0.40 |
| Ser | 210 | . | . | . | . | . | T | C | −0.44 | 0.33 | * | . | . | 0.45 | 0.68 |
| Leu | 211 | . | . | . | . | . | . | C | −0.86 | 0.51 | * | . | . | −0.20 | 0.36 |
| Ala | 212 | . | . | . | . | . | . | C | −0.57 | 0.87 | * | . | . | −0.20 | 0.32 |
| Gln | 213 | . | . | B | . | . | . | . | −1.17 | 0.83 | . | . | . | −0.40 | 0.32 |
| Leu | 214 | . | . | B | . | . | . | . | −0.82 | 1.13 | . | . | . | −0.40 | 0.32 |
| Phe | 215 | . | . | B | . | . | . | . | −0.82 | 0.44 | . | . | . | −0.40 | 0.52 |
| Ser | 216 | . | . | B | . | . | . | . | −0.87 | 0.33 | . | . | . | −0.10 | 0.40 |
| Leu | 217 | . | . | . | . | T | . | . | −0.49 | 0.57 | . | . | . | 0.00 | 0.36 |
| Asp | 218 | . | . | . | . | T | . | . | −1.38 | 0.31 | . | . | F | 0.45 | 0.65 |
| Ser | 219 | . | . | . | . | . | . | C | −0.78 | 0.21 | . | . | F | 0.25 | 0.34 |
| Val | 220 | . | . | . | . | . | . | C | −0.08 | 0.26 | . | * | F | 0.25 | 0.64 |
| Pro | 221 | . | . | . | . | . | . | C | 0.22 | −0.03 | . | . | F | 0.85 | 0.66 |

TABLE IV-continued

| Res | Pos | I | II | III | IV | V | VI | VII | VIII | IX | X | XI | XII | XIII | XIV |
|---|---|---|---|---|---|---|---|---|---|---|---|---|---|---|---|
| Ile | 222 | . | . | . | . | . | . | C | 1.03 | 0.37 | . | . | F | 0.25 | 0.86 |
| Pro | 223 | . | . | . | . | . | . | C | 1.03 | 0.39 | . | . | F | 0.66 | 2.00 |
| Gln | 224 | . | . | . | . | T | . | . | 0.99 | 0.14 | . | * | F | 1.12 | 2.24 |
| Gln | 225 | . | . | . | . | . | . | C | 1.63 | 0.14 | . | * | F | 1.18 | 3.16 |
| Gln | 226 | . | . | . | . | . | . | C | 1.84 | −0.11 | . | . | F | 2.04 | 3.16 |
| Gln | 227 | . | . | . | . | . | . | C | 2.13 | −0.54 | . | . | F | 2.60 | 3.16 |
| Gly | 228 | . | . | . | . | . | T | C | 1.96 | −0.33 | . | . | F | 2.24 | 1.80 |
| Pro | 229 | . | . | . | . | . | T | C | 1.57 | −0.30 | . | . | . | 1.83 | 1.33 |
| Glu | 230 | . | . | . | . | T | T | . | 1.18 | −0.27 | . | . | . | 1.62 | 0.98 |
| Met | 231 | . | . | . | . | . | T | C | 0.79 | −0.24 | * | . | . | 1.31 | 1.27 |

In another aspect, the invention provides an isolated nucleic acid molecule comprising a polynucleotide which hybridizes under stringent hybridization conditions to a portion of the polynucleotide in a TR13 nucleic acid molecule of the invention described above, for instance, the cDNA clone (HWLHM70) contained in ATCC Deposit No. PTA-349, the nucleic acid sequence disclosed in FIGS. 1A–D or the complementary strand thereof, and fragments thereof (e.g., as described herein).

By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C.

In another aspect, the invention provides an isolated nucleic acid molecule comprising a polynucleotide which hybridizes under stringent hybridization conditions to molecule of the invention described above, for instance, the TR13 cDNA clone (HWLHN83) contained in ATCC Deposit No. PTA-507, the nucleic acid sequence disclosed in FIGS. 7A–E or the complementary strand thereto, and fragments thereof (e.g., as described herein).

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below. In this context "about" includes the particularly recited size, larger or smaller by several (5, 4, 3, 2, or 1) nucleotides, at either terminus or at both termini.

By a portion of a polynucleotide of "at least 20 nt in length," for example, is intended 20 or more contiguous nucleotides from the nucleotide sequence of the reference polynucleotide (e.g., cDNA deposited as ATCC Deposit No. PTA-507, or the nucleotide sequence as shown in SEQ ID NO:39 or the complementary strand thereto, or a fragment thereof).

By a portion of a polynucleotide of "at least 20 nt in length," for example, is intended 20 or more contiguous nucleotides from the nucleotide sequence of the reference polynucleotide (e.g., cDNA desposited as ATCC Deposit No: PTA-349, or the nucleotide sequence as shown in SEQ ID NO:1 or the complementary strand thereto, or a fragment thereof).

Of course, a polynucleotide which hybridizes only to a poly A sequence (such as the 3' terminal poly(A) tract of the TR13 cDNA shown in SEQ ID NO:1 or SEQ ID NO:39), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated using oligo dT as a primer).

In another aspect, the invention provides an isolated nucleic acid molecule comprising a polynucleotide which hybridizes under stringent hybridization conditions to a portion of the polynucleotide in a TR14 nucleic acid molecule of the invention described above, for instance, a cDNA clone (HMSHK47) contained in ATCC Deposit No. PTA-348, the nucleic acid sequence disclosed in preferably in FIGS. 10A–H or, alternatively, in FIGS. 4A–E or the complementary strand thereto, and fragments thereof (e.g., as described herein).

By a portion of a polynucleotide of "at least 20 nt in length," for example, is intended 20 or more contiguous nucleotides from the nucleotide sequence of the reference polynucleotide (e.g., cDNA deposited as ATCC Deposit No: PTA-348, or the nucleotide sequence as shown preferably in SEQ ID NO:60 or, alternatively, in SEQ ID NO:4 or the complementary strand thereto, or a fragment thereof).

Of course, a polynucleotide which hybridizes only to a poly A sequence (such as the 3' terminal poly(A) tract of the TR14 cDNA shown preferably in SEQ ID NO:60 or, alternatively, in SEQ ID NO:4), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated using oligo dT as a primer).

In specific embodiments, the polynucleotides of the invention are less than 100000 kb, 50000 kb, 10000 kb, 1000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, nucleic acids of the invention comprise at least 15, at least 30, at least 50, at least 100, or at least 250, at least 500, or at least 1000 contiguous nucleotides of TR13 coding sequence, but consist of less than or equal to 1000 kb, 500 kb, 250 kb, 200 kb, 150 kb, 100 kb, 75 kb, 50 kb, 30 kb, 25 kb, 20 kb, 15 kb, 10 kb, or 5 kb of genomic DNA that flanks the 5' or 3' coding nucleotide set forth in FIGS. 1A–D (SEQ ID NO:1) or in FIGS. 7A–E (SEQ ID NO:39). In further embodiments, nucleic acids of the invention comprise at least 15, at least 30, at least 50, at least 100, or at least 250, at least 500, or at least 1000 contiguous nucleotides of TR13 coding sequence, but do not comprise all or a portion of any TR13 intron. In another embodiment, the nucleic acid comprising TR13 coding sequence does not contain coding sequences of a genomic flanking gene (i.e., 5' or 3' to the TR13 gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

In further, nucleic acids of the invention comprise at least 15, at least 30, at least 50, at least 100, or at least 250, at least 500, or at least 1000 contiguous nucleotides of TR14 coding sequence, but consist of less than or equal to 1000 kb, 500 kb, 250 kb, 200 kb, 150 kb, 100 kb, 75 kb, 50 kb, 30 kb, 25 kb, 20 kb, 15 kb, 10 kb, or 5 kb of genomic DNA that flanks the 5' or 3' coding nucleotide set forth preferably in FIGS. 10A–H (SEQ ID NO:60) or, alternatively, in FIGS. 4A–E (SEQ ID NO:4). In further embodiments, nucleic acids of the invention comprise at least 15, at least 30, at least 50, at least 100, or at least 250, at least 500, or at least 1000 contiguous nucleotides of TR14 coding sequence, but do not comprise all or a portion of any TR14 intron. In another embodiment, the nucleic acid comprising TR14 coding sequence does not contain coding sequences of a genomic flanking gene (i.e., 5' or 3' to the TR14 gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As indicated, nucleic acid molecules of the present invention which encode a TR13 polypeptide may include, but are not limited to the coding sequence for the mature polypeptide, by itself; the coding sequence for the mature polypeptide and additional sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86: 821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al, *Cell* 37:767–778 (1984). As discussed below, other such fusion proteins include, but are not limited to, the TR13 receptor fused to Fc at the N- or C-terminus.

As indicated, nucleic acid molecules of the present invention which encode a TR14 polypeptide may include, but are not limited to the coding sequence for the mature polypeptide, by itself; the coding sequence for the mature polypeptide and additional sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86: 821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778 (1984). As discussed below, other such fusion proteins include, but are not limited to, the TR14 receptor fused to Fc at the N- or C-terminus.

The present invention further relates to variants of the nucleic acid molecules of the present invention, which encode portions, analogs, or derivatives of the TR13 receptor. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides. The variants may be altered in coding or non-coding regions or both. Alterations in the coding regions may produce conservative or non-conservative amino acid substitutions, deletions, or additions. Especially preferred among these are silent substitutions, additions, and deletions, which do not alter the properties and activities of the TR13 receptor or portions thereof. Also especially preferred in this regard are conservative substitutions.

The present invention further relates to variants of the nucleic acid molecules of the present invention, which encode portions, analogs, or derivatives of the TR14 receptor. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides. The variants may be altered in coding or non-coding regions or both. Alterations in the coding regions may produce conservative or non-conservative amino acid substitutions, deletions, or additions. Especially preferred among these are silent substitutions, additions, and deletions, which do not alter the properties and activities of the TR14 receptor or portions thereof. Also especially preferred in this regard are conservative substitutions.

Further embodiments of the invention include isolated nucleic acid molecules comprising or alternatively consisting of, a polynucleotide having a nucleotide sequence at least 90% identical, and more preferably at least 95%, 96%, 97%, 98%, or 99% identical to: (a) a nucleotide sequence encoding the polypeptide having the amino acid sequence in SEQ ID NO:2; (b) a nucleotide sequence encoding the polypeptide having the amino acid sequence in SEQ ID NO:2, but lacking the amino terminal methionine (amino acid positions 2–750 of SEQ ID NO:2); (c) a nucleotide sequence encoding the polypeptide having the amino acid sequence encoded by the cDNA clone contained in ATGC Deposit No. PTA-349 (HWLHM70); (d) a nucleotide sequence encoding the mature TR13 polypeptide having the amino acid sequence encoded by the cDNA clone contained in ATCC Deposit No. PTA-349 (HWLHM70); (e) a nucleotide sequence encoding any combination of one, two, three or all four of the TR13 cysteine rich domains disclosed in FIGS. 1A–D (amino acids 105 to 170, amino acids 251 to 265, amino acids 331 to 410, and/or amino acids 580 to 610 of SEQ ID NO:2); (f) a nucleotide sequence encoding the polypeptide having the amino acid sequence at positions from about 105 to about 170 of SEQ ID NO:2; (g) a nucleotide sequence encoding the polypeptide having the amino acid sequence at positions from about 251 to about 265 of SEQ ID NO:2; (h) a nucleotide sequence encoding the polypeptide having the amino acid sequence at positions from about 331 to about 410 of SEQ ID NO:2; (i) a nucleotide sequence encoding the polypeptide having the amino acid sequence at positions from about 580 to about 610 of SEQ ID NO:2; and (j) a nucleotide sequence complementary to any of the nucleotide sequences in (a), (b), (c), (d), (e), (f), (g), (h), or (i), above. In this context "about" includes the particularly recited size, larger or smaller by several (5, 4, 3, 2, or 1) nucleotides, at either terminus or at both termini.

Further embodiments of the invention include isolated nucleic acid molecules comprising or alternatively consisting of, a polynucleotide having a nucleotide sequence at least 90% identical, and more preferably at least 95%, 96%, 97%, 98%, or 99% identical to: (a) a nucleotide sequence encoding the polypeptide having the amino acid sequence in SEQ ID NO:40; (b) a nucleotide sequence encoding the polypeptide having the amino acid sequence in SEQ ID NO:40, but lacking the amino terminal methionine (amino acid positions 2–1001 of SEQ ID NO:40); (c) a nucleotide sequence encoding the polypeptide having the amino acid sequence encoded by the cDNA clone contained in ATGC Deposit No. PTA-507 (HWLHN83); (d) a nucleotide sequence encoding the mature TR13 polypeptide having the amino acid sequence encoded by the cDNA clone contained in ATCC Deposit No. PTA-507 (HWLHN83); (e) a nucleotide sequence encoding the TR13 receptor mature extracellular domain (amino acid positions from about 42 to about 906 of SEQ ID NO:40); (1) a nucleotide sequence encoding the TR13 receptor transmembrane domain (amino acid positions from about 907 to about 931 of SEQ ID NO:40); (g) a nucleotide sequence encoding the TR13 receptor intracellular domain (amino acid positions 932 to about 1001 of SEQ ID NO:40); (h) a nucleotide sequence encoding the TR13 receptor extracellular and intracellular domains with all or a part of the transmembrane domain deleted (amino acid positions from about 42 to about 906 and 932 to about 1001 of SEQ ID NO:40); (i) a nucleotide sequence encoding the polypeptide having the amino acid sequence at positions from about 271 to about 421 of SEQ ID NO:40; (j) a nucleotide sequence encoding the polypeptide having the amino acid sequence at positions from about 271 to about 286 of SEQ ID NO:40; (k) a nucleotide sequence encoding the polypeptide having the amino acid sequence at positions from about 290 to about 300 of SEQ ID NO:40; (l) a nucleotide sequence encoding the polypeptide having the amino acid sequence at positions from about 301 to about 320 of SEQ ID NO:40; (m) a nucleotide sequence encoding the polypeptide having the amino acid sequence at positions from about 329 to about 361 of SEQ ID NO:40; (n) a nucleotide sequence encoding the polypeptide having the amino acid sequence at positions from about 404 to about 421 of SEQ ID NO:40; (o) a nucleotide sequence encoding the polypeptide having the amino acid sequence at positions from about 585 to about 595 of SEQ ID NO:40; (p) a nucleotide sequence encoding any one of the TR13 conserved domains as shown in FIGS. 7A–E; (q) a nucleotide sequence encoding the polypeptide having the amino acid sequence at positions from about 661 to about 674 of SEQ ID NO:40; (r) a nucleotide sequence encoding the polypeptide having the amino acid sequence at positions from about 710 to about 744 of SEQ ID NO:40; (s) a nucleotide sequence encoding the polypeptide having the amino acid sequence at positions from about 980 to about 991 of SEQ ID NO:40; (t) a nucleotide sequence encoding the polypeptide having the amino acid sequence at positions from about 45 to about 60 of SEQ ID NO:40; (u) a nucleotide sequence encoding the polypeptide having the amino acid sequence at positions from about 121 to about 135 of SEQ ID NO:40; (v) a nucleotide sequence encoding the polypeptide having the amino acid sequence at positions from about 145 to about 160 of SEQ ID NO:40; and (w) a nucleotide sequence complementary to any of the nucleotide sequences in (a), (b), (c), (d), (e), (f), (g), (h), (i), (j), (k), (l), (m), (n), (o), (p), (q), (r), (s), (t), (u) or (v) above. In this context "about" includes the particulauly recited size, larger or smaller by several (5, 4, 3, 2, or 1) nucleotides, at either terminus or at both termini.

By a polynucleotide having a nucleotide sequence at least, for example, 95% "identical" to a reference nucleotide sequence encoding a TR13 polypeptide is intended that the nucleotide sequence of the polynucleotide is identical to the reference sequence except that the polynucleotide sequence may include up to five mismatches per each 100 nucleotides of the reference nucleotide sequence encoding the TR13 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mismatches of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire TR13 encoding nucleotide sequence shown in FIGS. 1A–D (SEQ ID NO:1) or FIGS. 7A–E (SEQ ID NO:39) or any TR13 polynucleotide fragment (e.g., a polynucleotide encoding the amino acid sequence of any of the TR13 N- and/or C-terminal deletions described herein), variant, derivative or analog, as described herein.

As a practical matter, whether any particular polynucleotide sequence is at least 90%, 95%, 96%, 97%, 98% or 99% identical to, for instance, the nucleotide sequence shown in SEQ ID NO:1 or SEQ ID NO:39 or to the nucleotide sequence of the deposited cDNA clone (HWLHM70 or HWLHN83) can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full-length of the reference nucleotide sequence and that gaps in homology of up to 5% of the total number of nucleotides in the reference sequence are allowed.

Further embodiments of the invention include isolated nucleic acid molecules comprising a polynucleotide having a nucleotide sequence at least 90% identical, and more preferably at least 95%, 96%, 97%, 98%, or 99% identical to: (a) a nucleotide sequence encoding the polypeptide having the amino acid sequence in SEQ ID NO:61; (b) a nucleotide sequence encoding the polypeptide having the amino acid sequence in SEQ ID NO:61, but lacking the amino terminal methionine (amino acid positions 2–231 of SEQ ID NO:61); (c) a nucleotide sequence encoding the polypeptide having the amino acid sequence encoded by the cDNA clone contained in ATCC Deposit No. HMSHK47; (d) a nucleotide sequence encoding the polypeptide having the amino acid sequence in SEQ ID NO:5; (e) a nucleotide sequence encoding the polypeptide having the amino acid sequence in SEQ ID NO:5, but lacking the amino terminal methionine (amino acid positions 2–226 of SEQ ID NO:5); (f) a nucleotide sequence encoding the TR14 receptor extracellular domain (preferably preferably amino acid positions from about 1 to about 138 of SEQ ID NO:61 or, alternatively, amino acid positions from about 1 to about 133 of SEQ ID NO:5); (g) a nucleotide sequence encoding the TR14 cysteine rich domain (preferably amino acid positions from about 70 to about 90 of SEQ ID NO:61 or, alternatively, amino acid positions from about 65 to about 85 of SEQ ID NO:5); (h) a nucleotide sequence encoding the TR14 receptor transmembrane domain (preferably, amino acid positions from about 139 to about 155 of SEQ ID NO:61 or, alternatively, amino acid positions from about 134 to about 150 of SEQ ID NO:5); (i) a nucleotide sequence encoding the TR14 receptor intracellular domain (preferably, amino acid positions from about 156 to about 231 of SEQ ID NO:61 or, alternatively, from about amino acid positions 151 to about 226 of SEQ ID NO:5); (j) a nucleotide sequence encoding the TR14 receptor extracellular and intracellular domains with all or part of the transmembrane domain deleted (preferably amino acid positions from about 1 to about 138 and 156 to about 231 of SEQ ID NO:61 or, alternatively, amino acid positions from about 1 to about 133 and 151 to about 226 of SEQ ID NO:5); and (k) a nucleotide sequence complementary to any of the nucleotide sequences in (a), (b), (c), (d), (e), (f), (g), (h), (i), (j) or (k) above. In this context "about" includes the particularly recited size, larger or smaller by several (5, 4, 3, 2, or 1) nucleotides, at either terminus or at both termini.

By a polynucleotide having a nucleotide sequence at least, for example, 95% "identical" to a reference nucleotide sequence encoding a TR14 polypeptide is intended that the nucleotide sequence of the polynucleotide is identical to the reference sequence except that the polynucleotide sequence may include up to five mismatches per each 100 nucleotides of the reference nucleotide sequence encoding the TR14 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mismatches of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire TR14 encoding nucleotide sequence shown preferably in FIGS. 10A–H (SEQ ID NO:60) or, alternatively, in FIGS. 4A–E (SEQ ID NO:4) or any TR14 polynucleotide fragment (e.g., a polynucleotide encoding the amino acid sequence of any of the TR14 N- and/or C-terminal deletions described herein), variant, derivative or analog, as described herein.

As a practical matter, whether any particular polynucleotide sequence is at least 90%, 95%, 96%, 97%, 98% or 99% identical to, for instance, the nucleotide sequence shown preferably in SEQ ID NO:60 or, alternatively, in SEQ ID NO:4 or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full-length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules comprising a polynucleotide sequence at least 90%, 95%, 96%, 97%, 98%, or 99% identical to the nucleic acid sequence for example, shown in SEQ ID NO:1 or SEQ ID NO:39, or to the nucleic acid sequence of the cDNA deposited as ATCC deposit No. PTA-349 or PTA-507, irrespective of whether they encode a polypeptide having TR13 receptor activity. This is because even where a particular nucleic acid molecule does not encode a polypeptide having TR13 functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TR13 receptor activity include, inter alia: (1) isolating the TR13 receptor gene or allelic variants thereof in a cDNA library; (2) in situ hybridization (e.g., "FISH") to metaphase chromosomal spreads to provide precise chromosomal location of the TR13 receptor gene, as described in Verna et al., *Human Chromosomes: A Manual of Basic Techniques,* Pergamon Press, New York (1988); and (3) Northern Blot analysis for detecting TR13 receptor mRNA expression in specific tissues.

Preferred, however, are nucleic acid molecules having sequences at least 90%, 95%, 96%, 97%, 98% or 99% identical to for example, the nucleic acid sequence shown in SEQ ID NO:1 or SEQ ID NO:39, or to the nucleic acid sequence of the cDNA deposited as PTA-349 or PTA-507, which do, in fact, encode a polypeptide having TR13 receptor functional activity. By "a polypeptide having TR13 functional receptor activity" is intended polypeptides exhibiting activity similar, but not necessarily identical, to an activity of the TR13 receptor of the invention (either the full-length protein or, preferably, the mature protein), as measured, for example, in a particular biological assay.

Of course, due to the degeneracy of the genetic code, one of ordinary skill in the art will immediately recognize that a large number of the nucleic acid molecules having a sequence at least 90%, 95%, 96%, 97%, 98%, or 99% identical to, for example, the nucleic acid sequence of the deposited cDNA or the nucleic acid sequence shown in SEQ ID NO: 1 or SEQ ID NO: 39 will encode a polypeptide "having TR13 receptor functional activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having TR13 receptor activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in J. U. Bowie et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

The present application is directed to nucleic acid molecules comprising a polynucleotide sequence at least 90%, 95%, 96%, 97%, 98%, or 99% identical to the nucleic acid sequence for example, shown preferably in SEQ ID NO:60 or, alternatively, in SEQ ID NO:4, or to the nucleic acid sequence of the cDNA deposited as ATCC Deposit No. PTA-348, and even more preferably to the polypeptide coding regions of these sequences, irrespective of whether they encode a polypeptide having TR14 receptor activity. This is because even where a particular nucleic acid molecule does not encode a polypeptide having TR14 functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TR14 receptor activity include, inter alia: (1) isolating the TR14 receptor gene or allelic variants thereof in a cDNA library; (2) in situ hybridization (e.g., "FISH") to metaphase chromosomal spreads to provide precise chromosomal location of the TR14 receptor gene, as described in Verma et al., *Human Chromosomes: A Manual of Basic Techniques,* Pergamon Press, New York (1988); and (3) Northern Blot analysis for detecting TR14 receptor mRNA expression in specific tissues.

Preferred, however, are nucleic acid molecules having sequences at least 90%, 95%, 96%, 97%, 98% or 99% identical to for example, the nucleic acid sequence shown preferably in SEQ ID NO: 60 or, alternatively, in SEQ ID NO: 4, or to the nucleic acid sequence of the deposited cDNA, and even more preferably to the polypeptide coding regions of these sequences, which do, in fact, encode a polypeptide having TR14 receptor functional activity. By "a polypeptide having TR14 functional receptor activity" is intended polypeptides exhibiting activity similar, but not necessarily identical, to an activity of the TR14 receptor of the invention (either the full-length protein or, preferably, the mature protein), as measured, for example, in a particular biological assay.

Of course, due to the degeneracy of the genetic code, one of ordinary skill in the art will immediately recognize that a large number of the nucleic acid molecules having a sequence at least 90%, 95%, 96%, 97%, 98%, or 99% identical to, for example, the nucleic acid sequence of the deposited cDNA or the nucleic acid sequence shown preferably in SEQ ID NO:60 or, alternatively, in SEQ ID NO:4 will encode a polypeptide "having TR14 receptor functional activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having TR14 receptor activity. This is because the skilled artisan is fully aware of amino acid substitutions that are either less likely or not likely to significantly effect protein function (e.g., replacing one aliphatic amino acid with a second aliphatic amino acid).

Polynucleotide Assays

This invention is also related to the use of TR13 polynucleotides to detect complementary polynucleotides such as, for example, as a diagnostic reagent. Detection of a mutated form of TR13 polynucleotide associated with a dysfunction will provide a diagnostic tool that can add or define a diagnosis of a disease or susceptibility to a disease which results from under-expression over-expression or altered expression of TR13 or a soluble form thereof, such as, for example, tumors or autoimmune disease.

Individuals carrying mutations in the TR13 gene may be detected at the nucleic acid level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. (Saiki et al., *Nature* 324:163–166 (1986)). RNA or cDNA may also be used in the same ways, or through routine modification of these polynucleotides. As an example, PCR primers complementary to the nucleic acid encoding TR13 can be used to identify and analyze TR13 expression and mutations. For example, deletions and insertions can be detected by a change in size of the amplified product in comparison to the normal genotype. Point mutations can be identified using techniques known in the art, for example, by hybridizing amplified DNA to radiolabeled TR13 RNA or alternatively, radiolabeled TR13 antisense DNA sequences. Perfectly matched sequences can be distinguished from mismatched duplexes by, for example, RNase A digestion or by differences in melting temperatures.

This invention is also related to the use of TR14 polynucleotides to detect complementary polynucleotides such as, for example, as a diagnostic reagent. Detection of a mutated form of TR14 polynucleotide associated with a dysfunction will provide a diagnostic tool that can add or define a diagnosis of a disease or susceptibility to a disease which results from under-expression over-expression or altered expression of TR14 or a soluble form thereof, such as, for example, tumors or autoimmune disease.

Individuals carrying mutations in the TR14 gene may be detected at the nucleic acid level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. (Saiki et al., *Nature* 324:163–166 (1986)). RNA or cDNA may also be used in the same ways, or through routine modification of these polynucleotides. As an example, PCR primers complementary to the nucleic acid encoding TR14 can be used to identify and analyze TR14 expression and mutations. For example, deletions and insertions can be detected by a change in size of the amplified product in comparison to the normal genotype. Point mutations can be identified by hybridizing amplified DNA to radiolabeled TR14 RNA or alternatively, radiolabeled TR14 antisense DNA sequences. Perfectly matched sequences can be distinguished from mismatched duplexes by, for example, RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations also may be revealed by nuclease protection assays, such as RNase and S1 protection or the chemical cleavage method (e.g., Cotton et al., *Proc. Natl Acad. Sci. USA* 85: 4397–4401 (1985)).

Thus, the detection of a specific DNA sequence may be achieved by methods such as, for example, hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Vectors and Host Cells

The present invention also relates to vectors which include the isolated DNA molecules of the present invention, host cells which are genetically engineered with the recombinant vectors and/or nucleic acids of the invention and the production of TR13 polypeptides or fragments thereof by recombinant techniques.

The present invention also relates to vectors which include the isolated DNA molecules of the present invention, host cells which are genetically engineered with the recombinant vectors and/or nucleic acids of the invention and the production of TR14 polypeptides or fragments thereof by recombinant techniques.

Host cells can be genetically engineered to incorporate nucleic acid molecules and express polypeptides of the present invention. The polynucleotides may be introduced alone or with other polynucleotides. Such other polynucleotides may be introduced independently, co-introduced or introduced joined to the polynucleotides of the invention.

In accordance with the present invention the vector may be, for example, a clone vector, a single or double-stranded phage vector, a single or double-stranded RNA or DNA viral vector. Such vectors may be introduced into cells as polynucleotides, preferably DNA, by well known techniques for introducing DNA and RNA into cells. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed.

Appropriate trans-acting factors either are supplied by the host, supplied by a complementing vector or supplied by the vector itself upon introduction into the host.

The polynucleotides may be joined to a vector containing a selectable marker for propagation in a host. Generally, a clone vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces and Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, and pSport available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

The present invention also relates to host cells containing the above-described vector constructs described herein, and additionally encompasses host cells containing nucleotide sequences of the invention that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., TR13 coding sequence), and/or to include genetic material (e.g., heterologous polynucleotide sequences) that is operably associated with TR13 polynucleotides of the invention, and which activates, alters, and/or amplifies endogenous TR13 polynucleotides. For example, techniques known in the art may be used to operably associate heterologous control regions (e.g., promoter and/or enhancer) and endogenous TR13 polynucleotide sequences via homologous recombination (see, e.g., U.S. Pat. No. 5,641,670, issued Jun. 24, 1997; International Publication Number WO 96/29411, published Sep. 26, 1996; International Publication Number WO 94/12650, published Aug. 4, 1994; Koller et al., *Proc. Natl. Acad. Sci. USA* 86:8932–8935 (1989); and Zijlstra et al., *Nature* 342:435–438 (1989), the disclosures of each of which are incorporated by reference in their entireties).

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., TR14 coding sequence), and/or to include genetic material (e.g., heterologous polynucleotide sequences) that is operably associated with TR14 polynucleotides of the invention, and which activates, alters, and/or amplifies endogenous TR14 polynucleotides. For example, techniques known in the art may be used to operably associate heterologous control regions (e.g., promoter and/or enhancer) and endogenous TR14 polynucleotide sequences via homologous recombination (see, e.g., U.S. Pat. No. 5,641,670, issued Jun. 24, 1997; International Publication Number WO 96/29411, published Sep. 26, 1996; International Publication Number WO 94/12650, published Aug. 4, 1994; Koller et al., *Proc. Natl. Acad. Sci. USA* 86:8932–8935 (1989); and Zijlstra et al., *Nature* 342:435–438 (1989), the disclosures of each of which are incorporated by reference in their entireties).

The TR13 polypeptides of the invention may be expressed in a modified form, such as a fusion protein (comprising the polypeptide joined via a peptide bond to a heterologous protein sequence (of a different protein)), and may include not only secretion signals but also additional heterologous functional regions. Alternatively, such a fusion protein can be made by protein synthetic techniques, e.g., by use of a peptide synthesizer. Thus, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. For example, in one embodiment, polynucleotides encoding TR13 polypeptides of the invention may be fused to the pe1B pectate lyase signal sequence to increase the efficiency to expression and purification of such polypeptides in Gram-negative bacteria. See, U.S. Pat. Nos. 5,576,195 and 5,846,818, the contents of which are herein incorporated by reference in their entireties.

The TR14 polypeptides of the invention may also be expressed in a modified form, such as a fusion protein (comprising the polypeptide joined via a peptide bond to a heterologous protein sequence (of a different protein)), and may include not only secretion signals but also additional heterologous functional regions. Alternatively, such a fusion protein can be made by protein synthetic techniques, e.g., by use of a peptide synthesizer. Thus, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. For example, in one embodiment, polynucleotides encoding TR14 polypeptides of the invention may be fused to the pe1B pectate lyase signal sequence to increase the efficiency to expression and purification of such polypeptides in Gram-negative bacteria. See, U.S. Pat. Nos. 5,576,195 and 5,846,818, the contents of which are herein incorporated by reference in their entireties.

A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses, it would be desirable to be able to delete the Fc part after the fusion protein has been expressed, detected and purified in the advantageous manner described. This is the case when the Fc portion proves to be a hindrance to use in therapy and diagnosis, for example, when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, D. Bennett et al., *Journal of Molecular Recognition* 8:52–58 (1995) and K. Johanson et al., *The Journal of Biological Chemistry* 270:16:9459–9471 (1995).

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or non-glycosylated. In addition, polypeptides of the invention may also include an initial modified methionine residue, in some cases as a result of host-mediated processes.

In addition, TR13 polypeptides of the invention can be chemically synthesized using techniques known in the art (e.g., see Creighton, Proteins: Structures and Molecular Principles, W. H. Freeman & Co., N.Y. (1983), and Hunkapiller, et al., *Nature* 310:105–111 (1984)). For example, a TR13 polypeptide fragment of the invention can be synthesized by use of a peptide synthesizer. Furthermore, if desired, nonclassical amino acids or chemical amino acid analogs can be introduced as a substitution or addition into the TR13 polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, omithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

In addition, TR14 polypeptides of the invention can be chemically synthesized using techniques known in the art (e.g., see Creighton, Proteins: Structures and Molecular Principles, W. H. Freeman & Co., N.Y. (1983), and Hunkapiller, et al, *Nature* 310:105–111 (1984)). For example, a TR14 polypeptide fragment of the invention can be synthesized by use of a peptide synthesizer. Furthermore, if desired, nonclassical amino acids or chemical amino acid analogs can be introduced as a substitution or addition into the TR14 polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention additionally, encompasses TR13 polypeptides (proteins) which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

The invention additionally, encompasses TR14 polypeptides (proteins) which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of TR13 polypeptides (proteins) which may provide additional advantages such as increased solubility, stability and circulating time of the polypeptide, or decreased immunogenicity (see U.S. Pat. No. 4,179,337). The chemical moieties for derivitization may be selected from water soluble polymers such as, for example, polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

Also provided by the invention are chemically modified derivatives of TR14 polypeptides which may provide additional advantages such as increased solubility, stability and circulating time of the polypeptide, or decreased immunogenicity (see U.S. Pat. No. 4,179,337). The chemical moieties for derivitization may be selected from water soluble polymers such as, for example, polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59–72 (1996); Vorobjev et al, *Nucleosides Nucleotides* 18:2745–2750 (1999); and Caliceti et al., *Bioconjug. Chem.* 10:638–646 (1999), the disclosures of each of which are incorporated herein by reference.

The polyethylene glycol molecules (or other chemical moieties) should be attached to the polypeptide (proteins) with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire polypeptides (proteins) chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier*

Sys. 9:249–304 (1992); Francis et al., *Intern. J. of Hematol.* 68:1–18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

As mentioned the TR13 and TR14 polypeptides (proteins) of the invention may be modified by either natural processes, such as posttranslational processing, or by chemical modification techniques which are well known in the art. It will be appreciated that the same type of modification may be present in the same or varying degrees at several sites in a given TR13 or TR14 polypeptide. TR13 or TR14 polypeptides may be branched, for example, as a result of ubiquitination, and they may be cyclic, with or without branching. Cyclic, branched, and branched cyclic TR13 or TR14 polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., *Meth Enzymol* 182:626–646 (1990); Rattan et al., *Ann NY Acad Sci* 663:48–62 (1992)).

As mentioned the TR14 polypeptides (proteins) of the invention may be modified by either natural processes, such as posttranslational processing, or by chemical modification techniques which are well known in the art. It will be appreciated that the same type of modification may be present in the same or varying degrees at several sites in a given TR14 polypeptide. TR14 polypeptides may be branched, for example, as a result of ubiquitination, and they may be cyclic, with or without branching. Cyclic, branched, and branched cyclic TR14 polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., *Meth Enzymol* 182:626–646 (1990); Rattan et al., *Ann NY Acad Sci* 663:48–62 (1992)).

The TR13 polypeptides (proteins) of the invention can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

The TR14 polypeptides (proteins) of the invention can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

TR13 polynucleotides and polypeptides of the present invention, and agonsits or antagonists thereof, may be used in accordance with the present invention for a variety of applications, particularly those that make use of the chemical and biological properties of TR13. Among these are, for example, applications in treatment of tumors; resistance to parasites, bacteria and viruses; to regulate (i.e., induce) proliferation of T-cells, endothelial cells and hematopoietic cells; to treat restenosis, and graft vs. host disease; to regulate anti-viral responses; and to prevent certain autoimmune diseases after stimulation of TR13 by an agonist. Additional applications relate to diagnosis and to treatment of disorders of cells, tissues and organisms. These aspects of the invention are discussed further below.

TR14 polynucleotides and polypeptides of the present invention, and agonsits or antagonists thereof, may be used in accordance with the present invention for a variety of applications, particularly those that make use of the chemical and biological properties of TR14. Among these are, for example, applications in treatment of tumors; resistance to parasites, bacteria and viruses; to regulate (i.e., induce) proliferation of T-cells, endothelial cells and hematopoietic cells; to treat restenosis, and graft vs. host disease; to regulate anti-viral responses; and to prevent certain autoimmune diseases after stimulation of TR14 by an agonist. Additional applications relate to diagnosis and to treatment of disorders of cells, tissues and organisms. These aspects of the invention are discussed further below.

Transgenics and "knock-outs"

The TR13 polypeptides (proteins) of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

The TR14 polypeptides (proteins) of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., nucleic acids of the invention) into animals to produce the founder lines of transgenic animals. Such techniques include, but are not limited to, pronuclear microinjection (Paterson et al., *Appl. Microbiol. Biotechnol.* 40:691–698 (1994); Carver et al., *Biotechnology* (NY) 11:1263–1270 (1993); Wright et al., *Biotechnology* (N.Y.) 9:830–834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148–6152 (1985)), blastocysts or embryos; gene targeting in embryonic stem cells (Thompson et al., *Cell* 56:313–321 (1989)); electroporation of cells or embryos (Lo, *Mol Cell. Biol.* 3:1803–1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717–723 (1989); etc. For a review of such techniques, see Gordon, "Transgenic Animals," *Intl. Rev. Cytol.* 115:171–229 (1989), which is incorporated by reference herein in its entirety. Further, the contents of each of the documents recited in this paragraph is herein incorporated by reference in its entirety. See also, U.S. Pat. No. 5,464,764 (Capecchi, et al., Positive-Negative Selection Methods and Vectors); U.S. Pat. No. 5,631,153 (Capecchi, et al., Cells and Non-Human Organisms Containing Predetermined Genomic Modifications and Positive-Negative Selection Methods and Vectors for Making Same); U.S. Pat. No. 4,736,866 (Leder, et al., Transgenic Non-Human Animals); and U.S. Pat. No. 4,873,191 (Wagner, et al., Genetic Transformation of Zygotes); each of which is hereby incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64–66 (1996); Wilmut et al., *Nature* 385:810–813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (*Proc. Natl. Acad. Sci. USA* 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (*Science* 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of TR13 polypeptides, studying conditions and/or disorders associated with aberrant TR13 expression, and in screening for compounds effective in ameliorating such conditions and/or disorders.

Transgenic and "knock-out" animals of the invention have uses which include, but are not limited to, animal model systems useful in elaborating the biological function of TR14 polypeptides, studying conditions and/or disorders associated with aberrant TR14 expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of clones, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

TR13 Polypeptides

The TR13 proteins (polypeptides) of the invention may be in monomers or multimers (i.e., dimers, trimers, tetramers, and higher multimers). Accordingly, the present invention relates to monomers and multimers of the TR13 proteins (polypeptides) of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term TR13 homomer, refers to a multimer containing only TR13 proteins of the invention (including TR13 fragments, variants, and fusion proteins, as described herein). These homomers may contain TR13 proteins having identical or different polypeptide sequences. In a specific embodiment, a homomer of the invention is a multimer containing only TR13 proteins having an identical polypeptide sequence. In another specific embodiment, a homomer of the invention is a multimer containing TR13 proteins having different polypeptide sequences. In specific embodiments, the multimer of the invention is a homodimer (e.g., containing TR13 proteins having identical or different polypeptide sequences) or a homotrimer (e.g., containing TR13 proteins having identical or different polypeptide sequences). In additional embodiments, the homomeric multimer of the invention is at least a homodimer, at least a homotrimer, or at least a homotetramer.

As used herein, the term TR13 heteromer refers to a multimer containing heterologous proteins (i.e., proteins containing only polypeptide sequences that do not correspond to a polypeptide sequences encoded by the TR13 gene) in addition to the TR13 proteins of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the TR13 proteins of the invention. Such covalent associations may involve one or more amino acid residues contained in the polypeptide sequence of the protein (e.g., the polypeptide sequence recited in SEQ ID NO:2 or SEQ ID NO:40 or the polypeptide encoded by the cDNA deposited in ATCC Deposit No. PTA-349 or ATCC Deposit No. PTA-507. In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a TR13 fusion protein. In one example, covalent associations are between the heterologous sequence contained in a fusion protein of the invention (see, e.g., U.S. Pat. No. 5,478,925). In a specific example, the covalent associations are between the heterologous sequence contained in a TR13-Fc fusion protein of the invention (as described herein). In another specific example, covalent associations of fusion proteins of the invention are between heterologous polypeptide sequences from another TNF family ligand/receptor member that is capable of forming covalently associated multimers, such as for example, oseteoprotegerin (see, e.g., International Publication No. WO 98/49305, the contents of which are herein incorporated by reference in its entirety). In another embodiment, two or more TR13 polypeptides of the invention are joined through synthetic linkers (e.g., peptide, carbohydrate or soluble polymer linkers). Examples include those peptide linkers described in U.S. Pat. No. 5,073,627 (hereby incorporated by reference). Proteins comprising multiple TR13 polypeptides separated by peptide linkers may be produced using conventional recombinant DNA technology.

Another method for preparing multimer TR13 polypeptides of the invention involves use of TR13 polypeptides fused to a leucine zipper or isoleucine polypeptide sequence. Leucine zipper domains and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric TR13 proteins are those described in PCT application WO 94/10308, hereby incorporated by reference. Recombinant fusion proteins comprising a soluble TR13 polypeptide fused to a peptide that dimerizes or trimerizes in solution are expressed in suitable host cells, and the resulting soluble multimeric TR13 is recovered from the culture supernatant using techniques known in the art.

Certain members of the TNF family of proteins are believed to exist in trimeric form (Beutler and Huffel, *Science* 264:667, 1994; Banner et al., *Cell* 73:431, 1993). Thus, trimeric TR13 may offer the advantage of enhanced biological activity. Preferred leucine zipper moieties are those that preferentially form trimers. One example is a leucine zipper derived from lung surfactant protein D (SPD), as described in Hoppe et al. (*FEBS Letters* 344:191, (1994)) and in U.S. patent application Ser. No. 08/446,922, hereby incorporated by reference. Other peptides derived from naturally occurring trimeric proteins may be employed in preparing trimeric TR13.

In further preferred embodiments, TR13 polynucleotides of the invention are fused to a polynucleotide encoding a "FLAG" polypeptide. Thus, a TR13-FLAG fusion protein is encompassed by the present invention. The FLAG antigenic polypeptide may be fused to a TR13 polypeptide of the invention at either or both the amino or the carboxy terminus. In preferred embodiments, a TR13-FLAG fusion protein is expressed from a pFLAG-CMV-5a or a pFLAG-CMV-1 expression vector (available from Sigma, St. Louis, Mo., USA). See, Andersson, S., et al., *J. Biol. Chem.* 264:8222–29 (1989); Thomsen, D. R., et al., *Proc. Natl Acad. Sci. USA*, 81:659–63 (1984); and Kozak, M., *Nature* 308:241 (1984) (each of which is hereby incorporated by reference). In further preferred embodiments, a TR13-FLAG fusion protein is detectable by anti-FLAG monoclonal antibodies (also available from Sigma).

In another example, proteins of the invention are associated by interactions between Flag® polypeptide sequence contained in Flag®-TR13 fusion proteins of the invention. In a further embodiment, associated proteins of the invention are associated by interactions between heterologous polypeptide sequence contained in Flag®-TR13 fusion proteins of the invention and anti-Flag® antibody.

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

The polypeptides (proteins) of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the TR13 polypeptide can be substantially purified by the one-step method described in Smith and Johnson, *Gene* 67:31–40 (1988).

Accordingly, in one embodiment, the invention provides an isolated TR13 polypeptide having the amino acid sequence encoded by the cDNA deposited in ATCC Deposit No. PTA-349 or ATCC Deposit No. PTA-507, or the amino acid sequence in SEQ ID NO:2 or SEQ ID NO:40, or a peptide or polypeptide comprising a portion of the above polypeptides.

Polypeptide fragments of the present invention include polypeptides comprising or alternatively, consisting of, an amino acid sequence contained in SEQ ID NO:2, encoded by the cDNA contained in the clone deposited as ATCC Deposit No. PTA-349, or encoded by a nucleic acid which hybridizes (e.g., under stringent hybridization conditions) to the nucleotide sequence contained in the deposited clone, or shown in FIGS. 1A–D (SEQ ID NO:1) or the complementary strand thereto, or polynucleotide fragments thereof (e.g., as disclosed herein). Protein fragments may be "freestanding," or comprised within a larger polypeptide of which the fragment forms a part or region, most preferably as a single continuous region. Representative examples of polypeptide fragments of the invention, include, for example, fragments that comprise, or alternatively consist of, from about amino acid residues: 1 to 50, 51 to 100, 101 to 150, 151 to 200, 201 to 250, 251 to 300, 301 to 350, 351 to 400, 401 to 450, 451 to 500, 501 to 550, 551 to 600, 601 to 650, 651 to 700, and/or 701 to 750 of SEQ ID NO: 2. Moreover, polypeptide fragments can be at least 10, 20, 30, 40, 50, 60, 70, 80, 90, 100, 110, 120, 130, 140, 150, 175 or 200 amino acids in length. In this context "about" includes the particularly recited ranges, larger or smaller by several (5, 4, 3, 2, or 1) amino acids, at either extreme or at both extremes. Polynucleotides encoding these polypeptide fragments are also encompassed by the invention.

Polypeptide fragments of the present invention include polypeptides comprising or alternatively, consisting of, an amino acid sequence contained in SEQ ID NO:40, encoded by the cDNA contained in the clone deposited as ATCC Deposit No. PTA-507, or encoded by a nucleic acid which hybridizes (e.g., under stringent hybridization conditions) to the nucleotide sequence contained in the deposited clone, or shown in FIGS. 7A–E (SEQ ID NO:40) or the complementary strand thereto or polynucleotide fragments thereof (e.g., as disclosed herein). Protein fragments may be "freestanding," or comprised within a larger polypeptide of which the fragment forms a part or region, most preferably as a single continuous region. Representative examples of polypeptide fragments of the invention, include, for example, fragments that comprise, or alternatively consist of, from about amino acid residues: 1 to 50, 51 to 100, 101 to 150, 151 to 200, 201 to 250, 251 to 300, 301 to 350, 351 to 400, 401 to 450, 451 to 500, 501 to 550, 551 to 600, 601 to 650, 651 to 700, 701 to 750, 751 to 800, 801 to 850, 851 to 900, 901 to 950, and/or 951 to 1001 of SEQ ID NO: 2. Moreover, polypeptide fragments can be at least 10, 20, 30, 40, 50, 60, 70, 80, 90, 100, 110, 120, 130, 140, 150, 175, 200, 250, 300, 350, 400, 450, 500, 550, 600, 650, 700, 750, 800, 850, 900, 950, or 1001 amino acids in length. In this context "about" includes the particularly recited ranges, larger or smaller by several (5, 4, 3, 2, or 1) amino acids, at either extreme or at both extremes. Polynucleotides encoding these polypeptide fragments are also encompassed by the invention.

Polypeptide fragments of the present invention include polypeptides comprising or alternatively, consisting of from about amino acid residues: 105 to about 170, from 251 to about 265, from 331 to about 410, from 580 to about 610, from 139 to about 142, from 140 to about 143, from 153 to about 156, from 293 to about 296, from 325 to about 328, from 421 to about 424, from 466 to about 469, from 696 to about 699, from 728 to about 731, from 312 to about 315, from 454 to about 461, from 458 to about 461, from 50 to about 53, from 66 to about 69, from 80 to about 83, from 276 to about 279, from 311 to about 314, from 438 to about 441, from 559 to about 562, from 564 to about 567, from 698 to about 701, from 725 to about 728, from 80 to about 83, from 89 to about 92, from 180 to about 183, from 198 to about 201, from 214 to about 217, from 272 to about 275, from 306 to about 309, from 510 to about 513, from 529 to about 532, from 584 to about 867, from 609 to about 612, from 642 to about 645, from 698 to about 701, from 69 to about 74, from 149 to about 154, from 154 to about 159, from 163 to about 168, from 212 to about 217, from 248 to about 253, from 365 to about 370, from 383 to about 388, from 393 to about 398, from 588 to about 593, from 623 to about 628, from 661 to about 666, from 665 to about 670, and/or 456 to about 459 of SEQ ID NO:2. In this context "about" includes the particularly recited ranges, larger or smaller by several (5, 4, 3, 2, or 1) amino acids, at either extreme or at both extremes. Polynucleotides encoding these polypeptide fragments are also encompassed by the invention.

Polypeptide fragments of the present invention include polypeptides comprising or alternatively, consisting of from about amino acid residues: 42 to about 906, from 42 to about 1001, from 906 to about 931, from 932 to about 1001, from 271 to about 421, from 271 to about 286, from 290 to about 300, from 301 to about 320, from 329 to about 361, from 404 to about 421, from 585 to about 595, from 661 to about 674, from 710 to about 744, from 980 to about 991, from 45 to about 60, from 121 to about 135, from 145 to about 160, from 1 to about 262, from 264 to about 423, from 437 to about 789, from 791 to about 1001, from 310 to about 363, from 477 to about 519, from 769 to about 887, from 153 to about 156, from 11 to about 13, from about 18 to about 20, from 107 to about 109, from about 156 to about 158, from about 224 to about 226, from about 301 to about 303, from about 317 to about 319, from about 331 to about 333, from about 527 to about 529, from about 562 to about 564, from about 689 to about 691, from about 810 to about 812, from about 815 to about 817, from about 949 to about 951, from about 976 to about 978, from 42 to about 45, from about 59 to about 62, from about 81 to about 84, from about 146 to about 149, from about 282 to about 285, from about 331 to about 334, from about 340 to about 343, from about 431 to about 434, from about 449 to about 452, from about 465 to about 468, from about 523 to about 526, from about 557 to about 560, from about 761 to about 764, from about 780 to about 783, from about 780 to about 783, from about 835 to about 838, from about 860 to about 863, from about 893 to about 896, from about 949 to about 952, from from about 77 to about 82, from about 88 to about 93, from about 152 to about 157, from about 268 to about 273, from about 288 to about 293, from about 320 to about 325, from about 400 to about 405, from about 414 to about 419, from about 463 to about 468, from about 599 to about 604, from about 616 to about 621, from about 634 to about 639, from about 644 to about 649, from about 839 to about 844, from about 874 to about 879, from about 912 to about 917, from about 916 to about 921, from from about 50 to about 56, from from about 109 to about 116, from from about 153 to about 156, from 390 to about 393, from 391 to about 394, from about 404 to about 407, from about 544 to about 547, from about 576 to about 579, from about 672 to about 675, from about 717 to about 720, from about 947 to about 950, from and about 979 to about 982 of SEQ ID NO:40. In this context "about" includes the particularly recited ranges, larger or smaller by several (5, 4, 3, 2, or 1) amino acids, at either extreme or at both extremes.

In additional embodiments, the polypeptide fragments of the invention comprise, or alternatively consist of, one or more domains of the TR13 polypeptide disclosed in FIGS. 1A–D. Preferred polypeptide fragments of the present invention include a member selected from the group: (a) a polypeptide comprising or alternatively, consisting of, any combination of one, two, three, or all four of the TR13 cysteine rich domains disclosed in FIGS. 1A–D (predicted to constitute amino acid residues from about 105 to about 170, about 251 to about 265, about 331 to about 410, and about 580 to about 610 of SEQ ID NO: 2); (b) a polypeptide comprising, or alternatively, consisting of, one, two, three, four or more, epitope bearing portions of the TR13 receptor protein disclosed in FIGS. 1A–D (for example, those epitope bearing portions predicted to constitute amino acid residues from about 1 to about 170, or about 210 to about 318, or about 343 to about 480, or about 548 to about 592, or about 632 to about 742 of SEQ ID NO:2); (c) any combination of polypeptides (a)–(c). Polynucleotides encoding these polypeptides are also encompassed by the invention. In this context "about" includes the particularly recited ranges, larger or smaller by several (5, 4, 3, 2, or 1) amino acids, at either extreme or at both extremes. Polynucleotides encoding these polypeptide fragments are also encompassed by the invention.

In additional embodiments, the polypeptide fragments of the invention comprise, or alternatively consist of, one or more domains of the TR13 polypeptide disclosed in FIG. 7A-D. Preferred polypeptide fragments of the present invention include a member selected from the group: (a) a polypeptide comprising, or alternatively consisting of, amino acids 1 to about 41 of SEQ ID NO:40; (b) a polypeptide comprising, or alternatively consisting of, amino acids 42 to about 906 of SEQ ID NO:40; (c) a polypeptide comprising, or alternatively consisting of, amino acids 907 to about 931 of SEQ ID NO:40; (d) a polypeptide comprising, or alternatively consisting of, amino acids 932 to about 1001 of SEQ ID NO:40; (e) a polypeptide comprising or alternatively, consisting of, any combination of one, two, three, four or more of the TR13 cysteine rich domains disclosed in FIGS. 7A–D (predicted to constitute amino acid residues from about 271 to about 421, 271 to about 286, about 290 to about 300, about 301 to about 320, about 329 to about 361, about 404 to about 421, about 585 to about 595 of SEQ ID NO:40); (f) a polypeptide comprising, or alternatively, consisting of, one, two, three, four or more, epitope bearing portions of the TR13 receptor protein disclosed in FIGS. 7A–E (for example, these epitope bearing portions predicted to constitute amino acid residues from about 1 to about 262, or about 264 to about 423, or about 437 to about 789, or about 791 to about 1001, of SEQ ID NO: 40); and (g) any combination of polypeptides (a)–(f). In this context "about" includes the particularly recited ranges, larger or smaller by several (5, 4, 3, 2, or 1) amino acids, at either extreme or at both extremes. Polynucleotides encoding these polypeptides are also encompassed by the invention.

As discussed above, it is believed that the extracellular cysteine rich motifs of TR13 are important for interactions between TR13 and its ligands. Accordingly, in preferred embodiments, polypeptide fragments of the invention comprise, or alternatively consist of amino acid residues from about 105 to about 170, about 251 to about 265, about 331 to about 410 and/or about 580 to about 610 of the amino acid sequence disclosed in FIGS. 1A–D (SEQ ID NO:2). In a specific embodiment the polypeptides of the invention comprise, or alternatively consist of any combination of one, two, three or all four extracellular cysteine rich motifs disclosed in FIGS. 1A–D. In this context "about" includes the particularly recited ranges, larger or smaller by several (5, 4, 3, 2, or 1) amino acids, at either extreme or at both extremes. Polynucleotides encoding these polypeptides are also encompassed by the invention.

As discussed above, it is believed that the extracellular cysteine rich motifs of TR13 are important for interactions between TR13 and its ligands. Accordingly, in preferred embodiments, polypeptide fragments of the invention comprise, or alternatively consist of amino acid residues from about 271 to about 421, or 271 to about 286, or about 290 to about 300, or about 301 to about 320, or about 329 to about 361, or about 404 to about 421, or about 585 to about 595 of the amino acid sequence disclosed in FIGS. 7A–E (SEQ ID NO:40). In a specific embodiment the polypeptides of the invention comprise, or alternatively consist of any combination of one, two, three, four or more of the extracellular cysteine rich motifs disclosed in FIGS. 7A–E. In this context "about" includes the particularly recited ranges, larger or smaller by several (5, 4, 3, 2, or 1) amino acids, at either extreme or at both extremes. Polynucleotides encoding these polypeptides are also encompassed by the invention.

Among the especially preferred fragments of the invention are fragments characterized by structural or functional attributes of TR13 (SEQ ID NO:2 or SEQ ID NO:40). Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) TR13 (SEQ ID NO:2 or SEQ ID NO:40). Certain preferred regions are those set out in FIG. 3 (Table I) and FIG. 9 (Table III) and include, but are not limited to, regions of the aforementioned types identified by analysis of the amino acid sequence depicted in FIGS. 1A–D (SEQ ID NO:2) or FIGS. 7A–E (SEQ ID NO:40), respectively. Such preferred regions include; Garnier-Robson predicted alpha-regions, beta-regions, turn-regions, and coil-regions; Chou-Fasman predicted alpha-regions, beta-regions, and turn-regions; Kyte-Doolittle predicted hydrophilic and Hopp-Woods predicted hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

As mentioned above, even if deletion of one or more amino acids from the N-terminus of a protein results in modification of loss of one or more biological functions of the protein, other functional activities (e.g., biological activities, ability to multimerize, ability to bind TR13 ligand) may still be retained. For example, the ability of shortened TR13 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an TR13 mutein with a large number of deleted N-terminal amino acid residues may retain some biological or immunogenic activities. In fact, peptides composed of as few as six TR13 amino acid residues may often evoke an immune response.

Accordingly, the present invention further provides polypeptides having one or more residues deleted from the amino terminus of the TR13 amino acid sequence shown in FIGS. 1A–D, up to the aspartic acid residue at position number 745 and polynucleotides encoding such polypeptides. In particular, the present invention provides polypeptides comprising, or alternatively consisting of, the amino acid sequence of residues $n^1$-750 of FIGS. 1A–D, where $n^1$ is an integer from 2 to 745 corresponding to the position of the amino acid residue in FIGS. 1A–D (which is identical to the sequence shown as SEQ ID NO:2). In a specific embodiment, the present invention provides polypeptides comprising, or alternatively consisting of, the amino acid sequence of residues $n^1$-750 of FIGS. 1A–D, where $n^1$ is an integer from 2 to 610 corresponding to the position of the amino acid residue in FIGS. 1A–D. Polynucleotides encoding these polypeptides are also encompassed.

In one embodiment, N-terminal deletions of the TR13 polypeptides of the invention can be described by the general formula $n^2$-750, where $n^2$ is a number from 2 to 745, corresponding to the position of amino acid identified in FIGS. 1A–D (SEQ ID NO:2). N-terminal deletions of the TR13 polypeptide of the invention shown as SEQ ID NO:2 include polypeptides comprising, or alternatively consisting of, the amino acid sequence of residues: D-2 to R-750; Q-3 to R-750; S-4 to R-750; T-5 to R-750; Q-6 to R-750; A-7 to R-750; C-8 to R-750; A-9 to R-750; G-10 to R-750; E-11 to R-750; K-12 to R-750; H-13 to R-750; C-14 to R-750; H-15 to R-750; N-16 to R-750; R-17 to R-750; G-18 to R-750; G-19 to R-750; L-20 to R-750; H-21 to R-750; F-22 to R-750; R-23 to R-750; M-24 to R-750; L-25 to R-750; P-26 to R-750; L-27 to R-750; Q-28 to R-750; T-29 to R-750; W-30 to R-750; H-31 to R-750; V-32 to R-750; C-33 to R-750; R-34 to R-750; Q-35 to R-750; A-36 to R-750; G-37 to R-750; L-38 to R-750; L-39 to R-750; F-40 to R-750; L-41 to R-750; Q-42 to R-750; T-43 to R-750; L-44 to R-750; P-45 to R-750; S-46 to R-750; N-47 to R-750; S-48 to R-750; Y-49 to R-750; S-50 to R-750; N-51 to R-750; K-52 to R-750; G-53 to R-750; E-54 to R-750; T-55 to R-750; S-56 to R-750; C-57 to R-750; H-58 to R-750; Q-59 to R-750; C-60 to R-750; D-61 to R-750; P-62 to R-750; D-63 to R-750; K-64 to R-750; Y-65 to R-750; S-66 to R-750; E-67 to R-750; K-68 to R-750; G-69 to R-750; S-70 to R-750; S-71 to R-750; S-72 to R-750; C-73 to R-750; N-74 to R-750; V-75 to R-750; R-76 to R-750; P-77 to R-750; A-78 to R-750; C-79 to R-750; T-80 to R-750; D-81 to R-750; K-82 to R-750; D-83 to R-750; Y-84 to R-750; F-85 to R-750; Y-86 to R-750; T-87 to R-750; H-88 to R-750; T-89 to R-750; A-90 to R-750; C-91 to R-750; D-92 to R-750; A-93 to R-750; N-94 to R-750; G-95 to R-750; E-96 to R-750; T-97 to R-750; Q-98 to R-750; L-99 to R-750; M-100 to R-750; Y-101 to R-750; K-102 to R-750; W-103 to R-750; A-104 to R-750; K-105 to R-750; P-106 to R-750; K-107 to R-750; I-108 to R-750; C-109 to R-750; S-110 to R-750; D-112 to R-750; D-112 to R-750; L-113 to R-750; E-114 to R-750; G-115 to R-750; A-116 to R-750; V-117 to R-750; K-118 to R-750; L-119 to R-750; P-120 to R-750; A-121 to R-750; S-122 to R-750; G-123 to R-750; V-124 to R-750; K-125 to R-750; T-126 to R-750; H-127 to R-750; C-128 to R-750; P-129 to R-750; P-130 to R-750; C-131 to R-750; N-132 to R-750; P-133 to R-750; G-134 to R-750; F-135 to R-750; F-136 to R-750; K-137 to R-750; T-138 to R-750; N-139 to R-750; N-140 to R-750; S-141 to R-750; T-142 to R-750; C-143 to R-750; Q-144 to R-750; P-145 to R-750; C-146 to R-750; P-147 to R-750; Y-148 to R-750; G-149 to R-750; S-150 to R-750; Y-151 to R-750; S-152 to R-750; N-153 to R-750; G-154 to R-750; S-155 to R-750; D-156 to R-750; C-157 to R-750; T-158 to R-750; R-159 to R-750; C-160 to R-750; P-161 to R-750; A-162 to R-750; G-163 to R-750; T-164 to R-750; E-165 to R-750; P-166 to R-750; A-167 to R-750; V-168 to R-750; G-169 to R-750; F-170 to R-750; E-171 to R-750; Y-172 to R-750; K-173 to R-750; W-174 to R-750; W-175 to R-750; N-176 to R-750; T-177 to R-750; L-178 to R-750; P-179 to R-750; T-180 to R-750; N-181 to R-750; M-182 to R-750; E-183 to R-750; T-184 to R-750; T-185 to R-750; V-186 to R-750; L-187 to R-750; S-188 to R-750; G-189 to R-750; I-190 to R-750; N-191 to R-750; F-192 to R-750; E-193 to R-750; Y-194 to R-750; K-195 to R-750; G-196 to R-750; M-197 to R-750; T-198 to R-750; G-199 to R-750; W-200 to R-750; E-201 to R-750; V-202 to R-750; A-203 to R-750; G-204 to R-750; D-205 to R-750; H-206 to R-750; I-207 to R-750; Y-208 to R-750; T-209 to R-750; A-210 to R-750; A-211 to R-750; G-212 to R-750; A-213 to R-750; S-214 to R-750; D-215 to R-750; N-216 to R-750; D-217 to R-750; F-218 to R-750; M-219 to R-750; I-220 to R-750; L-221 to R-750; T-222 to R-750; L-223 to R-750; V-224 to R-750; V-225 to R-750; P-226 to R-750; G-227 to R-750; F-228 to R-750; R-229 to R-750; P-230 to R-750; P-231 to R-750; Q-232 to R-750; S-233 to R-750; V-234 to R-750; M-235 to R-750; A-236 to R-750; D-237 to R-750; T-238 to R-750; E-239 to R-750; N-240 to R-750; K-241 to R-750; E-242 to R-750; V-243 to R-750; A-244 to R-750; R-245 to R-750; I-246 to R-750; T-247 to R-750; F-248 to R-750; V-249 to R-750; F-250 to R-750; E-251 to R-750; T-252 to R-750; L-253 to R-750; C-254 to R-750; S-255 to R-750; V-256 to R-750; N-257 to R-750; C-258 to R-750; E-259 to R-750; L-260 to R-750; Y-261 to R-750; F-262 to R-750; M-263 to R-750; V-264 to R-750; G-265 to R-750; V-266 to R-750; N-267 to R-750; S-268 to R-750; R-269 to R-750; T-270 to R-750; N-271 to R-750; T-272 to R-750; P-273 to R-750; V-274 to R-750; E-275 to R-750; T-276 to R-750; W-277 to R-750; K-278 to R-750; G-279 to R-750; S-280 to R-750; K-281 to R-750; G-282 to R-750; K-283 to R-750; Q-284 to R-750; S-285 to R-750; Y-286 to R-750; T-287 to R-750; Y-288 to R-750; I-289 to R-750; I-290 to R-750; E-291 to R-750; E-292 to R-750; N-293 to R-750; T-294 to R-750; T-295 to R-750; T-296 to R-750; S-297 to R-750; F-298 to R-750; T-299 to R-750; W-300 to R-750; A-301 to R-750; F-302 to R-750; Q-303 to R-750; R-304 to R-750; T-305 to R-750; T-306 to R-750; F-307 to R-750; H-308 to R-750; E-309 to R-750; A-310 to R-750; S-311 to R-750; R-312 to R-750; K-313 to R-750; Y-314 to R-750; T-315 to R-750; N-316 to R-750; D-317 to R-750; V-318 to R-750; A-319 to R-750; K-320 to R-750; I-321 to R-750; Y-322 to R-750; S-323 to R-750; I-324 to R-750; N-325 to R-750; V-326 to R-750; T-327 to R-750; N-328 to R-750; V-329 to R-750; M-330 to R-750; N-331 to R-750; G-332 to R-750; V-333 to R-750; A-334 to R-750; S-335 to R-750; Y-336 to R-750; C-337 to R-750; R-338 to R-750; P-339 to R-750; C-340 to R-750; A-341 to R-750; L-342 to R-750; E-343 to R-750; A-344 to R-750; S-345 to R-750; D-346 to R-750; V-347 to R-750; G-348 to R-750; S-349 to R-750; S-350 to R-750; C-351 to R-750; T-352 to R-750; S-353 to R-750; C-354 to R-750; P-355 to R-750; A-356 to R-750; G-357 to R-750; Y-358 to R-750; Y-359 to R-750; I-360 to R-750; D-361 to R-750; R-362 to R-750; D-363 to R-750; S-364 to R-750; G-365 to R-750; T-366 to R-750; C-367 to R-750; H-368 to R-750; S-369 to R-750; C-370 to R-750; P-371 to R-750; P-372 to R-750; N-373 to R-750; T-374 to R-750; I-375 to R-750; L-376 to R-750; K-377 to R-750; A-378 to R-750; H-379 to R-750; Q-380 to R-750; P-381 to R-750; Y-382 to R-750; G-383 to R-750; V-384 to R-750; Q-385 to R-750; A-386 to R-750; C-387 to R-750; V-388 to R-750; P-389 to R-750; C-390 to R-750; G-391 to R-750; P-392 to R-750; G-393 to R-750; T-394 to R-750; K-395 to R-750; N-396 to R-750; N-397 to R-750; K-398 to R-750; I-399 to R-750; H-400 to R-750; S-401 to R-750; L-402 to R-750 C-403 to R-750; Y-404 to R-750; N-405 to R-750; D-406 to R-750; C-407 to R-750; T-408 to R-750; F-409 to R-750; S-410 to R-750; R-411 to R-750; N-412 to R-750; T-413 to R-750; P-414 to R-750; T-415 to R-750; R-416 to R-750; T-417 to R-750; F-418 to R-750; N-419 to R-750; Y-420 to R-750; N-421 to R-750; F-422 to R-750; S-423 to R-750 A-424 to R-750; L-425 to R-750; A-426 to R-750; N-427 to R-750; T-428 to R-750; V-429 to R-750; T-430 to R-750; L-431 to R-750; A-432 to R-750; G-433 to R-750; G-434 to R-750; P-435 to R-750; S-436 to R-750; F-437 to R-750; T-438 to R-750; S-439 to R-750; K-440 to R-750; G-441 to R-750; L-442 to R-750; K-443 to R-750; Y-444 to R-750 F-445 to R-750; H-446 to R-750; H-447 to R-750; F-448 to R-750; T-449 to R-750; L-450 to R-750; S-451 to R-750; L-452 to R-750; C-453 to R-750; G-454 to R-750; N-455 to R-750; Q-456 to R-750; G-457 to R-750; R-458 to R-750; K-459 to R-750; M-460 to R-750 S-461 to R-750; V-462 to R-750; C-463 to R-750; T-464 to R-750; D-465 to R-750; N-466 to R-750; V-467 to R-750; T-468 to R-750; D-469 to R-750; L-470 to R-750; R-471 to R-750; I-472 to R-750; P-473 to R-750; E-474 to R-750; G-475 to R-750; E-476 to R-750; S-477 to R-750; G-478 to R-750; F-479 to R-750; S-480 to R-750; K-481 to R-750 S-482 to R-750; I-483 to R-750; T-484 to R-750; A-485 to R-750; Y-486 to R-750; V-487 to R-750; C-488 to R-750; Q-489 to R-750; A-490 to R-750; V-491 to R-750; I-492 to R-750; I-493 to R-750; P-494 to R-750; P-495 to R-750; E-496 to R-750; V-497 to R-750; T-498 to R-750; G-4 99 to R-750; Y-500 to R-750; K-501 to R-750; A-502 to R-750; G-503 to R-750; V-504 to R-750; S-505 to R-750; S-506 to R-750; Q-507 to R-750; P-508 to R-750; V-509 to R-750; S-510 to R-750; L-511 to R-750; A-512 to R-750; D-513 to R-750; R-514 to R-750; L-515 to R-750; I-516 to R-750; G-517 to R-750; V-518 to R-750; T-519 to R-750; T-520 to R-750; D-521 to R-750; M-522 to R-750; T-523 to R-750; L-524 to R-750; D-525 to R-750; G-526 to R-750; I-527 to R-750; T-528 to R-750; S-529 to R-750; P-530 to R-750; A-531 to R-750; E-532 to R-750; L-533 to R-750; F-534 to R-750; H-535 to R-750; L-536 to R-750; E-537 to R-750; S-538 to R-750; L-539 to R-750 G-540 to R-750; I-541 to R-750; P-542 to R-750; D-543 to R-750; V-544 to R-750; I-545 to R-750; F-546 to R-750; F-547 to R-750; Y-548 to R-750; R-549 to R-750; S-550 to R-750; N-551 to R-750; D-552 to R-750; V-553 to R-750; T-554 to R-750; Q-555 to R-750 S-556 to R-750; C-557 to R-750; S-558 to R-750; S-559 to R-750; G-560 to R-750; R-561 to R-750; S-562 to R-750; T-563 to R-750; T-564 to R-750; I-565 to R-750; R-566 to R-750; V-567 to R-750; R-568 to R-750; C-569 to R-750; S-570 to R-750; P-571 to R-750 Q-572 to R-750; K-573 to R-750; T-574 to R-750; V-575 to R-750; P-576 to R-750; G-577 to R-750; S-578 to R-750; L-579 to R-750; L-580 to R-750; L-581 to R-750; P-582 to R-750; G-583 to R-750; T-584 to R-750; C-585 to R-750; S-586 to R-750; D-587 to R-750; G-588 to R-750; T-589 to R-750; C-590 to R-750; D-591 to R-750; G-592 to R-750; C-593 to R-750; N-594 to R-750; F-595 to R-750; H-596 to R-750; F-597 to R-750; L-598 to R-750; W-599 to R-750; E-600 to R-750; S-601 to R-750; A-602 to R-750; A-603 to R-750; A-604 to R-750; C-605 to R-750; P-606 to R-750; L-607 to R-750; C-608 to R-750; S-609 to R-750; V-610 to R-750; A-611 to R-750; D-612 to R-750; Y-613 to R-750; H-614 to R-750; A-615 to R-750; I-616 to R-750; V-617 to R-750; S-618 to R-750; S-619 to R-750; C-620 to R-750; V-621 to R-750; A-622 to R-750; G-623 to R-750; I-624 to R-750; Q-625 to R-750; K-626 to R-750; T-627 to R-750; T-628 to R-750; Y-629 to R-750 V-630 to R-750; W-631 to R-750; R-632 to R-750; E-633 to R-750; P-634 to R-750; K-635 to R-750; L-636 to R-750; C-637 to R-750; S-638 to R-750; G-639 to R-750; G-640 to R-750; I-641 to R-750; S-642 to R-750; L-643 to R-750; P-644 to R-750; E-645 to R-750; Q-646 to R-750; R-647 to R-750; V-648 to R-750; T-649 to R-750; I-650 to R-750; C-651 to R-750; K-652 to R-750; T-653 to R-750; I-654 to R-750; D-655 to R-750; F-656 to R-750; W-657 to R-750; L-658 to R-750; K-659 to R-750; V-660 to R-750; G-661 to R-750; I-662 to R-750; S-663 to R-750; A-664 to R-750; G-665 to R-750; T-666 to R-750; C-667 to R-750; T-668 to R-750; A-669 to R-750; I-670 to R-750; L-671 to R-750; L-672 to R-750; T-673 to R-750; V-674 to R-750; L-675 to R-750; T-676 to R-750; C-677 to R-750; Y -678 to R-750; F-679 to R-750; W-680 to R-750; K-681 to R-750; K-682 to R-750; N-683 to R-750; Q-684 to R-750; K-685 to R-750; L-686 to R-750; E-687 to R-750; Y-688 to R-750; K-689 to R-750; Y-690 to R-750; S-691 to R-750; K-692 to R-750 L-693 to R-750; V-694 to R-750; M-695 to R-750; N-696 to R-750; A-697 to R-750; T-698 to R-750; L-699 to R-750; K-700 to R-750; D-701 to R-750; C-702 to R-750; D-703 to R-750; L-704 to R-750; P-705 to R-750; A-706 to R-750; A-707 to R-750; D-708 to R-750; S-709 to R-750; C-710 to R-750; A-711 to R-750; I-712 to R-750; M-713 to R-750; E-714 to R-750; G-715 to R-750; E-716 to R-750; D-717 to R-750; V-718 to R-750; E-719 to R-750; D-720 to R-750; D-721 to R-750; L-722 to R-750; I-723 to R-750; F-724 to R-750; T-725 to R-750; S-726 to R-750; K-727 to R-750; N-728 to R-750; H-729 to R-750; S-730 to R-750; L-731 to R-750; G-732 to R-750; R-733 to R-750; S-734 to R-750; N-735 to R-750; H-736 to R-750; L-737 to R-750; P-738 to R-750; P-739 to R-750; R-740 to R-750; G-741 to R-750; L-742 to R-750; L-743 to R-750; M-744 to R-750; D-745 to R-750; of SEQ ID NO:2. Polynucleotides encoding these polypeptides are also encompassed by the invention.

Accordingly, the present invention further provides polypeptides having one or more residues deleted from the amino terminus of the TR13 amino acid sequence shown in FIGS. 7A–E, up to the aspartic acid residue at position number 996 and polynucleotides encoding such polypeptides. In particular, the present invention provides polypeptides comprising, or alternatively consisting of, the amino acid sequence of residues $n^1$-1001 of FIGS. 7A–E, where $n^1$ is an integer from 2 to 996 corresponding to the position of the amino acid residue in FIGS. 7A–E (which is identical to the sequence shown as SEQ ID NO:40). In a specific embodiment, the present invention provides polypeptides comprising, or alternatively consisting of, the amino acid sequence of residues $n^1$-906 of FIGS. 7A–E where $n^1$ is an integer from 42 to 595 corresponding to the position of the amino acid residue in FIGS. 7A–E. Polynucleotides encoding these polypeptides are also encompassed by the invention.

In another embodiment, N-terminal deletions of the TR13 polypeptide can be described by the general formula $n^2$-1001, where $n^2$ is a number from 2 to 996, corresponding to the position of amino acid identified in FIGS. 7A–E (SEQ ID NO:40). N-terminal deletions of the TR13 polypeptide of the invention shown as SEQ ID NO:40 include polypeptides comprising, or alternatively consisting of, the amino acid sequence of residues: A-2 to R-1001; E-3 to R-1001; P-4 to R-1001; G-5 to R-1001; H-6 to R-1001; S-7 to R-1001; H-8 to R-1001; H-9 to R-1001; L-10 to R-1001; S-11 to R-1001; A-12 to R-1001; R-13 to R-1001; V-14 to R-1001; R-15 to R-1001; G-16 to R-1001; R-17 to R-1001; T-18 to R-1001; E-19 to R-1001; R-20 to R-1001; R-21 to R-1001; I-22 to R-1001; P-23 to R-1001; R-24 to R-1001; L-25 to R-1001; W-26 to R-1001; R-27 to R-1001; L-28to R-1001; L-29 to R-1001; L-30 to R-1001; W-31 to R-1001; A-32 to R-1001; G-33 to R-1001; T-34 to R-1001; A-35 to R-1001; F-36 to R-1001; Q-37 to R-1001; V-38 to R-1001; T-39 to R-1001; Q-40 to R-1001; G-41 to R-1001; T-42 to R-1001; G-43 to R-1001; P-44 to R-1001; E-45 to R-1001; L-46 to R-1001; H-47 to R-1001; A-48 to R-1001; C-49 to R-1001; K-50 to R-1001; E-51 to R-1001; S-52 to R-1001; E-53 to R-1001; Y-54 to R-1001; H-55 to R-1001; Y-56 to R-1001; E-57 to R-1001; Y-58 to R-1001; T-59 to R-1001; A-60 to R-1001; C-61 to R-1001; D-62 to R-1001; S-63 to R-1001; T-64 to R-1001; G-65 to R-1001; S-66 to R-1001; R-67 to 1001; W-68 to R-1001; R-69 to R-1001; V-70 to R-1001; A-71 to R-1001; V-72 to R-1001; P-73 to R-1001; H-74 to R-1001; T-75 to R-1001; P-76 to R-1001; G-77 to R-1001; L-78 to R-1001; C-79 to R-1001; T-80 to R-1001; S-81 to R-1001; L-82 to R-1001; P-83 to R-1001; D-84 to R-1001; P-85 to R-1001; V-86 to R-1001; K-87 to R-1001; G-88 to R-1001; T-89 to R-1001; E-90 to R-1001; C-91 to R-1001; S-92 to R-1001; F-93 to R-1001; S-94 to R-1001; C-95 to R-1001; N-96 to R-1001; A-97 to R-1001; G-98 to R-1001; E-99 to R-1001; F-100 to R-1001; L-101 to R-1001; D-102 to R-1001; M-103 to R-1001; K-104 to R-1001; D-105 to R-1001; Q-106 to R-1001; S-107 to R-1001; C-108 to R-1001; K-109 to R-1001; P-110 to R-1001; C-111 to R-1001; A-112 to R-1001; E-113 to R-1001; G-114 to R-1001; R-115 to R-1001; Y-116 to R-1001; S-117 to R-1001; L-118 to R-1001; G-119 to R-1001; T-120 to R-1001; G-121 to R-1001; I-122 to R-1001; R-123 to R-1001; F-124 to R-1001; D-125 to R-1001; E-126 to R-1001; W-127 to R-1001; D-128 to R-1001; E-129 to R-1001; L-130 to R-1001; P-131 to R-1001; H-132 to R-1001; G-133 to R-1001; F-134 to R-1001; A-135 to R-1001; S-136 to R-1001; L-137 to R-1001; S-138 to R-1001; A-139 to R-1001; N-140 to R-1001; M-141 to R-1001; E-142 to R-1001; L-143 to R-1001; D-144 to R-1001; D-145 to R-1001; S-146 to R-1001; A-147 to R-1001; A-148 to R-1001; E-149 to R-1001; S-150 to R-1001; T-151 to R-1001; G-152 to R-1001; N-153 to R-1001; C-154 to R-1001; T-155 to R-1001; S-156 to R-1001; S-157 to R-1001; K-158 to R-1001; W-159 to R-1001; V-160 to R-1001; P-161 to R-1001; R-162 to R-1001; G-163 to R-1001; D-164 to R-1001; Y-165 to R-1001; I-166 to R-1001; A-167 to R-1001; F-168 to R-1001; N-169 to R-1001; T-170 to R-1001; D-171 to R-1001; E-172 to R-1001; C-173 to R-1001; T-174 to R-1001; A-175 to R-1001; T-176 to R-1001; L-177 to R-1001; M-178 to R-1001; Y-179 to R-1001; A-180 to R-1001; V-181 to R-1001; N-182 to R-1001; L-183 to R-1001; K-184 to R-1001; Q-185 to R-1001; S-186 to R-1001; G-187 to R-1001; T-188 to R-1001; V-189 to R-1001; N-190 to R-1001; F-191 to R-1001; E-192 to R-1001; Y-193 to R-1001; Y-194 to R-1001; Y-195 to R-1001; P-196 to R-1001; D-197 to R-1001; S-198 to R-1001; S-199 to R-1001; I-200 to R-1001; I-201 to R-1001; F-202 to R-1001; E-203to R-1001; F-204 to R-1001; F-205 to R-1001; V-206 to R-1001; Q-207 to R-1001; N-208 to R-1001; D-209 to R-1001; Q-210 to R-1001; C-211 to R-1001; Q-212 to R-1001; P-213 to R-1001; N-214 to R-1001; A-215 to R-1001; D-216 to R-1001; D-217 to R-1001; S-218 to R-1001; R-219 to R-1001; W-220 to R-1001; M-221 to R-1001; K-222 to R-1001; T-223 to R-1001; T-224 to R-1001; E-225 to R-1001; K-226 to R-1001; G-227 to R-1001; W-228 to R-1001; E-229 to R-1001; F-230 to R-1001; H-231 to R-1001; S-232 to R-1001; V-233 to R-1001; E-234 to R-1001; L-235 to R-1001; N-236 to R-1001; R-237 to R-1001; G-238 to R-1001; N-239 to R-1001; N-240 to R-1001; V-241 to R-1001; L-242 to R-1001; Y-243 to R-1001; W-244 to R-1001; R-245 to R-1001; T-246 to R-1001; T-247 to R-1001; A-248 to R-1001; F-249 to R-1001; S-250 to R-1001; V-251 to R-1001; W-252 to R-1001; T-253 to R-1001; K-254 to R-1001; V-255 to R-1001; P-256 to R-1001; K-257 to R-1001; P-258 to R-1001; V-259 to R-1001; L-260 to R-1001; V-261 to R-1001; R-262 to R-1001; N-263 to R-1001; I-264 to R-1001; A-265 to R-1001; I-266 to R-1001; T-267 to R-1001; G-268 to R-1001; V-269 to R-1001; A-270 to R-1001; Y-271 to R-1001; T-272 to R-1001; S-273 to R-1001; E-274 to R-1001; C-275 to R-1001; F-276 to R-1001; P-277 to R-1001; C-278 to R-1001; K-279 to R-1001; P-280 to R-1001; G-281 to R-1001; T-282 to R-1001; Y-283 to R-1001; A-284 to R-1001; D-285 to R-1001; K-286 to R-1001; Q-287 to R-1001; G-288 to R-1001; S-289 to R-1001; S-290 to R-1001; F-291 to R-1001; C-292 to R-1001; K-293 to R-1001; L-294 to R-1001; C-295 to R-1001; P-296 to R-1001; A-297 to R-1001; N-298 to R-1001; S-299 to R-1001; Y-300 to R-1001; S-301 to R-1001; N-302 to R-1001; K-303 to R-1001; G-304 to R-1001; E-305 to R-1001; T-306 to R-1001; S-307 to R-1001; C-308 to R-1001; H-309 to R-1001; Q-310 to R-1001; C-311 to R-1001; D-312 to R-1001; P-313 to R-1001; D-314 to R-1001; K-315 to R-1001; Y-316 to R-1001; S-317 to R-1001; E-318 to R-1001; K-319 to R-1001; G-320 to R-1001; S-321 to R-1001; S-322 to R-1001; S-323 to R-1001; C-324 to R-1001; N-325 to R-1001; V-326 to R-1001; R-327 to R-1001; P-328 to R-1001; A-329 to R-1001; C-330 to R-1001; T-331 to R-1001; D-332 to R-1001; K-333 to R-1001; D-334 to R-1001; Y-335 to R-1001; F-336 to R-1001; Y-337 to R-1001; T-338 to R-1001; H-339 to R-1001; T-340 to R-1001; A-341 to R-1001; C-342 to R-1001; D-343 to R-1001; A-344 to R-1001; N-345 to R-1001; G-346 to R-1001; E-347 to R-1001; T-348 to R-1001; Q-349 to R-1001; L-350 to R-1001; M-351 to R-1001; Y-352 to R-1001; K-353 to R-1001; W-354 to R-1001; A-355 to R-1001; K-356 to R-1001; P-357 to R-1001; K-358 to R-1001; I-359 to R-1001; C-360 to R-1001; S-361 to R-1001; E-362 to R-1001; D-363 to R-1001; L-364 to R-1001; E-365 to R-1001; G-366 to R-1001; A-367 to R-1001; V-368 to R-1001; K-369 to R-1001; L-370 to R-1001; P-371 to R-1001; A-372 to R-1001; S-373 to R-1001; G-374 to R-1001; V-375 to R-1001; K-376 to R-1001; T-377 to R-1001; H-378 to R-1001; C-379 to
R-1001; P-380 to R-1001; P-381 to R-1001; C-382 to
R-1001; N-383 to R-1001; P-384 to R-1001; G-385 to
R-1001; F-386 to R-1001; F-387 to R-1001; K-388 to
R-1001; T-389 to R-1001; N-390 to R-1001; N-391 to
R-1001; S-392 to R-1001; T-393 to R-1001; C-394 to
R-1001; Q-395 to R-1001; P-396 to R-1001; C-397 to
R-1001; P-398 to R-1001; Y-399 to R-1001; G-400 to
R-1001; S-401 to R-1001; Y-402 to R-1001; S-403 to
R-1001; N-404 to R-1001; G-405 to R-1001; S-406 to
R-1001; D-407 to R-1001; C-408 to R-1001; T-409 to
R-1001; R-410 to R-1001; C-411 to R-1001; P-412 to
R-1001; A-413 to R-1001; G-414 to R-1001; T-415 to
R-1001; E-416 to R-1001; P-417 to R-1001; A-418 to
R-1001; V-419 to R-1001; G-420 to R-1001; F-421 to R-1001; E-422 to R-1001; Y-423 to R-1001; K-424 to R-1001; W-425 to R-1001; W-426 to R-1001; N-427 to R-1001; T-428 to R-1001; L-429 to R-1001; P-430 to R-1001; T-431 to R-1001; N-432 to R-1001; M-433 to R-1001; E-434 to R-1001; T-435 to R-1001; T-436 to R-1001; V-437 to R-1001; L-438 to R-1001; S-439 to R-1001; G-440 to R-1001; I-441 to R-1001; N-442 to R-1001; F-443 to R-1001; E-444 to R-1001; Y-445 to R-1001; K-446 to R-1001; G-447 to R-1001; M-448 to R-1001; T-449 to R-1001; G-450 to R-1001; W-451 to R-1001; E-452 to R-1001; V-453 to R-1001; A-454 to R-100; G-455 to R-1001; D-456 to R-1001; H-457 to R-1001; I-458 to R-1001; Y-459 to R-1001; T-460 to R-1001; A-461 to R-1001; A-462 to R-1001; G-463 to R-1001; A-464 to R-1001; S-465 to R-1001; D-466 to R-1001; N-467 to R-1001; D-468 to R-1001; F-469 to R-1001; M-470 to R-1001; I-471 to R-1001; L-472 to R-1001; T-473 to R-1001; L-474 to R-1001; V-475 to R-1001; V-476 to R-1001; P-477to R-1001; G-478 to R-1001; F-479 to R-1001; R-480 to R-1001; P-481 to R-1001; P-482 to R-1001; Q-483 to R-1001; S-484 to R-1001; V-485 to R-1001; M-486 to R-1001; A-487 to R-1001; D-488 to R-1001; T-489 to R-1001; E-490 to R-1001; N-491 to R-1001; K-492 to R-1001; E-493 to R-1001; V-494 to R-1001; A-495 to R-1001; R-496 to R-1001; I-497 to R-1001; T-498 to R-1001; F-499 to R-1001; V-500 to R-1001; F-501 to R-1001; E-502 to R-1001; T-503 to R-1001; L-504 to R-1001; C-505 to R-1001; S-506 to R-1001; V-507 to R-1001; N-508 to R-1001; C-509 to R-1001; E-510 to R-1001; L-511 to R-1001; Y-512 to R-1001; F-513 to R-1001; M-514 to R-1001; V-515 to R-1001; G-516 to R-1001; V-517 to R-1001; N-518 to R-1001; S-519 to R-1001; R-520 to R-1001; T-521 to R-1001; N-522 to R-1001; T-523 to R-1001; P-524 to R-1001; V-525 to R-1001; E-526 to R-1001; T-527 to R-1001; W-528 to R-1001; K-529 to R-1001; G-530 to R-1001; S-531 to R-1001; K-532 to R-1001; G-533 to R-1001; K-534 to R-1001; Q-535 to R-1001; S-536 to R-1001; Y-537 to R-1001; T-538 to R-1001; Y-539 to R-1001; I-540 to R-1001; I-541 to R-1001; E-542 to R-1001; E-543 to R-1001; N-544 to R-1001; T-545 to R-1001; T-546 to R-1001; T-547 to R-1001; S-548 to R-1001; F-549 to R-1001; T-550 to R-1001; W-551 to R-1001; A-552 to R-1001; F-553 to R-1001; Q-554 to R-1001; R-555 to R-1001; T-556 to R-1001; T-557 to R-1001; F-558 to R-1001; H-559 to R-1001; E-560 to R-1001; A-561 to R-1001; S-562 to R-1001; R-563 to R-1001; K-564 to R-1001; Y-565 to R-1001; T-566 to R-1001; N-567 to R-1001; D-568 to R-1001; V-569 to R-1001; A-570 to R-1001; K-571 to R-1001; I-572 to R-1001; Y-573 to R-1001; S-574 to R-1001; I-575 to R-1001; N-576 to R-1001; V-577 to R-1001; T-578 to R-1001; N-579 to R-1001; V-580 to R-1001; M-581 to R-1001; N-582 to R-1001; G-583 to R-1001; V-584 to R-1001; A-585 to R-1001; S-586 to R-1001; Y-587 to R-1001; C-588 to R-1001; R-589 to R-1001; P-590 to R-1001; C-591 to R-1001; A-592 to R-1001; L-593 to R-1001; E-594 to R-1001; A-595 to R-1001; S-596 to R-1001; D-597 to R-1001; V-598 to R-1001; G-599 to R-1001; S-600 to R-1001; S-601 to R-1001; C-602 to R-1001; T-603 to R-1001; S-604 to R-1001; C-605 to R-1001; P-606 to R-1001; A-607 to R-1001; G-608 to R-1001; Y-609 to R-1001; Y-610 to R-1001; I-611 to R-1001; D-612 to R-1001; R-613 to R-1001; D-614 to R-1001; S-615 to R-1001; G-616 to R-1001; T-617 to R-1001; C-618 to R-1001; H-619 to R-1001; S-620 to R-1001; C-621 to R-1001; P-622 to R-1001; P-623 to R-1001; N-624 to R-1001; T-625 to R-1001; I-626 to R-1001; L-627 to R-1001; K-628 to R-1001; A-629 to R-1001; H-630 to R-1001; Q-631 to R-1001; P-632 to R-1001; Y-633 to R-1001; G-634 to R-1001; V-635 to R-1001; Q-636 to R-1001; A-637 to R-1001; C-638 to R-1001; V-639 to R-1001; P-640 to R-1001; C-641 to R-1001; G-642 to R-1001; P-643 to R-1001; G-644 to R-1001; T-645 to R-1001; K-646 to R-1001; N-647 to R-1001; N-648 to R-1001; K-649 to R-1001; I-650 to R-1001; H-651 to R-1001; S-652 to R-1001; L-653 to R-1001; C-654 to R-1001; Y-655 to R-1001; N-656 to R-1001; D-657 to R-1001; C-658 to R-1001; T-659 to R-1001; F-660 to R-1001; S-661 to R-1001; R-662 to R-1001; N-663 to R-1001; T-664 to R-1001; P-665 to R-1001; T-666 to R-1001; R-667 to R-1001; T-668 to R-1001; F-669 to R-1001; N-670 to R-1001; Y-671 to R-1001; N-672 to R-1001; F-673 to R-1001; S-674 to A-675 to R-1001; L-676 to R-1001; A-677 to R-1001; N-678 to R-1001; T-679 to R-1001; V-680 to R-1001; T-681 to R-1001; L-682 to R-1001; A-683 to R-1001; G-684 to R-1001; G-685 to R-1001; P-686 to R-1001; S-687 to R-1001; F-688 to R-1001; T-689 to R-1001; S-690 to R-1001; K-691 to R-1001; G-692 to R-1001; L-693 to R-1001; K-694 to R-1001; Y-695 to R-1001; F-696 to R-1001; H-697 to R-1001; H-698 to R-1001; F-699 to R-1001; T-700 to R-1001; L-701 to R-1001; S-702 to R-1001; L-703 to R-1001; C-704 to R-1001; G-705 to R-1001; N-706 to R-1001; Q-707 to R-1001; G-708 to R-1001; R-709 to R-1001; K-710 to R-1001; M-711 to R-1001; S-712 to R-1001; V-713 to R-1001; C-714 to R-1001; T-715 to R-1001; D-716 to R-1001; N-717 to R-1001; V-718 to R-1001; T-719 to R-1001; D-720 to R-1001; L-721 to R-1001; R-722 to R-1001; I-723 to R-1001; P-724 to R-1001; E-725 to R-1001; G-726 to R-1001; E-727 to R-1001; S-728 to R-1001; G-729 to R-1001; F-730 to R-1001; S-731 to R-1001; K-732 to R-1001; S-733 to R-1001; I-734 to R-1001; T-735 to R-1001; A-736 to R-1001; Y-737 to R-1001; V-738 to R-1001; C-739 to R-1001; Q-740 to R-1001; A-741 to R-1001; V-742 to R-1001; I-743 to R-1001; I-744 to R-1001; P-745to R-1001; P-746 to R-1001; E-747 to R-1001; V-748 to R-1001; T-749 to R-1001; G-750 to R-1001; Y-751 to R-1001; K-752 to R-1001; A-753 to R-1001; G-754 to R-1001; V-755 to R-1001; S-756 to R-1001; S-757 to R-1001; Q-758 to R-1001; P-759 to R-1001; V-760 to R-1001; S-761 to R-1001; L-762 to R-1001; A-763 to R-1001; D-764 to R-1001; R-765 to R-1001; L-766 to R-1001; I-767 to R-1001; G-768 to R-1001; V-769 to R-1001; T-770 to R-1001; T-771 to R-1001; D-772 to R-1001; M-773 to R-1001; T-774 to R-1001; L-775 to R-1001; D-776 to R-1001; G-777 to R-1001; I-778 to R-1001; T-779 to R-1001; S-780 to

R-1001; P-781 to R-1001; A-782 to R-1001; E-783 to R-1001; L-784 to R-1001; F-785 to R-1001; H-786 to R-1001; L-787 to R-1001; E-788 to R-1001; S-789 to R-1001; L-790 to R-1001; G-791 to R-1001; I-792 to R-1001; P-793 to R-1001; D-794 to R-1001; V-795 to R-1001; I-796 to R-1001; F-797 to R-1001; F-798 to R-1001; Y-799 to R-1001; R-800 to R-1001; S-801 to R-1001; N-802 to R-1001; D-803 to R-1001; V-804 to R-1001; T-805 to R-1001; Q-806 to R-1001; S-807 to R-1001; C-808 to R-1001; S-809 to R-1001; S-810 to R-1001; G-811 to R-1001; R-812 to R-1001; S-813 to R-1001; T-814 to R-1001; T-815 to R-1001; I-816 to R-1001; R-817 to R-1001; V-818 to R-1001; R-819 to R-1001; C-820 to R-1001; S-821 to R-1001; P-822 to R-1001; Q-823 to R-1001; K-824 to R-1001; T-825 to R-1001; V-826 to R-1001; P-827 to R-1001; G-828 to R-1001; S-829 to R-1001; L-830 to R-1001; L-831 to R-1001; L-832 to R-1001; P-833 to R-1001; G-834 to R-1001; T-835 to R-1001; C-836 to R-1001; S-837 to R-1001; D-838 to R-1001; G-839 to R-1001; T-840 to R-1001; C-841 to R-1001; D-842 to R-1001; G-843 to R-1001; C-844 to R-1001; N-845 to R-1001; F-846 to R-1001; H-847 to R-1001; F-848 to R-1001; L-849 to R-1001; W-850 to R-1001; E-851 to R-1001; S-852 to R-1001; A-853 to R-1001; A-854 to R-1001; A-855 to R-1001; C-856 to R-1001; P-857 to R-1001; L-858 to R-1001; C-859 to R-1001; S-860 to R-1001; V-861 to R-1001; A-862 to R-1001; D-863 to R-1001; Y-864 to R-1001; H-865 to R-1001; A-866 to R-1001; I-867 to R-1001; V-868 to R-1001; S-869 to R-1001; S-870 to R-1001; C-871 to R-1001; V-872 to R-1001; A-873 to R-1001; G-874 to R-1001; I-875 to R-1001; Q-876 to R-1001; K-877 to R-1001; T-878 to R-1001; T-879 to R-1001; Y-880 to R-1001; V-881 to R-1001; W-882 to R-1001; R-883 to R-1001; E-884 to R-1001; P-885 to R-1001; K-886 to R-1001; L-887 to R-1001; C-888 to R-1001; S-889 to R-1001; G-890 to R-1001; G-891 to R-1001; I-892 to R-1001; S-893 to R-1001; L-894 to R-1001; P-895 to R-1001; E-896 to R-1001; Q-897 to R-1001; R-898 to R-1001; V-899 to R-1001; T-900 to R-1001; I-901 to R-1001; C-902to R-1001; K-903 to R-1001; T-904 to R-1001; I-905 to R-1001; D-906 to R-1001; F-907 to R-1001; W-908 to R-1001; L-909 to R-1001; K-910 to R-1001; V-911 to R-1001; G-912 to R-1001; I-913 to R-1001; S-914 to R-1001; A-915 to R-1001; G-916 to R-1001; T-917 to R-1001; C-918 to R-1001; T-919 to R-1001; A-920 to R-1001; I-921 to R-1001; L-922 to R-1001; L-923 to R-1001; T-924 to R-1001; V-925 to R-1001; L-926 to R-1001; T-927 to R-1001; C-928 to R-1001; Y-929 to R-1001; F-930 to R-1001; W-931 to R-1001; K-932 to R-1001; K-933 to R-1001; N-934 to R-1001; Q-935 to R-1001; K-936 to R-1001; L-937 to R-1001; E-938 to R-1001; Y-939 to R-1001; K-940 to R-1001; Y-941 to R-1001; S-942 to R-1001; K-943 to R-1001; L-944 to R-1001; V-945 to R-1001; M-946 to R-1001; N-947 to R-1001; A-948 to R-1001; R-1001; L-973 to R-1001; I-974 to R-1001; F-975 to R-1001; T-976 to R-1001; S-977 to R-1001; K-978 to R-1001; N-979 to R-1001; H-980 to R-1001; S-981 to R-1001; L-982 to R-1001; G-983 to R-1001; R-984 to R-1001; S-985 to R-1001; N-986 to R-1001; H-987 to R-1001; L-988 to R-1001; P-989 to R-1001; P-990 to R-1001; R-991 to R-1001; G-992 to R-1001; L-993 to R-1001; L-994 to R-1001; M-995 to R-1001; D-996 to R-1001; of SEQ ID NO:40. Polynucleotides encoding these polypeptides are also encompassed by the invention.

Also as mentioned above, even if deletion of one or more amino acids from the C-terminus of a protein results in modification or loss of one or more biological functions of the protein, other functional activities (e.g., biological activities, ability to multimerize, ability to bind TR13 ligand) may still be retained. For example the ability of the shortened TR13 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an TR13 mutein with a large number of deleted C-terminal amino acid residues may retain some biological or immunogenic activities. In fact, peptides composed of as few as six TR13 amino acid residues may often evoke an immune response.

Accordingly, the present invention further provides polypeptides having one or more residues deleted from the carboxy terminus of the amino acid sequence of the TR13 polypeptide shown in FIGS. 1A–D (SEQ ID NO:2), up to the glutamine residue at position number 6, and polynucleotides encoding such polypeptides. In particular, the present invention provides polypeptides comprising, or alternatively consisting of, the amino acid sequence of residues 1-$m^1$ of FIGS. 1A–D, where $m^1$ is an integer from 6 to 749 corresponding to the position of the amino acid residue in FIGS. 1A–D.

Moreover, the invention provides TR13 polypeptides comprising, or alternatively consisting of, the amino acid sequence of residues: Q-6 to C-749; Q-6 to Q-748; Q-6 to T-747; Q-6 to L-746; Q-6 to D-745; Q-6 to M-744; Q-6to L-743; Q-6 to L-742; Q-6 to G-741; Q-6 to R-740; Q-6 to P-739; Q-6 to P-738; Q-6 to L-737; Q-6 to H-736; Q-6 to N-735; Q-6to S-734; Q-6 to R-733; Q-6 to G-732; Q-6 to L-731; Q-6 to S-730; Q-6 to H-729; Q-6 to N-728; Q-6 to K-727; Q-6 to S-726; Q-6 to T-725; Q-6 to F-724; Q-6 to I-723; Q-6 to L-722; Q-6 to D-721; Q-6 to D-720; Q-6 to E-719; Q-6 to V-718; Q-6 to D-717; Q-6 to E-716; Q-6 to G-715; Q-6 to E-714; Q-6 to M-713; Q-6 to I-712; Q-6 to A-711; Q-6 to C-710; Q-6 to S-709; Q-6 to D-708; Q-6 to A-707; Q-6 to A-706; Q-6 to P-705; Q-6 to L-704; Q-6 to D-703; Q-6 to C-702; Q-6 to D-701; Q-6 to K-700; Q-6 to L-699; Q-6 to T-698; Q-6 to A-697; Q-6 to N-696; Q-6 to M-695; Q-6 to V-694; Q-6 to L-693; Q-6 to K-692; Q-6 to S-691; Q-6 to Y-690; Q-6 to K-689; Q-6 to Y-688; Q-6 to E-687; Q-6 to L-686; Q-6 to K-685; Q-6 to Q-684; Q-6 to N-683; Q-6 to K-682; Q-6 to K-681; Q-6 to W-680; Q-6 to F-679; Q-6 to Y-678; Q-6 to C-677; Q-6 to T-676; Q-6 to L-675; Q-6 to V-674; Q-6 to T-673; Q-6 to L-672; Q-6 to L-671; Q-6 to I-670; Q-6 to A-669; Q-6 to T-668; Q-6 to C-667; Q-6 to T-666; Q-6 to G-665; Q-6 to A-664; Q-6 to S-663; Q-6 to I-662; Q-6 to G-661; Q-6 to V-660; Q-6 to K-659; Q-6 to L-658; Q-6 to W-657; Q-6 to F-656; Q-6 to D-655; Q-6 to I-654; Q-6 to T-653; Q-6 to K-652; Q-6 to C-651; Q-6 to I-650; Q-6 to T-649; Q-6 to V-648; Q-6 to R-647; Q-6 to Q-646; Q-6 to E-645; Q-6 to P-644; Q-6 to L-643; Q-6 to S-642; Q-6 to I-641; Q-6 to G-640; Q-6 to G-639; Q-6 to S-638; Q-6 to C-637; Q-6 to L-636; Q-6 to K-635; Q-6 to P-634; Q-6 to E-633; Q-6 to R-632; Q-6 to W-631; Q-6 to V-630; Q-6 to Y-629; Q-6 to T-628; Q-6 to T-627; Q-6 K-626; Q-6 to Q-625; Q-6 to I-624; Q-6 to G-623; Q-6 to A-622; Q-6 to V-621; Q-6 to C-620; Q-6 to S-619; Q-6 to S-618; Q-6 to V-617; Q-6 to I-616; Q-6 to A-615; Q-6 to H-614; Q-6 to Y-613; Q-6 to D-612; Q-6 to A-611; Q-6 to V-610; Q-6 to S-609; Q-6 to C-608; Q-6 to L-607; Q-6 to P-606; Q-6 to C-605; Q-6 to A-604; Q-6 to A-603; Q-6 to A-602; Q-6 to S-601; Q-6 to E-600; Q-6 to W-599; Q-6 to L-598; Q-6 to F-597; Q-6 to H-596; Q-6 to F-595; Q-6 to N-594; Q-6 to C-593; Q-6 to G-592; Q-6 to D-591; Q-6 to C-590; Q-6 to T-589; Q-6 to G-588; Q-6 to D-587; Q-6 to S-586; Q-6 to C-585; Q-6 to T-584; Q-6 to G-583; Q-6 to P-582; Q-6 to L-581; Q-6 to L-580; Q-6 to L-579; Q-6 to S-578; Q-6 to G-577; Q-6 to P-576; Q-6 to V-575; Q-6 to T-574; Q-6 to K-573; Q-6 to Q-572; Q-6 to P-571; Q-6 to S-570; Q-6 to C-569; Q-6 to R-568; Q-6 to V-567; Q-6 to R-566; Q-6 to I-565; Q-6 to T-564; Q-6 to T-563; Q-6 to S-562; Q-6 to R-561; Q-6 to G-560; Q-6 to S-559; Q-6 to S-558; Q-6 to C-557; Q-6 to S-556; Q-6 to Q-555; Q-6 to T-554; Q-6 to V-553; Q-6 to D-552; Q-6 to N-551; Q-6 to S-550; Q-6 to R-549; Q-6 to Y-548; Q-6 to F-547; Q-6 to F-546; Q-6 to I-545; Q-6 to V-544; Q-6 to D-543; Q-6 to P-542; Q-6 to I-531; Q-6 to G-540; Q-6 to L-539; Q-6 to S-538; Q-6 to E-537; Q-6 to L-536; Q-6 to H-535; Q-6 to F-534; Q-6 to L-533; Q-6 to E-532; Q-6 to A-531; Q-6 to P-530; Q-6 to S-529; Q-6 to T-528; Q-6 to I-527; Q-6 to G-526; Q-6 to D-525; Q-6 to L-524; Q-6 to T-523; Q-6 to M-522; Q-6 to D-521; Q-6 to T-520; Q-6 to T-519; Q-6 to V-518; Q-6 to G-517; Q-6 to I-516; Q-6 to L-515; Q-6 to R-514; Q-6 to D-513; Q-6 to A-512; Q-6 to L-511; Q-6 to S-510; Q-6 to V-509; Q-6 to P-508; Q-6 to Q-507; Q-6 to S-506; Q-6 to S-505; Q-6 to V-504; Q-6 to G-503; Q-6 to A-502; Q-6 to K-501; Q-6 to Y-500; Q-6 to G-499; Q-6 to T-498; Q-6 to V-497; Q-6 to E-496; Q-6 to P-495; Q-6 to P-494; Q-6 to I-493; Q-6 to I-492; Q-6 to V-491; Q-6 to A-490; Q-6 to Q-489; Q-6 to C-488; Q-6 to V-487; Q-6 to Y-486; Q-6 to A-485; Q-6 to T-484; Q-6 to I-483; Q-6 to S-482; Q-6 to K-481; Q-6 to S-480; Q-6 to F-479; Q-6 G-478; Q-6 to S-477; Q-6 to E-476; Q-6 to G-475; Q-6 to E-474; Q-6 to P-473; Q-6 to I-472; Q-6 to R-471; Q-6 to L-470; Q-6 to D-469; Q-6 to T-468; Q-6 to V-467; Q-6 to N-466; Q-6 to D-465; Q-6 to T-464; Q-6 to C-463; Q-6 to V-462; Q-6 to S-461; Q-6 to M-460; Q-6 to K-459; Q-6 to R-458; Q-6 to G-457; Q-6 to Q-456; Q-6 to N-455; Q-6 to G-454; Q-6 to C-453; Q-6 to L-452; Q-6 to S-451; Q-6 to L-450; Q-6 to T-449; Q-6 to F-448; Q-6 to H-447; Q-6 to H-446; Q-6 to F-445; Q-6 to Y-444; Q-6 to K-443; Q-6 to L-442; Q-6 to G-441; Q-6 to K-440; Q-6 to S-439; Q-6 to T-438; Q-6 to F-437; Q-6 to S-436; Q-6 to P-435; Q-6 to G-434; Q-6 to G-433; Q-6 to A-432; Q-6 to L-431; Q-6 to T-430; Q-6 to V-429; Q-6 to T-428; Q-6 to N-427; Q-6 to A-426; Q-6 to L-425; Q-6 to A-424; Q-6 to S-423; Q-6 to F-422; Q-6 to N-421; Q-6 to Y-420; Q-6 to N-419; Q-6 to F-418; Q-6 to T-417; Q-6 to R-416; Q-6 to T-415; Q-6 to P-414; Q-6 to T-413; Q-6 to N-412; Q-6 to R-411; Q-6 to S-410; Q-6 to F-409; Q-6 to T-408; Q-6 to C-407; Q-6 to D-406; Q-6 to N-405; Q-6 to Y-404; Q-6 to C-403; Q-6 to L-402; Q-6 to S-401; Q-6 to H-400; Q-6 to I-399; Q-6 to K-398; Q-6 to N-397; Q-6 to N-396; Q-6 to K-395; Q-6 to T-394; Q-6 to G-393; Q-6 to P-392; Q-6 to G-391; Q-6 to C-390; Q-6 to P-389; Q-6 to V-388; Q-6 to C-387; Q-6 to A-386; Q-6 to Q-385; Q-6 to V-384; Q-6 to G-383; Q-6 to Y-382; Q-6 to P-381; Q-6 to Q-380; Q-6 to H-379; Q-6 to A-378; Q-6 to K-377; Q-6 to L-376; Q-6 to I-375; Q-6 to T-374; Q-6 to N-373; Q-6 to P-372; Q-6 to P-371; Q-6 to C-370; Q-6 to S-369; Q-6 to H-368; Q-6 to C-367; Q-6 to T-366; Q-6 to G-365; Q-6 to S-364; Q-6 to D-363; Q-6 to R-362; Q-6 to D-361; Q-6 to I-360; Q-6 to Y-359; Q-6 to Y-358; Q-6 to G-357; Q-6 to A-356; Q-6 to P-355; Q-6 to C-354; Q-6 to S-353; Q-6 to T-352; Q-6 to C-351; Q-6 to S-350; Q-6 to S-349; Q-6 to G-348; Q-6 to V-347; Q-6 to D-346; Q-6 to S-345; Q-6 to A-344; Q-6 to E-343; Q-6 to L-342; Q-6 to A-341; Q-6 to C-340; Q-6 to P-339; Q-6 to R-338; Q-6 to C-337; Q-6 to Y-336; Q-6 to S-335; Q-6 to A-334; Q-6 to V-333; Q-6 to G-332; Q-6 to N-331; Q-6 to M-330; Q-6 to V-329; Q-6 to N-328; Q-6 to T-327; Q-6 to V-326; Q-6 to N-325; Q-6 to I-324; Q-6 to S-323; Q-6 to Y-322; Q-6 to I-321; Q-6 to K-320; Q-6 to A-319; Q-6 to V-318; Q-6 to D-317; Q-6 to N-316; Q-6 to T-315; Q-6 to Y-314; Q-6 to K-313; Q-6 to R-312; Q-6 to D-311; Q-6 to A-310; Q-6 to E-309; Q-6 to H-308; Q-6 to F-307; Q-307; Q-6 to T-306; Q-6 to T-305; Q-6 to R-304; Q-6 to Q-303; Q-6 to F-302; Q-6 to A-301; Q-6 to W-300; Q-6 to T-299; Q-6 to F-298; Q-6 to S-297; Q-6 to T-296; Q-6 to T-295; Q-6 to T-294; Q-6 to N-293; Q-6 to E-292; Q-6 to E-291; Q-6 to I-290; Q-6 to I-289; Q-6 to Y-288; Q-6 to T-287; Q-6 to Y-286; Q-6 to S-285; Q-6 to Q-284; Q-6 to K-283; Q-6 to G-282; Q-6 to K-281; Q-6 to S-280; Q-6 to G-279; Q-6 to K-278; Q-6 to W-277; Q-6 to T-276; Q-6 to E-275; Q-6 to V-274; Q-6 to P-273; Q-6 to T-272; Q-6 to N-271; Q-6 to T-270; Q-6 to R-269; Q-6 to S-268; Q-6 to N-267; Q-6 to V-266; Q-6 to G-265; Q-6 to V-264; Q-6 to M-263; Q-6 to F-262; Q-6 to Y-261; Q-6 to L-260; Q-6 to E-259; Q-6 to C-258; Q-6 to N-257; Q-6 to V-256; Q-6 to S-255; Q-6 to C-254; Q-6 to L-253; Q-6 to T-252; Q-6 to E-251; Q-6 to F-250; Q-6 to V-249; Q-6 to F-248; Q-6 to T-247; Q-6 to I-246; Q-6 to R-245; Q-6 to A-244; Q-6 to V-243; Q-6 to E-242; Q-6 to K-241; Q-6 to N-240; Q-6 to E-239; Q-6 to T-238; Q-6 to D-237; Q-6 to A-236; Q-6 to M-235; Q-6 to V-234; Q-6 to S-233; Q-6 to Q-232; Q-6 to P-231; Q-6 to P-230; Q-6 to R-229; Q-6 to F-228; Q-6 to G-227; Q-6 to P-226; Q-6 to V-225; Q-6 to V-224; Q-6 to L-223; Q-6 to T-222; Q-6 to L-221; Q-6 to I-220; Q-6 to M-219; Q-6 to F-218; Q-6 to D-217; Q-6 to N-216; Q-6 to D-215; Q-6 to S-214; Q-6 to A-213; Q-6 to G-212; Q-6 to A-211; Q-6 to A-210; Q-6 to T-209; Q-6 to Y-208; Q-6 to I-207; Q-6 to H-206; Q-6 to D-205; Q-6 to G-204; Q-6 to A-203; Q-6 to V-202; Q-6 to E-201; Q-6 to W-200; Q-6 to G-199; Q-6 to T-198; Q-6 to M-197; Q-6 to G-196; Q-6 to K-195; Q-6 to Y-194; Q-6 to E-193; Q-6 to F-192; Q-6 to N-191; Q-6 to I-190; Q-6 to G-189; Q-6 to S-188; Q-6 to L-187; Q-6 to V-186; Q-6 to T-185; Q-6 to T-184; Q-6 to E-183; Q-6 to M-182; Q-6 to N-181; Q-6 to T-180; Q-6 to P-179; Q-6 to L-178; Q-6 to T-177; Q-6 to N-176; Q-6 to W-175; Q-6 to W-174; Q-6 to K-173; Q-6 to Y-166; Q-6 to E-171; Q-6 to F-170; Q-6 to G-169; Q-6 to V-168; Q-6 to A-167; Q-6 to P-166; Q-6 to E-165; Q-6 to T-164; Q-6 to G-163; Q-6 to A-162; Q-6 to P-161; Q-6 to C-160; Q-6 to R-159; Q-6 to T-158; Q-6 to C-157; Q-6 to D-156; Q-6 to S-155; Q-6 to G-154; Q-6 to N-153; Q-6 to S-152; Q-6 to Y-151; Q-6 to S-150; Q-6 to G-149; Q-6 to Y-148; Q-6 to P-147; Q-6 to C-146; Q-6 to P-145; Q-6 to Q-144; Q-6 to C-143; Q-6 to T-142; Q-6 to S-141; Q-6 to N-140; Q-6 to N-139; Q-6 to T-138; Q-6 to K-137; Q-6 to F-136; Q-6 to F-135; Q-6 to G-134; Q-6 to P-133; Q-6 to N-132; Q-6 to C-131; Q-6 to P-130; Q-6 to P-129; Q-6 to C-128; Q-6 to H-127; Q-6 to T-126; Q-6 to K-125; Q-6 to V-124; Q-6 to G-123; Q-6 to S-122; Q-6 to A-121; Q-6 to P-120; Q-6 to L-119; Q-6 to K-118; Q-6 to V-117; Q-6 to A-116; Q-6 to G-115; Q-6 to E-114; Q-6 to L-113; Q-6 to D-112; Q-6 to E-111; Q-6 to S-110; Q-6 to C-109; Q-6 to I-108; Q-6 to K-107; Q-6 to P-106; Q-6 to K-105; Q-6 to A-104; Q-6 to W-103; Q-6 to K-102; Q-6 to Y-101; Q-6 to M-100; Q-6 to L-99; Q-6 to Q-98; Q-6 to T-97; Q-6 to E-96; Q-6 to G-95; Q-6 to N-94; Q-6 to A-93; Q-6 to D-92; Q-6 to C-91; Q-6 to A-90; Q-6 to T-89; Q-6 to H-88; Q-6 to T-87; Q-6 to Y-86; Q-6to F-85; Q-6 to Y-84; Q-6 to D-83; Q-6 to K-82; Q-6 to D-81; Q-6 to T-80; Q-6 to C-79; Q-6 to A-78; Q-6 to P-77; Q-6 to R-76; Q-6 to V-75; Q-6 to N-74; Q-6 to C-73; Q-6 to S-72; Q-6 to S-71; Q-6 to S-70; Q-6 to G-69; Q-6 to K-68; Q-6 to E-67; Q-6 to S-66; Q-6 to Y-65; Q-6 to K-64; Q-6 to

D-63; Q-6 to P-62; Q-6 to D-61; Q-6 to C-60; Q-6 to Q-59; Q-6 to H-58; Q-6 to C-57; Q-6to S-56; Q-6 to T-55; Q-6 to E-54; Q-6 to G-53; Q-6 to K-52; Q-6 to N-51; Q-6 to S-50; Q-6 to Y-49; Q-6 to S-48; Q-6 to N-47; Q-6 to S-46; Q-6 to P-45; Q-6 to L-44; Q-6 to T-43; Q-6 to Q-42; Q-6 to L-41; Q-6 to F-40; Q-6 to L-39; Q-6 to L-38; Q-6 to G-37; Q-6 to A-36; Q-6 to Q-35; Q-6 to R-34; Q-6 to C-33; Q-6 to V-32; Q-6 to H-31; Q-6 to W-30; Q-6 to T-29; Q-6 to Q-28; Q-6 to L-27; Q-6 to P-26; Q-6 to L-25; Q-6 to M-24; Q-6 to R-23; Q-6 to F-22; Q-6 to H-21; Q-6 to L-20; Q-6 to G-19; Q-6 to G-18; Q-6 to R-17; Q-6 to N-16; Q-6 to H-15; Q-6 to C-14; Q-6 to H-13; Q-6 to K-12; of SEQ ID NO:2. Polynucleotides encoding these polypeptides are also encompassed by the invention.

The present invention further provides polypeptides having one or more residues deleted from the carboxy terminus of the amino acid sequence of the TR13 polypeptide shown in FIGS. 7A–E (SEQ ID NO:40), up to the histidine residue at position number 6, and polynucleotides encoding such polypeptides. In particular, the present invention provides polypeptides comprising, or alternatively consisting of, the amino acid sequence of residues 1–$m^1$ of FIGS. 7A–E, where $m^1$ is an integer from 6 to 1001 corresponding to the position of the amino acid residue in FIGS. 7A–E.

Moreover, the invention provides TR13 polypeptides comprising, or alternatively consisting of, the amino acid sequence of residues: H-6 to C-1000; H-6 to Q-999; H-6 to T-998; H-6 to L-997; H-6 to D-996; H-6 to M-995; H-6 to L-994; H-6 to L-993; H-6 to G-992; H-6 to R-991; H-6 to P-990; H-6 to P-989; H-6 to L-988; H-6 to H-987; H-6 to N-986; H-6 to S-985; H-6 to R-984; H-6 to G-983; H-6 to L-982; H-6 to S-981; H-6 to H-980; H-6 to N-979; H-6 to K-978; H-6 to S-977; H-6 to T-976; H-6 to F-975; H-6 to I-974; H-6 to L-973; H-6 to D-972; H-6 to D-971; H-6 to E-970; H-6 to V-969; H-6 to D-968; H-6 to E-967; H-6 to G-966; H-6 to E-965; H-6 to M-964; H-6 to I-963; H-6 to A-962; H-6 to C-961; H-6 to S-960; H-6 to D-959; H-6 to A-958; H-6 to A-957; H-6 to P-956; H-6 to L-955; H-6 to D-954; H-6 to C-953; H-6 to D-952; H-6 to K-951; H-6 to L-950; H-6 to T-949; H-6 to A-948; H-6 to N-947; H-6 to M-946; H-6 to V-945; H-6 to L-944; H-6 to K-943; H-6 to S-942; H-6 to Y-941; H-6 to K-940; H-6 to Y-939; H-6 to E-938; H-6 to L-937; H-6 to K-936; H-6 to Q-935; H-6 to N-934; H-6 to K-933; H-6 to K-932; H-6 to W-931; H-6to F-930; H-6 to Y-929; H-6 to C-928; H-6 to T-927; H-6 to L-926; H-6 to V-925; H-6 to T-924; H-6 to L-923; H-6 to L-922; H-6 to I-921; H-6 to A-920; H-6 to T-919; H-6 to C-918; H-6 to T-917; H-6 to G-916; H-6 to A-915; H-6 to S-914; H-6 to I-913; H-6 to G-912; H-6 to V-911; H-6 to K-910; H-6 to L-909; H-6 to W-908; H-6 to F-907; H-6 to D-906; H-6 to I-905; H-6 to T-904; H-6 to K-903; H-6 to C-902; H-6 to I-901; H-6 to T-900; H-6 to V-899; H-6 to R-898; H-6 to Q-897; H-6 to E-896; H-6 to P-895; H-6 to L-894; H-6 to S-893; H-6 to I-892; H-6 to G-891; H-6 to G-890; H-6 to S-889; H-6 to C-888; H-6 to L-887; H-6 to K-886; H-6 to P-885; H-6 to E-884; H-6 to R-883; H-6 to W-882; H-6 to V-881; H-6 to Y-880; H-6 to T-879; H-6 to T-878; H-6 to K-877; H-6 to Q-876; H-6 to I-875; H-6 to G-874; H-6 to A-873; H-6 to V-872; H-6 to C-871; H-6 to S-870; H-6 to S-869; H-6 to V-868; H-6 to I-867; H-6 to A-866; H-6 to H-865; H-6 to Y-864; H-6 to D-863; H-6 to A-862; H-6 to V-861; H-6 to S-860; H-6 to C-859; H-6 to L-858; H-6 to P-857; H-6 to C-856; H-6 to A-855; H-6 to A-854; H-6 to A-853; H-6 to S-852; H-6 to E-851; H-6 to W-850; H-6 to L-849; H-6 to F-848; H-6 to H-847; H-6 to F-846; H-6 to N-845; H-6 to C-844; H-6 to G-843; H-6 to D-842; H-6 to C-841; H-6 to T-840; H-6 to G-839; H-6 to D-838; H-6 to S-837; H-6 to C-836; H-6 to T-835; H-6 to G-834; H-6 to P-833; H-6 to L-832; H-6 to L-831; H-6 to L-830; H-6 to S-829; H-6 to G-828; H-6 to P-827; H-6 to V-826; H-6 to T-825; H-6 to K-824; H-6 to Q-823; H-6 to P-822; H-6 to S-821; H-6 to C-820; H-6 to R-819; H-6 to V-818; H-6 to R-817; H-6 to I-816; H-6 to T-815; H-6 to T-814; H-6 to S-813; H-6 to R-812; H-6 to G-811; H-6 to S-810; H-6 to S-809; H-6 to C-808; H-6 to S-807; H-6 to Q-806; H-6 to T-805; H-6 to V-804; H-6 to D-803; H-6 to N-802; H-6 to S-801; H-6 to R-800; H-6 to Y-799; H-6 to F-798; H-6 to F-797; H-6 to I-796; H-6 to V-795; H-6 to D-794; H-6 to P-793; H-6 to I-792; H-6 to G-791; H-6 to L-790; H-6 to S-789; H-6 to E-788; H-6 to L-787; H-6 to H-786; H-6 to F-785; H-6 to L-784; H-6 to E-783; H-6 to A-782; H-6 to P-781; H-6 to S-780; H-6 to T-779; H-6 to I-778; H-6 to G-777; H-6 to D-776; H-6 to L-775; H-6 to T-774; H-6 to M-773; H-6 to D-772; H-6 to T-771; H-6 to T-770; H-6 to V-769; H-6 to G-768; H-6 to I-767; H-6 to L-766; H-6 to R-765; H-6 to D-764; H-6 to A-763; H-6 to L-762; H-6 to S-761; H-6 to V-760; H-6 to P-759; H-6 to Q-758; H-6 to S-757; H-6 to S-756; H-6 to V-755; H-6 to G-754; H-6 to A-753; H-6 to K-752; H-6 to Y-751; H-6 to G-750; H-6 to T-749; H-6 to V-748; H-6 to E-747; H-6 to P-746; H-6 to P-745; H-6 to I-744; H-6 to I-743; H-6 to V-742; H-6 to A-741; H-6 to Q-740; H-6 to C-739; H-6 to V-738; H-6 to Y-737; H-6 to A-736; H-6 to T-735; H-6 to I-734; H-6 to S-733; H-6 to K-732; H-6 to S-731; H-6 to F-730; H-6 to G-729; H-6 to S-728; H-6 to E-727; H-6 to G-726; H-6 to E-725; H-6 to P-724; H-6 to I-723; H-6 to R-722; H-6 to L-721; H-6 to D-720; H-6 to T-719; H-6 to V-718; H-6 to N-717; H-6 to D-716; H-6 to T-715; H-6 to C-714; H-6 to V-713; H-6 to S-712; H-6 to M-711; H-6 to K-710; H-6 to R-709; H-6 to G-708; H-6 to Q-707; H-6 to N-706; H-6 to G-705; H-6 to C-704; H-6 to L-703; H-6 to S-702; H-6 to L-701; H-6 to T-700; H-6 to F-699; H-6 to H-698; H-6 to H-697; H-6 to F-696; H-6 to Y-695; H-6 to K-694; H-6 to L-693; H-6 to G-692; H-6 to K-691; H-6 to S-690; H-6 to T-689; H-6 to F-688; H-6 to S-687; H-6 to P-686; H-6 to G-685; H-6 to G-684; H-6 to A-683; H-6 to L-682; H-6 to T-681; H-6 to V-680; H-6 to T-679; H-6 to N-678; H-6 to A-677; H-6 to L-676; H-6 to A-675; H-6 to S-674; H-6 to F-673; H-6 to N-672; H-6 to Y-671; H-6 to N-670; H-6 to F-669; H-6 to T-668; H-6 to R-667; H-6 to T-666; H-6 to P-665; H-6 to T-664; H-6 to N-663; H-6 to R-662; H-6 to S-661; H-6 to F-660; H-6 to T-659; H-6 to C-658; H-6 to D-657; H-6 to N-656; H-6 to Y-655; H-6 to C-654; H-6 to L-653; H-6 to S-652; H-6 to H-651; H-6 to I-650; H-6 to K-649; H-6 to N-648; H-6 to N-647; H-6 to K-646; H-6 to T-645; H-6 to G-644; H-6 to P-643; H-6 to G-642; H-6 to C-641; H-6 to P-640; H-6 to V-639; H-6 to C-638; H-6 to A-637; H-6 to Q-636; H-6 to V-635; H-6 to G-634; H-6 to Y-633; H-6 to P-632; H-6 to Q-631; H-6 to H630; H-6 to A-629; H-6 to K-628; H-6 to L-627; H-6 to I-626; H-6 to T-625; H-6 to N-624; H-6 to P-623; H-6 to P-622; H-6 to C-621; H-6 to S-620; H-6 to H-619; H-6 to C-618; H-6 to T-617; H-6 to G-616; H-6 to S-615; H-6 to D-614; H-6 to R-613; H-6 to D-612; H-6 to I-611; H-6 to Y-610; H-6 to Y-609; H-6 to G-608; H-6 to A-607; H-6 to P-606; H-6 to C-605; H-6 to S-604; H-6 to T-603; H-6 to C-602; H-6 to S-601; H-6 to S-600; H-6 to G-599; H-6 to V-598; H-6 to D-597; H-6 to S-596; H-6 to A-595; H-6 to E-594; H-6 to L-593; H-6 to A-592; H-6 to C-591; H-6 to P-590; H-6 to R-589; H-6 to C-588; H-6 to Y-587; H-6 to S-586; H-6 to A-585; H-6 to V-584; H-6 to G-583; H-6 to N-582; H-6 to M-581; H-6 to V-580; H-6 to N-579; H-6 to T-578; H-6 to V-577; H-6 to N-576; H-6 to I-575; H-6 to S-574; H-6 to Y-573; H-6 to I-572; H-6 to K-571; H-6 to A-570; H-6 to V-569; H-6 to D-568; H-6 to N-567; H-6 to T-566; H-6 to Y-565; H-6 to K-564; H-6 to R-563; H-6 to S-562; H-6 to A-561; H-6 to E-560; H-6 to H-559; H-6 to F-558; H-6 to T-557; H-6 to T-556; H-6 to R-555; H-6 to Q-554; H-6 to F-553; H-6 to A-552; H-6 to W-551; H-6 to T-550; H-6 to F-549; H-6 to S-548; H-6 to T-547; H-6 to T-546; H-6 to T-545; H-6 to N-544; H-6 to E-543; H-6 to E-542; H-6 to I-541; H-6 to I-540; H-6 to Y-539; H-6 to T-538; H-6 to Y-537; H-6 to S-536; H-6 to Q-535; H-6 to K-534; H-6 to G-533; H-6 to K-532; H-6 to S-531; H-6 to G-530; H-6 to K-529; H-6 to W-528; H-6 to T-527; H-6 to E-526; H-6 to V-525; H-6 to P-524; H-6 to T-523; H-6 to N-522; H-6 to T-521; H-6 to R-520; H-6 to S-519; H-6 to N-518; H-6 to V-517; H-6 to G-516; H-6 to V-515; H-6 to M-514; H-6 to F-513; H-6 to Y-512; H-6 to L-511; H-6 to E-510; H-6 to C-509; H-6 to N-508; H-6 to V-507; H-6 to S-506; H-6 to C-505; H-6 to L-504; H-6 to T-503; H-6 to E-502; H-6 to F-501; H-6 to V-500; H-6 to F-499; H-6 to T-498; H-6 to l-497; H-6 to R-496; H-6 to A-495; H-6 to V-494; H-6 to E-493; H-6 to K-492; H-6 to N-491; H-6 to E-490; H-6 to T-489; H-6 to D-488; H-6 to A-487; H-6 to M-486; H-6 to V-485; H-6 to S-484; H-6 to Q-483; H-6 to P-482; H-6 to P-481; H-6 to R-480; H-6 to F-479; H-6 to G-478; H-6 to P-477; H-6 to V-476; H-6 to V-475; H-6 to L-474; H-6 to T-473; H-6 to L-472; H-6 to I-471; H-6 to M-470; H-6 to F-469; H-6 to D-468; H-6 to N-467; H-6 to D-466; H-6 to S-465; H-6 to A-464; H-6 to G-463; H-6 to A-462; H-6 to A-461; H-6 to T-460; H-6 to Y-459; H-6 to I-458; H-6 to H-457; H-6 to D-456; H-6 to G-455; H-6 to A-454; H-6 to V-453; H-6 to E-452; H-6 to W-451; H-6 to G-450; H-6 to T-449; H-6 to M-448; H-6 to G-447; H-6 to K-446; H-6 to Y-445; H-6 to E-444; H-6 to F-443; H-6 to N-442; H-6 to I-441; H-6 to G-440; H-6 to S-439; H-6 to L-438; H-6 to V-437; H-6 to T-436; H-6 to T-435; H-6 to E-434; H-6 to M-433; H-6 to N-432; H-6 to T-431; H-6 to P-430; H-6 to L-429; H-6 to T-428; H-6 to N-427; H-6 to W-426; H-6 to W-425; H-6 to K-424; H-6 to Y-423; H-6 to E-422; H-6 to F-421; H-6 to G-420; H-6 to V-419; H-6 to A-418; H-6 to P-417; H-6 to E-416; H-6 to T-415; H-6 to G-414; H-6 to A-413; H-6 to P-412; H-6 to C-411; H-6 to R-410; H-6 to T-409; H-6 to C-408; H-6 to D-407; H-6 to S-406; H-6 to G-405; H-6 to N-404; H-6 to S-403; H-6 to Y-402; H-6 to S-401; H-6 to G-400; H-6 to Y-399; H-6 to P-398; H-6 to C-397; H-6 to P-396; H-6 to Q-395; H-6 to C-394; H-6 to T-393; H-6 to S-392; H-6 to N-391; H-6 to N-390; H-6 to T-389; H-6 to K-388; H-6 to F-387; H-6 to F-386; H-6 to G-385; H-6 to P-384; H-6 to N-383; H-6 to C-382; H-6 to P-381; H-6 to P-380; H-6 to C-379; H-6 to H-378; H-6 to T-377; H-6 to K-376; H-6 to V-375; H-6 to G-374; H-6 to S-373; H-6 to A-372; H-6 to P-371; H-6 to L-370; H-6 to K-369; H-6 to V-368; H-6 to A-367; H-6 to G-366; H-6 to E-365; H-6 to L-364; H-6 to D-363; H-6 to E-362; H-6 to S-361; H-6 to C-360; H-6 to I-359; H-6 to K-358; H-6 to P-357; H-6 to K-356; H-6 to A-355; H-6 to W-354; H-6 to K-353; H-6 to Y-352; H-6 to M-351; H-6 to L-350; H-6 to Q-349; H-6 to T-348; H-6 to E-347; H-6 to G-346; H-6 to N-345; H-6 to A-344; H-6 to D-343; H-6 to C-342; H-6 to A-341; H-6 to T-340; H-6 to H-339; H-6 to T-338; H-6 to Y-337; H-6 to F-336; H-6 to Y-335; H-6 to D-334; H-6 to K-333; H-6 to D-332; H-6 to T-331; H-6 to C-330; H-6 to A-329; H-6 to P-328; H-6 to R-327; H-6 to V-326; H-6 to N-325; H-6 to C-324; H-6 to S-323; H-6 to S-322; H-6 to S-321; H-6 to G-320; H-6 to K-319; H-6 to E-318; H-6 to S-317; H-6 to Y-316; H-6 to K-315; H-6 to D-314; H-6 to P-313; H-6 to D-312; H-6 to C-311; H-6 to Q-310; H-6 to H-309; H-6 to C-308; H-6 to S-307; H-6 to T-306; H-6 to E-305; H-6 to G-304; H-6 to K-303; H-6 to N-302; H-6 to S-301; H-6 to Y-300; H-6 to S-299; H-6 to N-298; H-6 to A-297; H-6 to P-296; H-6 to C-295; H-6 to L-294; H-6 to K-293; H-6 to C-292; H-6 to F-291; H-6 to S-290; H-6 to S-289; H-6 to G-288; H-6 to Q-287; H-6 to K-286; H-6 to D-285; H-6 to A-284; H-6 to Y-283; H-6 to T-282; H-6 to G-281; H-6 to P-280; H-6 to K-279; H-6 to C-278; H-6 to P-277; H-6 to F-276; H-6 to C-275; H-6 to E-274; H-6 to S-273; H-6 to T-272; H-6 to Y-271; H-6 to A-270; H-6 to V-269; H-6 to G-268; H-6 to T-267; H-6 to I-266; H-6 to A-265; H-6 to I-264; H-6 to N-263; H-6 to R-262; H-6 to V-261; H-6 to L-260; H-6 to V-259; H-6 to P-258; H-6 to K-257; H-6 to P-256; H-6 to V-255; H-6 to K-254; H-6 to T-253; H-6 to W-252; H-6 to V-251; H-6 to S-250; H-6 to F-249; H-6 to A-248; H-6 to T-247; H-6 to T-246; H-6 to R-245; H-6 to W-244; H-6 to Y-243; H-6 to L-242; H-6 to V-241; H-6 to N-240; H-6 to N-239; H-6 to G-238; H-6 to R-237; H-6 to N-236; H-6 to L-235; H-6 to E-234; H-6 to V-233; H-6 to S-232; H-6 to H-231; H-6 to F-230; H-6 to E-229; H-6 to W-228; H-6 to G-227; H-6 to K-226; H-6 to E-225; H-6 to T-224; H-6 to T-223; H-6 to K-222; H-6 to M-221; H-6 to W-220; H-6 to R-219; H-6 to S-218; H-6 to D-217; H-6 to D-216; H-6 to A-215; H-6 to N-214; H-6 to P-213; H-6 to Q-212; H-6 to C-211; H-6 to Q-210; H-6 to D-209; H-6 to N-208; H-6 to Q-207; H-6 to V-206; H-6 to F-205; H-6 to F-204; H-6 to E-203; H-6 to F-202; H-6 to I-201; H-6 to I-200; H-6 to S-199; H-6 to S-198; H-6 to D-197; H-6 to P-196; H-6 to Y-195; H-6 to Y-194; H-6 to Y-193; H-6 to E-192; H-6 to F-191; H-6 to N-190; H-6 to V-189; H-6 to T-188; H-6 to G-187; H-6 to S-186; H-6 to Q-185; H-6 to K-184; H-6 to L-183; H-6 to N-182; H-6 to V-181; H-6 to A-180; H-6 to Y-179; H-6 to M-178; H-6 to L-177; H-6 to T-176; H-6 to A-175; H-6 to T-174; H-6 to C-173; H-6 to E-172; H-6 to D-171; H-6 to T-170; H-6 to N-169; H-6 to F-168; H-6 to A-167; H-6 to I-166; H-6 to Y-165; H-6 to D-164; H-6 to G-163; H-6 to R-162; H-6 to P-161; H-6 to V-160; H-6 to W-159; H-6 to K-158; H-6 to S-157; H-6 to S-156; H-6 to T-155; H-6 to C-154; H-6 to N-153; H-6 to G-152; H-6 to T-151; H-6 to S-150; H-6 to E-149; H-6 to A-148; H-6 to A-147; H-6 to S-146; H-6 to D-145; H-6 to D-144; H-6 to L-143; H-6 to E-142; H-6 to M-141; H-6 to N-140; H-6 to A-139; H-6 to S-138; H-6 to L-137; H-6 to S-136; H-6 to A-135; H-6 to F-134; H-6 to G-133; H-6 to H-132; H-6 to P-131; H-6 to L-130; H-6 to E-129; H-6 to D-128; H-6 to W-127; H-6 to E-126; H-6 to D-125; H-6 to F-124; H-6 to R-123; H-6 to I-122; H-6 to G-121; H-6 to T-120; H-6 to G-19; H-6 to L-118; H-6 to S-117; H-6 to Y-116; H-6 to R-115; H-6 to G-114; H-6 to E-113; H-6 to A-112; H-6 to C-111; H-6 to P-110; H-6 to K-109; H-6 to C-108; H-6 to S-107; H-6 to Q-106; H-6 to D-105; H-6 to K-104; H-6 to M-103; H-6 to D-102; H-6 to L-101; H-6 to F-100; H-6 to E-99; H-6 to G-98; H-6 to A-97; H-6 to N-96; H-6 to C-95; H-6 to S-94; H-6 to F-93; H-6 to S-92; H-6 to C-91; H-6 to E-90; H-6 to T-89; H-6 to G-88; H-6 to K-87; H-6 to V-86; H-6 to P-85; H-6 to D-84; H-6 to P-83; H-6 to L-82; H-6 to S-81; H-6 to T-80; H-6 to C-79; H-6 to L-78; H-6 to G-77; H-6 to P-76; H-6 to T-75; H-6 to H-74; H-6 to P-73; H-6 to V-72; H-6 to A-71; H-6 to V-70; H-6 to R-69; H-6 to W-68; H-6 to R-67; H-6 to S-66; H-6 to G-65; H-6 to T-64; H-6 to S-63; H-6 to D-62; H-6 to C-61; H-6 to A-60; H-6 to T-59; H-6 to Y-58; H-6 to E-57; H-6 to Y-56; H-6 to H-55; H-6 to Y-54; H-6 to E-53; H-6 to S-52; H-6 to E-51; H-6 to K-50; H-6 to C-49; H-6 to A-48; H-6 to H-47; H-6 to L-46; H-6 to E-45; H-6 to P-44; H-6 to G-43; H-6 to T-42; H-6 to G-41; H-6 to Q-40; H-6 to T-39; H-6 to V-38; H-6 to Q-37; H-6 to F-36; H-6 to A-35; H-6 to T-34; H-6 to G-33; H-6 to A-32; H-6 to W-31; H-6 to L-30; H-6 to L-29; H-6 to L-28; H-6 to R-27; H-6 to

W-26; H-6 to L-25; H-6 to R-24; H-6 to P-23; H-6 to I-22; H-6 to R-21; H-6 to R-20; H-6 to E-19; H-6 to T-18; H-6 to R-17; H-6 to G-16; H-6 to R-15; H-6 to V-14; H-6 to R-13; H-6 to A-12; of SEQ ID NO:40. Polynucleotides encoding these polypeptides are also encompassed by the invention.

In another embodiment, N-terminal deletions of the predicted extracellular domain of the predicted mature TR13 protein, with the amino acid sequence shown in FIGS. 7A–E, can be described by the general formula $n^2$-906, where $n^2$ is a number from 2 to 900, corresponding to the position of amino acid identified in FIGS. 7A–E (SEQ ID NO:40). N-terminal deletions of the TR13 polypeptide of the invention shown as SEQ ID NO:40 include polypeptides comprising, or alternatively consisting of, the amino acid sequence of residues: T-42 to D-906; G-43 to D-906; P-44 to D-906; E-45 to D-906; L-46 to D-906; H-47 to D-906; A-48 to D-906; C-49 to D-906; K-50 to D-906; E-51 to D-906; S-52 to D-906; E-53 to D-906; Y-54 to D-906; H-55 to D-906; Y-56 to D-906; E-57 to D-906; Y-58 to D-906; T-59 to D-906; A-60 to D-906; C-61 to D-906; D-62 to D-906; S-63 to D-906; T-64 to D-906; G-65 to D-906; S-66 to D-906; R-67 to D-906; W-68 to D-906; R-69 to D-906; V-70 to D-906; A-71 to D-906; V-72 to D-906; P-73 to D-906; H-74 to D-906; T-75 to D-906; P-76 to D-906; G-77 to D-906; L-78 to D-906; C-79 to D-906; T-80 to D-906; S-81 to D-906; L-82 to D-906; P-83 to D-906; D-84 to D-906; P-85 to D-906; V-86 to D-906; K-87 to D-906; G-88 to D-906; T-89 to D-906; E-90 to D-906; C-91 to D-906; S-92 to D-906; F-93 to D-906; S-94 to D-906; C-95 to D-906; N-96 to D-906; A-97 to D-906; G-98 to D-906; E-99 to D-906; F-100 to D-906; L-101 to D-906; D-102 to D-906; M-103 to D-906; K-104 to D-906; D-105to D-906; Q-106 to D-906; S-107 to D-906; C-108 to D-906; K-109 to D-906; P-110 to D-906; C-111 to D-906; A-112 to D-906; E-113 to D-906; G-114 to D-906; R-115 to D-906; Y-116 to D-906; S-117 to D-906; L-118 to D-906; G-119 to D-906; T-120 to D-906; G-121 to D-906; I-122 to D-906; R-123 to D-906; F-124 to D-906; D-125 to D-906; E-126 to D-906; W-127 to D-906; D-128 to D-906; E-129 to D-906; L-130 to D-906; P-131 to D-906; H-132 to D-906; G-133 to D-906; F-134 to D-906; A-135 to D-906; S-136 to D-906; L-137 to D-906; S-138 to D-906; A-139 to D-906; N-140 to D-906; M-141 to D-906; E-142 to D-906; L-143 to D-906; D-144 to D-906; D-145 to D-906; S-146 to D-906; A-147 to D-906; A-148 to D-906; E-149 to D-906; S-150 to D-906; T-151 to D-906; G-152 to D-906; N-153 to D-906; C-154 to D-906; T-155 to D-906; S-156 to D-906; S-157 to D-906; K-158 to D-906; W-159 to D-906; V-160 to D-906; P-161 to D-906; R-162 to D-906; G-163 to D-906; D-164 to D-906; Y-165 to D-906; I-166 to D-906; A-167 to D-906; F-168 to D-906; N-169 to D-906; T-170 to D-906; D-171 to D-906; E-172 to D-906; C-173 to D-906; T-174 to D-906; A-175 to D-906; T-176 to D-906; L-177 to D-906; M-178 to D-906; Y-179 to D-906; A-180 to D-906; V-181 to D-906; N-182 to D-906; L-183 to D-906; K-184 to D-906; Q-185 to D-906; S-186 to D-906; G-187 to D-906; T-188 to D-906; V-189 to D-906; N-190 to D-906; F-191 to D-906; E-192 to D-906; Y-193 to D-906; Y-194 to D-906; Y-195 to D-906; P-196 to D-906; D-197 to D-906; S-198 to D-906; S-199 to D-906; I-200 to D-906; I-201 to D-906; F-202 to D-906; E-203to D-906; F-204 to D-906; F-205 to D-906; V-206 to D-906; Q-207 to D-906; N-208 to D-906; D-209 to D-906; Q-210 to D-906; C-211 to D-906; Q-212 to D-906; P-213 to D-906; N-214 to D-906; A-215 to D-906; D-216 to D-906; D-217 to D-906; S-218 to D-906; R-219 to D-906; W-220 to D-906; M-221 to D-906; K-222 to D-906; T-223 to D-906; T-224 to D-906; E-225 to D-906; K-226 to D-906; G-227 to D-906; W-228 to D-906; E-229 to D-906; F-230 to D-906; H-231 to D-906; S-232 to D-906; V-233 to D-906; E-234 to D-906; L-235 to D-906; N-236 to D-906; R-237 to D-906; G-238 to D-906; N-239 to D-906; N-240 to D-906; V-241 to D-906; L-242 to D-906; Y-243 to D-906; W-244 to D-906; R-245 to D-906; T-246 to D-906; T-247 to D-906; A-248 to D-906; F-249 to D-906; S-250 to D-906; V-251 to D-906; W-252 to D-906; T-253 to D-906; K-254 to D-906; V-255 to D-906; P-256 to D-906; K-257 to D-906; P-258 to D-906; V-259 to D-906; L-260 to D-906; V-261 to D-906; R-262 to D-906; N-263 to D-906; I-264 to D-906; A-265 to D-906; I-266 to D-906; T-267 to D-906; G-268 to D-906; V-269 to D-906; A-270 to D-906; Y-271 to D-906; T-272 to D-906; S-273 to D-906; E-274 to D-906; C-275 to D-906; F-276 to D-906; P-277 to D-906; C-278 to D-906; K-279 to D-906; P-280 to D-906; G-281 to D-906; T-282 to D-906; Y-283 to D-906; A-284 to D-906; D-285 to D-906; K-286 to D-906; Q-287 to D-906; G-288 to D-906; S-289 to D-906; S-290 to D-906; F-291 to D-906; C-292 to D-906; K-293 to D-906; L-294 to D-906; C-295 to D-906; P-296 to D-906; A-297 to D-906; N-298 to D-906; S-299 to D-906; Y-300 to D-906; S-301 to D-906; N-302 to D-906; K-303 to D-906; G-304 to D-906; E-305 to D-906; T-306 to D-906; S-307 to D-906; C-308 to D-906; H-309 to D-906; Q-310 to D-906; C-311 to D-906; D-312 to D-906; P-313 to D-906; D-314 to D-906; K-315 to D-906; Y-316 to D-906; S-317 to D-906; E-318 to D-906; K-319 to D-906; G-320 to D-906; S-321 to D-906; S-322 to D-906; S-323 to D-906; C-324 to D-906; N-325 to D-906; V-326 to D-906; R-327 to D-906; P-328 to D-906; A-329 to D-906; C-330 to D-906; T-331 to D-906; D-332 to D-906; K-333 to D-906; D-334 to D-906; Y-335 to D-906; F-336 to D-906; Y-337 to D-906; T-338 to D-906; H-339 to D-906; T-340 to D-906; A-341 to D-906; C-342 to D-906; D-343 to D-906; A-344 to D-906; N-345 to D-906; G-346 to D-906; E-347 to D-906; T-348 to D-906; Q-349 to D-906; L-350 to D-906; M-351 to D-906; Y-352 to D-906; K-353 to D-906; W-354 to D-906; A-355 to D-906; K-356 to D-906; P-357 to D-906; K-358 to D-906; I-359 to D-906; C-360 to D-906; S-361 to D-906; E-362 to D-906; D-363 to D-906; L-364 to D-906; E-365 to D-906; G-366 to D-906; A-367 to D-906; V-368 to D-906; K-369 to D-906; L-370 to D-906; P-371 to D-906; A-372 to D-906; S-373 to D-906; G-374 to D-906; V-375 to D-906; K-376 to D-906; T-377 to D-906; H-378 to D-906; C-379 to D-906; P-380 to D-906; P-381 to D-906; C-382 to D-906; N-383 to D-906; P-384 to D-906; G-385 to D-906; F-386 to D-906; F-387 to D-906; K-388 to D-906; T-389 to D-906; N-390 to D-906; N-391 to D-906; S-392 to D-906; T-393 to D-906; C-394 to D-906; Q-395 to D-906; P-396 to D-906; C-397 to D-906; P-398 to D-906; Y-399 to D-906; G-400 to D-906; S-401 to D-906; Y-402 to D-906; S-403 to D-906; N-404 to D-906; G-405 to D-906; S-406 to D-906; D-407 to D-906; C-408 to D-906; T-409 to D-906; R-410 to D-906; C-411 to D-906; P-412 to D-906; A-413 to D-906; G-414 to D-906; T-415 to D-906; E-416 to D-906; P-417 to D-906; A-418 to D-906; V-419 to D-906; G-420 to D-906; F-421 to D-906; E-422 to D-906; Y-423 to D-906; K-424 to D-906; W-425 to D-906; W-426 to D-906; N-427 to D-906; T-428 to D-906; L-429 to D-906; P-430 to D-906; T-431 to D-906; N-432 to D-906; M-433 to D-906; E-434 to D-906; T-435 to D-906; T-436 to D-906; V-437 to D-906; L-438 to D-906; S-439 to D-906; G-440 to D-906; I-441 to D-906; N-442 to D-906; F-443 to D-906; E-444 to D-906; Y-445 to D-906; K-446 to D-906; G-447 to D-906; M-448 to D-906; T-449 to D-906; G-450 to D-906; W-451 to D-906; E-452 to D-906; V-453 to D-906; A-454 to D-906; G-455 to D-906; D-456 to D-906; H-457 to D-906; I -458 to D-906; Y-459 to D-906; T-460 to D-906; A-461 to D-906; A-462 to D-906; G-463 to D-906; A-464 to D-906; S-465 to D-906; D-466 to D-906; N-467 to D-906; D-468 to D-906; F-469 to D-906; M-470 to D-906; I-471 to D-906; L-472 to D-906; T-473 to D-906; L-474 to D-906; V-475 to D-906; V-476 to D-906; P-477to D-906; G-478 to D-906; F-479 to D-906; R-480 to D-906; P-481 to D-906; P-482 to D-906; Q-483 to D-906; S-484 to D-906; V-485 to D-906; M-486 to D-906; A-487 to D-906; D-488 to D-906 T-489 to D-906; E-490 to D-906; N-491 to D-906; K-492 to D-906; E-493 to D-906; V-494 to D-906; A-495 to D-906; R-496 to D-906; I-497 to D-906; T-498 to D-906; F-499 to D-906; V-500 to D-906; F-501 to D-906; E-502 to D-906; T-503 to D-906; L-504 to D-906; C-505 to D-906; S-506 to D-906; V-507 to D-906; N-508 to D-906; C-509 to D-906; F-510 to D-906; L-511 to D-906; Y-512 to D-906; F-513 to D-906; M-514 to D-906; V-515 to D-906; G-516 to D-906; V-517 to D-906; N-918 to D-906; S-19 to D-906; R-520 to D-906; T-521 to D-906; N-522 to D-906; T-523 to D-906; P-524 to D-906; V-525 to D-906; E-526 to D-906; T-527 to D-906; W-528 to D-906; K-529 to D-906; G-530 to D-906; S-531 to D-906; K-532 to D-906; G-533 to D-906; K-534 to D-906; Q-535 to D-906; S-536 to D-906; Y-537 to D-906; T-538 to D-906; Y-539 to D-906; I-540 to D-906; I-541 to D-906; E-542 to D-906; E-543 to D-906; N-544 to D-906; T-545 to D-906; T-546 to D-906; T-547 to D-906; S-548 to D-906; F-549 to D-906; T-550 to D-906; W-551 to D-906; A-552 to D-906; F-553 to D-906; Q-554 to D-906; R-555 to D-906; T-556 to D-906; T-557 to D-906; F-558 to D-906; H-559 to D-906; E-560 to D-906; A-561 to D-906; S-562 to D-906; R-563 to D-906; K-564 to D-906; Y-565 to D-906; T-566 to D-906; N-567 to D-906; D-568 to D-906; V-569 to D-906; A-570 to D-906; K-571 to D-906; I-572 to D-906; Y-573 to D-906; S-574 to D-906; I-575 to D-906; N-576 to D-906; V-577 to D-906; T-578 to D-906; N-579 to D-906; V-580 to D-906; M-581 to D-906; N-582 to D-906; G-583 to D-906; V-584 to D-906; A-585 to D-906; S-586 to D-906; Y-587 to D-906; C-588 to D-906; R-589 to D-906; P-590 to D-906; C-591 to D-906; A-592 to D-906; L-593 to D-906; E-594 to D-906; A-595 to D-906; S-596 to D-906; D-597 to D-906; V-598 to D-906; G-599 to D-906; S-600 to D-906; S-601 to D-906; C-602 to D-906; T-603 to D-906; S-604 to D-906; C-605 to D-906; P-606 to D-906; A-607 to D-906; G-608 to D-906; Y-609 to D-906; Y-610 to D-906; I-611 to D-906; D-612 to D-906; R-613 to D-906; D-614 to D-906; S-615 to D-906; G-616 to D-906; T-617 to D-906; C-618 to D-906; H-619 to D-906; S-620 to D-906; C-621 to D-906; P-622 to D-906; P-623 to D-906; N-624 to D-906; T-625 to D-906; I-626 to D-906; L-627 to D-906; K-628 to D-906; A-629 to D-906; H-630 to D-906; Q-631 to D-906; P-632 to D-906; Y-633 to D-906; G-634 to D-906; V-635 to D-906; Q-636 to D-906; A-637 to D-906; C-638 to D-906; V-639 to D-906; P-640 to D-906; C-641 to D-906; G-642 to D-906; P-643 to D-906; G-644 to D-906; T-645 to D-906; K-646 to D-906; N-647 to D-906; N-648 to D-906; K-649 to D-906; I-650 to D-906; H-651 to D-906; S-652 to D-906; L-653 to D-906; C-654 to D-906; Y-655 to D-906; N-656 to D-906; D-657 to D-906; C-658 to D-906; T-659 to D-906; F-660 to D-906; S-661 to D-906; R-662 to D-906; N-663 to D-906; T-664 to D-906; P-665 to D-906; T-666 to D-906; R-667 to D-906; T-668 to D-906; F-669 to D-906; N-670 to D-906; Y-671 to D-906; N-672 to D-906; F-673 to D-906; S-674 to D-906; A-675 to D-906; L-676 to D-906; A-677 to D-906; N-678 to D-906; T-679 to D-906; V-680 to D-906; T-681 to D-906; L-682 to D-906; A-683 to D-906; G-684 to D-906; G-685 to D-906; P-686 to D-906; S-687 to D-906; F-688 to D-906; T-689 to D-906; S-690 to D-906; K-691 to D-906; G-692 to D-906; L-693 to D-906; K-694 to D-906; Y-695 to D-906; F-696 to D-906; H-697 to D-906; H-698 to D-906; T-699 to D-906; T-700 to D-906; L-701 to D-906; S-702 to D-906; L-703 to D-906; C-704 to D-906; G-705 to D-906; N-706 to D-906; Q-707 to D-906; G-708 to D-906; R-709 to D-906; K-710 to D-906; M-711 to D-906; S-712 to D-906; V-713 to D-906; C-714 to D-906; T-715 to D-906; D-716 to D-906; N-717 to D-906; V-718 to D-906; T-719 to D-906; D-720 to D-906; L-721 to D-906; R-722 to D-906; I-723 to D-906; P-724 to D-906; T-725to D-906; G-726 to D-906; E-727 to D-906; S-728 to D-906; G-729 to D-906; F-730 to D-906; S-731 to D-906; K-732 to D-906; S-733 to D-906; I-734 to D-906; T-735 to D-906; A-736 to D-906; Y-737 to D-906; V-738 to D-906; C-739 to D-906; Q-740 to D-906; A-741 to D-906; V-742 to D-906; I-743 to D-906; I-744 to D-906; P-745to D-906; P-746 to D-906; E-747 to D-906; V-748 to D-906; T-749 to D-906; G-750 to D-906; Y-751 to D-906; K-752 to D-906; A-753 to D-906; G-754 to D-906; V-755 to D-906; S-756 to D-906; S-757 to D-906; Q-758 to D-906; P-759 to D-906; V-760 to D-906; S-761 to D-906; L-762 to D-906; A-763 to D-906; D-764 to D-906; R-765 to D-906; L-766 to D-906; I-767 to D-906; G-768 to D-906; V-769 to D-906; T-770 to D-906; T-771 to D-906; D-772 to D-906; M-773 to D-906; T-774 to D-906; L-775 to D-906; D-776 to D-906; G-777 to D-906; I-778 to D-906; T-779 to D-906; S-780 to D-906; P-781 to D-906; A-782 to D-906; E-783 to D-906; L-784 to D-906; F-785 to D-906; H-786 to D-906; L-787 to D-906; E-788 to D-906; S-789 to D-906; L-790 to D-906; G-791 to D-906; I-792 to D-906; P-793 to D-906; D-794 to D-906; V-795 to D-906; I-796 to D-906; F-797 to D-906; F-798 to D-906; Y-799 to D-906; R-800 to D-906; S-801 to D-906; N-802 to D-906; D-803 to D-906; V-804 to D-906; T-805 to D-906; Q-806 to D-906; S-807 to D-906; C-808 to D-906; S-809 to D-906; S-810 to D-906; G-811 to D-906; R-812 to D-906; S-813 to D-906; T-814 to D-906; T-815 to D-906; I-816 to D-906; R-817to D-906; V-818 to D-906; R-819 to D-906; C-820 to D-906; S-821 to D-906; P-822 to D-906; Q-823 to D-906; K-824 to D-906; T-825 to D-906; V-826 to D-906; P-827 to D-906; G-828 to D-906; S-829 to D-906; L-830 to D-906; L-831 to D-906; L-832 to D-906; P-833 to D-906; G-834 to D-906; T-835 to D-906; C-836 to D-906; S-837 to D-906; D-838 to D-906; G-839 to D-906; T-840 to D-906; C-841 to D-906; D-842 to D-906; G-843 to D-906; C-844 to D-906; N-845 to D-906; F-846 to D-906; H-847 to D-906; F-848 to D-906; L-849 to D-906; W-850 to D-906; E-851 to D-906; S-852 to D-906; A-853 to D-906; A-854 to D-906; A-855 to D-906; C-856 to D-906; P-857 to D-906; L-858 to D-906; C-859 to D-906; S-860 to D-906; V-861 to D-906; A-862 to D-906; D-863 to D-906; Y-864 to D-906; H-865 to D-906; A-866 to D-906; I867 to D-906; V-868 to D-906; S-869 to D-906; S-870 to D-906; C-871 to D-906; V-872 to D-906; A-873 to D-906; G-874 to D-906; I-875 to D-906; Q-876 to D-906; K-877 to D-906; T-878 to D-906; T-879 to D-906; Y-880 to D-906; V-881 to D-906; W-882 to D-906; R-883 to D-906; E-884 to D-906; P-885 to D-906; K-886 to D-906; L-887 to D-906; C-888 to D-906; S-889 to D-906; G-890 to D-906; G-891 to D-906; I892 to D-906; S-893 to D-906; L-894 to D-906; P-895 to D-906; E-896 to D-906; Q-897 to D-906; R-898 to D-906; V-899 to D-906; and T-900 to D-906 of SEQ ID NO:40. Polynucleotides encoding these polypeptides are also encompassed by the invention.

The present invention further provides polypeptides having one or more residues deleted from the carboxy terminus of the predicted extracellular domain of the predicted mature TR13 protein, with the amino acid sequence shown in FIGS. 7A–E (SEQ ID NO:40), up to the alanine residue at position number 48, and polynucleotides encoding such polypeptides. In particular, the present invention provides polypeptides comprising, or alternatively consisting of, the amino acid sequence of residues 42-m$^1$ of FIGS. 7A–D, where m$^1$ is an integer from 48 to 906 corresponding to the position of the amino acid residue in FIGS. 7A–E.

Thus, the invention provides TR13 polypeptides comprising, or alternatively consisting of, the amino acid sequence of residues: T-42 to D-906; T-42 to I-905; T-42 to T-904; T-42 to K-903; T-42 to C-902; T-42 to I-901; T-42 to T-900; T-42 to V-899; T-42 to R-898; T-42 to Q-897; T-42 to E-896; T-42 to P-895; T-42 to L-894; T-42 to S-893; T-42 to I-892; T-42 to G-891; T-42 to G-890; T-42 to S-889; T-42 to C-888; T-42 to L-887; T-42 to K-886; T-42 to P-885; T-42 to E-884; T-42 to R-883; T-42 to W-882; T-42 to V-881; T-42 to Y-880; T-42 to T-879; T-42 to T-878; T-42 to K-877; T-42 to Q-876; T-42 to I-875; T-42 to G-874; T-42 to A-873; T-42 to V-872; T-42 to C-871; T-42 to S-870 T-42 to S-869; T-42 to V-868; T-42 to 1-867; T-42 to A-866; T-42 to H-865; T-42 to Y-864; T-42 to D-863; T-42 to A-862; T-42 to V-861; T-42 to S-860; T-42 to C-859; T-42 to L-858; T-42 to P-857; T-42 to C-856; T-42 to A-855; T-42 to A-854; T-42 to A-853; T-42 to S-852; T-42 to E-851; T-42 to W-850; T-42 to L-849; T-42 to F-848; T-42 to H-847; T-42 to F-846; T-42 to N-845; T-42 to C-844; T-42 to G-843; T-42 to D-842; T-42 to C-841; T-42 to T-840; T-42 to G-839; T-42 to D-838; T-42 to S-837; T-42 to C-836; T-42 to T-835; T-42 to G-834; T-42 to P-833; T-42 to L-832; T-42 to L-831; T-42 to L-830; T-42 to S-829; T-42 to G-828; T-42 to P-827; T-42 to V-826; T-42 to T-825; T-42 to K-824; T-42 to Q-823; T-42 to P-822; T-42 to S-821; T-42 to C-820; T-42 to R-819; T-42 to V-818; T-42 to R-817; T-42 to 1-816; T-42 to T-815; T-42 to T-814; T-42 to S-813; T-42 to R-812; T-42 to G-811; T-42 to S-810; T-42 to S-809; T-42 to C-808; T-42 to S-807; T-42 to Q-806; T-42 to T-805; T-42 to V-804; T-42 to D-803; T-42 to N-802; T-42 to S-801; T-42 to R-800; T-42 to Y-799; T-42 to F-798; T-42 to F-797; T-42 to I-796; T-42 to V-795; T-42 to D-794; T-42 to P-793; T-42 to I-792; T-42 to G-791; T-42 to L-790; T-42 to S-789; T-42 to E-788; T-42 to L-787; T-42 to H-786; T-42 to F-785; T-42 to L-784; T-42 to E-783; T-42 to A-782; T-42 to P-781; T-42 to S-780; T-42 to T-779; T-42 to I-778; T-42 to G-777; T-42 to D-776; T-42 to L-775; T-42 to T-774; T-42 to M-773; T-42 to D-772; T-42 to T-771; T-42 to T-770; T-42 to V-769; T-42 to G-768; T-42 to I-767; T-42 to L-766; T-42 to R-765; T-42 to D-764; T-42 to A-763; T-42 to L-762; T-42 to S-761; T-42 to V-760; T-42 to P-759; T-42 to Q-758; T-42 to S-757; T-42 to S-756; T-42 to V-755; T-42 to G-754; T-42 to A-753; T-42 to K-752; T-42 to Y-751; T-42 to G-750; T-42 to T-749; T-42 to V-748; T-42 to E-747; T-42 to P-746; T-42 to P-745; T-42 to I-744; T-42 to I-743; T-42 to V-742; T-42 to A-741; T-42 to Q-740; T-42 to C-739; T-42 to V-738; T-42 to Y-737; T-42 to A-736; T-42 to T-735; T-42 to I-734; T-42 to S-733; T-42 to K-732; T-42 to S-731; T-42 to F-730; T-42 to G-729; T-42 to S-728; T-42 to E-727; T-42 to G-726; T-42 to E-725; T-42 to P-724; T-42 to I-723; T-42 to R-722; T-42 to L-721; T-42 to D-720; T-42 to T-719; T-42 to V-718; T-42 to N-717; T-42 to D-716; T-42 to T-715; T-42 to C-714; T-42 to 713; T-42 to S-712; T-42 to M-711; T-42 to K-710; T-42 to R-709; T-42 to G-708; T-42 to Q-707; T-42 to N-706; T-42 to G-705; T-42 to C-704; T-42 to L-703; T-42 to S-702; T-42 to L-701; T-42 to T-700; T-42 to F-699; T-42 to T-4298; T-42 to T-4297; T-42 to F-696; T-42 to Y-695; T-42 to K-694; T-42 to L-693; T-42 to G-692; T-42 to K-691; T-42 to S-690; T-42 to T-689; T-42 to F-688; T-42 to S-687; T-42 to P-686; T-42 to G-685; T-42 to G-684; T-42 to A-683; T-42 to L-682; T-42 to S-681; T-42 to V-680; T-42 to T-679; T-42 to N-678; T-42 to A-677; T-42 to L-676; T-42 to A-675; T-42 to S-674; T-42 to F-673; T-42 to N-672; T-42 to Y-671; T-42 to N-670; T-42 to F-669; T-42 to T-668; T-42 to R-667; T-42 to T-666; T-42 to P-665; T-42 to T-664; T-42 to N-663; T-42 to R-662; T-42 to S-661; T-42 to F-660; T-42 to T-659; T-42 to C-658; T-42 to D-657; T-42 to N-656; T-42 to Y-655; T-42 to C-654; T-42 to L-653; T-42 to S-652; T-42 to T-4251; T-42 to I-650; T-42 to K-649; T-42 to N-648; T-42 to N-647; T-42 to K-646; T-42 to T-645; T-42 to G-644; T-42 to P-643; T-42 to G-642; T-42 to C-641; T-42 to P-640; T-42 to V-639; T-42 to C-638; T-42 to A-637; T-42 to Q-636; T-42 to V-635; T-42 to G-634; T-42 to Y-633; T-42 to P-632; T-42 to Q-631; T-42 to T-4230; T-42 to A-629; T-42 to K-628; T-42 to L-627; T-42 to I-626; T-42 to T-625; T-42 to N-624; T-42 to P-623; T-42 to P-622; T-42 to C-621; T-42 to S-620; T-42 to T-4219; T-42 to C-618; T-42 to T-617; T-42 to G-616; T-42 to S-615; T-42 to D-614; T-42 to R-613; T-42 to D-612; T-42 to I-611; T-42 to Y-610; T-42 to Y-609; T-42 to G-608; T-42 to A-607; T-42 to P-606; T-42 to C-605; T-42 to S-604; T-42 to T-603; T-42 to C-602; T-42 to S-601; T-42 to S-600; T-42 to G-599; T-42 to V-598; T42 to D-597; T-42 to S-596; T-42 to A-595; T-42 to E-594; T-42 to L-593; T-42 to A-592; T-42 to C-591; T-42 to P-590; T-42 to R-589; T-42 to C-588; T-42 to Y-587; T-42 to S-586; T-42 to A-585; T-42 to V-584; T-42 to G-583; T-42 to N-582; T-42 to M-581; T-42 to V-580; T-42 to N-579; T-42 to T-578; T-42 to V-577; T-42 to N-576; T-42 to I-575; T-42 to S-574; T-42 to Y-573; T-42 to I-572; T-42 to K-571; T-42 to A-570; T-42 to V-569; T-42 to D-568; T-42 to N-567; T-42 to T-566; T-42 to Y-565; T-42 to K-564; T-42 to R-563; T-42 to S-562; T-42 to A-561; T-42 to E-560; T-42 to H-559; T-42 to F-558; T-42 to T-557; T-42 to T-556; T-42 to R-555; T-42 to Q-554; T-42 to F-553; T-42 to A-552; T-42 to W-551; T-42 to T-550; T-42 to F-549; T-42 to Q-548; T-42 to T-547; T-42 to T-546; T-42 to T-545; T-42 to N-544; T-42 to E-543; T-42 to E-542; T-42 to I-541; T-42 to I-540; T-42 to Y-539; T-42 to T-538; T-42 to Y-537; T-42 to S-536; T-42 to Q-535; T-42 to K-534; T-42 to G-533; T-42 to K-532; T-42 to S-531; T-42 to G-530; T-42 to K-529; T-42 to W-528; T-42 to T-527; T-42 to E-526; T-42 to V-525; T-42 to P-524; T-42 to T-523; T-42 to N-522; T-42 to T-521; T-42 to R-520; T-42 to S-519; T-42 to N-518; T-42 to V-517; T-42 to G-516; T-42 to V-515; T-42 to M-514; T-42 to F-513; T-42 to Y-512; T-42 to L-511; T-42 to E-510; T-42 to C-509; T-42 to N-508; T-42 to V-507; T-42 to S-506; T-42 to C-505; T-42 to L-504; T-42 to T-503; T-42 to E-502; T-42 to F-501; T-42 to V-500; T-42 to F-499; T-42 to T-498; T-42 to 1-497; T-42 to R-496; T-42 to A-495; T-42 to V-494; T-42 to E-493; T-42 to K-492; T-42 to N-491; T-42 to E-490; T-42 to T-489; T-42 to D-488; T-42 to A-487; T-42 to M-486; T-42 to V-485; T-42 to S-484; T-42 to Q-483; T-42 to P-482; T-42 to P-481; T-42 to R-480; T-42 to F-479; T-42 to G-478; T-42 to P-477; T-42 to V-476; T-42 to V-475; T-42 to L-474; T-42 to T-473; T-42 to L-472; T-42 to I-471; T-42 to M-470; T-42 to F-469; T-42 to D-468; T-42 to N-467; T-42 to D-466; T-42 to S-465; T-42 to A-464; T-42 to G-463; T-42 to A-462; T-42 to A-461; T-42 to T-460; T-42 to Y-459; T-42 to I-458; T-42 to H-457; T-42 to D-456; T-42 to G-455; T-42 to A-454; T-42 to V-453; T-42 to E-452; T-42 to W-451; T-42 to G-450; T-42 to T-449; T-42 to M-448; T-42 to G-447; T-42 to K-446; T-42 to Y-445; T-42 to E-444; T-42 to F-443; T-42 to N-442; T-42 to I-441; T-42 to G-440; T-42 to S-439; T-42 to L-438; T-42 to V-437; T-42 to T-436; T-42 to T-435; T-42 to E-434; T-42 to M-433; T-42 to N-432; T-42 to T-431; T-42 to P-430; T-42 to L-429; T-42 to T-428; T-42 to N-427; T-42 to W-426; T-42 to W-425; T-42 to K-424; T-42 to Y-423; T-42 to E-422; T-42 to F-421; T-42 to G-420; T-42 to V-419; T-42 to A-418; T-42 to P-417; T-42 to E-416; T-42 to F-415; T-42 to G-414; T-42 to A-413; T-42 to P-412; T-42 to C-411; T-42 to R-410; T-42 to T-409; T-42 to C-408; T-42 to D-407; T-42 to S-406; T-42 to G-405; T-42 to N-404; T-42 to S-403; T-42 to Y-402; T-42 to S-401; T-42 to G-400; T-42 to Y-399; T-42 to P-398; T-42 to C-397; T-42 to P-396; T-42 to Q-395; T-42 to C-394; T-42 to T-393; T-42 to S-392; T-42 to N-391; T-42 to N-390; T-42 to T-389; T-42 to K-388; T-42 to F-387; T-42 to F-386; T-42 to G-385; T-42 to P-384; T-42 to N-383; T-42 to C-382; T-42 to P-381; T-42 to P-380; T-42 to C-379; T-42 to H-378; T-42 to T-377; T-42 to K-376; T-42 to V-375; T-42 to G-374; T-42 to C -373; T-42 to A-372; T-42 to P-371; T-42 to L-370; T-42 to K-369; T-42 to V-368; T-42 to A-367; T-42 to G-366; T-42 to E-365; T-42 to L-364; T-42 to D-363; T-42 to E-362; T-42 to S-361; T-42 to C-360; T-42 to I-359; T-42 to K-358; T-42 to P-357; T-42 to K-356; T-42 to A-355; T-42 to W-354; T-42 to K-353; T-42 to Y-352; T-42 to M-351; T-42 to L-350; T-42 to Q-349; T-42 to T-348; T-42 to L-347; T-42 to G-346; T-42 to N-345; T-42 to A-344; T-42 to D-343; T-42 to C-342; T-42 to A-341; T-42 to T-340; T-42 to U-339; T-42 to T-338; T-42 to Y-337; T-42 to F-336; T-42 to Y-335; T-42 to D-334; T-42 to K-333; T-42 to D-332; T-42 to T-331; T-42 to C-330; T-42 to A-329; T-42 to P-328; T-42 to R-327; T-42 to V-326; T-42 to N-325; T-42 to C-324; T-42 to D-323; T-42 to S-322; T-42 to S-321; T-42 to G-320; T-42 to K-319; T-42 to E-318; T-42 to P-317; T-42 to Y-316; T-42 to K-315; T-42 to D-314; T-42 to P-313; T-42 to D-312; T-42 to C -31 1; T-42 to Q-310; T-42 to H-309; T-42 to C-308; T-42 to S-307; T-42 to T-306; T-42 to E-305; T-42 to G-304; T-42 to K-303; T-42 to N-302; T-42 to A-301; T-42 to Y-300; T-42 to H-29 9; T-42 to N-298; T-42 to A-297; T-42 to P-296; T-42 to C-295; T-42 to L-294; T-42 to K-293; T-42 to C-292; T-42 to F-291; T-42 to S-290; T-42 to S-289; T-42 to G-288; T-42 to Q-287; T-42 to K-286; T-42 to D-285; T-42 to A-284; T-42 to Y-283; T-42 to T-282; T-42 to G-281; T-42 to P-280; T-42 to K-279; T-42 to C-278; T-42 to P-277; T-42 to F-276; T-42 to C-275; T-42 to E-274; T-42 to S-273; T-42 to T-272; T-42 to Y-271; T-42 to A-270; T-42 to V-269; T-42 to G-268; T-42 to T-267; T-42 to C-266; T-42 to A-265; T-42 to I-264; T-42 to N-263; T-42 to R-262; T-42 to V-261; T-42 to L-260; T-42 to V-259; T-42 to P-258; T-42 to K-257; T-42 to P-256; T-42 to V-255; T-42 to K-254; T-42 to T-253; T-42 to W-252; T-42 to V-251; T-42 to S-250; T-42 to F-249; T-42 to A-248; T-42 to T-247; T-42 to T-246; T-42 to R-245; T-42 to W-244; T-42 to Y-243; T-42 to L-242; T-42 to V-241; T-42 to N-240; T-42 to N-239; T-42 to G-238; T-42 to R-237; T-42 to N-236; T-42 to L-235; T-42 to E-234; T-42 to V-233; T-42 to S-232; T-42 to H-231; T-42 to F-230; T-42 to E-229; T-42 to W-228; T-42 to G-227; T-42 to K-226; T-42 to E-225; T-42 to T-224; T-42 to T-223; T-42 to K-222; T-42 to M-221; T-42 to W-220; T-42 to R-219; T-42 to S-218; T-42 to D-217; T-42 to D-216; T-42 to A-215; T-42 to N-214; T-42 to P-213; T-42 to Q-212; T-42 to C-211; T-42 to Q-210; T-42 to D-209; T-42 to N-208; T-42 to Q-207; T-42 to V-206; T-42 to F-205; T-42 to F-204; T-42 to E-203; T-42 to F-202; T-42 to I-201; T-42 to I-200; T-42 to S-199; T-42 to S-198; T-42 to D-197; T-42 to P-196; T-42 to Y-195; T-42 to Y-194; T-42 to Y-193; T-42 to E-192; T-42 to F-191; T-42 to N-190; T-42 to V-189; T-42 to T-188; T-42 to G-187; T-42 to E-186; T-42 to Q-185; T-42 to K-184; T-42 to L-183; T-42 to N-182; T-42 to V-181; T-42 to A-180; T-42 to Y-179; T-42 to M-178 ; T-42 to L-177; T-42 to T-176; T-42 to A-175; T-42 to T-174; T-42 to C-173; T-42 to E-172; T-42 to D-171; T-42 to T-170; T-42 to N-169; T-42 to F-168; T-42 to A-167; T-42 to I-166; T-42 to Y-165; T-42 to D-164; T-42 to G-163; T-42 to R-162; T-42 to P-161; T-42 to V-160; T-42 to W-159; T-42 to K-158; T-42 to S-157; T-42 to S-156; T-42 to T-155; T-42 to C-154; T-42 to N-153; T-42 to G-152; T-42 to T-151; T-42 to S-150; T-42 to E-149; T-42 to A-148; T-42 to A-147; T-42 to S-146; T-42 to D-145; T-42 to D-144; T-42 to L-143; T-42 to E-142; T-42 to M-141; T-42 to N-140; T-42 to A-139; T-42 to S-138; T-42 to L-137; T-42 to S-136; T-42 to A-135; T-42 to F-134; T-42 to G-133; T-42 to H-132; T-42 to P-131; T-42 to L-130; T-42 to E-129; T-42 to D-128; T-42 to W-127; T-42 to E-126; T-42 to D-125; T-42 to F-124; T-42 to R-123; T-42 to I-122; T-42 to G-121; T-42 to T-120; T-42 to G-l19; T-42 to L-118; T-42 to S-117; T-42 to Y-116; T-42 to R-115; T-42 to G-114; T-42 to E-113; T-42 to A-112; T-42 to C-111; T-42 to P-110; T-42 to K-109; T-42 to C-108; T-42 to S-107; T-42 to Q-106; T-42 to D-105; T-42 to K-104; T-42 to M-103; T-42 to D-102; T-42 to L-101; T-42 to F-100; T-42 to E-99; T-42 to G-98; T-42 to A-97; T-42 to N-96; T-42 to C-95; T-42 to S-94; T-42 to F-93; T-42 to S-92; T-42 to C-91; T-42 to E-90; T-42 to T-89; T-42 to G-88; T-42 to K-87; T-42 to V-86; T-42 to P-85; T-42 to D-84; T-42 to P-83; T-42 to L-82; T-42 to S-81; T-42 to T-80; T-42 to C-79; T-42 to L-78; T-42to G-77; T-42 to P-76; T-42 to T-75; T-42 to H-74; T-42 to P-73; T-42 to V-72; T-42 to A-71; T-42 to V-70; T-42 to R-69; T-42 to W-68; T-42 to R-67; T-42 to S-66; T-42 to G-65; T-42 to T-64; T-42 to S-63; T-42 to D-62; T-42 to C-61; T-42 to A-60; T-42 to T-59; T-42 to Y-58; T-42 to E-57; T-42 to Y-56; T-42 to H-55; T-42 to Y-54; T-42 to E-53; T-42 to S-52; T-42 to E-51; T-42 to K-50; T-42 to C-49; and T-42 to A-48 of SEQ ID NO:40. Polynucleotides encoding these polypeptides are also encompassed by the invention.

The invention also provides polypeptides having one or more amino acids deleted from both the amino and the carboxyl termini, which may be described generally as having residues $n^1$-$m^1$ and/or $n^2$-$m^1$ of FIGS. 1A–D (i.e., SEQ ID NO:2), where $n^1$, $n^2$, and $m^1$ are integers as described above. Thus, any of the above listed N- or C-terminal deletions can be combined to produce an N- and C-terminal deleted TR13 polypeptide.

The invention also provides polypeptides having one or more amino acids deleted from both the amino and the carboxyl termini, which may be described generally as having residues $n^1$-$m^1$ and/or $n^2$-$m^1$ of FIGS. 7A–E (SEQ ID) NO:40), where $n^1$, $n^2$, and $m^1$ are integers as described above. Thus, any of the above listed N- or C-terminal deletions can be combined to produce an N- and C-terminal deleted TR13 polypeptide.

It will be recognized in the art that some amino acid sequences of TR13 polypeptides can be varied without significant effect on the structure or function of the protein. If such differences in sequence are contemplated, it should be remembered that there will be critical areas on the protein which determine activity. Thus, the invention further includes variations of the TR13 polypeptide, which show substantial TR13 activity or which include regions of TR13 polypeptides, such as the polypeptide portions discussed herein. Such mutants include deletions, insertions, inversions, repeats, and type substitutions. As indicated above, guidance concerning which amino acid changes are likely to be phenotypically silent can be found in J.U. Bowie et al., *Science* 247:1306–1310 (1990).

Thus, the fragment, derivative, or analog of the polypeptide of SEQ ID NO:2 or SEQ ID NO:40, or that encoded by the cDNA deposited as ATCC Deposit No. PTA-349 or ATCC Deposit No. PTA-507, may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the TR13 polypeptide. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993), describes certain mutations resulting in selective binding of TNF-α to only one of the two known types of TNF receptors. Thus, the TR13 polypeptides of the present invention may include one or more amino acid substitutions, deletions, or additions, either from natural mutations or human manipulation.

As indicated, changes are preferably of a minor nature, such as conservative amino acid substitutions that do not significantly affect the folding or activity of the protein (see Table V).

TABLE V

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of FIGS. 1A–D or FIGS. 7A–E and/or any of the polypeptide fragments described herein (e.g., one or more of the cysteine rich domains, the mature extracellular domain, etc.) is 75, 70, 60, 50, 40, 35, 30, 25, 20, 15, 10, 9, 8, 7, 6, 5, 4, 3, 2, 1 or 30-20, 20-15, 20-10, 15-10, 10-1, 5-10, 1-5, 1-3 or 1-2.

Amino acids in the TR13 polypeptides of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

To improve or alter the characteristics of TR13 polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., *Nucl Acids Res.* 13:4331 (1986); and Zoller et al., *Nucl. Acids Res.* 10:6487 (1982)), cassette mutagenesis (see e.g., Wells et al., *Gene* (1985)), restriction selection mutagenesis (see e.g., Wells et al., *Philos. Trans. R. Soc. London Ser A* 317:415 (1986)).

Thus, the invention also encompasses TR13 derivatives and analogs that have one or more amino acid residues deleted, added, or substituted to generate TR13 polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the TR13 polypeptides of the invention, and/or an amino acid deletion at the second position of any one or more such recognition sequences will prevent glycosylation of the TR13 at the modified tripeptide sequence (see, e.g., Miyajimo et al., *EMBO J* 5(6):1193–1197). Additionally, one or more of the amino acid residues of the polypeptides of the invention (e.g., arginine and lysine residues) may be deleted or substituted with another residue to eliminate undesired processing by proteases such as, for example, furins or kexins.

The polypeptides of the present invention include a polypeptide comprising, or alternatively, consisting of the polypeptide encoded by the cDNA deposited as ATCC Deposit No. PTA-349, including the leader; a polypeptide comprising, or alternatively, consisting of the mature polypeptide encoded by the deposited cDNA minus the leader (i.e., the mature protein); a polypeptide comprising, or alternatively, consisting of amino acids from about 1 to about 750 of SEQ ID NO:2; a polypeptide comprising, or alternatively, consisting of amino acids from about 2 to about 750 of SEQ ID NO:2; a polypeptide comprising, or alternatively, consisting of amino acids from about 1 to about 331 in SEQ ID NO:2; a polypeptide comprising, or alternatively, consisting of any one or more of the four cysteine rich domains disclosed in FIGS. 1A–D (predicted to constitute amino acids from about 105 to about 170, 251 to about 265, about 331 to about 410, and about 580 to about 610 of SEQ ID NO: 2); as well as polypeptides which are at least 80% identical, more preferably at least 90% or 95% identical, still more preferably at least 96%, 97%, 98%, or 99% identical to the polypeptides described above (e.g., the polypeptide encoded by the deposited cDNA clone, the polypeptide of FIGS. 1A–D (SEQ ID NO:2) and polypeptide fragments thereof such as disclosed herein), and also include portions of such polypeptides with at least 30 amino acids and more preferably at least 50 amino acids. In this context "about" includes the particularly recited ranges, larger or smaller by several (5, 4, 3, 2, or 1) amino acids, at either extreme or at both extremes. Polynucleotides encoding these polypeptides are also encompassed by the invention.

The polypeptides of the present invention include a polypeptide comprising, or alternatively, consisting of the polypeptide encoded by the cDNA deposited as ATCC Deposit No. PTA-507, including the leader; a polypeptide comprising, or alternatively, consisting of the mature polypeptide encoded by the deposited cDNA minus the leader (i.e., the mature protein); a polypeptide comprising, or alternatively, consisting of amino acids from about 1 to about 1001 of SEQ ID NO:40; a polypeptide comprising, or alternatively, consisting of amino acids from about 2 to about 1001 of SEQ ID NO:40; a polypeptide comprising, or alternatively, consisting of amino acids from about 1 to about 906 in SEQ ID NO:40; a polypeptide comprising, or alternatively, consisting of amino acids from about 42 to about 1001 in SEQ ID NO:40; a polypeptide comprising, or alternatively, consisting of amino acids from about 42 to about 906 in SEQ ID NO: 40; a polypeptide comprising, or alternatively, consisting of amino acids from about 907 to about 931 in SEQ ID NO:40; a polypeptide comprising, or alternatively, consisting of amino acids from about 932 to about 1001 in SEQ ID NO:40; a polypeptide comprising, or alternatively, consisting of any of the seven cysteine rich domains disclosed in FIGS. 7A–E (predicted to constitute amino acids from about 271 to about 421, 271 to about 286, about 290 to about 300, about 301 to about 320, about 329 to about 361, about 404 to about 421, and about 585 to about 595 of SEQ ID NO:40); as well as polypeptides which are at least 80% identical, more preferably at least 90% or 95% identical, still more preferably at least 96%, 97%, 98%, or 99% identical to the polypeptides described above (e.g., the polypeptide encoded by the deposited cDNA clone, the polypeptide of FIGS. 7A–E (SEQ ID NO:40) and polypeptide fragments thereof, such as those disclosed herein), and also include portions of such polypeptides with at least 30 amino acids and more preferably at least 50 amino acids. In this context "about" includes the particularly recited ranges, larger or smaller by several (5, 4, 3, 2, or 1) amino acids, at either extreme or at both extremes. Polynucleotides encoding these polypeptides are also encompassed by the invention.

By a polypeptide (protein) comprising, or alternatively, consisting of, an amino acid sequence at least, for example, 95% "identical" to a reference amino acid sequence of a TR13 polypeptide is intended that the amino acid sequence of the polypeptide is identical to the reference sequence except that the polypeptide sequence may include up to five amino acid alterations per each 100 amino acids of the reference amino acid of the TR13 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98%, or 99% identical to, for instance, the amino acid sequence shown in SEQ ID NO:2 or SEQ ID NO:40, or to the amino acid sequence encoded by the cDNA clone deposited as ATCC Deposit No. PTA-349 or ATCC Deposit No. PTA-507, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full-length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (*Comp. App. Biosci.* 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present application is also directed to proteins comprising, or alternatively consisting of, a polypeptide sequence at least 90%, 95%, 96%, 97%, 98% or 99% identical to the TR13 polypeptide sequence set forth as $n^1$-$m^1$, and/or $n^2$-$m^1$ for polypeptide sequence shown in FIG. 1A–D or FIG. 7A–E herein. In preferred embodiments, the application is directed to proteins comprising, or alternatively consisting of, a polypeptide sequence at least 90%, 95%, 96%, 97%, 98% or 99% identical to polypeptides having the amino acid sequence of the specific TR13 N- and C-terminal deletions recited herein. Additional preferred embodiments are directed to fusion proteins comprising these polypeptide sequences. Polynucleotides encoding these polypeptides are also encompassed by the invention.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, J. G. Sutcliffe et al., "Antibodies That React With Predetermined Sites on Proteins," *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful, for example, to raise antibodies, including monoclonal antibodies, that bind specifically to a polypeptide of the invention. See, for instance, Wilson et al., *Cell* 37:767–778 (1984) at 777. Antigenic epitope-bearing peptides and polypeptides of the invention preferably contain a sequence of at least seven, more preferably at least 9 and at least 20, at least 25, at least 30, at least 40, at least 50 and most preferably between at least about 55 to about 100 amino acids contained within the amino acid sequence of a polypeptide of the invention. In this context "about" includes the particularly recited ranges, larger or smaller by several (5, 4, 3, 2, or 1) amino acids, at either extreme or at both extremes.

Non-limiting examples of predicted antigenic polypeptides that can be used to generate TR13 receptor-specific antibodies include: a polypeptide comprising, or alternatively consisting of, amino acid residues from about 1 to about 170 in FIGS. 1A–D (corresponding to about amino acid 1 to about 170 in SEQ ID NO:2); a polypeptide comprising amino acid residues from about 210 to about 318 in FIGS. 1A–D (corresponding to about amino acid 210 to about 318 in SEQ ID NO:2); a polypeptide comprising amino acid residues from about 343 to about 480 in FIGS. 1A–D (corresponding to about amino acid 343 to about 480 in SEQ ID NO:2); a polypeptide comprising amino acid residues from about 548 to about 592 in FIGS. 1A–D (corresponding to about amino acid 548 to about 592 in SEQ ID NO:2); and a polypeptide comprising amino acid residues from about 632 to about 742 in FIGS. 1A–D (corresponding to about amino acid 632 to about 742 in SEQ ID NO:2). As indicated above, the inventors have determined that the above polypeptide fragments are antigenic regions of the TR13 receptor protein. In this context "about" includes the particularly recited ranges, larger or smaller by several (5, 4, 3, 2, or 1) amino acids, at either extreme or at both extremes. Polynucleotides encoding these polypeptides are also encompassed by the invention.

Additional non-limiting examples of predicted antigenic polypeptides that can be used to generate TR13 receptor-specific antibodies include: a polypeptide comprising, or alternatively consisting of, amino acid residues from about M1 to about A9, about K12 to about L20, about N47 to about T55, about H58 to about S66, about D63 to S71, about P77 to about F85, about A90 to about Q98, about F136 to about Q144, about S152 to about C160, about R159 to about A167, about A211 to about M219, about M235 to about V243, about V266 to about V274, about W277 to about S285, about I290 to about F298, about A310 to about V318, about E343 to about C351, about I360 to about H368, about G391 to about I399, about F409 to about T417, about S436 to about Y444, about C453 to about S461, about I-472 to about S480, about Y548 to about S556, about C557 to about I565, about V567 to about V575, about T584 to about G592, about R632 to about G640, about W680 to about Y688, about Q684 to about K692, about T698 to about A706, about S726 to about S734, and about S734 to about L742 of SEQ ID NO:2 (FIGS. 1A–D) correspond to the highly antigenic regions of the TR13 protein, predicted using the Jameson-Wolf antigenic index (See FIG. 3 and Table I). These highly antigenic fragments correspond to the amino acid residues illustrated in FIG. 1A–D and in SEQ ID NO:2. As indicated above, the inventors have determined that the above polypeptide fragments are antigenic regions of the TR13 receptor protein. In this context "about" includes the particularly recited ranges, larger or smaller by several (5, 4, 3, 2, or 1) amino acids, at either extreme or at both extremes. Polynucleotides encoding these polypeptides are also encompassed by the invention.

Non-limiting examples of predicted antigenic polypeptides that can be used to generate TR13-specific antibodies include: a polypeptide comprising, or alternatively consisting of, amino acid residues from about 1 to about 262 in FIGS. 7A–E (corresponding to about amino acid 1 to about 262 in SEQ ID NO:40); a polypeptide comprising amino acid residues from about 264 to about 423 in FIGS. 7A–E (corresponding to about amino acid 264 to about 423 in SEQ ID NO:40); a polypeptide comprising amino acid residues from about 437 to about 789 in FIGS. 7A–E (corresponding to about amino acid 437 to about 789 in SEQ ID NO:40); and a polypeptide comprising amino acid residues from about 791 to about 1001 in FIGS. 7A–E (corresponding to about amino acid 791 to about 1001 in SEQ ID NO:40). As indicated above, the inventors have determined that the above polypeptide fragments are antigenic regions of the TR13 receptor protein. In this context "about" includes the particularly recited ranges, larger or smaller by several (5, 4, 3, 2, or 1) amino acids, at either extreme or at both extremes. Polynucleotides encoding these polypeptides are also encompassed by the invention.

Additional non-limiting examples of predicted antigenic polypeptides that can be used to generate TR13 receptor-specific antibodies include: a polypeptide comprising, or alternatively consisting of, amino acid residues from about M1 to about H9, about V14 to about I22, about H47 to about H55, about C61 to about R69, about L82 to E90, about D102 to about P110, about K109 to about S117, about F124 to about H132, about M141 to about E149, about S146 to about C154, about S157 to about W165, about F168 to about T176, about N182 to about N190, about Q207 to about A215, about P213 about M221, about M221 to about E229, about V233 to about V241, about T253 to about V261, about T282 to about S290, about N298 to about T306, about C308 to about Y316, about K315 to about S323, about P328 to about F336, about A341 to about Q349, about F387 to about Q395, about S403 to about C411, about T409 to about P417, about F443 about N451, about W451 to about Y459, about A462 to about M470, about G478 to about M486, about A487 to about A495, about V517 to about V525, about T527 to about Q535, about I541 to about F549, about A561 to about V569, about E594 to about C602, about I611 to about H619, about G643 to about I650, about P686 to about K694, about C704 to about S712, about R722 to about I730, about E727 to about T735, about P746 to about G754, about D776 to about L784, about Y799 to about S807, about C808 to about I816, about V818 to about V826, about T835 to about G843, about R883 to about G891, about K932 to about K940, about Q935 to about K943, about T949 to about A957, about S977 to about S985, about S981 to about P989, and about N986 to about L994 of SEQ ID NO:40 (FIGS. 7A–E) correspond to the highly antigenic regions of the TR13 protein, predicted using the Jameson-Wolf antigenic index (See FIG. 9 and Table III). These highly antigenic fragments correspond to the amino acid residues illustrated in FIG. 7A–E and in SEQ ID NO:40. As indicated above, the inventors have determined that the above polypeptide fragments are antigenic regions of the TR13 receptor protein. In this context "about" includes the particularly recited ranges, larger or smaller by several (5, 4, 3, 2, or 1) amino acids, at either extreme or at both extremes. Polynucleotides encoding these polypeptides are also encompassed by the invention.

The epitope-bearing peptides and polypeptides of the invention may be produced by any conventional means. R.A. Houghten, "General Method for the Rapid Solid-phase Synthesis of Large Numbers of Peptides: Specificity of Antigen-Antibody Interaction at the Level of Individual Amino Acids," *Proc. Natl. Acad. Sci. USA* 82:5131–5135 (1985). This "Simultaneous Multiple Peptide Synthesis (SMPS)" process is further described in U.S. Pat. No. 4,631,211 to Houghten et al. (1986).

As one of skill in the art will appreciate, TR13 receptor polypeptides of the present invention and the epitope-bearing fragments thereof, described herein (e.g., corresponding to a portion of the extracellular domain, such as, for example, amino acid residues 105 to about 170, about 251 to about 265, about 331 to about 410, and/or about 580 to about 610 of SEQ ID NO:2), can be combined with heterologous polypeptide sequences, for example, the polypeptides of the present invention may be fused with the constant domain of immunoglobulins (IgA, IgE, IgG, IgM) or portions thereof (CH1, CH2, CH3, and any combination thereof, including both entire domains and portions thereof), resulting in chimeric polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, polypeptides and/or antibodies of the present invention (including fragments or variants thereof) are fused with the mature form of human serum albumin (i.e., amino acids 1–585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

Such fusion proteins as those described above may facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric TR13 protein or protein fragment alone (Fountoulakis et al., *J. Biochem.* 270:3958–3964 (1995)). In this context "about" includes the particularly recited ranges, larger or smaller by several (5, 4, 3, 2, or 1) amino acids, at either extreme or at both extremes.

As one of skill in the art will appreciate, TR13 receptor polypeptides of the present invention and the epitope-bearing fragments thereof, described herein (e.g., corresponding to a portion of the extracellular domain, such as, for example, amino acid residues 1 to about 262, about 264 to about 423, about 437 to about 789, about 271 to about 421, and/or about 585 to 599 of SEQ ID NO: 40), can be combined with heterologous polypeptide sequences, for example, the polypeptides of the present invention may be fused with the constant domain of immunoglobulins (IgA, IgE, IgG, IgM) or portions thereof (CH1, CH2, CH3, and any combination thereof, including both entire domains and portions thereof), resulting in chimeric polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No.

5,766,883, issued Jun. 16, 1998, herein incorporated by reference in their entirety)). In a preferred embodiment, polypeptides and/or antibodies of the present invention (including fragments or variants thereof) are fused with the mature form of human serum albumin (i.e., amino acids 1–585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

Such fusion proteins as those described above may facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric TR13 protein or protein fragment alone (Fountoulakis et al., *J Biochem.* 270:3958–3964 (1995)). In this context "about" includes the particularly recited ranges, larger or smaller by several (5, 4, 3, 2, or 1) amino acids, at either extreme or at both extremes.

Preferred TR13 Fc fusions of the present invention include, but are not limited to constructs comprising, or alternatively consisting of, amino acid residues 1 to 750, 10 to 750, 20 to 750, 30 to 750, 40 to 750, 1 to 740, 1 to 730, 1 to 720, 1 to 710, 10 to 740, 10 to 730, and/or 10 to 720 of SEQ ID NO:2. Polynucleotides encoding these TR13 fusions are also encompassed by the invention.

Additional preferred TR13 Fc fusions of the present invention include, but are not limited to constructs comprising, or alternatively consisting of, amino acid residues 1 to 906, 42 to 906, 271 to 421, 585 to 595, 1 to 1001, 10 to 1001, 20 to 1001, 30 to 1001, 42 to 1001, 42 to 906, 1 to 990, 1 to 980, 1 to 970, 1 to 960, 10 to 990, 10 to 980, and/or 10 to 970 of SEQ ID NO:2. Polynucleotides encoding these TR13 fusions are also encompassed by the invention.

The polypeptides of the present invention have uses which include, but are not limited to, as sources for generating antibodies that bind the polypeptides of the invention, and as molecular weight markers on SDS-PAGE gels or on molecular sieve gel filtration columns using methods well known to those of skill in the art.

TR14 Polypeptides

The TR14 proteins (polypeptides) of the invention may be in monomers or multimers (i.e., dimers, trimers, tetramers, and higher multimers). Accordingly, the present invention relates to monomers and multimers of the TR14 proteins (polypeptides) of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term TR14 homomer, refers to a multimer containing only TR14 proteins of the invention (including TR14 fragments, variants, and fusion proteins, as described herein). These homomers may contain TR14 proteins having identical or different polypeptide sequences. In a specific embodiment, a homomer of the invention is a multimer containing only TR14 proteins having an identical polypeptide sequence. In another specific embodiment, a homomer of the invention is a multimer containing TR14 proteins having different polypeptide sequences. In specific embodiments, the multimer of the invention is a homodimer (e.g., containing TR14 proteins having identical or different polypeptide sequences) or a homotrimer (e.g., containing TR14 proteins having identical or different polypeptide sequences). In additional embodiments, the homomeric multimer of the invention is at least a homodimer, at least a homotrimer, or at least a homotetramer.

As used herein, the term TR14 heteromer refers to a multimer containing heterologous proteins (i.e., proteins containing only polypeptide sequences that do not correspond to a polypeptide sequences encoded by the TR14 gene) in addition to the TR14 proteins of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the TR14 proteins of the invention. Such covalent associations may involve one or more amino acid residues contained in the polypeptide sequence of the protein (e.g., the polypeptide sequence recited preferably in SEQ ID NO:61 or, alternatively, in SEQ ID NO:5 or the polypeptide encoded by the deposited cDNA clone). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a TR14 fusion protein. In one example, covalent associations are between the heterologous sequence contained in a fusion protein of the invention (see, e.g., US Pat. No. 5,478,925). In a specific example, the covalent associations are between the heterologous sequence contained in a TR14-Fc fusion protein of the invention (as described herein). In another specific example, covalent associations of fusion proteins of the invention are between heterologous polypeptide sequences from another TNF family ligand/receptor member that is capable of forming covalently associated multimers, such as for example, oseteoprotegerin (see, e.g., International Publication No. WO 98/49305, the contents of which are herein incorporated by reference in its entirety). In another embodiment, two or more TR14 polypeptides of the invention are joined through synthetic linkers (e.g., peptide, carbohydrate or soluble polymer linkers). Examples include those peptide linkers described in U.S. Pat. No. 5,073,627 (hereby incorporated by reference). Proteins comprising multiple TR14 polypeptides separated by peptide linkers may be produced using conventional recombinant DNA technology.

Another method for preparing multimer TR14 polypeptides of the invention involves use of TR14 polypeptides fused to a leucine zipper or isoleucine polypeptide sequence. Leucine zipper domains and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric TR14 proteins are those described in PCT application WO 94/10308, hereby incorporated by reference. Recombinant fusion proteins comprising a soluble TR14 polypeptide fused to a peptide that dimerizes or trimerizes in solution are expressed in suitable host cells, and the resulting soluble multimeric TR14 is recovered from the culture supernatant using techniques known in the art.

Certain members of the TNF family of proteins are believed to exist in trimeric form (Beutler and Huffel, *Science* 264:667, 1994; Banner et al., *Cell* 73:431, 1993). Thus, trimeric TR14 may offer the advantage of enhanced biological activity. Preferred leucine zipper moieties are those that preferentially form trimers. One example is a leucine zipper derived from lung surfactant protein D (SPD), as described in Hoppe et al. (*FEBS Letters* 344:191, (1994)) and in U.S. patent application Ser. No. 08/446,922, hereby incorporated by reference. Other peptides derived from naturally occurring trimeric proteins may be employed in preparing trimeric TR14.

In further preferred embodiments, TR14 polynucleotides of the invention are fused to a polynucleotide encoding a "FLAG" polypeptide. Thus, a TR14-FLAG fusion protein is encompassed by the present invention. The FLAG antigenic polypeptide may be fused to a TR14 polypeptide of the invention at either or both the amino or the carboxy terminus. In preferred embodiments, a TR14-FLAG fusion protein is expressed from a pFLAG-CMV-5a or a pFLAG-CMV-1 expression vector (available from Sigma, St. Louis, Mo., USA). See, Andersson, S., et al., *J. Biol Chem.* 264:8222–29 (1989); Thomsen, D. R., et al., *Proc. Natl. Acad. Sci. USA,* 81:659–63 (1984); and Kozak, M., *Nature* 308:241 (1984) (each of which is hereby incorporated by reference). In further preferred embodiments, a TR14-FLAG fusion protein is detectable by anti-FLAG monoclonal antibodies (also available from Sigma).

In another example, proteins of the invention are associated by interactions between Flag® polypeptide sequence contained in Flag®-TR14 fusion proteins of the invention. In a further embodiment, associated proteins of the invention are associated by interactions between heterologous polypeptide sequence contained in Flag®-TR14 fusion proteins of the invention and anti-Flag® antibody.

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

The polypeptides (proteins) of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the TR14 polypeptide can be substantially purified by the one-step method described in Smith and Johnson, *Gene* 67:31–40 (1988).

Accordingly, in one embodiment, the invention provides an isolated TR14 polypeptide having the amino acid sequence encoded by the cDNA deposited as ATCC Deposit No. PTA-348, or the amino acid sequence shown preferably in SEQ ID NO:61 or, alternatively, in SEQ ID NO:5, or a polypeptide comprising a portion of the above polypeptides.

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the TR14 polypeptide can be substantially purified by the one-step method described in Smith and Johnson, Gene 67:31–40 (1988).

Polypeptide fragments of the present invention include polypeptides comprising or alternatively, consisting of, an amino acid sequence contained preferably in SEQ ID NO:61 or, alternatively, in SEQ ID NO:5, encoded by the cDNA contained in the clone deposited as ATCC Deposit No. PTA-348, or encoded by a nucleic acid which hybridizes (e.g., under stringent hybridization conditions) to the nucleotide sequence contained in the deposited clone, or shown preferably in FIGS. 10A–H (SEQ ID NO:61) or, alternatively, in FIGS. 4A–E (SEQ ID NO:4) or the complementary strand thereto, or polynucleotide fragments thereof (e.g., as disclosed herein). Protein fragments may be "freestanding," or comprised within a larger polypeptide of which the fragment forms a part or region, most preferably as a single continuous region. Preferred representative examples of polypeptide fragments of the invention, include, for example, fragments that comprise, or alternatively consist of, from about amino acid residues: 1 to 50, 51 to 100, 101 to 150, 151 to 200, 201 to 231 of SEQ ID NO:61. Alternative, less preferred representative examples of polypeptide fragments of the invention, include, for example, fragments that comprise, or alternatively consist of, from about amino acid residues: 1 to 50, 51 to 100, 101 to 150, 151 to 200, 201 to 226 of SEQ ID NO:5, and the corresponding amino acid residues of SEQ ID NO:61 (as the sequence of amino acid residues T-78 to M-231 of SEQ ID NO:61 is identical to the sequence of amino acid residues T-73 to M-226 of SEQ ID NO:5). Moreover, polypeptide fragments can be at least 10, 20, 30, 40, 50, 60, 70, 80, 90, 100, 110, 120, 130, 140, 150, 175 or 200 amino acids in length. In this context "about" includes the particularly recited ranges, larger or smaller by several (5, 4, 3, 2, or 1) amino acids, at either extreme or at both extremes. Polynucleotides encoding these polypeptides are also encompassed by the invention.

Polypeptide fragments of the present invention include polypeptides comprising or alternatively, consisting of amino acid residues from about: 178 to about 180, 118 to about 121, 178 to about 181, 193 to about 196, 9 to about 14, and/or 65 to about 85 of SEQ ID NO:2. In this context "about" includes the particularly recited ranges, larger or smaller by several (5, 4, 3, 2, or 1) amino acids, at either extreme or at both extremes. Polynucleotides encoding the polypeptide fragments are also encompassed by the invention.

In specific embodiments, polypeptide fragments of the invention comprise, or alternatively consist of, amino acid residues from about: 1 to about 138, 139 to about 155, and/or 156 to about 231 as depicted in SEQ ID NO:61; or, alternatively, about 1 to about 133, 134 to about 150, and/or 151 to about 226 as depicted in SEQ ID NO:5. In this context "about" includes the particularly recited ranges, larger or smaller by several (5, 4, 3, 2, or 1) amino acids, at either extreme or at both extremes. Polynucleotides encoding these polypeptides are also encompassed by the invention.

In additional embodiments, the polypeptide fragments of the invention comprise, or alternatively consist of, one or more TR14 domains. Preferred polypeptide fragments of the present invention include a member selected from the group: (a) a polypeptide comprising or alternatively, consisting of, the TR14 extracellular domain (predicted to constitute preferably amino acid residues from about 1 to about 138 in FIGS. 10A–H and SEQ ID NO:61, or, alternatively, from about 1 to about 133 of SEQ ID NO:5 and FIGS. 4A–E, or from about 1 to about 133 of SEQ ID NO:5); (b) a polypeptide comprising or alternatively, consisting of, the TR14 cysteine rich domain (predicted to constitute preferably amino acids Cys-31 to Cys-104 of SEQ ID NO:61, or, alternatively, amino acid residues from about 65 to about 88 of FIGS. 4A–E, or from about 65 to about 85 in SEQ ID NO:5); (c) a polypeptide comprising or alternatively, consisting of, the TR14 transmembrane domain (predicted to constitute amino acid residues from about 139 to about 155 of FIGS. 10A–H and SEQ ID NO:61 or from about 134 to about 150 of FIGS. 4A–E and SEQ ID NO:5); (d) a polypeptide comprising or alternatively, consisting of, the TR14 intracellular domain (predicted to constitute amino acid residues from about 155 to about 231 of FIGS. 10A–H and SEQ ID NO:61 or amino acid residues from about 151 to about 226 of FIGS. 4A–E and SEQ ID NO:5); (e) a polypeptide comprising, or alternatively, consisting of, one, two, three, four or more, epitope bearing portions of the TR14 polypeptide (predicted to constitute preferably Asp-2 to Asp-10, Thr-17 to Asp-38, Pro-45 to Ser-52, Pro-88 to Arg-95, Thr-108 to Glu-115, Thr-131 to Glu-136, Phe-166 to Gly-174, Ala-180 to Ala-200, and Gln-224 to Met-231 of SEQ ID NO:61, or the corresponding amino acid sequences in SEQ ID NO:5, as the sequence of amino acid residues T-78 to M-231 of SEQ ID NO:61 is identical to the sequence of amino acid residues T-73 to M-226 of SEQ ID NO: 5. Additional epitope bearing TR14 polypeptides comprise or, alternatively, consist of amino acid residues from about 2 to about 24, 42 to about 52, 80 to about 115, and 155 to about 226 of SEQ ID NO:5 (or the corresponding amino acid sequences in SEQ ID NO:61, as the sequence of amino acid residues T-78 to M-231 of SEQ ID NO:61 is identical to the sequence of amino acid residues T-73 to M-226 of SEQ ID NO:5); and (f) any combination of polypeptides (a)–(e). In this context "about" includes the particularly recited ranges, larger or smaller by several (5, 4, 3, 2, or 1) amino acids, at either extreme or at both extremes. Polynucleotides encoding these polypeptides are also encompassed by the invention.

As discussed above, it is believed that the extracellular cysteine rich motifs of TR14 is important for interactions between TR14 and its ligands. Accordingly, in a specific embodiment, polypeptide fragments of the invention comprise, or alternatively consist of amino acid residues 31 to 104 of SEQ ID NO: 61 or 65 to 85 of SEQ ID NO: 5. Polynucleotides encoding these polypeptides are also encompassed by the invention.

Among the especially preferred fragments of the invention are fragments characterized by structural or functional attributes of TR14 (preferably SEQ ID NO:61 or, alternatively, SEQ ID NO:5). Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) TR14

(preferably SEQ ID NO:61 or, alternatively, SEQ ID NO:5). Certain preferred regions are those set out in FIG. 6 and Table II and include, but are not limited to, regions of the aforementioned types identified by analysis of the amino acid sequence depicted preferably FIGS. 10A–H (SEQ ID NO:61) or, alternatively, in FIGS. 4A–E (SEQ ID NO:5), such preferred regions include; Garnier-Robson predicted alpha-regions, beta-regions, turn-regions, and coil-regions; Chou-Fasman predicted alpha-regions, beta-regions, and turn-regions; Kyte-Doolittle predicted hydrophilic and Hopp-Woods predicted hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

As mentioned above, even if deletion of one or more amino acids from the N-terminus of a protein results in modification of loss of one or more biological functions of the protein, other functional activities (e.g., biological activities, ability to multimerize, ability to bind TR14 ligand) may still be retained. For example, the ability of shortened TR14 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an TR14 mutein with a large number of deleted N-terminal amino acid residues may retain some biological or immunogenic activities. In fact, peptides composed of as few as six TR14 amino acid residues may often evoke an immune response.

Accordingly, the present invention further provides polypeptides having one or more residues deleted from the amino terminus of the TR14 amino acid sequence shown depicted preferably FIGS. 10A–H (SEQ ID NO:61) or, alternatively, in FIGS. 4A–E (SEQ ID NO:5), up to the methionine residue at position number 231 of SEQ ID NO:61 (or, number 226 of SEQ ID NO:5) and polynucleotides encoding such polypeptides. In particular preferred embodiments for TR14, the present invention provides polypeptides comprising, or alternatively consisting of; the amino acid sequence of residues $n^{1-231}$ of FIGS. 10A–H, where $n^1$ is an integer from 1 to 231 corresponding to the position of the amino acid residue in FIGS. 10A–H. In alternative embodiments, the present invention provides polypeptides comprising, or alternatively consisting of, the amino acid sequence of residues $n^{1-226}$ of FIGS. 4A–E, where $n^1$ is an integer from 1 to 226 corresponding to the position of the amino acid residue in FIGS. 4A–E.

In specific embodiments, N-terminal deletions of the TR14 polypeptides of the invention can be described by the general formula $n^{2-231}$, where $n^2$ is a number from 2 to 226, corresponding to the position of amino acid identified in FIGS. 10A–H (SEQ ID NO:61). N-terminal deletions of the TR14 polypeptide of the invention shown as SEQ ID NO:61 include polypeptides comprising, or alternatively consisting of, the amino acid sequence of residues: D-2 to M-231; C-3 to M-231; Q-4 to M-231; E-5 to M-231; N-6 to M-231; E-7 to M-231; Y-8 to M-231; W-9 to M-231; D-10 to M-231; Q-11 to M-231; W-12 to M-231; G-13 to M-231; R-14 to M-231; C-15 to M-231; V-16 to M-231; T-17 to M-231; C-18 to M-231; Q-19 to M-231; R-20 to M-231; C-21 to M-231; G-22 to M-231; P-23 to M-231; G-24 to M-231; Q-25 to M-231; E-26 to M-231; L-27 to M-231; S-28 to M-231; K-29 to M-231; D-30 to M-231; C-31 to M-231; G-32 to M-231; Y-33 to M-231; G-34 to M-231; E-35 to M-231; G-36 to M-231; G-37 to M-231; D-38 to M-231; A-39 to M-231; Y-40 to M-231; W-41 to M-231; H-42 to M-231; S-43 to M-231; L-44 to M-231; P-45 to M-231; S-46 to M-231; S-47 to M-231; Q-48 to M-231; Y-49 to M-231; K-50 to M-231; S-51 to M-231; S-52 to M-231; W-53 to M-231; G-54 to M-231; H-55 to M-231; H-56 to M-231; K-57 to M-231; C-58 to M-231; Q-59 to M-231; S-60 to M-231; C-61 to M-231; I-62 to M-231; T-63 to M-231; C-64 to M-231; A-65 to M-231; V-66 to M-231; I-67 to M-231; N-68 to M-231; R-69 to M-231; V-70 to M-231; Q-71 to M-231; K-72 to M-231; V-73 to M-231; N-74 to M-231; C-75 to M-231; T-76 to M-231; P-77 to M-231; T-78 to M-231; S-79 to M-231; N-80 to M-231; A-81 to M-231; V-82 to M-231; C-83 to M-231; G-84 to M-231; D-85 to M-231; C-86 to M-231; L-87 to M-231; P-88 to M-231; R-89 to M-231; F-90 to M-231; Y-91 to M-231; R-92 to M-231; K-93 to M-231; T-94 to M-231; R-95 to M-231; I-96 to M-231; G-97 to M-231; G-98 to M-231; L-99 to M-231; Q-100 to M-231; D-101 to M-231; Q-102 to M-231; E-103 to M-231; C-104 to M-231; I-105 to M-231; P-106 to M-231; C-107 to M-231; T-108 to M-231; K-109 to M-231; Q-110 to M-231; T-111 to M-231; P-112 to M-231; T-113 to M-231; S-114 to M-231; E-115 to M-231; V-116 to M-231; Q-117 to M-231; C-118 to M-231; A-119 to M-231; F-120 to M-231; Q-121 to M-231; L-122 to M-231; S-123 to M-231; L-124 to M-231; V-125 to M-231; E-126 to M-231; A-127 to M-231; D-128 to M-231; A-129 to M-231; P-130 to M-231; T-131 to M-231; V-132 to M-231; P-133 to M-231; P-134 to M-231; Q-135 to M-231; E-136 to M-231; A-137 to M-231; T-138 to M-231; L-139 to M-231; V-140 to M-231; A-141 to M-231; L-142 to M-231; V-143 to M-231; S-144 to M-231; S-145 to M-231; L-146 to M-231; L-147 to M-231; V-148 to M-231; V-149 to M-231; F-150 to M-231; T-151 to M-231; L-152 to M-231; A-153 to M-231; F-154 to M-231; L-155 to M-231; G-156 to M-231; L-157 to M-231; F-158 to M-231; F-159 to M-231; L-160 to M-231; Y-161 to M-231; C-162 to M-231; K-163 to M-231; Q-164 to M-231; F-165 to M-231; F-166 to M-231; N-167 to M-231; R-168 to M-231; H-169 to M-231; C-170 to M-231; Q-171 to M-231; R-172 to M-231; G-173 to M-231; G-174 to M-231; L-175 to M-231; L-176 to M-231; Q-177 to M-231; F-178 to M-231; E-179 to M-231; A-180 to M-231; D-181 to M-231; K-182 to M-231; T-183 to M-231; A-184 to M-231; K-185 to M-231; E-186 to M-231; E-187 to M-231; S-188 to M-231; L-189 to M-231; F-190 to M-231; P-191 to M-231; V-192 to M-231; P-193 to M-231; P-194 to M-231; S-195 to M-231; K-196 to M-231; E-197 to M-231; T-198 to M-231; S-199 to M-231; A-200 to M-231; E-201 to M-231; S-202 to M-231; Q-203 to M-231; V-204 to M-231; S-205 to M-231; W-206 to M-231; A-207 to M-231; P-208 to M-231; G-209 to M-231; S-210 to M-231; L-211 to M-231; A-212 to M-231; Q-213 to M-231; L-214 to M-231; F-215 to M-231; S-216 to M-231; L-217 to M-231; D-218 to M-231; S-219 to M-231; V-220 to M-231; P-221 to M-231; I-222 to M-231; P-223 to M-231; Q-224 to M-231; Q-225 to M-231 and Q-226 to M-231 of SEQ ID NO:61.

In additional embodiments, N-terminal deletions of the TR14 polypeptides of the invention can be described by the general formula $n^{2-226}$, where $n^2$ is a number from 2 to 221, corresponding to the position of amino acid identified in FIGS. 4A–E (SEQ ID NO:5). N-terminal deletions of the TR14 polypeptide of the invention shown as SEQ ID NO:5 include polypeptides comprising, or alternatively consisting of, the amino acid sequence of residues: S-2 to M-226; T-3 to M-226; G-4 to M-226; T-5 to M-226; N-6 to M-226; G-7 to M-226; D-8 to M-226; G-9 to M-226; V-10 to M-226; S-11 to M-226; P-12 to M-226; A-13 to M-226; N-14 to M-226; G-15 to M-226; V-16 to M-226; V-17 to M-226; L-18 to M-226; D-19 to M-226; R-20 to M-226; S-21 to M-226; Y-22 to M-226; P-23 to M-226; R-24 to M-226; I-25 to M-226; V-26 to M-226; V-27 to M-226; M-28 to M-226; E-29 to M-226; R-30 to M-226; V-31 to M-226; E-32 to M-226; M-33 to M-226; P-34 to M-226; T-35 to M-226; A-36 to M-226; Q-37 to M-226; P-38 to M-226; A-39 to M-226; L-40 to M-226; L-41 to M-226; A-42 to M-226; V-43 to M-226; Q-44 to M-226; K-45 to M-226; Q-46 to M-226; L-47 to M-226; G-48 to M-226; P-49 to M-226; P-50 to M-226; Q-51 to M-226; M-52 to M-226; C-53 to M-226; R-54 to M-226; V-55 to M-226; A-56 to M-226; C-57 to M-226; T-58 to M-226; C-59 to M-226; A-60 to M-226; V-61 to M-226; I-62 to M-226; N-63 to M-226; R-64 to M-226; V-65 to M-226; Q-66 to M-226; K-67 to M-226; V-68 to M-226; N-69 to M-226; C-70 to M-226; T-71 to M-226; P-72 to M-226; T-73 to M-226; S-74 to M-226; N-75 to M-226; A-76 to M-226; V-77 to M-226; C-78 to M-226; G-79 to M-226; D-80 to M-226; C-81 to M-226; L-82 to M-226; P-83 to M-226; R-84 to M-226; F-85 to M-226; Y-86 to M-226; R-87 to M-226; K-88 to M-226; T-89 to M-226; R-90 to M-226; I-91 to M-226; G-92 to M-226; G-93 to M-226; L-94 to M-226; Q-95 to M-226; D-96 to M-226; Q-97 to M-226; E-98 to M-226; C-99 to M-226; I-100 to M-226; P-101 to M-226; C-102 to M-226; T-103 to M-226; K-104 to M-226; Q-105 to M-226; T-106 to M-226; P-107 to M-226; T-108 to M-226; S-109 to M-226; E-110 to M-226; V-111 to M-226; Q-112 to M-226; C-113 to M-226; A-114 to M-226; F-115 to M-226; Q-116 to M-226; L-117 to M-226; S-118 to M-226; L-119 to M-226; V-120 to M-226; E-121 to M-226; A-122 to M-226; D-123 to M-226; A-124 to M-226; P-125 to M-226; T-126 to M-226; V-127 to M-226; P-128 to M-226; P-129 to M-226; Q-130 to M-226; E-131 to M-226; A-132 to M-226; T-133 to M-226; L-134 to M-226; V-135 to M-226; A-136 to M-226; L-137 to M-226; V-138 to M-226; S-139 to M-226; S-140 to M-226; L-141 to M-226; L-142 to M-226; V-143 to M-226; V-144 to M-226; F-145 to M-226; T-146 to M-226; L-147 to M-226; A-148 to M-226; F-149 to M-226; L-150 to M-226; G-151 to M-226; L-152 to M-226; F-153 to M-226; F-154 to M-226; L-155 to M-226; Y-156 to M-226; C-157 to M-226; K-158 to M-226; Q-159 to M-226; F-160 to M-226; F-161 to M-226; N-162 to M-226; R-163 to M-226; H-164 to M-226; C-165 to M-226; Q-166 to M-226; R-167 to M-226; G-168 to M-226; G-169 to M-226; L-170 to M-226; L-171 to M-226; Q-172 to M-226; F-173 to M-226; E-174 to M-226; A-175 to M-226; D-176 to M-226; K-177 to M-226; T-178 to M-226; A-179 to M-226; K-180 to M-226; E-181 to M-226; E-182 to M-226; S-183 to M-226; L-184 to M-226; F-185 to M-226; P-186 to M-226; V-187 to M-226; P-188 to M-226; P-189 to M-226; S-190 to M-226; K-191 to M-226; E-192 to M-226; T-193 to M-226; S-194 to M-226; A-195 to M-226; E-196 to M-226; S-197 to M-226; Q-198 to M-226; V-199 to M-226; S-200 to M-226; W-201 to M-226; A-202 to M-226; P-203 to M-226; G-204 to M-226; S-205 to M-226; L-206 to M-226; A-207 to M-226; Q-208 to M-226; L-209 to M-226; F-210 to M-226; S-211 to M-226; L-212 to M-226; D-213 to M-226; S-214 to M-226; V-215 to M-226; P-216 to M-226; I-217 to M-226; P-218 to M-226; Q-219 to M-226; Q-220 to M-226; Q-221 to M-226; of SEQ ID NO: 5. Polynucleotides encoding these polypeptides are also encompassed by the invention.

In another embodiment, N-terminal deletions of the extracellular domain of the TR14 polypeptide can be described by the general formula $n^{2-133}$, where $n^2$ is a number from 1 to 128, corresponding to the position of amino acids identified in FIGS. 4A–E. N-terminal deletions of the extracellular domain of the TR14 polypeptide of the invention shown as SEQ ID NO:7 include polypeptides comprising, or alternatively consisting of, the amino acid sequence of residues: S-2 to T-133; T-3 to T-133; G-4 to T-133; T-5 to T-133; N-6 to T-133; G-7 to T-133; D-8 to T-133; G-9 to T-133; V-10 to T-133; S-11 to T-133; P-12 to T-133; A-13 to T-133; N-14 to T-133; G-15 to T-133; V-16 to T-133; V-17 to T-133; L-18 to T-133; D-19 to T-133; R-20 to T-133; S-21 to T-133; Y-22 to T-133; P-23 to T-133; R-24 to T-133; I-25 to T-133; V-26 to T-133; V-27 to T-133; M-28 to T-133; E-29 to T-133; R-30 to T-133; V-31 to T-133; E-32 to T-133; M-33 to T-133; P-34 to T-133; T-35 to T-133; A-36 to T-133; Q-37 to T-133; P-38 to T-133; A-39 to T-133; L-40 to T-133; L-41 to T-133; A-42 to T-133; V-43 to T-133; Q-44 to T-133; K-45 to T-133; Q-46 to T-133; L-47 to T-133; G-48 to T-133; P-49 to T-133; P-50 to T-133; Q-51 to T-133; M-52 to T-133; C-53 to T-133; R-54 to T-133; V-55 to T-133; A-56 to T-133; C-57 to T-133; T-58 to T-133; C-59 to T-133; A-60 to T-133; V-61 to T-133; I-62 to T-133; N-63 to T-133; R-64 to T-133; V-65 to T-133; Q-66 to T-133; K-67 to T-133; V-68 to T-133; N-69 to T-133; C-70 to T-133; T-71 to T-133; P-72 to T-133; T-73 to T-133; S-74 to T-133; N-75 to T-133; A-76 to T-133; V-77 to T-133; C-78 to T-133; G-79 to T-133; D-80 to T-133; C-81 to T-133; L-82 to T-133; P-83 to T-133; R-84 to T-133; F-85 to T-133; Y-86 to T-133; R-87 to T-133; K-88 to T-133; T-89 to T-133; R-90 to T-133; I-91 to T-133; G-92 to T-133; G-93 to T-133; L-94 to T-133; Q-95 to T-133 D-96 to T-133; Q-97 to T-133; E-98 to T-133; C-99 to T-133; I-100 to T-133; P-101 to T-133; C-102 to T-133; T-103 to T-133; K-104 to T-133; Q-105 to T-133; T-106 to T-133; P-107 to T-133; T-108 to T-133; S-109 to T-133; E-110 to T-133; V-111 to T-133; Q-112 to T-133; C-113 to T-133; A-114 to T-133; F-115 to T-133; Q-116 to T-133; L-117 to T-133; S-118 to T-133; L-119 to T-133; V-120 to T-133; E-121 to T-133; A-122 to T-133; D-123 to T-133; A-124 to T-133; P-125 to T-133; T-126 to T-133; V-127 to T-133; P-128 to T-133; of SEQ ID NO:7 (or the corresponding amino acid sequences in SEQ ID NO:61, as the sequence of amino acid residues T-78 to T-138 of SEQ ID NO:61 is identical to the sequence of amino acid residues T-73 to T-133 of SEQ ID NO:7). Polynucleotides encoding these polypeptides are also encompassed by the invention.

Also as mentioned above, even if deletion of one or more amino acids from the C-terminus of a protein results in modification or loss of one or more biological functions of the protein, other functional activities (e.g., biological activities), ability to multimerize, ability to bind TR14 ligand) may still be retained. For example the ability of the shortened TR14 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an TR14 mutein with a large number of deleted C-terminal amino acid residues may retain some biological or immunogenic activities. In fact, peptides composed of as few as six TR14 amino acid residues may often evoke an immune response.

Accordingly, the present invention further provides polypeptides having one or more residues deleted from the carboxy terminus of the amino acid sequence of the TR14 polypeptide shown in FIGS. 10A–H (SEQ ID NO:61), up to the glutamic acid residue at position number 7, and polynucleotides encoding such polypeptides. In particular, the present invention provides polypeptides comprising, or alternatively consisting of, the amino acid sequence of residues 1-m¹ of FIGS. 10A–H, where m¹ is an integer from 7 to 231 corresponding to the position of the amino acid residue in FIGS. 10A–H (which is identical to the sequence shown as SEQ ID NO:61).

Moreover, the invention provides polypeptides comprising, or alternatively consisting of, the amino acid residues: M-1 to E-230; M-1 to P-229; M-1 to G-228; M-1 to Q-227; M-1 to Q-226; M-1 to Q-225; M-1 to Q-224; M-1 to P-223; M-1 to I-222; M-1 to P-221; M-1 to V-220; M-1 to S-219; M-1 to D-218; M-1 to L-217; M-1 to S-216; M-1 to F-215; M-1 to L-214; M-1 to Q-213; M-1 to A-212; M-1 to L-211; M-1 to S-210; M-1 to G-209; M-1 to P-208; M-1 A-207 to W-206; M-1 to S-205; M-1 to V-204; M-1 to Q-203; M-1 to L-202; M-1 to E-201; M-1 to A-200; M-1 to S-199; M-1 to T-198; M-1 to E-197; M-1 to K-196; M-1 to S-195; M-1 to P-194; M-1 to P-193; M-1 to V-192; M-1 to P-191; M-1 to F-190; M-1 to L-189; M-1 to S-188; M-1 to E-187; M-1 to E-186; M-1 to K-185; M-1 to A-184; M-1 to T-183; M-1 to K-182; M-1 to D-181; M-1 to A-180; M-1 to E-179; M-1 to F-178; M-1 to Q-177; M-1 to L-176; M-1 to L-175; M-1 to G-174; M-1 to G-173; M-1 to R-172; M-1 to Q-171; M-1 to C-170; M-1 to H-169; M-1 to R-168; M-1 to N-167; M-1 to F-166; M-1 to F-165; M-1 to Q-164; M-1 to K-163; M-1 to C-162; M-1 to Y-161; M-1 to L-160; M-1 to F-159; M-1 to F-158; M-1 to L-157; M-1 to G-156; M-1 to L-155; M-1 to F-154; M-1 to A-153; M-1 to L-152; M-1 to T-151; M-1 to F-150; M-1 to V-149; M-1 to V-148; M-1 to L-147; M-1 to L-146; M-1 to S-145; M-1 to S-144; M-1 to V-143; M-1 to L-142; M-1 to A-141; M-1 to V-140; M-1 to L-139; M-1 to T-138; M-1 to A-137; M-1 to E-136; M-1 to Q-135; M-1 to P-134; M-1 to P-133; M-1 to V-132; M-1 to T-131; M-1 to P-130; M-1 to A-129; M-1 to D-128; M-1 to A-127; M-1 to E-126; M-1 to V-125; M-1 to L-124; M-1 to S-123; M-1 to L-122; M-1 to Q-121; M-1 to F-120; M-1 to A-119; M-1 to C-118; M-1 to Q-117; M-1 to V-116; M-1 to E-115; M-1 to S-114; M-1 to T-113; M-1 to P-112; M-1 to T-111; M-1 to Q-110; M-1 to K-109; M-1 to T-108; M-1 to C-107; M-1 to P-106; M-1 to I-105; M-1 to C-104; M-1 to E-103; M-1 to Q-102; M-1 to D-101; M-1 to Q-100; M-1 to L-99; M-1 to G-98; M-1 to G-97; M-1 to I-96; M-1 to R-95; M-1 to T-94; M-1 to K-93; M-1 to R-92; M-1 to Y-91; M-1 to F-90; M-1 to R-89; M-1 to P-88; M-1 to L-87; M-1 to C-86; M-1 to D-85; M-1 to G-84; M-1 to C-83; M-1 to V-82; M-1 to A-81; M-1 to N-80; M-1 to S-79; M-1 to T-78; M-1 to P-77; M-1 to T-76; M-1 to C-75; M-1 to N-74; M-1 to V-73; M-1 to K-72; M-1 to Q-71; M-1 to V-70; M-1 to R-69; M-1 to N-68; M-1 to I-67; M-1 to V-66; M-1 to A-65; M-1 to C-64; M-1 to T-63; M-1 to I-62; M-1 to C-61; M-1 to S-60; M-1 to Q-59; M-1 to C-58; M-1 to K-57; M-1 to H-56; M-1 to H-55; M-1 to G-54; M-1 to W-53; M-1 to S-52; M-1 to S-51; M-1 to K-50; M-1 to Y-49; M-1 to Q-48; M-1 to S-47; M-1 to S-46; M-1 to P-45; M-1 to L-44; M-1 S-43; M-1 to H-42; M-1 to W-41; M-1 to Y-40; M-1 to A-39; M-1 to D-38; M-1 to G-37; M-1 to G-36; M-1 to E-35; M-1 to G-34; M-1 to Y-33; M-1 to G-32; M-1 to C-31; M-1 to D-30; M-1 to K-29; M-1 to S-28; M-1 to L-27; M-1 to E-26; M-1 to Q-25; M-1 to G-24; M-1 to P-23; M-1 to G-22; M-1 to C-21; M-1 to R-20; M-1 to Q-19; M-1 to C-18; M-1 to T-17; M-1 to V-16; M-1 to C-15; M-1 to R-14; M-1 to G-13; M-1 to W-12; M-1 to Q-11; M-1 to D-10; M-1 to W-9; M-1 to Y-8 and M-1 to E-7 of SEQ ID NO:61. Polynucleotides encoding these polypeptides are also encompassed by the invention.

Alternatively, the present invention further provides polypeptides having one or more residues deleted from the carboxy terminus of the amino acid sequence of the TR14 polypeptide shown in FIGS. 4A–E (SEQ ID NO:5), up to the asparagine residue at position number 6, and polynucleotides encoding such polypeptides. In particular, the present invention provides polypeptides comprising, or alternatively consisting of, the amino acid sequence of residues 1-m¹ of FIGS. 4A–E, where m¹ is an integer from 6 to 226 corresponding to the position of the amino acid residue in FIGS. 4A–E (which is identical to the sequence shown as SEQ ID NO:5).

Moreover, the invention provides polypeptides comprising, or alternatively consisting of, the amino acid residues: M-1 to E-225; M-1 to P-224; M-1 to G-223; M-1 to Q-222; M-1 to Q-221; M-1 to Q-220; M-1 to Q-219; M-1 to P-218; M-1 to I-217; M-1 to P-216; M-1 to V-215; M-1 to S-214; M-1 to D-213; M-1 to L-212; M-1 to S-211; M-1 to F-210; M-1 to L-209; M-1 to Q-208; M-1 to A-207; M-1 to L-206; M-1 to S-205; M-1 to G-204; M-1 to P-203; M-1 to A-202; M-1 to W-201; M-1 to S-200; M-1 to V-199; M-1 to Q-198; M-1 to S-197; M-1 to E-196; M-1 to A-195; M-1 to S-194; M-1 to T-193; M-1 to E-192; M-1 to K-191; M-1 to S-190; M-1 to P-189; M-1 to P-188; M-1 to V-187; M-1 to P-186; M-1 to F-185; M-1 to L-184; M-1 to S-183; M-1 to E-182; M-1 to E-181; M-1 to K-180; M-1 to A-179; M-1 to T-178; M-1 to K-177; M-1 to D-176; M-1 to A-175; M-1 to E-174; M-1 to F-173; M-1 to Q-172; M-1 to L-171; M-1 to L-170; M-1 to G-169; M-1 to G-168; M-1 to R-167; M-1 to Q-166; M-1 to C-165; M-1 to H-164; M-1 to R-163; M-1 to N-162; M-1 to F-161; M-1 to F-160; M-1 to Q-159; M-1 to K-158; M-1 to C-157; M-1 to Y-156; M-1 to L-155; M-1 to F-154; M-1 to F-153; M-1 to L-152; M-1 to G-151; M-1 to L-150; M-1 to F-149; M-1 to A-148; M-1 to L-147; M-1 to T-146; M-1 to F-145; M-1 to V-144; M-1 to V-143; M-1 to L-142; M-1 to L-141; M-1 to S-140; M-1 to S-139; M-1 to V-138; M-1 to L-137; M-1 to A-136; M-1 to V-135; M-1 to L-134; M-1 to T-133; M-1 to A-132; M-1 to E-131; M-1 to Q-130; M-1 to P-129; M-1 to P-128; M-1 to V-127; M-1 to T-126; M-1 to P-125; M-1 to A-124; M-1 to D-123; M-1 to A-122; M-1 to E-121; M-1 to V-120; M-1 to L-119; M-1 to S-118; M-1 to L-117; M-1 to Q-116; M-1 to F-115; M-1 to A-114; M-1 to C-113; M-1 to Q-112; M-1 to V-111; M-1 to E-111; M-1 to S-109; M-1 to T-108; M-1 to P-107; M-1 to T-106; M-1 to Q-105; M-1 to K-104; M-1 to T-103; M-1 to C-102; M-1 to P-101; M-1 to I-100; M-1 to C-99; M-1 to E-98; M-1 to Q-97; M-1 to D-96; M-1 to Q-95; M-1 to L-94; M-1 to G-93; M-1 to G-92; M-1 to I-91; M-1 to R-90; M-1 to T-89; M-1 to K-88; M-1 to R-87; M-1 to Y-86; M-1 to F-85; M-1 to R-84; M-1 to P-83; M-1 to L-82; M-1 to C-81; M-1 to D-80; M-1 to G-79; M-1 to C-78; M-1 to V-77; M-1 to A-76; M-1 to N-75; M-1 to S-74; M-1 to T-73; M-1 to P-72; M-1 to T-71; M-1 to C-70; M-1 to N-69; M-1 to V-68; M-1 to K-67; M-1 to Q-66; M-1 to V-65; M-1 to R-64; M-1 to N-63; M-1 to I-62; M-1 to V-61; M-1 to A-60; M-1 to C-59; M-1 to T-58; M-1 to C-57; M-1 to A-56; M-1 to V-55; M-1 to R-54; M-1 to C-53; M-1 to M-52; M-1 to Q-51; M-1 to P-50; M-1 to P-49; M-1 to G-48; M-1 to L-47; M-1 to Q-46; M-1 to K-45; M-1 to Q-44; M-1 to V-43; M-1 to A-42; M-1 to L-41; M-1 to L-40; M-1 to A-39; M-1 to P-38; M-1 to Q-37; M-1 to A-36; M-1 to T-35; M-1 to P-34; M-1 to M-33; M-1 to E-32; M-1 to V-31; M-1 to R-30; M-1 to E-29; M-1 to M-28; M-1 to V-27; M-1 to V-26; M-1 to I-25; M-1 to R-24; M-1 to P-23; M-1 to Y-22; M-1 to S-21; M-1 to R-20; M-1 to D-19; M-1 to L-18; M-1 to V-17; M-1 to V-16; M-1 to G-15; M-1 to N-14; M-1 to A-13; M-1 to P-12; M-1 to S-11; M-1 to V-10; M-1 to G-9; M-1 to D-8; M-1 to G-7;

M-1 to N-6; of SEQ ID NO.5. Polynucleotides encoding these polypeptides are also encompassed by the invention.

Also as mentioned above, even if deletion of one or more amino acids from the C-terminus of a protein results in modification or loss of one or more biological functions of the protein, other functional activities (e.g., biological activities), ability to multimerize, ability to bind TR14 ligand) may still be retained. For example the ability of the shortened TR14 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an TR14 mutein with a large number of deleted C-terminal amino acid residues may retain some biological or immunogenic activities. In fact, peptides composed of as few as six TR14 amino acid residues may often evoke an immune response.

The present invention further provides polypeptides having one or more residues deleted from the carboxy terminus of the amino acid sequence of the TR14 polypeptide shown in FIGS. 4A–E (SEQ ID NO:5) and polynucleotides encoding such polypeptides. In particular, the present invention provides polypeptides comprising, or alternatively consisting of, the amino acid sequence of residues 133-$m^1$ of FIGS. 4A–E, where $m^1$ is an integer from 6 to 132 corresponding to the position of the amino acid residue in FIGS. 4A–E (which is identical to the sequence shown as SEQ ID NO:5).

Moreover, the invention provides TR14 polypeptides comprising, or alternatively consisting of, the amino acid sequence of residues: M-1 to A-132; M-1 to E-131; M-1 to Q-130; M-1 to P-129; M-1 to P-128; M-1 to V-127; M-1 to T-126; M-1 to P-125; M-1 to A-124; M-1 to D-123; M-1 to A-122; M-1 to E-121; M-1 to V-120; M-1 to L-119; M-1 to S-118; M-1 to L-117; M-1 to Q-116; M-1 to F-115; M-1 to A-114; M-1 to C-113; M-1 to Q-112; M-1 to V-111; M-1 to E-110; M-1 to S-109; M-1 to T-108; M-1 to P-107; M-1 to T-106; M-1 to Q-105; M-1 to K-104; M-1 to T-103; M-1 to C-102; M-1 to P-101; M-1 to I-100; M-1 to C-99; M-1 to E-98; M-1 to Q-97; M-1 to D-96; M-1 to Q-95; M-1 to L-94; M-1 to G-93; M-1 to G-92; M-1 to I-91; M-1 to R-90; M-1 to K-88; M-1 to R-87; M-1 to Y-86; M-1 to F-85; M-1 to R-84; M-1 to P-83; M-1 L-82; M-1 to C-81; M-1 to D-80; M-1 to G-79; M-1 to C-78; M-1 to V-77; M-1 to A-76; M-1 to N-75; M-1 to S-74; M-1 to T-73; M-1 to P-72; M-1 to T-71; M-1 to C-70; M-1 to N-69; M-1 to V-68; M-1 to K-67; M-1 to Q-66; M-1 to V-65; M-1 to R-64; M-1 to N-63; M-1 to I-62; M-1 to V-61; M-1 to A-60; M-1 to C-59; M-1 to T-58; M-1 to C-57; M-1 to A-56; M-1 to V-55; M-1 to R-54; M-1 to C-53; M-1 to M-52; M-1 to Q-51; M-1 to P-50; M1 to P-49; M-1 to G-48; M-1 to L-47; M-1 to Q-46; M-1 to K-45; M-1 to Q-44; M-1 to V-43; M-1 to A-42; M-1 to L-41; M-1 to L-40; M-1 to A-39; M-1 to P-38; M-1 to Q-37; M-1 to A-36; M-1 to T-35; M-1 to P-34; M-1 to M-33; M-1 to E-32; M-1 to V-31; M-1 to R-30; M-1 to E-29; M-1 to M-28; M-1 to V-27; M-1 to V-26; M-1 to I-25; M-1 to R-24; M-1 to P-23; M-1 to Y-22; M-1 to S-21; M-1 to R-20; M-1 to D-19; M-1 to L-18; M-1 to V-17; M-1 to V-16; M-1 to G-15; M-1 to N-14; M-1 to A-13; M-1 to P-12; M-1 to S-11; M-1 to V-10; M-1 to G-9; M-1 to D-8; M-1 to G-7; M-1 to N-6; of SEQ ID NO:7. Polynucleotides encoding these polypeptides are also encompassed by the invention.

The invention also provides polypeptides having one or more amino acids deleted from both the amino and the carboxyl termini, which may be described generally as having residues $n^1$-$m^1$, $n^2$-$m^1$, $n^1$-$m^2$ and/or $n^2$-$m^2$, where $n^1$, $n^2$, $m^1$, and $m^2$ are integers as described above. Thus, any of the above listed N- or C-terminal deletions can be combined to produce an N- and C-terminal deleted TR14 polypeptide.

It will be recognized in the art that some amino acid sequences of TR14 polypeptides can be varied without significant effect on the structure or function of the protein. If such differences in sequence are contemplated, it should be remembered that there will be critical areas on the protein which determine activity. Thus, the invention further includes variations of the TR14 polypeptide, which show substantial TR14 receptor activity or which include regions of TR14 polypeptides, such as the polypeptide portions discussed herein. Such mutants include deletions, insertions, inversions, repeats, and type substitutions. As indicated above, guidance concerning which amino acid changes are likely to be phenotypically silent can be found in J. U. Bowie et al., *Science* 247:1306–1310 (1990).

Thus, the fragment, derivative, or analog of the polypeptide encoded by the cDNA deposited as ATCC Deposit No. PTA-348 or shown, preferably, in SEQ ID NO:61 or, alternatively, in SEQ ID NO:5, may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the TR14 polypeptide. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993), describes certain mutations resulting in selective binding of TNF-α to only one of the two known types of TNF receptors. Thus, the TR14 receptor of the present invention may include one or more amino acid substitutions, deletions, or additions, either from natural mutations or human manipulation.

As indicated, changes are preferably of a minor nature, such as conservative amino acid substitutions that do not significantly affect the folding or activity of the protein (see Table IV).

In specific embodiments, the number of substitutions, additions or deletions in the amino acid sequence of FIGS.

10A–H (SEQ ID NO:61) and/or any of the polypeptide fragments described herein (e.g., the cysteine-rich domain, the extracellular domain, or intracellular domain) is 75, 70, 60, 50, 40, 35, 30, 25, 20, 15, 10, 9, 8, 7, 6, 5, 4, 3, 2, 1 or 30–20, 20-15, 20-10, 15-10, 10-1, 5-10, 1-5, 1-3 or 1-2.

In additional embodiments, the number of substitutions, additions or deletions in the amino acid sequence of FIGS. 4A–E (SEQ ID NO:5) and/or any of the polypeptide fragments described herein (e.g., the cysteine-rich domain, the extracellular domain, or intracellular domain) is 75, 70, 60, 50, 40, 35, 30, 25, 20, 15, 10, 9, 8, 7, 6, 5, 4, 3, 2, 1 or 30-20, 20-15, 20-10, 15-10, 10-1, 5-10, 1-5, 1-3 or 1-2.

Amino acids in the TR14 polypeptides of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro g proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

To improve or alter the characteristics of TR14 polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), restriction selection mutagenesis (see e.g., Wells et al., *Philos. Trans. R. Soc. London SerA* 317:415 (1986)).

Thus, the invention also encompasses TR14 derivatives and analogs that have one or more amino acid residues deleted, added, or substituted to generate TR14 polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the TR14 polypeptides of the invention, and/or an amino acid deletion at the second position of any one or more such recognition sequences will prevent glycosylation of the TR14 at the modified tripeptide sequence (see, e.g., Miyajimo et al., *EMBO J* 5(6):1193–1197). Additionally, one or more of the amino acid residues of the polypeptides of the invention (e.g., arginine and lysine residues) may be deleted or substituted with another residue to eliminate undesired processing by proteases such as, for example, furins or kexins.

The polypeptides of the present invention include a polypeptide comprising, or alternatively, consisting of the polypeptide encoded by the cDNA deposited as ATCC Deposit No. PTA-348; a polypeptide comprising, or alternatively, consisting of amino acids from 1 to about 231 of SEQ ID NO:61 or from 1 to about 226 of SEQ ID NO:5; a polypeptide comprising, or alternatively, consisting of amino acids from about from 2 to about 231 of SEQ ID NO:61 or 2 to about 226 of SEQ ID NO:5; a polypeptide comprising, or alternatively, consisting of amino acids from 1 to about 138 of SEQ ID NO:61 or from 1 to about 133 of SEQ ID NO:5; a polypeptide comprising, or alternatively, consisting of the extracellular domain of the polypeptide encoded by the cDNA deposited as ATCC Deposit No. PTA-348; a polypeptide comprising, or alternatively, consisting of the cysteine rich domain of the polypeptide encoded by the cDNA deposited as ATCC Deposit No. PTA-348, or as shown in amino acids about 31 to about 104 of SEQ ID NO:61, or shown in amino acids from about 65 to about 85 of SEQ ID NO:5; a polypeptide comprising, or alternatively, consisting of the transmembrane domain of the polypeptide encoded by the cDNA deposited as ATCC Deposit No. PTA-348 (predicted to constitute amino acids from about 139 to about 155 of SEQ ID NO: 61 or from 134 to about 150 of SEQ ID NO:5); a polypeptide comprising, or alternatively, consisting of the intracellular domain (predicted to constitute amino acids from about 155 to about 231 of SEQ ID NO:61 or from about 151 to about 226 of SEQ ID NO:5); a polypeptide comprising, or alternatively, consisting of the extracellular and intracellular domains with all or part of the transmembrane domain deleted; as well as polypeptides which are at least 80% identical, more preferably at least 90% or 95% identical, still more preferably at least 96%, 97%, 98%, or 99% identical to the polypeptides described above (e.g., the polypeptide encoded by the cDNA in ATCC Deposit No. PTA-348, the polypeptide of FIGS. 10A–H (SEQ ID NO:61); or the polypeptide of FIGS. 4A–E (SEQ ID NO:5)) or polypeptide fragments thereof, such as those disclosed herein), and also include portions of such polypeptides with at least 30 amino acids and more preferably at least 50 amino acids. In this context "about" includes the particularly recited ranges, larger or smaller by several (5, 4, 3, 2, or 1) amino acids, at either extreme or at both extremes. Polynucleotides encoding these polypeptides are also encompassed by the invention.

By a polypeptide (protein) comprising, or alternatively consisting of, an amino acid sequence at least, for example, 95% "identical" to a reference amino acid sequence of a TR14 polypeptide is intended that the amino acid sequence of the polypeptide is identical to the reference sequence except that the polypeptide sequence may include up to five amino acid alterations per each 100 amino acids of the reference amino acid of the TR14 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98%, or 99% identical to, for instance, the amino acid sequence shown in SEQ ID NO:5, or to the amino acid sequence encoded by the cDNA deposited as ATCC Deposit No. PTA-348, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full-length of the reference amino acid sequence and that gaps in homology of up to 5% of the total number of amino acid residues in the reference sequence are allowed.

In a specific embodiment, the identity between a reference (query) sequence (a sequence of the present invention) and a, subject sequence, also referred to as a global sequence alignment, is determined using the FASTDB computer program based on the algorithm of Brutlag et al. (*Comp. App. Biosci.* 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty= 0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present application is also directed to proteins cotaining polypeptides at least 90%, 95%, 96%, 97%, 98% or 99% identical to the TR14 polypeptide sequence set forth as $n^1$-$m^1$, $n^2$-$m^1$, $n^1$-$m^2$, and/or $n^2$-$m^2$ described herein. In preferred embodiments, the application is directed to proteins comprising, or alternatively consisting of, polypeptide sequence at least 90%, 95%, 96%, 97%, 98% or 99% identical to polypeptides having the amino acid sequence of the specific TR14 N- and C-terminal deletions recited herein. Polynucleotides encoding these polypeptides are also encompassed by the invention.

In certain preferred embodiments, TR14 proteins of the invention comprise fusion proteins as described above wherein the TR14 polypeptides are those described as $n^1$-$m^1$, and/or $n^2$-$m^1$ herein. In preferred embodiments, the application is directed to nucleic acid molecules at least 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

In another aspect, the invention provides a TR14 polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, J. G. Sutcliffe et al., "Antibodies That React With Predetermined Sites on Proteins," *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777. Antigenic epitope-bearing peptides and polypeptides of the invention preferably contain a sequence of at least seven, more preferably at least nine, at least 20, at least 25, at least 30, at least 40, at least 50 and most preferably between at least about 55 to about 100 amino acids contained within the amino acid sequence of a polypeptide of the invention. In this context "about"

includes the particularly recited ranges, larger or smaller by several (5, 4, 3, 2, or 1) amino acids, at either extreme or at both extremes.

Non-limiting examples of predicted antigenic polypeptides that can be used to generate TR14-specific antibodies include polypeptides comprising about: Asp-2 to Asp-10, Thr-17 to Asp-38, Pro-45 to Ser-52, Pro-88 to Arg-95, Thr-108 to Glu-115, Thr-131 to Glu-136, Phe-166 to Gly-174, Ala-180 to Ala-200, and Gln-224 to Met-231 of SEQ ID NO:61. Fragments and/or variants of these polypeptides, such as, for example, fragments and/or variants as described herein, are encompassed by the invention. Polynucleotides encoding these polypeptides (including fragments and/or variants) are also encompassed by the invention, as are antibodies that bind these polypeptides.

Additional non-limiting examples of predicted antigenic polypeptides that can be used to generate TR14-specific antibodies include: a polypeptide comprising, or alternatively consisting of amino acid residues from about 2 to about 24 in FIGS. 4A–E (corresponding to about amino acid 2 to about 24 in SEQ ID NO:5); a polypeptide comprising amino acid residues from about 42 to about 52 in FIGS. 4A–E (corresponding to about amino acid 42 to about 52 in SEQ ID NO:5); a polypeptide comprising amino acid residues from about 80 to about 115 in FIGS. 4A–E (corresponding to about amino acid 80 to about 115 in SEQ ID NO:5); and a polypeptide comprising amino acid residues from about 155 to about 226 in FIGS. 4A–E (corresponding to about amino acid 155 to about 226 in SEQ ID NO:5), and the corresponding amino acid sequences of SEQ ID NO:61, as the sequence of amino acid residues T-78 to M-231 of SEQ ID NO:61 is identical to the sequence of amino acid residues T-73 to M-226 of SEQ ID NO:5. As indicated above, the inventors have determined that the above polypeptide fragments are antigenic regions of the TR14 receptor protein. In this context "about" includes the particularly recited ranges, larger or smaller by several (5, 4, 3, 2, or 1) amino acids, at either extreme or at both extremes. Polynucleotides encoding these polypeptides are also encompassed by the invention.

Additional non-limiting examples of predicted antigenic polypeptides that can be used to generate TR14-specific antibodies include: a polypeptide comprising, or alternatively consisting of, amino acid residues from about T3 to about S11, from about V16 to about R24, from about Q44 to about M52, from about F85 to about G93, from about T103 to about V111, from about F161 to about G169, from about V187 to about A195, from about P218 to about M226 of SEQ ID NO:5 (FIGS. 4A–E, and the corresponding amino acid sequences of SEQ ID NO:61, as the sequence of amino acid residues T-78 to M-231 of SEQ ID NO:61 is identical to the sequence of amino acid residues T-73 to M-226 of SEQ ID NO:5) correspond to the highly antigenic regions of the TR14 protein, predicted using the Jameson-Wolf antigenic index (See FIG. 6 and Table II). These highly antigenic fragments correspond to the amino acid residues illustrated in FIG. 4A–E and in SEQ ID NO:5. In this context "about" includes the particularly recited ranges, larger or smaller by several (5, 4, 3, 2, or 1) amino acids, at either extreme or at both extremes. Polynucleotides encoding these polypeptides are also encompassed by the invention.

The epitope-bearing peptides and polypeptides of the invention may be produced by any conventional means. R. A. Houghten, "General Method for the Rapid Solid-phase Synthesis of Large Numbers of Peptides: Specificity of Antigen-Antibody Interaction at the Level of Individual Amino Acids," *Proc. Natl. Acad. Sci. USA* 82:5131–5135 (1985). This "Simultaneous Multiple Peptide Synthesis (SMPS)" process is further described in U.S. Pat. No. 4,631,211 to Houghten et al., (1986).

As one of skill in the art will appreciate, TR14 receptor polypeptides of the present invention and the epitope-bearing fragments thereof, described herein (e.g., corresponding to a portion of the extracellular domain, such as, for example, amino acid residues 1 to about 149, from about 2 to about 24, from about 42 to about 52, from about 80 to about 115, and/or from about 155 to about 226 of SEQ ID NO: 5), can be combined with heterologous polypeptide sequences, for example, the polypeptides of the present invention may be fused with the constant domain of immunoglobulins (IgA, IgE, IgG, IgM) or portions thereof (CH1, CH2, CH3, and any combination thereof, including both entire domains and portions thereof), resulting in chimeric polypeptides. By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, polypeptide,s and/or antibodies of the present invention (including fragments or variants thereof) are fused with the mature form of human serum albumin (i.e., amino acids 1–585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

Such fusion proteins as those described above may facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric TR14 protein or protein fragment alone (Fountoulakis et al., *J. Biochem.* 270:3958–3964 (1995)). In this context "about" includes the particularly recited ranges, larger or smaller by several (5, 4, 3, 2, or 1) amino acids, at either extreme or at both extremes.

Preferred TR14 Fc fusions of the present invention include, but are not limited to constructs comprising, or alternatively consisting of, amino acid residues: 1 to 138, 50 to 138, 70 to 90, 1 to 231, 10 to 231, 20 to 231, 30 to 231, 40 to 231, 1 to 221, 1 to 211, 1 to 201, 1 to 191, 10 to 221, 10 to 201, and/or 10 to 191 of SEQ ID NO:61. Polynucleotides encoding these TR14 fusions are also encompassed by the invention.

Additonal TR14 Fc fusions of the present invention include, but are not limited to constructs comprising, or alternatively consisting of, amino acid residues: 1 to 133, 50 to 133, 65 to 85, 1 to 226, 10 to 226, 20 to 226, 30 to 226, 40 to 226, 1 to 216, 1 to 206, 1 to 196, 1 to 186, 10 to 216, 10 to 206, and/or 10 to 196 of SEQ ID NO:5. Polynucleotides encoding these TR14 fusions are also encompassed by the invention.

The polypeptides of the present invention have uses which include, but are not limited to, as sources for generating antibodies that bind the polypeptides of the invention, and as molecular weight markers on SDS-PAGE gels or on molecular sieve gel filtration columns using methods well known to those of skill in the art.

Diagnostic Assays

The compounds of the present invention are useful for diagnosis or treatment of various immune system-related disorders in mammals, preferably humans. Such disorders include but are not limited to tumors (e.g., T cell, B cell and monocytic cell leukemias and lymphomas) and tumor metastasis, infections by bacteria, viruses and other parasites, immunodeficiencies, inflammatory diseases, lymphadenopathy, autoimmune diseases, and graft versus host disease.

TR13 and TR14 are expressed in immune cells and tissue. For a number of immune system-related disorders, substantially altered (increased or decreased) levels TR13 and/or TR14 gene expression can be detected in immune system tissue or other cells or bodily fluids (e.g., sera, plasma, urine, synovial fluid or spinal fluid) taken from an individual having such a disorder, relative to a "standard" TR13 and/or TR14 gene expression level, that is, the TR13 and/or TR14 expression level in immune system tissues or bodily fluids from an individual not having the immune system disorder. Thus, the invention provides a diagnostic method useful during diagnosis of an immune system disorder, which involves measuring the expression level of the gene encoding the TR13 and/or TR14 polypeptide in immune system tissue or other cells or body fluid from an individual and comparing the measured gene expression level with a standard TR13 and/or TR14 gene expression level, respectively, whereby an increase or decrease in the gene expression level compared to the standard is indicative of an immune system disorder or normal activation, proliferation, differentiation, and/or death.

In particular, it is believed that certain tissues in mammals with cancer (such as, for example, cancer of cells or tissue of the immune, gastrointestinal and or reproductive systems) express significantly enhanced or reduced levels of normal or altered TR13 and/or TR14 polypeptide and mRNA encoding the TR13 and/or TR14 polypeptide when compared to a corresponding "standard" level. Further, it is believed that enhanced or depressed levels of the TR13 and/or TR14 polypeptide can be detected in certain body fluids (e.g., sera, plasma, urine, and spinal fluid) or cells or tissue from mammals with such a cancer when compared to sera from mammals of the same species not having the cancer.

For example, polynucleotides of the invention (e.g., polynucleotide sequences complementary to all or a portion of TR13 and/or TR14 mRNA) and antibodies (and antibody fragments) directed against the polypeptides of the invention may be used to quantitate or qualitate concentrations of cells of T cell lineage and/or B cell lineage (e.g., B cell leukemia cells) expressing TR13 and/or TR14 on their cell surfaces. These antibodies additionally have diagnostic applications in detecting abnormalities in the level of TR13 and/or TR14 gene expression, or abnormalities in the structure and/or temporal, tissue, cellular, or subcellular location of TR13 and/or TR14. These diagnostic assays may be performed in vivo or in vitro, such as, for example, on blood samples, biopsy tissue or autopsy tissue.

For example, as disclosed herein, TR13 or TR14 is expressed in T cells. Accordingly, polynucleotides of the invention (e.g., polynucleotide sequences complementary to all or a portion of TR13 or TR14 mRNA) and antibodies (and antibody fragments) directed against the polypeptides of the invention may be used to quantitate or qualitate concentrations of cells of T cell lineage (e.g., T cell leukemia cells) expressing TR13 or TR14 on their cell surfaces. These polypeptides and antibodies additionally have diagnostic applications in detecting abnormalities in the level of TR13 or TR14 gene expression, or abnormalities in the structure and/or temporal, tissue, cellular, or subcellular location of TR13 or TR14. These diagnostic assays may be performed in vivo or in vitro, such as, for example, on blood samples, biopsy tissue or autopsy tissue.

Thus, the invention provides a diagnostic method useful during diagnosis of a immune system disorder (including cancers of this system) and/or cell proliferation disorder (e.g., cancer, such as a cancer disclosed herein) which involves measuring the expression level of the gene encoding the TR13 and/or TR14 polypeptide in immune system tissue or other cells or body fluid from an individual and comparing the measured gene expression level with a standard TR13 and/or TR14 gene expression level, whereby an increase or decrease in the gene expression level compared to the standard is indicative of an immune system disorder and/or cell proliferation disorder.

Where a diagnosis of a disorder in the immune system (including diagnosis of a tumor) and/or diagnosis of a cell proliferation disorder has already been made according to conventional methods, the present invention is useful as a prognostic indicator, whereby patients exhibiting enhanced or depressed TR13 and/or TR14 gene expression will experience a worse clinical outcome relative to patients expressing the gene at a level nearer the standard level.

By "assaying the expression level of the gene encoding the TR13 and/or TR14 polypeptide" is intended qualitatively or quantitatively measuring or estimating the level of the TR13 and/or TR14 polypeptide or the level of the mRNA encoding the TR13 and/or TR14 polypeptide in a first biological sample either directly (e.g., by determining or estimating absolute protein level or mRNA level) or relatively (e.g., by comparing to the TR13 and/or TR14 polypeptide level or mRNA level in a second biological sample). Preferably, the TR13 and/or TR14 polypeptide level or mRNA level in the first biological sample is measured or estimated and compared to a standard TR13 and/or TR14 polypeptide level or mRNA level, the standard being taken from a second biological sample obtained from an individual not having the disorder or being determined by averaging levels from a population of individuals not having a disorder of the immune system. As will be appreciated in the art, once a standard TR13 and/or TR14 polypeptide level or mRNA level is known, it can be used repeatedly as a standard for comparison.

By "biological sample" is intended any biological sample obtained from an individual, cell line, tissue culture, or other source containing TR13 and/or TR14 receptor protein (including portions thereof) or mRNA. As indicated, biological samples include body fluids (such as sera, plasma, urine, synovial fluid and spinal fluid) which contain free extracellular domains of the TR13 and/or TR14 polypeptide, immune system tissue, and other tissue sources found to express complete or free extracellular domain of the TR13 and/or TR14 receptor. Methods for obtaining tissue biopsies and body fluids from mammals are well known in the art. Where the biological sample is to include mRNA, a tissue biopsy is the preferred source.

Total cellular RNA can be isolated from a biological sample using any suitable technique such as, for example, the single-step guanidinium-thiocyanate-phenol-chloroform method described in Chomczynski and Sacchi, *Anal. Biochem.* 162:156–159 (1987). Levels of mRNA encoding the TR13 and/or TR14 polypeptide are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

The present invention also relates to diagnostic assays such as quantitative and diagnostic assays for detecting levels of TR13 polypeptide, or the soluble form thereof, in cells and tissues, including determination of normal and abnormal levels. Thus, for instance, a diagnostic assay in accordance with the invention for detecting over-expression of TR13, or soluble form thereof, compared to normal control tissue samples may be used to detect the presence of tumors, for example. Assay techniques that can be used to determine levels of a protein, such as a TR13 polypeptide of the present invention, or a soluble form thereof, in a biological sample derived from a host are well-known to those of skill in the art. Such assay methods include radioimmunoassays, competitive-binding assays, Western Blot analysis and ELISA assays. Preferred for assaying TR13 polypeptide levels in a biological sample are antibody-based techniques. For example, TR13 polypeptide expression in tissues can be studied with classical immunohistological methods. (M. Jalkanen et al., *J. Cell. Biol.* 101:976–985 (1985); M. Jalkanen et al., *J. Cell. Biol.* 105:3087–3096 (1987)). Other antibody-based methods useful for detecting TR13 gene expression include immunoassays, such as the enzyme linked immunosorbent assay (ELISA) and the radioimmunoassay (RIA).

The present invention also relates to diagnostic assays such as quantitative and diagnostic assays for detecting levels of TR14 polypeptide, or the soluble form thereof, in cells and tissues, including determination of normal and abnormal levels. Thus, for instance, a diagnostic assay in accordance with the invention for detecting over-expression of TR14, or soluble form thereof, compared to normal control tissue samples may be used to detect the presence of tumors, for example. Assay techniques that can be used to determine levels of a protein, such as a TR14 polypeptide of the present invention, or a soluble form thereof, in a biological sample derived from a host are well-known to those of skill in the art. Such assay methods include radioimmunoassays, competitive-binding assays, Western Blot analysis and ELISA assays. Preferred for assaying TR14 polypeptide levels in a biological sample are antibody-based techniques. For example, TR14 polypeptide expression in tissues can be studied with classical immunohistological methods. (M. Jalkanen et al., *J. Cell. Biol.* 101:976–985 (1985); M. Jalkanen et al., *J. Cell. Biol.* 105:3087–3096 (1987)). Other antibody-based methods useful for detecting TR14 gene expression include immunoassays, such as the enzyme linked immunosorbent assay (ELISA) and the radioimmunoassay (RIA).

Suitable antibody assay labels are known in the art and include enzyme labels, such as glucose oxidase, and radioisotopes, such as iodine ($^{131}$I, $^{125}$I, $^{123}$I, $^{121}$I) carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, 175Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

The tissue or cell type to be analyzed will generally include those which are known, or suspected, to express the TR13 and/or TR14 gene (such as, for example, cells of T cell lineage) or cells or tissue which are known, or suspected, to express the TR13 ligand and/or TR14 ligand gene (such as, for example, cells of monocytic lineage and the spleen). The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the TR13 and/or TR14 gene or TR13 ligand and/or TR14 ligand gene.

For example, antibodies, or fragments of antibodies, such as those described herein, may be used to quantitatively or qualitatively detect the presence of TR13 and/or TR14 gene products or conserved variants or peptide fragments thereof. This can be accomplished, for example, by immunofluorescence techniques employing a fluorescently labeled antibody coupled with light microscopic, flow cytometric, or fluorimetric detection.

The antibodies (or fragments thereof) or TR13 and/or TR14 polypeptides or TR13 ligand and/or TR14 ligand polypeptides of the present invention may, additionally, be employed histologically, as in immunofluorescence, immunoelectron microscopy or non-immunological assays, for in situ detection of TR13 and/or TR14 gene products or conserved variants or polypeptide fragments thereof, or for TR13 and/or TR14 binding to TR13 and/or TR14 ligand, respectively. In situ detection may be accomplished by removing a histological specimen from a patient, and applying thereto a labeled antibody, TR13 polypeptide, or TR14 polypeptide of the present invention. The antibody (or fragment) or TR13 and/or TR14 polypeptide is preferably applied by overlaying the labeled antibody (or fragment) onto a biological sample. Through the use of such a procedure, it is possible to determine not only the presence of the TR13 and/or TR14 gene product, or conserved variants or peptide fragments, or TR13 and/or TR14 polypeptide binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for TR13 and/or TR14 gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of TR13 and/or TR14 gene products or conserved variants or peptide fragments thereof, and detecting the bound antibody by any of a number of techniques well-known in the art.

Immunoassays and non-immunoassays for TR13 ligand and/or TR14 ligand gene products or conserved variants or peptide fragments thereof will typically comprise incubating a sample, such as a biological fluid, a tissue extract, freshly harvested cells, or lysates of cells which have been incubated in cell culture, in the presence of a detectable or labeled TR13 and/or TR14 polypeptide capable of identifying TR13 ligand and/or TR14 ligand gene products or conserved variants or polypeptide fragments thereof, and detecting the bound TR13 and/or TR14 polypeptide by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled anti-TR13 and/or TR14 antibody or detectable TR13 and/or TR14 polypeptide. The solid phase support may then be washed with the buffer a second time to remove unbound antibody or polypeptide. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

Assaying TR13 or TR14 protein levels in a biological sample can occur using any art-known method.

The binding activity of a given lot of anti-TR13 and/or anti-TR14 antibody or TR13 and/or TR14 polypeptide may be determined according to well known methods. Those skilled in the art will be able to determine operative and optimal assay conditions for each determination by employing routine experimentation.

In addition to assaying TR13 and/or TR14 polypeptide levels or polynucleotide levels in a biological sample obtained from an individual, TR13 and/or TR14 polypeptide or polynucleotide can also be detected in vivo by imaging. For example, in one embodiment of the invention, TR13 and/or TR14 polypeptide is used to image monocytic leukemias or lymphomas. In another embodiment, TR13 and/or TR14 polynucleotides of the invention (e.g., polynucleotides complementary to all or a portion of TR13 and/or TR14 mRNA) is used to image T cell leukemias or lymphomas.

Antibody labels or markers for in vivo imaging of TR13 and/or TR14 polypeptide include those detectable by X-radiography, NMR, MRI, CAT-scans or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

Where in vivo imaging is used to detect enhanced levels of TR13 and/or TR14 polypeptide for diagnosis in humans, it may be preferable to use human antibodies or "humanized" chimeric monoclonal antibodies. Such antibodies can be produced using techniques described herein or otherwise known in the art. For example methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Additionally, any TR13 and/or TR14 polypeptide whose presence can be detected, can be administered. For example, TR13 and/or TR14 polypeptides labeled with a radio-opaque or other appropriate compound can be administered and visualized in vivo, as discussed, above for labeled antibodies. Further such TR13 and/or TR14 polypeptides can be utilized for in vitro diagnostic procedures.

A TR13 and/or TR14 polypeptide-specific antibody or antibody fragment which has been labeled with an appropriate detectable imaging moiety, such as a radioisotope (for example, 131I, $^{112}$In, $^{99m}$Tc), a radio-opaque substance, or a material detectable by nuclear magnetic resonance, is introduced (for example, parenterally, subcutaneously or intraperitoneally) into the mammal to be examined for an immune system disorder and/or cell proliferation disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain TR13 and/or TR14 protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

With respect to antibodies, one of the ways in which the anti-TR13 and/or anti-TR14 antibody can be detectably labeled is by linking the same to an enzyme and using the linked product in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller et al., *J. Clin. Pathol.* 31:507–520 (1978); Butler, J. E., *Meth. Enzymol.* 73:482–523 (1981); Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect TR13 and/or TR14 through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by means including, but not limited to, a gamma counter, a scintillation counter, or autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, ophthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

TR13 and TR14 Binding Peptides and Other Molecules

The invention also encompasses screening methods for identifying polypeptides and nonpolypeptides that bind TR13 or TR14, and the TR13 or TR14 binding molecules identified thereby. These binding molecules are useful, for example, as agonists and antagonists of the TR13 or TR14 receptor proteins. Such agonists and antagonists can be used, in accordance with the invention, in the therapeutic embodiments described in detail, below.

This method comprises the steps of:

contacting a TR13 or TR14 protein or TR13 or TR14-like protein with a plurality of molecules; and identifying a molecule that binds the TR13 or TR14 protein or TR13 or TR14-like protein.

The step of contacting the TR13 or TR14 protein or TR13 or TR14-like protein with the plurality of molecules may be effected in a number of ways. For example, one may contemplate immobilizing the TR13 or TR14 protein or TR13 or TR14-like protein on a solid support and bringing a solution of the plurality of molecules in contact with the immobilized TR13 or TR14 protein or TR13 or TR14-like protein. Such a procedure would be akin to an affinity chromatographic process, with the affinity matrix being comprised of the immobilized TR13 or TR14 protein or TR13 or TR14-like protein. The molecules having a selective affinity for the TR13 or TR14 protein or TR13 or TR14-like protein can then be purified by affinity selection. The nature of the solid support, process for attachment of the TR13 or TR14 protein or TR13 or TR14-like protein to the solid support, solvent, and conditions of the affinity isolation or selection are largely conventional and well known to those of ordinary skill in the art.

Alternatively, one may also separate a plurality of polypeptides into substantially separate fractions comprising a subset of or individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface (e.g., a recombinant phage). Individual isolates can then be "probed" by the TR13 or TR14 protein or TR13 or TR14-like protein, optionally in the presence of an inducer should one be required for expression, to determine if any selective affinity interaction takes place between the TR13 or TR14 protein or TR13 or TR14-like protein and the individual clone. Prior to contacting the TR13 or TR14 protein or TR13 or TR14-like protein with each fraction comprising individual polypeptides, the polypeptides could first be transferred to a solid support for additional convenience. Such a solid support may simply be a piece of filter membrane, such as one made of nitrocellulose or nylon. In this manner, positive clones could be identified from a collection of transformed host cells of an expression library, which harbor a DNA construct encoding a polypeptide having a selective affinity for TR13 or TR14 protein or TR13 or TR14-like protein. Furthermore, the amino acid sequence of the polypeptide having a selective affinity for the TR13 or TR14 protein or TR13 or TR14-like protein can be determined directly by conventional means or the coding sequence of the DNA encoding the polypeptide can frequently be determined more conveniently. The primary sequence can then be deduced from the corresponding DNA sequence. If the amino acid sequence is to be determined from the polypeptide itself, one may use microsequencing techniques. The sequencing technique may include mass spectroscopy.

In certain situations, it may be desirable to wash away any unbound TR13 or TR14 protein or TR13 or TR14-like protein, or alternatively, unbound polypeptides, from a mixture of the TR13 or TR14 protein or TR13 or TR14-like protein and the plurality of polypeptides prior to attempting to determine or to detect the presence of a selective affinity interaction. Such a wash step may be particularly desirable when the TR13 or TR14 protein or TR13 or TR14-like protein or the plurality of polypeptides is bound to a solid support.

The plurality of molecules provided according to this method may be provided by way of diversity libraries, such as random or combinatorial peptide or nonpeptide libraries which can be screened for molecules that specifically bind to TR13 or TR14. Many libraries are known in the art that can be used, e.g., chemically synthesized libraries, recombinant (e.g., phage display libraries), and in vitro translation-based libraries. Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lemer, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R. B., et al., 1992, J. Mol. Biol. 227:711–718); Lenstra, 1992, J. Immunol. Meth. 152:149–157; Kay et al., 1993, Gene 128:59–65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

The variety of non-peptide libraries that are useful in the present invention is great. For example, Ecker and Crooke, 1995, Bio/Technology 13:351–360 list benzodiazepines, hydantoins, piperazinediones, biphenyls, sugar analogs, beta-mercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be a molecule with a known useful pharmacological activity. For example, the scaffold might be the benzodiazepine structure.

Non-peptide oligomer libraries utilize a large number of monomers that are assembled together in ways that create new shapes that depend on the order of the monomers. Among the monomer units that have been used are carbamates, pyrrolinones, and morpholinos. Peptoids, peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar and Pabo, 1993, Science 263:671–673; and CT Publication No. WO 94/18318.

In a specific embodiment, screening to identify a molecule that binds TR13 or TR14 can be carried out by contacting the library members with a TR13 or TR14 protein or TR13 or TR14-like protein immobilized on a solid phase and harvesting those library members that bind to the TR13 or TR14 protein or TR13 or TR14-like protein. Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited herein.

In another embodiment, the two-hybrid system for selecting interacting proteins in yeast (Fields and Song, 1989, Nature 340:245–246; Chien et al., 1991, Proc. Natl. Acad. Sci. USA 88:9578–9582) can be used to identify molecules that specifically bind to TR13 or TR14 or TR13 or TR14-like proteins.

Where the TR13 or TR14 binding molecule is a polypeptide, the polypeptide can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid or that positions 4, 8, and 9 of a decapeptide library be fixed to include only arginine. Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage vector with a DNA insert.

As mentioned above, in the case of a TR13 or TR14 binding molecule that is a polypeptide, the polypeptide may have about 6 to less than about 60 amino acid residues, preferably about 6 to about 10 amino acid residues, and most preferably, about 6 to about 22 amino acids. In another embodiment, a TR13 or TR14 binding polypeptide has in the range of 15–100 amino acids, or 20–50 amino acids.

The selected TR13 or TR14 binding polypeptide can be obtained by chemical synthesis or recombinant expression.

Epitopes

The present invention encompasses polypeptides comprising, or alternatively consisting of, an epitope of the TR13 and TR14 polypeptides described in detail above or encoded by a polynucleotide that hybridizes to the complement of the sequence of TR13 and TR14 coding sequences described in detail above, under stringent hybridization conditions or lower stringency hybridization conditions as defined supra. The present invention further encompasses polynucleotide sequences encoding an epitope of a polypeptide sequence of the, polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments that function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 15, at least 20, at least 25, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. Antigenic epitopes can be used as the target molecules in immunoassays. (See, for instance, Wilson et al., Cell 37:767–778 (1984); Sutcliffe et al., *Science* 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). The polypeptides comprising one or more immunogenic epitopes may be presented for eliciting an antibody response together with a carrier protein, such as an albumin, to an animal system (such as, for example, rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as, for example, rabbits, rats, and mice are immunized with either free or carrier-coupled peptides, for instance, by intraperitoneal and/or intradermal injection of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2): 76–82 (1998); Hansson, et al., J. Mol. Biol. 287:265–76 (1999); and Lorenzo and Blasco, Biotechniques 24(2): 308–13 (1998) (each of these patents and publications are hereby incorporated by reference in its entirety). In one embodiment, alteration of polynucleotides corresponding to SEQ ID NO:1 or 60 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide coding a polypeptide of the invention may be recombined with one or more components, motifs, sections, parts, domains, fragments, etc. of one or more heterologous molecules. (each of these patents and publications are hereby incorporated by reference). In one embodiment, alteration of TR13 and/or TR14 polynucleotides and corresponding polypeptides may be achieved by DNA shuffling. DNA shuffling involves the assembly of two or more DNA segments into a desired TR13 and/or TR14 molecule by homologous, or site-specific, recombination. In another embodiment, TR13 and/or TR14 polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of TR13 and/or TR14 may be recombined with one or more components, motifs, sections, parts, domains, fragments, etc. of one or more heterologous molecules. In preferred embodiments, the heterologous molecules are receptors for TNF-alpha, TNF-beta, lymphotoxin-alpha, lymphotoxin-beta, FAS ligand, and APRIL. In further preferred embodiments, the heterologous molecules are any member of the TNF family.

Antibodies

The present invention further relates to antibodies and T-cell antigen receptors (TCR) which immunospecifically bind a polypeptide, preferably an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine, donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues, or listed in the Tables and Figures. Antibodies that specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies that bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$M, $10^{-2}$M, $5\times10^{-3}$M, $10^{-3}$M, $5\times10^{-4}$M, $10^{-4}$M, $5\times10^{-5}$M, $10^{-5}$M, $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 90%, at least 80%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen, et al., Cancer Res. 58(16):3668–3678 (1998); Harrop et al., J. Immunol. 161(4):1786–1794 (1998); Zhu et al., Cancer Res. 58(15):3209–3214 (1998); Yoon, et al., J. Immunol. 160(7):3170–3179 (1998); Prat et al., J. Cell. Sci. 111(Pt2):237–247 (1998); Pitard et al., J. Immunol. Methods 205(2):177–190 (1997) Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

Figure 12:
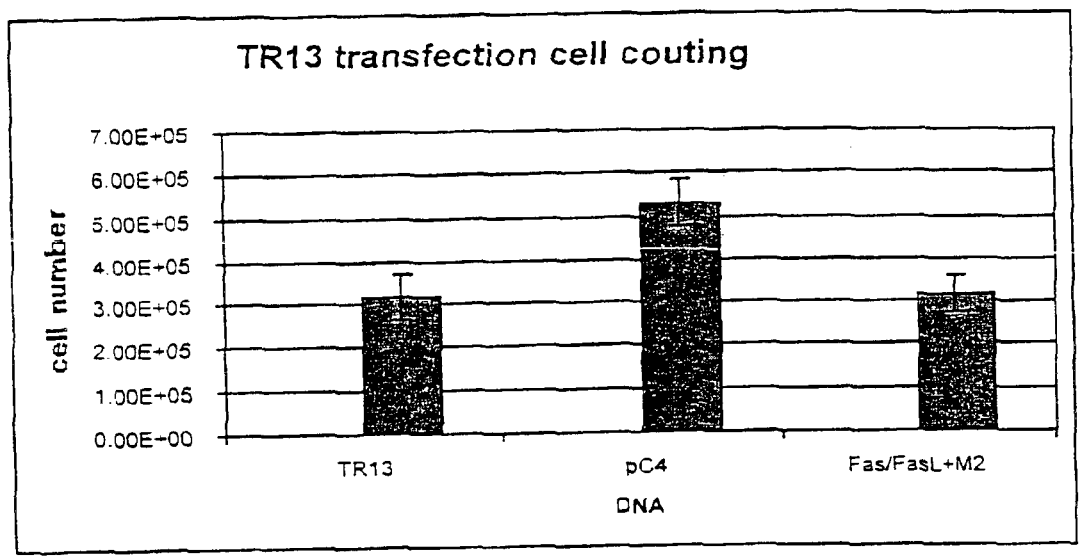
FIG. 12 provides experimental results from a HEK 293T cell survival assay carried out as described in Example 37 below. Briefly, human embryonic kidney (HEK) 293T cells were transiently transfected with expression construct DNAs, 48 hours post transfection viable cells were identified and counted using Trypan blue staining. TR13 was shown to restrict cell expansion when compared to a vector control, the extent of growth inhibition being similar to that caused by the apoptosis inducing receptor and ligand combination of Fas and Flag-FasL.

Agonistic antibodies of the invention may also be used to target and kill cells, including, for example, cancer cells, expressing TR13 on their surface and/or cells having TR13 bound to their surface. TR13 regulates survival and/or proliferation of epithelial cells as exemplified by HEK 293T cells. See Example 37 and FIG. 12. In specific embodiments agonistic antibodies of the invention are used to inhibit proliferation and/or survival of epithelial cells. In further specific embodiments agonistic antibodies of the invention are used to treat disorders of epithelial cell proliferation and/or survival, for example, cancer. Antibodies of the invention may be provided in pharmaceutically acceptable compositions as known in the art or as described herein.

In addition, antagonistic antibodies that bind TR13 so as to prevent ligand binding without triggering cell signalling may be used in accordance with the invention to prevent ligand (e.g., FasL or LIGHT)-induced cell death. TR13 regulates survival and/or proliferation of epithelial cells as exemplified by HEK 293T cells. See Example 37 and FIG. 12. In specific embodiments antagonistic antibodies of the invention are used to stimulate proliferation and/or survival of epithelial cells. In further specific embodiments antagonistic antibodies of the invention are used, for example, to promote wound healing. Antibodies of the invention may be provided in pharmaceutically acceptable compositions as known in the art or as described herein.

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., PCT publications WO 92/08495; WO 91/14438; WO 89/12624; U.S. Pat. No. 5,314,995; and EP 396,387.

Agonistic and/or antagonistic antibodies of the present invention may be used in an assay to identify compounds which can increase or decrease epithelial cell survival and/or proliferation. In specific embodiments antibodies of the present invention may be used to identify TR13 agonists. In further specific embodiments antibodies of the present invention may be used to identify TR13 antagonists.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well-known in the art and are discussed in detail in Example 5, below. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of inmunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Imnunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5): 489–498 (1991); Studnicka et al., Protein Engineering 7(6) :805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to TR13 or TR14 polypeptide of the invention, as described above.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, N.Y., which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., 1984, Proc. Natl. Acad. Sci. 81:851–855; Neuberger et al., 1984, Nature 312:604–608; Takeda et al., 1985, Nature 314:452–454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,694,778; Bird, 1988, Science 242:423–42; Huston et al., 1988, Proc. Natl. Acad. Sci. USA 85:5879–5883; and Ward et al., 1989, Nature 334:544–54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., 1988, Science 242:1038–1041).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as Escherichia coli, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; Cockett et al., 1990, Bio/Technology 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 24:5503–5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, 1984, Proc. Natl. Acad. Sci. USA 81:355–359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes can be employed in tk-, hgprt- or aprt- cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIB TECH 11(5): 155–215); and hygro, which confers resistance to hygromycin (Santerre et al., 1984, Gene 30:147). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY; Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

Antibody Conjugates

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides of the present invention may be fused or conjugated to the above antibody portions to increase the in vivo half life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995)0.

Moreover, the antibodies or fragments thereof of the present invention can be fused to marker sequences, such as a peptide to facilitates their purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc $^{186}$Re, $^{188}$Re, $^{142}$Pr, $^{105}$Rh, $^{97}$Ru.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. In specific embodiments, antibodies of the invention are attached to macrocyclic chelators useful for conjugating radiometal ions, including but not limited to, $^{111}$In, $^{177}$Lu, $^{90}$Y, $^{166}$Ho, and $^{153}$Sm, to polypeptides. In preferred embodiments, the radiometal ion associated with the macrocyclic chelators attached to antibodies of the invention is $^{111}$In. In preferred embodiments, the radiometal ion associated with the macrocyclic chelators attached to antibodies of the invention is $^{90}$Y. In specific embodiments, the macrocyclic chelator is 1,4,7,10-tetraazacyclododecane-N,N',N'',N'''-tetraacetic acid (DOTA). In other specific embodiments, the DOTA is attached to the Neutrokine-alpha and/or Neutrokine-alphaSV polypeptide of the invention via a linker molecule. Examples of linker molecules useful for conjugating DOTA to a polypeptide are commonly known in the art—see, for example, DeNardo et al., Clin Cancer Res. 4(10):2483–90 (1998); Peterson et al., Bioconjug. Chem. 10(4):553–7 (1999); and Zimmerman et al., Nucl. Med. Biol. 26(8):943–50 (1999) which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16. 1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the described disorders. Therapeutic compounds of the invention include, but are not limited to, antibodies of the invention (including fragments, analogs and derivatives thereof as described herein) and nucleic acids encoding antibodies of the invention (including fragments, analogs and derivatives thereof as described herein). The antibodies of the invention may be agonists or antagonists of TR13 and/or TR14. The antibodies of the invention can be used to treat, inhibit or prevent diseases and disorders associated with aberrant expression and/or activity of polypeptides of the invention, including, but not limited to, cancers and immune disorders. The treatment and/or prevention of diseases and disorders associated with aberrant expression and/or activity of a polypeptide of the invention includes, but is not limited to, alleviating symptoms associated with those diseases and disorders. Antibodies of the invention may be provided in pharmaceutically acceptable compositions as known in the art or as described herein. Antibodies that agonize the TR13 and/or TR14 receptor can be used to ameliorate or treat biological activities associated with epithelial cell proliferation, tooth development, growth of mucosal layers, and the growth of epithelial surfaces, including hair folicles, sweat glands, basal cells, and dermis. Accordingly, TR13 and/or TR14 agonistic antibodies may be used in the treatment of diseases and/or disorders relating to the epithelium (e.g., anhidrotic ectodermal dysplasia, hidrotic ectodermal dysplasia, sweat gland disorders, venous ulcers, psoriasis, prickly heat disorder, wounds healing, cancers of epithelial origins, male pattern baldness, and/or as described under "Epithelial Cell Proliferation and Wound Healing" below). Furthermore antibodies that antagonize the TR13 and/or TR14 receptor can be used to ameliorate or treat biological activities associated with epithelial cell proliferation, tooth development, growth of mucosal layers, and the growth of epithelial surfaces, including hair folicles, sweat glands, basal cells, and dermis. Accordingly, TR13 and/or TR14 antagonistic antibodies may be used in the treatment of diseases and/or disorders relating to the epithelium (e.g., anhidrotic ectodermal dysplasia, hidrotic ectodermal dysplasia, sweat gland disorders, venous ulcers, psoriasis, prickly heat disorder, wounds healing, cancers of epithelial origins, male pattern baldness, and/or as described under "Epithelial Cell Proliferation and Wound Healing" below).

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}$ M, $10^{-6}$ M, $5\times10^{-7}$ M, $10^{-7}$ M, $5\times10^{-8}$ M, and $10^{-8}$ M. Even more preferred binding affinities include those with a dissociation constant or Kd less than $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5): 155–215). Methods commonly known in the art of recombinant DNA technology which can be used are described in Ausubel et al. (eds.), 1993, Current Protocols in Molecular Biology, John Wiley & Sons, N.Y.; and Kriegler, 1990, Gene Transfer and Expression, A Laboratory Manual, Stockton Press, N.Y.

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody nucleic acids (Koller and Smithies, 1989, Proc. Natl. Acad. Sci. USA 86:8932–8935; Zijlstra et al., 1989, Nature 342:435–438). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429–4432) (which can be used to target cell types specifically expressing the receptors), etc. In another embodiment, nucleic acid-ligand complexes can be formed in which the ligand comprises a flisogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, viral vectors that contains nucleic acid sequences encoding an antibody of the invention are used. For example, a retroviral vector can be used (see Miller et al., 1993, Meth. Enzymol. 217:581–599). These retroviral vectors have been to delete retroviral sequences that are not necessary for packaging of the viral genome and integration into host cell DNA. The nucleic acid sequences encoding the antibody to be used in gene therapy are cloned into one or more vectors, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; Mastrangeli et al., 1993, J. Clin. Invest. 91:225–234; PCT Publication WO94/12649; and Wang, et al., 1995, Gene Therapy 2:775–783. In a preferred embodiment, adenovirus vectors are used.

Adeno-associated virus (AAV) has also been proposed for use in gene therapy (Walsh et al., 1993, Proc. Soc. Exp. Biol. Med. 204:289–300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598, dated Apr. 28, 1994; Stemple and Anderson, 1992, Cell 71:973–985; Rheinwald, 1980, Meth. Cell Bio. 21A:229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429–4432), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, 1990, Science 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (1990, Science 249:1527–1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosising a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, M., et al., J. Cell. Biol. 101:976–985 (1985); Jalkanen, M., et al., J. Cell Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I) carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, 175Yb, $^{166}$Ho, $^{90}$Y, $^{47}$Sc, $^{186}$Re, $^{188}$Re, $^{142}$Pr, $^{105}$Rh, $^{97}$Ru; luminescent labels such as luminol; and fluorescent labels, such as fluorescein and rhodamine, and biotin.

One aspect of the invention is the detection and diagnosis of a disease or disorder associated with aberrant expression of a polypeptide of the interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody.

The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Therapeutics

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (D. V. Goeddel et al., "Tumor Necrosis Factors: Gene Structure and Biological Activities," Symp. Quant. Biol. 51:597–609 (1986), Cold Spring Harbor; B. Beutler and A. Cerami, Annu. Rev. Biochem. 57:505–518 (1988); L. J. Old, Sci. Am. 258:59–75 (1988); W. Fiers, FEBS Lett. 285:199–224 (1991)). The TNF-family ligands induce such various cellular responses by binding to TNF-family receptors.

Epithilial Disorder-Related Therapeutic Embodiments for TR13 and/or TR14

TR13 and/or TR14 polynucleotides or polypeptides, or agonists or antagonists of the present invention, can be used in assays to test for one or more biological activities. If these polynucleotides or polypeptides, or agonists or antagonists of the present invention, do exhibit activity in a particular assay, it is likely that these molecules may be involved in the diseases associated with the biological activity. Thus, the polynucleotides and polypeptides, and agonists or antagonists could be used to treat the associated disease.

TR13 inhibits survival and/or proliferation of epithelial cells such as, for example, HEK 293T cells. See Example 37 and FIG. 12. Thus, Tr13 polynucleotides, polypeptides, antibodies, and agonists or antagonists of the present invention may be used to detect, diagnose, prognose, treat, prevent and/or ameliorate diseases, disorders, and/or conditions associated with and/or due to aberrant epithelial cell survival and/or proliferation.

TR14 polynucleotides and translation products are believed to be involved in further biological activities associated with tooth development, growth of mucosal layers, and the growth of epithelial surfaces, including hair folicles, sweat glands, basal cells, and dermis. Accordingly, compositions of the invention (including polynucleotides, polypeptides and antibodies of the invention, and fragments and variants thereof) may be used in the diagnosis, detection and/or treatment of diseases and/or disorders associated with aberrant TR13 and/or TR14 activity. In preferred embodiments, compositions of the invention (including TR13 and/or TR14 polynucleotides, polypeptides and TR13 and/or TR14 agonists or antagonists, including peptides and antibodies of the invention, and fragments and variants thereof) may be used in the diagnosis, detection and/or treatment of diseases and/or disorders relating to the epithelium (e.g., anhidrotic ectodermal dysplasia, hidrotic ectodermal dysplasia, sweat gland disorders, venous ulcers, psoriasis, prickly heat disorder, wounds healing, cancers of epithelial origins, male pattern baldness, and/or as described under "Epithelial Cell Proliferation and Wound Healing" below). Thus, polynucleotides, translation products and antibodies of the invention are useful in the diagnosis, detection and/or treatment of diseases and/or disorders associated with activities that include, but are not limited to, diseases and/or disorders of the epithelium and epithelial cell proliferation diseases and/or disorders.

More generally, polynucleotides, translation products and antibodies corresponding to this gene may be useful for the diagnosis, detection and/or treatment of diseases and/or disorders associated with the following systems.

Epithelial Cell Proliferation and Wound Healing

In accordance with yet a further aspect of the present invention, there is provided a process for utilizing polynucleotides or translation products, as well as agonists or antagonists of the present invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the present invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associted with systemic treatment with steroids, radiation therapy and antineoplastic drugs and antimetabolites. Polynucleotides or polypeptides, as well as agonists or antagonists of the present invention, could be used to promote dermal reestablishment subsequent to dermal loss.

In specific, preferred embodiments, TR13 and/or TR14 polynucleotides and polypeptides, antibodies thereto, as well asagonists or antagonists thereof(as described in the section on Antibodies, above), stimulate epithelial cell proliferation and/or development to ameliorate the diseases and disorders described in this section. Members of the TNF family of proteins are known to signal through the NF-κB singaling pathway. NF-κB is a transcription factor activated by a wide certain agents to stimulate cell activation and differentiation. It is believed that the TR14 receptor of the instant invention signals through the NF-κB pathway to activate proliferation and development of cells. Thus, TR14 polynucleotides and polypeptides of the invention as well as antibodies and peptides that agonize TR14 may be used in accordance with the invention to stimulate NF-κB-mediated epithelial cell proliferation, and thereby treat the epithelial disorders described above.

It is believed that TR13 and/or TR14 polynucleotides or polypeptides, as well as agonists or antagonists of the present invention, will also produce changes in hepatocyte proliferation, and epithelial cell proliferation in the lung, breast, pancreas, stomach, small intesting, and large intestine. Polynucleotides or polypeptides, as well as agonists or antagonists of the present invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. Polynucleotides or polypeptides, agonists or antagonists of the present invention, may promote proliferation of endothelial cells, keratinocytes, and basal keratinocytes.

Polynucleotides or polypeptides, as well as agonists or antagonists of the present invention, could be used to increase the adherence of skin grafts to a wound bed and to stimulate re-epithelialization from the wound bed. The following are types of grafts that polynucleotides or polypeptides, agonists or antagonists of the present invention, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. Polynucleotides or polypeptides, as well as agonists or antagonists of the present invention, can be used to promote skin strength and to improve the appearance of aged skin.

Polynucleotides or polypeptides, as well as agonists or antagonists of the present invention, could also be used to reduce the side effects of gut toxicity that result from radiation, chemotherapy treatments or viral infections. Polynucleotides or polypeptides, as well as agonists or antagonists of the present invention, may have a cytoprotective effect on the small intestine mucosa. Polynucleotides or polypeptides, as well as agonists or antagonists of the present invention, may also stimulate healing of mucositis (mouth ulcers) that result from chemotherapy and viral infections.

Polynucleotides or polypeptides, as well as agonists or antagonists of the present invention, could further be used in full regeneration of skin in full and partial thickness skin defects, including burns, (i.e., repopulation of hair follicles, sweat glands, and sebaceous glands), treatment of other skin defects such as psoriasis. Polynucleotides or polypeptides, as well as agonists or antagonists of the present invention, could be used to treat epidermolysis bullosa, a defect in adherence of the epidermis to the underlying dermis which results in frequent, open and painful blisters by accelerating reepithelialization of these lesions. Polynucleotides or polypeptides, as well as agonists or antagonists of the present invention, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, polynucleotides or polypeptides, as well as agonists or antagonists of the present invention, could be used to promote the resurfacing of the mucosal surface to aid more rapid healing and to prevent progression of inflammatory bowel disease. Treatment with polynucleotides or polypeptides, agonists or antagonists of the present invention, is expected to have a significant effect on the production of mucus throughout the gastrointestinal tract and could be used to protect the intestinal mucosa from injurious substances that are ingested or following surgery. Polynucleotides or polypeptides, as well as agonists or antagonists of the present invention, could be used to treat diseases associate with the under expression.

Moreover, polynucleotides or polypeptides, as well as agonists or antagonists of the present invention, could be used to prevent and heal damage to the lungs due to various pathological states. Polynucleotides or polypeptides, as well as agonists or antagonists of the present invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated using polynucleotides or polypeptides, agonists or antagonists of the present invention. Also, polynucleotides or polypeptides, as well as agonists or antagonists of the present invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

Polynucleotides or polypeptides, as well as agonists or antagonists of the present invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, polynucleotides or polypeptides, as well as agonists or antagonists of the present invention, could be used treat or prevent the onset of diabetes mellitus. In patients with newly diagnosed Types I and II diabetes, where some islet cell function remains, polynucleotides or polypeptides, as well as agonists or antagonists of the present invention, could be used to maintain the islet function so as to alleviate, delay or prevent permanent manifestation of the disease. Also, polynucleotides or polypeptides, as well as agonists or antagonists of the present invention, could be used as an auxiliary in islet cell transplantation to improve or promote islet cell function.

Additional Therapeutic Embodiments

TR13 nucleic acids, polypeptides (proteins), agonists and/or antagonists of the invention may be administered to a patient (e.g., mammal, preferably human) afflicted with any disease or disorder mediated (directly or indirectly) by defective, or deficient levels of, TR13. Alternatively, a gene therapy approach may be applied to treat such diseases or disorders. In one embodiment of the invention, TR13 polynucleotide sequences are used to detect mutein TR13 genes, including defective genes. Mutein genes may be identified in in vitro diagnostic assays using techniques known in the art, and by comparison of the TR13 nucleotide sequence disclosed herein with that of a TR13 gene obtained from a patient suspected of harboring a defect in this gene. Defective genes may be replaced with normal TR13-encoding genes using techniques known to one skilled in the art.

In another embodiment, the TR13 polypeptides, nucleic acids, agonists and/or antagonists of the present invention are used as research tools for studying the phenotypic effects that result from inhibiting TR13/TR13 ligand (e.g., Tr13/Fas ligand and/or TR13/AIM-II) interactions on various cell types. TR13 polypeptides and antagonists (e.g. monoclonal antibodies to TR13) also may be used in in vitro assays for detecting TR13 or TR13 ligand(s) or the interactions thereof.

In another embodiment, a purified TR13 polypeptide of the invention is used to inhibit binding of Fas ligand and/or AIM-II (i.e., "LIGHT") to endogenous cell surface Fas ligand and/or AIM-II receptors. Certain ligands of the TNF family (of which Fas ligand and AIM-II are members) have been reported to bind to more than one distinct cell surface receptor protein. AIM-II likewise is believed to bind multiple cell surface proteins. By binding Fas ligand and/or AIM-II, soluble TR13 polypeptides and TR13 fusion polypeptides of the present invention may be employed to inhibit the binding of Fas ligand and/or AIM-II not only to endogenous TR13, but also to Fas ligand and AIM-II receptor proteins that are distinct from TR13. Thus, in another embodiment, TR13 and TR13 fusion proteins are used to inhibit a biological activity of Fas ligand and/or AIM-II, in in vitro or in vivo procedures. By inhibiting binding of Fas ligand and/or AIM-II to cell surface receptors, TR13 polypeptides of the invention also inhibit biological effects that result from the binding of Fas ligand and/or AIM-II to endogenous receptors. Various forms of TR13 may be employed, including, for example, the above-described TR13 fragments, derivatives, and variants, including fusion proteins, that are capable of binding Fas ligand and/or AIM-II. In a preferred embodiment, a soluble TR13 polypeptide of the invention is administered to inhibit a biological activity of Fas ligand and/or AIM-II, e.g., to inhibit Fas ligand-mediated and/or AIM-II-mediated apoptosis of cells susceptible to such apoptosis.

In a further embodiment, a TR13 polypeptide of the invention is administered to a mammal to treat a Fas ligand-mediated and/or AIM-II-mediated disorder. Such Fas ligand-mediated and/or AIM-II-mediated (e.g., a human) disorders include conditions caused (directly or indirectly) or exacerbated by Fas ligand and/or AIM-II.

There are numerous autoimmune diseases in which FasL/Fas interactions play a role. In patients experiencing GVHD, serum levels of FasL were abnormally high as was the number of FasL$^+$ T cells . The CNS plaques from patients with MS have been shown to express high levels of Fas and FasL. This is particularly significant since Fas and FasL expression is normally absent in the mature CNS. As with NOD mice, patients with IDDM have a superabundance of FasL$^+$ T cells associated with their islet cells. As evidence of FasL/Fas mediated cell killing, patients with chronic renal failure have been reported to have a 50 fold increase in the number of apoptotic nephrons compared to normal. This has been ascribed to renal tubule epithelial cell expression of both FasL and Fas, leading to cellular fratricide . In the joints of rheumatoid arthritic patients, activated T cells expressing FasL are seen in conjunction with Fas expressing chondrocytes. In ulcerative colitis (UC), Fas expression is observed on colonic epithelial cells, and FasL on lamina propria lymphocytes. This lead to the observation that FasL positive lymphocytes are present only in the lamina propria of UC patients with active lesions but not in tissues from inactive UC patients.

Two clinical indications in which the role of FasL-mediated killing is most apparent are myelodisplastic syndrome (MDS) and the neutropenia associated with large granular lymphocyte (LGL) leukemia. In MDS, bone marrow hematopoetic cells suffer an abnormally high level of apoptosis, associated with the upregulation of bone marrow Fas expression and lymphocyte FasL expression. The neutropenia seen in patients with LGL leukemia has been attributed to the high levels of circulating serum FasL. When leukemic LGL serum was incubated in vitro for 24 hours with normal neutrophils, the degree of apoptosis significantly increased above that of cells incubated with normal serum.

As described in detail in Example 35, below, TR13-Fc may be administered to inhibit FasL-mediated killing. Thus, the FasL-associated disorders listed above may be treated and/or prevented, in accordance with the invention, through administration of the TR13-containing polypeptides, including TR13-human serim albumin fusions, and polynucleotides desribed herein.

Suitable animal models for examining the effectiveness of TR13 in treating disease include but are not limited to mouse models of graft versus host disease (GVHD), murine allergic encephalomyelitis (EAE), an assay used as a central nervous system (CNS) model of multiple sclerosis (MS); non-obese diabetic (NOD) mouse model of insulin-dependant diabetes mellitus (IDDM), which is characterized by $FasL^+$ T cell destruction of islet cells, while $Fas^-$ NOD mice fail to develop diabetes. NOD mice can also be used to model Sjogren's disease, since apoptosis in the salivary and lacrimal glands of these mice has been reported. In a mouse model of chronic renal failure, ROP-Os/+ mice developed spontaneous tubular atrophy and renal failure correlated with upregulation of Fas and FasL in these tissues. The invention encompasses the treatment and prevention of the human disesases corresponding to these animal models, through administration of the TR13 polypeptides and polynucleotides of the present invention.

In addition, TR13 may bind to LIGHT(AIM-II) (International application publication number WO 97/34911, published Sep. 25, 1997)), a regulator of T cell function. As detailed in Example 36, below, TR13-Fc may be tested for its ability to ameliorate the effects of transplantation, including the inhibition of transplant or graft rejection and the inhibition of graft versus host disease (GVHD). The methods encompass the treatment of graft rejection or GVHD wherein the grafted tissue or organ is one or more of a variety of tissues and/or organs, including, but not limted to, heart, lung, kidney, liver, pancreas, islet cells, bone marrow, and skin.

Other Fas ligand related disorders that may be prevented or treated by administering soluble TR13 polypeptides of the invention of TR13 antigonists include, but are not limited to Graft vs. host disease, multiple sclerosis, rheumatoid arthritis, chronic renal failure ulcerative colitis, graft rejection (including acute allograft rejection), chronic hepatitis, chronic active hepatitis (HBV and HCV associated), fullminant hepatitis, biliary cirrhosis, alcoholic liver disease, diabetes (IDDM), HIV infection, AIDS lymphopenia, heart disease, Alzheimer's disease, myelodysplastic syndrome (MDS), lupus (SLE), pulmonary fibrosis, Sjogren's, syndrome, toxic epidermal necrolysis, ocular disease, thyroid-associated opthalmopathy, stroke, Parkinson's disease, autoimmune gastritis, rheumatoid arthritis, Hashimoto's thyroiditis, pulmonary injury, chronic congestive heart failure, ischemic cardiac injury, proliferative glomerulonephritis, chronic renal failure, thrombotic thombocytopenic purpura (TTP), tumor growth; as well as prolonging transgene expression of adenovirus vector.

TR14 nucleic acids, polypeptides (proteins), agonists and/ or antagonists of the invention may be administered to a patient (e.g., mammal, preferably human) afflicted with any disease or disorder mediated (directly or indirectly) by defective, or deficient levels of, TR14. Alternatively, a gene therapy approach may be applied to treat such diseases or disorders. In one embodiment of the invention, TR14 polynucleotide sequences are used to detect mutein TR14 genes, including defective genes. Mutein genes may be identified in in vitro diagnostic assays using techniques known in the art, and by comparison of the TR14 nucleotide sequence disclosed herein with that of a TR14 gene obtained from a patient suspected of harboring a defect in this gene. Defective genes may be replaced with normal TR14-encoding genes using techniques known to one skilled in the art.

In another embodiment, the TR14 polypeptides, nucleic acids, agonists and/or antagonists of the present invention are used as research tools for studying the phenotypic effects that result from inhibiting TR14/TR14 ligand interactions on various cell types. TR14 polypeptides and antagonists (e.g. monoclonal antibodies to TR14) also may be used in in vitro assays for detecting TR14 or TR14 ligand(s) or the interactions thereof.

Cells which express the TR13 polypeptide and are believed to have a potent cellular response to TR13 ligands (e.g., Fas Ligand) include pancrease tumor, endometrial tumor, adult small intestine, colon cancer, breast cancer cell line, resting T-cell, amygdala, rectum, T-cell helper, pineal gland, apoptotic T-cell, epididymus, greater omentum, prostate BPH, osteoclastoma, endometrial stromal cells, stromal cell, substantia nigra, activated T-cell, tonsil, and testes tissue. By "a cellular response to a TNF-family ligand" is intended any genotypic, phenotypic, and/or morphologic change to a cell, cell line, tissue, tissue culture or patient that is induced by a TNF-family ligand (such as, for example, a TNF-ligand disclosed herein). As indicated, such cellular responses include not only normal physiological responses to TNF-family ligands, but also diseases associated with increased apoptosis or the inhibition of apoptosis. Apoptosis-programmed cell death is a physiological mechanism involved in the deletion of peripheral T lymphocytes of the immune system, and its dysregulation can lead to a number of different pathogenic processes (J. C. Ameisen, AIDS 8:1197–1213 (1994); P. H. Krammer et al., Curr. Opin. Immunol. 6:279–289 (1994)).

Cells which express TR14 polypeptide and that are believed to have a potent cellular response to TR14 ligands include activated T-cell, endometrial, thymus, and 12 week early stage human tissue. By "a cellular response to a TNF-family ligand" is intended any genotypic, phenotypic, and/or morphologic change to a cell, cell line, tissue, tissue culture or patient that is induced by a TNF-family ligand (such as, for example, a TNF-ligand described herein). As indicated, such cellular responses include not only normal physiological responses to TNF-family ligands, but also diseases associated with dysregulation of these physiological responses, such as, for example, diseases associated with increased apoptosis or the inhibition of apoptosis. Apoptosis-programmed cell death is a physiological mechanism involved in the deletion of peripheral T lymphocytes of the immune system, and its dysregulation can lead to a number of different pathogenic processes (J. C. Ameisen, AIDS 8:1197–1213 (1994); P. H. Krammer et al., Curr. Opin. Immunol. 6:279–289 (1994)).

In specific embodiments for treating cancer, including, for example, when underregulation of Fas ligand leads to excessive cancer cell growth, agonists of TR13, including antibodies and peptides that bind TR13, may be used to enhance the anti-tumor effect of Fas ligand.

Diseases associated with increased cell survival, or the inhibition of apoptosis, and that may be treated or prevented by the TR13 polynucleotides, polypeptides and/or agonists or antagonists of the invention include, but are not limited to, cancers (such as endometrial tumors, follicular lymphomas, carcinomas with p53 mutations, and hormone-dependent tumors, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostrate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis rheumatoid arthritis); viral infections (such as herpes viruses, pox viruses and adenoviruses); inflammation; graft vs. host disease; acute graft rejection and chronic graft rejection. In preferred embodiments, TR13 nucleic acids, polypeptides, agonists and/or antagonists of the invention are used to inhibit growth, progression, and/or metasis of cancers, in particular those listed above, or in the paragraphs that follow. In other highly preferred embodiments, agonistic anti-TR13 antibodies of the invention are used to inhibit growth, progression, and/or metastasis of cancers, in particular those listed above, or in the paragraphs that follow.

Additional diseases or conditions associated with increased cell survival and that may be treated or prevented by the TR13 polynucleotides, polypeptides, agonists and/or antagonists of the invention include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. In preferred embodiments, TR13 nucleic acids, polypeptides, agonists and/or antagonists are used to treat the diseases and disorders listed above.

In additional embodiments, TR13 nucleic acids, polypeptides, agonists and/or antagonists are used to treat pancreas tumor, endometrial tumor, colon cancer, breast cancer, prostate BPH and/or osteosarcoma.

Thus, in preferred embodiments TR13 polynucleotides or polypeptides of the invention and agonists or antagonists thereof, are used to treat or prevent autoimmune diseases and/or inhibit the growth, progression, and/or metastasis of cancers, including, but not limited to, those cancers disclosed herein, such as, for example, pancreatic cancer, endometrial cancer, colon cancer, breast cancer, osteocarcoma, and lymphocytic leukemias (including, for example, MLL and chronic lymphocytic leukemia (CLL)) and follicular lymphomas. In another embodiment TR13 polynucleotides or polypeptides of the invention and/or agonists or antagonists thereof, are used to activate, differentiate or proliferate cancerous cells or tissue (e.g., T cell lineage related cancers and B cell lineage related cancers (e.g., CLL and MLL), lymphocytic leukemia, or lymphoma) and thereby render the cells more vulnerable to cancer therapy (e.g., chemotherapy or radiation therapy).

Diseases associated with increased apoptosis and that may be treated or prevented by the polynucleotides, polypeptides and/or agonists or antagonists of the invention include, but are not limited to, AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis); myelodysplastic syndromes (such as aplastic anemia), graft v. host disease, ischemic injury (such as that caused by myocardial infarction, stroke and reperfusion injury), liver injury (such as hepatitis related liver injury, ischemia/reperfusion injury, cholestosis (bile duct injury) and liver cancer); toxin-induced liver disease (such as that caused by alcohol), septic shock, cachexia and anorexia. In preferred embodiments, TR13 nucleic acids, polypeptides, agonists and/or antagonists are used to treat the diseases and disorders listed above. In other highly preferred embodiments, soluble forms of the extracellular domain of the invention (e.g., amino acids 42–906 fused to an Ig Fc domain) or antagonistic antibodies (e.g., antibodies that bind TR13 but do not induce a signal or, antibodies that bind TR13 which do not induce signal transduction through TR13 and prevent TR13 ligands (e.g., Fas ligand) from binding TR13) are used to treat diseases and disorders associated with increased apoptosis.

Diseases associated with increased cell survival, or the inhibition of apoptosis, and that may be treated or prevented by the TR14 polynucleotides, polypeptides and/or agonists or antagonists of the invention include, but are not limited to, cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostrate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis rheumatoid arthritis); viral infections (such as herpes viruses, pox viruses and adenoviruses); inflammation; graft vs. host disease; acute graft rejection and chronic graft rejection. In preferred embodiments, TR14 nucleic acids, polypeptides, agonists and/or antagonists of the invention are used to inhibit growth, progression, and/or metasis of cancers, in particular those listed above, or in the paragraphs that follow.

Additional diseases or conditions associated with increased cell survival and that may be treated or prevented by the TR14 polynucleotides, polypeptides and/or agonists or antagonists of the invention include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. In preferred embodiments, TR14 nucleic acids, polypeptides, agonists and/or antagonists are used to treat the diseases and disorders listed above.

Thus, in preferred embodiments TR14 polynucleotides or polypeptides of the invention and agonists or antagonists thereof, are used to treat or prevent autoimmune diseases and/or inhibit the growth, progression, and/or metastasis of cancers, including, but not limited to, those cancers disclosed herein, such as, for example, lymphocytic leukemias (including, for example, MLL and chronic lymphocytic leukemia (CLL)) and follicular lymphomas. In another embodiment TR14 polynucleotides or polypeptides of the invention and/or agonists or antagonists thereof, are used to activate, differentiate or proliferate cancerous cells or tissue (e.g., T cell lineage cancers and B cell lineage related cancers (e.g., CLL and MLL), lymphocytic leukemia, or lymphoma) and thereby render the cells more vulnerable to cancer therapy (e.g., chemotherapy or radiation therapy).

Diseases associated with increased apoptosis and that may be treated or prevented by the TR14 polynucleotides, polypeptides and/or agonists or antagonists of the invention include, but are not limited to, AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis); myelodysplastic syndromes (such as aplastic anemia), graft v. host disease, ischemic injury (such as that caused by myocardial infarction, stroke and reperfusion injury), liver injury (such as hepatitis related liver injury, ischemia/reperfusion injury, cholestosis (bile duct injury) and liver cancer); toxin-induced liver disease (such as that caused by alcohol), septic shock, cachexia and anorexia. In preferred embodiments, TR14 nucleic acids, polypeptides, agonists and/or antagonists are used to treat the diseases and disorders listed above.

Many of the pathologies associated with HIV are mediated by apoptosis, including HIV-induced nephropathy and HIV encephalitis. Thus, in additional preferred embodiments, TR13 nucleic acids, polypeptides, and/or TR13 agonists or antagonists of the invention are used to treat AIDS and pathologies associated with AIDS.

Many of the pathologies associated with HIV are mediated by apoptosis, including HIV-induced nephropathy and HIV encephalitis. Thus, in additional preferred embodiments, TR14 nucleic acids, polypeptides, and/or TR14 agonists or antagonists of the invention are used to treat AIDS and pathologies associated with AIDS.

Another embodiment of the present invention is directed to the use of TR13 (especially the extracellular soluble domain of TR13 or fragments or variants thereof) to reduce cell death dependent upon a TNF family member, of T cells in HIV-infected patients. The state of immunodeficiency that defines AIDS is secondary to a decrease in the number and function of CD4$^+$ T-lymphocytes. Recent reports estimate the daily loss of CD4$^+$ T cells to be between $3.5 \times 10^7$ and $2 \times 10^9$ cells (Wei et al., Nature 373:117–122 (1995)). One cause of CD4$^+$ T cell depletion in the setting of HIV infection is believed to be HIV-induced apoptosis (see, for example, Meyaard et al., Science 257:217–219, 1992; Groux et al., J. Exp. Med., 175:331, 1992; and Oyaizu et al., in Cell Activation and Apoptosis in HIV Infection, Andrieu and Lu, Eds., Plenum Press, New York, 1995, pp. 101–114). Indeed, HIV-induced apoptotic cell death has been demonstrated not only in vitro but also, more importantly, in infected individuals (J. C. Ameisen, AIDS 8:1197–1213 (1994); T. H. Finkel and N. K. Banda, Curr. Opin. Immunol. 6:605–615 (1995); C. A. Muro-Cacho et al., J. Immunol. 154:5555–5566 (1995)). Furthermore, apoptosis and CD4$^+$ T-lymphocyte depletion is tightly correlated in different animal models of AIDS (T. Brunner et al., Nature 373:441–444 (1995); M. L. Gougeon et al., AIDS Res. Hum. Retroviruses 9:553–563 (1993)) and, apoptosis is not observed in those animal models in which viral replication does not result in AIDS. Id. Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (A. D. Badley et al., J. Virol. 70:199–206 (1996)). Further, the TNF-family ligand was detectable in uninfected macrophages and its expression was upregulated following HIV infection resulting in selective killing of uninfected CD4 T-lymphocytes. Id. Thus, by the invention, a method for treating HIV$^+$ individuals is provided which involves administering TR13 polynucleotides, polypeptides and/or TR13 agonists or antagonists of the present invention to reduce selective killing of CD4$^+$ T-lymphocytes. Modes of administration and dosages are discussed in detail below.

Activated human T cells are induced to undergo programmed cell death (apoptosis) upon triggering through the CD3/T cell receptor complex, a process termed activated-induced cell death (AICD). AICD of CD4⁺ T cells isolated from HIV-Infected asymptomatic individuals has been reported (Groux et al., supra). Thus, AICD may play a role in the depletion of CD4⁺ T cells and the progression to AIDS in HIV-infected individuals. Thus, the present invention provides a method of inhibiting a tumor-necrosis factor family member (e.g. Fas ligand or TRAIL) mediated T cell death in HIV patients, comprising administering a TR13 polypeptide of the invention (preferably, a soluble TR13 polypeptide, such as the extracellular soluble domain) to the patients. In one embodiment, the patient is asymptomatic when treatment with TR13 commences. If desired, prior to treatment, peripheral blood T cells may be extracted from an HIV patient, and tested for susceptibility to cell death mediated by a tumor necrosis factor family member, by procedures known in the art. In one embodiment, a patient's blood or plasma is contacted with TR13 ex vivo. The TR13 may be bound to a suitable chromatography matrix by procedures known in the art. The patient's blood or plasma flows through a chromatography column containing TR13 bound to the matrix, before being returned to the patient. In the event the immobilized TR13 bound to TRAIL, or another TNF family member(s), TRAIL and/or other TNF family member protein would be removed from the patient's blood.

In additional embodiments a TR13 polypeptide, polynucleotide, and/or agonist or antagonist of the invention is administered in combination with inhibitors of T cell apoptosis. For example, Fas-mediated apoptosis and TRAIL-mediated apoptosis have been implicated in loss of T cells in HIV individuals (See, e.g., Katsikis et al., *J. Exp. Med.* 181:2029–2036 (1995)). Thus, a patient susceptible to both Fas ligand mediated and/or TRAIL mediated T cell death may be treated by an agent that blocks Fas-ligand/TR13 interactions, Fas-ligand/Fas interactions and/or an agent that blocks TRAIL/TRAIL receptor interactions. Suitable agents for blocking binding of Fas-ligand to TR13 or Fas include, but are not limited to, soluble TR13 polypeptides, soluble Fas polypeptides; mulitmeric forms of soluble Fas polypeptides (e.g., dimers of sFas/Fc); ); anti-TR13 antibodies that bind TR13 without transducing the biological signal that results in apoptosis; anti-TR13-ligand antibodies that block binding of Fas-ligand to TR13; anti-Fas antibodies that bind Fas without transducing the biological signal that results in apoptosis; anti-Fas-ligand antibodies that block binding of Fas-ligand to Fas; and muteins of Fas-ligand that bind Fas and/or TR13 but do not transduce the biological signal that results in apoptosis. Preferably, the antibodies employed according to this method are monoclonal antibodies. Examples of suitable agents for blocking Fas-ligand/Fas interactions, including blocking anti-Fas monoclonal antibodies, are described in International application publication number WO 95/10540, hereby incorporated by reference.

Suitable agents, which block binding of TRAIL to a TRAIL receptor or FAS ligand to FAS that may be administered with the nucleic acids, polypeptides, and/or agonists or antagonists of the present invention include, but are not limited to, soluble TRAIL receptor polypeptides (e.g., a soluble form of OPG, DR4 (International application publication number WO 98/32856); TR5 (International application publication number WO 98/30693); and DR5 (International application publication number WO 98/41629)); multimeric forms of soluble TRAIL receptor polypeptides; and TRAIL receptor antibodies that bind the TRAIL receptor without transducing the biological signal that results in apoptosis, anti-TRAIL antibodies that block binding of TRAIL to one or more TRAIL receptors, and muteins of TRAIL that bind TRAIL receptors but do not transduce the biological signal that results in apoptosis. Preferably, the antibodies employed according to this method are monoclonal antibodies.

Another embodiment of the present invention is directed to the use of TR14 to reduce cell death dependent upon a TNF family member, of T cells in HIV-infected patients. The state of immunodeficiency that defines AIDS is secondary to a decrease in the number and function of CD4⁺ T-lymphocytes. Recent reports estimate the daily loss of CD4⁺ T cells to be between 3.5×10⁷ and 2×10⁹ cells (Wei et al., *Nature* 373:117–122 (1995)). One cause of CD4⁺ T cell depletion in the setting of HIV infection is believed to be HIV-induced apoptosis (see, for example, Meyaard et al., *Science* 257:217–219, 1992; Groux et al., *J. Exp. Med.,* 175:331, 1992; and Oyaizu et al., in *Cell Activation and Apoptosis in HIV Infection,* Andrieu and Lu, Eds., Plenum Press, New York, 1995, pp. 101–114). Indeed, HIV-induced apoptotic cell death has been demonstrated not only in vitro but also, more importantly, in infected individuals (J. C. Ameisen, *AIDS* 8:1197–1213 (1994); T. H. Finkel and N. K. Banda, *Curr. Opin. Immunol.* 6:605–615(1995); C.A. Muro-Cacho et al., *J. Immunol.* 154:5555–5566 (1995)). Furthermore, apoptosis and CD4⁺ T-lymphocyte depletion is tightly correlated in different animal models of AIDS (T. Brunner et al., *Nature* 373:441–444 (1995); M. L. Gougeon et al., *AIDS Res. Hum. Retroviruses* 9:553–563 (1993)) and, apoptosis is not observed in those animal models in which viral replication does not result in AIDS. Id. Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (A. D. Badley et al., *J. Virol.* 70:199–206 (1996)). Further, the TNF-family ligand was detectable in uninfected macrophages and its expression was upregulated following HIV infection resulting in selective killing of uninfected CD4 T-lymphocytes. Id. Thus, by the invention, a method for treating HIV⁺ individuals is provided which involves administering TR14 polynucleotides, polypeptides, and/or TR14 agonists or antagonists of the present invention to reduce selective killing of CD4⁺ T-lymphocytes. Modes of administration and dosages are discussed in detail below.

Activated human T cells are induced to undergo programmed cell death (apoptosis) upon triggering through the CD3/T cell receptor complex, a process termed activated-induced cell death (AICD). AICD of CD4⁺ T cells isolated from HIV-Infected asymptomatic individuals has been reported (Groux et al., supra). Thus, AICD may play a role in the depletion of CD4⁺ T cells and the progression to AIDS in HIV-infected individuals. Thus, the present invention provides a method of inhibiting a tumor-necrosis factor family member-mediated T cell death in HIV patients, comprising administering a TR14 polypeptide of the invention (preferably, a soluble TR14 polypeptide) to the patients. In one embodiment, the patient is asymptomatic when treatment with TR14 commences. If desired, prior to treatment, peripheral blood T cells may be extracted from an HIV patient, and tested for susceptibility to cell death mediated by a member of the TNF-family, by procedures known in the art. In one embodiment, a patient's blood or plasma is contacted with TR14 ex vivo. The TR14 may be bound to a suitable chromatography matrix by procedures known in the art. The patient's blood or plasma flows through a chromatography column containing TR14 bound to the matrix, before being returned to the patient. In the event the immobilized TR14 bound to TRAIL, or another TNF family member(s), TRAIL and/or other TNF family member protein would be removed from the patient's blood.

In additional embodiments a TR14 polypeptide, polynucleotide, and/or agonist or antagonist of the invention is administered in combination with inhibitors of T cell apoptosis. For example, TRAIL-mediated apoptosis and Fas-mediated apoptosis have been implicated in loss of T cells in HIV individuals (See e.g., Katsikis et al., *J. Exp. Med.* 181:2029–2036 (1995)). Thus, a patient susceptible to both Fas ligand mediated and TRAIL mediated T cell death may be treated as an agent that blocks TRAIL/TRAIL receptor interactions and/or an agent that blocks Fas-ligand/Fas interactions. Suitable agents for blocking binding of Fas-ligand to Fas include, but are not limited to, soluble Fas polypeptides; mulitmeric forms of soluble Fas polypeptides (e.g., dimers of sFas/Fc); anti-Fas antibodies that bind Fas without transducing the biological signal that results in apoptosis; anti-Fas-ligand antibodies that block binding of Fas-ligand to Fas; and muteins of Fas-ligand that bind Fas but do not transduce the biological signal that results in apoptosis. Preferably, the antibodies employed according to this method are monoclonal antibodies. Examples of suitable agents for blocking Fas-ligand/Fas interactions, including blocking anti-Fas monoclonal antibodies, are described in International application publication number WO 95/10540, hereby incorporated by reference.

Suitable agents, which block binding of TRAIL to a TRAIL receptor or FAS ligand to FAS that may be administered with the nucleic acids, polypeptides, and/or agonists or antagonists of the present invention include, but are not limited to, soluble TRAIL receptor polypeptides (e.g., a soluble form of OPG, DR4 (International application publication number WO 98/32856); TR5 (International application publication number WO 98/30693); and DR5 (International application publication number WO 98/41629)); multimeric forms of soluble TRAIL receptor polypeptides; and TRAIL receptor antibodies that bind the TRAIL receptor without transducing the biological signal that results in apoptosis, anti-TRAIL antibodies that block binding of TRAIL to one or more TRAIL receptors, and muteins of TRAIL that bind TRAIL receptors but do not transduce the biological signal that results in apoptosis. Preferably, the antibodies employed according to this method are monoclonal antibodies.

TR13 polypeptides, nucleic acids, and/or agonists or antagonists of the invention may be used to treat cardiovascular disorders, including peripheral artery disease, such as limb ischemia.

TR14 polypeptides, nucleic acids, and/or agonists or antagonists of the invention may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects, and conditions characterized by clotting of small blood vessels.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, thrombotic microangiopathies (e.g., thrombotic thrombocytopenic purpura (TTP) and hemolytic-uremic syndrome (HUS)), and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboanglitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subdlavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboanguitis obliterans, hypersensitivity vasculitis, Schoenlein-Henoch purpura, allergic cutaneous vasculitis, and Wegener's granulomatosis.

In one embodiment, TR13 polypeptides, polynucleotides and/or agonists or antagonists of the invention are used to treat or prevent thrombotic microangiopathies. One such disorder is thrombotic thrombocytopenic purpura (TTP) (Kwaan, H. C., *Semin. Hematol.* 24:71 (1987); Thompson et al., *Blood* 80:1890 (1992)). Increasing TTP-associated mortality rates have been reported by the U.S. Centers for Disease Control (Torok et al., *Am. J. Hematol.* 50:84 (1995)). Plasma from patients afflicted with TTP (including HIV+ and HIV– patients) induces apoptosis of human endothelial cells of dermal microvascular origin, but not large vessel origin (Laurence et al., *Blood* 87:3245 (1996)). Plasma of TTP patients thus is thought to contain one or more factors that directly or indirectly induce apoptosis. An anti-Fas blocking antibody has been shown to reduce TTP plasma-mediated apoptosis of microvascular endothelial cells (Lawrence et al., *Blood* 87:3245 (1996); hereby incorporated by reference). Accordingly, Fas ligand present in the serum of TTP patients is likely to play a role in inducing apoptosis of microvascular endothelial cells. Another thrombotic microangiopathy is hemolytic-uremic syndrome (HUS) (Moake, J. L., *Lancet,* 343:393, (1994); Melnyk et al., *(Arch. Intern. Med.,* 155:2077, (1995); Thompson et al., supra). Thus, in one embodiment, the invention is directed to use of TR13 to treat or prevent the condition that is often referred to as "adult HUS" (even though it can strike children as well). A disorder known as childhood/diarrhea-associated HUS differs in etiology from adult HUS. In another embodiment, conditions characterized by clotting of small blood vessels may be treated using TR13 polypeptides and/or polynucleotides of the invention. Such conditions include, but are not limited to, those described herein. For example, cardiac problems seen in about 5–10% of pediatric AIDS patients are believed to involve clotting of small blood vessels. Breakdown of the microvasculature in the heart has been reported in multiple sclerosis patients. As a further example, treatment of systemic lupus erythematosus (SLE) is contemplated. In one embodiment, a patient's blood or plasma is contacted with TR13 polypeptides of the invention ex vivo. The TR13 may be bound to a suitable chromatography matrix using techniques known in the art. According to this embodiment, the patient's blood or plasma flows through a chromatography column containing TR13 bound to the matrix, before being returned to the patient. The immobilized TR13 binds Fas ligand and/or AIM-II, thus removing Fas ligand protein from the patient's blood. Alternatively, TR13 may be administered in vivo to a patient afflicted with a thrombotic microangiopathy. In one embodiment, a TR13 polynucleotide or polypeptide of the invention is administered to the patient. Thus, the present invention provides a method for treating a thrombotic microangiopathy, involving use of an effective amount of a TR13 polypeptide of the invention. A TR13 polypeptide may be employed in in vivo or ex vivo procedures, to inhibit Fas ligand-mediated and/or AIM-II-mediated damage to (e.g., apoptosis of) microvascular endothelial cells.

TR13 polypeptides and polynucleotides of the invention may be employed in conjunction with other agents useful in treating a particular disorder. For example, in an in vitro study reported by Laurence et al. (*Blood* 87:3245, 1996), some reduction of TTP plasma-mediated apoptosis of microvascular endothelial cells was achieved by using an anti-Fas blocking antibody, aurintricarboxylic acid, or normal plasma depleted of cryoprecipitate. Thus, a patient may be treated in combination with an additional agent that inhibits Fas-ligand-mediated apoptosis of endothelial cells such as, for example, an agent described above. In one embodiment, TR13 polypeptides of the invention and an anti-FAS blocking antibody are administered to a patient afflicted with a disorder characterized by thrombotic microanglopathy, such as TTP or HUS. Examples of blocking monoclonal antibodies directed against Fas antigen (CD95) are described in International Application publication number WO 95/10540, hereby incorporated by reference.

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630–634 (1991); Folkman et al., *N. Engl. J. Med.,* 333:1757–1763 (1995); Auerbach et al., *J. Microvasc. Res.* 29:401–411 (1985); Folkman, Advances in Cancer Research, eds. Klein and Weinhouse, Academic Press, New York, pp. 175–203 (1985); Patz, *Am. J. Opthalmol.*

94:715–743 (1982); and Folkman et al., *Science* 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases or disorders associated with neovascularization by administration of the TR13 nucleic acids and/or polypeptides of the invention (including TR13 agonists and/or antagonists). Malignant and metastatic conditions which can be treated with the nucleic acids and polypeptides of the invention include, but are not limited to those malignancies, solid tumors, and cancers described herein and otherwise known in the art (for a review of such disorders, see Fishman et al., Medicine, 2d Ed., J. B. Lippincott Co., Philadelphia (1985)).

The present invention provides for treatment of diseases or disorders associated with neovascularization by administration of the TR14 nucleic acids and/or polypeptides of the invention (including TR14 agonists and/or antagonists). Malignant and metastatic conditions which can be treated with the nucleic acids and polypeptides of the invention include, but are not limited to those malignancies, solid tumors, and cancers described herein and otherwise known in the art (for a review of such disorders, see Fishman et al., Medicine, 2d Ed., J. B. Lippincott Co., Philadelphia (1985)).

Additionally, ocular disorders associated with neovascularization which can be treated with the TR13 nucleic acids and polypeptides of the present invention (including TR13 agonists and TR13 antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal* 22:291–312 (1978).

Additionally, disorders which can be treated with the TR13 nucleic acids and polypeptides of the present invention (including TR13 agonists and TR13 antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Additionally, ocular disorders associated with neovascularization which can be treated with the TR14 nucleic acids and polypeptides of the present invention (including TR14 agonists and TR14 antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978).

Additionally, disorders which can be treated with the TR14 nucleic acids and polypeptides of the present invention (including TR14 agonists and TR14 antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

The TR13 and/or TR14 nucleic acids, polypeptides and/or agonists or antagonists of the invention can also be employed to inhibit the proliferation and differentiation of hematopoietic cells and therefore may be employed to protect bone marrow stem cells from chemotherapeutic agents during chemotherapy. This antiproliferative effect may allow administration of higher doses of chemotherapeutic agents and, therefore, more effective chemotherapeutic treatment.

The TR13 and/or TR14 nucleic acids, polypeptides and/or agonists or antagonists of the invention may also be employed for the expansion of immature hematopoietic progenitor cells, for example, granulocytes, macrophages or monocytes (e.g., CD34+, kit+), by temporarily preventing their differentiation. These bone marrow cells may be cultured in vitro. Thus, TR13 may be useful as a modulator of hematopoietic stem cells in vitro for the purpose of bone marrow transplantation and/or gene therapy. Since stem cells are rare and are most useful for introducing genes into for gene therapy, TR13 can be used to isolate enriched populations of stem cells. Stem cells can be enriched by culturing cells in the presence of cytotoxins, such as 5-Fu, which kills rapidly dividing cells, where as the stem cells will be protected by TR13. These stem cells can be returned to a bone marrow transplant patient or can then be used for transfection of the desired gene for gene therapy. In addition, TR13 can be injected into animals which results in the release of stem cells from the bone marrow of the animal into the peripheral blood. These stem cells can be isolated for the purpose of autologous bone marrow transplantation or manipulation for gene therapy. After the patient has finished chemotherapy or radiation treatment, the isolated stem cells can be returned to the patient.

The TR14 nucleic acids, polypeptides, agonists and/or antagonists of the invention may also be employed for the expansion of immature hematopoietic progenitor cells, for example, granulocytes, macrophages or monocytes (e.g., CD34+, kit+), by temporarily preventing their differentiation. These bone marrow cells may be cultured in vitro. Thus, TR14 may be useful as a modulator of hematopoietic stem cells in vitro for the purpose of bone marrow transplantation and/or gene therapy. Since stem cells are rare and are most useful for introducing genes into for gene therapy, TR14 can be used to isolate enriched populations of stem cells. Stem cells can be enriched by culturing cells in the presence of cytotoxins, such as 5-Fu, which kills rapidly dividing cells, where as the stem cells will be protected by TR14. These stem cells can be returned to a bone marrow transplant patient or can then be used for transfection of the desired gene for gene therapy. In addition, TR14 can be injected into animals which results in the release of stem cells from the bone marrow of the animal into the peripheral blood. These stem cells can be isolated for the purpose of autologous bone marrow transplantation or manipulation for gene therapy. After the patient has finished chemotherapy or radiation treatment, the isolated stem cells can be returned to the patient.

In a specific embodiment, TR13 and/or TR14 nucleic acids, polypeptides, and/or agonists or antagonists of the invention and/or angonists and/or antagonists thereof may be used to increase the concentration of blood cells in individuals in need of such increase (i.e., in hematopoietin therapy). Conditions that may be ameliorated by administering the compositions of the invention include, but are not limited to, neutropenia, anemia, and thrombocytopenia.

In a specific embodiment, the TR13 and/or TR14 nucleic acids and/or polypeptides of the invention (and/or agonists or antagonists thereof) are used in erythropoietin therapy, which is directed toward supplementing the oxygen carrying capacity of blood. Nucleic acids and/or polypeptides of the invention (and/or agonists or antagonists thereof) may be used to treat or prevent diseases or conditions in patients generally requiring blood transfusions, such as, for example, trauma victims, surgical patients, dialysis patients, and patients with a variety of blood composition-affecting disorders, such as, for example, hemophilia, cystic fibrosis, pregnancy, menstrual disorders, early anemia of prematurity, spinal cord injury, aging, various neoplastic disease states, and the like. Examples of patient conditions that require supplementation of the oxygen carrying capacity of blood and which are within the scope of this invention, include,but are not limited to: treatment of blood disorders characterized by low or defective red blood cell production, anemia associated with chronic renal failure, stimulation of reticulocyte response, development of ferrokinetic effects (such as plasma iron turnover effects and marrow transit time effects), erythrocyte mass changes, stimulation of hemoglobin C synthesis, and increasing levels of hematocrit in vertebrates. The invention also provides for treatment to enhance the oxygen-carrying capacity of an individual, such as for example, an individual encountering hypoxic environmental conditions.

TR13 and/or TR14 nucleic acids, polypeptides and/or agonists or antagonists may also be employed to regulate hematopoiesis, by regulating the activation and differentiation of various hematopoietic progenitor cells, for example, to release mature leukocytes from the bone marrow following chemotherapy, i.e., in stem cell mobilization. TR13 and/or TR14 nucleic acids, polypeptides and/or agonists or antagonists may also be employed to treat sepsis.

TR13 and/or TR14 nucleic acids, polypeptides and/or agonists or antagonists may also be employed to inhibit T-cell proliferation by the inhibition of IL-2 biosynthesis for the treatment of T-cell mediated auto-immune diseases and lymphocytic leukemias (including, for example, chronic lymphocytic leukemia (CLL)).

TR13 and/or TR14 nucleic acids, polypeptides and/or agonists or antagonists may also be employed to stimulate wound healing, both via the recruitment of debris clearing and connective tissue promoting inflammatory cells. In this same manner TR13 and/or TR14 nucleic acids, polypeptides and/or agonists or antagonists may also be employed to treat other fibrotic disorders, including liver cirrhosis, osteoarthritis and pulmonary fibrosis.

TR13 and/or TR14 nucleic acids, polypeptides and/or agonists or antagonists may also be employed to enhance host defenses against resistant chronic and acute infections, for example, myobacterial infections via the attraction and activation of microbicidal leukocytes.

TR13 and/or TR14 nucleic acids, polypeptides and/or agonists or antagonists also increases the presence of eosinophils which have the distinctive function of killing the larvae of parasites that invade tissues, as in schistosomiasis, trichinosis and ascariasis.

TR13 nucleic acids and/or polypeptides of the invention, and/or angonists and/or antagonists thereof may be used in treatment of myeloid leukemias.

TR13 polynucleotides or polypeptides, or agonists of TR13, can be used in the treatment of infectious agents. For example, by increasing the immune response, infectious diseases may be treated. The immune response may be increased by either enhancing an existing immune response, or by initiating a new immune response. Alternatively, TR13 polynucleotides or polypeptides, or agonists or antagonists of TR13, may also directly inhibit the infectious agent, without necessarily eliciting an immune response.

TR14 polynucleotides or polypeptides, or agonists of TR14, can be used in the treatment of infectious agents. For example, by increasing the immune response, infectious diseases may be treated. The immune response may be increased by either enhancing an existing immune response, or by initiating a new immune response. Alternatively, TR14 polynucleotides or polypeptides, or agonists or antagonists of TR14, may also directly inhibit the infectious agent, without necessarily eliciting an immune response.

Viruses are one example of an infectious agent that can cause disease or symptoms that can be treated by TR13 nucleic acids, polypeptides, and/or agonists or antagonists. Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. TR13 nucleic acids, polypeptides, and/or agonists or antagonists of TR13, can be used to treat or detect any of these symptoms or diseases. In specific embodiments, TR13 nucleic acids, polypeptides, and/or agonists or antagonists are used to treat: meningitis, Dengue, EBV, and/or hepatitis (e.g., hepatitis B). In an additional specific embodiment TR13 nucleic acids, polypeptides, and/or agonists or antagonists are used to treat patients nonresponsive to one or more other commercially available hepatitis vaccines. In a further specific embodiment, TR13 nucleic acids, polypeptides, and/or agonists or antagonists are used to treat AIDS.

Similarly, bacterial or fungal agents that can cause disease or symptoms and that can be treated by TR13 nucleic acids or polypeptides, and/or agonists or antagonists of TR13, include, but not limited to, the following Gram-Negative and Gram-positive bacteria and bacterial families and fungi: Actinomycetales (e.g., *Corynebacterium, Mycobacterium, Norcardia*), *Cryptococcus neoformans, Aspergillosis, Bacillaceae* (e.g., *Anthrax, Clostridium*), *Bacteroidaceae, Blastomycosis, Bordetella, Borrelia* (e.g., *Borrelia burgdorferi, Brucellosis, Candidiasis, Campylobacter, Coccidioidomycosis, Cryptococcosis, Dennatocycoses, E. coli* (e.g., Enterotoxigenic *E. coli* and Enterohemorrhagic *E. coli*), *Enterobacteriaceae* (*Klebsiella, Salmonella* (e.g., *Salmonella typhi*, and *Salmonella paratyphi*), *Serratia, Yersinia*), *Erysipelothrix, Helicobacter, Legionellosis, Leptospirosis, Listeria, Mycoplasmatales, Mycobacterium leprae, Vibrio cholerae, Neisseriaceae* (e.g., *Acinetobacter,*

Gonorrhea, Menigococcal), *Meisseria meningitidis*, *Pasteurellacea* Infections (e.g., *Actinobacillus, Heamophilus* (e.g., *Heamophilus influenza* type B), Pasteurella), *Pseudomonas, Rickettsiaceae, Chlamydiaceae, Syphilis, Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), *Chlamydia*, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. TR13 nucleic acids or polypeptides, and/or agonists or antagonists of TR13, can be used to treat or detect any of these symptoms or diseases. In specific embodiments, TR13 nucleic acids, polypeptides, and/or agonists or antagonists thereof are used to treat: tetanus, Diptheria, botulism, and/or meningitis type B.

Moreover, parasitic agents causing disease or symptoms that can be treated by TR13 nucleic acids or polypeptides, and/or agonists or antagonists of TR13, include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. TR13 nucleic acids or polypeptides, and/or agonists or antagonists of TR13, can be used to treat or detect any of these symptoms or diseases. In specific embodiments, TR13 nucleic acids, polypeptides, and/or agonists or antagonists thereof are used to treat malaria. Moreover, parasitic agents causing disease or symptoms that can be treated by TR13 nucleic acids or polypeptides, and/or agonists or antagonists of TR13, include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. TR13 nucleic acids or polypeptides, and/or agonists or antagonists of TR13, can be used to treat or detect any of these symptoms or diseases. In specific embodiments, TR13 nucleic acids, polypeptides, and/or agonists or antagonists thereof are used to treat malaria.

Viruses are one example of an infectious agent that can cause disease or symptoms that can be treated by TR14 nucleic acids or polypeptides, and/or agonists or antagonists of TR14. Examples of viruses, include, but are not limited to the following DNA and RNA viruses and viral families: Arbovirus, Adenoviridae, Arenaviridae, Arterivirus, Bimaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. TR14 nucleic acids or polypeptides, and/or agonists or antagonists of TR14, can be used to treat or detect any of these symptoms or diseases. In specific embodiments, TR14 nucleic acids, polypeptides, and/or agonists or antagonists are used to treat: meningitis, Dengue, EBV, and/or hepatitis (e.g., hepatitis B). In an additional specific embodiment TR14 nucleic acids, polypeptides, and/or agonists or antagonists are used to treat patients nonresponsive to one or more other commercially available hepatitis vaccines. In a further specific embodiment, TR14 nucleic acids, polypeptides, and/or agonists or antagonists are used to treat AIDS.

Similarly, bacterial or fungal agents that can cause disease or symptoms and that can be treated by TR14 nucleic acids or polypeptides, and/or agonists or antagonists of TR14, include, but not limited to, the following Gram-Negative and Gram-positive bacteria and bacterial families and fungi: Actinomycetales (e.g., *Corynebacterium, Mycobacterium, Norcardia*), *Cryptococcus neoformans*, Aspergillosis, Bacillaceae (e.g., Anthrax, *Clostridium*), Bacteroidaceae, Blastomycosis, *Bordetella, Borrelia* (e.g., *Borrelia burgdorferi*, Brucellosis, Candidiasis, Campylobacter, Coccidioidomycosis, Cryptococcosis, Dermatocycoses, *E. coli* (e.g., Enterotoxigenic *E. coli* and Enterohemorrhagic *E. coli*), Enterobacteriaceae (*Klebsiella, Salmonella* (e.g., *Salmonella typhi*, and *Salmonella paratyphi*), *Serratia, Yersinia*), *Erysipelothrix, Helicobacter*, Legionellosis, Leptospirosis, *Listeria, Mycoplasmatales, Mycobacterium leprae, Vibrio cholerae*, Neisseriaceae (e.g., Acinetobacter, Gonorrhea, Menigococcal), *Meisseria meningitidis*, *Pasteurellacea* Infections (e.g., Actinobacillus, Heamophilus (e.g., *Heamophilus influenza* type B), Pasteurella), Pseudomonas, Rickettsiaceae, Chlamydiaceae, Syphilis, Shigella spp., Staphylococcal, Meningiococcal, Pneumococcal and Streptococcal (e.g., *Streptococcus pneumoniae* and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. TR14 nucleic acids or polypeptides, and/or agonists or antagonists of TR14, can be used to treat or detect any of these symptoms or diseases. In specific embodiments, TR14 nucleic acids, polypeptides, and/or agonists or antagonists thereof are used to treat: tetanus, Diptheria, botulism, and/or meningitis type B.

Moreover, parasitic agents causing disease or symptoms that can be treated by TR14 nucleic acids or polypeptides, and/or agonists or antagonists of TR14, include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., Plasmodium virax, Plasmodium falciparium, Plasmodium malariae and Plasmodium ovale). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. TR14 nucleic acids or polypeptides, and/or agonists or antagonists of TR14, can be used to treat or detect any of these symptoms or diseases. In specific embodiments, TR14 nucleic acids, polypeptides, and/or agonists or antagonists thereof are used to treat malaria. Moreover, parasitic agents causing disease or symptoms that can be treated by TR14 nucleic acids or polypeptides, and/or agonists or antagonists of TR14, include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. TR14 nucleic acids or polypeptides, and/or agonists or antagonists of TR14, can be used to treat or detect any of these symptoms or diseases. In specific embodiments, TR14 nucleic acids, polypeptides, and/or agonists or antagonists thereof are used to treat malaria.

An additional condition, disease or symptom that can be treated by TR13 nucleic acids, polypeptides, and/or agonists or antagonists of TR13, is osteomyelitis.

An additional condition, disease or symptom that can be treated by TR14 nucleic acids, polypeptides, and/or agonists or antagonists of TR14, is osteomyelitis.

Preferably, treatment using TR13 nucleic acids, polypeptides, and/or agonists or antagonists of TR13, could either be by administering an effective amount of TR13 polypeptide to the patient, or by removing cells from the patient, supplying the cells with TR13 nucleic acids, and returning the engineered cells to the patient (ex vivo therapy). Moreover, as further discussed herein, the TR13 polypeptide or nucleic acids can be used as an adjuvant in a vaccine to raise an immune response against infectious disease.

Preferably, treatment using TR14 nucleic acids, polypeptides, and/or agonists or antagonists of TR14, could either be by administering an effective amount of TR14 polypeptide to the patient, or by removing cells from the patient, supplying the cells with TR14 nucleic acid, and returning the engineered cells to the patient (ex vivo therapy). Moreover, as further discussed herein, the TR14 polypeptide or nucleic acid can be used as an adjuvant in a vaccine to raise an immune response against infectious disease.

Additional preferred embodiments of the invention include, but are not limited to, the use of TR13 and/or TR14 polypeptides and/or functional agonists or functional antgonists in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconsituted immune system from another animal (see, e.g., published PCT Application Nos. WO98/24893, WO/9634096, WO/9633735, and WO/9110741.

A vaccine adjuvant that enhances immune responsiveness to specific antigen. In a specific embodiment, the vaccine adjuvant is a TR13 and/or TR14 polypeptide described herein. In another specific embodiment, the vaccine adjuvant is a TR13 and/or TR14 nucleic acid described herein (i.e., the TR13 and/or TR14 nucleic acid is a genetic vaccine adjuvant). As discussed herein, TR13 and/or TR14 nucleic acids may be administered using techniques known in the art, including but not limited to, liposomal delivery, recombinant vector delivery, injection of naked DNA, and gene gun delivery.

An adjuvant to enhance tumor-specific immune responses.

An adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever. In another specific embodiment, the compositions of the invention are used as an adjuvant to enhance an immune response to the HIV gp120 antigen.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of: Vibrio cholerae, Mycobacterium leprae, Salmonella typhi, Salmonella paratyphi, Meisseria meningitidis, Streptococcus pneumoniae, Group B streptococcus, Shigella spp., Enterotoxigenic Escherichia coli, Enterohemorrhagic E. coli, Borrelia burgdorferi, and Plasmodium (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to Plasmodium (malaria).

As a stimulator of B cell responsiveness to pathogens.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to f all recovery of B cell populations.

As an agent to boost immunoresponsiveness among B cell immunodeficient individuals. B cell immunodeficiencies that may be ameliorated or treated by administering the TR13 polypeptides or polynucleotides of the invention, or agonists thereof, include, but are not limited to, SCID, congenital agammaglobulinemia, common variable immunodeficiency, Wiskott-Aldrich Syndrome, X-linked immunodeficiency with hyper IgM, and severe combined immunodeficiency.

As an agent to boost immunoresponsiveness among B cell immunodeficient individuals. B cell immunodeficiencies that may be ameliorated or treated by administering the TR14 polypeptides or nucleic acids of the invention, or agonists thereof, include, but are not limited to, SCID, congenital agammaglobulinemia, common variable immunodeficiency, Wiskott-Aldrich Syndrome, X-linked immunodeficiency with hyper IgM, and severe combined immunodeficiency.

As an agent to boost immunoresponsiveness among individuals having an acquired loss of B cell function. Conditions resulting in an acquired loss of B cell function that may be ameliorated or treated by administering the TR13 polypeptides or nucleic acids of the invention, or agonists thereof, include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering the TR13 polypeptides or nucleic acids of the invention, or agonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As an agent to boost immunoresponsiveness among individuals having an acquired loss of B cell function. Conditions resulting in an acquired loss of B cell function that may be ameliorated or treated by administering the TR14 polypeptides or nucleic acids of the invention, or agonists thereof, include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering the TR14 polypeptides or nucleic acids of the invention, or agonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As a regulator of antigen presentation by monocytes, dendritic cells, and/or B-cells. In one embodiment, TR13 (in soluble, membrane-bound or transmembrane forms) enhances antigen presentation or antagonizes antigen presentation in vitro or in vivo. Moreover, in related embodiments, said enhancement or antagonization of antigen presentation may be useful as an anti-tumor treatment or to modulate the immune system.

As a regulator of antigen presentation by monocytes, dendritic cells, and/or B-cells. In one embodiment, TR14 (in soluble, membrane-bound or transmembrane forms) enhances antigen presentation or antagonizes antigen presentation in vitro or in vivo. Moreover, in related embodiments, said enhancement or antagonization of antigen presentation may be useful as an anti-tumor treatment or to modulate the immune system.

As an agent to direct an individuals immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As a stimulator of B cell production in pathologies such as AIDS, chronic lymphocyte disorder and/or Common Variable Immunodificiency;

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance TR13 mediated responses.

As an antigen for the generation of antibodies to inhibit or enhance TR14 mediated responses.

As a means of activating monocytes/macrophages to defend against parasitic diseases that effect monocytes such as Leshmania.

As a means of activating T cells.

As pretreatment of bone marrow samples prior to transplant. Such treatment would increase B cell representation and thus accelerate recover.

As a means of regulating secreted cytokines that are elicited by TR13.

As a means of regulating secreted cytokines that are elicited by TR14.

TR13 polypeptides or nucleic acids of the invention, and/or agonists or antagonists may be used to modulate IgE concentrations in vitro or in vivo.

TR14 polypeptides or nucleic acids of the invention, and/or agonists or antagonists may be used to modulate IgE concentrations in vitro or in vivo.

Additionally, TR13 polypeptides or nucleic acids of the invention, and/or agonists or antagonists thereof, may be used to treat or prevent IgE-mediated allergic reactions. Such allergic reactions include, but are not limited to, asthma, rhinitis, and eczema.

Additionally, TR14 polypeptides or nucleic acids of the invention, and/or agonists or antagonists thereof, may be used to treat or prevent IgE-mediated allergic reactions. Such allergic reactions include, but are not limited to, asthma, rhinitis, and eczema.

All of the above described applications as they may apply to veterinary medicine.

Antagonists of TR13 include binding and/or inhibitory antibodies, antisense nucleic acids, ribozymes or soluble forms of the TR13 receptor(s). Antagonists or agonists of TR13 would be expected to reverse many of the activities of the ligand described above as well as find clinical or practical application as:

Antagonists of TR14 include binding and/or inhibitory antibodies, antisense nucleic acids, ribozymes or soluble forms of the TR14 receptor(s) Antagonists or agonists of TR14 would be expected to reverse many of the activities of the ligand described above as well as find clinical or practical application as:

A means of blocking various aspects of immune responses to foreign agents or self. Examples include autoimmune disorders such as lupus, and arthritis, as well as immuno-responsiveness to skin allergies, inflammation, bowel disease, injury and pathogens.

A means of blocking various aspects of immune responses to foreign agents or self Examples include autoimmune disorders such as lupus, and arthritis, as well as immuno-responsiveness to skin allergies, inflammation, bowel disease, injury and pathogens.

A therapy for preventing the B cell proliferation and Ig secretion associated with autoimmune diseases such as idiopathic thrombocytopenic purpura, systemic lupus erythramatosus and MS.

An inhibitor of graft versus host disease or transplant rejection.

A therapy for B cell malignancies such as ALL, Hodgkins disease, non-Hodgkins lymphoma, Chronic lymphocyte leukemia, plasmacytomas, multiple myeloma, Burkitt's lymphoma, and EBV-transformed diseases.

A therapy for chronic hypergammaglobulinemeia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and Ig associated with Chronic Myelogenous Leukemia.

An immunosuppressive agent(s).

TR13 polypeptides or nucleic acids of the invention, and/or agonists or antagonists may be used to modulate IgE concentrations in vitro or in vivo.

TR14 polypeptides or nucleic acids s of the invention, and/or agonists or antagonists may be used to modulate IgE concentrations in vitro or in vivo.

In another embodiment, administration of TR13 polypeptides or nucleic acids of the invention, and/or agonists or antagonists thereof, may be used to treat or prevent IgE-mediated allergic reactions including, but not limited to, asthma, rhinitis, and eczema.

In another embodiment, administration of TR14 polypeptides or nucleic acids of the invention, and/or agonists or antagonists thereof, may be used to treat or prevent IgE-mediated allergic reactions including, but not limited to, asthma, rhinitis, and eczema.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

The TR13 and/or TR14 nucleic acids, polypeptides and/or agonists and antagonists may be employed in a composition with a pharmaceutically acceptable carrier, e.g., as described hererin.

The TR13 and/or TR14 nucleic acids, polypeptides and/or agonists or antagonists may be employed for instance to inhibit the chemotaxis and activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. TR13 and/or TR14 nucleic acids, polypeptides and/or agonists or antagonists may also be employed to treat infectious diseases including silicosis, sarcoidosis, idiopathic pulmonary fibrosis by preventing the recruitment and activation of mononuclear phagocytes. They may also be employed to treat idiopathic hyper-eosinophilic syndrome by preventing eosinophil production and migration. Endotoxic shock may also be treated by the antagonists by preventing the migration of macrophages and their production of the TR16 polypeptides of the present invention. The TR13 and/or TR14 nucleic acids, polypeptides and/or agonists or antagonists may also be employed for treating TR13 and/or TR14 nucleic acids, polypeptides and/or agonists or antagonists antagonists may also be employed to treat histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated. The TR13 and/or TR14 nucleic acids, polypeptides and/or agonists or antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. TR13 and/or TR14 nucleic acids, polypeptides and/or agonists or antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies. The TR13 and/or TR14 nucleic acids, polypeptides and/or agonists or antagonists may be employed to interfere with the deleterious cascades attributed primarily to IL-1 and TNF, which prevents the biosynthesis of other inflammatory cytokines. In this way, the antagonists maybe employed to prevent inflammation. The TR13 and/or TR14 nucleic acids, polypeptides and/or agonists or antagonists may also be employed to inhibit prostaglandin-independent fever induced by TR16. The TR13 and/or TR14 nucleic acids, polypeptides and/or agonists or antagonists may also be employed to treat cases of bone marrow failure, for example, aplastic anemia and myelodysplastic syndrome. The TR13 and/or TR14 nucleic acids, polypeptides and/or agonists or antagonists may also be employed to treat asthma and allergy by preventing eosinophil accumulation in the lung. The TR13 and/or TR14 nucleic acids, polypeptides and/or agonists or antagonists may also be employed to treat subepithelial basement membrane fibrosis which is a prominent feature of the asthmatic lung. The TR13 and/or TR14 nucleic acids, polypeptides and/or agonists or antagonists may also be employed to treat lymphomas (e.g., one or more of the extensive, but not limiting, list of lymphomas provided herein).

Antibodies against TR13 and/or TR14 may be employed to bind to and inhibit TR13 and/or TR14 activity to treat ARDS, by preventing infiltration of neutrophils into the lung after injury. The antagonists and antagonists of the instant may be employed in a composition with a pharmaceutically acceptable carrier, e.g., as described hereinafter.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more than allograft rejection. In the case of disease recurrence, the immune system has already been activated, as evidenced by destruction of the native islet cells. Therefore, in disease recurrence, the immune system is already at the effector stage. Antagonists of the present invention are able to suppress the immune response to both allografts and xenografts because lymphocytes activated and differentiated into effector cells will express the TR13 polypeptide, and thereby are susceptible to compounds which enhance apoptosis. Thus, the present invention further provides a method for creating immune privileged tissues.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more than allograft rejection. In the case of disease recurrence, the immune system has already been activated, as evidenced by destruction of the native islet cells. Therefore, in disease recurrence, the immune system is already at the effector stage. Antagonists of the present invention are able to suppress the immune response to both allografts and xenografts because lymphocytes activated and differentiated into effector cells will express the TR14 polypeptide, and thereby are susceptible to compounds which enhance apoptosis. Thus, the present invention further provides a method for creating immune privileged tissues.

TR13 polynucleotides, polypeptides, and agonists of the invention may also be used to suppress immune responses. In one embodiment, the TR13 polynucleotides, polypeptides, and agonists of the invention are used to minimize untoward effects associated with transplantation. In a specific embodiment, the TR13 polynucleotides, polypeptides, and agonists of the invention are used to suppress Fas mediated immune responses (e.g., in a manner similar to an immunosuppressant such as, for example, rapamycin or cyclosporin). In another specific embodiment, the TR13 polynucleotides, polypeptides, and agonists of the invention are used to suppress AIM-II mediated immune responses.

Additionally, both graft rejection and graft vs. host disease are in part triggered by apoptosis. Accordingly, an additional preferred embodiment, TR13 polynucleotides, polypeptides, TR13 agonists and/or TR13 antagonists of the invention are used to treat and prevent and/or reduce graft rejection. In a further preferred embodiment, TR13 polynucleotides, polypeptides, TR13 agonists and/or TR13 antagonists of the invention are used to treat and prevent and/or reduce graft vs. host disease.

Additionally, TR13 polypeptides, polynucleotides, TR13 agonists and/or TR13 antagonists may be used to treat or prevent graft rejection (e.g., xenograft and allograft rejection (e.g, acute allograft rejection)) and/or medical conditions associated with graft rejection. In a specific embodiment, TR13 polypeptides, polynucleotides, , TR13 agonists and/or TR13 antagonists of the invention are used to treat or prevent acute allograft rejection and/or medical conditions associated with acute allograft rejection. In a further specific embodiment, TR13 polypeptides, polynucleotides, , TR13 agonists and/or TR13 antagonists of the invention are used to treat or prevent acute allograft rejection of a kidney and/or medical conditions associated with acute allograft rejection of a kidney.

Fas ligand is a type II membrane protein that induces apoptosis by binding to Fas. Fas ligand is expressed in activated T cells, and works as an effector of cytotoxic lymphocytes. Molecular and genetic analysis of Fas and Fas ligand have indicated that mouse lymphoproliferation mutation (1pr) and generalized lymphoproliferative disease (gld) are mutations of Fas and Fas ligand respectively. The 1pr of gld mice develop lymphadenopathy, and suffer from autoimmune disease. Based on these phenotypes and other studies, it is believed that the Fas system is involved in the apoptotic process during T-cell development, specifically peripheral clonal deletion or activation-induced apoptosis of mature T cells. In addition to the activated lymphocytes, Fas is expressed in the liver, heart and lung. Administration of agonistic anti-Fas antibody into mice has been shown to induce apoptosis in the liver and to quickly kill the mice, causing liver damage. These findings indicate that the Fas system plays a role not only in the physiological process of lymphocyte development, but also in the cytotoxic T-lymphocyte-mediated disease such as fulminant hepatitis and/or hepatitis resulting from viral infection or toxic agents. As discussed herein, TR13 binds Fas ligand, and thus functions as an antagonist of Fas-ligand mediated activity. Accordingly, the TR13 polypeptides and/or polynucleotides of the invention, and/or agonists thereof, may be used to treat or prevent lymphoproliferative disorders (e.g., lymphadenopathy and others described herein), autoimmune disorders (e.g., autoimmune diabetes, systemic lupus erythematosus, Grave's disease, Hashimoto's thyroiditis, immune-related glomerulonephritis, autoimmune gastritis, autoimmune thrombocytopenic purpura, multiple sclerosis, rheumatoid arthritis, and others described herein), and/or liver disease (e.g., acute and chronic hepatitis, and cirrhosis).

In a specific embodiment TR13 polynucleotides, polypeptides, and/or agonists or antagonists of the invention is used to treat or prevent hepatitis and/or tissue/cell damage or destruction and/or medical conditions associated with hepatitis. In a specific embodiment TR13 polynucleotides, polypeptides, and/or agonists or antagonists of the invention is used to treat or prevent fulminant hepatitis and/or medical conditions associated with fulminant hepatitis.

In a specific embodiment TR13 polynucleotides, polypeptides, and/or agonists or antagonists of the invention is used to treat or prevent systemic lupus erythematosus (SLE) and/or tissue/cell damage or destruction and/or medical conditions associated with SLE. In a further specific embodiment, TR13 polynucleotides, polypeptides, and/or agonists or antagonists of the invention are used to treat or prevent skin lesions in SLE patients.

In a specific embodiment TR13 polynucleotides, polypeptides, and/or agonists or antagonists of the invention is used to treat or prevent insulin-dependent diabetes mellitus and/or tissue/cell damage or destruction and/or medical conditions associated with insulin-dependent diabetes mellitus. In a further specific embodiment, TR13 polynucleotides, polypeptides, and/or agonists or antagonists of the invention are prior to, during, or immediately after the onset of diabetes to reduce or prevent damage to islet cells and/or to reduce exogenous insulin requirement.

In a specific embodiment TR13 polynucleotides, polypeptides, and/or agonists or antagonists of the invention is used to treat or prevent toxic epidermal necrolysis (TEN) and/or tissue/cell damage or destruction, and/or medical conditions associated with TEN. In a further specific embodiment, TR13 polynucleotides, polypeptides, and/or agonists or antagonists of the invention is used to treat or prevent Lyell's syndrome.

Hepatitis virus (e.g., Hepatitis B virus and Hepatitis C virus) is a major causative agent of chronic liver disease. In Hepatitis infection, Fas expression in hepatocytes is up-regulated in accordance with the severity of liver inflammation. When Hepatitis virus-specific T cells migrate into hepatocytes and recognize the viral antigen via the T cell receptor, they become activated and express Fas ligand that can transduce the apoptotic death signal to Fas-bearing hepatocytes. Thus, the Fas system plays an important role in liver cell injury by viral hepatitis. Accordingly, in specific embodiments, the TR13 polypeptides and/or polynucleotides of the invention and/or agonists or antagonists thereof, are used to treat or prevent hepatitis resulting from viral infection (e.g., infection resulting form Hepatitis B virus or Hepatitis C virus infection). In one embodiment, a patient's blood or plasma is contacted with TR13 polypeptides of the invention ex vivo. The TR13 may be bound to a suitable chromatography matrix by conventional procedures. According to this embodiment, the patient's blood or plasma flows through a chromatography column containing TR13 bound to the matrix, before being returned to the patient. The immobilized TR13 binds Fas-ligand, thus removing Fas-ligand protein from the patient's blood.

In a specific embodiment, TR13 polypeptides, polynucleotides, and/or agonists or antagonists of the invention may be used to treat or prevent renal failure (e.g., chronic renal failure), and/or tissue/cell damage or destruction (e.g., tubular epithelial cell deletion) and/or medical conditions associated with renal failure.

In a specific embodiment, TR13 polypeptides, polynucleotides, and/or agonists or antagonists of the invention may be used to regulate (i.e., stimulate or inhibit) bone growth. In specific embodiments TR13 polypeptides, polynucleotides, and/or agonists or antagonists of the invention are used to stimulate bone growth. Specific diseases or conditions that may be treated or prevented with the compositions of the invention include, but are not limited to, bone fractures, and defects, and disorders which result in weakened bones such as osteoporosis, osteomalacia, and age-related loss of bone mass.

TR13 nucleic acids, polypeptides and/or agonists or antagonists of the invention can further be used in the treatment of inflammatory diseases, such as inflammatory bowel disease, rheumatoid arthritis, osteoarthritis, psoriasis, and septicemia.

TR14 nucleic acids, polypeptides and/or agonists or antagonists of the invention can further be used in the treatment of inflammatory diseases, such as inflammatory bowel disease, rheumatoid arthritis, osteoarthritis, psoriasis, and septicemia.

TR13 and/or TR14 nucleic acids and/or polypeptides of the invention and/or agonists and/or antagonists thereof are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.))), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

TR13 and/or TR14 nucleic acids and/or polypeptides of the invention and/or agonists and/or antagonists thereof are useful in promoting angiogenesis, regulating hematopoiesis and wound healing (e.g., wounds, burns, and bone fractures).

TR13 and/or TR14 nucleic acids and/or polypeptides of the invention and/or agonists and/or antagonists thereof are also useful as an adjuvant to enhance immune responsiveness to specific antigen, anti-viral immune responses.

More generally, TR13 and/or TR14 nucleic acids and/or polypeptides of the invention and/or agonists and/or antagonists thereof are useful in regulating (i.e., elevating or reducing) immune response. For example, nucleic acids and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, TR13 and/or TR14 nucleic acids and/or polypeptides of the invention and/or agonists and/or antagonists thereof are useful as immunosuppressive agents, for example in the treatment or prevention of autoimmune disorders. In specific embodiments, nucleic acids and/or polypeptides of the invention are used to treat or prevent chronic inflammatory, allergic or autoimmune conditions, such as those described herein or are otherwise known in the art.

In one aspect, the present invention is directed to a method for enhancing apoptosis induced and/or TR13 mediated signaling induced by a TNF-family ligand, which involves administering to a cell which expresses the TR13 polypeptide an effective amount of TR13 ligand (e.g., Fas ligand), analog or an agonist capable of increasing apoptosis and/or TR13 mediated signaling. Preferably, TR13 mediated signaling is increased to treat a disease wherein decreased apoptosis or decreased cytokine and adhesion molecule expression is exhibited. An agonist can include monoclonal antibodies directed against the TR13 polypeptide.

In a further aspect, the present invention is directed to a method for inhibiting apoptosis induced and/or TR13 mediated signalling induced by a TNF-family ligand (e.g., Fas ligand), which involves administering to a cell which expresses the TR13 polypeptide an effective amount of an antagonist capable of decreasing apoptosis and/or TR13 mediated signaling. Preferably, TR13 mediated signaling is decreased to treat a disease wherein increased apoptosis or NFκB expression is exhibited. An antagonist can include soluble forms of TR13 and monoclonal antibodies directed against the TR13 polypeptide.

In one aspect, the present invention is directed to a method for enhancing apoptosis induced and/or TR14 mediated signaling induced by a TNF-family ligand, which involves administering to a cell which expresses the TR14 polypeptide an effective amount of TR14 ligand, analog or an agonist capable of increasing apoptosis and/or TR14 mediated signaling. Preferably, TR14 mediated signaling is increased to treat a disease wherein decreased apoptosis or decreased cytokine and adhesion molecule expression is exhibited. An agonist can include soluble forms of TR14 and monoclonal antibodies directed against the TR14 polypeptide.

In a further aspect, the present invention is directed to a method for inhibiting apoptosis induced and/or TR14 mediated signalling induced by a TNF-family ligand, which involves administering to a cell which expresses the TR14 polypeptide an effective amount of an antagonist capable of decreasing apoptosis and/or TR14 mediated signaling. Preferably, TR14 mediated signaling is decreased to treat a disease wherein increased apoptosis or NFKB expression is exhibited. An antagonist can include soluble forms of TR14 and monoclonal antibodies directed against the TR14 polypeptide.

By "agonist" is intended naturally occurring and synthetic compounds capable of enhancing or potentiating apoptosis. By "antagonist" is intended naturally occurring and synthetic compounds capable of inhibiting apoptosis. Whether any candidate "agonist" or "antagonist" of the present invention can enhance or inhibit apoptosis can be determined using art-known TNF-family ligand/receptor cellular response assays, including those described in more detail below.

One such screening procedure involves the use of melanophores which are transfected to express the receptor of the present invention. Such a screening technique is described in PCT WO 92/01810, published Feb. 6, 1992. Such an assay may be employed, for example, for screening for a compound which inhibits (or enhances) activation of the receptor polypeptide of the present invention by contacting the melanophore cells which encode the receptor with both a TNF-family ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular pH changes caused by receptor activation. For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique well known in the art involves expressing in cells a construct wherein the receptor is linked to a phospholipase C or D. Exemplary cells include endothelial cells, smooth muscle cells, embryonic kidney cells, etc. The screening may be accomplished as hereinabove described by detecting activation of the receptor or inhibition of activation of the receptor from the phospholipase signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Further screening assays for agonists and antagonists of the present invention are described in L. A. Tartaglia and D. V. Goeddel, *J. Biol. Chem.* 267:4304–4307(1992).

Thus, in a further aspect, a screening method is provided for determining whether a candidate agonist or antagonist is capable of enhancing or inhibiting a cellular response to a TNF-family ligand. The method involves contacting cells which express the TR13 polypeptide with a candidate compound and a TNF-family ligand (e.g. Fas ligand), assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., quntitating the amount of apoptosis in a cell population, or determining or estimating an increase or decrease in T cell proliferation by tritiated thymidine labeling). By the invention, a cell expressing the TR13 polypeptide can be contacted with either an endogenous or exogenously administered TNF-family ligand.

Thus, in a further aspect, a screening method is provided for determining whether a candidate agonist or antagonist is capable of enhancing or inhibiting a cellular response to a TNF-family ligand. The method involves contacting cells which express the TR14 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing the TR14 polypeptide can be contacted with either an endogenous or exogenously administered TNF-family ligand.

Antagonist according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites.)). Further preferred antagonists include, TR13 polypeptide fragments, and polyclonal and monoclonal antibodies raised against the TR13 polypeptide, or a fragment thereof. Preferred agonists include chemotherapeutic drugs such as, for example, cisplatin, doxorubicin, bleomycin, cytosine arabinoside, nitrogen mustard, methotrexate and vincristine. Others include ethanol and -amyloid peptide. (*Science* 267:1457–1458 (1995)). Further preferred agonists include, TR13 polypeptide fragments, and polyclonal and monoclonal antibodies raised against the TR13 polypeptide, or a fragment thereof. Such agonist antibodies raised against a TNF-family receptor are disclosed in L. A. Tartaglia et al, *Proc. Natl. Acad. Sci. USA* 88:9292–9296 (1991); and L. A. Tartaglia and D. V. Goeddel, *J. Biol. Chem.* 267:4304–4307 (1992). See, also, PCT Application WO 94/09137.

Antagonist according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Further preferred antagonists include, TR14 polypeptide fragments, and polyclonal and monoclonal antibodies raised against the TR14 polypeptide, or a fragment thereof. Preferred agonists include chemotherapeutic drugs such as, for example, cisplatin, doxorubicin, bleomycin, cytosine arabinoside, nitrogen mustard, methotrexate and vincristine. Others include ethanol and -amyloid peptide. (*Science* 267:1457–1458 (1995)). Further preferred agonists include, TR14 polypeptide fragments, and polyclonal and monoclonal antibodies raised against the TR14 polypeptide, or a fragment thereof. Such agonist antibodies raised against a TNF-family receptor are disclosed in L. A. Tartaglia et al., *Proc. Natl. Acad. Sci. USA* 88:9292–9296 (1991); and L. A. Tartaglia and D. V. Goeddel, *J. Biol. Chem.* 267:4304–4307 (1992). See, also, PCT Application WO 94/09137.

Agonists according to the present invention include naturally occurring and synthetic compounds such as, for example, the CD40 ligand, neutral amino acids, zinc, estrogen, androgens, viral genes (such as Adenovirus E1B, Baculovirus p35 and IAP, Cowpox virus crmA, Epstein-Barr virus BHRF1, LMP-1, African swine fever virus LMW5-HL, and Herpesvirus yl34.5), calpain inhibitors, cysteine protease inhibitors, and tumor promoters (such as PMA, Phenobarbital, and Hexachlorocyclohexane).

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); *Oligodeoxynucleotides as Antisense Inhibitors of Gene Expression*, CRC Press, Boca Raton, Fla. (1988). Triple helix formation is discussed in, for instance Lee et at., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA.

In specific embodiments, antagonists according to the present invention are nucleic acids corresponding to the sequences contained of TR13 (SEQ ID NO:1) and/or SEQ ID NO:39, or the complementary strand thereof, and/or to nucleotide sequences contained in the clone deposited as ATCC Deposit No. PTA-349 and/or ATCC Deposit No. PTA-507. In one embodiment, antisense sequence is generated internally by the organism, in another embodiment, the antisense sequence is separately administered (see, for example, Okano H. et al, *J. Neurochem.* 56:560 (1991), and Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, *Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al, *Science* 241:456 (1988); and Dervan et al., *Science* 251:1300 (1991). The methods are based on binding of a polynucleotide to a complementary DNA or RNA.

In specific embodiments, antagonists according to the present invention are nucleic acids corresponding to the sequences contained in TR14 (preferably SEQ ID NO:60 or, alternatively SEQ ID NO:4), or the complementary strand thereof, and/or to nucleotide sequences contained in the clone deposited as ATCC Deposit No. PTA-348. In one embodiment, antisense sequence is generated internally by the organism, in another embodiment, the antisense sequence is separately administered (see, for example, Okano H. et al., *J. Neurochem.* 56:560 (1991), and Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, *Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al, *Science* 241:456 (1988); and Dervan et al., *Science* 251:1300 (1991). The methods are based on binding of a polynucleotide to a complementary DNA or RNA.

For example, the 5' coding portion of a polynucleotide that encodes a mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the receptor.

In one embodiment, the TR13 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the TR13 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be clone, viral, or others know in the art, used for replication and expression in vertebrate cells. Expression of the sequence encoding TR13, or fragments thereof, can be by any promoter known in the art to act in vertebrate, preferably human cells. Such promoters can be inducible or constitutive. Such promoters include, but are not limited to, the SV40 early promoter region (Bernoist and Chambon, *Nature* 29:304–310 (1981), the promoter contained in the 3' long terminal repeat of Rous sarcoma virus (Yamamoto et al., *Cell* 22:787–797 (1980), the herpes thymidine promoter (Wagner et al., *Proc. Natl. Acad. Sci. U.S.A.* 78:1441–1445 (1981), the regulatory sequences of the metallothionein gene (Brinster, et al., *Nature* 296:39–42 (1982)), etc.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333–335 (1994). Thus, oligonucleotides complementary to either the 5'- or 3'- non-translated, non-coding regions of the TR13 shown in FIGS. 1A–D or FIGS. 7A–E could be used in an antisense approach to inhibit translation of endogenous TR13 mRNA. Oligonucleotides complementary to the 5' untranslated region of the mRNA should include the complement of the AUG start codon. While antisense nucleotides complementary to the TR13 coding region sequence could be used, those complementary to the transcribed untranslated region are most preferred.

Antisense oligonucleotides complementary to mRNA coding regions are less efficient inhibitors of translation but could be used in accordance with the invention. Whether designed to hybridize to the 5'-, 3'- or coding region of TR13 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The antisense nucleic acids of the invention comprise a sequence complementary to at least a portion of an RNA transcript of a TR13 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded TR13 antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a TR13 RNA it may contain and still form a stable duplex (or triplex as the case may be). One skilled in the art can ascertain a tolerable degree of mismatch by use of standard procedures to determine the melting point of the hybridized complex.

In one embodiment, the TR14 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the TR14 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be clone, viral, or others know in the art, used for replication and expression in vertebrate cells. Expression of the sequence encoding TR14, or fragments thereof, can be by any promoter known in the art to act in vertebrate, preferably human cells. Such promoters can be inducible or constitutive. Such promoters include, but are not limited to, the SV40 early promoter region (Bemoist and Chambon, *Nature* 29:304–310 (1981), the promoter contained in the 3' long terminal repeat of Rous sarcoma virus (Yamamoto et al., *Cell* 22:787–797 (1980), the herpes thymidine promoter (Wagner et al., *Proc. Natl. Acad. Sci. U.S.A.* 78:1441–1445 (1981), the regulatory sequences of the metallothionein gene (Brinster, et al., *Nature* 296:39–42 (1982)), etc.

The antisense nucleic acids of the invention comprise a sequence complementary to at least a portion of an RNA transcript of a TR14 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded TR14 antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a TR14 RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature* 372:333–335 (1994). Thus, oligonucleotides complementary to either the 5'- or 3'-non-translated, non-coding regions of the TR14 shown in FIGS. 4A–E could be used in an antisense approach to inhibit translation of endogenous TR14 mRNA. Oligonucleotides complementary to the 5' untranslated region of the mRNA should include the complement of the AUG start codon. While antisense nucleotides complementary to the TR14 coding region sequence could be used, those complementary to the transcribed untranslated region are most preferred.

Antisense oligonucleotides complementary to mRNA coding regions are less efficient inhibitors of translation but could be used in accordance with the invention. Whether designed to hybridize to the 5'-, 3'- or coding region of TR14 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The nucleic acids of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553–6556 (1989); Lemaitre et al., *Proc. Natl. Acad. Sci.* 84:648–652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., *BioTechniques* 6:958–976 (1988)) or intercalating agents. (See, e.g., Zon, *Pharm. Res.* 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625–6641 (1987)). The oligonucleotide is a 2'-0-methylribonucleotide (Inoue et al., *Nucl. Acids Res.* 15:6131–6148 (1987)), or a chimeric RNA-DNA analogue (Inoue et al., *FEBS Lett.* 215:327–330 (1987)).

Nucleic acids of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448–7451 (1988)), etc.

Potential antagonists according to the invention also include catalytic RNA, or a ribozyme (See, e.g., PCT International Publication WO 90/11364, Sarver et al, *Science* 247:1222–1225 (1990). While ribozymes that cleave mRNA at site specific recognition sequences can be used to destroy TR13 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585–591 (1988). There are numerous potential hammerhead ribozyme cleavage sites within the nucleotide sequence of TR13 in FIGS. 1A–D (SEQ ID NO:1) or FIGS. 7A–E (SEQ ID NO:39). Preferably, the ribozyme is engineered so that the cleavage recognition site is located near the 5' end of the TR13 mRNA; i.e., to increase efficiency and minimize the intracellular accumulation of non-functional mRNA transcripts.

As in the antisense approach, the ribozymes of the invention can be composed of modified oligonucleotides (e.g., for improved stability, targeting, etc.) and should be delivered to cells which express TR13 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous TR13 messages and inhibit translation. Since ribozymes unlike antisense molecules, are catalytic, a lower intracellular concentration is required for efficiency.

Potential antagonists according to the invention also include catalytic RNA, or a ribozyme (See, e.g., PCT International Publication WO 90/11364, Sarver et al, *Science* 247:1222–1225 (1990). While ribozymes that cleave mRNA at site specific recognition sequences can be used to destroy TR14 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585–591 (1988). There are numerous potential hammerhead ribozyme cleavage sites within the nucleotide sequence of TR14 (preferably FIGS. 10A–H (SEQ ID NO:60) or, alternatively, FIGS. 4A–E (SEQ ID NO:4)). Preferably, the ribozyme is engineered so that the cleavage recognition site is located near the 5' end of the TR14 mRNA; i.e., to increase efficiency and minimize the intracellular accumulation of non-functional mRNA transcripts.

As in the antisense approach, the ribozymes of the invention can be composed of modified oligonucleotides (e.g., for improved stability, targeting, etc.) and should be delivered to cells which express TR14 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous TR14 messages and inhibit translation. Since ribozymes unlike antisense molecules, are catalytic, a lower intracellular concentration is required for efficiency.

Endogenous gene expression can also be reduced by inactivating or "knocking out" the TR13 gene and/or its promoter using targeted homologous recombination. (E.g., see Smithies et al., *Nature* 317:230–234 (1985); Thomas & Capecchi, *Cell* 51:503–512 (1987); Thompson et al., *Cell* 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

Endogenous gene expression can also be reduced by inactivating or "knocking out" the TR14 gene and/or its promoter using targeted homologous recombination. (E.g., see Smithies et al., *Nature* 317:230–234 (1985); Thomas & Capecchi, *Cell* 51:503–512 (1987); Thompson et al, *Cell* 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

The techniques of gene-shuffling, motif-shuffling, exon-shuffling, and/or codon-shuffling (collectively referred to as "DNA shuffling") may be employed to modulate the activities of TR13 thereby effectively generating agonists and antagonists of TR13. See generally, U.S. Pat. Nos. 5,605,793, 5,811,238, 5,830,721, 5,834,252, and 5,837,458, and Patten et al, *Curr. Opinion Biotechnol.* 8:724–33 (1997); Harayama, *Trends Biotechnol.* 16(2):76–82 (1998); Hansson et al., *J. Mol. Biol.* 287:265–76 (1999); and Lorenzo and Blasco, *Biotechniques* 24(2):308–13 (1998) (each of these patents and publications are hereby incorporated by reference). In one embodiment, alteration of TR13 nucleic acids and corresponding polypeptides may be achieved by DNA shuffling. DNA shuffling involves the assembly of two or more DNA segments into a desired TR13 molecule by homologous, or site-specific, recombination. In another embodiment, TR13 nucleic acids and corresponding polypeptides may be alterred by being subjected to random mutagenesis by error-prone PCR, random nucleotide insertion or other methods prior to, or more preferrably, during recombination. In another embodiment, one or more components, motifs, sections, parts, domains, fragments, etc., of TR13 may be recombined with one or more components, motifs, sections, parts, domains, fragments, etc. of one or more heterologous molecules. In preferred embodiments, the heterologous molecules include, but are not limited to, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), TRAIL, AIM-II (International Publication No. WO 97/34911), APRIL (*J. Exp. Med.* 188(6):1185–1190), endokine-alpha (International Publication No. WO 98/07880), neutrokine alpha (International Publication No. WO98/18921), TWEAK, OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), RANK, TR9 (International Publication No. WO 98/56892), TR10 (International Publication No. WO 98/30694), 312C2 (International Publication No. WO 9854202), and TR12, and soluble forms CD154, CD70, and CD153. In further preferred embodiments, the heterologous molecules are any member of the TNF family.

The techniques of gene-shuffling, motif-shuffling, exon-shuffling, and/or codon-shuffling (collectively referred to as "DNA shuffling") may be employed to modulate the activities of TR14-thereby effectively generating agonists and antagonists of TR14. See generally, U.S. Pat. Nos. 5,605, 793, 5,811,238, 5,830,721, 5,834,252, and 5,837,458, and Patten et al., *Curr. Opinion Biotechnol.* 8:724–33 (1997); Harayama, *Trends Biotechnol.* 16(2):76–82 (1998); Hansson et al., *J. Mol. Biol.* 287:265–76 (1999); and Lorenzo and Blasco, *Biotechniques* 24(2):308–13 (1998) (each of these patents and publications are hereby incorporated by reference). In one embodiment, alteration of TR14 nucleic acids and corresponding polypeptides may be achieved by DNA shuffling. DNA shuffling involves the assembly of two or more DNA segments into a desired TR14 molecule by homologous, or site-specific, recombination. I n another embodiment, TR14 nucleic acids and corresponding polypeptides may be altered by being subjected to random mutagenesis by error-prone PCR, random nucleotide insertion or other methods prior to, or more preferably, during recombination. In another embodiment, one or more components, motifs, sections, parts, domains, fragments, etc., of TR14 may be recombined with one or more components, motifs, sections, parts, domains, fragments, etc. of one or more heterologous molecules. In preferred embodiments, the heterologous molecules are include, but are not limited to, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), TRAIL, AIM-II (International Publication No. WO 97/34911), APRIL (*J. Exp. Med.* 188(6):1185–1190), endokine-alpha (International Publication No. WO 98/07880), neutrokine alpha (International Publication No. WO98/18921), TWEAK, OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), RANK, TR9 (International Publication No. WO 98/56892), TR10 (International Publication No. WO 98/30694), 312C2 (International Publication No. WO 9854202), and TR12, and soluble forms CD154, CD70, and CD153. In further preferred embodiments, the heterologous molecules are any member of the TNF family.

In other embodiments, antagonists according to the present invention include soluble forms of TR13 (e.g., fragments of the TR13 shown in FIGS. 1A–D (SEQ ID NO:2) or FIGS. 7A–E (SEQ ID NO:39)) that include the ligand binding domain and/or any combination of one, two, three, four or more of the cysteine-rich domains from the extracellular region of the full-length receptor disclosed in the figures). Such soluble forms of the TR13, which may be naturally occurring or synthetic, antagonize TR13 mediated signaling by competing with the cell surface bound forms of the receptor for binding to TNF-family ligands. Antagonists of the present invention also include antibodies specific for TNF-family ligands, antibodies specific for TR13 polypeptides and TR13-Fc fusion proteins.

In other embodiments, antagonists according to the present invention include soluble forms of TR14 (e.g., fragments of the TR14 shown preferably in FIGS. 10A–H (SEQ ID NO:61) or, alternatively in FIGS. 4A–E (SEQ ID NO:5) that include the ligand binding domain, and/or the cysteine-rich domain from the extracellular region of the full-length receptor). Such soluble forms of the TR14, which may be naturally occurring or synthetic, antagonize TR14 mediated signaling by competing with the cell surface bound forms of the receptor for binding to TNF-family ligands. Antagonists of the present invention also include antibodies specific for TNF-family ligands, antibodies specific for TR14 polypeptides, and TR14-Fc fusion proteins.

By a "TNF-family ligand" is intended naturally occurring, recombinant, and synthetic ligands that are capable of binding to a member of the TNF receptor family and inducing and/or blocking the ligand/receptor signaling pathway. Members of the TNF ligand family include, but are not limited to, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), TRAIL, AIM-II (International Publication No. WO 97/34911), APRIL (*J. Exp. Med.* 188(6):1185–1190), endokine-alpha (International Publication No. WO 98/07880), Neutrokine-alpha (International Publications No. WO98/18921), TWEAK OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), RANK, TR9 (International Publication No. WO 98/56892), ), TR10 (International Publication No. WO 98/30694), 312C2 (International Publication No. WO 98/06842), and TR12, and soluble forms CD154, CD70, and CD153.

TNF-α has been shown to protect mice from infection with herpes simplex virus type 1 (HSV-1). Rossol-Voth et al., J Gen. Virol. 72:143–147 (1991). The mechanism of the protective effect of TNF-α is unknown but appears to involve neither interferons nor NK cell killing. One member of the family has been shown to mediate HSV-1 entry into cells. Montgomery et al., *Eur. Cytokine Newt.* 7:159 (1996). Further, antibodies specific for the extracellular domain of this block HSV-1 entry into cells. Thus, TR13 antagonists of the present invention include both TR13 amino acid sequences and antibodies capable of preventing mediated viral entry into cells. Such sequences and antibodies can function by either competing with cell surface localized for binding to virus or by directly blocking binding of virus to cell surface receptors.

Antibodies according to the present invention may be prepared by any of a variety of methods using TR13 immunogens and/or antigens of the present invention. As indicated, such TR13 immunogens and/or antigens include the full-length TR13 polypeptide and TR13 polypeptide fragments such as, the extracellular domain, any one of the four cysteine rich domains disclosed in FIGS. 1A–D and/or FIGS. 7A–E, the ligand binding domain, or any combination thereof.

Polyclonal and monoclonal antibody agonists or antagonists according to the present invention can be raised according to the methods disclosed herein and and/or known in the art, such as, for example, those methods described in Tartaglia and Goeddel, *J. Biol. Chem.* 267(7):4304–4307(1992); Tartaglia et al., *Cell* 73:213–216 (1993), and PCT Application WO 94/09137 (the contents of each of these three publications are herein incorporated by reference in their entireties), and are preferably specific to TR13 polypeptides of the invention having the amino acid sequence of SEQ ID NO:2 or SEQ ID NO:40.

TNF-α has been shown to protect mice from infection with herpes simplex virus type 1 (HSV-1). Rossol-Voth et al., J Gen. Virol. 72:143–147 (1991). The mechanism of the protective effect of TNF-α is unknown but appears to involve neither interferons nor NK cell killing. One member of the family has been shown to mediate HSV-1 entry into cells. Montgomery et al., *Eur. Cytokine Newt.* 7:159 (1996). Further, antibodies specific for the extracellular domain of this block HSV-1 entry into cells. Thus, TR14 antagonists of the present invention include both TR14 amino acid sequences and antibodies capable of preventing mediated viral entry into cells. Such sequences and antibodies can function by either competing with cell surface localized for binding to virus or by directly blocking binding of virus to cell surface receptors.

Antibodies according to the present invention may be prepared by any of a variety of methods using TR14 immunogens and/or antigens of the present invention. As indicated, such TR14 immunogens and/or antigens include the full-length TR14 polypeptide (which may or may not include the leader sequence) and TR14 polypeptide fragments such as the extracellular domain, the cysteine rich domain, the ligand binding domain, the transmembrane domain, and the intracellular domain, or any combination thereof Polyclonal and monoclonal antibody agonists or antagonists according to the present invention can be raised according to the methods disclosed herein and and/or known in the art, such as, for example, those methods described in Tartaglia and Goeddel, *J. Biol. Chem.* 267(7):4304–4307(1992); Tartaglia et al., *Cell* 73:213–216 (1993), and PCT Application WO 94/09137 (the contents of each of these three publications are herein incorporated by reference in their entireties), and are preferably specific to TR14 polypeptides of the invention having the amino acid sequence of SEQ ID NO:61 or SEQ ID NO:5.

Antagonists according to the present invention include soluble forms of TR13, i.e., TR13 fragments that include the ligand binding domain, and/or any combination of one, two, three, four or more of the cysteine-rich domains from the extracellular region of the TR13 polypeptide sequence shown in FIGS. 1A–D or FIGS. 7A–E. Such soluble forms of the receptor, which may be naturally occurring or synthetic, antagonize TR13 mediated signaling by competing with the cell surface TR13 for binding to TNF-family ligands (See, for example, Examples 34 and 35). Additionally, soluble TR13 may bind to apoptosis inducing TNF ligands such as TRAIL, FasL, or AIM-II and more effectively compete for TRAIL, FasL, AIM-II, binding, or other TNF family member, reducing the available TRAIL, FasL, AIM-II, or other TNF family member, for binding to receptors with functional death domains. Thus, soluble forms of the receptor that include the ligand binding domain and/or one or more cysteine rich domains of TR13 are novel cytokines capable of inhibiting apoptosis induced by TNF-family ligands (See, for example, Examples 34 and 35). These are preferably expressed as dimers or trimers, since these have been shown to be superior to monomeric forms of soluble receptor as antagonists, e.g., IgGFc-TNF receptor family fusions. Other such cytokines are known in the art and include Fas B (a soluble form of the mouse Fas receptor) that acts physiologically to limit apoptosis induced by Fas ligand (D. P. Hughes and I. N. Crispe, *J. Exp. Med.* 182:1395–1401 (1995)).

Antagonists according to the present invention include soluble forms of TR14, i.e., TR14 fragments that include the ligand binding domain and/or cysteine rich domain from the extracellular region of the full-length receptor. Such soluble forms of the receptor, which may be naturally occurring or synthetic, antagonize TR14 mediated signaling by competing with the cell surface TR14 for binding to TNF-family ligands. Additionally, soluble TR14 may bind to apoptosis inducing TNF ligands such as TRAIL, FasL, or AIM-II and more effectively compete for TRAIL, FasL, AIM-II binding, or other TNF family member, reducing the available TRAIL, FasL, AIM-II, or other TNF family member, for binding to receptors with functional death domains. Thus, soluble forms of the receptor that include the ligand binding domain and/or the cysteine rich domain of TR14 are novel cytokines capable of inhibiting apoptosis induced by TNF-family ligands. These are preferably expressed as dimers or trimers, since these have been shown to be superior to monomeric forms of soluble receptor as antagonists, e.g., IgGFc-TNF receptor family fusions. Other such cytokines are known in the art and include Fas B (a soluble form of the mouse Fas receptor) that acts physiologically to limit apoptosis induced by Fas ligand (D. P. Hughes and I. N. Crispe, *J. Exp. Med.* 182:1395–1401 (1995)).

Proteins and other compounds which bind the TR13 domains are also candidate agonists and antagonists according to the present invention. Such binding compounds can be "captured" using the yeast two-hybrid system (Fields and Song, *Nature* 340:245–246 (1989)). A modified version of the yeast two-hybrid system has been described by Roger Brent and his colleagues (J. Gyuris, *Cell* 75:791–803 (1993); A. S. Zervos et al., *Cell* 72:223–232 (1993)). Preferably, the yeast two-hybrid system is used according to the present invention to capture compounds which bind to either a TR13 ligand binding domain, one, two, three, or all four cystein-rich domains, or to the full-length, or partial-length, TR13 protein. Such compounds are good candidate agonists and antagonists of the present invention.

Proteins and other compounds which bind the TR14 domains are also candidate agonists and antagonists according to the present invention. Such binding compounds can be "captured" using the yeast two-hybrid system (Fields and Song, *Nature* 340:245–246 (1989)). A modified version of the yeast two-hybrid system has been described by Roger Brent and his colleagues (J. Gyuris, *Cell* 75:791–803 (1993); A. S. Zervos et al., *Cell* 72:223–232 (1993)). Preferably, the yeast two-hybrid system is used according to the present invention to capture compounds which bind to either the TR14 ligand binding domain, cysteine-rich domain, or to the TR14 intracellular domain. Such compounds are good candidate agonists and antagonists of the present invention.

Modes of Administration

TR13 nucleic acids, polypeptides, and/or agonist or antagonists of the invention can be administered in vitro, ex vivo, or in vivo to cells which express the receptor of the present invention. By administration of an "effective amount" of an TR13 nucleic acid, polypeptide, and/or agonist or antagonist is intended an amount of the compound that is sufficient to enhance or inhibit a cellular response to a TNF-family ligand. In particular, by administration of an "effective amount" of an TR13 nucleic acid, polypeptide, and/or agonist or antagonists is intended an amount effective to enhance or inhibit TR13 mediated signalling and/or TR13 mediated apoptosis. Of course, where it is desired for apoptosis to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or prodrug form. The agonist or antagonist may be administered in compositions in combination with one or more pharmaceutically acceptable excipients.

TR14 nucleic acids, polypeptides, and/or agonist or antagonists of the invention can be administered in vitro, ex vivo, or in vivo to cells which express the receptor of the present invention. By administration of an "effective amount" of an TR14 nucleic acid, polypeptide, and/or agonist or antagonist is intended an amount of the compound that is sufficient to enhance or inhibit a cellular response to a TNF-family ligand. In particular, by administration of an "effective amount" of an TR14 nucleic acids, polypeptide, and/or agonist or antagonists is intended an amount effective to enhance or inhibit TR14 mediated signalling and/or TR14 mediated apoptosis. Of course, where it is desired for apoptosis to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or prodrug form. The TR13 and/or TR14 nucleic acid, polypeptide, agonist or antagonist may be administered in compositions in combination with one or more pharmaceutically acceptable excipients.

It will be understood that, when administered to a human patient, the total daily usage of the compounds and compositions of the present invention will be decided by the attending physician within the scope of sound medical judgment. The specific therapeutically effective dose level for any particular patient will depend upon factors well known in the medical arts.

As a general proposition, the total pharmaceutically effective amount of TR13 polypeptide administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TR13 polypeptide is typically administered at a dose rate of about 1 ug/kg/hour to about 50 ug/kg/hour, either by 1–4 injections per day or by continuous subcutaneous infusions, for example, using a mini-pump. An intravenous bag solution may also be employed.

As a general proposition, the total pharmaceutically effective amount of TR14 polypeptide administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TR14 polypeptide is typically administered at a dose rate of about 1 ug/kg/hour to about 50 ug/kg/hour, either by 1–4 injections per day or by continuous subcutaneous infusions, for example, using a mini-pump. An intravenous bag solution may also be employed.

Dosaging may also be arranged in a patient specific manner to provide a predetermined concentration of an agonist or antagonist in the blood, as determined by the RIA technique. Thus patient dosaging may be adjusted to achieve regular on-going trough blood levels, as measured by RIA, on the order of from 50 to 1000 ng/ml, preferably 150 to 500 ng/ml.

Pharmaceutical compositions containing the TR13 polynucleotide, polypeptide, and/or agonist or antagonist, of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

Pharmaceutical compositions containing the TR14 polynucleotide, polypeptide, and/or agonist or antagonist of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use.

In addition to soluble TR13 polypeptides, TR13 polypeptides can also be used when appropriately solubilized by including detergents, such as CHAPS or NP-40, with buffer.

In addition to soluble TR14 polypeptides, TR14 polypeptides containing the transmembrane region can also be used when appropriately solubilized by including detergents, such as CHAPS or NP-40, with buffer.

TR13 compositions of the invention are also suitably administered by sustained-release systems. Suitable examples of sustained-release compositions include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

TR14 compositions of the invention are also suitably administered by sustained-release systems. Suitable examples of sustained-release compositions include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(−)-3-hydroxybutyric acid (EP 133,988).

Sustained-release compositions also include liposomally entrapped compositions of the invention (see generally, Langer, *Science* 249:1527–1533 (1990); Treat et al., in *Liposomes in the Therapy of Infectious Disease and Cancer*, Lopez-Berestein and Fidler (eds.), Liss, New York, pp. 317–327 and 353–365 (1989)). Liposomes containing TR13 polypeptide may be prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal TR13 polypeptide therapy.

Sustained-release compositions also include liposomally entrapped compositions of the invention (see generally, Langer, *Science* 249:1527–1533 (1990); Treat et al., in *Liposomes in the Therapy of Infectious Disease and Cancer*, Lopez-Berestein and Fidler (eds.), Liss, New York, pp. 317–327 and 353–365 (1989)). Liposomes containing TR14 polypeptide may be prepared by methods known per se: DE 3,218,121; Epstein et al., Proc. Natl. Acad. Sci. (USA) 82:3688–3692 (1985); Hwang et al., Proc. Nat. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal TR14 polypeptide therapy.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527–1533 (1990)).

The compositions of the invention (e.g., TR13 and/or TR14 nucleic acids, polypeptides, and/or agonists or antagonists) may be administered alone or in combination with other adjuvants. Adjuvants that may be administered with the compositions of the invention include, but are not limited to, alum, alum plus deoxycholate (ImmunoAg), MTP-PE (Biocine Corp.), QS21 (Genentech, Inc.), BCG, and MPL. In a specific embodiment, compositions of the invention are administered in combination with alum. In another specific embodiment, compositions of the invention are administered in combination with QS-21. Further adjuvants that may be administered with the compositions of the invention include, but are not limited to, Monophosphoryl lipid immunomodulator, AdjuVax 100a, QS-18, CRL1005, Aluminum salts, MF-59, and Virosomal adjuvant technology. Vaccines that may be administered with the compositions of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The compositions of the invention (e.g., TR 13 and/or TR14 nucleic acids, polypeptides, and/or agonists or antagonists) may be administered alone or in combination with other therapeutic agents. Therapeutic agents that may be administered in combination with the compositions of the invention, include but are not limited to, other members of the TNF family, chemotherapeutic agents, antibiotics, steroidal and non-steroidal anti-inflammatories, conventional immunotherapeutic agents, cytokines, chemokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), TRAIL, AIM-II (International Publication No. WO 97/34911), APRIL (*J. Exp. Med.* 188(6):1185–1190), endokine-alpha (International Publication No. WO 98/07880), Neutrokine-alpha (International Publication No. WO 9818921), OPG, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), RANK, TR9 (International Publication No. WO 98/56892), TR10 (International Publication No. WO9854202), 312C2 (International Publication No. WO 98/06842), and TR12, and soluble forms CD154, CD70, and CD153.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat AIDS and/or to prevent or treat HIV infection.

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDNE™, and/or ATOVAQUONE™ to prophylactically treat or prevent an opportunistic *Pneumocystis carinii* pneumonia infection. In another specific embodiment, compositions of the invention are used in any combination with ISONLAZID™, RIFAMPIN™, PYRAZINAMIDE™, and/or ETHAMBUTOL™ to prophylactically treat or prevent an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, compositions of the invention are used in any combination with GANCICLOVIR™, FOSCARNET™, and/or CIDOFOVIR™ to prophylactically treat or prevent an opportunistic cytomegalovirus infection. In another specific embodiment, compositions of the invention are used in any combination with FLUCONAZOLE™, ITRACONAZOLE™, and/or KETOCONAZOLE™ to prophylactically treat or prevent an opportunistic fungal infection. In another specific embodiment, compositions of the invention are used in any combination with ACYCLOVIR™ and/or FAMCICOLVIR™ to prophylactically treat or prevent an opportunistic herpes simplex virus type I and/or type II infection. In another specific embodiment, compositions of the invention are used in any combination with PYRIMETHAMINE™ and/or LEUCOVORIN™ to prophylactically treat or prevent an opportunistic *Toxoplasma gondii* infection. In another specific embodiment, compositions of the invention are used in any combination with LEUCOVORIN™ and/or NEUPOGEN™ to prophylactically treat or prevent an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

Additional immunosuppressants preparations that may be administered with the compositions of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGAM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, compositions of the invention are administered in combination with CHOP (cyclophosphamide, doxorubicin, vincristine, and prednisone) or any combination of the components of CHOP. In another embodiment, compositions of the invention are administered in combination with Rituximab. In a further embodiment, compositions of the invention are administered with Rituxmab and CHOP, or Rituxmab and any combination of the components of CHOP.

In an additional embodiment, the compositions of the invention are administered in combination with cytokines. Cytokines that may be administered with the compositions of the invention include, but are not limited to, GM-CSF, G-CSF, IL-1 alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, anti-CD40, CD40L, IFN-gamma and TNF-alpha. In one embodiment, the compositions of the invention are administered in combination with one or more chemokines. In specific embodiments, the compositions of the invention are administered in combination with an $\alpha(C \times C)$ chemokine selected from the group consisting of gamma-interferon inducible protein-10 ($\gamma$IP-10), interleukin-8 (IL-8), platelet factor-4 (PF4), neutrophil activating protein (NAP-2), GRO-$\alpha$, GRO-$\beta$, GRO-$\gamma$, neutrophil-activating peptide (ENA-78), granulocyte chemoattractant protein-2 (GCP-2), and stromal cell-derived factor-1 (SDF-1, or pre-B cell stimulatory factor (PBSF)); and/or a $\beta$(CC) selected from the group consisting of: RANTES (regulated on activation, normal T expressed and secreted), macrophage inflammatory protein-1 alpha (MIP-1$\alpha$), macrophage inflammatory protein-1 beta (MIP-1$\beta$), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 gamma (MIP-1$\gamma$), macrophage inflammatory protein-3 alpha (MIP-3$\alpha$), macrophage inflammatory protein-3 beta (MIP-3$\beta$), macrophage inflammatory protein-4 (MIP-4/DC-CK-1/PARC), eotaxin, Exodus, and I-309; and/or the $\gamma$(C) chemokine, lymphotactin.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In a preferred embodiment, the compositions of the invention are administered in combination with Stem Cell Factor or IL-3. In a most preferred embodiment the compositions of the invention are administered in combination with Stem Cell Factor and IL-3.

The invention also encompasses combining the polynucleotides and/or polypeptides of the invention (and/or agonists or antagonists thereof) with other proposed or conventional hematopoietic therapies. Thus, for example, the polynucleotides and/or polypeptides of the invention (and/or agonists or antagonists thereof) can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations of the compositions of the invention with compounds generally used to treat aplastic anemia, such as, for example, methenolene, stanozolol, and nandrolone; to treat iron-deficiency anemia, such as, for example, iron preparations; to treat malignant anemia, such as, for example, vitamin $B_{12}$ and/or folic acid; and to treat hemolytic anemia, such as, for example, adrenocortical steroids, e.g., corticoids. See e.g., Resegotti et al., *Panminerva Medica*, 23:243–248 (1981); Kurtz, *FEBS Letters*, 14a:105–108 (1982); McGonigle et al., *Kidney Int.*, 25:437–444 (1984); and Pavlovic-Kantera, *Expt. Hematol.*, 8(supp. 8) 283–291 (1980), the contents of each of which are hereby incorporated by reference in their entireties.

Compounds that enhance the effects of or synergize with erythropoietin are also useful as adjuvants herein, and include but are not limited to, adrenergic agonists, thyroid hormones, androgens, hepatic erythropoietic factors, erythrotropins, and erythrogenins, See for e.g., Dunn, "Current Concepts in Erythropoiesis", John Wiley and Sons (Chichester, England, 1983); Kalmani, *Kidney Int.*, 22:383–391 (1982); Shahidi, *New Eng. J. Med.*, 289:72–80 (1973); Urabe et al., *J. Exp. Med.*, 149:1314–1325 (1979); Billat et al., *Expt. Hematol.*, 10:133–140 (1982); Naughton et al., *Acta Haemat*, 69:171–179 (1983); Cognote et al. in abstract 364, *Proceedings 7th Intl. Cong. of Endocrinology* (Quebec City, Quebec, Jul. 1–7, 1984); and Rothman et al., 1982, *J. Surg. Oncol.*, 20:105–108 (1982). Methods for stimulating hematopoiesis comprise administering a hematopoietically effective amount (i.e., an amount which effects the formation of blood cells) of a pharmaceutical composition containing nucleic acids and/or poylpeptides of the invention (and/or agonists or antagonists thereof) to a patient. The nucleic acids and/or polypeptides of the invention and/or agonists or antagonists thereof is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin $B_{12}$, folic acid and/or adrenocortical steroids.

In additional prefered embodiments, the compositions of the invention are administered in combination with hematopoietic growth factors. Hematopoietic growth factors that may be administered with the compositions of the invention included, but are not limited to, LEUKINE™ (SARGRAMOSTIM™) and NEUPOGEN™ (FILGRASTIM™).

In additional embodiments, the compositions of the invention are administered in combination with other therapeutic or prophylactic regimens, such as, for example, radiation therapy.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a TR13 receptor gene. This can be accomplished using a variety of well known techniques and libraries, which generally are available commercially. The genomic DNA is then used for in situ chromosome mapping using well known techniques for this purpose.

In certain preferred embodiments in this regard, the cDNA herein disclosed is used to clone genomic DNA of a TR14 receptor gene. This can be accomplished using a variety of well known techniques and libraries, which generally are available commercially. The genomic DNA is then used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with cDNA as short as 50 or 60 bp. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man*, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Expression and Purification of the TR13, TR13-α, and/or TR14 Polypeptides in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6× His tag") covalently linked to the carboxyl terminus of that polypeptide. However, in this example, the polypeptide coding sequence is inserted such that translation of the six His codons is prevented and, therefore, the polypeptide is produced with no 6× His tag.

The DNA sequence encoding the desired portion of the TR13 and/or TR14 protein lacking the hydrophobic leader sequence is amplified from the deposited cDNA clone using PCR oligonucleotide primers which anneal to the amino terminal sequences of the desired portion of the TR13 and/or TR14 protein and to sequences in the deposited construct 3' to the cDNA coding sequence. Additional nucleotides containing restriction sites to facilitate cloning in the pQE60 vector are added to the 5' and 3' sequences, respectively.

For cloning a TR13 polypeptide, the 5' primer has the sequence:

5'-CGC<u>CCATGG</u>ATGGACCAAAGTACC-3' (SEQ ID NO: 23) containing the underlined NcoI restriction site followed by nucleotides complementary to the amino terminal coding sequence of the mature TR13 sequence in FIGS. 1A–D, respectively. One of ordinary skill in the art would appreciate, of course, that the point in the protein coding sequence where the 5' primer begins may be varied to amplify a desired portion of the complete protein shorter or longer than the described form.

For cloning a TR14 polypeptide, the 5' primer has the sequence:

5'-CGC<u>CCATGG</u>ATGAGTACTGGGACC-3' (SEQ ID NO: 24) containing the underlined NcoI restriction site followed by nucleotides complementary to the amino terminal coding sequence of the mature TR14 sequence in FIGS. 4A–E, respectively. One of ordinary skill in the art would appreciate, of course, that the point in the protein coding sequence where the 5' primer begins may be varied to amplify a desired portion of the complete protein shorter or longer than the described form.

For cloning a TR13 polypeptide, the 5' primer has the sequence:

5'-GCAGCA<u>CATATG</u>ATGGCTGAGCCTGGGCAC-3' (SEQ ID NO: 42) containing the underlined NdeII restriction site followed by nucleotides complementary to the amino terminal coding sequence of the mature TR13 sequence in FIGS. 7A–E, respectively. One of ordinary skill in the art would appreciate, of course, that the point in the protein coding sequence where the 5' primer begins may be varied to amplify a desired portion of the complete protein shorter or longer than the described form.

The 3' TR13 primer has the sequence:

5'-GCAGCA<u>TCTAGA</u>GCGGCACTGAGTCAAATCCATC-3' (SEQ ID NO:25) containing the underlined HindIII site followed by nucleotides complementary to the 3' end of the non-coding sequence in the TR13 sequence in FIGS. 1A–D.

The 3' TR14 primer has the sequence:
5'-CGC<u>AAGCTT</u>CATTCAGGCCCCTGCTG-3' (SEQ ID NO:26) containing the underlined HindIII site followed by nucleotides complementary to the 3' end of the non-coding sequence in the TR14 DNA sequence in FIGS. 4A–E.

The 3' TR13 primer has the sequence:
5'-GCAGCA<u>TCTAGA</u>GCGGCAGTGAGTCAAATCCATC-3' (SEQ ID NO:43) containing the underlined HindIII site followed by nucleotides complementary to the 3' end of the non-coding sequence in the TR13 DNA sequence in FIGS. 7A–E.

The amplified TR13 and/or TR14 DNA fragments and the vector pQE60 are digested with Nco I and HindIII and the digested DNAs then ligated together. Insertion of the TR13 and/or TR14 protein DNA into the restricted pQE60 vector places the TR13 and/or TR14 protein coding region (including its associated stop codon) downstream from the IPTG-inducible promoter and in-frame with an initiating AUG. The associated stop codon prevents translation of the six histidine codons downstream of the insertion point.

The ligation mixture is transformed into competent E. coli cells using standard procedures. Such procedures are described in Sambrook et al., *Molecular Cloning: a Laboratory Manual*, 2nd Ed.; Cold Spring Harbor Laboratory Press, Cold Spring Harbor, N.Y. (1989). E. coli strain M15/rep4, containing multiple copies of the clone pREP4, which expresses lac repressor and confers kanamycin resistance ("Kan'"), is used in carrying out the illustrative example described herein. This strain, which is only one of many that are suitable for expressing TR13 and/or TR14 protein, is available commercially from Qiagen, Inc., supra.

Transformants are identified by their ability to grow on LB plates in the presence of ampicillin and kanamycin. Clone DNA is isolated from resistant colonies and the identity of the cloned DNA confirmed by restriction analysis, PCR, and DNA sequencing.

Clones containing the desired constructs are grown overnight ("O/N") in liquid culture in LB media supplemented with both ampicillin (100 ug/ml) and kanamycin (25 ug/ml). The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from the lac repressor sensitive promoter, by inactivating the laci repressor. Cells subsequently are incubated further for 3 to 4 hours. Cells then are harvested by centrifugation.

The cells are then stirred for 3–4 hours at 4° C. in 6M guanidine-HCl, pH8. The cell debris is removed by centrifugation, and the supernatant containing the TR13 and/or TR14 is loaded onto a nickel-nitrilo-tri-acetic acid ("NiNTA") affinity resin column (available from QIAGEN, Inc., supra). Proteins with a 6× His tag bind to the NI-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH8, the column is first washed with 10 volumes of 6 M guanidine-HCl, pH8, then washed with 10 volumes of 6 M guanidine-HCl pH6, and finally the TR13 and/or TR14 is eluted with 6 M guanidine-HCl, pH5.

The purified protein is then renatured by dialyzing it against phosphatebuffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M–1M urea gradient in 500 mM NaCl, 20% glycerol, 20 mM Tris/HCl pH7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH6 buffer plus 200 mM NaCl. The purified protein is stored at 4° C. or frozen at −80° C.

Example 2
Cloning and Expression of TR13 and/or TR14 Polypeptides in a Baculovirus Expression System In this illustrative example, the clone shuttle vector pA2 is used to insert the cloned DNA encoding the complete protein, including its naturally associated secretary signal (leader) sequence, into a baculovirus to express the mature TR13 and/or TR14 protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI and Asp718. The polyadenylation site of the simian virus 40 ("SV40") is used for efficient polyadenylation. For easy selection of recombinant virus, the clone contains the beta-galactosidase gene from E. coli under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al, *Virology* 170:31–39 (1989).

The cDNA sequence encoding the TR13 and/or TR14 receptor protein in the deposited clone (s), lacking the AUG initiation codon and the naturally associated leader sequence shown in FIGS. 1A–D (SEQ ID NO:2), FIGS. 7A–E (SEQ ID NO:40), and FIGS. 4A–E (SEQ ID NO:5), and respectively, is amplified using PCR oligonucleotide primers corresponding to the 5' and 3' sequences of the gene.

The 5' TR13 primer has the sequence 5'CGC <u>GGATCC</u>ATGGATGGACCAA AGTACC 3' (SEQ ID NO:27) containing the underlined BamHI restriction enzyme site, an efficient signal for initiation of translation in eukaryotic cells, as described by M. Kozak, *J. Mol. Biol.* 196:947–950 (1987), followed by bases of the sequence of the mature TR13 protein shown in FIGS. 1A–D, beginning with the indicated N-terminus of the mature protein.

The 5' TR14 primer has the sequence 5'CGC <u>GGATCC</u>ATGGATGAGTACTG GGACC 3' (SEQ ID NO:28) containing the underlined BamHI restriction enzyme site, an efficient signal for initiation of translation in eukaryotic cells, as described by M. Kozak, *J. Mol. Biol.* 196:947–950 (1987), followed by bases of the sequence of the TR14 polypeptide shown in FIGS. 4A–E, respectively, beginning with the indicated N-terminus of the mature protein.

The 5' TR13 primer has the sequence 5'GCAGCA TCTAGACCGCCATC ATGGCTGAGCCTGGGCA-CAGCCACCATC 3' (SEQ ID NO:44) containing the underlined XbaI restriction enzyme site, an efficient signal for initiation of translation in eukaryotic cells, as described by M. Kozak, *J. Mol. Biol.* 196:947–950 (1987), followed by bases of the sequence of the TR13 polypeptide shown in FIGS. 7A–E, respectively, beginning with the indicated N-terminus of the mature protein.

The 3' primer for TR13 has the sequence 5'CGC GGTACCGCGGCACTGAG TCAAATC 3' (SEQ ID NO:29) containing the underlined Asp718 restriction site, followed by nucleotides complementary to the 3' noncoding sequence in FIGS 1A–D.

The 3' primer for TR14 has the sequence 5'CGC GGTACCCATTCAGGCCCC TGCTG 3' (SEQ ID NO:30) containing the underlined Asp718 restriction site followed by nucleotides complementary to the 3' noncoding sequence in FIGS. 4A–E, respectively.

The 3' primer for TR13 has the sequence 5'GCAGCA TCTAGAGGCGGCACT GAGTCAAATC 3' (SEQ ID NO:45) containing the underlined XbaI restriction site, followed by nucleotides complementary to the 3' noncoding sequence in FIGS 7A–E, respectively.

The amplified fragment is isolated from a 1% agarose gel using a commercially available kit ("Geneclean," BIO 101 Inc., La Jolla, Calif.) The fragment then is digested with Ba mnHI or Xba I and Asp718 or XbaI and again is purified on a 1% agarose gel. This fragment is designated "F1."

The clone is digested with the restriction enzyme Bam HI or XbaI and optionally can be dephosphorylated using calf intestinal phosphatase, using routine procedures known in the art. The DNA is then isolated from a 1% agarose gel using a commercially available kit ("Geneclean" BIO 101 Inc., La Jolla, Calif.). The vector DNA is designated herein "V1."

Fragment F1 and the dephosphorylated clone V1 are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria are identified that contain the clone with the human TR13 and/or TR14 nucleic acids using the PCR method, in which one of the primers that is used to amplify the nucleic acids and the second primer is from well within the vector so that only those bacterial colonies containing the TR13 and/or TR14 nucleic acid fragment will show amplification of the DNA. The sequence of the cloned fragment is confirmed by DNA sequencing. This clone is designated herein pBacTR13 and/or pBacTR14.

Five ug of the clone pBacTR13 and/or pBacTR14 is co-transfected with 1.0 ug of a commercially available linearized baculovirus DNA ("BaculoGold™ baculovirus DNA", Pharmingen, San Diego, Calif.), using the lipofectin method described by Felgner et al., *Proc. Natl. Acad. Sci. USA* 84:7413–7417 (1987). 1 ug of BaculoGold™ virus DNA and 5 ug of the clone pBacTR13 and/or TR14 are mixed in a sterile well of a microliter plate containing 50 ul of serum free Grace's medium (Life Technologies, Inc., Rockville, Md.). Afterwards, 10 ul Lipofectin plus 90 1 Grace's medium are added, mixed, and incubated for 15 minutes at room temperature. Then, the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours, the transfection solution is removed from the plate and 1 ml of Grace's insect medium supplemented with 10% fetal calf serum is added. The plate is put back into an incubator and cultivation is continued at 27° C. for four days.

After four days, the supernatant is collected and a plaque assay is performed, as described by Summers and Smith, cited above. An agarose gel with "Blue Gal" (Life Technologies, Inc., Rockville, Md.) is used to allow easy identification and isolation of gal-expressing clones, which produce blue-stained plaques. (A detailed description of a "plaque assay" of this type can also be found in the user's guide for insect cell culture and baculovirology distributed by Life Technologies, Inc., Rockville, Md., pages 9–10). After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-TR13 and/or V-TR14.

To verify the expression of the TR13 and/or TR14 nucleic acid, Sf9 cells are grown in Grace's medium supplemented with 10% heat inactivated FBS. The cells are infected with the recombinant baculovirus V-TR13 and/or TR14 at a multiplicity of infection ("MOI") of about 2. Six hours later the medium is removed and is replaced with SF900 II medium minus methionine and cysteine (available from Life Technologies, Inc., Rockville, Md.). If radiolabeled proteins are desired, 42 hours later, 5 uCi of $^{35}$S-methionine and 5 uCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 3

Cloning and Expression of the TR13 and/or TR14 Polypeptides in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g. RSV, HTLVI, HIVI and the early promoter of the cytomegalovirus (CMV). However, cellular signals can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela 293, H9 and Jurkat cells, mouse NIH3T3 and C127 cells, Cos 1, Cos 7 and CV1, quail QC1–3 cells, mouse L cells, and Chinese hamster ovary (CHO) cells.

Alternatively, the gene can be expressed in stable cell lines that contain the gene integrated into a chromosome. Co-transfection with a selectable marker such as dhfr, gpt, neomycin, or hygromycin allows the identification and isolation of the transfected cells.

The transfected gene can also be amplified to express large amounts of the encoded protein. The dihydrofolate reductase (DHFR) marker is useful to develop cell lines that carry several hundred or even several thousand copies of the gene of interest. Another useful selection marker is the enzyme glutamine synthase (GS) (Murphy et al., *Biochem. J.* 227:277–279 (1991); Bebbington et al., *Bio/Technology* 10:169–175 (1992)). Using these markers, the mammalian cells are grown in selective medium and the cells with the highest resistance selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology* 5:438–447 (March 1985)), plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3A

Cloning and Expression of the Extracellular Soluble Domain of TR13, and/or TR14 Polypeptides in COS Cells The expression clone, pTR13-HA and/or TR14-HA, is made by cloning a cDNA encoding TR13 and/or TR14 polypeptides into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cell; (2) an ampicillin resistance gene for selection of clone-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire TR13 and/or TR14 precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37:767 (1984). The fusion of the HA tag to the target protein allows easy detection of the recombinant protein with an antibody that recognizes the HA epitope.

The clone construction strategy is as follows:

The TR13 and/or TR14 cDNA of the deposited clone(s) is amplified using primers that contain convenient restriction sites, much as described above regarding the construction of expression vectors for expression of TR13 and/or TR14 polypeptides in *E. coli*.

To facilitate detection, purification and characterization of the expressed TR13 and/or TR14 polypeptides, one of the primers contains a hemagglutinin tag ("HA tag") as described above.

Suitable primers for TR13 and/or TR14 include the following, which are used in this example:

The 5' TR13 primer, 5'CGC GGATCCATGGACCAAAGTACCCAA 3' (SEQ ID NO:31) contains the underlined BamHI site, an ATG start codon and 5 codons thereafter. The 3' primer for TR13, which contains the underlined XbaI site, stop codon, hemagglutinin tag, and the last 18 nucleotides of the 3'coding sequence (at the 3' end), has the following sequence: 5' CGC TCTAGATCAAGCGTAGTCTGGGACGTCGTATG GGTAGCGGCACTGAGTCAAATC 3' (SEQ ID NO:32).

The 5' TR14 primer, 5'CGC GGATCCATGAGTACTGGGACCAAT 3' (SEQ ID NO:34) contains the underlined BamHI site, an ATG start codon and 5 codons thereafter. The 3' primer for TR14, which contains the underlined XbaI site, stop codon, hemagglutinin tag, and the last 18 nucleotides of the 3'coding sequence (at the 3' end), has the following sequence: 5' CGC TCTAGATCAAGCGTAGTCTGGGACGTCGTATGG GTACATTCAGGCCCCTGCTG 3' (SEQ ID NO:33).

The 5' TR13 primer of the sequence described in FIGS. 7A–E (SEQ ID NO:39), 5'CGC GGATCCATGGCTGAGCCTGGGCAC 3' (SEQ ID NO:46) contains the underlined BamHI site, an ATG start codon and 5 codons thereafter. The 3' primer for TR, which contains the underlined XbaI site, stop codon, hemagglutinin tag, and the last 18 nucleotides of the 3' coding sequence (at the 3' end), has the following sequence: 5'CGC TCTAGATCAAGCGTAGTCTGGGACGTCGTAT GGG-TAGCGGCACTGAGTCA AATC 3' (SEQ ID NO:47).

The PCR amplified DNA fragment and the vector, pcDNAI/Amp, are digested with BamHI and XbaI and then ligated. The ligation mixture is transformed into *E. coli* strain SLRE (available from Stratagene Cloning Systems, 11099 North Torrey Pines Road, La Jolla, Calif. 92037) the transformed culture is plated on ampicillin media plates which then are incubated to allow growth of ampicillin resistant colonies. Clone DNA is isolated from resistant colonies and examined by restriction analysis and gel sizing for the presence of the TR13, and/or TR14-encoding fragment.

For expression of recombinant TR13 and/or TR14 polypeptides, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of TR13 and/or TR14 polypeptides by the vector.

Expression of the TR13-HA, and/or TR14-HA fusion protein is detected by radiolabelling and immunoprecipitation, using methods described in, for example Harlow et al., *Antibodies: a Laboratory Manual*, 2nd Ed., Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and then lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 3B

Cloning and Expression of TR13 and/or TR14 Polypeptides Using the CHO Expression System The vector pC4 is used for the expression of the TR13 and/or TR14 polypeptide. Clone pC4 is a derivative of the clone pSV2-dhfr (ATCC Accession No. 37146). The clone contains the mouse DHFR gene under control of the SV40 early promoter. Chinese hamster ovary- or other cells lacking dihydrofolate activity that are transfected with these clones can be selected by growing the cells in a selective medium (alpha minus MEM, Life Technologies, Rockville, Md.) supplemented with the chemotherapeutic agent methotrexate (MTX). The amplification of the DHFR genes in cells resistant to MTX has been well documented (see, e.g., F. W. Alt et al., *J. Biol. Chem.* 253:1357–1370 (1978); J. L. Hamlin and C. Ma, *Biochem. et Biophys. Acta* 1097:107–143 (1990); M. J. Page M. A. Sydenham, *Biotechnology* 9:64–68(1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and overexpressed. It is known in the art that this approach may be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Clone pC4 contains, for expressing the gene of interest, the strong promoter of the long terminal repeat (LTR) of the Rous Sarcoma Virus (Cullen et al., *Molecular and Cellular Biology* 5:438–447 (March 1985)), plus a fragment isolated from the enhancer of the immediate early gene of human cytomegalovirus (CMV) (Boshart et al, *Cell* 41:521–530 (1985)). Downstream of the promoter are the following single restriction enzyme cleavage sites that allow the integration of the genes: Bam-HI, XbaI, and Asp718. Behind these cloning sites, the clone contains the 3'intron and the polyadenylation site of the rat preproinsulin gene. Other high efficiency promoters can also be used for the expression, e.g., the human B-actin promoter, the SV40 early or late promoters or the long terminal repeats from other retroviruses, e.g., HIV and HTLVI. Clontech's Tet-Off and Tet-On gene expression systems and similar systems can be used to express the TR13 and/or TR14 polypeptide in a regulated way in mammalian cells. For the polyadenylation of the mRNA, other signals, e.g., from the human growth hormone or globin genes, can be used as well.

Stable cell lines carrying a gene of interest integrated into the chromosomes can also be selected upon co-transfection with a selectable marker such as gpt, G418, or hygromycin. It is advantageous to use more than one selectable marker in the beginning, e.g., G418 plus methotrexate.

The clone pC4 is digested with the restriction enzyme BamHI and then dephosphorylated using calf intestinal phosphates, by procedures known in the art. The vector is then isolated from a 1% agarose gel.

The DNA sequence encoding the complete TR13 and/or TR14 polypeptide is amplified using PCR oligonucleotide primers corresponding to the 5' and 3' sequences of the desired portion of the gene.

The 5' oligonucleotide primer for TR13, containing the underlined BamHI restriction site, a Kozak sequence, and an AUG start codon, has the sequence: 5'CGC GGATCCGCCATCATGGACCAAAGTACC 3' (SEQ ID NO:34). The 3' primer for TR13, containing the underlined Asp718 restriction site, has the sequence: 5' CGC GGTACCGCGGCACTGAGTCAAATC 3' (SEQ ID NO:35).

The 5' oligonucleotide primer for TR14, containing the underlined BamHI restriction site, a Kozak sequence, and an AUG start codon, has the sequence: 5' CGC GGATCCATGAGTACTGGGACC 3' (SEQ ID NO:36). The 3' primer for TR14, containing the underlined Asp718 restriction site, has the sequence: 5' CGC GGTACCTTCATTCAGGCCCCTGCTG 3' (SEQ ID NO:37).

The amplified fragment is digested with BamHI and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into clone pC4 using, for instance, restriction enzyme analysis.

Chinese hamster ovary cells lacking an active DHFR enzyme are used for transfection. Five ug of the expression clone pC4 are cotransfected with 0.5 ug of the clone pSVneo using the lipofectin method (Felgner et al., supra). The clone pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of MTX plus 1 mg/ml G418. After about 10–14 days, single clones are trypsinized and then seeded in 6-well petri dishes or 10 ml flasks using different concentrations of methotrexate (50 nM, 100 nM, 200 nM, 400 nM, 800nM). Clones growing at the highest concentrations of methotrexate are then transferred to new 6-well plates containing even higher concentrations of methotrexate (1 uM, 2 uM, 5 uM, 10 uM, 20 uM). The same procedure is repeated until clones are obtained which grow at a concentration of 100–200 uM. Expression of the desired gene product is analyzed, for instance, by Western blot analysis and SDS-PAGE, or by reversed phase HPLC analysis.

Example 4
Protein Fusions of TR13 and/or TR14

TR13 and/or TR14 polypeptides of the invention are optionally fused to other proteins. These fusion proteins can be used for a variety of applications. For example, fusion of TR13 and/or TR14 polypeptides to His-tag, HA-tag, protein A, IgG domains, and maltose binding protein facilitates purification. (See EP A 394,827; Traunecker, et al., *Nature* 331:84–86 (1988)). Similarly, fusion to IgG-1, IgG-3, and albumin increases the halflife time in vivo. Nuclear localization signals fused to TR13 and/or TR14 polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made using techniques known in the art or by using or routinely modifying the following protocol, which outlines the fusion of a polypeptide to an IgG molecule.

Briefly, the human Fc portion of the IgG molecule can be PCR amplified, using primers that span the 5' and 3' ends of the sequence described below (SEQ ID NO:38). These primers also preferably contain convenient restriction enzyme sites that will facilitate cloning into an expression vector, preferably a mammalian expression vector.

For example, if the pC4 (Accession No. 209646) expression vector is used, the human Fc portion can be ligated into the BamHI cloning site. Note that the 3'BamHI site should be destroyed. Next, the vector containing the human Fc portion is re-restricted with BanHI, linearizing the vector, and TR13 and/or TR14 polynucleotide, isolated by the PCR protocol described in Example 1, is ligated into this BaniHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

line (SP2O), available from the ATCC. After fusion, the resulting hybridoma cells are selectively maintained in HAT medium, and then cloned by limiting dilution as described by Wands et al. (Gastroenterology 80:225–232 (1981). The hybridoma cells obtained through such a selection are then assayed to identify clones which secrete antibodies capable of binding the TR13 or TR14 polypeptide.

```
Human IgG Fc region:
GGGATCCGGAGCCCAAATCTTCTGACAAAACTCACACATGCCCACCGTGC  (SEQ ID NO:38)

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCAGACGGCCGCGACTCTAGAGGAT
```

Example 5
Production of an Antibody against TR13 or TR14
Hybridoma Technology

The antibodies of the present invention can be prepared by a variety of methods. (See, Current Protocols, Chapter 2.) As one example of such methods, cells expressing TR13 or TR14 are administered to an animal to induce the production of sera containing polyclonal antibodies. In a preferred method, a preparation of TR13 or TR14 protein is prepared and purified to render it substantially free of natural contaminants. Such a preparation is then introduced into an animal in order to produce polyclonal antisera of greater specific activity.

Monoclonal antibodies specific for protein TR13 or TR14 are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with TR13 or TR14 polypeptide or, more preferably, with a secreted TR13 or TR14 polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell Alternatively, additional antibodies capable of binding to TR13 or TR14 polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the TR13 or TR14protein-specific antibody can be blocked by TR13 or TR14. Such antibodies comprise anti-idiotypic antibodies to the TR13 or TR14 protein-specific antibody and are used to immunize an animal to induce formation of further TR13 or TR14 protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed infra. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Isolation of Antibody Fragments Directed Against TR13 or TR14 from a Library of scFvs Naturally occurring V-genes isolated from human PBLs are constructed into a library of antibody fragments which contain reactivities against TR13 or TR14 to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 E. coli harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 μg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing.

Example 6
Tissue Distribution of TR13 and TR14 mRNA Expression

Northern blot analysis was carried out to examine TR13 and/or TR14 gene expression in human tissues, using methods described by, among others, Sambrook et al., cited above. A cDNA probe containing the entire nucleotide sequence of TR13 (SEQ ID NO:1) and/or TR14 (HMSHK47) was labeled with $^{32}P$ using the rediprime™ DNA labeling system (Amersham Life Science), according to manufacturer's instructions. After labeling, the probe was purified using a CHROMA SPIN-100 column (Clontech Laboratories, Inc.), according to manufacturer's protocol number PT1200-1. The purified labeled TR13 and TR14 probes were then separately used to examine various human tissues for TR13 and TR14 mRNA, respectively.

Multiple Tissue Northern (MTN) blots containing various human tissues (H) or human immune system tissues (IM) were obtained from Clontech and were examined with labeled probe using ExpressHyb™ hybridization solution (Clontech) according to manufacturer's protocol number PT1190–1. Following hybridization and washing, the blots were mounted and exposed to film at −70° C. overnight, and films developed according to standard procedures.

Expression of TR13 was detected in pancreas tumor, endometrial tumor, adult small intestine, colon cancer, breast cancer cell line, resting T-cell, amygdala, rectum, T-cell helper, pineal gland, apoptotic T-cell, epididymus, greater omentum, prostate BPH, osteoclastoma, endometrial stromal cells, stromal cell, substantia nigra, activated T-cell, tonsil, and testes tissue.

Expression of TR14 was detected in activated T-cell, endometrial tumor, thymus, and 12 week early stage human tissue.

Northern Blot Analysis of TR13 and/or TR14 in Various Cell Lines Cells

Unless stated otherwise, cell lines are obtained from the American Type Culture Collection (Rockville, Md.). The myeloid (Koeffler et al. (1980); Koeffler (1983); Harris and Ralph (1985); and Tucker et al. (1987) and B-cell lines (Jonak et al. (1922)) studied represent cell types at different stages of the differentiation pathway. KG1a and PLB 985 cells (Tucker et al. (1987)) are obtained from H. P. Koeffler (UCLA School of Medicine). BJA-B is from Z. Jonak (SmithKline Beecham). TF274, a stromal cell line exhibiting osteoblastic features, is generated from the bone marrow of a healthy male donor (Z. Jonak and K. B. Tan, unpublished). Primary carotid artery endothelial cells are purchased from Clonetics Corp. (San Diego, Calif.) and monocytes are prepared by differential centrifugation of peripheral blood mononuclear cells and adhesion to tissue culture dish. CD19+, CD4+ and CD8+ cells (>90% pure) are isolated with cell type specific immunomagnetic beads (Drynal, Lake Success, N.Y.).

RNA Analysis

Total RNA of adult tissues are purchased from Clontech (Palo Alto, Calif.). Total RNA is extracted from cell lines (in exponential growth phase) and primary cells with TriReagent (Molecular Research Center, Inc., Cincinnati, Ohio). 5 to 7.5 ug of total RNA is fractionated in a 1% agarose gel containing formaldehyde cast in a Wide Mini-Sub Cell gel tray (Bio-Rad, Hercules, Calif.) as described (Sambrook, et al.) with slight modifications. The formaldehyde concentration is reduced to 0.5M and the RNA is stained prior to electrophoresis with 100 g/ml of ethidium bromide that is added to the loading buffer. After electrophoresis with continuous buffer recirculation (60 volts/90 min), the gel is photographed and the RNA is transferred quantitatively to Zeta-probe nylon membrane (Biorad, Hercules, Calif.) by vacuum-blotting with 25 mM NaOH for 90 min. After neutralization for 5–10 min, with 1M Tris-HCl, pH 7.5 containing 3M NaCl, the blots are prehybridized with 50% formamide, 8% dextran sulfate, 6×SSPE, 0.1% SDS and 100 ug/ml of sheared and denatured salmon sperm DNA for at least 30 min at 42° C. cDNA inserts labeled with $^{32}$P-dCTP by random priming (Stratagene, La Jolla, Calif.), are denatured with 0.25M NaOH (10 min at 37° C.) and added to the prehybridization solution. After 24–65 hr at 42° C., the blots are wasted under high stringency conditions (Sambrook, et al.) and exposed to X-ray films.

Example 7
Method of Determining Alterations in the TR13 and/or TR14 Gene

RNA is isolated from entire families or individual patients presenting with a phenotype of interest (such as a disease). cDNA is then generated from these RNA samples using protocols known in the art. (See, Sambrook.) The cDNA is then used as a template for PCR, employing primers surrounding regions of interest in SEQ ID NO:1 SEQ ID NO:60, and/or SEQ ID NO:4. Suggested PCR conditions consist of 35 cycles at 95° C. for 30 seconds; 60–120 seconds at 52–58° C.; and 60–120 seconds at 70° C., using buffer solutions described in Sidransky, D., et al., *Science* 252:706 (1991).

PCR products are then sequenced using primers labeled at their 5' end with T4 polynucleotide kinase, employing SequiTherm Polymerase. (Epicentre Technologies). The intron-exon borders of selected exons of TR13 and/or TR14 are also determined and genomic PCR products analyzed to confirm the results. PCR products harboring suspected mutations in TR13 and/or TR14 is then cloned and sequenced to validate the results of the direct sequencing.

PCR products of TR13 and/or TR14 are cloned into T-tailed vectors as described in Holton, T. A. and Graham, M. W., *Nucleic Acids Research,* 19:1156 (1991) and sequenced with T7 polymerase (United States Biochemical). Affected individuals are identified by mutations in TR13 and/or TR14 not present in unaffected individuals.

Genomic rearrangements are also observed as a method of determining alterations in the TR13 and/or TR14 gene. Genomic clones isolated using techniques known in the art are nick-translated with digoxigenindeoxy-uridine 5'-triphosphate (Boehringer Manheim), and FISH performed as described in Johnson, Cg. et al., *Methods Cell Biol.* 35:73–99 (1991). Hybridization with the labeled probe is carried out using a vast excess of human cot-1 DNA for specific hybridization to the TR13 and/or TR14 genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., *Genet. Anal. Tech. Appl.,* 8:75 (1991).) Image collection, analysis and chromosomal fractional length measurements are performed using the ISee Graphical Program System. (Inovision Corporation, Durham, N.C.) Chromosome alterations of the genomic region of TR13 and/or TR14 (hybridized by the probe) are identified as insertions, deletions, and translocations. These TR13 and/or TR14 alterations are used as a diagnostic marker for an associated disease.

Example 8
Method of Detecting Abnormal Levels of TR13 and/or TR14 Nucleic Acids in a Biological Sample TR13 and/or TR14 polypeptides can be detected in a biological sample, and if an increased or decreased level of TR13 and/or TR14 is detected, this polypeptide is a marker for a particular phenotype. Methods of detection are numerous, and thus, it is understood that one skilled in the art can modify the following assay to fit their particular needs.

For example, antibody-sandwich ELISAs are used to detect TR13 and/or TR14 in a sample, preferably a biological sample. Wells of a microtiter plate are coated with specific antibodies to TR13 and/or TR14, at a final concentration of 0.2 to 10 ug/ml. The antibodies are either monoclonal or polyclonal and are produced using technique known in the art. The wells are blocked so that non-specific binding of TR13 and/or TR14 to the well is reduced.

The coated wells are then incubated for >2 hours at RT with a sample containing TR13 and/or TR14. Preferably, serial dilutions of the sample should be used to validate results. The plates are then washed three times with deionized or distilled water to remove unbounded TR13 and/or TR14.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

75 ul of 4-methylumbelliferyl phosphate (MUP) or p-nitrophenyl phosphate (NPP) substrate solution is then added to each well and incubated 1 hour at room temperature to allow cleavage of the substrate and flourescence. The flourescence is measured by a microtiter plate reader. A standard curve is preparded using the experimental results from serial dilutions of a control sample with the sample concentration plotted on the X-axis (log scale) and fluorescence or absorbance on the Y-axis (linear scale). The TR13 and/or TR14 polypeptide concentration in a sample is then interpolated using the standard curve based on the measured flourescence of that sample.

Example 9
Method of Decreasing Levels of TR13 and/or TR14

The present invention relates to a method for treating an individual in need of a decreased level of TR13 and/or TR14 biological activity in the body comprising, administering to such an individual a composition comprising a therapeutically effective amount of TR13 and/or TR14 antagonist. Preferred antagonists for use in the present invention are TR13 and/or TR14-specific antibodies.

Antisense technology is used to inhibit production of TR13 and/or TR14. This technology is one example of a method of decreasing levels of TR13 and/or TR14 polypeptide, preferably a soluble and/or secreted form, due to a variety of etiologies, such as cancer.

For example, a patient with decreased levels of TR13 and/or TR14 polypeptide receives a daily dose 0.1–100 ug/kg of the polypeptide for six consecutive days. Preferably, the polypeptide is in a soluble and/or secreted form.

Example 10
Method of Treating Increased Levels of TR13 and/or TR14

The present invention also relates to a method for treating an individual in need of an increased level of TR13 and/or TR14 biological activity in the body comprising administering to such an individual a composition comprising a therapeutically effective amount of TR13 and/or TR14 or an agonist thereof.

Moreover, it will be appreciated that conditions caused by a decrease in the standard or normal expression level of TR13 and/or TR14 in an individual can be treated by administering TR13 and/or TR14, preferably in a soluble and/or secreted form. Thus, the invention also provides a method of treatment of an individual in need of an increased level of TR13 and/or TR14 polypeptide comprising administering to such an individual a pharmaceutical composition comprising an amount of TR13 and/or TR14 to increase the biological activity level of TR13 and/or TR14 in such an individual.

For example, a patient diagnosed with abnormally increased levels of TR13 and/or TR14 is administered intravenously antisense polynucleotides at 0.5, 1.0, 1.5, 2.0 and 3.0 mg/kg day for 21 days. This treatment is repeated after a 7-day rest period if the is determined to be well tolerated.

Example 11
Method of Treatment Using Gene Therapy—Ex Vivo

One method of gene therapy transplants fibroblasts, which are capable of expressing soluble and/or mature TR13 and/or TR14 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 C for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., *DNA*, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding TR13 and/or TR14 can be amplified using PCR primers which correspond to the 5' and 3' end encoding sequences respectively. Preferably, the 5'primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform *E. coli* HB101, which are then plated onto agar containing kanamycin for the purpose of confirming that the vector contains properly inserted TR13 and/or TR14.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the TR13 and/or TR14 gene is then added to the media and the packaging cells transduced with the vector. The packaging cells now produce infectious viral particles containing the TR13 and/or TR14 nucleic acid (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether TR13 and/or TR14 protein is produced.

The engineered fibroblasts are then transplanted onto the host, either alone or after having been grown to confluence on cytodex 3 microcarrier beads.

Example 12
Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) TR13 and/or TR14 sequences into an animal to increase or decrease the expression of the TR13 and/or TR14 polypeptide. The TR13 and/or TR14 polynucleotide may be operatively linked to a promoter or any other genetic elements necessary for the expression of the TR13 and/or TR14 polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al., *Cardiovasc. Res.* 35:470–479 (1997); Chao J. et al., *Pharmacol. Res.* 35:517–522 (1997); Wolff J. A. *Neuromuscul. Disord.* 7:314–318 (1997); Schwartz B. et al., *Gene Ther.* 3:405–411 (1996); Tsurumi Y. et al., *Circulation* 94:3281–3290 (1996) (incorporated herein by reference).

The TR13 and/or TR14 polynucleotide constructs may be delivered by any method that delivers injectable materials to the cells of an animal, such as, injection into the interstitial space of tissues (heart, muscle, skin, lung, liver, intestine and the like). The TR13 and/or TR14 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the TR13 and/or TR14 polynucleotides may also be delivered in liposome formulations (such as those taught in Felgner P. L., et al. *Ann. NY Acad. Sci.* 772:126–139 (1995), and Abdallah B., et al. *Biol Cell* 85(1):1–7 (1995)) which can be prepared by methods well known to those skilled in the art.

The TR13 and/or TR14 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The TR13 and/or TR14 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked TR13 and/or TR14 polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked TR13 and/or TR14 polynucleotide constructs can be delivered to arteries during angioplasty by the catheter used in the procedure.

The dose response effects of injected TR13 and/or TR14 polynucleotide in muscle in vivo is determined as follows. Suitable TR13 and/or TR14 template DNA for production of mRNA coding for TR13 and/or TR14 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The TR13 and/or TR14 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for TR13 and/or TR14 protein expression. A time course for TR13 and/or TR14 protein expression may be done in a similar fashion except that quadriceps from different mice are harvested at different times. Persistence of TR13 and/or TR14 DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using TR13 and/or TR14 naked DNA.

Example 14

Gene Therapy Using Endogenous TR13 and/or TR14 Gene

Another method of gene therapy according to the present invention involves operably associating the endogenous TR13 and/or TR14 sequence with a promoter via homologous recombination as described, for example, in U.S. Pat. No. 5,641,670, issued Jun. 24, 1997; International Publication Number WO 96/29411, published Sep. 26, 1996; International Publication Number WO 94/12650, published Aug. 4, 1994; Koller et al, *Proc. Natl. Acad. Sci. USA* 86:8932–8935 (1989); and Zijlstra et al., *Nature* 342:435–438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous TR13 and/or TR14, flanking the promoter. The targeting sequence will be sufficiently near the 5' end of TR13 and/or TR14 so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous TR13 and/or TR14 sequence. This results in the expression of TR13 and/or TR14 in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2

HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Clone DNA is prepared according to standard techniques. For example, to construct a clone for targeting to the TR13 and/or TR14 locus, clone pUC18 (MBI Fennentas, Amherst, N.Y.) is digested with HindIII. The CMV promoter is amplified by PCR with an XbaI site on the 5' end and a BamHI site on the 3' end. Two TR13 and/or TR14 non-coding sequences are amplified via PCR: one TR13 and/or TR14 non-coding sequence (TR13 and/or TR14 fragment 1) is amplified with a HindIII site at the 5' end and an Xba site at the 3' end; the other TR13 and/or TR14 non-coding sequence (TR13 and/or TR14 fragment 2) is amplified with a BamHI site at the 5' end and a HindIII site at the 3' end. The CMV promoter and TR13 and/or TR14 fragments are digested with the appropriate enzymes (CMV promoter-XbaI and BamHI; TR13 and/or TR14 fragment 1-XbaI; TR13 and/or TR14 fragment 2-BamHI) and ligated together. The resulting ligation product is digested with HindIII, and ligated with the HindIII-digested pUC18 clone.

Clone DNA is added to a sterile cuvette with a 0.4 cm electrode gap (Bio-Rad). The final DNA concentration is generally at least 120 µg/ml. 0.5 ml of the cell suspension (containing approximately $1.5. \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 15

Assays to Detect Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL5, IL6, IL-7, IL10, IL-13, IL14 and IL15. Interestingly, these signals are by themselves weak effectors but can, in combination with various co-stimulatory proteins, induce activation, proliferation, differentiation, homing, tolerance and death among B cell populations. One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

Experimental Procedure

In Vitro assay-Purified TR13 and/or TR14 protein, or truncated forms thereof, is assessed for its ability to induce activation, proliferation, differentiation or inhibition and/or death in B-cell populations and their precursors. The activity of TR13 and/or TR14 protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R (B220). Various dilutions of each sample are placed into individual wells of a 96-well plate to which are added $10^5$ B-cells suspended in culture medium (RPMI 1640 containing 10% FBS, $5 \times 10^{-5}$M βME, 100 U/ml penicillin, 10 µg/ml streptomycin, and $10^{-5}$ dilution of SAC) in a total volume of 150 ul. Proliferation or inhibition is quantitated by a 20 h pulse (1 uCi/well) with $^3$H-thymidine (6.7 Ci/mM) beginning 72 h post factor addition. The positive and negative controls are IL2 and medium respectively.

In Vivo assay—BALB/c mice are injected (i.p.) twice per day with buffer only, or 2 mg/Kg of TR13 and/or TR14 protein, or truncated forms thereof. Mice receive this treatment for 4 consecutive days, at which time they are sacrificed and various tissues and serum collected for analyses. Comparison of H&E sections from normal and TR13 and/or TR14 protein-treated spleens identify the results of the activity of TR13 and/or TR14 protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from TR13 and/or TR14 protein-treated mice is used to indicate whether TR13 and/or TR14 protein specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and TR13 and/or TR14 protein-treated mice.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 16
T Cell Proliferation Assay

A CD3-induced proliferation assay is performed on PBMCs and is measured by the uptake of $^3$H-thymidine. The assay is performed as follows. Ninety-six well plates are coated with 100 µl/well of mAb to CD3 (HIT3a, Pharmingen) or isotype-matched control mAb (B33.1) overnight at 4° C. (1 µg/ml in 0.05M bicarbonate buffer, pH 9.5), then washed three times with PBS. PBMC are isolated by F/H gradient centrifugation from human peripheral blood and added to quadruplicate wells ($5 \times 10^4$/well) of mAb coated plates in RPMI containing 10% FCS and P/S in the presence of varying concentrations of TR13 and/or TR14 protein (total volume 200 µl). Relevant protein buffer and medium alone are controls. After 48 hr. culture at 37° C., plates are spun for 2 min. at 1000 rpm and 100 µl of supernatant is removed and stored −20° C. for measurement of IL-2 (or other cytokines) if effect on proliferation is observed. Wells are supplemented with 100 µl of medium containing 0.5 µCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of TR13 and/or TR14 proteins.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 17
Effect of TR13 and/or TR14 on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1–3 days with increasing concentrations of TR13 and/or TR14 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the Production of Cytokines

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of TR13 and/or TR14 for 24 hours. LPS (100 ng/ml) is added to the cell culture as positive control. Supernatants from the cell cultures are then collected and analyzed for IL-12 content using commercial ELISA kit (e.g., R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of TR13 and/or TR14 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte Activation and/or Increased Survival

Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. TR13 and/or TR14, agonists, or antagonists of TR13 and/or TR14 can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

1. Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2 \times 10^6$/ml in PBS containing PI at a final concentration of 5 µg/ml, and then incubated at room temperature for 5 minutes before FAC Scan analysis. PI uptake has been demonstrated to correlate with DNA fragmentation in this experimental paradigm.

2. Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of 5×10⁵ cells/ml with increasing concentrations of TR13 and/or TR14 and under the same conditions, but in the absence of TR13 and/or TR14. For IL-12 production, the cells are primed overnight with IFN- (100 U/ml) in presence of TR13 and/or TR14. LPS (10 ng/ml) is then added. Conditioned media are collected after 24 h and kept frozen until use. Measurement of TNF-α, IL-10, MCP-1 and IL-8 is then performed using a commercially available ELISA kit (e.g., R & D Systems (Minneapolis, Minn.)) applying the standard protocols provided with the kit.

3. Oxidative burst. Purified monocytes are plated in 96-well plate at 2–1×10⁵ cell/well. Increasing concentrations of TR13 and/or TR14 are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 riM PMA). The plates are incubated at 37° C. for 2 hours and the reaction is stopped by adding 20 $\mu$l 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 18

The Effect of TR13 and/or TR14 on the Growth of Vascular Endothelial Cells

On day 1, human umbilical vein endothelial cells (HUVEC) are seeded at 2–5×10⁴ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. TR13 of SEQ ID NO:2 and/or TR14 protein preferably of SEQ ID NO:61 or, alternatively, SEQ ID NO:5, respectively, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that TR13 and/or TR14 may proliferate vascular endothelial cells.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 19

Stimulatory Effect of TR13 and /or TR14 on the Proliferation of Vascular Endothelial Cells For evaluation of mitogenic activity of growth factors, the calorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 ml serum-supplemented medium and are allowed to attach overnight. After serum-starvation for 12 hours in 0.5% FBS, conditions (bFGF, VEGF₁₆₅ or TR13 and/or TR14 in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. In Vitro *Cell. Dev. Biol.* 30A:512–518 (1994).

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 20

Inhibition of PDGF-Induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2–3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4° C. for 2 h after exposing to denaturing solution and then with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., *J. Biol. Chem.* 6;271(36):21985–21992 (1996).

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR 13 and/or TR 14.

Example 21

Stimulation of Endothelial Migration

This example will be used to explore the possibility that TR13 and/or TR14 may stimulate lymphatic endothelial cell migration.

Endothelial cell migration assays are performed using a 48 well microchemotaxis chamber (Neuroprobe Inc., Cabin John, Md.; Falk, W., Goodwin, R. H. J., and Leonard, E. J. "A 48 well micro chemotaxis assembly for rapid and accurate measurement of leukocyte migration." *J. Immunological Methods* 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, 2.5×10⁵ cells suspended in 50 ul M199 containing 1% FBS are seeded in the upper compartment.

The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 22

Stimulation of Nitric Oxide Production by Endothelial Cells

Nitric oxide released by the vascular endothelium is believed to be a mediator of vascular endothelium relaxation. Thus, TR13 and/or TR14 activity can be assayed by determining nitric oxide production by endothelial cells in response to TR13 and/or TR14.

Nitric oxide is measured in 96-well plates of confluent microvascular endothelial cells after 24 hours starvation and a subsequent 4 hr exposure to various levels of a positive control (such as VEGF-1) and TR13 and/or TR14. Nitric oxide in the medium is determined by use of the Griess reagent to measure total nitrite after reduction of nitric oxide-derived nitrate by nitrate reductase. The effect of TR13 and/or TR14 on nitric oxide release is examined on HUVEC.

Briefly, NO release from cultured HUVEC monolayer is measured with a NO-specific polarographic electrode connected to a NO meter (Iso-NO, World Precision Instruments Inc.). Calibration of the NO element is performed according to the following equation:

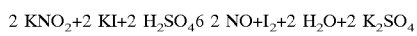

$$2\ KNO_2 + 2\ KI + 2\ H_2SO_4 \rightarrow 2\ NO + I_2 + 2\ H_2O + 2\ K_2SO_4$$

The standard calibration curve is obtained by adding graded concentrations of $KNO_2$ (0, 5, 10, 25, 50, 100, 250, and 500 nmol/L) into the calibration solution containing KI and $H_2SO_4$. The specificity of the Iso-NO electrode to NO is previously determined by measurement of NO from authentic NO gas. The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) to maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1 \times 10^6$ endothelial cells. All values reported are means of four to six measurements in each group (number of cell culture wells). See, Leak et al. *Biochem. and Biophys. Res. Comm.* 217:96–105 (1995).

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 23

Effect of TR13 and/or TR14 on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 µl/well) for 30 min. at 37° C. CADMEC are seeded onto the coated wells at 7,500 cells/well and cultured overnight in Growth Medium. The Growth Medium is then replaced with 300 µg Cell Applications' Chord Formation Medium containing control buffer or TR13 and/or TR14 (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 24

Angiogenic Effect on Chick Chorioallantoic Membrane

Chick chorioallantoic membrane (CAM) is a well-established system to examine angiogenesis. Blood vessel formation on CAM is easily visible and quantifiable. The ability of TR13 and/or TR14 to stimulate angiogenesis in CAM can be examined.

Fertilized eggs of the White Leghorn chick (*Gallus gallus*) and the Japanese quail (*Coturnix coturnix*) are incubated at 37.8° C. and 80% humidity. Differentiated CAM of 16-day-old chick and 13-day-old quail embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors, and the protein to be tested, are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 25

Angiogenesis Assay Using a Matrigel Implant in Mouse

In order to establish an in vivo model for angiogenesis to test TR13 and/or TR14 protein activities, mice and rats are implanted subcutaneously with methylcellulose disks containing either 20 mg of BSA (negative control), 1 mg of TR13 and/or TR14, or 0.5 mg of VEGF-1 (positive control). The negative control disks should contain little vascularization, while the positive control disks should show signs of vessel formation.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 26
Rescue of Ischemia in Rabbit Lower Limb Model

To study the in vivo effects of TR13 and/or TR14 on ischemia, a rabbit hindlimb ischemia model is created by surgical removal of one femoral arteries as described previously (Takeshita, S. et al, Am J. Pathol 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al., Am J. Pathol 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked TR13 and/or TR14 expression clone by arterial gene transfer technology using a hydrogel-coated balloon catheter as described (Riessen, R. et al, Hum Gene Ther. 4:749–758 (1993); Leclerc, G. et al., J. Clin. Invest. 90: 936–944 (1992)). When TR13 and/or TR14 is used in the treatment, a single bolus of 500 mg TR13 and/or TR14 protein or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 27
Rat Ischemic Skin Flap Model

The evaluation parameters include skin blood flow, skin temperature, and factor VIII immunohistochemistry or endothelial alkaline phosphatase reaction. TR13 and/or TR14 expression, during the skin ischemia, is studied using in situ hybridization.

The study in this model is divided into three parts as follows:
 Ischemic skin
 Ischemic skin wounds
 Normal wounds The experimental protocol includes:
 Raising a 3×4 cm, single pedicle flill-thickness random skin flap (myocutaneous flap over the lower back of the animal).
 An excisional wounding (4–6 mm in diameter) in the ischemic skin (skin-flap).
 Topical treatment with TR13 and/or TR14 of the excisional wounds (day 0, 1, 2, 3, 4 post-wounding) at the following various dosage ranges: 1 mg to 100 mg.
 Harvesting the wound tissues at day 3, 5, 7, 10, 14 and 21 post-wounding for histological, immunohistochemical, and in situ studies.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 28
Peripheral Arterial Disease Model

Angiogenic therapy using TR13 and/or TR14 is a novel therapeutic strategy to obtain restoration of blood flow around the ischemia in case of peripheral arterial diseases. The experimental protocol includes:
 One side of the femoral artery is ligated to create ischemic muscle of the hindlimb, the other side of hindlimb serves as a control.

TR13 and/or TR14 protein, in a dosage range of 20 mg–500 mg, is delivered intravenously and/or intramuscularly 3 times (perhaps more) per week for 2–3 weeks.

The ischemic muscle tissue is collected after ligation of the femoral artery at 1, 2, and 3 weeks for the analysis of TR13 and/or TR14 expression and histology. Biopsy is also performed on the other side of normal muscle of the contralateral hindlimb.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 29
Ischemic Myocardial Disease Model

TR13 and/or TR14 is evaluated as a potent mitogen capable of stimulating the development of collateral vessels, and restructuring new vessels after coronary artery occlusion. Alteration of TR13 and/or TR14 expression is investigated in situ. The experimental protocol includes:
 The heart is exposed through a left-side thoracotomy in the rat. Immediately, the left coronary artery is occluded with a thin suture (6–0) and the thorax is closed.

TR13 and/or TR14 protein, in a dosage range of 20 mg–500 mg, is delivered intravenously and/or intramuscularly 3 times (perhaps more) per week for 2–4 weeks.

Thirty days after the surgery, the heart is removed and cross-sectioned for morphometric and in situ analyzes.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 30
Rat Corneal Wound Healing Model

This animal model shows the effect of TR13 and/or TR14 on neovascularization. The experimental protocol includes:
 Making a 1–1.5 mm long incision from the center of cornea into the stromal layer.

Inserting a spatula below the lip of the incision facing the outer corner of the eye.

Making a pocket (its base is 1–1.5 mm form the edge of the eye).

Positioning a pellet, containing 50 ng–5 ug of TR13 and/or TR14, within the pocket.

TR13 and/or TR14 treatment can also be applied topically to the corneal wounds in a dosage range of 20 mg–500 mg (daily treatment for five days).

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 31

Diabetic Mouse and Glucocorticoid-Impaired Wound Healing Models

Diabetic db+/db+ Mouse Model

To demonstrate that TR13 and/or TR14 accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D.G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1–7 (1983); Leiter et al, *Am. J. of Pathol.* 114:46–55 (1985)). Peripheral neuropathy, myocardial complications, and microvascular lesions, basement membrane thickening and glomerular filtration abnormalities have been described in these animals (Norido, F. et al., *Exp. Neurol.* 83(2):221–232 (1984); Robertson et al., *Diabetes* 29(1):60–67 (1980); Giacomelli et al. *Lab Invest.* 40(4):460–473 (1979); Coleman, D. L., *Diabetes* 31 (Suppl): 1–6 (1982)). These homozygous diabetic mice develop hyperglycemia that is resistant to insulin analogous to human type II diabetes (Mandel et al., *J. Immunol.* 120:1375–1377 (1978)).

The characteristics observed in these animals suggests that healing in this model may be similar to the healing observed in human diabetes (Greenhalgh, et al., *Am. J. of Pathol.* 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and were 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rilkin, D. B.,*J. Exp. Med.* 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

TR13 and/or TR14 is administered using at a range different doses of TR13 and/or TR14, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for fur ther processing.

Three groups of 10 animals each (5 diabetic and 5 non-diabetic controls) are evaluated: 1) Vehicle placebo control, 2) TR13 and/or TR14.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 was 64 mm², the corresponding size of the dermal punch. Calculations were made using the following formula:

$$[\text{Open area on day 8}]-[\text{Open area on day 1}]/[\text{Open area on day 1}]$$

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with TR13 and/or TR14. This assessment included verification of the presence of cell accumulation, inflammatory cells, capillaries, fibroblasts, re-epithelialization and epidermal maturity (Greenhalgh, D. G. et al., *Am. J Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer served as a positive tissue control and human brain tissue is used as a negative tissue control. Each specimen included a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

Steroid Impaired Rat Model

The inhibition of wound healing by steroids has been well documented in various in vitro and in vivo systems (Wahl, S. M. Glucocorticoids and Wound healing. In: Anti-Inflammatory Steroid Action: Basic and Clinical Aspects. 280–302 (1989); Wahl, S. M. et al., *J. Immunol.* 115: 476–481 (1975); Werb, Z. et al., *J. Exp. Med.* 147:1684–1694 (1978)). Glucocorticoids retard wound healing by inhibiting angiogenesis, decreasing vascular permeability (Ebert, R. H., et al., *An. Intern. Med.* 37:701–705 (1952)), fibroblast proliferation, and collagen synthesis (Beck, L. S. et al., *Growth Factors.* 5: 295–304 (1991); Haynes, B. F. et al., *J. Clin. Invest.* 61: 703–797 (1978)) and producing a transient reduction of circulating monocytes (Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck, L. S. et al., *Growth Factors.* 5: 295–304 (1991); Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989); Pierce, G. F. et al., *Proc. Natl. Acad. Sci. USA* 86: 2229–2233 (1989)).

To demonstrate that TR13 and/or TR14 can accelerate the healing process, the effects of multiple topical applications of TR13 and/or TR14 on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and were 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue was no longer visible and the wound is covered by a continuous epithelium.

TR13 and/or TR14 is administered using at a range different doses of TR13 and/or TR14, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) were evaluated: 1) Untreated group 2) Vehicle placebo control 3) TR13 and/or TR14 treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 was 64 mm$^2$, the corresponding size of the dermal punch. Calculations were made using the following formula:

$$[\text{Open area on day 8}] - [\text{Open area on day 1}]/[\text{Open area on day 1}]$$

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin was improved by treatment with TR13 and/or TR14. A calibrated lens micrometer is used by a blinded observer to determine the distance of the wound gap.

Experimental data are analyzed using an unpaired t test. A p value of <0.05 is considered significant.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 32

Lymphadema Animal Model

The purpose of this experimental approach is to create an appropriate and consistent lymphedema model for testing the therapeutic effects of TR13 and/or TR14 in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 3–4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located.

The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (A J Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5–7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma protein measurements: Blood is drawn, spun, and serum separated prior to surgery and then at conclusion for total protein and Ca2+ comparison.

Limb Weight Comparison: After drawing blood, the animal is prepared for tissue collection. The limbs were amputated using a quillitine, then both experimental and control legs were cut at the ligature and weighed. A second weighing is done as the tibio-cacaneal joint was disarticulated and the foot was weighed.

Histological preparations: The transverse muscle located behind the knee (popliteal) area is dissected and arranged in a metal mold, filled with freezeGel, dipped into cold methylbutane, placed into labeled sample bags at −80EC until sectioning. Upon sectioning, the muscle was observed under fluorescent microscopy for lymphatics. Other immuno/histological methods are currently being evaluated.

The studies described in this example test the activity in TR13 and/or TR14 protein. However, one skilled in the art could easily modify the exemplified studies to test the activity of TR13 and/or TR14 polynucleotides (e.g., gene therapy), agonists, and/or antagonists of TR13 and/or TR14.

Example 33

Assay for TR13 and/or TR14 Inhibition of B Cell Proliferation in an in Vitro Co-Stimulatory Assay This example provides a co-stimulatory assay using *Staphylococcus Aureus* Cowan 1 (SAC) as priming agent and Neutrokine-alpha (International Application Publication No. WO 98/18921) or IL-2 as a second signal to assay for TR13 and/or TR14 polypeptide antagonists of Neutrokine-alpha (or IL-2) mediated B cell proliferation.

A soluble TR13 or TR14 polypeptide is prepared (e.g., a soluble form of TR13 or TR14 corresponding to a portion of the TR13 or TR14 extracellular domain linked to the Fc portion of a human IgGI immunogloulin molecule). The ability of this protein to alter the proliferative response of human B cells is assessed in a standard co-stimulatory assay. Briefly, human tonsillar B cells are purified by magnetic bead (MACS) depletion of CD3-positive cells. The resulting cell population is routinely greater than 95% B cells as assessed by expression of CD19 and CD20 staining. Various dilutions of rHuNeutrokine-alpha (Internatioanl Application Publication No. WO 98/18921) or rHuIL2 are placed into individual wells of a 96-well plate to which is added $10^5$B cells suspended in culture medium (RPMI 1640 containing 10% FBS, $5\times10^{-5}$M 2ME, 100U/ml penicillin, 10ug/ml streptomycin, and $10^{-5}$ dilution of formalin-fixed *Staphylococcus aureus* Cowan I (SAC) also known as Pansorbin (Pan)) in a total volume of 150 ul. The TR13 or TR14 polypeptide is then added at various concentrations and the plates are placed in the incubator (37° C. 5% $CO_2$, 95% humidity) for three days. Proliferation is quantitated by a 20 h pulse (1 $\mu$Ci/well) of $^3$H-thymidine (6.7 Ci/mM) beginning 72 h post factor addition. The positive and negative controls are SAC exposed B cells with rHuNeutrokine-alpha (or rHuIL2) and medium (in the absence of the TR13 or TR14 polypeptide), respectively.

Antagonists of rHuNeutrokine-alpha (or rHuIL2) mediated B cell proliferation demonstrate a reduced level of B cell proliferation in the samples containing the TR13 or TR14 polypeptides when compared to the positive control.

Example 34

Demonstration that TR13 Binds Fas Ligand

Fas (CD95/Apol) and Fas ligand (FasL/CD95L), are a pair of pro-apoptotic mediators of the TNF receptor and ligand family that induce apoptosis upon receptor/ligand engagement. Fas/FasL-mediated apoptosis is a normal and important homeostatic mechanism useful in the down-regulation of hyper-immune responses and the deletion of activated lymphocytes. Fas/FasL-induced apoptosis is also important in host protection and surveillance, preventing damage to immune privileged sites, and eliminating virus-infected or transformed cells. While necessary for normal physiological processes, unregulated apoptosis mediated by the Fas/FasL system is implicated in organ-specific tissue injury both in experimental animal models and several human disease states.

To determine the ability of TR13 to bind Fas ligand, co-transfection experiments were performed. Cells (that do not express endogenous TR13) were either transfected with expression vectors containing the TR13 receptor or a soluble form of flag-tagged Fas ligand, APRIL, or Neutrokine-alpha (ligand vectors) or cotransfected with TR13 vector and a ligand vector. FACS analysis, using fluorochrome labelled anti-FLAG antibody (using streptavidin-PE as a secondary reagent to detect the anti-FLAG antibody) and propidium iodide staining, was used to evaluate the ability of the recombinantly expressed TR13 receptor to bind flag-tagged Fas ligand, APRIL, or Neutrokine-alpha and to evaluate the viability of the cells.

Untreated control cells or control cells that were transfected with ligand vectors alone did not stain with anti-FLAG antibody and showed minimal cell death by propidium iodide staining. Cells that were cotransfected with TR13 and APRIL or Neutrokine-alpha expression vectors also did not stain with anti-FLAG antibody but propidium iodide staining showed increased cell death. These results indicate that TR13 does not bind either APRIL or Neutrokine-alpha and that expression of TR13 induce cell death. Control cotransfection experiments using the Neutrokine alpha/APRIL receptor, TACI, instead of TR13, and Neutrokine-alpha or APRIL expression vectors did however, show staining with the anti-FLAG antibody and minmal cell death. Cells that were cotransfected with TR13 and Fas ligand expression vectors did stain with anti-FLAG antibody indicating that TR13 binds Fas Ligand. In addition, cells cotransfected with TR13 and Fas ligand expression vectors showed the greatest amount of cell death, indicating that Fas ligand/TR13 interactions induce cell death.

Thus, in accordance with the invention, agonists that bind TR13, including anti-TR1 3 antibodies and antibody fragments and peptides, can be used to selectively kill cells expressing TR13, including cancer cells.

Example 35
In Vitro and In Vivo Inhibition of FasL Mediated Killing by TR13

This example describes the synthesis and biological activity of a fusion protein that can be produced using the full length coding region of TR13 (or fragment or variant thereof such as amino acids 1 to 906 of SEQ ID NO:40) and an Fc domain of IgG1. Biochemical and biological characterization of this TR13-Fc may be used to determine the ability of TR13-Fc to bind FasL and thereby inhibit apoptosis in-vitro. TR13-Fc may also be used to assess the ability of a soluble form of TR13 to block the mortality associated with iv injection of cross-linked FasL into Fas+ mice. Results from these such experiments would determine the therapeutic potential of TR13-Fc in diseases where Fas/FasL is implicated in mediating organ damage.

Methods of Example 35

Animals

Female Balb/c mice (20–25 g) may be obtained from Charles River Laboratories (Raleigh, N.C.). Female MLR/lpr mice (30–35 g) may be obtained from Jackson Laboratories (Bar Harbor, Me.). Mice are generally housed five per cage, and kept under standard conditions for one week before being used in experiments. The animals are maintained according to National Research Council standards for the care and use of laboratory animals.

Human TR13-Fc, TR13-Non Fc and Fas-Fc Expression Vectors

Cells infected with baculovirus clone encoding the TR13-Fc fusion protein (e.g., pA2Fc:TR13 (M1-D906)), are grown in media containing 1% ultra low IgG serum. Conditioned culture supernatant (20 L) is adjusted to pH 7.0, filtered through 0.22 micron filter and loaded on a Protein A column (BioSepra Ceramic HyperD) previously conditioned with 20 mM phosphate buffer with 0.5 M NaCl, pH7.2. The column is washed with 15 CV of 20 mM phosphate buffer containing 0.5 M NaCl, pH 7.2, and followed by 5 CV of 0.1 M citric acid (pH 5.0). TR13-Fc is eluted with 0.1 M citric acid (pH 2.4)/20% glycerol, and fractions are neutralized with 1M Tris-HCl, pH 9.2. The human TR13-Fc positive fractions are determined by SDS-PAGE. The peak fractions are pooled and concentrated using an Amicon concentrator. The TR13-Fc concentrate is then loaded onto a Superdex 200 column containing PBS containing 0.5 M NaCl (Pharmacia) and TR13-Fc positive fractions are determined by non-reducing SDS-PAGE. The TR13-Fc positive fractions eluting as disulfide-linked dimers are pooled and further concentrated with CentriPlus 10K cutoff spin concentrators.

The TR13-Fc protein bound to the Protein A resin may contain both disulfide-linked Fc dimers and higher disulfide-linked aggregates. Aggregates may be removed by Superdex 200 size-exclusion chromatography. The yield for TR13-Fc can be determined using Reverse-Phase HPLC assay and N-terminal sequence assay. Due to processing of the signal sequence, The N terminus is predicted to be Thr-42. The biological activity of pure TR13 protein may be assessed using, for example, BIAcore analysis to determine the properties of the interaction of TR13-Fc with Fas ligand.

To confirm purity, TR13-Fc protein may be blotted to a ProBlott membrane cartridge (PE Biosystems, Inc). After staining with Ponceau S (0.2% in 4% acetic acid), the membrane is placed in a "Blot Cartridge", and subjected to N-terminal amino acid sequence analysis using a model ABI-494 sequencer (PE Biosystems, Inc.) and the Gas-phase Blot cycles. Proteins are then subjected to reverse-phase HPLC (Beckmann) analysis to access purity.

A human Fas(M1-G169)-Fc fusion protein was purified from CHO conditioned media by capture on a Poros 50 protein A affinity column with elution at 0.1M citrate pH 2.0 as described for TR13-Fc. Further purification was effected by size separation on a Superdex-200 gel filtration resin in PBS/glycerol. N-terminal sequence of Fas-Fc was blocked and protein identity was confirmed post digestion with pyroglutamate aminopeptidase to deblock the N-terminus and 16% SDS-PAGE, respectively. The protein behaved as disulfide linked dimer as expected for a Fc fusion protein.

BIAcore Chip Preparation and Analysis

BIAcore chip technology provides the opportunity to identify and characterize ligands that bind to a given receptor, in this case TR13. The protein ligand can be immobilized and challenged with TR13 to calculate relative binding units (RU). Conversely, the TR13 receptor can be immobilized and exposed to various ligands to identify proteins with an affinity for the TR13 receptor.

The extra-cellular portion of FasL (Oncogene Research Products), amino acids 103–281, are dialyzed against 10 mM sodium acetate buffer, pH 5 and a BIAcore flow cell prepared. TR13-Fc and Fas-Fc fusion proteins are analyzed at 5 ug/mL in 50 uL HBS buffer and are injected onto the FasL chip at a flow rate of 15 ul per minute. After injection of the sample the flow cell is equilibrated with HBS and the amount of net bound protein is determined.

In Vitro Soluble Human FasL Mediated Cytotoxicity

The HT-29 cell line, a human colon adenocarcinoma cell line obtained from the ATCC (code ATCC HTB-38) is sensitive to FasL mediated cytotoxicity, presumably through activation of its Fas receptor. HT-29 cells may be grown in D-MEM/10% FBS/2 mM Glutamine/pen/strep. To measure FLAG-FasL induced cytotoxicity, target cells are trypsinized, washed and plated in a 96-well plate at 50,000 cells/well. HT-29 cells are treated with cross-linked FLAG-FasL+FLAG antibody (1 ng/ml), or with cross-linked FLAG-FasL in combination with Fas-Fc, or TR13-Fc. Although uncross-linked FasL can induce cytotoxity in this assay, antibody cross-linking of FasL via its FLAG domain significantly enhances the ability of FasL to mediate apoptosis, and thus the FLAG antibody is included. The final volume in each well is 200 ul. After 5 days of culture, the plate is harvested and 20 ul of Alamar Blue reagent added. To assess final viability, cells are incubated for four hours and the plate analyzed in a CytoFluor fluorescence plate reader with excitation of 530 nm and emission of 590 nm. The Jurkat human T cell line, which also expresses the Fas receptor, and is sensitive to FasL, may also be tested in an in vitro cytotoxicity assay similar to that used on HT-29 cells.

Additionally, Jurkat cells may be evaluated by FACS analysis in an apoptosis assay. Jurkat cells (RPMI+5% serum) seeded at 50,000 cells per well are treated with FLAG-FasL and anti-FLAG mouse monoclonal antibody (200 ng/ml) and incubated at 37C for 16 hrs to induce apoptosis. When TR13-Fc or Fas-Fc is included in the assay, the Fc protein was pre-incubated with FasL and anti-FLAG antibody for 15 mins. To determine the degree of apoptosis, cells are harvested, stained with annexin and propidium iodide and evaluated using FACS analysis.

In Vitro Membrane Bound Murine FasL Mediated Cytotoxicity

To analyze the in vitro killing of Fas+target cells by murine FasL, murine effector L929 cells ($2.5 \times 10^5$ cells/well) are transfected with murine FasL and incubated with Fas+ murine A20 target cells ($5 \times 10^3$ cells/well) labeled with Eu DTPA. After an 18 hour incubation at an effector:target cell ratio of 50:1, cells are centrifuged, and % release of Eu DTPA is quantified as a measure of cell death.

In Vivo Cross-linked FLAG-FasL Induced Mortality

Soluble human FLAG-FasL was synthesized at HGS. To induce cross-linking of Fas receptors, FasL is incubated with FLAG antibody (Sigma, St Louis, Mo.) and injected iv into mice following a variation of the procedure used by Schneider et al (*J. Exp. Med.*, 187:1205–13 and *Methods Enzymol.* 322:325–45). Fc-fusion proteins may be injected iv or sc at various time points prior to FasL injection, and mortality recorded over time. Liver samples one centimeter square, are fixed in 10% neutral buffered formalin for 24 hours, then transferred to 70 percent methanol until time for embedding in paraffin. Sections are stained with H&E, and evaluated histologically. Blood may be drawn from the heart and used in the measurement of serum alanine (ALT) and aspartate (AST) aminotransferase levels. To control that the mortality of mice is indeed a result of crosslinking of the Fas receptor in these mice, the same experiments may be performed on MRL/lpr mice whose Fas receptor is non-functional, thus crosslinking of the Fas receptor should not idnduce mortality in these mice.

Example 36
Modulation of T Cell Responses by TR13: Ability of Soluble TR13 to Inhibit Alloactivation and Heart Allograft Rejection The ability of TR13 to interact with AIM-II (LIGHT) (International application publication number WO 97/34911, published Sep. 25, 1997) and the role of TR13 in modulating T cell activities and immunological responses that may be associated with AIM-II may be analyzed according to the experiments detailed below.

Materials and Methods of Example 36

Mice

Twelve week-old female C57BL/6 (B6, H-$2^b$), BALB/c, and BALB/cxC57BL/6 F1 (H-$2^{bXd}$) mice may be obtained from Jackson Laboratory (Bar Harbor, Me.) or Charles River (LaSalle, Quebec, Canada). 2C TCR transgenic mice are bred in an animal facility as described in Chen, H., et al., 1996. *J. Immunol.* 157:4297, which is hereby incorporated by reference in its entirety.

Expression and Purification of the Human TR13-Fc Fusion Protein

Full-length human TR13 cDNA or a fragment or variant thereof (e.g., a polynucleotide encoding amino acids 1 to 906 of SEQ ID NO: 40) is fused to the sequence coding for the Fc domain of human IgG$_1$ and subcloned into a baculovirus expression vector pA2. The construct is designated pA2-Fc:TR13. Sf9 cells infected pA2-Fc:TR13 may be grown in media (100 L) containing 1% ultra low IgG serum (100 L). Conditioned culture supernatant from a bioreactor can be harvested by continuous flow centrifugation. The pH of the supernatant is adjusted to pH 7.0, filtered through 0.22 um filter and loaded on to a Protein A column (BioSepra Ceramic HyperD, Life Technologies, Rockville, Md. 30 ml bed volume) previously conditioned with 20 mM phosphate buffer, 0.5 M NaCl (pH 7.2). The column is then washed with 15 column volumes (CV) of 20 mM phosphate buffer (pH 7.2) containing 0.5 M NaCl followed by 5 CV of 0.1 M sodium citrate (pH 5.0). TR13-Fc can be eluted with 0.1 M citric acid (H 2.4), and 2 mL fractions were collected into tubes containing 0.6 ml Tris-HCl (pH 9.2). The TR13-Fc positive fractions may then be determined by SDS-PAGE. The peak fractions are pooled and concentrated with a Protein A column (7 mL bed volume) as described above. The concentrated TR13-Fc is then loaded onto a Superdex 200 column (Amersham Pharmacia, Piscataway, N.J. 90 ml bed volume) and eluted with PBS containing 0.5 M NaCl. TR13-Fc positive fractions are determined by non-reducing SDS-PAGE. The pooled positive fractions are then dialyzed against 12.5 mM HEPES buffer, pH 5.75 containing 50 mM NaCl. The dialysate is then passed through a 0.2 m filter (Minisart, Sartorius AG, Goettingen, Germany) followed by a Q15X-anion exchange membrane (Sartobind membrane, Sartorius AG, Goettingen, Germany).

Expression and Purification of Full-Length Human TR13 (without Fc)

Sf9 cells are infected with the pA2-FC:TR13 viral construct and the culture supernatant of the infected cells are loaded onto a Poros HS-50 column (Applied Biosystems, Foster City, Calif.) equilibrated in a buffer containing 50 mM Tris-HCl, pH 7, and 0.1M NaCl. The column is washed with 0.1 M NaCl and eluted stepwise with 0.3M, 0.5M, and 1.5M NaCl. The eluted fractions are analyzed by SDS-PAGE, and the 0.5 M NaCl fraction containing TR13 protein is diluted and loaded onto a set of Poros HQ-50/CM-20 columns in a tandem mode. TR13 may be eluted from the CM column with a linear gradient from 0.2M to 1.0 M NaCl.

Expression and Purification of Human TR2-Fc, MCIF-Fc, and Fas-Fc Fusion Proteins The cDNA sequences coding for the extracellular domain of TR2 (aa 1–192), the extracellular domain of Fas (aa 1–169) and a beta chemokine MCIF (aa 1–92) were fused with the cDNA sequence coding for the Fc domain of human IgG$_1$ and cloned into a eukaryotic expression vector pC4. The construct was stably transfected into CHO cells. The Fc fusion proteins from the CHO supernatant were purified with methods described for TR13-Fc.

Expression and Purification of the Human AIM-II Protein

The coding sequence of the natural secreted form of AIM-II (aa 83–240) was cloned into a prokaryotic expression vector pHE4, and expressed in *E. coli*. Inclusion bodies from the transformed bacteria were dissolved for 48–72 hours at 4 C in 3.5 M guanidine hydrochloride containing 100 mM Tris-HCl, pH 7.4 and 2 mM $CaCl_2$. The solution was quickly diluted with 20–30 volumes of a buffer containing 50 mM Tris-HCl, pH8 and 150 mM NaCl, adjusted to pH 6.6 and chromatographed with a strong cation exchange column (Poros HS-50). The protein was eluted with 3–5 CV of a stepwise gradient of 300 mM, 700 mM, and 1500 mM NaCl in 50 mM MES at pH 6.6. The fraction eluted with 0.7 M NaCl was diluted 3-fold with water, and applied to a set of strong anion (Poros HQ-50) and cation (Poros CM-20) exchange columns in a tandem mode. The CM column was eluted with 10–20 CV of a linear gradient from 50 mM MES pH6.6, 150 mM NaCl to 50 mM Tris-HCl pH 8, 500 mM NaCl. Fractions containing purified AIM-II as analyzed by SDS-PAGE were combined.

Quality Control of the Recombinant Proteins

The endotoxin levels in the purified recombinant proteins can be determined by the LAL assay on a Limulus Amebocyte Lysate (LAL)-5000 Automatic Endotoxin Detection System (Associates of Cape Cod, Inc. Falmouth, Mass.), according to the standard procedure recommended by the manufacturer. All the recombinant proteins are subjected to N-terminal sequence using an ABI-494 sequencer (PE Biosystems, Inc. Foster City, Calif.) for their authenticity. The proteins are dialyzed against PBS containing 20% (v/v) glycerol for storage at −80° C. For applications such as CTL, cytokine secretion and heart transplantation, the proteins are subsequently dialyzed against PBS to remove the glycerol in the solution.

BIAcore Analysis

The binding of human AIM-II to human TR13-Fc may be assessed by BIAcore analysis (BIAcore Biosensor, Piscataway, N.J.). TR13-Fc or TR2-Fc fusion proteins are covalently immobilized to the BIAcore sensor chip (CM5 chip) via amine groups using N-ethyl-N'-(dimethylaminopropyl)carbodiimide/N-hydroxysuccinimide. Various dilutions of AIM-II are passed through the TR13-Fc- or TR2-Fc-conjugated flow cells at 15 microliters/min for a total volume of 50 microliters. The amount of bound protein is determined during washing of the flow cell with HBS buffer (10 mM HEPES, pH 7.4, 150 mM NaCl, 3.4 mM EDTA, 0.005% Surfactant P20). The flow cell surface is regenerated by washing off the bound proteins with 20 microliters of 10 mM glycine-HCl pH 2.3. For kinetic analysis the flow cells are tested at different flow rates and with different density of the conjugated TR13-Fc or TR2-Fc proteins. The on- and off-rates are determined according a kinetic evaluation program in the BiaEvaluation 3 software using a 1:1 binding model and the global analysis method.

Generation of Stable Cell Lines that Express Human AIM-II

The full-length human AIM-II gene were PCR amplified and subcloned into pcDNA3.1. The parental vector and the AIM-II expression vectors were then transfected into 293F cells (Life Technologies, Grand Island, N.Y.) using Lipofectamine (Life Technology) and stable clones resistant to 0.5 mg/ml geneticin were selected.

Flow Cytometry

Cells are incubated with Fc-fusion proteins in 100 ul FACS buffer (d-PBS with 0.1% sodium azide and 0.1% BSA) for 15–20 minutes at room temperature. The cells are washed then once and reacted with goat F (ab)$_2$ anti-human IgG (Southern Biotechnology, Birmingham, Ala.) for 15 minutes at room temperature. After wash, the cells are resuspended in 0.5 ug/ml propidium iodide, and live cells are gated and analyzed on a FACScan (BD Biosciences, Mansfield, Mass.).

Stimulation of Human T Cells for AIM-II Expression

Briefly, T cells are purified from human peripheral blood and stimulated with anti-CD3 in the presence of rhuIL-2 for 5 days. The cells are then restimulated with PMA (100 ng/ml) and ionomycin (1 mg/ml) for additional 4 hours. AIM-II expression on the cells may be assessed by the binding of TR13-Fc, TR2-Fc, or Fas-Fc to the cells using flow cytometry. If TR13 is shown to bind activated T cells, the binding can be shown to be specific to AIM-II if control Fc fusion protein (e.g., Fas-Fc) does not bind to these cells, and if the binding could be competed off with soluble TR13. Additionally the specificity of the binding of TR13 for AIM-II, is demonstrated if the same soluble TR13 protein can also compete off the binding of TR2-Fc and LTbetaR-Fc from the T cells, TR2 and LTbetaR being receptors of AIM-II.

Three-Way MLR of Human PBMC

It has been shown that soluble AIM-II can enhance a 3-way MLR, and soluble recombinant TR2-Fc can inhibit the 3-way MLR or dendritic cells-stimulated alloresponse of the T cells. These immune regulations are likely via the interaction between soluble AIM-II and its cell surface receptor TR2. To determine if TR13 could interfere with the interaction between AIM-II and TR2, the ability of TR13 to alter T cell alloresponses might be analyzed by testing the effect of TR13 in a three-way human MLR.

PBMC from human donors are purified by density gradient using Lymphocyte Separation Medium (LSM, density at 1.0770 g/ml, Organon Teknika Corporation, West Chester, Pa.). PBMC from three donors are mixed at a ratio of 2:2:0.2 for a final density of $4.2 \times 10^6$ cells/ml in RPMI-1640 (Life Technologies) containing 10% FCS and 2 mM glutamine. The cells are then cultured for 5–6 days in round-bottomed microtiter plates (200 microliters/well) in triplicate, pulsed with [$^3$H] thymidine for the last 16 h of culture, and the thymidine uptake was measured as describe before (Chen, H., et al., 1996. *J. Immunol.* 157:4297, which is hereby incorporated by reference in its entirety).

One-Way Ex Vivo MLR After In Vivo Stimulation in Mice

It has been shown previously that T cells stimulated by alloantigen in vivo have increased spontaneous proliferation ex vivo, and alloreactive T cells depend on AIM-II for some costimulation in certain cases. In order to test whether TR13 had any immune regulatory effects in vivo on alloantigen-stimulated T cells, the following assy migt be performed.

The F1 of C57BL/6xBALB/c mice (H-$2^{bxd}$) are transfused i.v. with $1.5 \times 10^8$ spleen cells from C57BL/6 mice (H-$2^b$) on day 1. TR13-Fc or a control fusion protein is administered i.v. daily for 9 days at 3 mg/kg/day starting one day before the transfusion. The spleen cells of the recipient F1 mice are harvested on day 8 for in vitro proliferation and cytokine assays.

Ex Vivo Mouse Splenocyte Proliferation

Single splenocyte suspensions from normal and transfused F1 mice are cultured in triplicate in 96-well flat-bottomed plates ($4 \times 10^5$ cells/200 microliters/well) for 2–5 days as with the human MLR. After removing 100 microliters of supernatants per well on the day of harvest, 10 microliters alamar Blue (Biosource, Camarillo, Calif.) is added to each well and the cells are cultured for additional 4 h. The cell number in each well is assessed according to $OD_{590}$ using a CytoFlu apparatus (PerSeptive Biosystems, Framingham, Mass.).

Mouse Cytokine Assays

Cytokines in the culture supernatants of mouse spleen cells can be measured with commercial ELISA kits from Endogen (Cambridge, Mass.) or R & D Systems (Minneapolis, Minn.), for example.

Mouse Cytotoxic T Lymphocyte (CTL) Assay $L^d$-specific transgenic 2C T cells may be used as a model system to evaluate the effect of TR13 on the differentiation of alloantigen-specific CD8 cells into effector cells, since the CD8 cells are mainly responsible to the alloresponsiveness, and the high alloreactive CD8 CTL precursors in the 2C mice gives out elevated read-out signals for easy detection of possible changes exerted by TR13.

Transgenic mice carrying $L^d$-specific TCR (2C mice) are used in this experiment. In the 2C mice, the majority (about 75%) of T cells are CD8$^+$, and almost all the CD8$^+$ cells express a clonotypic TCR recognized by mAb 1B2. The 2C mice in our colony are of an H-2$^b$ background. 2C spleen cells are stimulated with an equal number of mitomycin C-treated BALB/c spleen cells in 24-well plates at a final density of 4×10$^6$ cells/2 ml/well. After 5 days of culture in the presence of 10 U/ml recombinant human IL-2, the viable cells are counted and assayed for their H-2$^d$-specific cytotoxic activity using $^{51}$Cr-labeled P815 cells (H-2$^d$) as targets. A standard 4-h $^{51}$Cr release assay (Chen, H., et al., 1996. *J. Immunol.* 157:4297, which is hereby incorporated by reference in its entirety) is carried out in 96-well round-bottomed plates with 0.15×10$^6$ target cells/well/200 microliters at different ratios of effector/target cells (10:1, 3:1, 1:1 and 0.3:1). After 4-h incubation, 100 microliters of supernatant are collected from each well and counted in a gamma-counter. The percentage lysis of the test sample is calculated as follows:

% lysis=cpm of the test sample−cpm of spontaneous release cpm of maximal release−cpm of spontaneous release where the spontaneous release is derived from 100 microliters supernatant of the target cells cultured alone for 4 h, and the maximal release is derived from 100 microliters lysate of 0.15×106 target cells that were lysed by SDS in a total volume of 200 microliters.

Mouse Heart Transplantation

The ability of TR13 to down regulate an allograft rejection may be assessed with the following assay. Three- to four-month-old C57BL/6 mice (H-2$^b$) are used as recipients, and 2- to 3-month-old BALB/c mice (H-2$^d$) are used as donors. The procedure of heterotopic heart transplantation was detailed in Chen, H., et al., 1996. *J. Immunol.* 157:4297, which is hereby incorporated by reference in its entirety. The contraction of the transplanted heart is assessed daily by abdominal palpation. The duration between the day of the operation and the first day when a graft totally lost its palpable activity was defined as the graft survival time. Animals that lose palpable activity of the graft within three days after transplantation are classified as technical failures (<5%) and are omitted from the analysis.

Example 37

HEK 293T Cell Survival Assay

A human embryonic kidney (HEK) 293T cell survival assay was performed by measuring numbers of viable cells using a Trypan blue dye exclusion staining technique. The assay was performed as follows. HEK 293T cells (3×10$^5$ cells per well) were transiently transfected with 2 ug of expression construct DNAs. 48 hours post transfection viable cells were counted using Trypan blue staining. Results from this experiment are presented in FIG. 12 as described above. The results show that introduction of TR13 restricted cell expansion compared to the vector control pC4. The extent of growth inhibition was similar to that observed following transfection of the apoptosis inducing receptor and ligand combination of Fas and Flag-FasL (the anti-Flag antibody M2 was included in the media to stimulate FasL driven apoptosis at a final concentration of 100 ng/ml).

The studies described in this example were used to test the activity of TR13 polynucleotides. However, one skilled in the art could easily modify the exemplified studies to test the activity of TR14 polynucleotides (e.g., gene therapy), as well as TR13 and/or TR14 polypeptiodes, and agonists and/or antagonists of TR13 and/or TR14.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. This application claims the benefit of priority under 35 U.S.C. § 119(e) of U.S. Provisional Application Nos. 60/144,087, filed Jul. 16, 1999; 60/149,450, filed Aug. 18, 1999; 60/149,712, filed Aug. 20, 1999; and 60/153,089, filed Sep. 10, 1999; each of which is hereby incorporated by reference in its entirety.

Further, the Sequence Listing submitted herewith, in both computer and paper forms, is hereby incorporated by reference in its entirety.

What is claimed is:

1. An isolated nucleic acid molecule comprising a polynucleotide encoding a TR13 polypeptide selected from the group consisting of:
   (a) a TR13 polypeptide having the amino acid sequence encoded by the cDNA clone contained in ATCC Deposit No. PTA-507;
   (b) the mature TR13 polypeptide having the amino acid sequence encoded by the cDNA clone contained in ATCC Deposit No. PTA-507; and
   (c) the TR13 extracellular domain encoded by the cDNA clone contained in ATCC Deposit No. PTA-507.

2. The nucleic acid molecule of claim 1, wherein said nucleotide sequence is (a).

3. The nucleic acid molecule of claim 1, wherein said nucleotide sequence is (b).

4. The nucleic acid molecule of claim 1, wherein said nucleotide sequence is (c).

5. The nucleic acid molecule of claim 1, wherein said nucleotide sequence is (d).

6. A method for making a recombinant vector comprising inserting an isolated nucleic acid molecule of claim 1 into a vector.

7. A recombinant vector produced by the method of claim 6.

8. A method of making a recombinant host cell comprising introducing the recombinant vector of claim 7 into a host cell.

9. A recombinant host cell produced by the method of claim 8.

10. A recombinant method for producing a TR13 polypeptide, comprising culturing the recombinant host cell of claim 9 under conditions such that said polypeptide is expressed, and recovering said polypeptide.

11. An isolated nucleic acid molecule comprising a nucleotide sequence complementary to the polynucleotide of claim 1.

12. An isolated nucleic acid molecule comprising a polynucleotide encoding an amino acid sequence selected from the group consisting of:
   (a) amino acid residues 1 to 1001 of SEQ ID NO:40;
   (b) amino acid residues 2 to 1001 of SEQ ID NO:40;
   (c) amino acid residues 42 to 1001 of SEQ ID NO:40;
   (d) amino acid residues 1 to 906 of SEQ ID NO:40;
   (e) amino acid residues 2 to 906 of SEQ ID NO:40; and
   (f) amino acid residues 42 to 906 of SEQ ID NO:40.

13. The isolated nucleic acid molecule of claim 12, wherein said amino acid sequence is (a).

14. The isolated nucleic acid molecule of claim 12, wherein said amino acid sequence is (b).

15. The isolated nucleic acid molecule of claim 12, wherein said amino acid sequence is (c).

16. The isolated nucleic acid molecule of claim 12, wherein said amino acid sequence is (d).

17. The isolated nucleic acid molecule of claim 12, wherein said amino acid sequence is (e).

18. The isolated nucleic acid molecule of claim 12, wherein said amino acid sequence is (f).

19. An isolated nucleic acid molecule complementary to the isolated nucleic acid molecule of claim 12.

20. The isolated nucleic acid molecule of claim 12, wherein said nucleic acid is DNA.

21. The isolated nucleic acid molecule of claim 12, wherein said nucleic acid is RNA.

22. The isolated nucleic acid molecule of claim 12, wherein said nucleic acid is double-stranded.

23. The isolated nucleic acid molecule of claim 12, wherein said nucleic acid is single-stranded.

24. A composition comprising the nucleic acid molecule of claim 12 and a carrier.

25. The isolated nucleic acid molecule of claim 12 wherein the nucleic acid molecule further comprises a heterologous polynucleotide sequence.

26. The isolated nucleic acid molecule of claim 25, wherein said heterologous polynucleotide sequence encodes a heterologous polypeptide.

27. The isolated nucleic acid molecule of claim 26, wherein said heterologous polypeptide is human serum albumin.

28. The isolated nucleic acid molecule of claim 26, wherein said heterologous polypeptide is a human IgG Fc region.

29. A recombinant vector comprising the isolated nucleic acid molecule of claim 12.

30. The recombinant vector of claim 29 wherein the nucleic acid molecule is operably associated with a heterologous regulatory sequence that controls gene expression.

31. A recombinant host cell comprising the isolated nucleic acid molecule of claim 12.

32. The recombinant host cell of claim 31 wherein the nucleic acid molecule is operably associated with a heterologous regulatory sequence that controls gene expression.

33. A method for producing a polypeptide comprising an amino acid sequence selected from the group consisting of:
    (a) amino acid residues 1 to 1001 of SEQ ID NO:40;
    (b) amino acid residues 2 to 1001 of SEQ ID NO:40;
    (c) amino acid residues 42 to 1001 of SEQ ID NO:40;
    (d) amino acid residues 1 to 906 of SEQ ID NO:40;
    (e) amino acid residues 2 to 906 of SEQ ID NO:40; and
    (f) amino acid residues 42 to 906 of SEQ ID NO:40;
comprising culturing a host cell comprising the nucleic acid molecule of claim 12 under conditions suitable to produce the polypeptide of (a), (b), (c), (d), (e), or (f) and recovering the polypeptide of (a), (b), (c), (d), (e), or (f).

34. An isolated nucleic acid molecule comprising a polynucleotide encoding an amino acid sequence selected from the group consisting of:
    (a) the amino acid sequence of the full-length TR13 polypeptide encoded by the cDNA contained in ATCC Deposit No. PTA-507, minus the N-terminal methionine residue;
    (b) the amino acid sequence of the extracellular domain of the full-length TR13 polypeptide encoded by the cDNA contained in ATCC Deposit No. PTA-507, minus the N-terminal methionine residue; and
    (c) the amino acid sequence of the extracellular domain of the mature TR13 polypeptide encoded by the cDNA contained in ATCC Deposit No. PTA-507.

35. The isolated nucleic acid molecule of claim 34, wherein said amino acid sequence is (a).

36. The isolated nucleic acid molecule of claim 34, wherein said amino acid sequence is (b).

37. The isolated nucleic acid molecule of claim 34, wherein said amino acid sequence is (c).

38. A method for producing a polypeptide comprising an amino acid sequence selected from the group consisting of:
    (a) the amino acid sequence of the full-length TR13 polypeptide encoded by the cDNA contained in ATCC Deposit No. PTA-507;
    (b) the amino acid sequence of the full-length TR13 polypeptide encoded by the cDNA contained in ATCC Deposit No. PTA-507, minus the N-terminal methionine residue;
    (c) the amino acid sequence of the mature TR13 polypeptide encoded by the cDNA contained in ATCC Deposit No. PTA-507;
    (d) the amino acid sequence of the extracellular domain of the full-length TR13 polypeptide encoded by the cDNA contained in ATCC Deposit No. PTA-507;
    (e) the amino acid sequence of the extracellular domain of the full-length TR13 polypeptide encoded by the cDNA contained in ATCC Deposit No. PTA-507, minus the N-terminal methionine residue; and
    (f) the amino acid sequence of the extracellular domain of the mature TR13 polypeptide encoded by the cDNA contained in ATCC Deposit No. PTA-507;
comprising culturing a host cell comprising the nucleic acid molecule of claim 34 under conditions suitable to produce the polypeptide of (a), (b), (c), (d), (e) or (f) and recovering the polypeptide of (a), (b), (c), (d), (e) or (f).

* * * * *

UNITED STATES PATENT AND TRADEMARK OFFICE
CERTIFICATE OF CORRECTION

PATENT NO. : 6,951,738 B2  Page 1 of 1
DATED : October 4, 2005
INVENTOR(S) : Ni et al.

It is certified that error appears in the above-identified patent and that said Letters Patent is hereby corrected as shown below:

Title page,
Item [54], Title, delete "HUMAN TUMOR NECROSIS FACTOR RECEPTORS TR13 AND TR14" and insert -- NUCLEIC ACIDS ENCODING TUMOR NECROSIS FACTOR RECEPTOR TR13 --;
Item [56], References Cited, OTHER PUBLICATIONS,
delete "AII48969" and insert -- AI148969 --; delete "A1623092" and insert -- AI623092--; delete "AII52363" and insert -- AI152363 --; and delete "AA9996710" and insert -- AA999670 --.

Signed and Sealed this

Twenty-seventh Day of December, 2005

JON W. DUDAS
*Director of the United States Patent and Trademark Office*